US006117654A

United States Patent [19]

Pan

[11] Patent Number: 6,117,654

[45] Date of Patent: Sep. 12, 2000

[54] NUCLEIC ACID MOLECULES ENCODING TANGO-77-POLYPEPTIDES

[75] Inventor: Yang Pan, Brookline, Mass.

[73] Assignee: Millennium BioTherapeutics, Inc., Cambridge, Mass.

[21] Appl. No.: 09/128,155

[22] Filed: Aug. 3, 1998

Related U.S. Application Data

[60] Provisional application No. 60/054,646, Aug. 4, 1997, and provisional application No. 60/091,650, Jul. 2, 1998.

[51] Int. Cl.[7] .............................. C12N 5/10; C12N 15/19; C12N 15/63; C07K 14/52

[52] U.S. Cl. ....................... 435/69.5; 435/70.1; 435/71.1; 435/71.2; 435/471; 435/325; 435/252.3; 435/320.1; 536/23.1; 536/23.5; 536/24.3; 536/24.31; 530/351

[58] Field of Search .................................... 530/350, 351; 536/23.1, 23.5, 24.3, 24.31; 435/659.5, 70.1, 71.1, 71.2, 471, 325, 252.3, 254.11, 363, 320.1

[56] References Cited

PUBLICATIONS

Cunningham et al. (1989) Science vol. 244, pp. 1081–1085.

Rieger et al. (1976) Colonary of Genetics & Cytogenetics. Fourth Edition, pp. 16–19, Springer–Verlag.

George et al. (1988) Macromolecular Sequencing & Synthesis, Ch 12, pp. 127–149, Alan R. Liss, Inc. New York.

Auron et al., "Nucleotide Sequence of Human Monocyte Interleukin 1 Precursor cDNA", *PNAS USA*, 81(24):7907–11 (1984).

Carter et al., "Purification, Cloning, Expression and Biological Characterization of an Interleukin–1 Receptor Antagonist Protein", *Nature*, 344:633–38 (1990).

Lennard et al., "Cloning and Chromosome Mapping of the Human Interleukin–1 Receptor Antagonist Gene", *Cytokine*, 4(2):83–89 (1992).

March et al., Cloning, Sequence and Expression of Two Distinct Human Interleukin–1 Complementary DNAs, *Nature*, 315(6021):641–47 (1985).

GenBank Accession No. P01584, Auron et al., Jul. 15, 1998.

GenBank Accession No. P18510, Carter et al., Jul. 15, 1998.

Sonnenfield et al., "The Drosphila tango gene encodes a bHLH–PAS protein that is othologous to mammalian . . . " Development 124(22):4571–82, 1997.

Pan et al., "Mutations in the V2 vasopressin receptor gene are associated with X–linked nephrogenic . . . " Nature Genetics 2(2):103–106, 1992.

*Primary Examiner*—Prema Mertz
*Attorney, Agent, or Firm*—Fish & Richardson, P.C.

[57] ABSTRACT

Novel Tango-77 polypeptides, proteins, and nucleic acid molecules are disclosed. In addition to isolated, full-length Tango-77 proteins, the invention further provides isolated Tango-77 fusion proteins, antigenic peptides and anti-Tango-77 antibodies. The invention also provides Tango-77 nucleic acid molecules, recombinant expression vectors containing a nucleic acid molecule of the invention, host cells into which the expression vectors have been introduced and non-human transgenic animals in which a Tango-77 gene has been introduced or disrupted. Diagnostic, screening and therapeutic methods utilizing compositions of the invention are also provided.

43 Claims, 118 Drawing Sheets

```
GTCGACCCACGCGTCCGCAGACGTCTACCTGGGGGTCCCGTCTGCGCTCCCGGGATGGAAAACGCCCAGGGGAAACTTA  79

GGCAGGCGAGCGGACGGGCACCTCCCGCGGGACGAACTCACTCGGTGGCCTCCTACTTCCCCGGCCGTGTTCCAACGCC  158

TGAGAATAACGGGAACAGCGGTCGTACTCACCGACAGCGGCAGCAGCGGCCTCTCTCAATTGGGCAAAGCACTCCAGAC  237

CTTTTGGAAGAGTGACACCAAAGGCAAGCACCTGCTTGGCAGGCCCCTCAGCTTCTACGCAAGTATAAGTCTTGGACTT  316

                                         M   S   F   V   G   E   N   S   G   V    10
CATTCCATTTTCTGTTGAGTAATAAACTCAACGTTGAAA ATG TCC TTT GTG GGG GAG AAC TCA GGA GTG  385

 K   M   G   S   E   D   W   E   K   D   E   P   Q   C   C   L   E   D   P   A    30
AAA ATG GGC TCT GAG GAC TGG GAA AAA GAT GAA CCC CAG TGC TGC TTA GAA GAC CCG GCT  445

 G   S   P   L   E   P   G   P   S   L   P   T   M   N   F   V   H   T   K   I    50
GGA AGC CCC CTG GAA CCA GGC CCA AGC CTC CCC ACC ATG AAT TTT GTT CAC ACA AAG ATC  505

 F   F   A   L   A   S   S   L   S   S   A   S   A   E   K   G   S   P   I   L    70
TTC TTT GCA TTA GCC TCA TCC TTG AGC TCA GCC TCT GCG GAG AAA GGA AGT CCG ATT CTC  565

 L   G   V   S   K   G   E   F   C   L   Y   C   D   K   D   K   G   Q   S   H    90
CTG GGG GTC TCT AAA GGG GAG TTT TGT CTC TAC TGT GAC AAG GAT AAA GGA CAA AGT CAT  625

 P   S   L   Q   L   K   K   E   K   L   M   K   L   A   A   Q   K   E   S   A   110
CCA TCC CTT CAG CTG AAG AAG GAG AAA CTG ATG AAG CTG GCT GCC CAA AAG GAA TCA GCA  685

 R   R   P   F   I   F   Y   R   A   Q   V   G   S   W   N   M   L   E   S   A   130
CGC CGG CCC TTC ATC TTT TAT AGG GCT CAG GTG GGC TCC TGG AAC ATG CTG GAG TCG GCG  745

 A   H   P   G   W   F   I   C   T   S   C   N   C   N   E   P   V   G   V   T   150
GCT CAC CCC GGA TGG TTC ATC TGC ACC TCC TGC AAT TGT AAT GAG CCT GTT GGG GTG ACA  805

 D   K   F   E   N   R   K   H   I   E   F   S   F   Q   P   V   C   K   A   E   170
GAT AAA TTT GAG AAC AGG AAA CAC ATT GAA TTT TCA TTT CAA CCA GTT TGC AAA GCT GAA  865

 M   S   P   S   E   V   S   D   *                                               179
ATG AGC CCC AGT GAG GTC AGC GAT TAG                                              892

GAAACTGCCCCATTGAACGCCTTCCTCGCTAATTTGAACTAATTGTATAAAAACACCAAACCTGCTCACTAAAAAAAAA  971

AAAAAAAAGGGCGGCCGC                                                               989
```

FIG. 1

```
                1                                                              50
IL1ra-human     MEICRGLRSH LITLLLFLFH SETICRPSGR KSSKMQAFRI WDVNQKTFYL
T77-human       ~~~~~~~~~~ ~~~~~~~~~~ ~~~~~~~~~~ ~~~~~~~~~~ ~~~~~~~~~~
IL1b-human      ~~~~~~~~~~ ~~~~~~~~~~ ~~~~APVRSL NCTLRDSQQK SLVMSGPYEL
Consensus       ---------- ---------- ---------- ---------- ----------

                51                                                            100
IL1ra-human     RNNQLVAGYL QGPNVNLEEK IDVVPIEPH. ALFLGIHGGK MCLSCVKSGD
T77-human       ~~~~MNFVHT KIFFALASSL SSASAEKGS. PILLGVSKGE FCLYCDKDKG
IL1b-human      KALHLQGQDM EQQVVFSMSF VQGEESNDKI PVALGLKEKN LYLSCVLKDD
Consensus       ---------- ---------- ---------- ---LG----- --L-C-----

                101                                                           150
IL1ra-human     ETR..LQLEA VNITDLSENR KQDKR.FAFI RSDSGPTTSF ESAACPGWFL
T77-human       QSHPSLQLKK EKLMKLAAQK ESARRPFIFY RAQVGSWNML ESAAHPEWFI
IL1b-human      K..PTLQLES VDPKNYP..K KKMEKRFVFN KIEINNKLEF ESAQFPNWYI
Consensus       -----LQL-- ---------- ------F-F- ---------- ESA--P-W--

                151                                   192
IL1ra-human     CTAMEADQPV SLTNMPDEGV MVTKFYFQED E~~~~~~~~~ ~~
T77-human       CTSCNCNEPV GVTDKFENRK HI.EFSFQPV CKAEMSPSEV SD
IL1b-human      STSQAENMPV FLGGT.KGGQ DITDFTMQFV SS~~~~~~~~ ~~
Consensus       -T------PV ---------- ----F--Q-- ---------- ~~
```

FIG. 2

>Contig1
GAAGTGAAGATATAATGTATAGTAGTAATATATAATGTTAGGTGAATTAA
AGGAAATAGAATATATTGGGGAGTAATTATGGGTGTAAAGAAATATAGTA
GGGAAGTATTTAGATTTGAGAAAAAAAAAAAAGGAATTTAGTGTAGGTGAA
NAATAAAAGNANAAGGTTAAAAATTAAAAAAAAATTAAATATAAATAAAT
AAATAAAAATAAAAATAAAATAAAAAATTTAAAAAATTAAAAAAATATAA
AAAATAAAGAAATGGAAGTGGATTCTTAGAAAAAAAAGAAAGTAAGGTGA
TATGAGGAGATAGAGAGGATGTGGTGTGAGATGATTGGTTTAATTAGAAA
ATAGGTTTTGAATAGAGTGGGAAAGTAGAGTTTTGGTAAATGTGGGGGA
AGAGGGTAATGTTGTTTGAGTGAAAGAAAAAATGGTATATTTTTATAAAA
TAATGAGGAAAGTGTGTGAAAAAAAAATTATTGGGATTTGGGAAGGTGAT
ATATAAAGTTGTGGAAAATTTGGGGGGTGGGGTTTATTTAGGATTAAAAA
GTTATTTAAAGAATGAAAATGAATTTTTGTTTGTAATTTGGGGATAAGAA
ATTAATGTTTAGAAAGAAAGGGAAAAAATTGAAGAAAAAAATTTAGATTT
TGGAAATTTAAAAATATTGTGGGTGTAAATAGGAAGGATTTTTAAAGGTA
ATTGTGGAAGGGATTTGTGTGGAAAATAATAGGGAGAAAAAATGGGG
>Contig2
GCATCTAACTGGAGCCTGCATTATTACAGATTTAGCATCACCAAAGTCTA
AACAATTAGACTGACTAAGGCAGAACTGCCCTTATGACAGCAGACATAAG
AAGGAAAAGGCCAAAACACTGTGTTAAAAATTATCCAAATGTGAGGAAAA
GGCAAAGAGAGTAGGTGTGCCTTTTTAGTGTCTAAGCTGCCTGCCCAAGG
GGCATCTGATGCTCTCAGGCAGGAGTCCACAAATTTTTTTTGTAAAAGA
TCAGATAGTAAATCTTTTCAGCGTGAAGAGCATGAGGTCTCTGTCACAAA
TACTCAACCACCATTACAACATGAAAGCAGCCAACAGACAACACATGACA
AATGAGTGTGGCTGTGTTCCAGTAAATCTTGATTACAAAAACAGGCAAGA
GGCCAGAGCTGACCCATGGGCCATAGTTTGCTGACCCCTTCTGTAAAGGA
AAGTATTTTTGTTTGACTTGCTGTTTACCATTGATTGAACACAAGGCTCT
GTAAAGTTACTTGTTAACTTGCAGAAGATTGATGAGTGGCAAGTAATTTT
TATTCACCAGAATATAAAATTATTTCTGTTCAGTAGAAAAGATAAACCAA
CTGTGATATTATGGTCCTG
>Contig3
GGGGTGTCTGTCTACCATGTGCTCGCAGTTCTGTAATAAATGTTCTCTCA
AGATCCTTAAAATCTCTTGGAAATTATAAAAATATTGGAAAGAGAAGAAC
AGTTTTTAAAATATATATATATATATATATATTTTTTTTGAGATGGAGTCTT
GCTCTGTCGTCCAGGCTGGAGTGCAGTGGCGCAAACTTGGTTCACCACAA
CCTCTGCCTCCCGGGTTCAAGCGATTCTTCTGCCTCAGCCTCCTGAGTAG
CTGGGACTACAGGCGCCCGCCACCACGCCCAGCTAATTTTTGTATTTTTA
GTAGAGACGAGGTTTTACTATGTTGGCTAGGCTGGTCTCAAACTCCTGAC
CTTGTGATCTGCCCGCCTTGGCCTCCCAAAGTGCTGGGATTACAGGTGTG
AGCCACTGCACCTGGCCAGTTTTTTAAATATATTTTTAAAAACACTTGAA
TAAGAGTCAGTGTAAACTAGAAGTTTAAAAATGCTTCACAGAACACCCAG
GGTTTACATTACAAGATTCTCACAACAAACCTATTGTAAAGGTGAGTAAG
GCATGTTATTACAGAGAAAAGTTTGGGAGCAAAACTGTAAAAAATTATAT
TTTTGTTGTATTTTCTAAGAGAAAGAGTATTGTTATGTTCTCCTAACCTC
TGTTGATTACTACTTTAAGTGATTTCCTTGAGAGCACATGATGATCC
>Contig4
GCCGTTCATAGAAAACTGAAAGCAATAAGATGACTAGGTAAGCATGACAT
TTAAAAGGTATTCATGGGACGTGGTTACAAAACCAACTCACAACTAAAAA
GTCTTAGGACCTCTCGCTGACTTAGGAGCCTGATCCCAACTCTGAGAATG
ACTCAGTGTGTTACCCTGTGGCTAGTGTAGACCAATGATCCTGTCTCAGA
GTCACTAGCCAACAGCCCATATCAAGTACTTGAAACTTTGACTCAGAAAC
CTCAGTGTCAGAACCTTTGACCTAGGAACCACCTGTAGTGGTTAACTGCA
ATTTGCACCCCTTAGTTCAGGGCTTTACAACACCGGGGGCGGGGAGGGGA
AAGGCATANANCTGATGACCTAAAGGAAACCCATTGCAGCAACGCTTTTG
TGTTAAGTGTACAAATAAGTGTTGTTTTAGAATCCTCCAGGTAATGCCTT
TGTTATTTAATGTGTCTGAGACAATTCTGCACATTAAAGAATATAAAATA
TTACCTTGTAATTCCAATTTGAAATGTGTAATTGACATTAGACTTCTATT
TGAATTTGAAATGTCTAAAACAATGTGGTTAAGTTTGTAAAAGGTGTGTG
AATTTTGAGTCTGATTTACTACATTTTTTTTTAATTTTCTTTTTTTTTGG
AGTTTTAGGGATTGCTTAGATGGCTAGAAAGATTTTATTCATCAGATTTT

FIG. 3A

TAAGTCTGCCTTGGCAGGCACTTGCAGTGTTTGAAAGAATCAGATATATC
AAATTTGTAGTTTAAAATATTTAAGGGAACTCAATTAACTATGCTAGAAA
AGAGAATTAAGTATTTAGGAGGATTTAATATGGTGTGAAAGTTGTGAAAA
TCAAAATGGAGACACTAATGTTAAGAAAACCCTGATAAATGGAACCAGGG
AAAGGCATGAAGATAGAGTTCTCACACTTGTATCCCTGATCATGAAAAAG
ATCTGC
>Contig5
GGGTTTTTCCGCGTTTTTACCCGAAATCTTCAAGGGATGGAAAAAGAAA
ATTGCTAAAAAATCTCGGTTTTTTGGTTTTAACAGATATTTACACCNTGG
ATCCCATTTATTATGTTGTCCCCAAGGTTTTCGGTGGGTTCCCAATCAGT
TAGCCCCCCTCCACAGTGAAAGCACTTTACTTTATCACCTTCACCTAAAG
CATAAAATCCAGCTCTTGAAAGCTGCTCCTTGTTAACTGAATATATCCAC
ATCCCAAAAGTAATGATCCATGCTTCATAATCTGCCACGGATGGATGGAT
GGATGGATGGATGGATGGATGGATGGATGAATGGATGGATTGATTTCTTG
GAGGATTTGTTGAATTTGGGAAATTCCACGCCAGGACAGCTGGCCCAAAC
TGCCCGCGACAATCTGCTCGGTACAAGGGGAGGGTCCTGGAGAGGGTGCG
GCCCGAGCCCCAGTTTGGAAATGCCAACTTGGCTCTGCAGCCGGGCCTTA
GCCACTTGGGTCTGGCGTCCCTCCATTATTAGCGCCATGCCGGCTCGGGG
TGCTGCCAAGTCCCTGAGAGCACAAGCC
>Contig6
CGCGCTCAAGAAAAGCTGAAGTGTGAATGTTCTGTCTACCTTCACAGTAA
ATGCTAAGAGAATGACCCAAGAGCAGAGGGTATCACTCTGCTACGGAGGA
TTGATTGTAACTGGCTCTCCTGCCTTAGCAAGAAATGCCAGAACCATGGT
CATTCAAGTTCTTGACCAAAAACTGCCTTCATGAGAATCAACTTCCCCAA
GAAAAAAAAAGCAGAAACAGGCAAAGCTTCCAGCATGGTAGGTAATACTG
ACCCTTCTTCCCTCCTTCCTTTGGAGATTCACACAGTAATAATGCATAAA
GCTTTGCCAATGGACTAAGCACTGCCCAGGGGTTTTTGTCATGCCTGGAC
TGAAATGCTCTTTTTGCGTTATCATAGAATCCCAGTGCAGTCTGAGTAGA
CTCTAAGCAAAAGGGACATTTTTCAAAAAGGCTTTAAATTGCTAGTACAA
AGAAGGCAACAAAACTTGCGTAACTGTGGACAGATTAACTCACTTGGTGT
TTTGGCTCTTCAGTTTTCCCTTGGCTGCGAAGTACTCCTGAAGCTTTCTC
TGCGGCTCTTCCTGCAAGCAGGCAAGCAAAAAAACGACTGAACTTTATTT
CGAGAT
>Contig7
GAAGAGCCGCTAACTTGCTGTAGTGATAAGGAATGAACTAAGGCTAGGGA
CATATTAACATCCGCTGGTGGTGACTCTTTAGCCTAGATCTTACCCCACT
CCTGCTCCTTCCATATGGTTCGGTCTCAGGCTCACTACCGATCAATGGCG
TACTAAAAGCACTAACTATAGACTCCAACACGTCTGTCGTGTGTTTCACG
ACAAGCCGTGGAGTTAATCCCTCTGACAGTAGCTCAGATAAGGATGGGCT
ATCATGGGCCCGGAACTGGGGCATGACGCTCGTCACCAACGCATGAGCTC
CCCAAGTATGCTATACCTGTCCCTATGAAGGGCTTCCAACTCTATGTGCA
GTCCCCATGTGGAGAGTCAGGTATTGATTGATCAAGCCAGGGGTGTGGTG
AATGGGGAGCTTCCTACAGGGGTAATGATAATTGAAATGCACGGTGATGG
GGATTTTCATATTGGTCTCCTAAGGAGATAACAGATTGGATGCGGGGTCG
ATATTCCACTGCCCAGGGTGTGTACCGAGGGTATCTGCAGGTGGATCTCC
TCCCCACGTTTGATTAATACTCCTGTCTTGGGAAGCATAGACGGGCGGGG
GAAATGATGAAGGGTGACCACTCCCC
>Contig8
GGGAACGCAGTGCTCTGTACGATGGCCTTGATTGCGAATTCCTGCAGGGG
GGG
>Contig9
GGCAAGAGATTTAATATTCATTCCATCTTCATTTGGAAGATGAAAAATTG
GGGACCAGAGAGGGGAGGGGACTGGGCCAAGTTTTCAAAGAAAAGTCAGT
AGGAATTGTGAATTCCTGGGGGCCGGGGCCCATTAGTGCTGTTTTGGATC
AGTAAATGGAGATGTGAGTTTCAACAGTAACAGGGACATTTTAAAATTAA
AATGATTTAACCTTTAGAAAATGTCCTATTTTGTAATAATGATGGATTCA
CAGGAAGGTACAAAGAAATGTCCAGAGAGTTCNTGAGCCCCCTTCAGCCA
GCTTCTTCCAATGTTAACATCTTGCATTATTATAGTACAACATCAAAACT
GGGAAATCGATATTGGTACTGTCCAGATAGCTTACTCAGATTTTGCCAGT
TATACTTCCACTCATTTGTGTGTGTGTGTGTGTGTGTGTGTGTGTGTGTG

FIG. 3B

TGTGTGTAGCTCTATGCAATTTTATGTGTGTAGCTTCATGTAACCACCAC
AATCACAATACTTAACTATGCCCTCATCACAAGACTCTCTCTTGCTATGC
TTTACAGCTGTATCCTCTTCATCTCCAAACCCTAAGCCCACCTCACCGCC
TCCACCATCTCTAATCCCTGGCAACCACTATTCTGTGCTCCATCTCTGTA
ATTAATTGTGTTAATTAATGTTATACAAATGGAATCATGAAGTATGTGTC
CTTTGAGATTGGGCTGTTAATTTTTCACTCAGCACAATTTCCGTGAGTCT
AATCCAACTTGTGTGTAGCAGTAATTCTTTCCTTATTATTGCTGAATAAT
ATGCCATGGTATGGATGTATCACAGTGTGTCTAATCCTTTGCCCATTGAA
AGGAATTTGGATAATTTCCAGGTTTTGGCTATTATGAATAAAGTGAACAT
AAGACATGTGTGTACAAATTTTGGTGTGATCAAAAGTCTCATTTCTCTGG
GATAAATGCCCGGTAATGAAATGGCTGGGTTGTGTGGG
>Contig10
GCAAGAACACAGGCGCGTATTATAACCTTACTACCAAGACCTGAACCCAT
ATAAAGGTTTATGCGTAACAATCATCATCCCTGTTCCAGAAGATTACACG
TACGACCACGCCTGGCTCACCGACTCACGTGGCCAGTACCAGAAATTCT
CCCAAACAAACAGTCGTGTCTGAAAACAATCGCGGTGACCTCCACGGTTA
GAAAAGCCTGTTTTCAAGTCCTGGAATTGCCACATATTAGCTGGGTAACT
TTGGGCATCACATTTACTCTCTCCGAATTTCAGATTGCAAAAACTCATTG
GATTGTTTTGTGGATTGAAAGAAATAATGTAAATTTAGGCCGAGTGCTTT
GACTTACGCCTGTAATCCTATCACTTTGGGAGGCCAAAGCAGGAGGGTCA
CTTGAGCTCAGGAATTTGAGACCACCTCTGGCAACATAGTGAGATCCTGT
CTCTACAAAAAATTTTTTTAAATTATCCAGCATGGTGGTACACGCCTGT
ATTCCCAGCTACTCAGGAGACTGAGGTGTGAGGATTGCTAGAACCTGGGA
GATCAAGTCAACAGTGAGCCGTGGTTGTGCCACTGCCCTCCAACCTCAGT
GACAGAGGAAGACCCTGTCTCAAAAAAAAAAAAAAAAGTAGTAAGTTTAA
AGAACTTAGTGTAGGCCTGGCATATAAATGATATTGTTGATGTTGATGTT
AGCTTGAAGGCACATTTATAGGAGTAGGGATTTTATAACATTATGAGCCT
GAGAGCACATATAATGTTCCC
>Contig11
GGTCTAACATGCTCCAACTGAAGAAACCCCACACTTGTCCGGCAAGGAAA
CTACTACAGATTTCCTGACCTACTGTGCAATTCGGGGCATGCGACGGGAC
TGTGTTTCTGGGTACGCTGTCTCAGGTTCGTCTGGGATGTAAGAATTCAA
CTTCAGTAGTTCTCTCATAGACGCCGACGAGAGGGGCGTCTCTTTTCTCT
GATGAATCTGCCAGATCTTCCACTTCATAGAGTCTAAATCCTCCGATTCG
ATCTACTGGAGACCCCCACGTTACAAAAACGTCTAACGTCGGTGACAGCT
CCCCACATAGGGAAAGATCACCTGAGTCTCACTACCTCACATTAGTGCTA
TCTCCAGCCCCATGCTATCTACGAGATGGTCACGCGAGGTTTAAGGGGTC
TCCGATTCCGGTGGTCCGATTCAGCTAATCGTGGCCCTACGTGAACGATC
ACTCCTGCTCGTAACATCGATACAGGGTCGCGCTGACAAATGGTACTACG
TAGGTTCTCAGGTCAATGCCGCGTCACGAATGAGCCTAACTACCCCATAA
GTGCACGTACTGTGTTACCTTTCCTGTTCGGCCAAACCTGCTACTGTATG
CTGTGCTTGTTT
>Contig12
AGGCTCCATGTGCTCTAGCCTGATTATCTTTTCAAGTGTTTTATTTGCTA
ATCTATAAGGCCCCTTTCGTAAAATGTTCACTCATTTTCTAATTAGATAT
TTTTTTTAATGTTGAGTTTTGAGAGTTCTTTAGATATTTTAGATACAAGT
CCATTGTCAAATATGTGATTTACAAATATTTTCTCTCAATCTGTAATTTA
GTTTTCATCCTCTTAACAGGGTCTTTTGGAGAGCAAATAATTTGATTTTC
ATAAGGTTCAAATTATTAATTTTTTCTTGTATAGTTCACACTTCTAGTGT
TAAGTCTAAAAACTGTGCCTTGTCATAGGTACCAAAGGTTTTCTCCAGTT
TTTTTTCTAGAAGTTTAGAGTTTCATGTTTTACATTGGAGTCCATGATCC
ATTGTTAATTAATTTTTGTATATAGGTAGATGTTTAGGTTTAGGGTTTTT
TTAAAAAAAAATTACATATGTTTAATTGCTCCAGTTCCCTTTCATTGAAA
AGGGTATCCTTCCTCCATTGAATTGCCTTTGTCAGAAATTAATTGGACAT
ATTTGTGTGAGTCTATTTCTGGGCTCTTTATCATGTTACTTTTAAAAAAT
GCATCAGTTCCTCCACCAATACCTCATTGTCTTGATTATTGCAGTTATAT
AGTAAGCCTTAGCATTAGGAAAAGTGTTTTTCCTGCTTTATTCTTTNTCA
AAAAATTTTTGGATATTCTAGGGCCTTTACATATAAATTTTAAAATAACT
TTGTCTATGTCTAACCGAAAGCCTTATGAAGATTTTGATAAGAATTGCAT
TATGCCTATACATTAATTTAAAAAGAACTGATGTCTTTATTCAGTTGATT

FIG. 3C

CTGCTAATCTATGAACATAGCATCTCTCTCAAAGCATTTAGTCTTTCTTT
AATTTCTGTCATTAATTTTTAAAATTTCATCCTAAAGATTCTGTATAT
GTTTTGTTGAATTTATGCTTAAGCATTTCACTTTCTTGGTAACAATTATA
AATGATTTTGTGTTTTTATTCCACTAGTTCATTTTCAGTGTGTAGAAAA
GCAATGAATTTTTGTGTGTTGATCTTTGTTCCTACATCTTGCAACATTAT
TGAACTCATTTATTAGTTCTAGGAGGTTTTTCATTTTTCTTGTAGATAC
CTTGAGATTTTCTATATAGACAGTCATGTTGTCTGCAAACAGGCACAGTT
TTATTTCTTCCTTTTCAATCTATATGCCTTTTTTTTTTTTTTTGCCTTAT
TGCAGTGGCTAGAACTTCTAGCACTATGTCAAATAGCATTGGTGAAAGCA
GACATCCTTGTTCCTTGTCTTAGAGGAACATTTGGTCTTTAATCTTGGAT
TGCG
>Contig13
GCGCCTCCTTTTCTCTTCCAAAATTTCTCTTGTCTAGTTATTTGTCCAGG
GAAATTTGAAAGCTCACTTACTGTGCAAGTCAGCAGGAAACAACTGGGTC
TGTGCACAGCACCTAGCAAAGTTCTGCTCTAGGAATTACACTTTGGCCCT
GAGGTAGATTTCTACAAGAACCTTACCTTCTAAGCAGCACTGGGGTTCAT
CTTTTTCCCAGTCCTCAGAGCCCATTTTCACTCCTGAGTTCTCCCCCACA
AAGGACATTTTCAACGTTGAGTTTATTACTCAACAGAAAATGGAATGAAG
TCCAAGACCTAAGGAGATAGAAAGGGGACCAGTTATGGCATCTTCTCACC
CCAGGACACCTTGCTGCATGTCTCTAGTGCTGAACAGACCACTGGCCTTG
CTCTGTAGTTTGAAATGCTCGCTGCAACCAGAAAGGCACCAAGGGGCCAG
ACCATGCTCTCCTGTCTATCACGCCTTCAAAGCAGAATTTCCCAAACCTT
GAGTCACAGTGCTAACACACGGGGTGCCATAACATTTTTGTTGATTTTGG
CATTTTACAAAAATAAAATAAAAAAGTTAAAAATGCATTGCTCTATTCTT
GGGGCTGGCACACTATTGCCTTTGGCCAAATCCGGTCCCTGACTGTTTTT
TTAAATAAAGTTTTATTGAAACACAACCATGCTCTTGTGTACATATTGTC
TCTTGGCTGCTTCGAAGCTACAATA
>Contig14
GTGTTCGCTTTTTAACACTTACCTAAAATTACTCTGTAATCCATGGATCC
TTAATTTATTTAAAAAACTAATGTTAATGAGTAGCTTTATTTTCCTCCCA
TCTAATTTAAGGCCCACAGAACACCTTCACTTACCTCAATCCTCTCCCAA
CTTACATGCTTTTAATGTCATATATGTTAATACCGTATACTTTTAAAACT
TTCTAAAATAGCATTATTTTATAGCATGAGTGTTCATTTACATTTTTGCA
TATATTTAGAATTTTCTTTGCTCTTCGTTTCTTCTTCTATTTATGACTCC
CCTCTGGGATCATTTTCCTTCTACTTGAAGTACATAGTTTAGAACTGCAC
TATTCAATACAGTAGCCACTAGCCATGTGTAGCTATTGAAGTTTAAACTA
AGTAAAATTGAGTAATATTAAAAACTCAGTTCCTTCATCTCACTAGCCAC
ATTTCAAGTGCTCAGCAGCCACGTGCGACTAATGACTACTGTACATCAAA
CATATAGAACATTTCCATCATGGCAAAGAGCTCTATTGATAGTGTTCATC
CAGAGTTTCTGTTCCAGGACCAAACTGAGGGTTGGGCTGCTATTTCTCAT
GGCCCAATAACAAGATGCAGATGAGCTGGGGAGGAAGAGAGTTTTTATTT
CTGCNACCATTTACCGGGAGAAGGCCTGGAAATCATCACCAGGCCAACTC
AAAATTATTACGTTTTCCAGAGCTTATATACCTTCTAAGCTATATGTCTA
CGTGTAAGTGTGCATTCACCTGAAGACGTTAGTGATTAACTTCTTTTAAT
CTGTAACTAAGGTCTGAGTCCGGAAGATCTTCCCCTGGAGCCTCAGTAAA
TTTACTTAATCTAAATGGGTCCAGGTGCTGGGGTAATTACCCTTATCTTG
TCCCCTGCTAAATCATGGAGGTTTGGGGATTCCTTTAGAGCACCAATAAA
CTTGTTTGTGGAGGCCTGGGGGTTTCTTCTGACCCACAATAAAACTTGTT
TAATCCTAAATGGGTCCTGTTAAGAATTCCTTCTTTATTTGTCATATTT
TAAGGCCCAGAAAAGGCCTGGGCAAAACTCTTGATGGGCTTTTGTTACAT
TCCAGCCTTTGTATAAGAACACTGGTTTTTAATATTTAACTTAACCATTT
AGTCAGTACTGAAACAGTTGTTATAGAGATCTGCATTAGTGAGACCTGGC
CTGCCACATTTCCTTTTCTGAAGATCTTATGGTAGTGATCACCTTTGTGA
AAGGAAAATAAATCTTGGGACCTCAAAATCACTAAGCCAAAGAAAAAAGT
CAAGCTGGGAAGAATCTGACACTTAAATCCAACACTGCTAACTCATTCAT
CTCACTCATTCATTCATTTTATTTTCTTTTTTCTTTCTTTTTTTTTTTTT
TTTTTTGAAACGAAGTCTTGCTCTGTCACCCAAGCTGGAGTGCAGTGGAT
CTCAGGTCACTGCAACCTCCACCTCCCGGGTTCAAGCGATTCTCCTACCT
CAGACTCCTGAGTAGCTGGAATTACAGGCACCTGCCACCACGCCTGGCTA
ATTTTTATATTTTTAGTAGAGACGGGGTTTCACCATGTTCATCAGGCTGG

FIG. 3D

TCTCGAACTCCTGACCTCGTGATCCGCACCCCCCTCGGCCTTGTTTGCTT
GAGGTACTGTCTAAATGCTGGAACTGAAAATGGCAAGCAAGACATCCCTA
CCCTTGAGGAAACTGTAATCTAGTCGGAAATACAGATGTCAACCAAGTCT
CACACAAGAANATTGTACAAAACCCCTAGGA
>Contig15
GGAAAAACCTATCACCGCCTCCTATGGAACTTAAAACAAAAAGAAAAGTA
ACAAAGGAAATGAATATTTCATTCTGGAAGAACATTGAAAAAGAACAGGA
AGAAGAGAAAGCACAACTCGAACTGTCCACTAGAATTGACAACACTCTGA
CAGAATGTCTGAACCTCATCGAAGGGGTAAGTGAAAAAAATAAGCTCCTC
CAGCTTTGGCCCAAAGTCTTATAATTTTTAAACATATTCCTAAATATAAT
ATAGGAGAGATAGCCTTCATCTAAGTAGAAATTTAGCTACTCTTGTAAAT
ACAGAGTAATAATAATAATGACATGCCCATAAACAGTGTCTTTTGTGTAT
CTGTGCTTTTATAAGCACTTAGCTAAGATTATCTCACATAATTATCATAA
CCACTGTTACTATGACCACTTTACAAACAAAACTGAGGCACAAAGAAGTT
GGAAAACTAATCCAAACAAACTGGCTCCAAAAGGAACTTTGCTTTCTTTG
GGTATCAAGTTCTGAAGAGTACACATTTAACATTGAAACTGAGGTCAGAA
GGCAAGTTTCTATGTAAAGTTGGAGTATTCTGAATACTCTGGGTAGCTAC
AAATAGTATTTAAATTTTATCTTGGATTCTGCAGATAAGGATAAAATAGA
TGGTAGGCAAAGAGTATGATCCTTAGGAGAAATTTTTCCTGAAGGAAAAA
TATATTAATAAAAAATGATGGAATAAACTTCTAAGATCCTTGCCTAGAGC
AAAACTCATTCAGTCCTTTGGCTGGTAATGTTGAACATCAACAAAAAAAA
GGAAAAGTTCAGTTTAAGTCTACTCCAGGCAACATTTTCACAACATCCAG
TTAAATATTAACTATTTCTCTTTGTGGAATTGAACTAGAGTTCTTTTTCT
TATCCTCTTTTTTGGTTGTTGTATTATTTAAAAATGAGTACCTTTTTATT
ATTGAAATCATTTCAAGTAATGCAGATAAATGATCAGCCCTCTCCCTGTA
CAAACATACATACTTAGGCATCCCAAACTTCTCTCTGGAGGTGACCACCA
TTGCCAGTCATTCATTCTGTTTTCATGCATGTCCATACAGTATAGGTATG
TCGAGAAATGAAGTATTATATTTTTGTGAGTTGCAATTCTTTTATTCACA
TTTTTGTGTACTTTGGTTGTCTTTTCTTGTGTTTTCCTAGTACCAATGTT
ATGCTGACTTAGGCAGATGAGTTGAGTATTTTCCTTTTTGCCCTATAAAC
TGAAAATAGTTTGTATGACATGAGAATTATTTTTATTTTTTGAAGGTTTG
ATAAAAACTTGCCCATAAAAATCGTCTGGACCGGTTTCTTGAGGATGCCT
GTGTTAGAGCC
>Contig16
CGCTTTAACCTGGGCTACCAATGGTTCGTCAAGTTCTAGATTCTCTATTA
ATACCTTTTTCTTGTGTCTTTCTCTGGTCTGTTTTCAGCCCCGAGTCTCT
TAGATCTGTCCTCTAATATTCCTATTGACTTTACTTCATTTTCTAAGTCT
TTATCCTTTTGCTTTACTTTCCGAGAGACCTGCTTAACCTTATCTCCCAA
CTCTTTTATTGAATTTCATTTCTTTTACTATATATTTTTTACTTTGAATA
CACCTCTCTCTTCCTCACATTTTCCCCCATAGTATTTTGTCTTCAATTGA
CAGTTCTACTATCTTATTACTCTGGAGATATTAATAATAGTTTTTAAATT
TTTATTTATTTTTATTTTCAAAACAGTGTCTTACTCTGTCACTCACGCTG
GAGTGCAGTGGTGTGATCATGGATCACTGCAGCCTTGATCTCTGAGCTCA
AGCTATCCTCCTGCTTCAGCCTCCCAAGTAGCTGGAACCACAGGCATGTG
TCACCATACCCAGCTAATTTTTTTGTTTTTGAGGTGGAGTCTCACTCTGT
AGCCCGGTCTGGAGTGCAGTGGTGCAATCTGGGCTCACAGCAACCTCTGC
CTCCTGGGTCCTGGTTCAAGCAATTCTCCTGCCTCAGCCTCCTGAGTAGC
TGGGATTACAGAAACACACTACCATGCCCAGCTAATTTTTGTATTTTTGT
AGAGACAGGGTTTCACCATGTTGGCCAGGCTGGTCTTGAACTCCTGACCT
TGTGATCTGCCCACCTTGGCCTCCCAAAGTGCTGGGATTACAGGCGTGAG
CCACTGCACCCGGCCACTAATTTTTAAATTGTTAATAAAGACGAGGTCTT
GCTATGTTGCCCAGTATGGTCTTGAACTCCTGGGCTTAAGTAATCCTCCT
GCCTCAGCCTCCCAAAGTGTTGGGATTACAGGTGTGAGCCACTGAATCTG
ACATTTTTTAAAAGTTTTCTTCTCTTTACCAAGTCTTTTTTCCCCTTTCT
GCTTTTTTGGGTTGTTTTATTTTGATCTCTATCTTGCTAGAAACTTTCTG
CAGACGTTTAGTAATACTAGATTTTGAGAGTGGGCAACTGGAAAGCTGA
TTGGAAACTCTGAATACATGGGTGAGGCTTGTTGGCTGTGAGTGTCATTG
CTTGATGTCCTGGCAAGGCCAATGGGTTTGGGACCCCTACTATTAGTATA
GGCCTGATTCCCTGGGAAAGGCTCTTTTGATCTCCTGCCTGGAGGATAAA
GGCCTGGCTACCAGCCTTCTGTGTGTAATGTGAGGGAGAAGGGCTGGAGT

FIG. 3E

ATTCAACATCATGCTGAATCCTTTCAATGATCATCTTGTTTTTAGTAATC
TCCTACCTTAACTCTCTGTCTTCTGCTAGTATGGGAAAGATGACCTGAAA
ATCTAACCATTTATTTTTCCCCCATTAATATCATTTTATGATTATTCAGA
AGTTAAATAATTGTCATGCTGTCCTCCAAAAAGACTGAATCAACTAGCAA
CAAATAAGAATTTTCTCACAGCTCTGCCAGCATTTTAAAAGAATAGCTTT
ATTGAGCCCAGGAGGTCAAGGCTGCAGTGAGCTGTGATTACACCACTCTA
CCCCAGCCTGGGTGACAGAGCAAAACCCTGTCTCAAAAAAGAAATTTAAG
GAACAGCTTTATTGTTGTAAAATAGACATACAATAAACAGAGCACATATT
TAAATTGTGCAACTTATACTTTGATATAACCCTGTGAAAACATCACCACA
ATCAAGATAGTGAATATATTTATCACCTCCTGATACAGTTTAGCTCTGTG
TCCCCACCTAAGTCTCATGTTGAATTGTAATCCCCAATGCTGGGGGAGGG
GCTTTGTGGGAGGTGATTGAATTGTGGGGGTGCACTTCCCCCTTGCTGTT
CTTGAGATAGTGAATGAGCTCTCATGAGCTCCCCTTCACTCACTCTCTTT
CCTGCTGCCATGTGAGGATGTGCTTGCCTCTTCTTTGCCCTTCTGCCATG
ATGTGTTTCCTGAGTCCTCCCTAACCATGCCTCCTGTACAGCTTGCAGAA
CTGTGAGTCAGTTAAATCTCTTTTCTTCATAAATTACCCAGTCTCAGGTG
GCTCTTTATAGCAGTGTGAAAAGGAACTAATATACCTCCTAAGTTACCTC
AAGCTTGTTTTTAATTCCTTCTCCTCCCTTCCTTCATTGCCAAGCAAACA
ACCACCTGTTTTCTGTCACTATAGATTAGTTTACATTTTGTGGGTTTTTT
TTTTTTTTGAGACAAGGTCTGACTCTGTTGCACAGGAGCAGAGCAGCGTA
TC
>Contig17
CGCGTTATAGGAGATGCGAACTTAAGAAATGATGATAAGGAGACTTTATT
AAATATAATTTTGAATTATTTTGCCATTACAGAAATTCTAATTATTTAAA
ATTCTATTCATAATTTTTAATCACTGTACTTCCCAAGCTTAGCTTAGAAT
CCTTCTGTGCTGAGGATTAATTTTAATTTGTCTTTTATAGGCCTTATCTA
AAATCCAAGAATAATTGCCAGAATCAACCACCTTCTAAATCTGTAAGTAG
AAATTAGTCTTTTTAAAAATATGCATTCATAAGTATGATTAGTAATAAAA
ATAATAAAGATGTTAGCAACCTAAAGAACATGTATTTGAAAGGTATTTCT
TACAGATATAAAAACAGTTTGGTTTAATAAGAGACAATCATTTTTTGAAA
AGTATGACATTTTTTGAAAAGTAGTTTAGTTTTATTAACCAAGAAAAGCC
TCAAGTGAACTTTAGTCCTCTTGATAGCTAACATTTATTGAATGCTTACT
GTGTGCCTGATACTTTTCTGACTTGCATTACCTCACTGAGTCCTCACAAT
CTTATGAGGCTACTATTAGTAGCCCCACTTTACAGATGAGCAAACTAAGT
CACAGAAAGGTTAAATAGGTCGTATAGCTATTAAGTGACAAAGCTGAGAG
CCTGTGATCTTAACCACTTTGGTATGCTGCCATGAAGTTAAATAGCTCAG
TAGTCATTAAAAGAGAACATTTGCATTGAACCTTCCAAGCCACTTAACAA
GTATATGCTTCCTAATCAATTTAATTTAGCTACATTAGATAGAATGGTAA
AGGATCCTTAACTTAAAGTTTAAATGGAAGAAATTAGCCCTCTGAAAGAG
GCACAGATTATTCATCTGCAATAAAAATCTCACCTTTAGTTTTTTAAAAC
ATAGTTTTTATCTGTGTTCTGAAATGTAACTAAAACAGTGCTTCCTGAAG
TGAAAAATTCTCACTGGTGAGAATTTTAATAAGTTTTAATGATTCACCAA
ATCACTTCAGTCATATTTCAGTCATATGCATATGCATATATAGACATATA
AGTTTTTATCTGTGTTCTGAAATGTAACTAAAATAGTGCTTCCTGAAGTG
AAAAATTCTCACTGGTGAGAATTTTAATAAGTTTTAATGATTCACCAAAT
CACTTCAGTCATATTTCAGTCATATGCATATGCATATGTAGACATATATA
TGTTGTATGTATACATGACATCATTAGACACTGTGAAGGATAGCAAAATG
TATATAAGGCAAAATTTATGAACAATGGTTTAACGTTTGGGAAGCACTGG
GTTACACTTTTACTTTATGCAGATTGAACCAGTATAGTATGCAAGTCTTA
AGGAAAAATCTACTGGAAAGGGCCCTCATTCAGACTTCCCAGAGGCTTCT
CTGGAAGTTGACAATACTGACTTCAGTACATCAGCTCGTAAATGAGGATG
ATACCTACCTTATCTGCTTTACACAGTTGTAAAAGTAAAAAGTGAACTCA
GGAAGGGAATTACAGAATTTAGGAGAAACTAAAAGCACGATGTAAATAAT
AGTCATCATTACAGTTATATAATGCTTGACAATTTATATAACACTTTCGA
TACATGACAACAATAACTAACACCCAGACATGTTTATATACATTACCTCA
CTCAGAACAACCATGTGAGGAAGTTGGCCATATGCTTTAATGTCCAAACC
AGGACACTTTTGAGAGTAAAAAGCAGTACTCTTTGACCAACAGGCATAAA
TCAAAACTATCTTGTGAAAACCGGGATATATGGCATCCTTCCTAGATAAT
AGATACTTTTACTATTATTAATTTTGCTGTGAATCTAAACCTGCTCTAAA
AAAGTTAATTTTAAAAAGTAATGAAGTACTGATACATGCTACAACATGGG

FIG. 3F

TAAATCTTGAAAACGTTATGCTAAGTGAAAGAAGCCAGACAGAAAAGGCC
ACATATTACATGATTCCATTTATATGACACATCTAAAATAGGCACATCTA
TAGACATACAGAGACAGAAAGTAGACTAGCGGTTGCCAAGAACTGCAGGG
AGCAGAAGATGGGGAGTGACTGCCAATANGAAAACGCATTACGT
>Contig18
TGAATCGCAATGATATGTGCCACTTTGCACTCTCTGTGACATATATAATT
ATTTTTAATGCATTCATTTTTTTCTCAGAGTGCATTCGTTTGAAAACATA
GACGGGAAATACTGGTAGTCTTCCTTGTCAGTTAGAAACACCCAAACAAT
GAAAAATGAAAAAGTTGCACAAATAGTCTCTAAAAACAATGAAACTATTG
CCTGAGGAATTGAAGTTTAAAAAGAAGCACATAAGCAACAACAAGGATAA
TCCTAGAAAACCAGTTCTGCTGACTGGGTGATTTCACTTCTCTTTGCTTC
CTCATCTGGATTGGCATATTCCTAATATCCCCTCCAGAACTATTTTCCCT
GTTTGTACTAAACTGTGTATATCATCTGTGTTTGTACATAGACATTAATC
TGCACTTGTGATCATGGTTTTAGAAATCATCAAGCCTAGGTCAGCACCTT
TTAGCTTCCTGAGCAATGTGAAATACAACTTTATGAGGATCATCAAATAC
GAATTCATCCTGAATGACGCCCTCAATCAAAGTATAATTCGAGCCAATGA
TCAGTACCTCACGGCTGCTGCATTACATAATCTGGATGAAGCAGGTACAT
TAAAATGGCACCAGACATTTCTGTCATCCTCCCCTCCTTTCATTTACTTA
TTTATTTATTTCAATCTTTCTGCTTGCAAAAAACATACCTCTTCAGAGTT
CTGGGTTGCACAATTCTTCCAGAATAGCTTGAAACACAGCACCCCCATAA
AAATCCCAAGCCAGGGCAGAAGGTTCAACTAAATCTGGAAGTTCCACAAG
AGAGAAGTTTCCTATCTTTGAGAGTAAAGGGTTGTGCACAAAGCTAGCTG
ATGTACTACCTCTTTGGTTCTTTCAGACATTCTTACCCTCAATTTTAAAA
CTGAGGAAACTGTCAGACATATTAAATGATTTACTCAGATTTACCCAGAA
GCCAATGAAGAACAATCACTCTCCTTTAAAAAGTCTGTTGATCAAACTCA
CAAGTAACACCAAACCAGGAAGATCTTTATTATCTCTGATAACATATTTG
TGAGGCAAAACCTCCAATAAGCTACAAATATGGCTTAAAGGATGAAGTTT
AGTGTCCAAAAACTTTTATCACACACATCCAATTTTCATGGCGGACATGT
TTTAGTTTCAACAGTATACATATTTTCAAAGGTCCAGAGAGGCAATTTTG
CAATAAACAAGCAAGACTTTTTCTGATTGGATGCACTTCAGCTAACATGC
TTTCAACTCTACATTTACAAATTATTTTGTGTTCTATTTTTCTACTTAAT
ATTATTTCTGCAATTTTCCCAATATTGACATCGTGTATGTATTTGCCATT
TTTAATATCACTAGACAATTCAATCAGGTTGCTACGTTGGTCCCTTGGGT
TTACTCTAAATAGCTTGATTGCAAATATCTTTGTATATATTATTGTTTTT
TCTCCTATCTTGTAATTTCTTTGAGCACATCCCAAAGAGGAATGCCTAGA
TCAATGGGCACAAATAATTTGACAGCTCTTATTAAACATTATTCTGTAAG
TAAAAACTGAACTACTTTTCAGTATCACTAGCAACATATGAGTGTATCAG
CTTCCTAAACCCCTCCATGTTAGGTCATTATGAACTTATGATCTAACAAA
TTACAGGGTCTTATCCCACTAATGAAATTATAAGAGATTCAACACTTATT
CAGCCCCGAAGGATTCATTCAACGTAGAAAATTCTAAGAACATTAACCAA
GTATTTACCTGCCTAGTGAGTGTGGAAGACATTGTGAAGGACACAAAGAT
GTATAGAATTCCATTCCTGACTTCCAGGTATTTACACCATAGGTGGGGAC
CTAACTACACACACACACACACACACACACACACACACACACACACACAC
CATGCACACACAATCTACATCAACACTTGATTTTATACAAATACAATGAA
TTTACTTTCTTTTTGGTTCTTCTCTTCACCAGTGAAATTTGACATGGGTG
CTTATAAGTCATCAAAGGATGATGCTAAAATTACCGTGATTCTAAGAATC
TCAAAAACTCAATTGTTTGTGACTGCGCAAGAAGAAAACCACCCATGCTG
CTGAAAGTCAGTTGTCCTTTGTCTCCAACTTTACTTCCTTTACCTCTCAT
ATGTTTGTGAATAAGCCCAATAAGCAGACNCCTCCTACAAAGTGAACCTG
GTCTCTTTCCTCCTAACAGGG
>Contig19
GTCTTGTAACACAGGTAAGACGAGTTCAAGTTTTATTTCTTGNTTTTAGA
ACGGTAGTGAGCGGTTTTCAGCNTGAGACCACACCTAAGGTAAGTAGCTG
AATTGGGGTTTTGTCTTGGCTAAAGTTTAACAACCAGCTGGTCTTAATTT
CTCCTTACCATTAGAGCACTCAGTAATCATATAAGTTGTGTGATCATTCA
TTTTGCTTAACTGTTTGTTTCTGTTTTTATTGCTGTTTCAGTCTTTTTCC
CATTGGGTTTGACCTACTCTATCTGACTTGATCAAATCCAAAGGAAATTT
CCAAATTATGGGGAATGAGGCCTCTGAAGTGGCTAAATTCCCACCCTCCC
ACACACACAAACGTGGTATGGTGGGGGAAAAAACGGCCAGCAAAAGAAAA
AAAAAAAGGAAAAGATGTTTCATTTTGACCACCAAACGGGCTTTATTTAC

FIG. 3G

ATAACAAGGCCACCTTTTTGCTAGCCAGGCCATACTGAAAGAGCAATGGC
TGTTGCCCCATGCTGTGGGTTCCATAGCTAACGTTCTGCCTTTTTTCCTA
CCACGACAGCCTGGGTTTGGTTCCTAAATCAAGCCTTTTCTGGTTTGATA
CTTGGTAATGCTGAAATAGCAGCAATTTGTCCTAGCTGAAATATCGTAAT
AAGATTTTAAAAGATTTATTTTAAAGGACCTCAATAGTTAAAAGTCAGCT
TAATTAAAAGCTAACATCCAAGATGTGTGCATGTGTATGTATGCGTCTTT
GTATTTAAATAGCCCTCATGTTTTTTTTTTCTTTCCTAGGAACTTGCCTT
TTTTTGAGCAAAAGTTTTTTTCTTCTCTGTTGACTGGATTCTGTTTTCTT
CATTTACTTCTGCTGTCTCTCCTTTCTCTTGCACCGTCTGCTGCATGAGA
GCCCTAAAATAGTTTATAATAGCCTGGGGTTCCTTAAAGAAAATGGAGAA
GGTGCCAGGCTCCCTTTTAGGGAGAAACTTCTATTTTTCCTTATGGAATC
CCTAGAGTGTAAACAGACAAGTTCATTTCAGCTCTTAAACTGCTTGCGTT
TGTGTTGTGTTACCTGATTTTTTTGACTATTATATTTTTGACTAGCTATT
GCAACAGAAGCTACTCTTGGGTTTTCAAGGAAGATTGTAGTTTAGACATG
TAGAAATGTCTTTTAAAAAAAAAACAAACTTTTTTTAAGTGCACTGTAA
AAGCATCATATGGTCTAGCCTCCTAATAATTTTCCCTTTTTGGAGACCAG
GATTCAGGGTGGGCTCTGCCCAGAGCTCAGAGATCCAGTTAAAAGAGAGG
TAGTCTCGGCCGGGCGTAGAGGCCCAGCCTGTAATCCCAGCACTTTGGGA
GGCCGAGGCGGGCGGATCACGAGGTCAGGAGATCGAGACCATCCTGGCCA
ACATGGTGAAACCCCGTCTCTACTAAAAATACAAAAATTAGCTGGGTGTG
GTGGCAGGTGCCTGTAGTCCCAGCCACTCGGGAGACTGAGGAAAGAGGAG
AATCGTTTGAACCCGGGAGGCGGAGCTTGCAGTGAGACGAGATGGCGCCA
CTGCACTCCAGCCTGGCGACAGTGAGACTCCGTCTCAAAAAAAAAAAGAT
AGGTAGACTCGATGTTGTCGTACCCGAGCAAGTTAGAGCAACGCCACACT
TTGAGACGAATTTAAGAGTCCTTTATCAGCCGGCGACCAAGAGACGGCTA
ACGCTCGAAATTCTCTCGGCCCCTTGGAAGGGGCTTGATTTTCCTTTATG
CTTTGGTTTAGGAAGGGGAGGGGAGCTCAGTTGCAACAATTCTACAGGAG
TAAAAACATGCAAAGAAATTAAAAAGACAAGTGGTTACAGGGAAACAAAC
AGTTCCAGGTGCAGGGGCTCTAAATCTATCATAAGATGTTAGGTATGGGG
GCTCTGCCGGACACAAACTCAAGGCTTTATGCTGTTATCTCTTGAGCGAA
ATCCTGGGAACTTCGTACATTGCTTGCTTCAGTACCTTATCAGTTAATCG
GACTCTTTGATATGTTGGGAGTCAGCGTACACAAGTTAACTCCTTGAGGA
AGGGGGTGGGTAAGGAGTCCTTGATGTCTGGTAAATGAAGGAGCGAAATC
GAGTTCCTCTGGCTTTCTCAGCTAAGGGAGAGCTTATTCATGTGGAAACA
AGGCTAAGTGATTAAGGGAGAAAGGGAGAGTCTGAAAACAAGGTTAGGTA
TTACAATGTCAATAAAATTGGTCTCCTTATACAGTCCTATGGTAGATTTC
TTTCCATCTTTAATCTCCCTCTAGCACCACCAGACTTTTTCTCTCTGTAC
CTTGAGATGTAAATTTTGCTATCTGAATTTTCGTCTAAGAGTTGTTTCCT
TTAATATGCAAATTTAGGGTTATTTAGCTGACAACTGCCAAAGTAGTGAA
ACAAGTTATCAAGAACTTGAACGTCTAAGGTAGGAAAAAAAAAAGTCTTT
ATGAATCTATAAGATGTACTTCTATTGGCATGCCTAATACGTCTATGTAT
TTACGTGTTGTGTACACAGTTTTTCACTACTGAAAATATATAGAGGAGTT
CTAATTAATTGACTTAAGACAATAAAAGCGCTTGAATCAAATACCTTATC
AGGAAAAAGGAAAAGACAAGTCAAATGCTTGTTCAAGTCTATATAACTTA
AGTAAAATCTTTAATAAATAAGCTAGCTTTAACATTATTTGAAATGTCTT
AAGAATTGCCAGCAGGTTCTGGGTTACAGAACTAGTGGGGGTGCAGTGGG
GTGAGGGTTGGTGGGGTGGGNGGTNNNACNNNNNCNCCCCCCCCCCCCCC
CCCCCCCCCCCCCTCCCCCCCCGCCCCGNGCGGGCCGCGCCCCCCCCCGC
CCCCCCGGCCCGCCCCCCGCGGCCCCCACCCCCCCCCCCCCCCCCCCGC
GCCCCGCCCCCCCCCCCGCGCCCCCCACCCCCCCGCCCCCCCGCCCCCCC
CCCCCCCCCCCACCCCCCACACCCGGCCCACACGCACCCCCCACCCCGAC
GCCCCCGCCCCCCCCCCCCGCAGCCGACGCCCCCCCCCCGCCCGCCCCG
CCCCGCACCCCCGACCCCCCCCCGCCGCCCCGCCCCCGCCCCCCCCCCCCG
GCCCCCCCCCCGCCGGCGCGGCGCCCCACCCCCCCCCCCCAGCCCCGACC
GCGCGCCCCCCCCACCCCCCCCCCCAGCCCCCGCCCCCCGCCCCGACCC
>Contig20
GGCAGTACGCTATAATTCCCTCTTCACCTTACCTCATCTGTTCTCTGATG
GATGTACTTTTTTTTTTAGTTTCTAAATTCCCTTTTCCTTTGCTCTGGAG
ATGGGTGATTGATGTAGTCTGGGTATTTGTTCCCTCCAAATCTCATGTTG
AAATGTAATCCCCAGTGTTGGAGGTAGGGCCTGGTGGGAGGTGTTTGGAT

FIG. 3H

CATGGGGGCAGATCCCTCATGAATAGCTTGGTACTGTCCTCTCAATAGTG
AATGAGTTCTCCTGAGATATGGTTGTTTAAAAGTGTGTGGCACTCCCCCA
TTGCTCTCTTGTTACTGCTTTCGACATGTGACATCCCTGCTCCCCTTCGC
TCTCTGCCATGATTGAAAGTTTCCTAAGGCTTCGCCAAAAGCTGAGCAGA
TGTGGGTGCCATGCTTGTACAGCCTGCAGAACTGTGAGCCAAAATAAACT
TCATTTCCATATAAATTACCCAGCCTCAGATATTTCTTTATAGCAACATA
AGAGTGGCTTAATACAGGCTGGGCATGGTGGCTCACGCCTGTAATCCCAG
CACTGTGGGAGGCTGAGGGGGGTGGAACATGAGGTCAGGAGATTGAGACC
ACCGGCTAACACGGTGAAACTCCATCTCTACTAAAAATACAAAAAATTAG
TCGGGCGTGGTGGTGGGCGCCTGTAGTCCCAGCTACTCTGGAGGCTGAGG
CAGGAGAATGGCATGAACCCGGGAAGCGGAGCTTGCAGTGAGCCGAGATT
GCACCACTGCACTCCAGCCTGGGCGACAAGAGTGAAACTCCATTTAAAAA
GAAAAAACAAAATTTCAAACAGAACAAAATGAAAAAAATACCAAGTGAAA
GGCCCCTATAAAAACCCCTCTGGGGCCCATCCTCCCACCCCCTCAAGTGA
AACCACATTTAACAATTTGGTGCATATCTTTCCAAACCTTTTGTTGTACA
CATATAAAAAACATACATGCTTTGATTTGGCTCAGACTGTACATAGTGTT
TTCCCTCTTGCATTTTACACTTAATATATCTTTGACATCTTTCTATGTCA
GTGCATGTTGGCTCGATGATATTCTATCATTAAATACCCTTCCAAAAATG
GTAAAATCATTTTAAAAAATCATTCACACAAGTACATATTTACAATTTTA
AAAGAAAACAGAATCCCAAAACACAACGACAAACCTCTAAAAATAATCTC
TATCTTTCCACCAGCATGGAACAGTTCATTCCTTTTTCACATAAAACGAA
TTATGTGATTGGAAAGATTAACTCTAATCTACACATTTATATACAGAATG
TTCTATTTGTTAAGCCTATCTGAAAATAAAAAATTCAGATGATTAATTCA
CTTACACTTAGAAATTAAGTCAATATACTATGAATACACATTGTGATCAG
TTATAATATGATGCTTCTTAGTCTAGGGTTTCAATTAAATAACAGTAAAA
AAAATTGGATAAATAAGACAGCTAATAACTGAAAAATCCAGAAATTCAAA
GATTATATTGCCAACTAAAACACTGCCATTTACATTTTTTTTCCTACTT
GGTAGCAAATGCTAATGGAATTCAATCCTGATTACTTAAAGTCAGTTCAC
ATCACACATTCAATCAGGATAATACGAACATAATATGCCTACTATAGCGT
TAGATTAAGACATAAAATTTTTTTGCTTGAAAGTAATGACTGCGTACCAC
TTGAGACATTTGTCAACCACTTCAGCACATTGTTTACGAGTGACTGGATG
TCCACAAGGAATAAAAACGACAGCAATATTTCTATCCATACAGATTTTGC
AAAGCTTCTCCTCTTGCAGGTGTCTTAGCTGCTCTTCAGTACTAATCTCT
TTCTGCAATGAAGTCTGACTTGATTCGTCTTGTGTACTGTCTTTCTGAGC
CTTCACTGGATCTGCAATCAGAACCTCAAGTGATTTACAGTTGCTCCCAG
ATGTCTGAATTTTTTCCTCCATTATTTTCTTAATGTCTTTGAAACTGAAC
CCCATTCATATAGCTTCTTGTACCATAGGATTATGGAAGATGGTATCAAT
TTTTCTAGTTAGTGATGGCGTTTTTTCAGCAGTTCTTACCAGACACTCCT
CAAGTGAATGGGATAAATGAATATTGTTTATATATTTTCGTGTCTTCTGT
TCTAACAGATATTTACACCCTGGATGCCATTAACATGTTGTCCCAAGGGT
CTTNCTGGGCT
>Contig21
CTTTCTCCCTTTTTACCCCCATTTTCGTAGGGATTTGGTTAAAACCCATG
TAAAAAATCCAAACACCGGCGGGGAACGGGGGTTCAAGCTCGTATCCCCA
CCACTTTGGGAACCCAAGGTGGCAGGATTGTCGGAAGCCAGGCATTTGAG
CCCACCCTTGGGAAAAAAAAGAGAACCCCCATTTTTTTTGAACAAAAACC
CCAACCCTCCCAGGAAAGAAATAAGTATGGCTGGGTTGAAGTCACCAAAG
ATGGCCGACTGGCTGGTCAAGTAACTTTACCTGATGGTTCGTAGAATATT
TACCTTCACCCAGGTGGGAGAATTGCTTGAGCCAACCCTCAGTGTGGATT
CAGGAACTTGATTTAATTGGTATCGTGATTGTGGATTAGATTCTCAGGGA
TGCATTCACTAAGTAAAAGTGATAATAGCTACTTTTAAGTAAAATAATGA
ATGAATCAAACACTCTAAATCCATGGTGCTATGCTAAGCTCTTTCTGTAT
TTTATCTCATTTGATATTACAAATATTTGATGTGTTAATAGTAATGACTA
TCTCCATTTTTACAAGTAAGGAAACTGACATTGAGAGATTAAAAGACTAG
CACAAATCACAAAGTAAATGAGATTTGAATCCGGTCTTGATTCCAAACTC
TACAGTATTCTAAATTCAAGGAGACTAAATTATAAGATGGAGAGCCAATT
TTACTTTATAACAGGGTTAGAATGGCAGAAGAGACCTGACATTCACACCT
CTAGCCAGTGCATCATCTTCCTGTAGGCAAATATGCAGGAAATCTATAAT
AAGAACGTCCTTTGGTGAAGGCCAGGTGCAGGGGCTTACACTTGTAATTC
CAGCACTTTGGGAGGTCAAGGTGGGAGGGTCGCTTGATGACAGGAGTTTG

FIG. 3I

AGAACAGCCTGGGCAACATAGTGAGACCCTGTCTCTACAAACAAAAACAA
ACACAAAACAACTTCAAGAAAACTCCTTTGGTATGGATCAGAACAAGATG
AATTATCTATCTGATCCAAATGCTTAATGACATTAAGCCACAGTCCACTC
ACTGCCACAATAGAGATATACCTGCCAATGCCACTCAGGTAATCCCATCA
AAAGTGGTAATGAGGTCTGCAGCATGACTTGTTCTTAGTGATCCCAGCCT
GAGACCTTGAGATTGCAGCATTTTATTCTACATATGCACAAAACATCTGT
TGAAAAATCTTCTAAATTGATGCAATACATTCGTATCAAGAATACCTGTC
TGTAATCTCCATAAACCCTCTCCTTTCTGTTTTAAAAAATAGTAACAGCA
TTTCTCCTTACATGACAAAGAAATGACTTCACCATCTACGAAATAGTGAA
TAGGAGCTGTGTGGAAGGAAATTAGCTCTACTTCTTGGTGGAGATGAGAA
GGGAGTGTTCCTCTGAAAATCAAGGCTCTTGTCATGCTAGGAGCCAAAGT
CGTTTTTTAGAGTGTGGACAGTTGAGAAGATAAGACAGGGACCATCCACT
CATGTTTTTCTTATTCCATAGGCCTCTCTCAATTGGGCAAAGCACTCCAG
ACCTTTTGGAAGAGTGACACCAAAGGCAAGCACCTGCTTGGCAGGCCCCT
CAGCTTCTACGCAAGTATAAGTGAGTATATAAAATGGGGGTACTTGTGCT
GTTGAGTACCTTATTTCCAAATGAGGCCTGCCGGTGTCCCTGTGGCTGTG
AGAAGGCCTCTACTGGATAGGTGGAAGTTGTGTGTTCTCATCTTTTCTAA
CCCTGGATTGACTTGCCCAAAAGGAAGCCATTATTAACACTATAATAAAA
CCATCCTTAATCTGGGACTCTCTTCATGCAGTGGTTCTTAACCAGTGATA
AACATGAGAGTTACTTTTGGAGCTTAAAAAAATTAAGATGCTCAAGGTCT
ACCCAAACTGACTGAATCTCCAGAGGTGAGGCCCAGGGATGTATACTTTT
GAGCCAGACCTCAGTTTACCCTGCAGAGCTCATAAGGTTGCATAACACCC
TTTGTCAGCCACTCTGATGAAAAGAAAAATTGGTGAGGAATAAGTTTTAG
AGAAGAAGGAGCAAAGGTGTTCTTGGCCAGTGAGAGCCAATGACAGGGAA
ATGCAAACAATGTATCCACAAGAAAGGTAAATTACCCTATAGAGCATTTT
AGGATAAATGAACATCTCATGCCTAGGGTTGAGAGAGGGTACAAAAAAAA
AAAAAAAAAAGACCACTCTGGATACACAACGCGATAAATGGAATAAAGAA
TTTTTTCCTTGTAAATTAAAAAAATCCTTTGTTACTGAGGTATAATTTAA
TCTATTTTATGTATAGTTCAATGAGGTGTTATAGATAATAAATTTTTTTT
GTAAATTATTATATTGTCATATACTCATACATTCATTTTTAAAAGTCAGA
AATGTATATAACCATTAAACTTATAAATCATTCAGTCATTCAGAGATATA
GATACACGAGCATATTTTATATCCACCACAATAATTATTACCATCTCAAC
AATTCCATCACCCCTCAAATTTCAAGCGTAGGGGTTTTTAAATGTCAAAG
GAGTCTACTCAGTGGGAAGAAAGTTAAGGAAAAAACCTTTGGGGCTTTGG
GCTCCTTCCCCCTGGGGTTAAAAAGGCAGGAAATTGGGCTTACCCCCCCT
GAAATTGGGAACTGAAATTTTGGGAAGTTTAAAAAAAAAAAAA
>Contig22
TCAAGCAGCCTTCCTTCCTTGGCTTCCCAAATTGTTGGGATTACAGGCAT
GAGTCAGGATTCCTGGCTTAGTTTACATTTTCTAGAGTTTTGTATAAATG
GAAACATACAGAATGTATTTTTTTGCGGAGTGGGGGAGTGTTTCTATTTC
TTTCTTTCCATTTTCCCCCCCCCNCCCCCCCGAGACGGAGTCTCGCTCTG
TCTGTTGCCCAGGCTGGAGTGCAGTGGTGCGATCTCGGCTCACCGCAAGC
TCCACCTCCCGGGTTCAAGCAATTCTCCTGCCTCAGCCTCCTGAGTAGCT
GGGATTACAGGCGCCCGCCACCACACCTGGCTAATTTTTTTGTATTTTT
GGTAGAGACGGGGTTTCACCATGTTAGCCAGGATGGTCTCGATCTCCTGA
CCTCGTGATCTGCCCGCTTCGGCCTCCCTAAGTGCTGGGATTACAGGCGT
GAGCCACCGTGCCCGGCCCAAGTGTTTCTATTTCTTAACCAGCTTTCATG
CAATCTTTTTTTATTTTACCATCTCTGTGATCCCACTCCCAAAGGTACTA
GATGTCGATTGGTCCTTAGGATCAGCTACCATTTGCCCAACTGCTTTCCA
GCCTTCCAAAAATTTTTTTCTTTTTTTCTTAAAGATACTCCTGTGTGAGG
CTCAGAACTCTTGAATTGCTACTGCAAATATGAACTCGGTGATGTGAATG
CCAGGGAATTGCCTGATTGATCAAAGAAATGTATCCCCTTCTCCCTCACT
CTTGCTGTCTTCTCATTTGTTTTCCCCATCCTTGTGGATTCGTGAATTTA
AATATCCCTTTAATGTTATAATATTTTAATGGCGTTTGGCGAAAAGTACA
GAATTAGGTGCAAGAGTGCATAGCTGTTATTTTTTTTTTGGCCTCTGAGA
CTGTTCATATATGCAAGTTATTTAACAGAAAGTTCTGCAGTGACCTGAGA
TGTCAGGGGGGTCTGATAGAGTACGTTTGAAGGCAGTTACTGGAAAAAAA
TAATGCCATTTCTGGTTTGTACTTCGGTAAGTTCAGATGACCCAATATAT
TGTTTACATGTGGCATTCAGTAAAAAAGTAGCTTCCCCTCCCTTTCTTCT
TCCTTTTCTCCTTTCCTGCTTCTATAAAGCATCTGCTTTGGGAAACTTCT

FIG. 3J

TAGGAGGAGAGCTTGCCAGCCCGTGGGTAATGGAGAGGTCTTGCAGAGAT
AAAAGAGATGCTCCCACTCAATGCAGGATGGTGTGGAGGTAAATGGGGAT
ACGTCTGGCATCACTCAGGAATGGGCCTTCCTGGCAGGGAAAAAAAGGGA
GGGGAAAGAGGAAGGGAATTCNNANATNAATTGCTGAATACGGGGATTCC
ATGGCCTGGATCCAGGAAGAGAACTTTGGGAGGTGTGAACCTGGAAGGCA
TCANCTGATGAGGAGCAGCCTGAACTCCGGGGAGGACCTGTTTTTGGTGG
CCCGGAAAAAAATGCCTTCCACACACAGGGAGGCCACCCGGCTGATGGGC
TGGGGGTTGGACGGACAGCCCTAGGACAGGCTTGGGAAACCAGGCTCAGG
TAGGGCCTGCGAGGTTCTCGCTGCGTCTCTTTCCTTCCTGGTCTTAGAAA
ATAGAATCCAAGGCCTCTTGAGAGTGGAAGGTGGGTTGGGAGGAGGGCAG
ATGGGGCTTAGGCCCAGGACACCCGTAGAGCTACTGCCCAGCTGTCTCTC
AGGGACTCTGCTGAGGTCACTCCAAGGATCATTCTTAGCCTTGCTAGACA
GTACTGACAGAGGGAACCGTAGTATCGCACCCACTTCCTTCTCTTTCAAT
GAAAGTTTAAAGGTCACCATTTCCTCTGGCAAAGGAAGTTCCACAAATAT
TCCATTTCCGGTCTTAGAAACAGCAAGGTATCAAGCAATTGCAAACTTCC
TGTGCTGGGGAATTCCCAAGGAAGTAGGGGCAGAGTTCTGGTGGAGACAA
AGTGAATTCCGAGTGATTAGTCAGTAGCAGTAGCAGTAGCAGTAGCAGTA
GCAGTAGCAGTAGCAGTAGCAGTAGCAGTAGCAGTAGCAGCAGCAGAACC
AGAATTTCCCCGCACGTGTCTCAGGCTCTCATTTGCCAACTCAGTCTCTA
AGTATTTTTATTGGCAGGAAAAATAAAATAGCTATGAGTGAAATAATTCA
TTAGACCTGAGCCTCCATCAATTTTGTGTTTAAAGGCCTGACTCTCTTTA
CCTTTCCCTGGGATGGAAGATGCAAATGTTCCTGATCTCACTGTCAAAAA
AGAAGAACCAGTGGGTATATTGTATGCTTGAGTTCCAGCCATTAGTCACA
AGACATAGAGATGACTGCCATGTGTGTAGACTTTCTATAGACTGTGTGCT
AAACCCGACCTGCCACTTCCAAGGAGTAGATGAGGAATGTCCATGGTTCT
GGGGAGCCCTACCCCAATTTGGGGCAGACATTCCAAAGCTCATTTTCTGT
GGAGGGGGTTGATGGTTAAAGGAACGGCTGGGATTTACTCTTCTTTCTAG
GGCCAAGAAAATGACATGCTGCCTCCATGTTTAATCATCCTTCCCCCTGT
TAATAACTATGGCTTTAAGTCCCCGGTTAGGGCCTTCCTCCAAAATTGGG
GAAAAAAATTCCCCTCCCCCCCTAAAAATTTTTTTTTAAAAAAACCTTT
TTTTTTGGGGGTTGGGAAAAAAACCAAAAATTTTTTTTCCCCAGGGGTTT
TTTAATTTAAATTTCTCCCCAAAAATTTGTTTTTTTTTTTCCGCGAAAAA
AAGACCCCCCCAAAAAAAAAAAGTTTTTGGCGGAAAAAAAAATATTTTT
TTTGTGTTAAGAAATGGAGAAGAAGGGGGGTTTTTTTTTCTTCTCCCCC
CACCCGCCAAAGGAAAGGTTGTTCACAGATTGTTTTGTGTCTCCCGCCCA
T
>Contig23
ATGTGCCTGCGAAATCATCCTTCCAGAAATATTTGCCCCTTTCTTTTGTT
ATAGAGTGGCACTGCCCTATATGGTGACCACTTGCCACATGTGGCTGTTG
AACACTTGAAATTGGCTTGTCAGAATTGCAGTGTAAAGTGTAAAACACAT
ACCAAATTTCAAAGACATGGCACATAATAAAAAATGTAAAATATCTCATT
AACAATTTTTATATTGACTGTGTAAGTAACATTTTGAATATATTGGATTA
AATACATGGATGATGCCCCAACACCCACAGTCCCTTATCAAGTCTCTACT
TCACATTTTTGTACTTCTGACTTAGAAATAGCACTGGCGTCTAAGAGCCT
ATTAATGTCGTCAATAGGTTCTTGGGAACCACAATTTTAAACAAAATGAC
ATATAAGAAAACGAATAACATTGAACAAAATGACATTATTCGAGGACCTG
CTGCATGTTGTTTCACTTAAAGTCAGTGTCCAAGAAACTATCAGTGACAT
TTAGTGAGGAATTGCTGTCCTTCCTGTTTACAGGAACCTGGGCAAGTTAC
TTAATTCCTCTAAGCCCGGTTTATATCCCTGCAAAGAGAGAAGGATAATA
ATCACCAGTACTTAGTGATGTCGTAAGGAGAAAATAAAATAATAAATATG
AAATGGCTGACAGTGTCCTTGTCACACAGAAGATGTGTGATCCACAGTAG
CTGCTATTGTCTGCCTCACTTCACTAGTAATGGTCCAGGGAGGCCTTTAA
TGTGCATGGTGCAGTACATTCACATGTTGGACATGGGTGAAGGGAAAGAC
CAGGCTCATCTAAACACAATAGGATGCTTGTGGTGTTTTGAGGAGGAATC
AAGGACTAGTTATCCACAGCTGTAACATGCATGGATCAAAAGAGATAAGG
CACACAAAAGACTTTGTCAGTAGCAAAGCATTACAAAATGCAGAGACCAG
CTGTGGGTGGTGGTGAGTCAGACCCAGCTTCCCTCTGTGCCTGGCTGAGT
GGTTCTGGGCAAGTCACGCCATCTGTCTTGATGCCCTTCCCCATCTATAG
AGAGGGAGCAACTGAGGCCCCTTCCAATACTGAAGTCCTTTATTTCTGCT
ACTTTAGAAATATCCACATTTTTGGTAAATTCAAATGATCCAATGATTCC

FIG. 3K

ATTTCCTAATGTTCAAAACTAGCCCCAGAAACATCTAAATGAATCAAACA
AATAAAATATTTATTGTGTATGTTTTGATTGCTGAAACTTCTATTTTAGC
AACACACACACACACACACACAGAACCCATAAGCCTTCATCTTTCCTTGGAT
AAACGAGCCTTCCTGTCTGGCCATTTAAGTCACGATTAAGTAAATGATTT
CCAACTCGCCTTTTGCAGCAGTTCAGATGGGTCTTTCCTGCGTGGCAGTG
GCCCTCCTGACTTATGATTTCCTGTGTGTCGGCCTGTTACCACTGCAGCT
TAACTGAGGAAACAAGAACAAAACAGCCTCTGACCCCAAGAGACTGTTGG
AGGCAAAGGCTTCAGTCCCAAGAACCTCACACGTGGGGAGCCCGAGAGCC
CAGCCCTGACCTTTTCTCCAGTAATAACATAAGAAACAACAGGCACTGGC
CTTATTTTGGATACAAAGAGTGGTGCTTTTCCTTAAATCTTCCTTTAGTC
AGGGGTACCCCTTCATGGACGCCCCAACATCCATGGTTCCTGCTTGAGTC
CCTGCTTCCATATTCCTGCACTTCTCACTTGAAATATCCCTGGAGTACGT
TAAGCAGCCAGGTTTGGAAGTTCTTGCTGTGCAGGCGGGTGTGTGCATGT
CCTCTCTCTCAACAGGACACAAGCTCCCCAAATCAGACGGTATGCCTCCA
CGCCCCTTCCCAAGCCTCCCCAGCAGCACCGAGCATGTGAGGGGAGCTGG
GGCCCAGGCCATGATGGGAAGCACTCTCTGCCTAAAGACTAGGGTGATGC
GCCCTCAACTGTGGGAATGAGCCCCAGCTCTGGTGTCTGCCTCGGTTTTT
CCTCCTGGACAATCAACATGAACTCCTCACCCCTCTTATCCACTTTGCAT
AAACTGAAAATAACAAACCCAGGGTCTTTCTGTCACAGGAAAGGGTTTTT
TTTTATAAGATTAAACAGAGATGATTCAACACACCCAGGATATAACACAT
GGGCCATGAGTCAAGGCCAGGCATTGCTCTGGTCAGCCTGTTGTTTGGGC
CCCCTTGGCAGGGCTCTCCCCTGAATCTTCCCCCTCTTGACTCCCCATCA
CCACAGCACGTCCAGCTTTGGGTACAAGGCCAGTAAATGGGGAAGGGGGT
CAGATGACATAAAGAGCCCTTTCCTGTCCCATTGAAATATATTTGGATAA
CAGATGGCATTTCCCCCTGTGTCTTGCCCAGGGCCCAGAGCCTCCACTTG
CTAGAGGCAGACAGAGGATGGAGAGCCCCTTCATTAGTGGGAGGACATCA
CAGGTGGGCAAGAAACCACAAGCTTGCACTGAGGCCCAGCCTTGAAATAG
CAGCACCTGCCGGCACCTGTGGTCTGGGGACAGGGTCACAGGATGGAGGG
GCCTCCTAAGCCTTTTATCTCTATGTACTAAGTACAACCCATTTTCCCAC
CTCACAGAGCCAGATCAGCCTCTGTGAGGTCCTGGTGGCAAAAGGATAAT
TGCCTGCCCGCCTGCCCGCGGTGGGGTGCTTGTGCTTGCATTCCTGGGAA
GGTTGTTGGGTTACTCTGCAATAGGTCTCTCTGACCAGCTCACCCTCCTA
CTGCAAACCTCAAACCAACTTCAAAGAAGATCCAGCACC
>Contig24
CGCGTAGTCTAAAGACTGAGTCTGAAGCTGTCCCTTCCTGCTATGGACTT
CAGATTTTAGCCCACTTGAATTGCTCCATATCCTCCAAGCCATGGCCATC
CCTTGACTCTCTGGGCTCCCAAGCACTTGCTGCCTTCATCACACAGTTTG
AGTTAAGGCAGAAAGACTGGTTTCCATGTACACTTTGTGGAAGCTTTCTC
ATTTCTTTATATAATCTCTGTCCTTTGTCTACTGCTTTAAAATCTAGAAA
TTGTTTACAAACACAAAGGTGATCCTTTAAAAGCTCAAAGCTGATTGTGT
CACCAATATATACCACTCTTAATGGCTTCCCATTAAACTTTGAGTAAAGA
CTTTATGGAGCCTACATAAGGCCATGACTACCTGGCTCTTATTTTCCTCC
TCATCCTCATCTCACCAACTCACTCTCCACTCCTATACCCCTCACTCCTT
CCCCCTCCTCTCTCTGAGCTCCAGACTCCCAATTACCTACTTCCACCCTT
TTTGACCCCCAGGGACTTATCTCAGCCTGGAATTTTCCCTCTTTGCTCTC
CACTGAACTGTCCACTCCCAGTCTAAGACATGTGCTTATGTCACACGCCC
TTACCGTGCTTATCTCAGTTTGTAATTATCTACTCATTTAGAAAAGTGTT
GATGAAGGTCTTCACTGTCAGCTTTCAGGATAGCAGGAATCATAGCTGAT
TTTACTTACTTAACGGGGTTTCATTCTTTGTAACTTTTTTTTTTTTTGAG
ATGGAGACTCACTCTTGCCCAGGCTGGAGTGCAATGGCATGATCTCGGCT
CACTGCAACCTCCACCTCCTGGGTTCAAGTGATTCTCCTGCTTCAGCCTC
CCGAGTAGCTGGGATTACAGATGCCTGTCACCACGCCCAGCTAATTTTTT
GTATTTTTTGTAAAGACGGGGTTTCATCATGTTGGCCAGGCTGGTCTCGA
TCTCCTGACCTCAGGCGATCCACCCACCTCAGCCTCCCAAAGTGCTGTGA
TTACAGGCATGAGCCACGGCACCCAGCCACTCCTTTTTTACTTATGGGTG
AGAAGCCATTAGAGATCATTTCTTCTTTTCTTTCTCTCTTCACTAAGGCA
CCAGGGTCACTAAGTAGTAGGATACTTTGAACTAGAACTCAAGAAATTGA
GTTTTAATTTTACCTCACACTCTCATATGAATTCTCCATGTGACCTCGGG
CCATACTTCCCCTGTACCCTGTTTCCTCTTTTATAAAAGTAAGAGTTTAA
ACTAGATGGTCTCCGACATGCATCCTTCTCTAACATATTCTGGAACCTTC

FIG. 3L

AATAAACTAAGATAAAGCAGAATAATTAAAACTTAATTTAAAAGAACACA
GGAAAGGAAGCAGTTACATTAAGCAAAAGAGACATCTTCATGGTTGAAGA
AGTGTATGCCCTGGTGTCTGGATCCCATTTAGGAAACTTGGTAACCTTGC
AATCTTGGGCAGATTGCTTAATTTCTCTAGACCATGACTTCCTCTTCTGT
AAGATGTGATAAGAACATCTACCTCACAGGTTTCATGAGAGGATTAAATG
AGATAATGTATTATAATCCCTTGAACATGGTAGGCTGTTATGTTAAGTCC
TTTCCTCCTTCTCTGTAGCTATCATGGAATTTAAAAACACATTATAACTA
GAGCATGAGTTGCGACTAAAGGCTCAATTGTCTCTGCATGTGTTGGCTCA
TGCATGCTTTATTCCTCTGAAGAGCTTTTATACCAAGTGAAAGGAAATAA
TTGCATTTCCCTGAAAATTCACAGGAAAAAGTTATGTTTTTCTCTTCATT
CAAGTGATTCTGTTAGACCCAACCACATGCAACAATTTTAAAGTTGCTTC
CAAATATATTTACAAATATTTCCTGTCTTCAAGGAACAATGGCAAGACCA
TGACTCAGGTTCACATCCGGATTCCACCACTAACCATGTACCCAATTACT
TCAGTCACCTTCATTCAGGTCTTACATATCACAGAATAAAATCAGATTTC
ATCAGAGGAGGTGAAGACAGGGAGAGGAGATATTTCAATCCCTTCTCCGC
AACCCCCGTTTTTTTTTTTTTTTAACAAGGATCCTAGAGTTACTGAATG
ATAGCACGTTTGAGGGGGAAAGACCCTAAGGATGATCTTTATAAGCCATC
ACTTGGTGTTGGTGGTGATAAAAAACTCGAGTATCTTTATGCAGTGGAAA
GAGAAGATTGGACTCGGAATCAGAAGCTTGAGTTCAAGCACTGGTTTCAT
CAGTCTTGTGATCTTGGGTTGGTCACTTAACCTCTTCAAGGGTCCTCAGC
TGTGAAAGAAGATAGTATCAGCTAATTCTTGTATGTGCAGTGAGGAGGCA
GTGAGATAGTGCAGGTAAACTATAAAACAATTGTCACATGAAACGCATCA
CAGTGATTCTTTGGACCCACAAGCTCCAATCTTATAAAACATATCCAGTC
ACCCACCAACATAGATCATCTCACCTTGCATATCTGATTTTGTGGATCAT
GGGGAAAAACTGCTGATTCCTAGCAAAACCCATGGCATAGGATAAGTGCA
CAATAATTTTTTTTTCCTAAATGATTTAGATGACAGTGACTCATTAAGGG
TTTCCTGAGGCCTCCTCAGAGTCGAGAGGTGGGTGCCTGAAGCCACCCAA
AGTCCCTGTCACAGGATGGCTCCCAACGCACACACCCACAGGCCTGCCCAG
TATGTTCCACTATCTACCCAGTAGAGCCCTGCCCAGTACGTTCCACTGTC
CCTTCCCTAGAAGAGGTGACTGTTGTTCACAGTCCCAGAAAAGCGGGCTC
CCCAAAACAATGCAAGGACCCACCTCTCTCTGAACCTCACCCACCCTAGT
TTTCCTTTAAAAATCAATTTACAAGAAGATCATGTGAAGGAAAAGGTTGG
GTGATATTCTAACCCAAGTTAGCTGTTTCTCAACCAAGTTCTCTTTGAAA
AATTCAACAACCACCTTTGGGGAATTATTTACAACAGAGGAGTGAGGATG
GGACCAGGATAGGTATTGCCTATGTTGGTGGAACCAGGGTTTTTTTCCTG
GATTACCAAAGAGATGGTATGCATTGCTCCCAGAAGCTAAATATCTTCAG
GCTTTCAATGGTGGCCTTCACCTGAAAATGTTATCCCTGTTGAAGCTTTC
AAGCCAGTATTTTCATAAGAACTATATTTTCTTTGGTGAACTGAGGCATT
ATAATGATGACTATACAGGTTCTTGAGTGACTGAAGCCATCATTAGCATT
GTCATTATTTTTGTTTAGTTGCATCTCCATAGCAGCTCACATTCACAATG
TGCTTTGCAATTGTTCCTTAGCAATAGCCCTCACAAGATTCTCAGGAGGA
GAGGGTTAATCCGGATTAACATTTCTGTGAAGCCTAGCGAGATTAATCGC

>Contig25
AAGAGTTTTAAAATTAAGTAAGGACGCCGGGAAACAAATCAATCCCAGCA
AACATTTTGTTGGGATTTATCATTCAAGCAATTTTACAGTTATCCCTGTC
AAATACATTAAGTGTTCAAAATTGGGCATAGGGGGAACAAAATAATAAAC
CCAGCCAAAACAGAATAATCCCTGTTTGTTCAATGTTGGATAAAAAAGAC
ATTACTATTGGTGTAAGGAAATTAGATACATCTTCCATTATTTAGTAAAA
TTACCATAACTTCTAACTTTGTGGCTTTAGGCAGTCTAGTCCACAGGCAG
GAAGGAGGTTTGTTTTGGCAAATGACTGTTATCATCTTCTGTTTCAAAGC
TAAACCATAAACTAAGTTCCTCCCAAAGTTAATTCAGCATATGCCCAGGA
ATGAACAAGGACAGCCTGGACGTTAGAAGCAAAATGGAGTCAGGTAGGTC
AGATCTTCTTCACTGTCTCAGTGATGGCAGTTTCATAACTTTAAATGATG
GCTATCACAGTTTTCATAAATAATCTAGATAAACAGTTAAAATAAAATAA
TTAGGTAAATGTAGTGCGATAAATATTAGTAGACAAACTCACCATAATTT
AGAATCTAAAGTTAAATTAAATAATAATATTTCATTATTTGGTATTTTCC
AAGAAAAACATATTGTAGGAAACCATTCTTTTTAAAAAAAAAAGTGTCCT
TTTAAAAAGGTGAATAATTTTTGTCTAATTCAAAGTTTATTGAAAAGTTA
TGTATAAAACAAGGTAAAAGGAACAAGGAAATAAGGGAAATGTAAAGAAA

FIG. 3M

ATTATAGAAATAAAGTGGTATTTTTTGGTAAGAAAGCTTAAAGAGAAATA
ATTTTAGGTAAGAAAGAATCTTACCTAAAATTTTGTGCTAGAATAAAGTG
ACTGGCTAAGAAAGGGATGTTCAAAGCTATTTATGACAAACCCACAGCCA
ATATCATACTGAATGGGCAAAAGCTGGAAACATTCCCTTTGAGAACTGGC
ACAAGACAAGGATGTCCTCTCTCACCACTCCTATTCAACATAGTATCGGA
AGTTCTGGCCAGGGCAATCAAGCAAGAGAAAGAAATAAAGGGTATTCAAA
TAGGAAGAGAGGAAGTCAAATTTTCTCCGTTTGCAGATGCATGATTGCAT
ATTTAGAAAACCCCATCATTTCAGCCCCAAAACTCCTTAAGCTGATAAGC
AACTTCAGCAAAGTCTCAGGATACAAAATCAATGTGCAAAAATCACAGGC
ATTCCTATACACCAATAATAGACTAACAGAGAGCCAAATCATGAGTGAAC
TCCCATTCACAATTGCTACAAAGAGAATAAAATACCTGGGAATACAACTT
ACAATGGACATGAAAGACCTTTTCAGGGTGAACTGCAAACCACTGCTCAA
GGAAATAAGAGAGGAAACAAGCAAATGGAAAAACATTCCATGCTTATGGA
TAGGAAGAATCAATATCGTGAAAATGGCCATACTGCCCAAGTAATTTATA
GATTCAATGCTATCCCCATCAAGCTACCATTGACTTTCTTCACAGAATTA
GAAAAAACTAATAGCCAAGACAATCCTAAGCAAAAAGAACAAAGCTGGAG
GCATTGTGCTACCTGACTTCAAACTATACTACAAGGCTGCAGTAACCAAA
ACAGCATGGTACTGGTACCAAAACAGATATATAGACCAAAAGAACAGAAC
AGAGGCCTCAGATATAACACCACACATCTACAACCATCTGATCTTTGACA
AACCTAACAAAAATAAGCAATGGGGAAAATAATTCCCTATTTAATAAATG
ATGTTGGGAAAACTGGTTAGCCATATGCTGAAAACTGAAACTGGACCCCT
TCCTTACAACTTATACAAAAATCAACTCAAGATGGATTAAAGATTTAAAC
ATGGCTGGGCATGGTGGCTCACGCCTGTAATCCCAGCACTTTGGGAGGCC
GAGATGGGTGGATCATGAGGTCAGGAGATGGAGACCATCCTGACTAACAC
AGTGAAACCCTGTCTCTACTAAAAAATACAAAAAATTAGCTGGGCATGGT
GGTGGGCGCCTGTAGTCCCAGCTACTTGGGAGGCTGAGGCAGGAGAATGG
TGTGAAACCAGGAGGTGGAGCTTGCAGGGAGTGGAGATCACGCCACTGCA
CTCCAGCCTGGGCAACAGAGTAAGACTCCATCTCAAAAAAAAAAAAAAAA
AAAAAAAGAAGGATTTAAACATAAGACCTAAAACCATAAAAACCATAGAA
GAAAACCTAGGCAATACCATTCAGGACATAGGCATGAGCAAAGACTTCAT
GATTAGAACACCAAAAGCAATTGCAACAAAAGCCAATTGACAAATGGGAT
CTAATTAAACTGAAGAGCTTCTGCACAGCAAAAGAAACTATTGTCAGAGT
GAACAGGCAACCTACAGAATAGGAGAAAATTTTTTCAATCTATCCATCTG
ACAAAGGGCTAATATCCAGAATCTACAAGGAATTTAAACAAATTTGCAAG
AAAAAAAAACCCATCAAAAAGTGGGCAAAAGATATGAACAGACACATCTC
AGAAGAAGACATTTATGTGGCCAACAAACATGAAAAAAAGCTCATCATCA
CTGGTCATTAGAGAAATGCAAATTGAAACCACAATGAGATACCATCTCAT
GCCAGTTAGAATGGCGATTATTAAAAAGTCAGGAAACAACAGATGCTGGA
GAGGATGTGGAGAAATAGGAATGCTTTTACACTGTTGGTGGGAGTGTCAG
TTAGTTCAACCATTGTGGAAGACAGTGTGGCAATTCCTCAAGGATCTGGA
ACCAGAAATACCATTTGACCCAGCAATCCCATTACTGGGTATATACCTAA
AGGATTAGAAATCATTCTATTGTAAAGACACATGCACATGTATGTTTATT
GCAGCACTATTCACAATAGCAAAGACTTGGAACAACCCTAATGCCCACC
AATGATAGACTGTGTAAAAAAATGTGGACGTATACCCCATGGAATACTAT
GCAGCCATAAAAAAGAATGAGTTCATTCTTTTGCACGGAACTGGATGAAG
CTGGAAGCCATCATTCTCAGCAAACTAACACAGGAACAGAAAACCAAACA
CTGCATGTTCTCACTCATAAGTGGGAGTTGAACAATGAGAACACATGGAC
ACAGGGAGGGGAATGTCACACACCAGGGCCTGTCAGGAGGTGGGGGGCAA
GGGGAGGGATAACATTAGGAAAAATACCTAATATAGATGACGGGTTAATG
GGTGCAGCAAACCACCATGGCACATGTACACCTACGTAATAAACCTCCAT
GTTCTTCACATGTATCCCAGAACGTAAAGTAAAATTTAAAAAAGAAAGAA
AGAAAGAAAAGGATGTTCACGACAAACCAGAAAGTCCAAGCATGTCATGA
ATAGTCTGTGTAAGTCACAATAAGAGGATTTATTTAAAAAAACTTTTATA
TGATAAAGTTGTCTATAATTAAAGGGAAATTATAATGGTCTTTCTAGAGA
TTGGGTTGATGTTAAAAAACTACTTATATATTAAAAAATTGGTTAGAACA
ATGAAATTTTCTTACGGGGTTGATTCACTCTTAATAAATTATAAGAGACT
TAAGAATTTTTTTTTAACCCAAAGTTCAGCTTTTATTGCATCTTGCTGTT
TTAGGTTTTCTCTCCCCTTTAAAAGGGTGGGAAATAGTAATGCCCTCCTT
CAACTCCCTTCAGCTCATATACGTTTTTTACCCTCAGATTCTGTTTGTTG
TGTCCTGATGCTAACAATGTTTTCTTAAAGGTCTAAAGGAAATGTTTTCT

FIG. 3N

TCCAACATAATATTCTGTGCATTGCAGAAGGTCTTTTCTTTTGCCTTTTG
GTAACTGGCTTAACAGATTTTATGTTTTATTGAAATAATTTCTATGCCAT
TATTATTAAGTTTTGGTTTGCTTAGAAAACACTGAGATTAATACAATTTT
TTAAAAATTATGATTATTACATCCATATATCTTTATGTATGTGCTTTTAA
AGTCCTTGTGACATTGAGTTCTAGGGCTTGACTCCTGGGTCTTAAAAGGA
CAAGTCCTGCTAAATCTTAAATACTGACAGCAATTAAAGGCTCATCTTCA
GGACTGGTAGAAAATGCCAATCAAAATAAACTGCATTCTTGAAACACAGA
GCCAGAAATTAAAGCTATTCAACTCAAGGCCCAGGAACTATAGTGGAAGA
GGTGGGTGTGTGAGATTGTAAGGGCCAATTTTGAGAGATAAAATAAGTTC
AATTTCTCTATAAATTAATCATAATCATTGATGTCCAAGCCACACTGATG
CAAGATCAGCATATGGGTCCTGTGTCAGATTAACAAGGTTTTCTTGAAGC
ATTAACCTACTCCTTAATAAAGGTTATAGAGGTTATAAAAGGCTTCTGGA
AGTTATAGCTATGGTCAAGATAAAAATTTCATAGATTGTTAATACAATTT
TGGAAAACAAATTTAATTGGCTTCTTGCTGTTTTTATTAGGGCTTATTGT
TTGGAAAATTAAGTCTCGTCTCTCAAAGAATGAAGGCTTTCACCTTTTTT
TTTTTTTTTTTAATCCTTGAGTTATCACTTTGGTCAAATGAATGACTTA
TTTTACAATGACCTTTCATCAAGTGTTTTAAACCTTTCAAATTTGACAAA
CTTTCCAAAATCAAACTACAAATTATGTCTTTTTATGACCTAATGAATCC
TTTAAAATACTAGGTTCCCTAAAGTCCAAAAAAAAAAAAAAAATAACATAA
TGTGGCTTATTTGGTATAAAAATTTTACAAGAAACATTGTCAAATATAAA
ATATTGTGTGGTTTTGTTTGGGCTGTATTTGTATAAATATGTTATTGGTA
TGTGTTCCAAAATTATAGGAAACTCCTATAATTCTGATATGACTTGGTGT
ACATTATCAGTAATAATTATAATTGTTATGGTAAATTATTGTGTGCCATG
GAGGTAACAAATTTCCTCATCAAGTGTGTCTTTGACTATGGTTGCCCTAA
AACTTTTTGCCATTCACAGACAATTGTCTTGCTTTGGTCCTCTTTAGAAG
GTGGTTTTATAATCAGCTATAAAACTCTAACGGGTGCTCTTGAATGCAGG
CTTAAGATAGCTTTGGAGACTGTGACATCAGAATAGAGGAAAAACTTTCA
GTATTCATGGAGTGCTGAAATATTCATGAATATCAAGCAAAACAGGAATT
AACTTCATAGATGGAACTAAAAGAATGCTGAAGTAATCTTTTTGACTTTT
TTTCTTAGAATGTTGATCCTTCGTTTTGTTTTTCAGAGTCNAGGAAATTT
TTCTGTTGAGATATTGACAGCTTTAACAATTAAGTATACTCCAGTGAACA
CAATTTGGAGCA

>Contig26

ATCTAGTCATTCCCCAGCCTGACCAATTCAATGGCCCCCATCTTAGTTAA
AATTCCTCACCCTGACAAGGCCCCATCTACGCCTCTGACCTCATGCCCTC
CACTCTCAGTCTTGCACTCACCCTGCCACACTCAAGGGCTTCCCCAGGTT
CCTTCTTAGATTCCACCGATAGCTCAGGGACTTTGCACATGCTACGGTCT
CTGCCTGGCTCCTCCCCAGATCTTCTCATGCCTAGCTGCTTCTCATCAGC
ACCCCTCAGAGACTGTCCCTGCCCCACCTCTCCAGGTTCCATACCTGCCA
CCCTCCCCCAATCACGTAACAGTTTCTTCACAGAGCGAGTTACCATCCCA
GTATTTCCCTAACTTATTTTTTGTGACTGGTCTGTTGCCTGTCTCCACCA
CAAGAACATAAGCTGCATGTGAACAGGAGCCTTGTCTATCTTGTCACCCC
AGTGGCTGTGACATAACCTGATACACATTAGATGCTCAATGATGTTTGAT
GAATGAAGTGCTGGTAGTCCAACTGTGTTTCCTTGTCTGTGTAAGTATGT
CTGTTGTGGTTTCCTAAGAACCTACAGCTCTCCCACTGTGACTCCTGTTC
TATGGTCCTGATTTGCTGGACTAGAATCCTAACCTACATGCTTACTCTTA
GTGTCCTCCCCCAGAGGCTGAATCCCAGTCCCTAAACCTCCACCAAATGG
CTAAGACCTAGCTTCCAACCAGACAGGCCTACGCTGAGACCTCAGCACCG
CCCTTCTGCGGTCTCATCCTTAACGCATCCTTCAGGGCCCAGCTTAAATG
TCTCTTCTCCAAGGAAGGCTATCCTCTTTCTGCCCCTCAGTGCTCTCCAT
GCCTCCTCTATGCCTCCATGCCTGCTTTCAACCCTGCAGAAGTGGAGAAA
TTGCTAATCTGCTGTGTTGACACTGTGCTGGGGTGCCTTGGGCCAGGGAG
CAGGCTGGTGGTGTGCTGATAGCCCGTGGCTGTGCCCAGGTCCATGCTCA
CTTCCTGAGCCCCAGTGGAGTAGGCTCCCTTTCCCTTATTGCAGCACTCA
GAGGAAGGACGTGCTTCTTAGGACAGATCTGGCCAACCTCTCCCTCGTGA
GAGAAGGCCCAGCCATCCTCTTGCCCTCTTTCTTTCTCCTGCCCCCGAGT
AATAAAGGTGCCTGGTCAGAGCCTTCTAGAAGGAGACCCAAACATCCACC
ACACATTCCCAGTTCCAACCGTCATCCACATGGCTGGCTGTGCAGGTAAA
CGCAGAGTCTGTTTCACACACCCAACCATCTAGTATTGGATGGGAGGACA
GTAGCGTGACACTCTTCTCCAGCCTTGAGCCCTACTGTGGGCCCCACCCA

FIG. 3O

ACCCAGATACCAGAGGAGCCCTGTACTGGGATGCTATTGGATGCTTGTCC
AGTCATGTACAAAGTTAGCCCTTTGTTATATAGAGTTAGCTACGTACATC
TTCCTCTGTAGGGAACCCAAGAGGGGAGAAGAGATATGTAGTAGGATTTA
ACCTGCAAATCCTCTGCTGAGCACCCTGCACTACATACAGTGGGTAGCAT
GTGGTAGGTGCTCAATAACTATTGACCGATAGATTGAATACAGGTAGGAT
GGTGACACAATCTAAGATCCCAGGGGTGGGAGACCACACGCTTGGTTAG
GGAGACCCAAAGTGGACCGTGTGGCCAGAAGAGTCCCGCACTGCACTCTA
GTGACAGTGCAGAAAGTCACTGTGGGAAATCTAGAAGTTTCTACAGGTTG
CTATTTCATCATAGCACTGTGCAGGCCAACCCTTCCTGCTCCACTGGCTG
TTGGGAAAAGCTTTCTCTTTTCTTCCTAGCCAGGGAGCTCTCAAAGTGTT
CCACTCTCTCACCTCCACCCAGGCGTCCAGGTGTGGAGGACACTTGCCGG
CTGCTTGTCTGCTGACTCATCCCTTGGTTTCACTTGGAAAACCTACCACC
AGCTGGCCTCTTTCCAAGCATCAGCCTCCTCATTTTCTTAATCCCTTAGG
TGTGATCTCACCTCCACACAGTAGATTGCCTCAAGGCCCAATTCCAATAT
GAATAAAAATGATTATTTTGTCATCTTCCAATCTTCCTTTTAAAATATTA
TTTTATAATTCCCTTTAGGAGGATCACCTAAGTGAAGACTATTTTTACCT
AAGAAATGTTAAAATGTAAAGACATGGTTGTAATCTGGGGATTCCTGTTA
AAATGGCTAGCAGACAGAAGTCAGACGACAGGCTAGAAATGTGTGAAGAG
TGGTTGCCTTTGAAAGGCGGAGTTGGTAATGATTTTCTTCCATTTTTCCA
TGCTTTCCAATTCTCTACAAAGGCCTTAATATTACTTCGATAACCAGGAC
CTCTGATAACCTGCCCCCACCGAGTAAAGACTTAGCTGGGAAAGTCAGCT
TCATGTGAGGTAAAAGGAACCAGGTAATACACAATTCCCACTGCCAACTG
TCGGGTGTGCAGGCCTGAGCTTCCTGCATGTGGGAGGAAAGAGAAAGAAG
AGAGAAACTCCAAGATCCAAGAGATCCAGCAAGAAGGCTGGAGTCTGAGG
ACGCAGAAAGCTGAATGGCACAGTTACCACTATTGTGCTGAGGTTCTGTG
GCCTCTGGGTCTCTTGACAACTGGGCAAAGACCCACAGAAAACTATCTCT
AGACCCTACCTGTGGGAGGGGAAAGTGCTTAAGATCATTTACAGGACAGC
CACCTGGACCTCAAATGGCTTACAGTTCCTTCATCCAGAGGGTCTTCATT
TAGTACATACCAGGTGCTAAGCTGGGTGCTGGAGACATGACGGGGAACCC
ATTTACCATGGCTTTGTTACTGTGACATTCACATCTAGGGAAAGCCAGCA
AAGGGGAGGGATCGAGGAGAGCTTGTTAGGCAGAGAAAATACCCAAGGGC
AAGGGAGAAGCCAGCCTGTTCTGAGCACACACAGTGGTTCCATCTAACTG
GGCCTCAGTGCCAGGTTGGACTGGAGATGGGGCTGAGGAGCTGTCACAGA
GCATTCTGGACACAGATGTCACATAGTCCCTTGAGGTTAGGGTCCTTAGG
CATGGCAGCATTGCTTTGAGTTTTTCCTTTTGTAATGTTGCCATTCATGA
CAATGTGGAAGATGGGTCCTTGCAGAGAAGGGCAGGGCTGTGAGACCAGT
TAGGAGACTAAGATGTGAGCCAAGGAAAATGAGGAACACCTGAACACTGG
GGCAGGTGCAGGGCCCAGAGAGAAGCAGATGGCTTCCTGAGGTTTTAAGT
AGGTAGAATCAAGGCAGCTGGTACAGATCTTTTATTACATATAAACTGGA
ATAAGCCATCTGTTCCAAGACAAAAGAGTAGGCGGAAAACAATACAAGAC
AGAAATGGAATTAGAACAAACCTGGGAGGAATGTGGAATTAGAGTAGAGA
GTCCAACACTGGCTGCAATCATAAAAATGTAAAACAAACAAAAATTTGCT
AGGTGTGCTTACTTAGAAATAATTAGCTGTCATATTAAGTTCACTTGTGT
TATGGCTTAAATGTGTCCCCCAAAATGTGATGTGTTGGAAACTTGATCCC
CAATGCAACAGAGTTGAGAGATGGGACCTTTAAAAGGTGATTAGGTCATA
AGGGTTCTGCCCTCATAAATGAATTAATACTGTTATCATGAGAGTAGATT
CCTGATAAAAGGATGATCTCTGCCTCCTCCCCACAGCCCTCTTGTGCATG
CTTTCCTGCCTTTCCACCTTCTGCTATGGGATGACACAGCAAGAAGGCCC
TCACCAAATGCAGCTCCTTGATCTTGGACTTTCCAGCCTCCAAAACTGTA
AGCCAAACAAATTTCTGTTTATTATAAATTACCCAGTCTCAGGTATTCTG
TTCTAGAAACACAAAATGGACTAAGATCATTAAATTATCATTTTTATCA
GACTGTTGA
>Contig27
AAAATATAACAGAGAGTAAGAGGAAAATTACCTTCTTTCTTTTTCCTTTC
CCTGCCTGACCTTATTCACCTCCCATCCCAGAGCATCCATTTATTCCATT
GATCTTTACTGACATCTATTATCTGACCTACACAATACTAGACATTAGGA
CAATGTGGCCTGCCTCCAAGAAACTCAAATAAGCCAACTGAGATCAGAGA
GGATTAATCACCTGCCAATGGGCACAAAGCAACAAGCTGGGAGCCAAGTC
CCAAAATGGGGCCTGCTGCTTCCAGTTCCCCTCTCTCTGCATTGATGTCA
GCATTATCCTTCGTCCCAGTCCTGTCTCCACTACCACTTTCCCCCTCAAA

FIG. 3P

CACACACACACACAACAGCCTTAGATGTTTTCTCCACTGATAAGTAGGTG
ACTCAATTTGTAAGTATATAATCCAAGACCTTCTATTCCCAAGTAGAATT
TATGTGCCTGCCTGTGCTTTTCTACCTGGATCAAGTGATGTCTACAGAGT
AGGGCAGTAGCTTCATTCATGAACTCATTCAACAAGCATTATTCACTGAG
AGCCTTGTATTTTTCAGGCATAGTGCCAACAGCAGTGTGGACAGTGGTGC
ATCAAAGCCTCTAGTCTCATAGAACTTAGTCTTCTGGAGGATATGGAAAA
CAGACAACCCAAACAACCAACAAAAGAGCAAGATGCTGCAAAAAAAAAAA
AAATGAATAGGGTGCTAAGATAGAGAAAAGTGGGAGAGTGCTATTTAGAC
AAAGTGGTAAAAACAAAGCCCCTTGTGAGATGAGAGCTGCCGACAGGAGG
GGGCGGGTCATGGTTGTGGGTTTTTGGGTAGGACATTCAGAGGAGGGGGC
GGGTCGTGGTTGTGGGTTTTTGGGTAGGACATTCAGAGGAGGGGGCGGGT
CGTGGTTGTGGGTTTTTGGGTAGGACATTCAGAGGAGGGGGCGGGTCGTG
GTTGTGGGTTTTTGGGACATTCAAAAGAGTCTGAATGCACCCAGGCCTAC
AACTTCAAGATGGTAAAGGACAGCTCCAAGGATCAGAAGAAGCATGCTTG
GAACTGGGGCATTTTGAGAAGGAGGAAAAATATGCAGAGACTAGTGCTTG
CAGAGCTTGCATGTGGATTTCATTTGAGGTACAATGAAAACCCATTAATG
GGTTTCACACAGTGCAATGGCCTGACCTCACTTATATTTCCTAAAATAGA
AAACAGATCAGAAGGAAGGCAATAGAGAAGCAGAAAGTCCAATGAGGAGG
TTTCACAGCAGTCATGGGGGTGGGGTAAGGAAAAGAAGTGGAAAGAAACA
GACAGAATTGGGTTATATTTTGGAGATAGAACCAACAGAAGGAAGAGGAG
AAACAACATTTACTGAGAAGGGAAAAAGTAGGAGAGGAATAGGTTTGGGA
AATAAATCCTGCTGACATTGGAAACCCCAAGGAAGCCTCAAAAGTATATT
TACTTGCTTTAGATTTAAAAGAATAGGAAAGAAGCATCTCAACTTGGAAT
TTGAAATCTATTTTTCCATAAAAGTATTGTTAAATTCTACTCATACTCAC
AAGAAAAGTACATTCTAAAGAGTATATTGAAAGAGTTTACTGATATACTT
AGGAATTTTGTGTGTATGTGTGTGTGTGTATGCGTGTGTGTGTGTTTAAC
CTTCAATTGTTGACTTAAATACTGAGATAAATGTCATCTAAATGCTAAAT
TGATTTCCCAAAGGTATGATTTGTTCACTTGGAGATCAAAATGTTTAGGG
GGCTTAGAATCACTGTAGTGCTCAGATTTGATGCAAAATGTCTTAGGCCT
ATGTTGAAGGCAGGACAGAAACAATGTTTCCCTCCTACCTGCCTGGATAC
AGTAAGATACTAGTGTCACTGACAATCTTCATAACTAATTTAGATCTCTC
TCCAATCAACTAAGGAAATCAACTCTTATTAATAGACTGGGCCACACATC
TACTAGGCATGTAATAAATGCTTGCTGAATGAACAAATGAATGAAGAGCC
TATAGCATCATGTTACAGCCATAGTCCTAAAGTGCTGTTTCTCATGAAGG
CCAAATGCTAAGGGATTGAGCTTCAGTCCTTTTTCTAACATCTTGTTCTC
TAACAGAATTCTCTTCTTTTCTTCATAGGAGATGCCTGAGATACCCAAAA
CCATCACAGGTAGTGAGACCAACCTCCTCTTCTTCTGGGAAACTCACGGC
ACTAAGAACTATTTCACATCAGTTGCCCATCCAAACTTGTTTATTGCCAC
AAAGCAAGACTACTGGGTGTGCTTGGCAGGGGGGCCACCCTCTATCACTG
ACTTTCAGATACTGGAAAACCAGGCGTAGGTCTGGAGTCTCACTTGTCTC
ACTTGTGCAGTGTTGACAGTTCATATGTACCATGTACATGAAGAAGCTAA
ATCCTTTACTGTTAGTCATTTGCTGAGCATGTANTGAGCCTTGTAATTCT
AAATGAATGTTTACACTCTTTGTAAGAGTGGAACCAACACTAACATATAA
TGTTGTTATTTAAAGAACACCCTATATTTTGCATAGTACCAATCATTTTA
ATTATTATTCTTCATAACAATTTTAGGAGGACCAGAGCTACTGACTATGG
CTACCAAAAAGACTCTACCCATATTACAGATGGGCAAATTAAGGCATAAG
AAAACTAAGAAATATGCACAATAGCAGTTGAAACAAGAAGCCACAGACCT
AGGATTTCATGATTTCATTTCAACTGTTTGCCTTCTACTTTTAAGTTGCT
GATGAACTCTTAATCAAATAGCATAAGTTTCTGGGACCTCAGTTTTATCA
TTTTCAAAATGGAGGGAATAATACCTAAGCCTTCCTGCCGCAACAGTTTT
TTATGCTAATCAGGGAGGTCATTTTGGTAAAATACTTCTTGAAGCCGAGC
CTCAAGATGAAGGCAAAGCACGAAATGTTATTTTTTAATTATTATTTATA
TATGTATTTATAAATATATTTAAGATAATTATAATATACTATATTTATGG
GAACCCCTTCATCCTCTGAGTGTGACCAGGCATCCTCCACAATAGCAGAC
AGTGTTTTCTGGGATAAGTAAGTTTGATTTCATTAATACAGGGCATTTTG
GTCCAAGTTGTGCTTATCCCATAGCCAGGAAACTCTGCATTCTAGTACTT
GGGAGACCTGTAATCATATAATAAATGTACATTAATTACCTTGAGCCAGT
AATTGGTCCGATCTTTGACTCTTTTGCCATTAAACTTACCTGGGCATTCT
TGTTTCATTCAATTCCACCTGCAATCAAGTCCTACAAGCTAAAATTAGAT
GAACTCAACTTTGACAACCATGAGACCACTGTTATCAAAACTTTCTTTTC

FIG. 3Q

TGGAATGTAATCAATGTTTCTTCTAGGTTCTAAAAATTGTGATCAGACCA
TAATGTTACATTATTATCAACAATAGTGATTGATAGAGTGTTATCAGTCA
TAACTAAATAAAGCTTGCAACAAAATTCTCTGACACATAGTTATTCATTG
CCTTAATCATTATTTTACTGCATGGTAATTAGGGACAAATGGTAAATGTT
TACATAAATAATTGTATTTAGTGTTACTTTATAAAATCAAACCAAGATTT
TATATTTTTTTCTCCTCTTTGTTAGCTGCCAGTATGCATAAATGGCATTA
AGAATGATAATATTTCCGGGTTCACTTAAAGCTCACATTACACATACACA
AAACATGTGTTCCCATCTTTATACAAACTCACACATACAGAGCTACATTA
AAAACAACTAATAGGCCAGGCACGGTGGCTCAGACCTGTAATCCCAGCAC
TTTGGGAGGCCAAGGTGGGAAGATCACTTGAGGTCAGGAGTTCAAGACCA
GCCTAGGCAACATAGTGAGATCTCATCTCTACAAAAAAAAAATGAAAAAT
TAAAAAATGAGCTGGACATGGTAGTACACACCTGTAGTCCCAGCTACTCG
GGAGGCTTGAGGTGGGAGGATCACTTGAGCCTGGGAGATGGAGGCTGCAG
TGAGCCATAATCACACCATTGCACCCCAACCTGGGCAACAGAGTGAGACC
CAGTCTCAAAAGATAAATTTTTAAAAATGTTAAAAAATATATAAAAGAGA
ATTTTAAAAGAACAACTAATAGATCAAAGCATGGATGCAAGATATATTTA
GTTGGAAAATCAAGGTTAAAATCAAGGGATCTTGGAATTAGGTGTGGTAG
ATTTGGGTAAGGAGTAGTCTAAGATGACCCTGTTTCTTGGTACTGGAGAC
TGGATGAGTGGCAGCGTCTTAACCATATTTTTGGTAGAAATATGGAGGTC
TTCTCCATTCCAGGATGAATGATGAGTAAAATTTTAGGCATGTAATTTGA
GCTACTAGAAGGACACTCAATTGCAGATGTACAATGGGGAGATGATAACC
TATCTGGAACTCAGAAAAATAACTGTATATAGATATGAAAGACATCAGTA
GGTATGTAGTAGATAAAATCCTAAAAGTGATGTCAAAGGGAGAAGAGAAG
TATATGGTGAACACTGTTGTTTGTCCATGCAATTGCCATCTCTTCTTCTT
CCTTACTGACAGAACCCTGATTTCACTGAGAAGTCAACATGCCCTTCCCC
AATTGATGAATCCAATTGGTTGAAGATTATGTTCATTCTATTCTTACATG
ACTAAGTCACGTTGACTTAATCCTATCAAATGAGATGTCGATCTGGAAAC
AACTTCTGGAAAAGATTTTCTACCTTGATAAAATAAAGAGCCATATAGAT
GGTCCTTTATCTTCCTTCTTCCTTGAATGAGATATGTTCTATGAGGAAGT
GAAGCTTAGAACTGTGGTCAGCAACTTGCAACGACTGGGAAGTCAGAGCC
ACACAATGAAGAATGCAGAGTGGAAGGAGAAAAAGAGCCAGCATCTCTGA
CAACATTGTTACACCGAGAACCTACCTCCAGATTTTAAGAAAACAAGAAA
TGCTACTGTTATTAAGCCATTTCACTGGGTTTGCTATGACTTGCAGTCAA
ATCTAGCTTAACTGATACAGAGCACCACAGAGAACTGGTCTCTCATTTGT
CTCATCCTGTTCTTTCTAGCAGCCACGACTTTCCTAGGGTTTCCTTAGCC
CAAGTCTGGCTAGAGCAAGACTAAGTAAGACTTGATTCCTTAATGTCCTT
TTGTTTTAAGAAATATTAAAGAATTATTTTTATATTAATATATTTTAAGA
AATAAGGAAATACAAAACACTGAGCAAGCAACACAAATTCAAGAAATCTT
AAAAAGTATAATAGCTGCTCAGTCTCTGATTAACAGTGAAATATGGAATC
ATTGTAGAAATGGCCTTGGAGCGTTATTCTCCCAGGCCAGCTATCCTTAT
GGTCTGCCCCACCTCCCTCATTGCCTAAACAGTAAGAGAGTCCCATGGTG
AGACTCAACAGTCTTAGCACAGAACTTGTTACAGTCTATTTCTTTTCTTA
CAGTCCTATATATCAATTCCAAATCAATGAGAGTAAAGCCCAATCCCTGC
CTTTAAACCCAAAGGACAGAAGCCCAAAGCCCAAAGATATTCCCTAACCT
TCTCCCCCT
>Contig28
CCTGTCGCTCCCTATGTTTAAAGCTGGGGATCTCTTTTTCCTGTGTCTAA
TTATTTTCCTCATTGGCTTGAAAAATCTGATAAAACATTTTAGGACTGTG
TATAAAATAGAATTAGCCAAGTGCAATGTCTTTATTCAGAAGAAATTTCA
TGGACGTTGTGCCTACTCTCTTGGCTTCCTGGCTTCATGGCTTTCCAGAT
CCCACAGTAAGCTCTGGATAGTAGAAGTTATAGTAAGACTGACTTCTAAA
TAAATGAAGTGACTTTAACCTTACTGATATGGCTTAAAGAAAAGGAGTGG
CCTTTAAGATCCATGAACTTCTCAAACAAAAGTGATAACGTTATCTCCAT
GCATATATAATACTAAATATAATGCAACTGAGAGAAGTAGGCTGTGGTAA
GAAAGGAGACCCAAGTGCCATCTGAAGGCAGCACTTACCACTCTGCTTCA
TCCCACCGAGGAAACAAAGCATGAGTATTGCCAGATTTTCTTCTGTTTCA
AGAAAAGCCAGAAATCCAGGTTTTTGCGTGAAATGTCCTGATTTTAATGT
TGGGAACTAATTTATATTTTGAAATAACATTGTGTGGGACAAGTGAACTT
GTATGTGGAACTGCTTTCTCCCAGTGGCGACCAGTTTGGACCGTTGATAC
TCAGCAAGTTCAGCCAAGTGCGCCTTGTCATTGTCAGTCATCAAGGTGAT

FIG. 3R

GTGTGATTGGTCAAACAATTAGTTTTGCTCAGCATCTCGTGTGTTTTCAA
AGGACCTGAGGGTTCATTTGCCCATGCAGATCTTGTAGTCCTGTTTATTC
TATTAATTTATCTTGCAAATCTATAATGTTTTATTTTAAGCAGCGAGAGC
CGTGGCAGCCTTTGGTCTGGACCCTTTCTAATGATCATTTAGTATCAGGC
TATGTGGGAGTTGATTGTTTTGCATTGCCTGAAAGCCAACAGTATCACTC
CTCCTCTAGGTGTGGCAGAGATGTGAGAGAGGGAGACTGACAGTCTGTGG
GTGTGTATGCAGTGTTGGGGGAAGCGAGGCACAGGGGACAATACTGTGGT
GTATAAAACTAGTCTAAGGTAGCATCAGGAAGTTCATGAAGCCAAAATGA
TTTTCATAACAGCACAAGACATTATTTGTTTTTGCCTCCCTCTCATTTTT
TTTTTTTTTTGAGACAGAGTCTTGCTCTGTCATCCATGCTCGTGTGCAGT
GGTGCAATCTCGGCTCACTGCAACCTCCACCTCCAGGGTTCAAGCAATTC
TCATGCCTCAGCCTCCTGAGTAGCTGATTACAGGTCTGCACCACCCCGCC
GGCTAGTTTTTGTATTTTTAGTAGAGATGGGGTTTTGTAATGTTGGCCAG
GCTGCCCTGTCATTTTTTTTTTACTAGTGTCCAGTGGAGTTTTTTAGGGG
CTACATAACATGATACTGTCATTAATCTAATGGCTAATGAAAGGGATATG
TATATGTTTTTGTGTTTAAAACAAACTTCTTTGGGGTCCTCAATAATTTT
TAAGAGTATAAAGGGGTCCTGAGATCAAAGAGTTTGAGTTCTGCTGGACT
GGGACAGTGGTTGTCAACCCAGATTGTACATTAGGGTCATCTGGGAAGCT
TTAAAATAGTACTGATGCCCAACCTTACCGCAAACCAATTAAGCCAGAAT
CTCTGTGGATGAGAAGTCTTCATTGTCATCATCACCATGACCATCATCAT
TGTCACCGTCACTACACCATTATCATCATCATCATATCATCTTCATTATC
ATTGTTAGTATCTCCATCACCATCATCAGCATCACCATTATTATCATCAT
CATCATCCCCACCATCATCCTCATCGGAACTTCACCTGCATGGAGGACAA
TCCACTATGCATTAGGTGCTATGCTATTTGCTATACTCCTTATTCTCACA
ACTGCCCAGAGAGGCTGATATTATCTCACTTTATAACAGGAGGAATCTGG
ATCGGAAAAGTTAAGGTAAGCTAATTCACAGAGCGAGAAGAGATAGAGCC
AGGATTCGAAACCAGTTCTCTGCTACATCAATGTTCCCAGTCCTTGCACT
ATTGAGAACCTCTTTAGTTATGCTTTCACCCCTCCAACACCACAGTAAAT
TTTTTCTTTTTTTAAAAAAATTATACTTTAAGTTATAGGGTATATGTGCA
TAATGTGCAGGTTTGTTACATATGTATACATGTGCCATGTTGGTGTGCTG
CACTCATTAACTCGTCATTTACATTAGGTATATCTTCTAATGCTATCCCT
CCCCGCTCTCCCCACCCCATGACAGGCCCTGGTGTGTGATGTTCCCCACC
CTGTGTCCAAGTGTTCTCATTGTTCAGTTCCCACCTATGAGTGAGAACAT
GTGGTGTTTGGTTTTCTGTCCTTGTGATAGTTTGCTCAGAATGATGGTTT
CCAGCTTCATCCACGTCCCTACAAAGGATATGAACTCATCCTTTTTTATG
GCTGCATAGTATTCCATGGTGTATGTGTGCCACATTTTCTTAATCCAGTC
TATCATTGCTGGACATTTGGGTTGGTTCCAAGTCTTTGCTATTGTGAATA
GTGCCACAGTGAACATTCATGTGCATGTGTCTTTATAGCAGCATGATTTA
TAATCCTTTGGGTATATACCCAGTAATGGGATGGCTGGGTCAAATGGTAT
TTCTAGTTCTAGATCCTTGAGGAATTGCCACACTGTCTACCACAATGGTT
GAATTAGTTTATAGCCCCACCAACAGTGTAAAAGCATTCCTATTTCTCCA
CATCCTCTCCAGCACCTGTTGTTTCGTGACTTTTTAGTGATTGCCATTCT
AACTGGCACCACAGTAAATTTTTATAGATTTTATAAGCAAATTGTATTTA
CTGTGCAAGAATTGGTTTATTTTTTAAACCATGTGTTGCAAACATACAAT
GGTTAATTGTGATATTTGCTCAGTACAAGATCATCAGATCACTACACAGA
CTTGAGGTAATTCCACCTAAAAGCAAAGAGAACTGACCCCACATTAACTG
AGAAGTCTTTACTTATTTATTCCCTATAAACGAGCCAATATGAAGAGAAG
GCCTTAATGTGGTTAACTATGTAATTTTTTTCTGACTTTTTGAAATACTG
AGAAGAGCTCATGACTCTCCCATCTCCTAATTCTACCTTGGTGGATTTTA
GACTGACCACAACTCATGGGTAAATGAGGGAAGACGAATAAGAAACCTTG
CTTTTTTTTCCTCCTTGTTTTTGGCTGGCTGCAGTGGCTCACACCTGTAA
TCTCATCACTTTGGGAGGCCAAGGTGGGAAGATCACTTGAGCTCAGGATT
TCAAAACTGGCCTGGGCAACATAGTGAGACCCCATCTCTAAAAAAAAAAA
AAAAAAAAAAAAAGGCGACAGGCGGTGCGTGCCTGTAATCCTACCTACTC
AAGAAGCCGAGGTGGAAAGATCACTTGAGCATGGGAGGTCAAAGCTGCAG
TGAACCTTGATTGCACCACTTCATTCCAGCCTGGGTGACAAAGCAGGACG
CTGCCTCAAGAAAACAAAAACAAAACCTTAATTTTTTGGCTATTCTTTTC
TGGTAAGAATGGTATAGAGATGGGGATGAGGATGGCTATTGTATGAGAGA
GCAAACAGGGTCCAAGCAGTGCTCTGGGCTGTCTAAGGACCAGTAGTCAG
CTTAACTTCTCAAATTTCCAGGGAAGGAGTTCGGAGTGGTAGAATATCCT

FIG. 3S

GGGTATGCCCAAAGCATCACCTTGCAAATAGCCTGTCATGAATAATTTGT
TTCATTTGTTATGACTGGAAACTGGCTTTGTGTATGCCAGAGAATGGGGG
CAGGAAAGAGAGATTGGTGTCTTGAGCTCTCTGTGCCTCTGGGGCAGTGA
TGCTTTTCCTCTCATGTGGAAGGAGAGCATGACTGAAAAGGTGCACAAAT
AAGGTGTCTGTGAGAGAAATTAACCTTCCAGATACAGAGACACAACCTTC
CCCAAGAGGTCCTCATTGCTCTGCCTTTTTCCTTTTTTTGCTTGTTCT
ACCATTAATAACAGAAACTGATTATGACCTCAAAAGAGAGGAGAAAGCGA
CTCTCCCCACCCTAGAGCTAGTTAACCACCATATCTTCCTAGATATCCTT
GAGAGCAATGTAACCC
>Contig29
GTGAACTCGTTTTACCTGTGTAGCAGACCAAGCCGCAGACAAAATCCNTC
AGACACCAAATTAAAGAAGGAAGGGCTTTATTGGGCCTGGAGCTGCGGCA
AGACTCACGTCTCCAACAACCGAGCTCCCCGAGTGTGCAATTCCTGTCCC
TTTTAAGGGCTCACAACTCTAAGGCGGTCCACATGAGAGAGTCGTGATAG
ATTGAGCAAGCAGGGGGTATGTGACTGGGGGCTGCATGCACCTGTAGTTA
GAATGGAACAGAACATGACAGGGATCTTCACAGTGCTTTTCTTATGCAAA
TAACCGATTAGATCAGGGGTCGATCTTTACCAGGCCCAGGGTGTGTCACC
GGGCTGTCTGCTTGTGGATTTCATTTCTGCCTTTTAGTTATTACTTCTTT
CTTTGGAGGCAGAAATTGGGCATAAGACAATATGAGGGGTGGTCTCCTCT
CTTACCTGCGGGGAGTGAGCTCAAACTCCTTAAAGGAGTTACCTGCCTTC
CATCATCAGGGAAGCAGGAAATCTTGCCTTCCTTGTTGGAAGCAAGTAAA
ACTCAAAACAAACAAAGAAAAAAACAGGGAGTTGTACAGCAAAATAAACT
TTTGATTTTGACCAAATTTTGGGAGATCAGGAATTCTCTGAAGGAGATGC
TTTCAGACCTCAGCAAATTGTCCTGTTGGTTTGAGCCATAAAGTTAGCTC
ATGCTGGTACCAAACACCAGTAGGAGATTTGTCAAAGGTAAGAGGCATCT
CCACTCAGAATCCCTTCGTGGTTACCAACATGTGAACCTTGGAAATCTGA
GACAGGTCTCAGTTAATTTAGAAAGTTTATTTTGCCACGGTTGAGGACAC
CCACCCATGACAGAGCATCAGGAGGTCCTGACCACATGTGCTCAGGGTGG
TCTGAGCACAGCTTGGTTTTACACATTTTAGGGAGACATGAGACATCAGT
GAATATATGTAAGATGTACACTGGTTCCCTCCAGAAAGGCAGAACAACTT
GAAGCAGGGAGGGAGCTTCCAGGTCACAGGTAGGTGAGAGACAAACAATT
GCATTCTTCTGAGTGTCTGATTAGCCTTTCCAAAGGAGGCAATCAGATAT
GCATTTATCACAGTGAGCAGAGGGGTGACTTTGAATAGAATGGAGGCAG
GTTTGCCCTAAGCAGTTCCCAGCTTGACTTTTCCCTTTAGCTTAGTGATT
TGGAGGCCCCAAGATTTATTTTCCTTCTACATCACTGTGGGCAGCTGACT
AGGAAAGCTTTGTAGGACTGGTGGGCAGTGTGAGAGCCCAGTGGGGGGTG
GTGGTCCTGTGCCAATGGTAGCAACCACCTGTGAGGCTGAGTAAACTCAT
TTCCCAACCTCCTCTAGCAGCCCCAGTGGAGATACAGAGGAAGCAGACTA
GCGATACAACCCAGCCTGAAGTTTTGTCTGGTGAGTGTAATGGAATAAAA
ATGGGAAGGGTGCTGAAGAGACCAGCAAGAAAATGGTTGAAGAGATGGGG
CACAGAAATTAAGCTGGATCAAAAAGGACGGAAAAGCAGAAAGGGCCGAT
AGAGAGAGGGGATATCTATGGGTTCGCGATTCTGAAAAGGACAAATCACT
GGTGCTTTGAGAAGAGAGAGGGTGAGAAAGCAGGAAGGCTGGAGGCTGTC
ATCCAAGAGGCGGACATCTGTGAACATGATTCCAAGAGTCACCAGACCAT
GGGGGTGGCCAAAGGGAGTGCCTCTTCTCACCTCCTACTCTTAATTCCTT
GTACTCAAGATAATAAGTTCCCAGAAGAGAAGTACCCATATTTAATTCAT
CTGTGTCTTCCTAGCAGTACTAAAAATATTATATGAAAGGTATCAAACCT
TTGAGAATGTGTGCTGCTAAATTGTTAAGGATGCTGGAAAACTCAAGACG
TCCCTGATCCTGAGCCTGAGTATGAGCCTGTGGTGAGCCCAATGCAGGTC
TCCATTCAGACAAAGGCCTCAGGGAACGGATGAGACCTAGGGACAGAGAT
GCATGCTGGAGCAGCATTCCCCATCCCTACTGCAGCTCAGGCCAGCTGAC
TGCTTTATGAGTAAACGTTACCAGGGAACACTTTGCAGTCTTAACACACA
TGCCCACCTGTGACCACTGATCCCTGTTGGGTGACCACTGACATCAGAGA
TTCGATGGCAGCAATGAAGACAAGGCTATCCTCATTAGGAAGGAAAGGAA
GGAGGAGGGAGGAGGGCAAACGAATCTTTCCTGCTTGTCAACCACGTCCA
TCTCTGTTAGGTGATTTCCCATGTGTGACTTTGTTTATCTTTATAATAAC
TCTGAGAGGTAGGTCTTGATGTCCACATTTTGAACATGAGGACATCCAGC
CAGGAAGTTGAGTTCTGGGGACATAGCTGAGAGGGCAAAGCTACATATAA
ACCCCTCTTTGTTTTTTCTGGCTTATCCACTGAGTGCCCCCTGCAATCCA
CCAGCCCATTTGTGAAGTGCATACTATAGGTAAGTTGGCACAGGAGGAGT

FIG. 3T

GGATGTGGGCGATTTTGTCACAGCTCTCCAGGAACTTACACACTGGTGAG
GAGGGCCAGGTATGTTCCTGACCAGTCACAATCAAAGCAACCTCCTACTA
ATCAGGGAGGCTTGGTACCTGGGGAATGCTATGTTGAAAGGTTCTTTTCT
GGGTTTTAAAATGATGGGTCTATTTCCTTATTCTTAAGATTGCTTTTTTT
CTGGCTAGAACTTAAAAGAAATTTTCAGTAAAATTTCCCTTCCCTGGCAC
AAAGTGAGCTTGAAATGAATTCCCAGGTGGCCTTGATACTTTAAAATATT
GCCTCCTATAAAATCAACCTTTAGAAGAAGGAAGTCAAAGAACATGCTAG
ATTTCACAAAGGTTAATTCCTTGAAATCCAGTTATCTACAGGACAATGTT
GTCAAAGAAAAAATTATTTGGCCAGGCACGGCGGCTCATGCCTATAATCC
CAGCACTTTGGGAGGCTGAGGCAGGTGATCACCTGAGGTCAGGAGTTCGA
GACCAGCCTGGCCAACATGGTGAAACCCCATCTCTACTAAAAATACAAAA
AAAATTAGCCAGGTGTGGTGGTGGGCACCTGTAATCCCAGCTACACGGGA
GGCTGAGGCAGGAGAATCGCTTGAACCCGGGAGGAGGAAGTTGCAGTGAG
CCAAGTTCAAGCCACTGCACCCCAGCCTGGGCAACAGAGCAAGACTTTGT
CTCCAAAAAAAAAAAAAAATTCAATGATATTTTTAAATTCATGGTAAGGAA
GATTTCATTCAGAACCAGCACAGAAGATATAGGAAACACTGCAATGGGAC
TTTGCGGTGGGGGAGAGAGATTGAACACAACTACATATACAGCACGGGCA
AGGACATATTCATAGCCAGGAAGCAGAGCAAAGATCAGTGGATGCGAAAT
TACTAAGAGGAAACATGAAAAATAAGGGAGCTTCTGCCTAAACCCACCTA
ACCGGATCCTTGCTGAAGACAGGACAGGGTGATTGGACACCACTTTGGGG
ATGGTGGAGGATGGGGAATCCAGTGAGATTTCAAGGGTGATGCGATATTG
AACATACAAAGTTCTTGCTAAAAAAGGATTTTACAAGAAAGTGTACAAAT
GTGCCTGGGACAAGGTGCAGGAGCCCGACGGAGATGTGGTCCAGCAGAGA
ATATGTGCCGAGATGATAGGTGAGTTCTCTGACGAAGGATATATGCTGAT
CCAGCCAGGGTGAAATGCTCAGAGAAAGCACGGAGGGGCTATGTCCGTTG
CCCCAGTCTCCACGCGGTCAAATCTGATCCCGTTGTGAGTGTGGCCGTTT
GTAGAAAGCAATCAGGGGGGGTCCCTCCCC
>Contig30
AATATATATTTTTTATANNATNTGAGACAGGTTCTCACTAGGTTGCCCAG
GCTGGTCTTGAATTCCTGCCTTCAAGTGACTCTCCCACCTTAGCCTACTG
CATAGCTGGGATTACAGGCACAAACCACTGCATGCAGCTAACTTTGCTTC
TCATTCCAGCACTTTTTATTCCACTGATTATATGTATATGTATATCTGCA
TCATCTCTCTCTCTCTCTCTCTCTCTCTCTCTCTATATATATATATATAT
ATGGAAATATCTCTCTCTCTCTCTATATATATATATATGGAAATATATATCT
CAGTCTCTCCTATCCTCCTTTAATCAGTTTTGCTATCCTGTCAATTCCCC
CAACGAGTGTGATGTTGTGAAATATATATTTGTTCTTCATCTCCTGTTTC
CTGACATACAGCTTTTAAAAACCCTTGGAATCTCTGGAATAATAAGAGTG
TCTTTTGCATGCTAATAGATGACTGCTGGCTGGCAGCCCCAATGCAGTAG
CTTCATGATGGGGTTTGTCACAGGAAAGACCAAGGCAGGATTGGAGACTT
GAGACTGTTAGCCCCACTCCCCAACCACTGGAGGGAGTGGAGGGGCTGAA
GGTTGTGTCAGTCACCAATGGCCAATGGTTCGGTCAATCATGTGTATGTA
ATAAAGCCACTCTTAAAAACCCAAAAAGGACAGGGTTTGGAAGGGCTCCC
AGATAGCTGGACACATGAAGGTTCCTGGAGGGTGGTGCCCCAGAGGGGCA
TGGAAGCTCCACACCCCTTCTCACATGCTTTGCTCTGCGCATCTCTTCAT
CTGGTGTTCATCTGTATCCTTTGTAATATCTTTTAGAATAAACTGGTAAA
CTTAAGTGTTTTCCTGAGTTCTGTGAGCTGCTCTAGCAAATTCACGGAAC
CCGAGGGAAGCAAACCCAGATTTATAGCCATCAGTCAGAAGCATAGGTGA
CAACCTACCACTTGTAACTGGCACCTGAAGTGGGAGGCAGTCTTGTGAGA
CTGAGCCCTCAACCTGTGGGATCTAACGCTAACTCCAGGTAGATAGTGTT
GGAGTGAATTAGGACACCCAACTGGTGTCGGCTGCTGGAGGACTAGTGGT
GGGAGAAATCCCCAAGCATTTCGGTGACTAGAGGTCACAGAAGAACTCAG
TGTTGAGGTGTTGTGACAGTATGGTAGGGAAAACTGCGTCTGGTTTTTTC
CTTTTACAATCAGTTAAATATTTAACACAAGTCTACTGTATATTAGTAAA
AGGGTTACATTTTTTAATGTCTTGACAGTTGCACTTTGACAACTTCCATA
TCAATCACTTTTTTTCGTGTCCGTTTGGAACCAAAATCACTTGGGATACC
ATGAACCAGGCTGCAGCGTATTCCCCAGGCCTTGAAAGCTTGGAGGCCAT
TTTGCCAGCCNTAATCCCTGTGAATACCAGGCTTCGTGGATTTAAAAAAT
AGACTTGAGGCCAGGCCTGGTGGCTCACACCTGTAAGCCCAGCACTTTGG
GAGGCAGAGGCGGATAGATCACAAGGTTAGGAGTTCGAGACCAGCGTGGC
CAACATGGTGAAACCCCGTCTCTACTAAATATACAAAAAAAAATTAGCCG

FIG. 3U

GGCGTGATGTTACACGCCAGTAGTGCCAGATACTCAGGAGGCTGAGGCAG
GAGAAATACTTGAACCTGGGAGGCAGAGGTTGAAATGAGTCAAGATCGTG
CCACTGCACTCCAGCTTGGGCGACAGAGTGAGACTCAGTTTTCAGGGGAG
TTAAAACAATACAAAAAAAGAAAAAGACTTGAACAATGAGGCTCCACTGG
ATGGATTTAGGGGAATTACAGGAAGCAGGACCTGACGGTGCAATGCCACA
CTCCACCTGTCCAGAATTGGACCTCACCAAGGGAGGTCTGTGGGGACAGG
GAGAGGCCCTCTGCCTCCACCCCCTCCTCTACTCCCCAAACCCTGAGTCA
GGCTGAATGTAGTAAACCTGGAACAGAAAAGTTCAGTTTGGCAATAGGTA
TCTGAAGGACTCCAGGTGCTTCTCCCTTGATTCAAAATTTTACTTATAAA
AAAAATTATAAGAAAATTCTACTTAAAAGAAATAATCAGGGAGGTACAAC
AAATTGTACTTTTTTTTTTTTTTTTTTTTTTTTGAAATGGAGTCTCACTG
TTGCCCATGCTGGAGTACAGTAGTGTGATCTCGGCTCACTGCAACCTCCG
CCTCCTAGGTTCAAGTGATTTTCCTACTTCAGCCTCCCAAGTAGCTGCGA
TTACAGGTGTGTGCCACCACACCCGGCTAATTTTTGTATTTTTGGTAGAG
ACGGGGTTTCACCATGTTAACCAAGATGGTCTCGAACTCCTGACCTCAGG
TGACCCACCTGCCTCAGACTCCCAAAGTGTTGGGATTACAGGGGTGAGCC
ACTAAGCCCAGCCATTGTACATATTTTGTGGGTATTTACTAAAACATTAT
TCAAAATAGTAAAAAAAAAATTGAAATAAACTGGGGACTGGTTAAATAATT
TTGGGTACAACCACATGATGGAATACTATACAGCCATTAAAAATTACATT
GAGGCCAGGTGTGGTGGCTCATGCTTGTAATCTTAGCACTTTGGGAGGCC
AAAGTGGGAGGATTGCTTGGACCCAGGAGCTCAAGACCAGCTTGGGCAAT
GTGGCAAAACCCTGTCTCTAAAAAAAAAAATACAAAAAAAAATTAAAAAGCT
GGGTGTGGAGGCACACACCTCTAGTCCCAGCTACTCAAAGGGCTAAGGTG
GGAAGATCACTTGAACCGGGGAGGTCAAGGCTGCAGTGACCCAAAATCGG
GTCATTGCACTCCAGCCTGGGCAACAAAGCAAGACCCTGTCTCAAAAAAA
AAAAAAATACATTGAAGAATATCTTACGGTATGGATAAATATTCATTTTA
CAGTGATAGATGCAAATAAAAGCAAATTACAAAATATACAGTTTAATTCC
AACTTTGATACTACATATGTATATATGAATACATGCATATGTTATGTATG
TATATGTAAATATAACAATATATGTTCTATATATGGATATTATATATTTA
CACATACATACACACATATATAATATCTTCTCTAGAGAGCAGAAAGAGAG
TAGACAGATAATGAAGATAGGATACAACTCCAGTCCAGCTCAACCTAGGG
GACTTGTTTTAAAGCCTCAGGAGAGAGAAGTTGGGACTAGAAAGCAAGGC
AGCTATTTGTAAGCATCTTTGTGTTTCATGCTATTGGGGTGGGAAACAAC
AGCACAACTTTTGAAAGCCCCTTTCTACTCACCCCACAAACTGCAGAGCA
GCTTTAGGACCCTCAGAGTTCAAGAAGACCATTTGCAGAGTAGAAGAAGT
AAAAACATGTATGAACTTGACCCTGAGCTCATGGACTGTGCCATGAGGGA
AATTCCTAAAACAGCAGGAGAGGCCCTGGAGGAAGGCAGAGGCCCTGCAT
CAGCAAGTCCAGGCAAAAGCCTGCATTCCATAGATGCTCATCTCTCTGGC
TGGTGAGGTCTAAAGACGTTTGGTCTCAATATTAAGTCTCGTGAGAGAGG
TCACAAACCCAGTCCCTTGGCCACAAAAGGAAATAAATTCTGGCTTGAGA
CATTAGGGAGGAACAGGGCAAGGGGAGGTTCAAGAAAGTTTTAATGGATG
AGATGATATTTAAGCAAGGCCCTGGAAAATGAGAATTTCAACCAATAGCC
ATATGGTAGGTCAGAAAGCAAAGATAAGGAGGGGGCAAGTGCAAGGGGCA
ACATCAGATATGACCAGGGTGTCGTGGGGCATGGCTGATGGAGAAGAAGA
TTAGACTGGAGTTTGGGAATGCCACAGTATCGAGGTTGGATTTAATCCTA
TGGGTAATAAAGCCAACTGTTCAACCCCCAACCCACTTGCAATATGGCTC
CAAAATAGCAGGTGTTTGATAAAATGACTACTTTTACTCTACTATTCCCT
CCCTCTTAAGAAGAAAAAGAAAGTGGAGGCTCAGAGAAAGGCAGTGGCTT
GTCCCAATCACACTATGATTTGGCCACAAAACAAGAACGAAATGTTACAC
CCAAAAATGCTGCCTCCACCTCCCTTCCTTGCTTTCCTCCCTGCTGGACT
ACAGACTATCTCAAGAGTGACGTACACCATCAGGGCTTCAGCTTTTCCCC
GAAACAATGCCAAAATATTAGCCATACGTCACTGTAGTAAGAGCCCTGAA
TTGGGAATCCCAGCTTTGACGCAGACATGCTGATTGACTCTGTGACCATT
CTCTTCACTTCTCCACTCTATTCTTCCCCACCTGTAAAGTGAGGTCCTTT
CCAGTTATAAAAACAGATGATGCTATTGTCCTGTTTTGTATCTAATCTTG
CTGTGTTATAAAAAAAAAAATAAGGCTCTGTACATTCATCTTGGCCAATTC
CCTTCTTATCTCTACTTCCCACAGCCCCTTTTTCTACAGAAAACCAGCAT
TGTTCTTCTGGATCCATCTCTTAAGAAAGCGCTTTGCCTCCCCGGTTATT
TAGGTGATAAGAAGTGTCCTAGATGACAGCCCTGGAATGGGCTGGAGGCA
ACAAAAAAGCAAGTGAAATAGACAGTTACAGCGACGACAATAATAACAAC

FIG. 3V

CAACACCTCTCACTAAAGAGAAAGAAATAAAAAAGAAAATTAAAATCTGC
CGCAATGCCCACACAGTCATTGAATAACTGCATGTGTACAGCACTTGGTT
ACTTTTACATACTTCATATTTTAGCCTTCATAGCAGCTCACAGGGGTGGA
TTTAATTTTTAGTCCAACTCCTGTCACGGTGCCTGGCACAAGTATAATAA
ATGTTCTGTGAATAAATGACCCTCTTTTTAGATGAGGAAATCGAGGCTCA
AGGAGAACAAGCAATGTAATGTCCCCCTCCTGTTCAGCCATCTGCCTTTC
ACGCCACTGAATGCAGTAGTCCTCAGTGCCCTGAACTTGACCCTCTTCTG
CTTTTCGGACTGGTCCTTCTAATCCCGTTGTGACTCACTACACCACCTCT
CCTGCATATGACATCTACATTTTAAAACAAACCGTATGGAAATAACACAT
TAGTCGGCTTGTTCCCCCACCCCCGCAAAAAAAAAGGCCTCTTTATAACA
GAAACTTCTCAGGCTGGTAGGGGAATTTTATTCCCCCATTTATGGTAGAA
AGGCCCTAACCTTGGACCTCACGCCATAGCTATTCACATGGGGGAATGAT
GAATAACATGGGGAGCAGCATGTAAATATCATTGAGCCGTAGTCCAGACC
TATAACACATC
>Contig31
GGGGGAGCTGCATGTGCCTGTCGAGATCTGGGGGAGGAACAGGAAGATCA
AGAGTTCTGTGTAGGACATGTTAAGTTGAAGGTGCTTACAGGATAGCCAG
ATGAAGCATCAGGTGTGCAGTCAAAGATATGAGTCTGGAGCAGCACATCC
TAAGTCACCTCCTGCACCAACACAGAACTTCCAGGCCACTCACTTGAGCT
CTCCCAAATAGTTTCCAAGTGTCATTATGTTAATAACCTATGAGCTTGAA
CACCAGATTCAAACCCCACTGCATGGCTTTTAAAGACCATCTCAAGGGCT
TGACACTCCAGGGAGCCAACTAAAGATGCCTGGTCCTACCATCAACCTCC
ACCCCATTTTTTATAGAAAATGTTTCTACCTGTCCTAAGGCAGGGTCCTG
CCCCACTCCCAGGCCCCTTTAGATCCCCAATATTCCTCCTCCCTGAACCA
AAACCCTCATCATCTTCCAGCATGGGTGGGGCCTCCATTCTTGCTTCTGC
TCCCCTGAGCAGAAGCAAGTTTCTCCCAACTTGACCTGATTCTCCTCCTA
AGTACCAGTCACTGCTTTGTTTCTGGAATGAGAGAAAAAGACAGAGTGAG
AGAGACAATCCAGAACTCTTGCTCACTCACAGCTAGGCTGGGCATCTGGG
AGGATGGCTGTGTCCATGGGAACCTGGGAAAAGCCACACCCTTGGCACCC
TGGTCACCCACCTGTCTCCCTGGCAGATTCCGCACTGCTCTCTTGCACCC
TCTACCAGGGCTAACCGGCCTGCTCACTCTCCCCAGCATGTCTTCCCACG
CCCACTCTCTAATTATTACATTCCCTTCACATAAACTGCCCTTCTCTCCC
AATCACCACATGTTCACTTCCCACCCAGCTGTCAAAGTCTGGCTCAACCT
CATTCTTGAAAAGGAAAAAACAAACAAACAAACAAACAAACAAGCAAAAA
ACCTATGATGGATTAAGAACACACTTCATTCCAGGAACATGCTTATCTCC
TCTAACTCTCACAACAACTACAGCAGGTAGGTGTTATCACACCCATCTCT
CAGGTGAGAAAACAGGCTCAACGAGTGCAGGAGGACACAGCAAGTCAGTG
ACAAAGCTTAAATTCAAGCCCAAGCCTGTTGGCAACCAACGTCTGTACCC
TTGATAGCTACCTCATTTACCACCAAATCCAGTGGCCTCAGGCCTGGCTG
CACACTGGGATCACCTGGTGCCCAGACCACATCTTAGACCAGTCATACAG
AATCTCTTGGGCTGGGATCCTCCACGGTACATTTTAAGGGTCCCCAGGTG
AGTTCCACCATGGACCCAGAATTGAGGACCCAATACCGTATACCATCTCC
TTCTTCATCTCTTCTAAGGCATCTCTTACTCGCTGTGCACTCCCATACCA
CTTTGTTCAATCATCCAATCATTCATTCATTGAGTCAGTTAGTCAGGAGC
TACTCACTAGTCCCCTGCCAGGTCCTAGTCATGACATAGGGCTCTGGGGA
CCAACAAGAAGCAGGACCCATGCCTCCTGCTCTCATGGAGCTTGCTCTGC
AGCAGAGGAAGCAGTCAGTGAGATGTAGCAAATGTGAAATGTGCACAGAT
GGGAAAAGCAAAACTTTAAAACTTTTAGGACAAAATACACAAGAAATCTT
TGCAACTTTGGGACAGGAAGGAACAACATTCCTTACACATGACACCAAAG
GAATCAACCATAAATAAAAAGGTGATCAATTTGACCTCATTTAAGTGTTA
AGCTTTTTTCATTGAGAGACACCATTAAAAATTAAAAATACATGCCACAA
ACTGGGATACAATATTTACAACACTTATGTCTCACAAAGGATTAGTTTTC
AGAATATATAAAGAACTCCCGGCCGGGTATGGCCGCGCACGCTGGAATCT
CAGCACTTTGGGAGGCCAGCGGATCACATGAGGTCAGGAGTTCAAGACCA
GCCTGGCCAACATGGCAAAACTCCGTCTCTACTAAAAATACAAAAATTAG
CCAGGCATGGTGGCGGGCGCCTGTAATCCCAGCTACTCAGGAAACTGAGG
CAGGAGAATCACTTGAGCCCAGAAAACAGAAGTTGCAGTGAGCTGAGCTC
ACATCACTGTAAGCCTCGGTGACAGAGTAAGACTGTCAAAAAAACGAAAA
CAAAAACAAAAACTCCTACAAATAAATAAGAAAAAAATAGCCCAGCAGGA
AAAAGTATATACATTTCATAAAAGAATAAATACATTCTGTCAGTTTTCTA

FIG. 3W

ACATATATTTTTTAAGAGTAAATACAAATGGTTAGGAAACATTTTTTAAA
ATGCCCAACCTCATTAAAAATTATAGAAGTGAAAATTAAGCCACAATAAG
ATACGATTTTATACCAAATACAGTGTCAACACTTTGCAAGTCTGACCTCA
CCAAGTGTTACCAGACGTGTGCACTGACGTGGCTGCTGAGATACTGATGG
TGGGTGTGTAAATCTGTACTACAAACAATTGCAATAAAATGTAATAAATA
TACAATAGGTGGAGCAGGAAGTGACCTGCAACCATATAGCAGATAGGGCA
GGAAAAAGCCTATGAAAGCTGACATCAAAGGGATAAGTTCCAGTTACCCA
GCTGAAGGGAAGGAGGGTGTTTCAGATAGAGGAAGGATAAGCATGACCTA
TTCAAGGCCAGTGAAAGAAGCGTGCAACGGCCAAGTCAGGAGAACCTGAA
ATTGTGTCAAAGAGCTTGGATGCAAAGAGCCGTGGGAGACTATTGGGGGT
TTTAAGCAGGGATATAATATTCATTCAAGCATGCAGTAAAAGGTCACTGG
CACCTGCCATGGGCCAGGACTCGGGCTCTACATGATTGCGTCTGTTTTGG
AAATATCACCCTGGCTGTGAGATGAAGAACAGGTAGGAGGGTCACAAAAC
TTGAAGCAGAGAGACTGTTGAGGAAGTAAGCTGTTTTTGTGTGGACTGTG
GCAATCACAGAGGCAGAGGATATAAATGCACAGAGACACAAGGCATGTGG
GAGGCAGAAGGAATCAAATACAATGAGTGATCAGATGTGGGGTTAGAGTG
GTGAGTGAGAAGACATACTCAAGGTGACACGCCCAGGTATCTGGGTGGAT
GGTAAGACATTCATGGACTAGGATCGAGGAANGAGGTGGGGAATGGGACC
ATACCTGCAGTTTATAAGGGGTGGACGAGGGAAGATTATGCGGGAGACTG
AGAGAGGAATAGACAAAGGAATCCCGGTGCAGTATTACAGAAACTGGGGT
GGGAGGGGGTTGTANTTCAAAAAGGAAAGAAAATTGTCAAATAGTATGAA
ATGCTGCAGAGAAACTCACGGATTTTTTTTTTAAGCTTAGAATTATTCAT
TGACTATGTGAATAAGAATAACTTTTATGAAAGAAGTTTTGCTTAAGTAG
TAGGAAGAAGCAAAATTGTTGAGGGCTGATGAGTGGGAGGAGAAGTAATT
GAAGGCACTCTTTCAAGAGAAACAAAGCAGAAGGTGAGGAGAATACTAAT
GAAGGAGTTACGGCCTTCACTATTTTGTTTTGCTTTAGATAAGCAAGACT
TGAGTGGGTCTGGTGAGGAGAAACAAGTAGAGTACAAAGTTAAAGGAGAG
ACAGACAGAGATAGAGATAGGGACAGAGAGAGAGACAGAGACAGAGCACA
AAAGAGCAAGGTCCCTGAGAACACGGGCCTTCTGTTTAAACCCCAGCCAG
ATGTATTGCAATTCAATTCCAGTACTAACCACCCAGAGTTTGTGTAGACT
CTACAAGTTAAAGAGCATGGTCCCCAACAAGACTGCTTCTACGTCAGATG
CCAGGCACACTTCAGGGGTCCCCAAGCCACTCATGTTTTTGAATGACTG
CCATAAGTTCAAAAATTCCCACAATTCTCTCAGATTCAATAACTGGGTAT
AACCACTCATAGAACTCAAGAAAATGCTATCATTATTATTACAATTTTAT
TATAAAGGATACAAATCAGAAGGACTAGCCAAATGAGGAGACACATAGAG
AGAGGACTAGTAAAAAACAGAGCTTCTGCGTCCTACCTTCAAGGAATCAG
GATGCACCACCCTCCCAGCACATCAAGTGCTCATCAACCAGGAAGTTCCT
CTGAGCTCCAATGTCCAGAGATTTTAGGGAGGATTCATTACATAGGTATC
ATTGATTAAATCATTGGCCATGTACTTGAACTCAATCTCCAGTGTCCCTC
TTCTCCCTAGAGGTCTGAAGGGTTGGCTAATATCATGTGGCTCAAAGCCC
CAACTCTAATTACCTTTTTGGTCTTTTCAGGGACTAGACCCCATCCTGAA
GCTATCTACAGGCCCTGCCATGAGTTAGCTCATTAACATAACAAAGACAC
TTATATTACTCAGAAAATTCCAACAGTTTTAGAAGCTCCATGTCAGGAAC
CTGGGACATAGATCAAATTCTTTTTTTTTTTTTTTTTTGGAGACAGGGT
CTTGCTGTGTTGCCCAGGCTAGAGTGCAACGACAGATCACAGCTCAATGC
AGCTTCAACTTCCCAGGCTTAAGTGACCTTTCCACCTTAACCTTCCAAGT
ATCTGGGACCACAGAAAATGGCTAATTATCCTGGCTGATTTTTAAACTTT
TTTTTTTTGTAGGGATGGATCGCCCTGTGTTGCCAAGGTTGGTCTCAAA
CTCCTGGGTTCAAGCAATCATTCTGCCCTGGCCTCTGTGATGGTTAATAC
TGAGTGTCAACTTGATTGGATTGAAGGATACAAAGTATTATTTTTGGGTG
TGTCTGTGAGGGTGTTGCCAAAGGAGATTACATTTGAGTCAGTGGACTGG
GAAAGTCCACCCTTTCCCAGTGGACTGGGAGACCCACCCTCAATCCAGGT
AAACACAATCTAATCAGCTGCCAGTGTGGTCAGAATAAAAGGAGGCAGAA
GAACAGGGAAACACTAGACTGGCTTAGTCTTCCAGCCTACATCTTTCTCT
CATGCTGAATGCTTCCTACCCTCGAACATCAGCCTCCAAGTTCTTCAGTT
TTTGGACTCTTGGACCTTCAACCACAGATTGAAGACTGCAGTGTTGGCTT
CCCTGTTTTTGAGGTTTTGGGACTCAGACTGGCTTCCTTGCTCCTCAGCT
TGCAGATGGCCAATTGTGGGACTTTAACTTGTGATCATGTGAGTCAATAT
TCCTTAATAAACTCAGATATATATATATATGTATCAGACATATATATATATC
CTATTGTATATTATATACAGATATATAATATCCTATTATATACAGATATA

FIG. 3X

TAATATCCTATTATATACAGGTATATATATATATATGTATCATATATATA
TATCCTATTGGTTCTATCCCTCTTGAGAATCCTGACTAATACAGCCTCCC
AAAATGCTGAGATTACAGGAGTGAGCCACAGCCACCATGCCCAGCCCCAA
ATTCTTAATTATACAACAATGGGTCCAGAGATCAGGGCCTGGGTAGGATG
CAGCAATAAGAAAACAGATGGTGGATGGGGACACATGTTGGAAGTGTGGC
AGGACATGGCTGAGGGAACTCATAGGATGGTGTCTATTTTCATGGCTGAG
TGTGAGGAACAGCATAAGGTCAAAATTTCAGGTCAATGGTGAGTTTTTA
AATTGTTGCTGTGAACCCCAAAAATCTGACCCAGGTCTCAGTTAATTTAG
AAAGTCTATTTTTCCAAGGTTGAGAACACCCACCCACTCACGACAAGAGC
ATCAGGAGGTCCTGACCACATGTGCCCAAGGTGGTAAGAGCACAGCTTGG
TTTTATATATTTTAGGGAGACGTAAGTCATCAATCAATATATGTAAGATG
TACACTGGTTCTGCCTAGAAAGGCAGGACAACTTGAAGCAGGGAGGGGGC
TTCCATGTCACAGGTAGGTGAGAGACAAACAGTTGCATTCTTTGAGTTTC
TGATTATCCTTTCCAAAGGAGGCAATCAGATGTGCAATTATCTCAGTGAG
CAGAGGGATGACTTTGAATAGAAAGACAGGCAGGTTTGCCCTAAGAAGTT
CCCAGCTTGACTTTTTCCTTTAGCTTTGTGATTTGGAGGCGCCAAGATTT
ATTTTCCTTTCACATTTCCCCCCCTTTCTTTTTAAGAATCTTTTAAAGAA
AGCTTTTAAAAAGAAAATGAGTCTCTGGTCCCAGGTTTCATCTGAATTCT
CGAGGGGAGGATGGTTTATCCTAAACGGGTGGTTCTGAATTTTGAGAAAG
TGCATTGTAC
>Contig32
AAAAGCCATACGAATGAGGAAGAATTAAGGGCCAGAACAAAACAAGAAGA
TGAGGGAAAGTTTGGAACTTCTTAGAGACTGGCTAAATGGTTGTGACCAA
AATGCTGATAGTGATACGGACAATGAAGTCCAGGGTGACAAAGTCTCAGA
TGGAAATGGGGAATTTGTTGGGAACTGGGCAAAGGTCACCCTTGCTATGA
CTCAGCAAAGAAATTGGGTGCATTGTGTTCATGTCCTGGGGATCTGTGGA
AGTTTGAATGTAAGAGTGATGACTTACGGTAGGGTATCTAGTGGAAGAAA
CCTCTAAGCAACAAAGTGTGTTGCTTAGAAATTTCTTTCTTTCTTTTTTT
TTTTTTTTTGAGCTGGAGTTTTGCTGTGTCGCCCAGGCTGGAGCGCAGTG
GCGCAATCTTGGCTCACTTCAAGCTCTGTCTCCTGGGTTCATGCCATTCT
CCTGCCTCAGCCTCCCAAGTAGCTGGGACTACAGGCGCCTGCCACCATAC
CTGGCTAATTTTTTAGTATTTTAGTAGAGACGAGGTTTCACCATGTTAGC
CAAGATGGTCTCAATCTTCTGACCTCGTGATCCACCCGCCTTGGCCTCCC
AAAATGCTGGGGTTACAAGCATGAGCCACCCCGCCTGGCCTGCTTAGAAA
TTTCTAAGCCAGGATATGGCCTGTCTGCTTCTAACAGCCTGTGCTCAGGG
GTAAAGAAATGACTTAAAGTTGGAACCTATGTTTAAAATGGAAGTAGAGT
CTAAAAATTTGGAAAATTTGCAGCCTGGCCTTGTGGCAGAGAAAGAATCC
AAGTAGGCTGCAGAGCAATCATTGCTAGAGAGATTAGCATGACTAAAAGG
GAGCCAAGTGCTAATATTCAAGACAATGTTAAAAAGGCCTTGAGGGCATT
TCAGAGATCTATGAAGCAGCCCCTCCCATCACAGGTGCAGAGGTTTGGTG
CACTAGGCCCAGAGGTTTTATGGGCCANNGCCAGGGCCACACTGCTATGC
ACAGCTTTGGGACACTGCTGCCCGCATCCAGGCCACTCTGCTCTGGCTCC
ACCCTTGGCTCAAACGGGCCAAGATAGAGCTTGGACCACTGCTCCCGAGG
GCACAAGCCATAAGCCTTGGTGGTTTCCATGTGGTGTTAAGCCTGCAGGT
GCCCAGAATGCAAGATTGAGGGAGCTTGGGCACTTCCACCTAAATTTCAG
AGGATGTGTCAGAAACCCTAGGTTCCCAGGCAGAAGCATGATACAGGGGC
AGAGCCCTTGCAGAGAACCTCTACTAGGGCAATGCCAAAGGAAAATGTGG
GGTTGGAGTCCTCACACATGGTCCCCACTGGGGCACTACCTGGTGATACT
GTGGGAATGGGGCTGCTGCCCTCCAGACCCCAGAATGGTAGATGCACTGG
CAGCTGGCACCCTGAGCCTGGAAAAGCTGCAGGCACTCAACTCCAACCCA
TGAGATCAGCCACATGGGCTACTCCCAGGGAAGCCCACAGAGGCAGGGCT
GTCTAAGGCCTTGGGAGCCTACCCCTTGAACCAGCTTGCAGGACATGGAA
TCAAAGATTATGTTGCAGCTTTAAGGCTTAATGTTTTCCCTGTCAATTTC
AGGCTTGTGTGGGACCTGTTGCTTTTTTTTTTTTTTTTTTTTTTTTTGGT
CACAGGTGTTTGAACCAGAACAATTCCATCTTGAATAGGGGCTGGGTAAA
ATAAGGCTGAGACCTACTGAGCTGCATTCCTAGGAGGTTAGGAATTCTAA
GTCACAGGAGGAGATAGGAGGTCGGCACAAGATACAGGTAGCGAAGACCT
CGCTGATAAAATAAGTTGCAGTAAAGAAGCCAGCCAAAACTCACAAAGCC
AAAATGGTGATATGGTTTGGCTCTATGTCCCCACCCAAATCTCATCTCAA
ATTATAATTCCCATAATCCCCACATGTTGAGGGGAGGACCTGGTTGGAGG

FIG. 3Y

TGATTGGATTATGGAGGCAATTTCCCCCATGCTGTTCTGGTGATACTGAG
TGAGTTCTCATAAGATCTAATGGTTTTATAAGTGTTTGGAAGTTCCTCCT
ACACACATGCTCACACTCTCTCCTGCAGCTTTATGAAGAAGGTACTTGCT
TTCCTTTCTGCCATGATTGTAAGTTTCCTGAGGCTTCCCAGCTATGCAGA
ACTGTGAGTCAATTAAACCCGTTTTCTTTATACATTACCAGTCTTGGGCA
GTTCTTTACAGCAGTGTGAGAACTGCTGGCGATGAGAGTGACCTCTGGTT
GTCCTCACTGCTCATTATATGCTAATTATAATGTATTAGCATGCCAAAAG
ACACTCCCACCATGACCCCAACAGTCATGCCTGTGCCGGTCTCAGCACCA
TGACAGTTTACAGATGGCATAGCAACGTCTAAAAGGTACCCCATATGGAC
TAACAAGGGGAGGAACCCTCAGCTCTGGGAAGTGCCTACCTCGTTCCCAG
AAAGCTTGTGAATAATCCACTGCTTGTTTAACATATAATTAAGAAATAAC
TATTAAGCATCCTTAGTTCAGCAGCCCAAGCTGCTGTTCTGCCTATGGAG
TAGCCATTCTTTATTCCGTTACTTTCTTAATAAAATTGCTTTTACTTTAC
TGTATGTACTCGCCTGGAATTCTTTCTTGTACGAGGTCCAGAGCCCTCTC
TTGGGTCTGGATCGGGACCCCTTTCTGGTAACATTTTGACCAATTTCTCC
CTTCTGGAATGGGAATGTTTACACAATGACTGTATCACTTTTGAATCTTG
GAAGTAAATAATTTGTTTTTGACTTTACAGCCTCATAGGTGGAAGGAACT
TGACTTGAATTTCAGATGAGACTTTGGACTTTGGGACTTTTGGGTTGGGG
CTGGAATGAGTTAAAAGTTGGGGGGATTATTGGGAAGGCACGATTTTATT
TTGCAATATGAGAAGCACATGAGATTTGGGGGACCAAGGGTGGAATAATA
TGGTTTGGATGTTTGCCCCCTCCAAATCTCACATTGAAATGTAATCCCCA
GTGTTGAAGTGAGGCCTGCTGGAAAATGTTTGGATTACAAGGCTGTCGAG
CACATTGGATAAGACGTGTAGGNCCC
>Contig33
CGCAGCTCGCTGGTTAATTCTGTGGCTCCTGTGACCACTATTATAGCACC
AGGTCTATGACCAGGAGAATTAGACTGGCATTAAATCAGAATAAGAGATT
TTGCACCTGCAATAGACCTTATGACACCTAACCAACCCCATTATTTACAA
TTAAACAGGAACAGAGGGAATACTTTATCCAACTCACACAAGCTGCTTTC
CTCCCAGATCCATGCTTTTTTGCGTTTATTATTTTTTAGAGATGGGGGCT
TCACTATGTTGCCCACACTGGACTAAAACTCTGGGCCTCAAGTGATTGTC
CTGCCTCAGCCTCCTGAATAGCTGGGACTACAGGGGCATGCCATCACACC
TAGTTCATTTCCTCTATTTAAAATATACATGGCTTAAACTCCAACTGGGA
ACCCAAAACATTCATTTGCTAAGAGTCTGGTGTTCTACCACCTGAACTAG
GCTGGCCACAGGAATTATAAAAGCTGAGAAATTCTTTAATAATAGTAACC
AGGCAACACCATTGAAGGCTCATATGTAAAAATCCATGCCTTCCTTTCTC
CCAATCTCCATTCCCAAACTTAGCCACTGGCTTCTGGCTGAGGCCTTACG
CATACCTCCCGGGGCTTGCACACACCTTCTTCTACAGAAGACACACCTTG
GGCATATCCTACAGAAGACCAGGCTTCTCTCTGGTCCTTGGTAGAGGGCT
ACTTTACTGTAACAGGGCCAGGGTGGAGAATTCTCTCCTGAAGCTCCATC
CCCTCTATAGGAAATGTGTTGACAATATTCAGAAGAGTAGGAGGATCAAG
ACTTCTTTGTGCTCAAATACCACTGTTCTCTTCTCTACCCTGCCCTAACC
AGGAGCTTGTCACCCCAAACTCTGAGGTGATTTATGCCTTAATCAAGCAA
ACTTCCCTCTTCAGAAAAGATGGCTCATTTTCCCTCAAAAGTTGCCAGGA
GCTGCCAAGTATTCTGCCAATTCACCCTGGAGCACAATCAACAAATTCAG
CCAGAACACAACTACAGCTACTATTAGAACTATTATTATTAATAAATTCC
TCTCCAAATCTAGCCCCTTGACTTCGGATTTCACGATTTCTCCCTTCCTC
CTAGAAACTTGATAAGTTTCCCGCGCTTCCCTTTTTCTAAGACTACATGT
TTGTCATCTTATAAAGCAAAGGGGTGAATAAATGAACCAAATCAATAACT
TCTGGAATATCTGCAAACAACAATAATATCAGCTATGCCATCTTTCACTA
TTTTAGCCAGTATCGAGTTGAATGAACATAGAAAAATACAAAACTGAATT
CTTCCCTGTAAATTCCCCGTTTTGACGACGCACTTGTAGCCACGTAGCCA
CGCCTACTTAAGACAATTACAAAAGGCGAAGAAGACTGACTCAGGCTTAA
GCTGCCAGCCAGAGAGGGAGTCATTTCATTGGCGTTTGAGTCAGCAAAGG
TATTGTCCTCACATCTCTGGCTATTAAAGTATTTTCTGTTGTTGTTTTTC
TCTTTGGCTGTTTTCTCTCACATTGCCTTCTCTAAAGCTACAGCCTCTCC
TTTCTTTTCTTGTCCCTCCCTGGTTTGGTATGTGACCTAGAATTACAGTC
AGATTTCAGAAAATGATTCTCTCATTTTGCTGATAAGGACTGATTCGTTT
TACTGAGGGACGGCAGAACTAGTTTCCTATGAGGGCATGGGTGAATACAA
CTGAGGCTTCTCATGGGAGGGAATCTCTACTATCCAAAATTATTAGGAGA
AAATTGAAAATTTCCAACTCTGTCTCTCTCTTACCTCTGTGTAAGGCAAA

FIG. 3Z

TACCTTATTCTTGTGGTGTTTTTGTAACCTCTTCAAACTTTCATTGATTG
AATGCCTGTTCTGGCAATACATTAGGTTGGGCACATAAGGAATACCAACA
TAAATAAAACATTCTAAAAGAAGTTTACGATCTAATAAAGGAGACAGGTA
CATAGCAAACTAATTCAAAGGAGCTAGAAGATGGAGAAAATGCTGAATGT
GGACTAAGTCATTCAACAAAGTTTTCAGGAAGCACAAAGAGGAGGGGCTC
CCCTCACAGATATCTGGATTAGAGGCTGGCTGAGCTGATGGTGGCTGGTG
TTCTCTGTTGCAAAAGTCAAGATGGCCAAAGTTCCAGACATGTTTGAAGA
CCTGAAGAACTGTTACAGGTAAGGAATAAGATTTATCTCTTGTGATTTAA
TGAGGGTTTCAAGGCTCACCAAAATCCAGCTAGGCATAACAGTGGCCAGC
ATGGGGGCAGGCCGGCAGAGGTTGTAAAGATGTGTACTAGTCCTGAAGTC
AGAGCAGGTTCAGAGAAGACCCAGAAAAACTAAGCATTCAGCATGTTAAA
CTGAGATTACATTGGCAGGGAGACCGCCATTTTAGAAAAATTATTTTTGA
GGTCTGCTGAGCCCTACATGAATATCAGCATCAACTTAGACACAGCCTCT
GTTGAGATCACATGCCCTGATATAAGAATGGGTTTTACTGGTCCATTCTC
AGGAAAACTTGATCTCATTCAGGAACAGGAAATGGCTCCACAGCAAGCTG
GGCATGTGAACTCACATATGCAGGCAAATCTCACTCAGATGTAGAAGAAA
GGTAAATGAACACAAAGATAAAATTACGGAACATATTAAACTAACATGAT
GTTTCCATTATCTGTAGTAAATACTAACACAAACTAGGCTGTCAAAATTT
TGCCTGGATATTTTACTAAGTATAAATTATGAAATCTGTTTTAGTGAATA
CATGAAAGTAATGTGTAACATATAATCTATTTGGTTAAAATAAAAAGGAA
GTGCTTCAAAACCTTTCTTTTCTCTAAAGGAGCTTAACATTCTTCCCTGA
ACTTCAATTAAAGCTCTTCAATTTGTTAGCCAAGTCCAATTTTTACAGAT
AAAGCACAGGTAAAGCTCAAAGCCTGTCTTGATGACTACTAATTCCAGAT
TAGTAAGATATGAATTACTCTACCTATGTGTATGTGTAGAAGTCCTTAAA
TTTCAAAGATGACAGTAATGGCCATGTGTATGTGTGTGACCCACAACTAT
CATGGTCATTAAAGTACATTGGCCAGAGACCACACTGAAATAACAACAAT
TACATTCTCATCATCTTATTTTGACAGTGAAAATGAAGAAGACAGTTCCT
CCATTGATCATCTGTCTCTGAATCAGGTAAGCAAATGACTGTAATTCTCA
TGGGACTGCTATTCTTACACAGTGGTTTCTTCATCCAAAGAGAACAGCAA
TGACTTGAATCTTAAATACTTTTGTTTTACCCTCACTAGAGGTCCAGAGA
CCTGTCTTTCATTATAAGTGAGACCAGCTGCCTCTCTAAACTAATAGTTG
ATGTGCATTGGCTTCTCCCAGAACAGAGCAGAACTATCCCAAATCCCTGA
GAACTGGAGTCTCCTGGGGCAGGCTTCATCAGGATGTTAGTTATGCCATC
CTGAGAAAGGCCCCGCAGGCCGCTTCACCAGGTGTCTGTCTCCTAATGTG
ATGTGTTGTGGTTGTCTTCTCTGACACCAGCATCAGAGGTTAGAGAAAGT
CTCCAAACATGAAGCTGAGAGAGAGGAAGCAAGCCAGTTGAAAGTGAGAA
GTCTACAGCCACTCATCAATCTGTGTTATTGTGTTTGGAGACCACAAATA
GACACTATAAGTACTGCCTAGTATGTCTTCAGTACTGGCTTTAAAAGCTG
TCCCCAAAGGAGTATTTCTAAAATATTTTGAGCATTGTTAAGCAGATTTT
TAACCTCCTGAGAGGGAACTAATTGGAAAGCTACCACTCACTACAATCAT
TGTTAACCTATTTAGTTACAACATCTCATTTTTGAGCATGCAAATAAATG
AAAAATCTTCCTAAAAAAATCATCTTTTTATCCTGGAAGGAGGAAGGAAG
GTGAGACAAAAGGGAGAGAGGGAGGGAAGCCTAATGAAACACCAGTTACC
TAAGACCAGAATGGAGATCTTCCTCACTACCTCTGTTGAATACAGCACCT
ACTGAAAGAACTTTCATTCCCTGACCATGAACAGCCTCTCAGCTTCTGTT
TTCCTTCCTCACAGAAATCCTTCTATCATGTAAGNTATGGCCCACTCCAT
GAAGGCTGCATGGATCAATCTGTGTCTCTGAGTATCTCTGAAACCTCTAA
AACATCCAAGCTTACCTTCAAGGAGAGCATGGTGGTAGTAGCAACCAACG
GGAAGGTTCTGAAGAAGAGACGGTTGAGTTTAAGCCAATCCATCACTGAT
GATGACCTGGAGGCCATCGCCAATGACTCAGAGGAAGGTAAGGGGTCAAG
CACAATAATATCTTTCTTTTACAGTTTTAAGCAAGTAGGGACAGTAGAAT
TTAGGGGAAAATTAAACGTGGAGTCAGAATAACAAGAAGACAACCAAGCA
TTAGTCTGGTAACTATACAGAGGAAAATTAATTTTTATCCTTCTCCAGGA
GGGAGAAATGAGCAGTGGCCTGAATCGAGAATACTTGCTCACAGCCATTA
TTTCTTAGCCATATTGTAAAGGTCGTGTGACTTTTAGCCTTTCAGGAGAA
AGCAGTAATAAGACCACTTACGAGCTATGTTCCTCTCATACTAACTATGC
CTCCTTGGTCATGTTACATAATCTTTTCGTGATTCAGTTTCCTCTACTGT
AAAATGGAGATAATCAGAATCCCCCACTCATTGGATTGTTGTAAAGATTA
AGAGTCTCAGGCTTTACAGACTGAGCTAGCTGGGCCCTCCTGACTGTTAT
AAAGATTAAATGAGTCAACATCCCCTAACTTCTGGACTAGAATAATGTCT

FIG. 3A'

GGTACAAAGTAAGCACCCAATAAATGTTAGCTATTACTATCATTATTATT
ATTATTTTATTTTTTTTTTTGAGATGGAGTCTCACTCTGTTGCCCAGGC
TGGAGTGCAGTGGCGCAATCTTGGCTCACTGCAAGCTCTGCCTCCTGGGT
TCACGCCATTTTCCTGCCTCAGCCTCCCGAGTAGCTGGGACAACAGGCAT
GTGCCACCATGCCCAGCTAATTTTTTGTATTTTTAGTAGAGATGGGGTT
TCACTGTGTTAGCCAGGATGGTCTCTATTTCCTGATCTCATGATCCGCCT
GCCTTGGCCTCCCAAAGTGCTGGGATTACAGGCGTGAGCCACCGCGCCCG
GCCTATTATTATTATTATTACTACTACTACTACCTATATGAATACTACCA
GCAATACTAATTTATTAATGACTGGATTATGTCTAAACCTCACAAGAATC
CTACCTTCTCATTTTACATAAAAGGAAACTAAGCTCATTGAGATAGGTAA
ACTGCCCAATGGCATACATCTGTAAGTGGGAGAGCCTCAAATCTAATTCA
GTTCTACCTGAGTAAAAAAATCATGGTTTCTCCTCCATCCCTTTACTGTA
CAAGCCTCCACATGAACTATAAACCCAATATTCCTGTTTTTAAGATAATA
CCTAAGCAATAACGCATGTTCACCTAGAAGGTTTTAAAATGTAACACAAT
ATAAGAAAATAAAAATCACTCATATCGTCAGTGAGAGTTTACTACTGCCA
GCACTATGGTATGTTTCCTTAAAATCTTTGCTATACACATACCTACATGT
GAACAAATATGTCTAACATCAAGACCACACTATTTACAACTTTATATCCA
GCTTTTCTGACTTAGCAATGTATTGATGACATTATGCATGCTTAGACCTC
C
>Contig34
GTATTCTATTCTCGGTTATAACACAATCACAGTGATTTGTCATATCTTTC
CAGGATTTGTTAATTTCACTTCTTCAGCTGTTTCCCCCTTGTTGGCTGGA
ACTGATTTTCTATCTTCTGGGAGAATCTTCAGCAAGCCAACTCAGGATTT
GTTGGGTGCATTTTGTCAAGTCTAGGACCCAGGCTCTGGGTGACTGATTT
CCTCTAATTACCGAGCAATGTAAAATGAGGAAGTCTGATTGTGTAAAGGT
GTTAAACTTTTGTGTGACGGCAAAACTTTAATACCATGAATAGAGATTCC
AGAATTTTCCAACTTCTAACGGGATTCCTTTCACTCCCTGACATTAGAAT
GTTAGAAAATCTACCACAAAACATCTGTGAGGCTATCCTACAAGGCCCGT
TTTTCAAAATAGGTTTTTACAAGGATTGCTATTTGGGATGATAGTTTCAG
AAAGGCGCTATCAAAGTTAATTGATGATGTGTGCAAGCTGAAAGTTATAT
GTTAGAACTAGCAGTGATTTCAAAAATATCCCTTTTAGGCTTTTTGCTAA
TATATCTGCTCATTTTCAAAGTTCCCAATATTATAAAACTTTTTAAAGCA
GAAAGAAGAACCCTCCATTTCTGCTGGCCCCTTCCCTGTTCAACTAAAAA
GTATTTTCCCAGGCAATGCTATCCCAGGACTCACACTCCATCCATCCATC
ACCTACCATAAGTTCTTTGAAGGGCTCATTCTGAGCGCTTCCTGAGTGCC
TGGGATCTGTTATTTCTCTCCATTTCTGCTGCTGCATGGTAGTCCAAGTC
CTCCTCCCTTTTCCCCTAGGCCATTTGAATCATCTGCTAATTGGTTTTCC
TGATTGCCACGGAAACTTCCTCCATCCCTTCCTCACATATCAGCCACAGA
AGTATCTCCAAAAAGCAAATCTGGTGACATGAAGCCCTTGCACAAAACCC
ATTCATTACTGGTTCCACACCTCCTTTGTGGATAAGTTCAAGCTCCTGAG
TGTGGCAAGCAGGGCCCACCTGGAATCCCCTGCCCTCCTCTCCTATCCCA
CGCATCAATCTTTCCTGTCTATTTGCAGTTCCTTGAATGTGATATTCTTT
CTAGTCTCTGTGCTTTTGCATAACCTGTTCTTCCTGACTGGAAACTCCTT
CTCCTCCTTGTAGTTTGGCTAATTTCTAGTCTTTCAAGACTCAGCTCATG
CTTCACCCCCTCTATAACAAGTCCTTTCCCAAGCTGGGTGGTGGATGCTC
CTCTGTGCTGTGTGAGTCTTGAACATCCTCAGCAAACCTCAGCTTTGTTT
GCTTGTCTCCCTTGCTGTCAATGCACCTGATTCAGGGCTGGCATATACTG
TTCACCTCCATGACTGGCTCATGGTGGTGCTCCGTGAATATCATCCACCC
AAACGGATGAGAGCTACCATGCCATCACTTGTGACTTCCATCTGGAGCTA
ACCTCCCCCGACAGGAAAGCGTTTCCTTAGGAAAGAATATCTTTGGGTTA
AATAGAAGTAGAGACTCACCAGAAGCACTATGTCCAGCTCAGAATGAACT
GCTCAGTAAGCAGCCTTGTCAATGAGGAGGCAGCAGGCCAGCCCCAGAGG
CCTCAAAGTGGGAGAGTAGAGAAGCGCAGTTCCTGCCACAAAGGCACAGT
GGACACCTTGCTCCCCTGGCTGGCTGGAAGCAGATGGTGTCCACCTGCTT
CCATGGGAATTCTGCACCTTTAATAAAGTTTTATGGGACAGGAAGGTGAC
TGGCATTGACATTGTAACGAGGAATGGGTGGTGCCACCTTTGCTGTGTCT
TACCAGAAATACCTGTGGCAGGTAAATTTCTAGAGAGACCCTCCCATTTC
TCCCATATAGCAATTTTGAAATGTTTCCTGAGGGCTTTCCAAATTCATCT
GGGAACATAGGAGTTCCAGAAAGATGAAATCAAAGGTGATGGTATGCCAA
AGAAAGTAGCTTTTAGAATGACTTACATTAGCCATTCATCCATTCAGCAC

FIG. 3B'

ACCAGGCATTCAGTTTGAGGGGTGTGTGTGTGTGTGCGCGCGCGCGTG
CGTGCATGAGTGCATGCGCGCGCGTGTACATAGGGGAAGGGAAACAAAAC
AAAAGTACACAAGACATGATAGTTGTCCTCAAGGAGTTTTTGCAAATGTT
CACAATTTAAGAGAATATGCTGTGCTGTGGCTGGTGTATAAACCAACTGC
TAGGGAGAGGCCTTCCACACACACTTGGGGCAAATGCGACCTCTAGGACT
GCCAGTGGAATCTGGGCATGCTGTTTGTGGTCGATAAACCCTGGTCCCTT
GATCAGGGACCTATGTTTACTTTTCCTCTCCCTGGAAGTCTTCATTAGTG
GGCATCCAGAAGGTCTTGCACAGGGCAGAGGGAGGCACAAAGACAAGAGT
TTGAAACCAGCCTGGACAACAAAATGAGTTTCTATCTTTACAAAAAAAAT
TTTTAAAAAATTAGCCAGGTAGGATTGCATGTGCCTGTAGTCCCAGCTAT
TCAGGAAGCTGAGGCAGGAGGATTCCCTGAGACCAGGAATTTTGAGGCTG
CAGTGAGCTATTAAGTTGGCGCAAAAGTAATCGTGGTTTTTATCATTAAA
AGTAATGGCAAAACTTTTAATGACAAAAACCGTGATTACTTTTGCACCAA
TTTAATATGATTGCACGACTGCACTGTGCTCCAGCCTGGGCAACAGAGTG
GGACCCTGTCACAAAATAATAAATAAATAAAATGTAAACATGTAAAAAAA
ACCCCAAAAACAAAAAAAATGGGTGTTGAGACCCCTGAATTGAGGAATAA
TAGGAAGGAGTGTGATTCTGTGTGTGCATGCATGGGTGTGCACCCCTCAGT
GCCTGGGTGGCTTACCCTGGGCTAGTTCAGGTGGCAAATGGTTTTCCTCC
AGCTGGGCTACCACCATCTTCCCCCAGGGCCTGTCCATGTATTTGGTGGC
AAGATACCTATGGACTAGAGTCCCTCCTCAGAGGAAAGGCTCCTCCCATT
TCTCTGGCTTTCAGGTAGTAGTCCATGACTTCAACAGGTCCCCACTGCAA
TGTTATGGGTTAGTTTAGGTGGGGTCTCCTCTGAGAGCCTCCCATAGCCC
AAAAGGCCCTGTCCTAGCTGGCACTGCATCTCCCTCTTCCCAGCTCTCAG
CCTTTCTCTTTGCTCATCCCACTCCGCACAGGCTTTCTGCCTGATCCTTG
GATGTGTCAATCCTGCCCCTAAGGGATGCAAGGCAATTTGTCCTTTTATT
ATTAAGATCTCTCCTGAGGCCACGTGTGGTGGCTCACACCTGTAGTCCTA
GAACTTTGGTAGGCCAAGGTAGGAGAATTGCTTGAGCTCAGGAGTTCCAG
GCTGTAGTGAACCATGATTGCACCATTGCATTCCAGCCTGTGTGACACAG
CGAGACCCTGTCTTTTTTCTTTTTTTTTTTGAGACAGGGTCTCGCTCTGT
CATCCAGGCTAGAGTGCAGCGGTGTTTTTCTGCTCACTGCAGCCTCAACC
TGCACATTTTTTGTAGAGACGGTGTCTTGCTATGTTGCCCAGAGTGGCCT
CAAACTCCTGGGCTCAAGAGATCTTTCCACCTCAGCCTTCCAAAGTGCTG
GGACTACAGGCGTGAGCTACCGCGCCCAACAAAGACCCTGTCTTAAAAAG
AAAACAAAAATAAACAACTCCCTCAAGTCTTTTTTTTTTTTTTGAGACGG
AGTCTCGCTCTGTCGCCCAGGCTGGAGGGCAGTGGCGCAATCTTGGCTCA
CTGCAAGCTCTGCCTCCCGGGTTCACGCCATTCTCTTGCCTCAGCCTCCC
GAGTAGCTGGGACTACAGGTGCCCGCCACCACGCCTGGCTAATATTTTGT
ATTTTTAGTAGAGATGGGGTTTCACTGCGTTAGCCAGGATGGTCTTGATC
TCCTCACCTTGTGATCCGCCCGCCTCGGCCTCCCAAAGTGCTGGGATTAC
AGGCATGAGCCACCGCGCCCAGCCAGACCTCTTGAGTCTTAAACTCCTCT
GTAGTTCCAGCCACCCTTTAGCACATGACTCTGTTAATTTTGTTCTCACT
GTCTGAAATCATCTCCTGTCCACTCTTGACTGACAGGTCTCTGCACTAGC
CCACTGCTTAATCAGAGTAGGTCCCTGTCAACTTATTCATATTGTGTCCC
CATGCCAGTGTGGATGATTAAAATTGTTGAGTGGAGGCTGATCAGATGAG
CCATCTCCTTCCAAGTCCTCACTTGCTGGCTCCTGTCTTAGTTTTAGTCC
CCATTCTTCAAAGAACGTGAGCCCTGGAAAGTATTTTAGTCATTTAGTTC
AGTGCCTTTGGATGGGAGGATCACATCCCTGGGTCCCGTCCTGCAGACTG
TTTTGCTCTAGCTGACTAGGCAGGATTCCCTGCCTTCTCTCACTTCGGCA
TGGGACTTCCTTCTGAAATTGCTGCTCAGTCAAGAGAATGACCTTCCCCA
ACATAATCCTACTCCACAGGGACTTAAAGGTGTGTCAGAGATCTCTTGCT
CATCTTTCTGGCCAGGTGCCAACGTCAGTTTATAGCCAAGGGACAAGACT
AGTTAGCAGATCAGGCAGGTCTTAGACCCCAGCGTAAGTGCCAGACTTCT
AGCTGCAGTTGTTCCTGCCCACACTGGGCGTTCAGGTGGAGAGAGGGCAT
GGCACTACACTGAGCTCTCGGCGAAACCCAGGACTCTGAAATCTCGGTGT
CAGCCACAGGCCACTCTTTTCAGCAGGACTTCAGTCAGTCCTGTCACTAG
GCTGTCGAGCACATGGTAGGCTTTACCCC
>Contig35
AAGGAGTGTGCTTGCTGATAGCATGTGTGANGGGACGAGGAGTAAATAAT
TTCTGCCTTCAAGAAATTGCAAACTAGTAATGGAGATAAAATCAACAGAG
GAACAATTAGAGTATAAGGTAAAATCTAAGGGCCATAAGAGAGGAGAAGA

FIG. 3C'

AGTATGGGAGTTCAGAGGTAGGGGGTAAATGAGGGGAGTAGGTGGGTAGA
AAAGGTTAAAAGTAAATAATGATGGGAAGGAAGACAAAAAGACGACAGGG
GTGCCAAAGGACTCTTAACCTCATCTGAACGGAGTTGCCCTGTTTTGCTC
TCTGATGCTCATGTATCTATCCTTAGAGACAGCTTGGCGGGCAATGTAGA
GCGTAGGGGCTGACATAGGGGGTTGGAGTCCCACCTCCGTGACTTCTAGC
AAATTAGCAAACTTTGCTGCTGCTAAGCCTATAAGGCGGACAGAAATGCC
ATCTTTAAAGCTTGTTATGTAAAGTGCCTAGGACCTCGTAGGCATCAACA
GGAATAATGGATGAAACAAAACAACGGTGCGTATCTTGGAGAAAGTGGCA
TCTGAGCAGGAGTATTTTGAAAGGTAGGAAAGGGCTCCAAGCACATCTAA
GAGATTAGGGAACGCAGAAGCCTTAGCCCTGGGTGCAGATTTAACCAATC
AACTTCTAACCACCGCAGGCTGAGAGGTGTGGAGTGAGAGCCCCGCCAGA
GGCAGGAGACCCGGGCTTCGGCCAGACCCCGCCTCCTGGTACAGAGGACC
ACGCCCGGCTCTGCCTGGAGCCAAATGTGGATCAAAACAGCGCGCAGCTT
CCCACTGCTGGTGAAAACCCGAGCAAGGGGCCTCAGTTTCTTTATCCGGA
ACGTGGTGACAATGACATCTCTTTGCAAGGCTGCTGCAGGGCTTTCTGGA
AATACGCCCGTGAGGTATCTGGGCCTGCGCACAGCCTCCCCCGCCCAGGA
CCCAGACGTCTACCTGGGGGTCCCGTCTGCGCTCCCGGGATGGAAAACGC
CCAGGGGAAACTTAGGCAGGCGAGCGGACGGGCACCTCCCGCGGGACGAA
CTCACTCGGTGGCCTCCTACTTCCCCGGCCGTGTTCCAACGCCTGAGAAT
AACGGGAACAGCGGTCGTACTCACCGACAGCGGCAGCAGCGGTAGGCCCG
GGCCCCACCATGACTCTTCAGTGACAGTTTTTCTTCAAACGCCGCGCCTG
TAGCCAGGACCGGCGTGCCGCGCGTCCACGCGTCCTCATTGGCTCCTGCG
GGTTTGAAACTCGCTAGTCGTCAGCACGGGAGGGCGGGACAACAGGCAAT
AGGCTCTTTGCGGTTGGCTCTGGCCTTGAGAACCCGACCTTGGGGCCCTT
TGATTGGAAGAACGTGCAGCGCACCTCGGCATTGAGGGCGGCTTCCTCGG
GGCGCGGCGCCGCCCGCCTCTGAGTGCGCCTGTGAGTGCGCCTCCGAGTG
GGCGTGGGACCCTCCGTGGGGGCCTCAGCCGGGCTGGTGGTTGGGGGGCG
GTTACGCTGAATCCAGCTGGGGTTGGCGCGCCGGGAGTCCCTGGGCGGAG
AGACAGGGCGGTCCTCCCAGGATGCTGGGGCCGCTACCTGATTCTGTCCT
TTCAAAGTCTCAGACTCACAGGAGCTGTGAAAAAATAATATTATAAAGAG
GACATATGGGTCTTATGCATCTAAAGGCTCCTAGTTCTTAGTACTGCAGG
GTGGCTCGTTTAATTGTGGTAAAATATGCATAACATCACATATACCATTT
TAACCATTTTAAAGTGTTAAATTTTTCAAAAATGTGCAGTTTAGTGGTAT
TAAGTACCCTCACATTGTGGCACAGCCACCACTACTGTCCTTTCCAGAAC
TTTTTCATCTTCCCAAATGAAACCCTGTACCCGTCACTAACTCCGCACTC
CTCCCTCCCCCAGCCCCAGGCAATCACCATTCTAGTTTCTGTCTCTATGG
ATTTGACAACTGTAGGTGCCATATAAGTAGAATCATGCAGTATTTGTTCT
GTGACTGGCTTGTTTCACTTAGCATAAAGTATTCAAGGTTCATCCATGTG
TAGCATGTGTCAGAATTTCCTTTCCTTTTAAGGGGGAATAGCATTTCGTT
GTGTGGAGATGCCACATTTTGCTTCTTGGTCCATCCCTCTCCGGACACTT
GAGTTGCTTCCACTTTTTGGCTATTGTGAATAATAATATGAACATGAATG
CACAAATAACTCTTTGAGACTCTCCTTTTCATTCTTTTGGGTATATACCA
CGAAGTGGTATTGTTGGATCAAACGGCAATTCTATTTTTAATTTTTTGAG
AAACTGCCTTACTCCTCTCACGGTGATCTCTTGTTCAAGGTATATTTTCG
ATTTCACCTGATCAGCTGACTATAAGGCCATAAGGCTAACGGAGAAACGC
AGGCCTAGTTTCTCCTAGTTACTAGGAGATCGCAGGCCTCGTTGTCCTGA
ATCCCTAGACACACTTCATTCCCCTTGTTTAATCCTAAATTTTTTTTCT
TTTGAAGTTTGTCCTGTTTCATCTATTCTCCAGTTTCTTAAAGAGGTCTG
GAAAATGCTTTTGGCTCCTTGTGTATGAAGGTTCCTCTTCCATGGATGCT
GGAGAAGTCGTGTGTGGAGGGGCAGTCATATCTGGGCACCTGTTGGCCAG
GTTCAGCTTACCAGTTGGGTACTCAGCAGGGCATGAAGCCACTGCAGCAG
CCCTTCTCTTTAGCCGTAAATAGGGAGTTTGGAAGAGAGCCAGGGTTTCT
GGATTTATGCATTTTGATATTTTCAATAGTGTATTAAATGTTTAAAATAG
GAAAACTGATCATTATTTTTGTTAATGACTGAGAAAGGGACTCCTTCACC
AACAGTTTCAGAAAAGTGAAGGCGGTTTTGTTTTGGTCTTTGTAGAATCT
AGGTGGTTGAATGCATGTCAGTTGTAGAAGTCACCTTGCCTGATATCCCA
CGCAGTGCTGGAGTATTCCACAGACCCCATGTAGGTACTGCACCTTTGCA
GGTATACTGCTGGTGTTGGTGAGCTGCCTTACCTGTCCTGTTATTGGAGA
CCCCTGCTTATTAGGAAACTTAAAATGAACTCAAATGAGCTTCCTTGCTT
ACTGGTCCTAGTCCTTTGGAGCAACATAGGCCAGTTCTGCCTCGTTTTTT

FIG. 3D'

TCCATCCTTTGGGTATTTGACGGTCTATTTTGTAGGACACAAAATGTGGG
AAAATAGCTAGGCAGGTTTAAAAATTCTCAACTCTACCAAGCATGGTGGC
TTATGTCTGTAATCAATCCCAGCACTTTGTGAAGCTGAGGCAAGAGGATT
GCTTGAGCCTAGGAGTTTGAGACCAGACTGGGCAACATAGCAAGACCTCG
TTTCTTAAAAAAAAAAAAAAAATTACAAAAATTAACCAGGCATGGTGGCA
CACACCTGTAGTCCCTTCTACTCAGGAGGCTGAGGTGGGAGGATCACTTG
AGCCCAAAAGTTGAAGGATGCAGTGCACTGTGGTCATGCCACCGCACTCC
AGCATGGGAGGCAGAGCAAGACCCTGTCTCCAAATAAATACATAAATTAA
ATTCTTAACTCATTCATCAAAGTATCCACTGTAGCTTTCCATCATCCTGG
TGTTGTTTTTTTTAGAAGGATCTGGCTCCATTGCCCGGCTAGAGTGCAGT
GGCATGATCTCAGCTCACTGCAGCCCCCACCTCTCTGGCTTAAGCGATCA
CCCACTTCAGTCACCCATCTGGGTAATTTTTGTATTTTTTGTAGAGATGG
GGTTTTGCCATGTTGCCCCAGGTTGGTCTTGAACTCCTGGCTCAAGCGAT
CCATCTGCCTCCATCTCCTAAAGTGTTGGGATTACAGGTGTGAGCCACCA
CACCAGGACAATCCTGGTGGCTTTTAACGGTTTTCCATTGCTCTCAGGCT
AATGACCTATAAGCCCCTGCGGGCTTGGCCTTTTACTCCCTCAGCATTAG
CCACCTCCCTTAGCCTTAGCCCACACTACTCTCCCCTTGCTCAGTGTTAT
CCAGACACTTTGTTTTTCCTTTCCATACTCCTCTCTGTCTGGGAATCCA
ACCTTTCTTTCTCATTTCTCTAGTTGATTATTATTATTTTTACTCTAGCA
GCCTTATTGAGATATTTACATACCGTACGATTCTCCCACTTACAGTGTAC
AATTCAATTTTCTAACATTTTCATCACCCCCTAAAGAAACCCTATACTCA
TTAGCAGTCACTCCCCATTCTCCCCTCCTCTCAGCCCCTAGAAACCATGA
ATCTACTATCCATCTCTATAGATTTGCCTTCTGGACATTTCATATGTATG
AAATTATGCAATTTGTGGTCTCTGATGGGCTTCTTTTGTTACCAAAATAT
CATGGGTTTGATCTAGGTCCTGCTGCTCGCTGCACAGAAAGCCAGCCACT
GAGATGACAAGTATTGCCAAGGAAGAAGGCTTTAGTCAGGTGCTGCAGCT
GAGGAGATGGGGGCTCAATCTCAAATCCATCTCGCTGACCTAAAACCAGG
GGTTTGGATAGCAGGGAAGAAATGTAACAATGCGTAAGAAAACAGGAACC
AGGGAGGGGCAAGGAAGCAATCCTGATGAATGAGTGGTCCAAAGTCTCAT
TGCCTGGATGTGGTGATCTGGCGAGTTTCAGTTCTTTGATACTTTTTTTG
AGAGGCCTGAAGTCTTTTCCCCAGGAAGGAACTCAAACAAAACAAATACA
AGCTTCCAGCTTTAAGACCAGAAGCGTCAATTTCTATGTTTATCCGAAAG
AACAGTCTATGGGACTATTGGTTAAGTTTCACTTTCACTTAGTATGCTGT
TTTCAAGGTTTATCCACATAGCATGTGTCAGTACTTCATTCTTTTATGAC
TGGGTATTCTATTGTGCGGATATACAATATTTTATTTGCCATTCATCAGT
TGATGGACATCTAGGTTCTTTCCACTTTTTGGCTATTATGAATAATGCTG
TTATGAACTTTCATGTATAAGTTTTTGTGTAGACATATGTTTTCAACACT
CATGGGTATATACCTAATGAGAGGAATTACTGTGTCATACGATAATTCTA
TCTTTAACCATTTGAGGAACTGCCAGACTGTTTTCCAAAGCAGCTGCAGC
ATTTTACATTCCTACCAGCAGTGTATGAAAGTTCCAGTTTCTTTACATCC
TCAACAACACTTGTTATTGTCCATCTTTTAAATTACAACCATCCTAGTGG
TTGTGAAATGGTATCACATTGTGGTTTTTATTTGTATTTCCTTGATGACT
AATGATGTTAAGCATCTTTTTATGTGTTTACTGGCCATTTGTATATCTCT
ATTCAGAGTCTTTGCCAATTTTTAAATTGGGTCAGTTGTCTTCTTCCTTT
TTTTTTGAGATGGAGCCTCACTCTGTTTCCCAGCTGGAATACAGTGGTGT
GATCTCAGCTCACTGCAACTTCCACCTCCTGTGTTCAAGTGATTCTGGTG
CCTCAGCCTCCCAAGTAGCTGGGATTACACGCACCTGCCACCATTCCCAG
CTAATTTTTTTCTTTGTATTTTGAGTAGAGACGGGGTTTCACCATGTTGG
CCAGGCTAGTCTCTTTGTTGACTCTTAACCATCCTTCAGTCTCAGACAAA
ACATCCCTTTCTCAAGGATTGTGATTAGCTTGATTATTTGCTTATCTTTC
TCCCTGCTAGTCTGTAAACTGAGGGTAGGCCACTATATTCATTGTTCTTG
GCACCAAATAGAAACTAAATTAATGTCTTTTGAATGAATAGGGCTTTCTC
CTTTTAAAGATCCCTTCAATACAGTAACCACACTATATATAAGTAGCCAC
AAGCCCATTCAATAATACTACTAGTNCTTGCGCCAAACC
>Contig36
GGCTCAGCGTTACTATACTGGTCTCAAACTCCTGGGCTCAAGCGATCTGC
CCCCCTCGGCTTCCCAAAGTGTTGGGATTATAGGCGTGAGCCACGGTGCC
TGGCCTCAAATAACTATTTAAGTGAAACAAAACTAGTATGGCACTAATGA
AAAATGTATAAATCCATAATCGCAGAGGGATTTCAACTTACTTCTTTCGA
TTATGTAAAGGTCAAACAGACAAAAGACAATGACAAAACTTAATGCAATG

FIG. 3E'

AACACTTTTGATTTAATGAACATATATTGGATATGTACCCAAGAATTAGA
GAATACATACTAGTTTTGAGTTTATGCAGAACATTTACAAAAATTTAGTG
GAAGCCTAAATTATAAAAAGTTGCTGTCACGTAGAATAACACACAAACCC
CTGAGTCCGGAATTCAAAGCCCTCCACACTCTCCTCTACCTTTGCATCTT
TATCCTCCACCACACTGCAGTGCATACTCTGGGCTACTACTCACTGTTCT
TGATTCAAATTCCATGTTCTGTCAGCTCAAATCATTCTCTCTGCCTGGAA
TAACTACTTCATACATATTCTGCTATTGAATTCTTGTCTTAGCACCCCAT
CTACTCCAAGACGATGTCCAGTTGGGGTTACTCCCTGTCCCATTTTCTTT
GATTACACTTTTTTTTTCTACTTCCATTATATTATTGATCACATCTGTGC
CACAGTTTTTGACTTTGTGTCTGCTTTTACTCTTTTCTAGACCCTGATAG
CTCCTGAAGGGTTGGGTCATTTCTTTTTTATTTGCTCATTCCTCATGGCA
CAGTGAGTGCTTAATAAATGGCTATTGACTGAAATTAAACTGTATCTAAA
TGGACATATTCCACTTCTGGGCCATTCATTCTTTCTTTCTATTGGAACCA
GGAGATGGGGAACCATAACAAAGGTAAGGTTGTGCCATGTGAAAGAACAT
GGAACCTTCCCCTGAGGGCCAAAAAAGAGCAGGGAAAGGTGCAAAGACAA
AATCTTCCATTTTTAAACAATGTAAGAATGTGGTCCACCTCATGCTCAGG
TGGGACTTTATCATGACGTTATTTTTGGGGACTTATAGCTGCATCATTTA
CCCCATATACATTTACCTTTAGTGTAGGGAACTGAGGACAGGAATTTTGT
TGATGCAGACTCTTGCTAATGAGGCTAACACTTGGAGAATTTTTATCATG
CATTCAAGAAGCTTGTTTTACATTTCTTCATTAATACTTTAGTTGGTGGT
TTAGCTTTAGTTGTAGGCTTATCAGATATTTGGAGATATCTTCATAAACG
ATGGCTTTGGTTTTAGAAGAGTTATTCTGAAGCTACTATTTCTGGCAATA
ATCAAACAGCATGGCCATTTGTTTTGTAAGGCCTTTCCTAGAATATGACG
GTAAAATCTACGTGTGGAAAAATGCTTATTCTTCTGTCCTCTATAAATGT
GAATCTAGTTTGTCTTCAAAATGAAATCAAGTGATTAAAATGTAGTTTTC
TAAGAAGATAAATGGAGCAAAGCACTCTGTGTTTCACAGTGTTGGAAATC
ACTCATCCCTCATAAAACTGTCCCAACTGATCCTGACTCACATGAATGAA
TTAAAATAAGAGTTAATAACATCAATTTACATTTTTAAAGACACTTTCCC
ATGTTTTAGACTATTGGTTGGAAAAGCTGGTAGGTGTACAATTTGTGGAG
AGTTGGCTGTTTTTGTCTGTCGTTGTTTGACGTATTTCAAAGCCATATCT
AATTTTGTTGCAGAATGGTCTGAATTCTACAAAAATGTTGAGTTGTGTAG
TGTGGAGAAGTACGGAGCCATTTACTGAAAGGCTGGGGGAAATGACGAG
ACCCTGAGATAAGGCAGTAGTGGTGCGAACAGAGTGGAAGGGAGGTAGTT
GAGATATGTTCAGAGTAGAATCAGAATGGACATAGTGAACAACTGGATGC
AGGTGGGGGCTGAGGAAGCAAAGTTGAGGATAATTCTGAGACTTCTAGGT
TGATCCACTGAAGTTACATTATTCAACACCACAAGGAAACTAGGGGAATG
AGAAGGCATACTGGTTTGCTTTGGAGTGGAAGGGCAGTGATGTAAGAGGA
GTTAATGAGTTAAAGTTTGGATATGCCTGAACTTCAATTTGATATGTGCA
TCTGATATACCCTTGGGGTGACCCTCCAGGCAATGGTTGAACATGTGTAT
TTCTTAGTAACTGATAGGCATCACAGACTCACATCAGTAAGGAAGCAACA
GCAAACTTGATTGGACGATATACCTGGAACTCAGTACCCTATGACTGGAG
CAAGTCTCTGTCAGTGAAATGAGGATAAGAAGAATCTTGACCTTGTGGAA
TATGTTGTTAGGAATATATGTGATGAACAACATAGGATACTTCCTACAGG
GCTCCACATGTAGTAAGGGCTTTATAAATGCTTGATAAATATTATTGTTG
TAATTTATTTCCAAAGTAAGATGCCACTGGAGGAATCTTTGGAACCCAAA
TTAATAACAAATAGGACTGGATGCAATGGCTCACACCTGTAATCCCAGCA
CTTTGGAAGGCCAAGGCAGGAGGATCTCTTGAGCCCAGAAATTCAAGACC
AGCCTGGGTGACACAGGGAGACCTTGTATCTATGAAGAATTAAAAAAAAT
TAACCAGATGTGGTGGTGCACGCCTATAGTCCCTGCTGCTTGAGAGGCTG
AGGTGGGAGGATTGCTTGAGCCCATGAGGTTGAGGCTGCAGTGAGCCATA
ATTGTGCCACCACACTCCAGACTGGGTGACAGAGTGAGACCCTATCTCAA
ATAAATAAATAAATAAATAAATAAATAAGTACAAACCAGCAAACACTAAT
CCTTTCTAGAGATTATTGAACTCTGGAGGGCAGATCTGAATGGAGCCAGC
AGAGGGACCTATGGAGATCAGCCTGGCCCTGGACAGCACCAGGCAATGGG
GTTGCTAGAGAGGTAATGGGGTTGAACAGGGTTTAAGCCATGAGGTCTCA
AGAATCCGTGAAGACTCAGACTAATTTTTTTTTTTTTGCATGAGGATTAG
GTGTTCCTAGGAATTTCAATGAGAGCAGGGTTAATGAAGGAATGCAGGGT
AGGAGAGCTGAGGGAAGGCATCTGAGAGAGCCTGGCTTATGAATGGCTGC
GTCAGTATGGCTCACCTGCTTTCCTTGTATCTACTTAGCAGATGATCCCA
CCCCAGGCCTCCAGGGCCAAGGTCATTTCCACATAGTCATGGGCCCTTGA

FIG. 3F'

GGGCCTGGAGCAGTGTAAGGAAGACAGAGTCTTAAGAAATTGCATTAACA
GTCATGGTGCTTGGCAAGTGTCGTCATCCTATGCCAAGCCTGATCTGAAG
GGGTGCATGCTCATAGGTAGCTGCTGCCCAAGATTACAGCAGCTTCTTCA
ATCCCAGATCCATGCTCTCCTATATTCATTTTTCCAGGGGTTCCTGTCCT
TCGACAGTGATGAGATGCAGAATGACTTATTGAGTTATTCTCCTGATAGT
TGCCAACTTTTCCAAATGACAATGGGGCATGGAGCTTGAGAGTGGAAATG
AGGCCCTAGGGATAGCGTGCTTAGGAAAACACTCCCAGCCTGATGTAATT
CTGGGGGTACAATGGCATTTTCATCATCAAGACTGATGTAAAGGGTGACT
AGCAGTGAGTTGGGGGTGACTCGCACTGGGGCTAGGTTTCTGATTCTGCC
TAATCCAGACAGAGCAGAAGCACTAGTGGGCTGGTAGAGGGCCTCCAGGG
CCTCACTTAATGTCCTGGAAAAACAGCTCCAGATTGTTGGTTCACGTTCT
GAGGACAAGCTTGGGTACTACAGGATAGAGAGAGTGGTGGGAGATGCCGT
GGCCTGCCCTGCTGATGCCTGCCCTGCCATTCCTGCGTGTGATGTCTCTG
GGGCATCTTGCCTTCCCTGCCCAGACCTGTAGTTCAGCTGAGGGCATGTG
GAGGCCAAATGGCTTCTTAGAGTGTTACTTTCCTTGAACAGCTCTGCTGG
GAGAACTGGAGGAGCTAGCTAGTCACGGTAACTGCAGCAGTCAAAGGATC
GTCCCGGTGGAGGTGGGGTGGAAAGGTAGAGAAAGAGAACATATAGCGTT
TTCCTTGGAGATGTGTGGGCATGTCATAGAGGAAATACCCAATTCCTGAG
CCTTGAGCCCTCCAGGAAACCTTGGAATATTAGGTTAGTCATCCCCAAGG
AAGTCTAAGAATTCTGGTCTCACCCATCTCCTTTAATTCCCACAATGATC
CTACATGATATTAAGGAACACGGGCCAGTAACCCTCCAAGCAATGGATGT
GGTGGTGAAGTTTGACCTCATGATGGAGCGGAGGTTGGTTTGAAACCTAA
GAATTTAATTTATTGTTTCAAACTGTTCTCCACTCAGCGTTATTAAAGCA
TACATAATTGACACATAAAAATTGTATATGTCTACGGTGTACAATGTGAT
GTTTCGATCTATGTATACATTGTGAAATGATTACAACAAGCTAAATAACA
TACCCATTCATCGTGTTTCAAAGGAATTAAACTCAAGCACAAAAGAGAGG
TGCTGTTGAAGAGTAGGGCTGCTCTATCTAAGTAGTATGTCTGGGGTTGT
CCTGGATCAGGGTCCTTTTGTGCTAGTAATAAACCAGCCCTTCTGGGGCT
GCTCCACTTTCCCCACATTTTCTTCTGGAGCCTCCCTAAGAATTAGGACA
TGGCCACTTTCTCTGCATAGGCTTCCTACTTCAACAAGGACAGGGCTTGT
GCTGCCCCATGCCACTTGAGTGTCCCTACAGCACAGAGCTGAGTGCACAC
TGGCTGAGTGAGGAAATCCCCCAGATTAATCTTGGTTCTAAGCATCATGG
CTGTATTTCACACGTATATGAATTACAAATTACAGCATAGTCGAATAAGG
ATTTTTGTGCTACAACTGGAATCCCAGATTATGCAAATTGGATAGTATAA
TATTGAAATTCCTAGGACTTTTTATTAGTTTTAAAAAATTATACAAGCTT
AGAGTAAGAAATTAAACAGTGCAAAAGAATTCACTGTGAAAAGTAAAATG
CTCTGTCTCTGCTGAGAGACAGATATTGCAGCCCAGATACTACTGGGGTC
AATAGTTTCCTTTAAGCATGCCATTTTGATGGTTTATGGGACTTACAGCT
CAAGAAGCTTGACACTAGGGTTGATCTCAGAAAATCATTGTTGCAGGTAT
TAGATATGACCGTCTCATAAAGATACACACACAGACACAGCGATTGGAGA
TATTCACTGGGGCTTATGGGCTGCTTGTCCTTTCTGCTCTGTGCCTAAGT
TGGGCTCAGAGTAGCCTGGCATCGGCTGTGGGGAGAATGCTGGCATGGGG
TTAGCAGGAGCCCACTTAACATGTCCTAAGCCACCTGGAAGAGTCCTTCA
AGGAGACCAGACTCCAGAGGCCCTAAGGAAGGAAGGACTTTTGCCCGTTT
TTAGGTATTCTAGTCCCAGAGTTTAGGGAGGAATGGTTTGGCTTTGGGTC
GTGTGCCCCTTTACCGAGTGGGATGGGATGTGCCCATGAGCTGTTGAGCT
GGCTCTTGGAGAAGACAGCAAAAGCGGGAATAAGAGGTCAGGAAGCTGTG
TGGTTGTAGGAAATCCCAGCAGAGGGCCTGGGGGTCAAAAGTGGTCATGG
TAGTGACGGTGGAGGCTGAGGTGGTAGAAAATCAGAGGACAAACCCCATG
GGCTGCTGGTGATCTGACCGAGCTCCTATGCTCTCCTGGTTCATTTTAGG
CTCTGTAGCAGCAGATGATTGGCTGGTGTGAGAGCAGTGCACCTGCCATA
TCAGGCAATCCAAGACAAGTCCAAGCTACGCTGGGAGGAAACCTGAAGGC
AGCAGCAGGTAGACTGGCTGAAGACAGACAGGCAGGCAACTTGTCAATCA
GATTTGTGTTTTTAAGGACTTTTAACTGGGGAGCCCTCCGGGACAGATCA
GATGAGAGTGAAATGTGCTCCGCCTTAGCC
>Contig37
GGCCGTTCGCAATTCTGTAAAAGGGAGAGTGGTTTTATTTATTTTTAAAC
ATAGTCAAGCTGCTAAAGTATATGATATGTATAGATAGAGTATAATTAAA
TACTTTCAACTACAGACAAAATCAGGAGAATGGAATTAAAAAACAATTTA
CAAATGGGTAATGGCAGCATTGGGTTGCGCCCACCCACGAGAAGGCAGAC

FIG. 3G'

ACCAAGATTCTAAGATCACACGTGGCCAGCACTTCAGACTTCAAATAGAA
TTCGTGATTATGCATTATTTTTCTCGGAAAGTTTTCACTTCACTATATGC
TACTTGACACTTGCTTTCCTAAGACATCCCTCTATTTTTGAGATGACTAA
CTCAGCAATTCATTTCTCTCACGCATAAGCTGTCACTCAACCCAAACCCA
CCAAGCCTGCATTCTACCCTCAATAAGGTCTTGGTGTGTAAACTGACCCA
CTTCACCTAGTTCCTTAGCCCTCTCTTGACCAGACATGACTCTTTCATAA
GCTAGACCTATAAAGTCAGGGCTCTTAAGTAGCTGATCTCTGATAGTGCC
AAGTGTCCCCCACTGTTCACATTTTCCACTCCAGCTTCTAACAGGTGATA
GACTGCTTTTTGGGGGTAGGGGCACCAAAACATATAGACCTCATGTTTGG
ATGTAGACACTCCAGTTTCTTTAAATTACAACTACATATTAATAATGACT
TCCAAGTGTACATTTCAGTCCAGATCTCTCCCTGGATCCCCAAACTTTGT
AAAACCCACCGCCTAGTTGATATCTTTTGATGTCTGACAGGCATTTCAAA
TTTAATACTGTCACAAACAAAGTTATTGATTTTCATCTCTGCATCTGTTA
CAAATTTTTCTTACTTTGGTAAATAGCACCCCAGGCTGTGTCACTGCCAA
GAACTTTCCACAGCTCTTGGAATAAAATTCAAAATATTTTCCAAGGCAGA
AAGGCACAGTGTAATCTGGCTCCTGCCTACCTCTCCAACCTCGTATCACA
CTAGTCTCCCTGTCACTCACCCCCTCCAGGAGCTCAGGTATCCTTAAAGT
TTCTTTTCTTTTTTTTTTTTTTTTTTTTTTTGAAACAGTTTTGCTCTGTT
GCCCAGGCTGGAGTGAAGTGGCATGATCTCAGGTCACTGCAACCTCCGCC
TCCTGGGTTCAAGTGATTCTTGTGCCTCAGCCTCCCAAGTAGCTGCAATT
ACAGGCGCGTGCCACCACACCCGGCTAATTTTTGTATTTTTAGTAGAGAT
GGGGTTTCACAATGTTGGCTAAACCGGTCTCAAACTCCTGACCTCAAGTG
ATCTGACCACTTCAGCCTCCCAAGGTGCTGGGATTACAGGCGTGAACCAT
TGTACCCTGCCTCCTTGAAGTTTCTTGATCCAGACTCATTCCTGCCTTAA
GGTCTTGCATCTTCAGTCCTCCCCTCAAATGACACCTCCATGAAGACGCA
ATTACCTGTAATTACCGTGTCTTATTTAGTCAATGTGTTGGTTTTCTGTC
TCCTCCACTACAGTGTAAGCTCTATGAAGGCAGAAACCTTGGCAGTCCAG
TTCCCAGCACAGTGCCTAGCACACATAGGTATTTAATAACACACAGTAAA
ATTCACCTTTTAGTGTGCAATTCTGAGTTTTGACAAATGCATCAAGTCAT
TTAAGTCTGACTATTATCAAGCTATAAGATGGTTGCAACACTATCACTAA
TTCCCTCATGCTCCTTGGTAGTCAGTCTCACCCCTAACGCCCCCCTCCTG
GCAATCACTGATCCGTTTTTTGTCTTTATAGTTTTGGTTTTTCCAGAATG
CCAATAACTAAGTTTTGAATGAATGAATGCTATTAACTCTCATTTCTGAC
TCCAGAGCAACATCCATGCAATATTTATTATTTCAGCCCCAAATACTGCC
CCCTCACCTTCACTCCAACCACCTACTTGATGATACAAGGTGAGACATTT
GGCATGTGCTTCCTCCATGTTCCTAGCATTTTCCCTATCTCCTTAGCCTT
CCTTCTAATCATAAACGAAGAGTGAACTTTCCCTTTCTAAAGGCAACTTA
CTCCTAGGACCTCGATGCCATAATTTTGTTTCTCTAGTACTTTCTATATA
TACACCAAACAATTAGCTCCAGAAAGGTAAAGACTCACTGTGTGCTCATC
ACTGTGTCTCCTAGCGCCTGGCACACTGCAGGTGCTGAAGAAACACCTAC
AGAATGAGTGAATGAATCTCTCCCTCTCTAGACTCCTTCTCTTTTGTAAT
CAAACATGTTCAACCTGCAACACAGTCTTATGACCAATCCTCTGTTGTCT
GACCTAGGCTGAGCTCCAGGGCTGGGACCCTGACTTCCTTATTCACCACC
TCAAGGTCTCTGCACTCACTTCTCTTTCTGCTCAGGATTGTTTTTCTTCT
TGTCACCAGTCTTTTCTCAGACTTAGGTCTCAGCTCAGACATTGCTGTTG
AAAGTACTTCTACTGATCCTTTTATCTAAAGCAGCCATTCCAGCCCTACT
CTCTTGATCATAGCACCCTGAATTAAGTTGTTTACTTACTGTCTCTTCAG
GAGGGCAAGGAGCTTGGTGGTGGTGTTCAGGGCTGTACCAAGCTGTACCT
TGCTTCACCCTGCTACACTTTTTAGCAACCATCTAATTTTACATGCTCCC
TTCACTCGTCAGAAATTTCCTTATTTTCTACTTCAAGCAGGTATACATAT
GTGCTTCTCCTGGGAGGCTCACCCACTTCATGAGACTACATTTGGTCCTG
GGTAGAAAGTGTACAAAATCCACTGGCTCAGTTTTAATCAATGTATGTTA
ATATTAACCAACCTGAGATCTTGATTTCCACGCCTGGCTAATTTTGTATT
TTTAGTAAAAACAGGGTTTCTCCATGTTGGTCAGGCTGGTCTCGAACTCC
CGACCTCAGGTGATCCGCTCACCTCGGCCTCCCAAAGTGCTGGGACTACA
GGCATGAGCCAGCGTGCCCGGCCTAAGATCTTGATTTCTACCATCTGAAC
TCTGTATTTGAACTGACTGCTCCTGCTTGAGCTTACTGGCCAAAACTTGG
CCCACTCAGACTCACGGAAGTTTCTGGTTCTTCCCTGGTAACTTTTCTGA
ACTTAACCACTGGTTTGCTTGACAAGAGATTACCATCTTCTCACTTCCTA
GCTATGTGAACTCACTTATCTGCTCTATTGCTGTTCAGTCTAGCACGGCA

FIG. 3H'

CTTATTGAACGAGTGTCTACATCTGCACCCCCTACTTCTTACTCATCCAT
TCTGTTTCAATTTCTTAAAAAGAAAAAAAAAAAGCTATTGTAAACATACG
ATTACAGAAAATGATTTATAACATGTGTATGTACCACCTAGCCCTGTCAA
GTCTTAATATTTGTTATATTTGCTTCAAATCTTTTTTCAGACTGTAGTTA
AAAATTACTTAGGAGCCATTATTTATGGCCTATTTCCTGACCTAGTCTTC
TTGATGGTCAATTTGCCTAATCATCTTAAGTTGCAAAAGCTTAGAATTAA
AGCAAAGTACCTTCGATCCTCTGCTGTTGCCTTCTTTTAATATTTGGGT
TTGTTTGGGTCCCATTTACGGTTGTGACATCAGCTTGAGTTTTGGGAGCT
GTCTTGTTCAGAAAATGGTTCTGGGGAACAGCCTTTTTCAACTTGGAGTC
CAAAGTCTGTGCTTTTTGCTGAAAGCCATTATTGTTATGTTTATTACCAC
TGGTTCCATTTGGTCTTATGCTAGGGGTGCTTGGAATGGCTGAATTAAAT
CTGCCAACTGTCAAATTAGGCCTCTGGCTTACGGCTTTTGACTTTTGCAG
TACACATGATGTCTGAGGTATACAAACTTGGCTGGACTTCTGATCTTGCT
TGATGTTTGGATGTCTGTTGTTATATTCACCCTGAAGCAAACTGGGGTAT
GTTCTGGGTTTGGTGTGCTTCACTCTCTGTTCAGTAACAGGGTATGACCG
TATCTTAGTTTCATTTGGTCTTTCATATTGACTCCTATTAACCTTTATAT
CTTTGATGTTCTTGACTACTGGTTTCTTTGATGACTGAACTTTACTAAGG
GTCCGAATAAAGTGAGAGGGAACCGTCCTTGAGGGTTTTACTCCTGGTCT
TGCAAGATCTGCTCCTCTAGAGAGTTGCTGTGATTTTACTGGGAAAGTCC
TGCTTTGTGTTTCTCCAACAAATTGTTTATTAACCCTATCTTTCAGAACA
GCACTATTAACTGAACTTTTGCCCAAGGCTTGTTTAGGAACTAAACTGTT
CTTGGTTTGATTATAAGAGTCAGTCTTTGGCTTACTTCTGGTATATAATT
TAGGATCTGGCTTCCTCTCAGGTTCTGTTAAGATATCTAGCAAGTTCTCT
TTGTTTGTTTCTTTTAGAAAGTTATCCAAAGATTCGTTTTCAACATGGAT
ATTATTCATAAAGTCTATACATTTACCATTTCCTTGATCTGTTAACTGCT
GCTTTGTAGTTTTCAATTGCTCTATATTAAGTGACCCCACAGGTTTTCTT
GACAGTCCTCCTGTGGTGGACTATCTAGCTTCACACTGTTGAAAACTCTT
GCTGAAAAGCTTAGACTATGGGTTAGAAGAAACACATTTTGAAGTCCGCC
TTTTGCCCAGAAGTTTTGGTGGCTCTAACTTCAGCTTCTGGGACCCTGCA
GTATTAGGTGGTCTGGGCTGGAGTTTAATGCTGATGGACCTTTTAGGTTT
GACAGGCAAAACAACATGGTTGGTAACATCATTTTTGGGTCTAATAGTCT
GAAAAAACAAAGAAAATACATATTAAAAAATCCTTAACATATCTTATTGT
TTTTAAAATAATAACTGTGTTTAACACATGCTAAAAAAAAAATCATTTTT
AGAATTTCATCTAAGAAAGTTGAATCCTCAGAAAGTAAAGAAAGACTCAC
TAATAGGTAGTTTTTGTGTTTTTTTTTTTTTTTTTTTTTGAGACAGGATC
TTGCTCTGTCACCCAGTCTGGTGTGCAGTGATGCAATCTTGGCTCATTGC
AACCTCTGCCTCCTGGGTTGAAGCAATTCTCCCACCCCAACCTCGCAAGT
GGCTGGACTACAGGCGCATGTCACTACACCTGGCTACTTTTTTGTATTTT
TAGTAAAGTTGGGGTTTCACCATATTGGCCAGGTTGGTCTTGAAATCCTG
ACCTCCAGTGATCCACGCACCTTGGCCTCCCAAAGTGCTGGGATAACAGG
TATGAGCCACCACACCTGTCCTAACAGGTAGTTTTTACAACTTGAGTTCC
TATCAGAAGTATATTAGAATCTTTTAGCTTGACAGAATTAAGCAGAGATG
CAGTGAATATACAAAACTTGCTCTTTCAAAAATGAATTTGCCTCAAACAG
TAGTTGTTGAATGCCTATTATATCCTAAGTGCCCTCCAAAGAACCCTGAA
AAAATACATACATAATGAACTTATGTTAGGGTACCTCCCAACAAATCTCT
CCTAGTACTTTGTATAGCCACACTATATGTTTTTTAAACCACTGCCTTTG
TAAACATCACAGTATCACTCAAGAACCTCTGTCTCATCCCTGGAGATCAG
TGACAAGGAGATAGGTGGCAGATGATGTGAGGCCTGAGATATGCTGCCAC
AGCTCTCAATAAACATGTAACATCTTAATAGTCATATTTGTAAAATCAGC
CAGGACAGGGTTTTAAGGTTAGAGTCTATGTTAATAATAAACAAATGTTT
AGTCATGTGATTTAAGTTTGGATAAGAAAGGTAGGACTCGATTACAGAGA
ATTTTGAAAACTAGGGAAGGGAGTTTAGAATTCATATGGTAAGTAATTGG
GCAAGCCACTATGAATTCCTGAGCATCTCTCATGAAAGCAATTACTCAGA
AAGGAGAATTTCACAGAGATTTATGGAATATGTTTCCAGGGTAAGATATG
GGAATGCTAGAGTTACCACTCTATTTTTGATTTGACAAATATTGTGAAGA
ATCACTACATAAACTTGGCGAGTATGTAAAGGATTTCTAACCAGAACCAT
TTGGCATTGAGGGCAAAGAAATGTCTACTCTGGATGATAGCGGTGTGTGT
GGTGTTACTAGGAGTGAAACAGCGGAGTTGGGAGTGGGAGGCAGAGAGAT
GGATGGTATACCCACAATGGCTATATCTGGATTAATCTTTGAGCACCAAC
ATTTATATACACCTCGGATCTCTCCATCATTGCTTACTGAAGAGGTGGAG

FIG. 3I'

GGACGTTGGCATGAAAGCTTCCAAATGTGTTTTTTTAGTTGCTTTCTTAT
ATATTAAAAACGAATTGATATAATCCACAAACCATAAAATTCACCATTTT
AGTAAGTGCACACTTCTGTGGATTTTAGTATAGCCACACTATTATACAGC
AATCACCACTGTCTAATTCCAGAACATATTCATCACCCCTAGAAAGAGAC
TTGGGTTTACTTGTTGGCAGTCCCTCCCCA
>Contig38
GGTCTACATGTGCTCGCAAGATTGGATATTGAAATATCAGCAAGAAATTA
AATGACATAGTAGTCATTATGCCTAAATTATTGTTATTTTTTGATTGAAA
AAAGTTGAATATTTCAAATATCAAGGTAGTAGTGAGATATAATAAAGAGA
GAGTCAGTTCTAAGTATAGAATTGCTGATTCAGTTAAGCTCTGTTCTCCA
ACATTTGGGCCACATTGAAGAGACCATGTAGCTGCTTTCAGCCTCGGTTT
CCTCCTTTGCAAAATGGGGATTACACTACCTGCCTCACAGAGATGTAAAC
TTATGACATGTTATCATGATTGCCAGGGCCCACCTGTTTTCTTTTAAACA
TTGAAATCACTGTGCCTGAAACAGGGATTTCCCTGCCCTTTGTGCAAGCT
CCAGAAACAGGAGTCAGCCTGAGTCCCGCAGCTAAGAACGTGGATTCTGG
TCATTTTCTCATAGCGAACACACTTCACAGGTCCTTCAAGGGAGTACATT
TTCCTATAACTCACCTTAATCTCAGTTGAAGCCTCGTTTCTTATTTTGCA
CTGTGGCCAAAAACTAAATCTCATTTCTTTCACGTAAACTTCAGCAATTC
AATAATAGTACAGTCATTTTATGTTTCAACTGAACCAAGTCAGGGTTCCA
CTCCTGCCTCCCCTTTCTGCTCTGAGGACATCCATGAAGTGGAGGGGGTC
TATGTAGCCTGGAGCTATTGGTGAGGGGCGATGGGTCCGTGGTGGTCTTG
GGGAACTGCGGGGCTGTGTCTGGCTGGTCTGGTGTCTGGTGATTGGCCTT
GTTCCACGCGGTTCACGCTGCAGGACAGTTCGTGTCCTTCTTGTCCTAAT
GATCAGCTTTTAGGCTCACGGGCCTGTCTCTGCTGAGATATGGAATAGGA
CAGCCTCTGGATCTTCTTTAAACTCTCCTGGGGCCACAGGGGACTCTGTT
TGTGTCTGTGCCCACATAGGATGATTCTGCCCAGACCTTTGCTGCCATTT
CTTGCTGTTCTGCTGTTTTTAGTCTCTGGAGGGCTTGCAGTTTCCTTGGG
GTCCCTGTGGAAGCAAAGCAAAGTCCTCTCCACGCTCAGATGTCTAAACG
TATCTGGGTTTTATCGTCCACCCATCCCAGAGCTCAGTCTAGAGGAGGGG
GCAGCCTTCGGGTTCTCTCCTTCCTCCCAGAGCCTCTTCCTTTGCACCAG
GGCAGCCTCTTCCTATCTGTTGGAAAGGGCTGTCTGGTTCTTGAATATAG
AGTTGCAGGTTTGAGGGGTGTAGGCTGAGGTAAGGCAAACTATCACATGG
AATAAAAATTACCCTGTGTCAAGGAACAACCAGAGCTGGACAGTTTTTAA
ATGTGAAAACCAATTTTATTCAGGACTATGGCGAGAGGTGAAGTAAGACC
TCAGTATAGAACTGGGCTCAATTCCGAATGCAGCATGGGCAAATGGGAAT
GTATAGCCTAGGAGCAGGGTGGGAACCTGTGGATGAAGAATTACTAAAAG
GGCATATCAGGGGTGAGGGGGCGTCCTGGCTACACCCACTAACTACTGTT
GCTGAAGAAAGGCCTGGTGACATCACTGGGGAATGGTGGGGGATGAAGAA
TCCAATCAGATGGATATTGAGGATAAGGGGATCTTGATAAACTGGCTTAG
GAGGGTTTTTGCTAAAACTGGTTTTCATAGGTAAGTCCACAGACAGGTCT
TGGAGAAAGTTCAGGGACCTACGGTTTGTTCGGGCAGATGCTTTGTCATC
TGTCACACTGGCACTGTCACCTGGCTTTCCTTTAGTCCCTCCCCCCCTTT
TTTTTTTCTGGAGTAGTTTTGGGAGACCAGAGGAGCAGGGAGTTAGGGAG
AGTAGTCAGAAAAGGCCAGAGAAAATAAGGAGGTGTCTGTAGGGAAAATC
CTTAAATCCTCTAATTAAATTAATTTAATTTATTTATCTGGGACAAGGTC
TCACTCTGTTGCCCAGGCTGAAGTGCAGTGGTGTGATCTCGGCTCACTGC
AGCCTCGACCTCAGGGCTCAAGCAGTTTTGCCACCTCAGCCTCCTGAGTA
GCTGGGGCTCACAGGTGTGCACTACCATGCCCGGGTAATTTTTGGGTTTT
TTTTTTTTTTTTTTTTTTTTTTTTTTTGTAGAGATGAGGTTTCGCCATG
TTGCCCAGGCTTGGTCTCGAACTCCTAAGTGATCCATCCACGTCGACCTC
CCAAAGTGCTGAGATTACAGGCATGAGCCACTGTGCCCGGCCTAAATTCT
CCAATTTTTAAATGCTTCCCTGTTCCCTGTTCCAGATTTGGGATATTGAC
TGCTGTTAAATCAGCGATTTCTCCCTGTGGAGAGGTAGCCAATAGGAAGC
AACAAGAGTGAGGAGTCCTTATATCGAAATAGAGGGTAAGAGAAGAGACA
GATGTTATCTTGGCAGTGATTTAAGAACAGCGAGTCTGTAAGCAAAGCAA
AGCAAGGCTCCCAGGTGCTGAGAAACAATGGCTTTCTGGGGAAGCGTCTG
TGTTCAGAACCTTAAGTTGGAAACATCTCTGAAGATGTTTGCCATGAAGG
TTTTCTTCTGAAGTTGAGTCTTTCATCACTAGGTAGGCGTGTTTTGGAGT
CTCTATCAAACAGATCCTGTGTTTATTAGGAAGCTGTGGTTCATAAAGCC
CCATGCTAATTTTGCAGGTAGCAGGGTGGCCCTGGCCTGACCCGGGGACA

FIG. 3J'

GAGTGGCTGTCCTCCCTCCAGGCAGGAAACTCTCTCCTGCCACCTAGTGG
CTGCATACCCACATTTCAAGGGAGCTTCTGGGTGGTGAGTTTACCAGACT
ATGGTCTGAGGTAGAGTTAAGCAAAACAAAACTAAACTGCATAAAGAAAC
AGAAAGAAAATCAGGTGTTATAAAAACAATTTGGCATTTGTTTGTGTTTC
AGCTCCGTGTCGATTTATTGCTTCCACAAATAGTGCCGATATGCACCAGG
CACTGTTGTAAAACTGAAAATATGTTTTTGGATGTGCCCAGTCTGTGAGT
ATTAAACGATGGTTGATTTGAAATTTGCTATGATTCATATTTCTGGGGGT
AAGATGCAGGATTTCTTTGGGGGCCTACGATGTGGCATTCTAGAATTCT
CAAAGAATCAACCCTGGTGGGACCAGGAAGAGCTGAGCTGAGGCCTCTCT
GCTCATGTGTACTTACTGGAGATCATGGAGACAGGTGAGCCTGAGTGCAC
GTCTCACCAAAGCCACAGCAGAGGGGGAGGAGGCGGAAAGAGAGCTCTCT
CCATTTCTGAGAAGTTAATGGTAACAATGGCATACATACCTACTTTACAG
TTGAAATTGGAAACCACAGCATTAAGTGTTTCCAATGAAATTTGGCAATT
TGGGAGTTTTCTGAGCTGCATTGGATGTGGTTTTGCATGCTGTTAGGATG
AGCAAGAGATGATGGAGAACATCTTCCTTTTGAGCTTCCTCTTGGACGTG
GGTCACTCCCACTCATGGAATTAGAAAGCTTAGACCTAGACTTGAATCTC
ACCTTCTCAAGGTGCTCCCGGGCAAATCACTTAAGATCCATCTTCTTCTC
CTCCTGCTCCTTCTCCTCCTTCTGAGTTTTTTTTTTTCTTTCCAAAATTC
AAATGACACGGTACTGGTAGAAGAAAAGGTCCAAGTCTGCTTTTACAGCT
CCCCTCATCCCCAAATGTACTCCGACCCCAAGATGACCATGTTATCATTT
GATTGACATCCTTCTAGTTTCAACTCATTTCTTTGCATGTATATGCACGT
ACATATACACTATTTTATTTTGCCAGGGGTCACCGTTTAGCTGCATTAAT
TTCTTATAAAATAATCTATATTTACTTATGGTTTACGTAAAACAACATAC
ACATGTAAGTGTATAGCTTGATAAGTCTTCACTGTAAACCAAAAATAAAA
TTCGAAGCCCCCCCAACCGTCTGAATGGACCCCTCTTCTTGGCCAAGAGC
ATTCCAAAGTTAACCTGAAAAAACTAGTTCAGGTCATGATGGAAGGGAAG
GTTGGACATGCCCCAGTATACCCTTCTCCCTTTTGGAATTCAGGAAAAGC
TGACCAGCATTAACATCAACACAGACCTTATGTCTGATAGGAAACTTTGA
CAATCTATTCCCTCTGAAGCTTGCTACCCGGAGGCTTCATCTACAAGATA
AAACCTTGGTCTCCACAACCGCTTATCATAACCCAGACATTCCTTTCTGT
TGAGAATAATTTACCTTGTAACCTGGAAGCTCCCTGCTTCAAGTTCCCTC
ACCTTTCCAGATTGAACCAATGTAAACCTTACATGCATTGATTGATGTAT
TATGTCTCCCTAAGATGAATAAAAGCAAGCTGTATGTTGACTGCCTTCAG
CACAGGTTGTCAGGACCTCCTGAGGCTGGGTCACGGATGCATCCTTAACC
TTGGCAAAATAAACTGTCTAGATTGACTGAGACCTATCTCAGATACTGTT
GGGTTCAAATATATAACTTATGAAACTAATACACAAATCAAGTCATAGAA
TATTTCCATCACTCCTCATCTACCCCCAAATTTCCTTATGCGTCTTTGCA
GTCAACCTCCCACCCCATCCCCAGGCAACTGCAGATCTACTTTTTGTCTC
TGCACCTTCAACTGACCCTTTCTGTGATTTCATATGAATGGAATCATGCG
CTGAGCAGTCTTTTGTGTCTGGCTTCTTTTGCTCAGCATAATGTTTTTGA
GGTTTGTCCATGTTTTTGTGTTTGTCAATGGTTAATTTCTCTCCATTGCA
GAGTAGTTTTCTATTGTACATGTGTACCACAATTTGTATATCCATTCCAT
TGCTGATGGACATTTGATTTGTTTCCAGATTTTGGCAATTATGAATAGAG
CTACCATGAACACCCAGGTACAAGTCTTTGTGTGGACTTATGTTTTCATT
TCTCTTGGAATGGAACTGTCATATCAATAAGTATATGTTTAACTTTGTAA
GAAACTGACAACAAATTATCTGCGATGGTTATGCCATTTTGTTTTTCTAC
CAGCAATACACGAGCATTTCAGTTGCTCCACAACTTTGCCAAAACTTGTT
TTCTTTAATTTGGACATTTAAGTGGTGTACAGAGGCATCTCATTGTGGTT
CTAGTTTTCTTTGCCCTGATGACCAATGGTGTTGAACATCTTTTCATGTG
CTTTTTGACCATTTACATATCCTCTTTTGTGAAGTGTCTGTTCAAATATT
TTTGCCCATTTAAAACATTTGGGGGTTTGTCTTATTATTGTGTTGGGAGA
GTTCCATATTTATTTATTTATTGAGATGGAGTCTCACTCTGTTGCCCAGG
CTAGAGTGCAGTGGCGTGATCTTGGCTCACTGCAACCTCCACTTCCTGGG
TTCAAGCAATTCTCCTGCCTTAGCCTCCTGAGTAGCTGGGATTACAGGCA
TGTGCCACCACACTGGCTAAGTTTTTGTATTTTTAGTAGAGATGGGGTTT
CATCATGTTGGCCAGACTGGTCGCAAATTCCTGACCTCAAGCAATCCACC
TGCCTCGGCCCTACAAAGTGCTGGGATTACAAGCATGAGCCACTGTGCCT
GGCCCATATTTATTTTTATTCTTTATTTTGTATACAAGTTCTTGGTCAG
ATACAATAATACCTGGTCAGATGAGATAATGAGTTGGAAAATGCTTTGCA
AATGGGGGAGAATAATTTAAATGTTATTTATTTATTAAGAGCAGAGGCCC

FIG. 3K'

TTCCTGTTGCGGTCACAGAAGCCGTTTGCTTCTTCTGCCTTTTATAAACC
AGCAGAGTCGAGCTACACAGGCTGTCTGTGTTGGCTGCTATTAGTTAATC
AGAGAGTTTTTTTTTTCTTGCCTTGTCATTCTAATTTGTGACACATAATT
AGCCACAATATGTGTTTTCAGTTGTGACACTGGCCTGGGAAACCAAGGGA
TGTTTAGAGTGGATTTCCTTGATTTTGCAATAATTGTGTGTTTTTCTGCA
TCTTCTGTTAAACACAAATTCATGGAAGCAAAACATGGAAGCAAAGTACC
CTGGACATCCCCCCTTCTTTATGAAATTGATTTCTCTTAAATGTAATGTT
TGCTTGTTCCCTTACTTTAAAAGCAATTTAAGAGTTTATTGAGAAAGTGA
GCCCTGGAAACATAGATGCATAGAGAGAAAATTCTACCACCCTCAGGTCC
CTATTGTCTTCTCTCATAAAGTGTAGTTTCAGGGCCTTTTAGAAGTTTCT
TTTCTGCTCTGATTTGCATGTTTGTGAGTGTTGCTATTTTAAGTATTTGG
ATTTGGTCTGCAAATCCTATGAGAGATGGCAACAGAGTAGGGATCTCAAA
GCCTGCAGGTTGTATTAAGTCCAGCAGGGCCTTGTATTTACAACAGAGGG
TCCTTGAAGACATTCCATATATTATGCTAGGGGAGTGGCCAAGCAAACTT
TAATGTGTCCCTATGGTGGGATATTTGGGGTTAATACCTGCCCTTCTCTT
AATTTCTTTTTCTTTTCTTTTTTTCTTTTTCTTTCTTTTTTTTTTTTGAAA
TGTAGTCTTGCTTTGTCACCCANGCTGGATTGGAGTGCAGTGGTATGATC
TCAGCTCACTGCAACCTCCACCTCCTGGGTTCAAGCAATTCTCCTGCCTC
AGCCTCCCAAGTAGCTGGGACTATAGGCACACACCACCATGCCTGGCTAG
TTTTTTTTTTTTTTTTTTGAAACNGAATCTCGCTCTGTCGCCCAGGCGGGA
CTGCGGACTGCAGTGGCGCAATCTCGG
>Contig39
CGCTCGCATCCCTCATATCCATGAGTGTTCTGTGGGCCCTGCCTCTGAAA
TAAATCCTGCCTTTGTCTCCCAGTTCACTCCAGCCACCCATCCTGGGGCT
GCACCCTCCTCCTTCCAAGCCCTCTCCCTTTCCTTCCTGGTGCTGCCTGT
CATGTCAAGCATATGCATCAGTGCGACCAGGACATTTGAAATGCAACCAG
TACAATTGGGCGCGGTTATGCCTACCAGTTTTTCTTCCTTAAACATTTTA
TATTTATGTTTGAAAGCATGCCACCTTTCTTCACTTGCCAACTTGACAGA
TTTATTAGTTGACAACATCCGCTGATAGCATCAGTAATAAGTTAATTGTT
TTTGCACATGTAGCTTTAATTATTCTCATTATCATTTATAGGAGTTATTC
TTTGTAAAGGGTAACTGAGTTTTCCAAAACAAACAGAAATTTGGGGTGGG
CCCATGGAGCGTGACTCATGAAATCAGATTCTTAGAAGGACCTCGGCAAG
TCTCTGGGTTGCTGTTAATGAGCCTGGCTGGCTGCCAGGGGTGTGTCTGC
CCTTTATGAGGCCACCACTGTTCAAATGCTTGCCTGCAGCATTACTTGCC
TAGGTAGTGCTTGTTTCTACTGAACTGTCAGGGATCCAATTCTTTGTGGT
CTAAGTAACAATACTCAGATTCACAAGGAATTGATTAATAAGCCAGAATG
CCAATGTATTACATTTTTGATGAAGACCATATTTACAGTGATTGTATCTG
CTCAAGCTCAAATTAGGATTAGAGTTCTGACAAATACATATGTGAGAAGT
ATGAGGTTAAATACTTGAAATTTGGACTTTTCTAGAAAATCTGAATGTGA
TTGCCATTCACATACCTTTCTGGGGATGATGATTCTTGTACTTTTATTTT
AAAAGACATAGAAAACTAACTTAAGAATCAGATTGCTTGGCTGGGCACAG
TGGCTCATGCCTGTAATGCCAGCACTTTGGGAGGCCAAGGTGAGTGGATT
GCTTGAGCTCAGGAGTTTGAGATCAGCCTGGGCAACATGGTGAAATCCCA
TCTCTACCAAAAATACAAAAAAAAAAAAAAAAACAACCAAAAAGAATAAA
TTAGCTAGGTGTGATGGTGCGTGCTTGTAGTTCCAGCTACTTGGGAGGAT
GAGGTGGAAGAATTGCTTGAGCCCAGGAGGTGGAGGTTTCAGTGAGCTGG
GGTTGCAACAGTGTACTCCAGCCTGGGCGATAGAGTGAGACTCCGTCTCA
AAAAAAAAAAAATCAGATTGCTTTATTGCTGGTTTTCTTTCTAAAACTGA
GATTGGGTCCCATCATCCCCTGGCCCCCATTGGTTAATGGTTCCTCCTTT
GTCTATTGAATAAAATACAGATGTCTGCTTTTGGCAACATGGTTGAATGT
AGACACTGCAGGGTCTTCCTGACTCAAAATGAGTAAGGCTTAGATAAAAC
ACATTTTGAAATGCATTTCTGGATGAACAGCAAGGAAAGGAGATCTCTTA
AAATCCTCTTTCTGTTCCCCTCTCCCTACCCCCTCCAAGTGGGCTTAAGT
AGGAAGGGTGGTGAGCGGCAGGTAAACACACGTCAAAGGCAGTCTTCCTC
TCTGAGGGAAAACACTTGTATAAGCATTGCAATCAATGGGCCTCTTTAAT
TATGTGCCAGTGGCAAGAGCGGGTGCTGAACCCAGGGGCCTGCCTCAATC
CGGGGCCTTTGAGGCAGAATAAAGTGGTCTCAGGTTGTTGGCATTTCCTT
GCCCTTCCACCCGAAGCAGACACAAATCCTCTCTGGAGGCAAGTTCCCCA
ATTCAGCCAGTACAACTCCCACAGACTAAGATCAATCATGTACAAGCTCA
CAGACAAAGGTCACCAAACACACAGAGCAATAAACAAATTCATGAGTGAC

FIG. 3L'

GTGAATGAGAATAAACAGAAACAATAACCACCAGCTGGGATGCTCTAAGT
CTTCAGCTGTTAGAATTCCTGAATATAGAATAAAACTGCCACAATGGCAA
ACATGCATCTAGTACTTACTGTGTGCTGGGTTCTAAGAATTTTGCACATT
GTGCCAGATACCGACTCAGCTTCACACTCACCCTCCTACTGTGCCCTCTT
AATTTGCACTAGATTAAAAGGTAGAAAGGAAGAGGCAGCTATTCTGTTCT
TGGCTGTGCCTCTGGCAGCACATGCAAAATGGGCAGTAACAGTGGCAGTC
ACAGGTAAGTAGCCTTCTCACAGTGTGGAGTTAAAGGCATGGACTGAGA
CGAGCAAGGTTCCTAAAGGGACAGTGGCCAGTAGATGACCAGGGGCTACT
GGAGTGGCTGCATGGCTCTGTGGAAGCTCAGAGGAGCCTTGGGTCCTGCA
GGTGCAGTAGCAGCTTTCTGTAGTTCCTGATCTCTGGGTCCCACAATCTT
CCCCGTTTTTGCTCCTCCACTTCTAATTTTGTAACTGACTTCCCTGTGTG
TACTTCTCTCTCTGATTGAAATAGCCAGACTGGTTTCTGTTTCCTGATAA
GACATTGTCTGGTACGAACACAGTAACTCATTTAATCCGATATCTCTATG
AAGGAGGTACAATAATTATTCCTATTTTACAGATGAGGAAACACAGCAGA
GAAATAAAGTCAATTGTCTAAGGTTGCACATTTAGTCAAGGGAAGGGTTG
ATATAACATATAATTATTTAGAAAACATCTAAGGAAATAAAAGGCATAAT
TTAAAAATAAAACTAGGCAGGTTTAAAAAAATGAAGTAATCTATAAGTAA
AAAAGTATAATTGTTGAAATACATATCTTAGTGGATGGGTTAAATAGCTG
AAGAAATGATTAATGAACTGGAAGGTAGTTCTGAGGAAATCAGAATTCAG
CATAGATAGAAAAAATGGGAATTTACAAAAGTACACAGGAATTATAAAAG
AGGTTAAATTATAGGGAGGGTAGAATGAGAATTAACATTGGTCTAACTGG
AATTTTGGAAGAAGAGAATAGAGAGAATGAACAAGGCAATATTTAAAGAG
GTGGCTGAGAATTTTTCAGAACCAACACAAACTATGACTTTACCAGTAGA
GAAAACAATGTACACTGAGGAGGATAAATAAATATACTATGAACAAATTG
TAATAATAATACTCAACAAAGACAAAGAGAAGATGTTAAAATCAGCAAAA
AAAGAAAGTCAGACTTAGAAAGAAATGACAATGGCAGACTACTCAACAAC
AACAATGGAATCCAAATTCGGTCAAACAGTATTTTCTTCATGCTAGCATA
TAGC
>Contig40
GGGAGTCCGCTATGCTCCTAAAGATTTGCACCTCTGATCTGGTTTGTAGT
TAGTCTCTTTTATTGCTTTATCCTACTCAACTAATTTTTTTAGTGCCTGT
TTTTTTTTTTTTTAATGTGTGTTGATGACTACAATTCTAAACTCATTCTA
CTGATTCATGGGTGCTTTAAAATCTGAGCAGTCTTTCGCATTTACTGCCT
GTGATGGCCCATCCCACCAGCTAAAGTGTGTGGCCACTGCTTACAGCACC
ATGTGATAACGAGTAAGGGAGAGATGCCGCCCAGACTCTTCTAGGAGCAG
CCAGTAGGACCTTCCAGGGGTTGCAAGCAAACCACAGCAATATGTGGAGT
GTGGCAGAGGATGGCCCCAAGAGGATGTGGCAGCGGCTAGTGCAGCTCAG
CTTAGTCTGAGAGGAAATGCTGGAGAGGAGAGCCCAGTCTGTACAGGCAT
GACAGCCACAAGGACTTCAACAGCTAACATGGCTGAGTGGACTTTATGTG
CTATCTCATTCAGAAAACAGGAGCAATCAGAAAGGAGTCACCTCCTATTT
GTACCCCAGGAATTGCTAACCTACTTGCATCTGAATGATGTCCATCACTT
CCCTTCATCACCTCCTCTGGGGGCTCTGCAAGGATTTGACTCCTGCATTA
GTGATCTGTCTCACCTACGTTGTGATTCACATGAACTTACTAATGTGCTA
TGTGACAACTACCATCTTAAACACAAAAACCCTCTTTTGATTCTGTGGCT
CCCTCCAGCTACCCCTGCATTTCTCTGTCCCCCTGCCCCGTCTCTGCACT
CACTTTTATTTTACAGCAAAACTACTCAAGGGAGTCTCAGTGCTCCTTGG
CTCCATGTCTCCACCTTTCATTCTCTCCTCAGTTCACTCCTGTCAGGCTT
CCGTCCTCAAGCTCTTCTTCACTTTTGTTCTAGGGCCGCTGACATCCTCT
TTCTTGCCAAATTCAGTGGCCAGGTCCTCACTTACTCAACTGCTCAGCAT
TGTTGGGCCTGGTGGACCACATTCTCCTTCACCCACCTTTTGCTGCTCTC
TCTTCTCTCCAGATGTTTCTCTCTTCTCACTGGCTACTCCTCTTTTGTCT
CCTTTGTTAGCTCCATTTCTTCCTTCCAACCTCACTGTGCTGGTGTGCCC
AGTGCTCAGTTTTTAGCTATTCTCTCTTTTCCAGTGGCATTCATTAGATG
GTATCATGTGACCCATGGCATTATATGCCTTCTACATGACAGTTACTCCT
GAATATGAATCTCAGGAAAGATTTGGATTTATTTTTAATTAATTTTTTTA
AATTTTATTTTAATAAATGAGGTCTCTCTCTGTCATCCAGGCTGGAGTGT
AGTATTGAGTGATGTGATTATAGCTCACTGCAGCCTTGAACCATGGGCTC
AAGTGATCCTCCTGCCTCAGCTTCCTGAGTAGCTGGGACTACAGGCATGT
GCCACCATGCCTGGATGACTTTTTGTGTGTGTGTGTGTGTGTGGAGACAG
GGTCTTGCTCTATTGCCCAGGCTGATCACAAACTCCTGGCCTCAAGTGAT

FIG. 3M'

CCTCTCACCTCAGCCTCCCAAAGTGCTGGGATTACAGGTGTGAGACCATC
CTGGGCTAAGATTCAGATTTTGTATTCAATTGACTGTTTGACATCTTCAC
TTGGACACCTAAGAGGTATCTCAAATATTAATTAACTTGGCCAAAATACA
GAACTTTTGACCCCTGCCCCCACAATACTTGCCCCTTCCCCAGACTTCTC
CATTTCTGTTAAATATCCCCAGTTACTCAACCCTCAAACCTATGAATGCC
CTTTGATTTCTTTCTTTCCCTCATCTCCTACGTTGACGCCATCAGCTAGT
TTTGTTGCCTTTATGCCCAGAATATAATCCTCACCACCTTCTCTCCTATT
GCCCGAGTATAAGATGTCAGTTTTTCCTGCACAGTCCATTGCCCTGACCT
CCTGAGTGGTTTGCTTCCACTTTTGACATTTGTATTCCTCTTTCCCCCAG
GGTCAATTTTTCACAGCAAGAGTGGCATTTTTTTTTTTTTTTTTTTTTTG
AGACGGAGTCTCGCTCTGTCGCCCAGGCCGGACTGCGGACTGCAGTGGCG
CAATCTCGGCTCACTGCAAGCTCCGCCTCCCGGGTTCACGCCATTCTCCT
GCCTCAGCCTCCCGAGTAGCTGGGAATACAGGCGCCCGCCACCGCGCCCG
GCTAATTTTTTGTATTTTTAGTAGAGACGGGGTTTCACCTTGTTAGCCAG
GATGGTCTCGATCTCCTGACCTCATGATCCACCCGCCTCGGCCTCCCAAA
GTGCTGGGATTACAGGCGTGAGCCACCGCGCCCGGCCAAGAGTGGCATTT
TTAAAACCATATATTAGATCATTGCTTTTGTGTTTGGGAACCTCCAAGGG
CTTTGCATCATATATCAAGTTGACACCTCTCCTACCCAAGCCTGGCTCTT
TCCTGCTCCTCTGTCCTCTCAGCCCCTCCACCCATTGTTCATGCTGCTTC
AGCCACACTGGCCTTCTTGCCATGCCACATTTGTGCTAAGCCCACATCCA
ATCTCGGGGCCTTTGCACTCGCATTTCCTCTGCTTGGCATGCTGTACCCC
AGATCTTTCATGATTGGCAGCTTCTGTACATTCAGCCACCTGCTCAAGCC
ACCCTTTCAGAGGGCCTTCCCTGGCCACCTCACCTGAAATAGCACCTCCG
ATTGCACCCATCCGGTTATTCTCCATCCTGTTCTCTTGCTTGGTGATTTT
CCATCACTGATGAGGAAATGAACCATGGAATGCTAGGGCTGATGACCAGA
ACTTTCCCCCACCCCCACATTATTACAGAGGAGGAAATGAGGTCGGAGGT
AAGATGGGCCCAGGATTTCTACTCCCGCCTGGACTGCAGGCACAGCACTG
ACCTCAGCTGTGCTCACTCTTGGCATTCACCCAACCCTTCTATCTCCAAC
TGCCCCATTTACCAGAAAGTGAAATGTTCTCAGAGACGGTGAGCCACCTG
ACTTGGACAGCAGCCCAGGGCCCCTGGCACCCTGCTTTCTTCCTCCCTGC
CATCCTTTCCTCTCCAAGACCTACCTTTCCCTGTGATTCTTGCCCACATG
CTGCATTTCATGGTTTTATGACCTGATTTCTGAGAGGGATTTGAATTTTC
ATGATTATTTATGTAAGCAAATCATTATGCTTATACAAATGAGAAAAGGA
GTGCTTCTGGACTTCCCAGGGACAAAATCTTGTCACTTGGCTTGCTTTCA
TATTGCTAATTAAGGACCCAGGATGTGGGTGAGATGTGCTAAAAGCTGAG
AGGAGGCTCTGGACTCTGACTATGGGCCCACACCCCTGGGCAGGCATCAC
ACTAGTCCTTTAGGTCATCCTCAACCCAGCTTCCAGTTGAATCAGATGTT
TGTGAATAACTCAGCAAGGCTGTATGGGAAATGAAGAATGAGGTGGGGAA
GAGGCCTGTGCAGAAGACACACTGACTTACCCCTCTACCTCTAACTAGGG
TGTTGTAGCAGCCACCCACCCACCAAGTCTGTCTTCCAGACCACGTATGC
TTTCCTCCACCTTTGCATCTTTTATCTTCTGCCAGCCCAGATGCTTGCTG
ACTCCAGCCCAAGCCTATAGGATAAGCTACAGCCTGTCCCTACAGACTAC
GCATTGCAGAATCTAAGACATCAAGTCAAGTTCGGAAGCACTTGCCTTCT
CCTCTCCAGGTACACAGGCTCTCCTGGAAAGCTGGTAGCAGCTGTGGAGG
TGTGGTGTGTTACCTGCTGCAGGTGCAGAGAAGTTGACTTCACAGCCCTT
CAGAAAGACTGCCTTCTTCCAGTTGTATTTGTGTACTTGCTTGGGTGTGG
GGAGGATTCTCAGCTTTCTCCACTCAAATTATCAGACCCTTTCCATTTAG
TGGTAGACCATTTCCCTCGTCCAGGCCAAGGGCACATAGTACAGAGAAAT
AGGGAGTTGTTACCCAGGGAGAGAACTTGGCTCTAAACCTGTAATAGAAA
GGTCAGTTCTGGTCTGGAGGGTCAATTTTGATCTTTGGCTCAGATCCAGG
AATTGGAACCAAGGCTTTTGAACATTTTAATGCAGGGGATTAAAAAAATG
ATACGAGTCATTCACGAATATATTTGCTTAACATCTAAAGAGATCCCTCA
AAACACTAGAAAAAATAAGAACAAAAATCTAATAAAACAAAATTTGTTAA
ACACATTTACCAAATTTTTTTTTTTGGTAAAAATTCAAATGTCATAAATA
AAGCTAAAGTTCCTCTTGATGACTCGCTCCTCTGCCCTATTCCACTCCAA
GTAACCACTATTATCAGTCTTGCCAATACCCTTCCAGACCTCTCTACCTC
TATATACCATTAGAAGCACATGGTTTTGCATTGAGGATGTGCAGTGTTTT
GTTTTACGTAAATGTTATCACTCTGTTCTTGTTCCATAATTTGCCTTTTT
CTCTCAATGATTTGCTTGGCTATCTTTCTATTTCAGTAGCATCTCCTTTC
TTTTTAACTTACCATTGTTTATTTAACCTTGCCTCTATCAACAGATATGT

FIG. 3N'

AGGTTGTTTCTAGTTGATTTCATTAAGTATTTATAAACAACGCATCAGTA
GATGTCCATAAATTTCTTTACGGAAGATGGCAAGTAGTGGAATTGCTGAG
CCAAAGAACATGTTTAAAAAACCCAAAAAAACTAGACGCTACCAATTTTC
TCTCCAAAATGGCCATACCCACTTACCCATACAGAGATGATTTGGAATCT
GGCTTCCTCACAAGGTGAGATGCCTTCACAGTTTCATTCTTCCTGGCATG
TCTTCCCTTTTGTATCTGAGAGAGCTGGCAGAATTGTGTCACTAAATCAA
GGATAGAGGGTCAAATGACAGCTCAAGCTCACAGGCACCTCTGCTTTCTT
CCCAGACCACCTGCTTTCCTGCCACCAGCTCTGTTCCATCTTATAGAATG
GTTGCCACTTGGGTGTCTGCTCCGACAGCCATGTCATCCTTTGCACTGCA
GTTATGAAGCAGACAGAGCTAGGAGAGGGGCTTTGCCAGCCTCTGCCCTA
GCTTGGAGAATTTCAAAGAAGGAGGGTATTGAGAGTGAGCTGCCGAAGAC
TGGCAGCTCCCTCAACTCAACAGTTGTCCTTCCACAAGAAGTCAGATACA
TTTTTTTGGGATAAAATATTTAAAAATTATTATTTATTTCTGAATAATA
TATTTACATGATTCAAAAATCAAACTGTAGGCCAGGCATGGCTGCTTATG
CCTGTAATCCTAGCAATTTAGGAGGCCGAGGCGGGAGGATCACTTCAGCC
CAGGAGTTCAAGACCAGCCTGGGTAACATAGTGAGACCCTGTATCTACAA
AAATTTAAAAACAAAAATTAGTTGGGCATGGTGGCTGATATGGTTTGGCT
CTGTGACCCAACTCAAACCTCATGTTGAATTTTAATCCTCAATGTTGAGG
GAGGGTCCTGGTGGGAGGTGATTGGATCATGGGGGTGGGTTCTCCCTTGC
TGTTCTCATGATAGTGAGTGAGTTCTCACAAGACCTGGTTATTTGAAAGT
GTGTAGCACCTCCCCCTTCACTCTCTCACTCTCCTGCTCCGCCATAGTAA
GATGTGTGTGTTTCCCCTTTGCCTTCCGCCATGATTGTAAGTTTCCTGAA
GCCTCCCAGCTATGCTTCCTGTACAGCCTGTAGAACTGTGAATCAGTTAG
ACCTCTTTTCTTCATAAATTACCCAGTCTCAGGTCATTCTTTATAGCAGT
GTGAGAGTGGATGAATATAGTGCCATATGTTTGTATTCCCAGCTACCCAG
GAGGCTGAGGTAAGAGGATTGCTTGAGCCTGGGAGTTTAAGGCTGCAGTG
AGCCATGACTGTACCACTGCTCTCCAGCCTGGGTGACAGCGAGACCTTGT
CTCCAAAAAAAAAAAACCCAAACTGTGTAAAATGTGTTCATAAAAGTGTC
TTGCTCCCACACCTGTCCCTATATATCTTATTCCTCAGCCTCCGACAACT
ACTTTATTCATTTCTTATGTATCTTCCAGAATCAAAAAAAAAAAATCAAA
TACAAGCACAGTGGAATGTATTGCCCTTCTTCCCCTCCCTTTTGTTACAT
CAGAGTTAGCATATCATAAATACGGTCTGCATTTTCTTCTTTTTCAGCTA
TCAGCATGTTTTGGAGAGGATTTCATATTCGTGCAGACAGCATGTATTAG
TCAGTCCTTGCATTGCTATAAGGAAATACCTGAGACTGCATAATTTATAA
AGAAAAGAGGTTTAATTGGCTCACAGCTTCGCAGGCTGTTCCACAGGAAG
CATGGCAGCATCTGCTTCTGGGGAGGCCTTAGGAAGCTTTTACTCATGCA
GAAGACAAAGCGGGAGTGGATGTCTTATATGGCAGGAGCAGGACTGAGAG
AGAGAGAGAGAGAGAGAGAAAGGATGCCACATACTTTTAAACAACCAGATCT
TGTGGGAACTCTGTCACGAGAACAGCACCAAAGGGATAGTGCTAAACCAT
TCATAAGAACTCCACCCCCATGATCCAATCACCCCACACCAGGCCCCACC
TCCAACATCGGGGATTACAATTTGACATGAGATTTGGGCTGGGACACAGA
ACCAAACAATACCAGAGTGCTTTCTCATTCTTTTCTATAGCTGCCTAGTA
TTCTATGTCCTTTACTTCATTTAGGCAGTCTCTTGTTGATAGACACTTGG
GTTACTTCCAATTTTTCCTATTACAAATGATGTGCAATGAATAATTTTGA
TCATTTTCCATTTCACATGGGTTATGTCCATCTGTGGGATAAATCTCCAG
GAGTGAAATTGCTGGATCAAAGGGGAAGTGCACTTGTGATTTTCATAGTT
AGCAAATTTTGTTCTATAAGGGTCATATCAATTTATAGTCCCACGCGTAA
TATTTAACAGTGGGGATTTCCCGACAGTTTGACCAACAAGGTCTGTTGTT
AAACTTTTGATTTTTGTCAATCTGATGGGAAAATACTAGTATCTCAAAGT
GCTTTTAATTTGACTTTCTTATTACAATGTTAAGCATCATTTTACTCTGC
CCAAGATCAAATAGTATTTTCTTTTCTGTGAACAGACTGTTAAGATCCCT
TGCCTCTTGTTTTGCTGGATTTTTGTTCTTTTTTTTCAAATGTTTTGAGG
CAGTTCTTTACATGTGAAACAAGTTATCTCTTTATCTGGGGTGTGAGTTA
CAACTACTTTTCCTCTGGCTTGTTTTGCGCTTTGACTTTGCTTCTGGTGA
TTCCCGCAATTCTGAAAGTGTACTTTTTGCATCATTCATTCTTATACACC
CATGCTCTTGTTCACGCTGGTTCCTCTACCTGAGGGCTTTTTCTTTTCTG
CTTCTATCTGGGAACATTTTTTTGAGAGAGAGTCTCACTCTCTCGCCCAG
GCTGGAGTAGTGCAATGGCGCGATCTTAGCTCACTGCAACCTCCACCTCC
TGGGTTCAAGCAATTCTCCTGCCTCAGCCTCCCAAGTAGCTGGGATTACA
GGAGCCCACCACCAAGCCCAGCTAATTTGTTGATTTATTTATTTATTTTT

FIG. 3O'

TGTAGAGATGGGAGTCTCACTATGTTGCCCAGGCTGGTCTTGAACTCCTG
GGCTCAAGCGATCCACCCACCTCGGCCACCCAAAGTGCTGGGATTACAGG
CGTAAGCCACCATGCCCAGCCCATGTGTGGAAATCTTCTGTTTATCCCTT
TAGGCTTGATTCTTATGTCGTTCTCCTCCCTCCTTCCTGGATACTCCTCT
TGTTCTTTATCTTACTCTACTTGTCATGTTACCTTGTTTCTGCTTATAAC
TAGCTGCCTCTCCTATCTGAGGAGGGACTTGTGACTGTTCTCATCTCTGT
ACTCCCAGCTCCTAGTACATAGCGCTTGCTCAACAGATGTTTGGTGCATT
GATAGATAAATCACTGGTAGCTGTTACTACCAGTCCTGACTCCCTGCAGT
GCTTCAGCTGATCCTGTTCCAGATGTGCACTGAATATCCTTCTGTTGAAC
AACAGAAATAAAGGGGATGGGTGAGGAGGATAGTCTTCGGTGGCCAAGGA
TATTTTTAGGTACTTTGCAGCACTCAGCAATGAGGAGTGGGCTTTAGTCC
CCCAAGAACTCTCACAGCCCTGGGTGTCTTTACTGTTCAGTGTCAAATCC
AAGACAAGTCAATGATCAGGAAAGACCATTTTTTTTTGTTCAGTGAAGTT
TATTTCAGAATCATTGAACAGTATGATATTTGGTAATTTCATAAATATTC
CCACTTAAAATGATCGGAGCAGATATATTTTCAGTCGTAATTAAAGGACA
TGATTTAAAGAGAGCACACCAGTCCAAATTGAAATGATTCCATAGCTATT
AAAAAACTAGGGTTTTTTACAGACAATGATACTTTTTGCCCCCTTTGAAT
AGATTAGACCAATGAATAAAACAAACAAACAAATAAATAAATAAATAGGG
AAGCGGTTGCTCATCAGAATGTGGGAGCGAATGACAGAGGGTTTCTTAGA
ACCAAATGTGGCCGTGGTTTCTGTCAGGCGTGCTTTAAGTGAGTAGGAGA
GGTGAGAGAGGCCTGGCTCAACAAAAGGGCTGGGGATTGTCCCTGAAGAA
CCAGAGCTGANTTNCATCAGGAGTAACANAGGTAGATAG
>Contig41
CCGCGTTGAGGTTCCACGCAGTTCAAATTATGTCCAATTATCAACATTAA
TGCACATTTTCAATAGAACCTGTTCCGGCTTTTCTTAGGAGGGGGGCGGG
GAGACGTTGTTCTCTGGGAATAAGTGTACGCAGGAGGCTGAGAAGGCTTC
ATTCCATAGCATTCACTTACCTCCAGCTGTAGAGTGGGCTTATCATCTTT
CAACACGCAGGACAGGTACAGATTTTTTTCTTTGAGGCCCAAGGCCACAG
GTATTTTGTCATTACTTTCTTCTCCTTGTACAAAGGACATGGAGAACACC
ACTGAAGAAAGAAGGGGGTCTTGTGGTTAGGGACACAGCAGTGCAGGGTC
ACCCCAACCCCTAGGCCCCATGAGTAGGATACATGTAATTTGGTAGCCTC
TGTGGGAACCCACAGTGAGGTTCCTTGGCCTAAGACACAGGATAACTTGA
CTTCTCACAGACAATAGCAGGGTCATTTTGTTGATTTAGGGTTTCCCCTC
AAAGGCCTGAGGGTTTCTCAGAGCCTCATAGCAGTAGGAACGGAGAATGA
AAGAGGGTCTACATTTTAAATGCTGAAGGAAGGAAGGAAGGAAGCCATTG
TGTCACTGGCTGGCAATGTGCCCATCCACAGGAGCGGAACAACTTGATCA
ATGTGGAAGGAAAGGAAAGAGGTGAGGCTGTACTTCTGCCAGAAATCAGG
CACCAGAACTGTTTCAGGAACAGAGAGTAGCCCATGGAAGAAACTGGGA
GAGGAGAGGCTGAGCTGGGAAAGTGGCTCCAAAGAGAGACACTCATTTTG
ATCTTCCTCAGTCACAGCAGTGTCAATTGGAGGCCCTGGGATCACTCTTA
CTACCCGATTCCAAAGAAACAGGATTTTCTTGGCCTGGCTGAGAGCAAAT
AGCTTCCCCCTGAGTGAGGCTGTCCTTCAAAGTCAGCAGCCTTAGTTGCC
CACACTCCTGTGCAGAGGCTTTGGCTACTGTGGCACGATGCCAGGCAGAT
CACCACAGCTAATGATGGGTTCACCGCACTTGAAACTTTTGCCCGTTACA
GCGGAGAGATATAAGTTCCTGCTGGGCGGTAAAATTTCCCTACAAGGAAC
CACCTGGCATTGGGTGGGACGGATGTTGGGGCAAGGGGGGAAGACTGGGG
AGGGGGATGGACACATTATCGCTCCAGCACTCTTGTTTCAGCCTCAACAA
CAGGAAGAGAGAACCCACAGGCAGTTAGGCCATGTCCATCAAATGACCCC
ATATTGTGGAAGAATTGACATTGCACTATGCCCAAGAGACTTGGGTGGAC
ATGGTCCTGGGAGTGCTTGAGCCGTCTAATTTCTCAGGGTCACACTCCTG
TTAACAAATGCACTGGCCAGTGCAATCAAATGTGCCATTTCTAGGACCAA
AGTTTGTATATTCCTTTTTAATATTTTTTTTCACTTGTGTTGATCATTTG
CCTTAAATTAACTTTCTACTTTGTTTAAAACATGGAGAATTAGCAAGCTG
CCAGGAGGCCAGGCAGGGAAACCAGGATGTTTCCATTTACCTTGTTGCTC
CATATCCTGTCCCTGGAGGTGGAGAGCTTTCAGTTCATATGGACCAGACA
TCACCAAGCTTTTTTGCTGTGAGTCCCGGAGCGTGCAGTTCAGTGATCGT
ACAGGTGCATCGTGCACATAAGCTTCGTTATCCCATGTGTCGAAGAAGAT
AGGTTCTGAAATGTGGAGCACATGTTGTTTAGGTATAAAATCAGAAGGGC
AGGCCTCGTGAGGCGAGGTGGCAAAATTTGATTTCTTGGAGGACACCTGA
GCATATACGGTCAAAGTCTGATGACAACACCAGTAGGGATGAAGCTGGGA

FIG. 3P'

GTGGGGTGGCTAAGAACACTGGACCTGACACTATTAGACATGGGTTCCAG
CTTCAGGTCTATTACTGCTCACTGTGGCCGAGCAACAGAGCTACTTAGGT
AAAATGGTGATGGTCATAACACTAGCCCACAGGGAGGTTACGAACCTCTG
GTGACAATGTAAGTGAAAGGCCCCTGAGAAAGAGTGAGGGAGTTGCAAAT
GTCAGTAGCCATCAAGATCTTCTTTAAGAATAGTTTCCACTAAAGAGATG
ATTGCTTTGGTTTCCAGCCTTCTTTGTTTTGTCTCCCCGCTGGGCCTTCT
ACCTTTAAAGGGCTTTGGCTCTGGGGGAATTGAGTTGGCTGGGGCTTGAT
GACTTCCAAGAGGACACAAGTGGAGATCTACTGCCTGCTCTTGGCTAACT
ACCTTCTTCAAAGATGAAGGGAAAGAAGGTGCTCAGGTCATTCTCCTGGA
AGGTCTGTGGGCAGGGAACCAGCATCTTCCTCAGCTTGTCCATGGCCACA
ACAACTGACGCGGCCTGCCTGAAGCCCTTGCTGTAGTGGTGGTCGGAGAT
TCGTAGCTGGATGCCGCCATCCAGAGGGCAGAGGTCCAGGTCCTGGAAGG
AGCACTGCGGAGAGAGCGAGGGAGGGAGCCTGGTGAGGTGGTCCTGCCAG
GAACCATGCTTTGACATCAGAGAGTAGAAAGCTCAGAGAGGAGGAAAGGG
CTTGAAAGAATCCCGAGCTTCTAAAGATCATCCCTCTCTGGGCCAGGCGT
GGTGGCTCATGCCTGTAATCCCAGCACTTTGGGAAGCCGAGGTGGATGAA
TCATTTAGGTCAGGACTTCAAAACCAGCCTGGCCAACATGGCGAAACCCC
TTCTCTACTAAAAATACAAAAATTAGCTGGGTGTGGTGGGGTGCACCTGT
AATCCTAGCTATTCAGGAGACTGAGGAAGGAGAATCGCTTGAACTCAGGA
GGTGGAGGATGCAGTAAGCCAAGATTGTACCACTGCACTCCAGCCTGGGC
AACAGAGTGAGACTCTGTCTCATAAAACAAAACAAAACAAAACAAAACAA
AATAAAATAAAATAAAATAAAAAGATTATCCCTCTCTGAAGCTCAAGGAG
GTTAAGGGTGTACTCAAGGGCACACAGCAGGTTAGAGGCAGACTCAAGAT
TAGAATGTGGGCTTTCTGACACCTTACAGGCTATTCTTTTAGAATAAATC
CCATTTCTACTTTGTTCATCTTTTTTGTACATGCCCCACCTACACCATAC
ATGTATACCTTCTCTATATCTTTTTGTATCCCTAATGCTGTCACACTATG
ATTTGCTTTTTCATGCAGATGACCATAACATTTTCCATTCACCTATGCTC
ACTCAGCAAGTATTCAATTTTTCTACACTGTTCTTTTTTTTCCTTTTTCA
TAACACTGTCTCATAGGCATTCTGCAAATCCTGTGAGAGTACTTTTTGTG
AAATGTTACCACTTTCCTCTTATTCAGAGAAGCTCCGTATTAAGGCTTCA
CTGAGGTTGCCTTAAGGCATGATAATGGTTCAAAGGCTTGAAAGACAGTT
AAAGAGACCTGTAAGTGCACAAAAGAAAGTTGAGCAGGAGAGAATTTCCT
GCCTGGAGCAGAGCCAAGCTGCTGGAAGAGGCAATGGGGGCAAAGGCCAG
GCAGACAAGCCAATGGGCTCCTCCCACAGCTGCAGCCAACAAGTTATGCC
AGTCTTAAAACTTCTAAAGAAATATGTTTTTAACAAGATTGAGGACTGGA
TTATGAGGCTAGGGGAGGCTATCACAAACTGGAATAAAATAAAGCCAGAG
AAAAGTGGCTGCCTTCCAACCTGCACAACTGACCTAGCTAGGCTGATGGC
TGGGCCACCTAGGAAGGCTACTGAGCATCATATAAAACAGAAGGGACAGC
AGGAATATAACATGGCTCTTTGTAAGGATGAGTCTGAAAAATGACCATTT
GCTGCCCAAATGCCCTTAGCTACAACTGAAAATATTTCAGAACTGGAGGT
TGCAGGATGCTGGAATCTCAGAGATCATCCAGCTCAGCCCTTTATTTTTC
AGATGAGGTCCAAAGCGGGTAAAATGACTTGTCAAGGTCAAACAGCAAGT
GAATGGTTTTCTTTCAAGTCTCAATTCATCTTTTTGTTTATATCATCTAT
GTCTTGTTGTTATAAGCTTCACCCCAGGTAGCAAAAAACTATTCTACTCA
AAAGGGGTAGACATATGTTAGTTCTCAAGATCATCTCTTGGTTTCAGAGT
TTAACTCAAGTGATTGGCATAGGCTGAATCCATCTCTTAAAAGGATAATC
AAATTTATGTTGAAGACTTGGTTGTCTTCCTACTATGAAATGGGAAACAT
TATCACTACTCCTCCCCTGTCACCACCAAGTGTGGCCACCACCACCAACG
TTAGTGAGTGACTGTGGTGATATGATGACCAAGTGGCCAGGTCAGCAAGT
GGTGCAGCCTGTGTCTCACTGGAAGAGGTTAAAGTCTTTCTAAAACAAAA
TACCATGGCATCAAAGTGGCCCAGAACTCCCTTCTTTGAGCTTTCCCTGT
GTTAGAGCCCTTCCTTGGGTTGGGAGTTAAACCCATAGTCTTACCTTCAT
CTGTTTAGGGCCATCAGCTTCAAAGAACAAGTCATCCTCATTGCCACTGT
AATAAAAACAGGGACATGTCTCAATTATGTCTTCTAAACAGGTTTATTTT
TCCTTCCCTGTGTACAAGACTTGACTGTTCATAAGAAACTGCAAACAGCC
TGCCTCTCAAAGCTGCCTGAAACACCTGGCAAGTTTCACAGTGATATGCG
CAGAACAGTCCAGAAGGCAGATTCTAGGCCTGGCAGGTGGGCACCCTGGG
TGCTCCCTGTTGGATCTTGAGGCCTAACCTCTAGCCCAGCAGAGTCAGCT
AAAATCTGAGCTCTCCCTCTCCCTCCAAGCCACACTTTGCAAAGGGATTC
CTTGTATTGTGGGCTTGGAATCTTTTCTCCCCATTTGCCTCTGCAGGAAG

FIG 3Q'

CCCTTGCAACAACACATCTGGATAGCCTCCAGGTCCCAAGGCTGGAGGGA
CTTGTAATGGGAAAGTAGTCTTTAAATCAGATTTACTTGGCACCCTGTTT
GCCACTGAAAGAGGCAATTTAGGGGAAAAATCTGGTCTCCAAGCACAGAT
AACACTCTACTCTTGAAAGAGGAGACCTGCTCATGTTACTGGTCTCAGCG
TCTCCACTGACCTGTAATAAGCCATCATTTCACTGGCGAGCTCAGGTACT
TCTGCCATGGCTGCTTCAGACACCTGTGTAAAAAGGAGAAAATGAGTGAC
TTCCCCATGACGGCTACGTTCATGTGTGATTTCTCTCAGCATCCAGTGCA
TGGCAGTCATGCAAAGAAATGATCTCTGAGTAAATGAATGAATGTGTGAA
AGAGAAGTCCTTTGGGTCTAGAGAAAAGCATTTGCTAAACCAAACCCCAA
CTAGCAATGTATTGGCTAGGAGAGCTGGAGCAGAGGCTTTGACACTAACC
TTTAGGGTGTCAGCTGTTAGATAAGCAGTATCCATTCCCAGAATATTTCC
CGAGTCATAAGCATTATATTACACCTGGCATTTTTGCAAAAAGCTGAGAG
AGGGAGGCAGAGAGGGAAGGAGAGGGAGAGACAGAGAAAGAAAGAGAGAG
AGAGAGAGAATATGCATACACACAAAGAGGCAGAGAGACAGAGAGACTCC
CTTAGCACCTAGTTGTAAGGAAGATTAAAGTCATACTTGAGCAATGAAGA
TTGGCTGAAGAGAATCCCAGAGCAGCCTGTTGTGCCTTGTGCCTCGAAGA
GGTTTGGTATCTGCCAGTTTCTCCCTCGCTGTTTTATAGCTTTCAAAAG
CAGAAGTAGGAGGCTGAGAAATTTCTCTGTTGAATACCTGATTTCACAAT
CAAGTTAAAGGAAAGGGGAAAAGAGTATTGGTGGAAGCTTCTTAGGGGAG
GGGACTAATAAACTGAGATAATTCTCTGGTTCATGGAAGGGCAAGGAGTA
GCAAACTATGACACATTTTGCAAATGTATCACCATGCAAATATGCATTGT
TTTCCTGACAATCGTTGTGCAGTTGATGTCCACATTAAAATACTGGATTT
TCCCACGTTAGAAGAATGTTTAAATTTAGTATATGTGGGACAAAGTGGAA
GACACACAGATTTATACATGCACATACTTTTCTTCATTCACTTCTTTGTA
CTTAAGTTTAGGAATCTTCCCACTTACAGATGGATAAATGGGTACAATGA
AGGGCCAATAGCCCTCCCTGTCTGTATTGAGGGTGTGGGTCTCTACCTTG
GGTGCTGTTCTCTGCCTCGGGAGCTCTCTGTCAATTGCAGGAGCCTCTGA
GGAGAAAATTGACCTTTCTTGGCTGGGGCAGAGAACATACGGTATGCAGG
GTTCAGGCTCCTGACGGAGTTGGGGCAACCCTGGAGATAAGCTCACACAA
CCCTGCAAGACCAGGTGCTGTTACCCTAGCCAATCTCATGGATGAACCAG
ATCAATGCCAGATGAGCTCTGCCTAAAATGATTTTTTGGTGAACTCTGAA
AAGTGGAATATTGTTTCTGTAAGAATATCCATCTGAGACTCTATCTCTTG
GTAATACCAAGAGTTATCAGTTTCTCTTTAACCGAGACACCAGCAAAGTG
CCTGCTCCAGGGTAATGCCCAGGGGAGCCCTCCATTTGTAGAATGAATGA
GAGTCCAGGTTATGAACAGTGCCTGGAGTGTAGGAACACCCTCCTTTGCC
TCTTTGACAGGTCTGCATCATAACACTTTTTTTTTTTTTTTGAGACAGAG
TCTCACTCTGTCGCCCAGGCTGGAGTGCAGTGGCACGATCTCGGCCCCCT
GCAAGTTCCGCCTCCCGGGTTCACACCATTCTCCTGCCTCAGCCTCCCCA
GCAGCTGGGACTACAGGCACCTGCCGCCACGCCCGGCTAATTTTTTGTAT
TTTTAGTAGAGACAGGGTTTCACCATGTTAGCCAGGATGGTCTCGATCTC
CTGACCTTGTGATCTGCCCGCCTCGGCCTCCCAAAGTGTTGGGATTACAG
GCGTGAGCCACCGTGTCCAGCCTGTAACACTTCTTATAGCACTGAGTTGA
AACCTTGCTCCTCCTGGTTCCTCCAGGAAACTGAAATCTTTTTGAGCCAA
GTCTAGCACAGTGCCTGGCATGTACATTCAGGTGGTAGAGTTTGCTGCTT
GAATGGGTGAATGGGAATTTGACAGCATTTTTATTCAAATTAGTATGTGC
CAGGTATCGTGCTCGCTCTGCATTATCCAAGGGAGTGAGCCTCTGTGCAA
GTATTTGAGACACGAGGGAAATAGGTTCTACTGTGGGAAAAAGAGCATTT
CATGGACTTGCTCTCCAAGCAGCCTTCTGATTTTTAATTTGGCTCCCAGT
ATCTTGATATCAGGAGTCAGTCACAAGAACTCCATCTTTAGTAAGTTATA
TTTTCCACAGGAAATCTAAAAGCTGTTCAACATGTTAGTTTCCTGTGAAT
TTGATAAGCCATAATCCATTCCTAACACTGAGCCCTCCTGAAATTTGGTG
TCTGGTCCTGCAGATAGCTAAAAGCCCTGTCTGGGTGGCCTAGGGACTCC
TCTGTTTTGCCTCCACAGGATCCACTTTGCAAATTAACCACTGGTTCTCC
CGTTGTAGGAACTGCCACCTTCCTCAGAGCCTGTCTTTCTTCCTTCCTTC
CTTCCTTCCTCTTTCTTTTTCTTTCTCTCTCTCTTTCTTTCTTTTCTTTT
CTTTCTTTCTTTCTTTCTTTCTTTCTTTCTTTCTTTCTTTCTTTCTTTCT
TCCTTTCTTTCTCTTTCTCTCTTTCTCTCTTTCTCTTTCTTTCTTTCTCT
CTCCCTCCCTCCCTCTCTCTCTTTCTTTCTTTTTCTTTCTTTTCTCTTTT
CTTTCTCTCTTTCTTTCTCCCTCCCTCTCTCTCTTTTTCTTTGTCTCTCC
CTCCCTTCTCTCTCTCTTTCTCTTTCTCTCTCTCTCTCTCCTAGACAGGA

FIG. 3R'

TCTACCTTTATCCCCCAGGCTGGAGTGCAGTGGTACAATCATGCATTCAT
TGCATGATCACAGCAGCCTCAAACCCTTCCTCAGAGTCTTTATGCGGCAA
CCAGCAGGGTCTGGAGGGTTGGTGGCTCTGTGAACTCTCCTGACAGAACA
CAGAGATGTCTTTGGTCTGTTGATGTGATTACAAGCTGAACGAAGGAAGA
TCAAAGCCAGTGACAGGAAGGGAGATATGCAAGGGACCCGAGCATCAGCT
CTGAGTTAGTCCATTCTGCTTCTGGGACTTGGGATACAGGTCAGAAACCT
TGAGCTTCTACTTCTCCATCTTCCAATTGTAGCATCCAGGACCTCAGAAT
CTGCCAGCTAAGAGGAGCCCTAATGATTGTCTGGTGGGATATGGTGGGAC
CACAGAGATGAAGACATGAATAGCTATTTGAATGTGAACAGCAGACGAAG
AAATCAAGGCTAGGAGGGTGGAAGTGACTCATCCAATAGCACAGTGTGGT
TGAAGCAGCACTAGTATCCAGGTTGCATGAGCCCCTGATGCTTTCGCTCG
AGGGAAATTTTGGAGCCATGGGGCAATGCCCCCTGACGTAACAGTCTCCA
CAGTTCTGCCATGTCTCATCCTGGCCCTGTAACCTGGACCCAAATCTGCT
ACCATCCCATCCATCTCAGGAAGTGAAACCTCTTATGTCAAATAGGTTGT
GCAACGTATGTATCAGATCCTGTCTTCCCAAGGAGACCGCTCAGGCCACA
GCACTTCCTTCCGATCCCCAATGAGCAGAAAATATCTCGCTATAAACATA
GTTGGCACTAAGGGAGGGAGTGGAAGAGTGATGATGATGTAGATGGTGAT
GTAGCCCCAAGGAAGTGGAACAAGCAGAGATGGGGAGCTGGAAATGCCAG
GATGCTCCAGCTTTTGGGGAATTATTCAGCTCTTGAGTCACTAAAGCCTT
TCTCAGCTGCAAGTTCCTCTTTACCCTGTCAGGTCATTCTTCCAAGACAG
GAGACTGACATTTATTCAAAGCAGCAAGTGCCCTGATACCATCTTGTGTC
TAATCATGGGCTTCGCAGCCAGTTATCAAGGTTGATCTCATCTCATTGGT
CTTCAATCATTTTGAACAAGAAGACAAGCAAAATAATCATGGGTTAGTTC
TTATATTATTGTGTGTACATGCAGTGATGTCTGTTCTTTGTAGTGAGCTG
TTCCTTCCTTGTTCACCCTCTTGCTTAGAACAGAACTAAGCAATCTGCCC
CCAACATTTTCCCCAATTTCCCATCTCATTCTTGGCACTGGCTTCCTAAT
ATTTGTTCTTATGAGTCATTTTCTTGTATCATTTCCATGAGTCCCTCTGG
GATCTTAAAGTATGAAAAATGTTGTGTGTACCCACACCTGTCTTTGTGGA
TATTTCTCTCCTTTCCCTTCTGCTTCTGGGATTATTTGGGAATGGGCACT
ATGATTTTTATCATATCGCTTCCACTTCCTTTATGGCATCATCTCCAATG
GGCTTCTTCTCCCTCTTGGATCCAGGTTCTCAGATTGGGGACATGCAGAG
TCCAAGGAACATTCCATTCTCCTCCCTGGTCTAGAACAAGGAGGGCTTAG
ATATATGAGCAGGTGGCTGGGGCTGGCGAGCTATGTAGTCTCCAATGGCT
TTTCCCTGATGTCGGAGTTGTTATGTCAGTTCTGGGAGACCAATAAGACC
TTGTCCTTCCTTTGGATCCATCAGAAAAAGCCCCTGGGTGGGTAAGATGG
ATGGCAGGGCTCTCCTACTCTATGTCTTTTCTCACACCTAGTGGGTATAA
GAGAGGGGACCACAAACAGAGGGGGCTCTGGTACCACTTATCCAGGGTCT
GGAAACATTTTCTGTAAAGGGCCAGATAATAAATGTTTCAGGTACAACTA
CTCAACCTTGCATCATTTCAGAAAAGCAGTCAGATAATACATAAATGAAT
GGGTGTGGCTGGACTTGTCCTGCGGTCCCCTGTCTTATATCATTGTATTA
TATCATTTTTTCTTACATACAAATTTAGAAGCAATACTTAAAAAAAAAAA
GCCGTCCTTTATTGAGCACCTACTAAGTGCCAGGTACCTTTTTTTCCCTC
ATTATCTTATTAACTCTTCATAATAACCTTTAAAGTAGATAATATTGAAC
CATTTGACCTATGCAGAAACTGAGGTTGAGACAATAAATTATTTAAGACC
GCACAAACAGTAAATGCTGGAACTACGACTCAAATATGGGTTAACTGAAC
CAAAACCAGATCTTTATTTCTCACTTTTAATTGTTACATATGTTTATTGC
CTCATCTCCTGTCCACATGGTGCCCATCGGCAGACTCCTTTCTCATTCTC
AGTGATTGAGTGACATTCTAAACTACATTGGCCTGGCAGATTCACCTCTG
TCCCCTAAATGTTTCCACATTGTCCTTTTAGGATTGAGATCCTCTCTGTT
CCCTTGTCTTCCCTCCTTTCTTCTTCTGGCGGTGACGTGCTGTGTGAATT
TGTTTCTTTCTCCTCTCAGGGTAGTACTGGGACTTTCCAAATCAGGGTTT
TTAGTGATCTCTCTTCCCTTTTCTGAGTTTCTTCCTTATTCCCATTCACT
TTCTCATCTATAAGTGGCAGCTTTGTTGCTGGAGGATTTCCTTTGTCCTT
TTATTCTTCTTTAAGACTTTGTCATAACTGTCAAAAGCAATCCCTTGAAG
GTATCTGTCCTTGGAATTGTGTGCTTATGATGCTGAAAAATACTCTCTTC
CTAAAGCTATTATAAATGCT
>Contig42
GGCTAGCTGCAACTCTTGAATACAAACACATTCAGACATGCACACACTTT
CTGGCTCCCAAAAAGAAAAAAAAAAATCAATTTATAATAATTCTGATCCT
TTGCTTATTTCCACAAACTCCATGAAAATTGTACATTGTCCAAGCAACAT

FIG. 3S'

TTCTTAATATTCTCTTTTTCTCTCATATCCATTTTCCTTACTGCTGTCTC
CACCTATCTCTTCCAAACTCCCTGTTAAAATCCCTGCCCCAGCGAACTTT
TATTCAATTTTGTGGAATGGAGGCTGCACTGATTTAAATTAAAAAAAAAA
AAAAAATCCCTACTCCATGTCCCAGATCCCTAGTTGTTTTTTGTTTTTTG
TTTTCCTGAGACAGGGTCTTGTGTCTTCCATGCTGGAGTGCAGTGGCATG
ATCATGGCTCACTGCAGCCTCAACCTCCTGGGCTCAAGTAATTCTCTTGC
CTCAGCCTCCCCAGTAGCTGGGAGTTCAGGTATGTGCTACCATGCCTAGC
TAATTTTTTTCTTTTATTTTGTAGAGACACGGTCTTGCCAGGTTGCCCAG
GCTGGTCTAGAACCCCTGGGCGGACGTGATCCGCCTGCCTCGGCCTCCCA
AAGTGCTGGGATTACAGGCGTGAGCCACTGCTCCCGGCCTTGGGTGCAAA
TTTGAGCTTTCTCACTTATTAGTGTAAGACATACAGCTAATTTCTAAATC
TTCCAAACCTCAGATTTTTCATCCATGAAGTGAGGATTATTATAGAGCTC
ACTAATAACATGGCTTCAAAAATATATAATGCCAAAATTGAGATCAAAAT
AATAAATCTATATTACATGGGAGATCTTAATGTACCTCTTATATTATTGA
TAGACTAAGATGATCAAAAAAATAGAAAGAGAGCAGTAAGGAGAGCAAGC
ATTTAATCAATAGGACCAATACATTTTAATCAATAGGATCCTCAGGAATA
TATACAGAATACCAAACCTAACAACTGCAGAAAACATGCCAAACATTTAG
GTACAGACATTGTTGGAAAATGCAATCTTGAAACGAGTGGACTGACATTC
AGAAGATATTAATAAGAGCACTAATGATGGGGATTGCAACCATGTCTTTA
CTGACTTCCAGAAGCTTCTTACAGTAAACATGAAATCACATAATTTCTTC
CACTTTCCTACTGTTTCTTGTTCTGGGCTCTGTCCTGCTTACTGTCTAAT
ATCTTGGCCCCTTAAAAGTTGCTAATCTTCCAAACCTCATTCCTGTGACT
GGGCCGCTGGTCCTTGTTCATGGGCCTTGAAAATACTGACTGTACACTTA
TCTGGAGCATCCAGTGCCTACCACCTGACCCAGATTCCTCATTGCGCTCC
TCCCTCCTCCACCTATTGGAATTTGCTCATACCCGTGTGAGACCCCTCCC
TTTCCCCCCATCTGAATTTTTATCAAGACAACGCACTGCCATACTCCCTC
GTACCCTGCTCTGGGCATCAGACTGAATGTTTGTTTCCATTGAGGATCTG
CAGCTGCATCAGTTTCCCCAGCACCGTCCAACCCCTTGAGCATGGCTAGT
CCTAAAGCAGAGAATTAGCCTTTCTATCCCTGCTGCTATACATGCTGGGA
CAAATAATAAGAAATGACAGCATTTTATGATAATGCAGGCTGCAGGAGGC
AGGAGGCAGGAATCAAATTCGTGCTTATCAAATAGTGCTCCAATTCTTTG
AATATTGGACTATAGAATATGTCATGGATCTATGCTCAGGTGGGTTCCCT
ATTACTCACTCCACTGAGGCCAGGTTGTGGGATTAGCTGTCCAAGAGGGA
GTTTCAGTCTCACAGCATAGGGTCATTCTGAGAATTACTGGCCCACACTT
GTGTGGAGACCTCCAGAGAACAGAATCTGGGTTGGTGCCATGTACTTCCA
GGAGGAGAGAAGTGGCAGGATGCCCAGCCCCACAATCAGAGGGGAAGGGG
CAGAGCCACATGTATGAAGATCCTCTCCCCAGTACGTGCCAATCACAGGG
CTTCCTAGCTTTTGGGCCAAGGAAACAATGTGGGAAGCAAAAAAGGACAA
TTTTCTCCTCCCTTTGCATGAAGACTGAGCAGTTTTACCAGATTCCCAGG
GAAACACCCTTCCACTCTGGGTTGAATGTGAGTGAGAGACATTCAGCTGG
AACACTAGAAAAACTATTTCCTGAGCCACTCACCTTTAGCCCTAGAAAGT
GTTGGATTTGTCCTTCATCTTTGCCACAGTAGAGACTGCTGATAGCATCA
GAACTTGGGCTCTGGAATTAGACAGATATGGGTACAAATCTGAGCTCTCT
CACTTATTAGTGTGGGATGTAGAGCAACTTTTAAAATCCTTCCAAACCTC
AGACTTCTCATGCATGATGTGAGGATTGTAATAGGGCCCACCTAATAGGG
GTTTTTGAGAATTAAAAAAGTTATTCAATGAACAGCATTTAGCAAGATGC
CTGACCATTGAGAAAATAACAAATTGTTTATTATTATTGTTATTATTAAA
CATCTTTCCTGCACCTTCTGACTGGGGGCATCGTATCATCAGAAATACTT
AGGATGGGATGGATTCCTGCATGGGCTGAGTCAAGGGTGCAATAATGGAG
GAGTGAAGAAGGAAGAAATGGAGGCAGAAATCCCCAGGAGCCCAGCATGG
TACAAGGCTGAGCTAGTGCTGCAGAGCCTCCTTGGAACAGCCACAGAGCT
TGCATCTGGCCCTGGGAGGAACCTCTTCTAGCTGGCAGGACCAGCCACAA
CAGTGGCCAGGGGATTTCCCAGGGCGTGGGCTCCTAGGAGTTCATTTGGA
CCAAGCCTGCCTGGAGAGGGGTTATAACAGGGATCCTTCCCTACTGGCAG
GTGATTTACCCCTCGGTGAGAAGCTCAGGCATTTGTTTGATGGAAGGTGG
AAGGCCCTGTGCTGGGCCAGTGACTATCAGGGATGGGCGGTGGCTGGAA
AATAGCAAATAAGACAATATGATAACACAGTTAACCACCACACTATGTGA
AGCTACAATATGGGTATCTGTAATAGACAATTCCAATGTAGAGAATAATT
CTAAGGTGTCATTCTCCCCGCCAATGCCATAAGCACACGGCCTCTGCCTG
GGTTTCTCACTGTGGAATGTCCTCCTGGTCTCCTCATGCCCAGAGAGTGG

FIG. 3T'

GAAGTACTCCTACTTTAACACCGGCTTTCCTGTCATCTCCCTGCAGCCCT
CCTCAGCCCCCTCTGCACAGGGAGGTTTCCTCCCTGCTGCTGCAGTGCTT
TGTACTTGTTAGTGGTACCTGCACACAGGTATTGGTGTCCTTGTCTCACC
ACCCTACATCACTGTAAGCTCCCCAGGAGCAGGCTTCCTGTTTGACTCAC
CTGTGATCCTCCACCTCCCACCCTGTAGTGCCTCAAGCATTGAGGACAAT
CACTGGCTGCCCCTTAACCCAGAAATGCTGCCGAGACAGGAGGCCATGGC
CCAAGTTCCTGGAATGGGGTATTACTATGTCAGCACAAAGGCCTTTGCAC
AAATGAAGGCTTTAAAAATGCAGTCCTAGTCAGGTGGAGGAGGGCTTATA
GGATTCCCAGGAATCTGGATCATTCTCTTGAGAGCTTTCCCTTGTCTCTG
TTAAAACTCACATCCTACGGCCCAAATAACAACAAAAAATGGATGTAAAT
TCTTGAAATAACTTGTGGATGGGGGAACAAGGCCCACCCCCCAGATCTGC
CAGAAGCTTCAGGTGAGGGTCCCAAATGCCAAAAAGTCTGGTATCAGAGA
GGATGGCCAGTGACCTGGGGACACATGCCCTTTGCTGTGTCACTCAAGGA
GCAGCAGCCTCGGCCCCGCACAGTGACCAGGACCCTGGCTTCCCACGCTG
GGCAGGAGCTGGTGTCTGATGAAGGGAATGCCTGGCAGCACGTGCTGTCT
GTCTCCTCGTGTCAGCTTACCTGGCTTTGCTGCGAAGAGGCCACTCGCAT
TTCTCAATTTTTTATATTTTTTTAATTTTTTAAATTTTTTATTTTATTTT
TATTTTTATTTATTTATTTATTTTAATTTTTTTTTAATTTTTTAAATTA
TGCTTTAAGTTTTAGGGTACATGTGCACATTGTGCAGGTTAGTTACATAC
GCATACATGCGCCATGCTGGTGCGCTGCACCCACTAACTCGTCATCTAGC
ATTAGGTATATCTCCCAGTGCTATCCCTCCCCCCTCCCCCCACCCCACAA
CAGTCCCCAGAATGTGATGTTCCCCTTCCTGTGTCCATGTGATCTCATTG
AATTTCTTTAAAGGTGGAATCTCTCAGTGGGGTCTAATCTGTTCAGAAAT
ATCAAAAGAGTATCCTTGGGAATGACTGGAATTCCAGAGTCATCTGGTAA
TCCTCATAAAACAACTCCTGGATGTCTCTCAGCACATCTCCCACCTTGAA
CGCAGGAGGCTGGTTCAAATGGAGGAGCATCGCTCTACTGCACTTTTTTT
TTTTTTTGGCCTAAAGTGCAAAAGGGGATACGTTTCATGTAAATAAATCA
ACTGCAAATCGCTAGTTATGCTGAGCCCTGTCCCGTGCTGTGGACACAAA
GGAACCAAAGGCTTTTCTCCCCGCCCAACACACACACATAACACACACACAA
AATCATAAAAACATACATACCCCCAACACATAACAACACACAACACACAC
ACAAAATATATACACACAACACACACCAAACATGCCCACAAACCTGTGTC
CAGAGATAGATCCTACTGGTGGGTTTGTGGTCTCGCTGACTTCAAGAATG
AAGCCGTGGACCTTCGCAGTGAGTGTTACAGCTCTTAAAGATGGCATGGA
TCCAAAGAGTGAGCAGTAGCAACGTTTACTGTGAAGAGCAAAAGGACAAA
GCTTCCACAACCCAGAAGGGGACCCCAGCAGGGTTGCTGGTTGGGGTGGC
CAGCTTTTACTTCCTTTTGGCCCCTCCCATGTTCTGTTTCCATCCTATCA
GAGTGCCCTTTTTTCAATCCTCCCTGTGATTGGCTACTTTTAGAATCCTG
CTGATTGGTGCATTTTACAGAGTGCTGATTGGTGCGTTTTACAATCCCCT
TGTAAGACAGAAAAGTTCCTGATTGGTGTGTTTTACAATCCTCTTGTAAG
ACAGAAAAGTTCCCCAAGTCCCCACTGGACCCAGGAAGTCCACGTGGCCT
CACCTTTCAACTCCATAATGGCATGAAAATACATATGTTGTACAAAACAT
ACATACACAAAGTATACATGCATCTCCCCAAATATACACATACCACAGAA
ACATACACACAGGAACTCAGCTACCTGTCAAAAGTCTGCATGGTGATTGC
CTCTGCAGTGAGTAGTTAGAAAAGTGAATTTGTTTTTCAATAAATTGGAG
TCCTTAAAAATCGTTGTAAGATAGAAAATTTTTAAAAGTATATAAAATAA
AATATGTATGTCCTTTGGTCTAGCATTTACACATGTAGGAATTTATCCTA
GTGGAGTAATCAATGATATATGCAAAGATTTGGACAAGCATATTAAGCAC
AGAATTATGTATGCATATGTGTGTGTATATATATATATATCTCATACATA
TAATAATGTAAAAGTGAAAATAACTCAGATGTTCAAAATTGAGGATTAGT
TAGACTATGATCTGTCCATATGTGACATACAAGTTAGCTGCCCCTTATTC
TCTCGAGCTTCAACCTCCTATAAACAGTGTCCCTTGTATATCAGTATTGG
TACAGATAATCGAACTTATTGAGGTTTTACATGGGGCAATAAAGGCAAGA
GTTTATGAATACTCCATACTACACTAGGTAGCACCCCCTATTAAAGACAA
ACTCTTCTCTCTCATTTCCCTTCCTTTCCGGAACCACTTGGTTGAATCTC
TACAAGTCTCTATTGCAACTGCCTCAACATGGCACCCTCCCTGCATCTCC
ATCTTCCCTGTCCTGAGAGCAATGGCCTGCTGCCCCCACACTCACATCCT
CATTCATTCCAGAAGTGAGCACCACAGAAGTGCCTACAGTTACCCCAACC
ACCTTCTTAGAAGATAAGTTAGTGTTTGTTTTGACTTTTTAAAATTTTTA
CTTCCTCTTTTCCTTCACAATCTCATCCCATCCCAAGAGGTTTATCAAGA
AGTTCTCTAAAGATATGTGTCTCCTTATGGAATTTAACAGAAATCAGGGA

FIG. 3U'

TTTGTATTCTAGCCATCAAGGGAATAACATTTTTCCAGGTCTTTAGACAA
ATAATGGAATACCTTGCAGTAATTAGATACACTATTGTAGAAAAGTATTG
ATGAAATGGAACGATGTTTGAGATATCATATTGAGTAGAAAAGGCAAGAT
ACATTAAGTAGGAAATGTATCTTACAAAATAATTTGTCAGACACACTCCT
ATATTTGTATGTTATATAAATGCGTATGTGAAGAAAGGCTAGAGGATGAG
ACCACAGTCTTCGGTGAAGTTTAAGAGATGATGCTGCAGCATGCTCAGAA
AGGCTTGGTATAGTTTTTTCCAGTAATTAAGGACTGATCTTAGGTAAATT
GTCCATCCTCTCTAAACTGCACCACCTTTTGTCTGTAAAACAGGAAGGAT
GGTATTTACCCCCAGGGTCATCAAAGGATTTGGTTGGAGAAAAATAAATA
AATGGGCTGAGCCCAGACCTGGCACAGTGAGAGCACAGTGGTTGACTATT
GTGCTGGCCTGTTGTTCCTGTGTTATTGACATGCTGCTGGTGGTGGTCCA
GAAGCTATTACCTTAATTGGTTATGTGGATTTCCCCTCATACTGAGCAGC
TGTGTGTGGTGTTGTAAAACATAGCCATACACAGTAACTGACAAGGGCAA
ATGTGATGGAAAAATGCAAGGAAGTGCAGATAAATAGCTAATGGGCTGTA
GAAGGAAGCTAGTCCTTGGAGGGCTTGATCAAGGAAGGTCCTTTTGCATG
TCACCTTTGAAGAAGAGGGGACATAGAAGAGGTATAGTGCATCCCGGAGT
GTACCTGGAAGGGAACATGAAAAGAGGACATTTTTCTCTGGGACATGGGG
ACTCCACTTGCATGAACTCTGGAATTGGGGCAAAGAACCATCATGAGAAC
AAGGGCTTCCTTGAACCTCCCAGGCTCATTGGCTGATCTAAACCCTGTGT
CCCCTCTTTCCTTCACTCTCCTCTGTTTTCTATACCTGTATTATTGGACT
GGACTGGAAGCCACCTGATCTATCACAAGTACCTTGAAATGTGTTGAATA
GGTGTGGCACAGTCCTTAGCAGAGTGGCACTACCCCCACAGGAATTTGTT
TATACCTTTGGCATGGAAAATAGCAGGAAATGAGTGATCACTGATAACTG
AGGATGCTATTTATTATTGGCCAAAGGAATACTTGTGTTGTATTTGCATA
ACCACTCACAAACTGTTGATTACAAATGAGTACCAGACCTAGCTCCTTCA
AGTAAAGGATCTTGAGAACTGAAGGCAAACAGAGCTCCAGGAGTCCAAGA
CAGAGCCACAGACCACGAGGATCCCTGGCCCAGGTAGGTGGTCCTCCTGC
ACTGGCTTTCAAGGCCAACAGGATGGATGGGGAAGTAGAGTAGCATCTGG
CCATCTAGACCCTTGCTTTTTATCCCCACTGGAAGCACATCTGAATTTCT
AAATATGATCTCTGAGACCTGCCCAGAACACCTTGCTCTCAGCCCCAGTA
GCAGCCTGCTCTCTCCCAGGAGGGCTTCCACTAACAAGTAGGGCATTGCT
GGAGGGCCAGGCAGACACTAGCTTAGGAAATCCACCAACCCTGGAAATGC
TAGTCCCTTCTCTGAAGGCTCAGAAGACTGACTTTAGAGTCTAGAAAATA
TTGGTCCTTGGGAACAGATTTTGAGTGCAAAGAGATGGACTTCAGATGGC
CAGATGCACTGCTTCTTTAGGGAATTCTGTGAAAGCTCCCTGCATTTATC
TTAATACAGGCAGCAGATTTCATGAGTACCCCCGAGGGATGGCCCCAGGT
CCTCCAGCCTGTGAGCATCCTTCTGTCCTTCAGCAGCACCACAGTATCTT
TATATGTCTTTGGATACCTACGTTTCTGCCAGACATCTCTTGCTCTGATG
TTCTGGCTGCCAAATTCTCTGTCAAGCGCCTCCAATTTTTTGTGTCCTTT
GATTTACCCCAACATGACAAAGGCAGTTGTGCTTCATGTATTCAGGGATA
CTGCCAAACCACAAACAGGTTAAAATCAAATAGCAGATATCCCTGTTCCT
AAAGACCCATCAGCTCTACCCACCTGCTCCTGCTCACCGTCCTTATTGTT
GAGTCCTGAAGCCCTTCCTTGTCATTTTTATTTTTTGCATGAACAATTTA
GTTCCCTTTGTCTCACTCCTAAACCTTTCTCAAAGGATTGGATTTGTACA
CAAACTGCCTATCTCTGCAATCTTAGAAGTGATATGATTCTGAACAAATC
ACTTAACTTTTGATTTTTTATTGGTAAGATGGGAATACCAATTTTTGCTC
CACTTCTGTCCTATGTTGGCCTGGGCTGATGTTGAAAGCTCTCGGTCAAC
TGAGATAGGGTGTGCAGAATTTATATATATAAATATATCTCCTCCAACCC
CTCCCAATGAAGCAAGTCACGTGAGTCAATCCTACCCTAAGATATTAGGG
ATTGAGCCTCCTGGGACATTTGGTGGCTTAGGTTTTCATGAAAAGAGGTT
GCAGAGCAACTGCTTTTTGTTAGGCAAAGATTAGGCTACTGCAGAGACTC
AGCAAACTTCTATAGAAGGTGTCAGATGGTAAGTATTTTAGGCTTTGCTT
GCCAGATGATCTCTCAACTAGTTAACCATGCTATTGTAGCCTCGAAGCAG
CCAGAGACGATCTGTAAACAAGAGCATGTAGTGTTGGCATAAATATAGTA
CCGCG
>Contig43
GCAATAAGTCTATTTACTGTAAAGTTAATCAAATTTACATTTCAGAACAC
TTAATCTGCAAGAGTCCTTTCCAAGACCCTATACCTAATTTTGTGTTTAC
AATTTTATATTTGTTTTCTTAAAGAAGACCACCAATATAAACTATATCCA
GCCTTCATGATAAGTACATAAGAAACTATGCAAATAAGGGGGAAAAAAAA

FIG. 3V'

CAAAGAAAAATACCTAGTTTACTAATGGTTCACTTCTGAATAGCACATAT
TCATAATGATACAAGCACTCATTACTAGTCTAGGAAAATGAAGATATAAT
TGCATTAGGAAGATCAAGAGGTAGGAAATGTGGATGTGTGTGGTATAGAC
TAGGGCAGGACAAAGAACCTAAATCCTCATTTTCTAAAGATAATTGTTAA
TACGTAAAACTCAAAATTCAAGAAGTAACAGTAAAAGCGGTCATTAAGAA
ACAAGCACTAAACACCAGATAGGAAGCGAGAGATGGGGGAAGAGGGCAAG
AATCTGATTATTTTTTGCAACAAATTTTGTAAAACCATTTGACTGTTTAC
ATGTAGAACTTGGATCTTTTTTAAAAAACACAAAATAATAATACTATTAT
TTTTTAACTGGATTTTTGAAAAAGAAGATAAAAGTCTCATTTTAGTAATT
AAAACTCATTCCAGGTTAGTCCACTCAAAACTTATATTCGAAAATTAAAA
CTTTGGGAGGCTGAGGCAGGCAGATCACCTGAGGTTGGGAGTTCGAGACC
AGCCTGACCAACACGGAGAAACCCCGTCTCTACTAAAAATACAAAATTAG
CTGGGCGTTGTGCATGCCTGTAATCCCAGCTACTCGGGAGGCTGAGGCAG
GAGAATTGCTTGAACCCGGGAGGCAGAGGTTGCAGTGAGCCGAGATCACA
CCATTGCACTCCAGCCTGGGCAACAAGAGTGAAACTCCATCTCAAAAAAA
AAAAAAAAAAAAAATTAAAACCTCTGGAAGTTGAGTTTGCAGATATTCAT
TATGCTCATTTTTAACTTGTATGTTTGGAAAATGTCATGATGAGAATTGA
GGTTGGGGGATGAGAAAAAAAGAAAAACATCAACCCCACAGCCCATTCAA
TTTTCAGCCCGACCCACAGCTCCGGGGAAGGGCAGCAGGTCCATCCTTCA
CTCTTTCTTCACCTCTTTCCCCTCCTTCTGGCTCTTCCACCTCTAAGTTG
GAGCCCAAGAAGAGGCACTGGGAAATGGAAAAGTCTTTTGTACGTGGTAC
TTGCCGGGGAAGCTGCCATGAAGACCTGGCCCCACGGTGGGGAGGGAATG
CCCAGCTGAGGCCTCGTGCCCATGCTAGGATAGACTCGTCCAGACATGTC
AGGTGGTCTGACAGGGCAAGCAGCAGGAAGTCATGTATGAGTATGAACTG
ATCTGTATGCAAGGGCGGGGAGAACACGCGGAGGAATGGGGCGTGAGAAA
ACAGCACAGTACGTTTCTTTAGCAGCTGTCTCTGCTCAGCCATGGGAGTC
ACCAGAGAAAGAGGCTTGGAGGCGTTATTTCACTGTGAGATGTGAGTGT
AAAAAAGTGCCCAAGACACAGTGAGTACCAGGGAGATGCCCTCTTTCCCT
ACCCGAATGCAGAATGGCCACAGGCCTTAAAACACACACATGGTTCCTCA
GAGGAGAGAGGCCTCCACAGTGGACACCCGCATTCTCCCCTGGTCAGCAG
CAGCAGGGCGAGTGCTGGGCCATCATGAAGCTTCACAGGCAATGAGCTCT
CAGCAATAACAGGAACAGTGCCTGGGGGACTGTAGCTGCAAGACCGATTT
TCATGTAAGATGGCCTCTGAGGACTCCGAGATACACCAGGCTGAGACTAG
CTGGCAGCTCCAAGTTCTTGGTCAGAAGAGAACAGGAACTAGGGAAATTG
GAATTACTGTTACTACAATTCCTTTACATCCGCACAACCATGAGGTCCAG
AGAGTCTCTCTTATTTTTTTTTAAAGACAGGGTCTCACTCTGTCGCCCA
GCCTAGAGTGCACTGGTGTGATCATGGTTCAGTACAGTCTTCACCTCCCA
GGCTCAAGTGACCCTCCTGCCTCAGCCTCTCAAGTGGCTGGGACAGCAGT
TGCATGCTACCAGGCCTGGCTTTTTTTTTTTTTTTTTTTTTTTTTTTTT
TCGGTAGAGACTGGGTCTCTCTGTATTGCCCAGGCTAGTCTCGAACTCCT
GGGCTCAAGTGATCCTCTGGCCTCAGCCTCCCAAAGTGTTGGAATTACAG
GCATGAGACACTGCACCCAGCCAGTATAGTCTTTTAACAGCTTTATTGAG
GTACGGCTAACATTGAAAAAACTACACAAATGTAAAGTATGCAATTTGAT
AATTTTGACAAATGTACACACCAGTGAAACTATCACTACAGTCAAAATAA
TGAACATATCCATCACTCCCAATTTCCTCACGCCCCTTGGTAACCCCTCT
CTCCCAACTCCCTGCCCCCTAACATCAGACAACTACTGATGCATTCTGTC
TCCATAGGCTCATTTACATTTTCTAGAATTTTACATAAATAAAATGACAG
AGTATATACTCCTTCATGTATGGCTTCTTTCAGCCCAATTATGTCAAGAT
TCATGCTTATGGCTGTGCGTATCCTTAGCCCATCTCTTTGTCTTGCTGAG
TAGGATACCATTGCATAGACAGACCACAGCTTGCTCATCCATTCACTCTT
GACAACGTTGAATTGTCTCTGTTTTTTGCAATGACAAATAAGGTTGCTAT
GTACATTCCTGTATAGACATTTGTAAAAGCACAGCATTTCATTTCTCTTG
GGTAAAGACCTAAAAGTGGAAAGGCTGAGTCATATGGTAAATATATATGT
CTAACTTTTTAAGAAACTGTCAAACTGTTACCCAAAGGGATTGTACAATT
TTACATCCCCACCAGCAGTGTATGAAAATTCCCGTACTTCCACATCCTCA
CCAATATATGGTGTGGTCAATCTTTTTAATTTTGGACATGNTAATGAGTG
CAAAATGAGGCCCAGAGTGTCTGAAGTTACATTTGTATCCTTTTTGGCAT
CCAAAACAGGTGTCAAGCATAGAAAAAACACTTGTTCCTTGAATGGTCAG
TCATTTACAAGTGGAATTCATTACAAACCGGTAGTTCTACTGGGTTAAAC
TATGCCTTACTGTCAACAGGCACATACACATACAGACAGACAGGAAGGCA

FIG. 3W'

CAGAGACAAGGCAGAGCATTGATAAGAAGGTGACCTGGGCTCTAGCTCTG
GCCTATCACCTAGTAAAATATTAGTTAAGTAGCCATGAGTAACTCACTTA
ACTTACCACAGGCTCCATTTTCTTATCTGTAAAATAGGAACATTGAAACA
GCTAATCCCCAAGGTTTGTGGATAATCAGAATTACAAAGATCAATGACAT
TTCTATGAGAGAAACATATTTCCAAGTATTTGATGGAGTACATCAGACAC
AAAGGAAAGGAAACTGAATATTTTTGAGGTTTTTTTTTTTTACCAAGAAA
TTCACATTTTGTTAAATTTTCAGAACTACCTCCTGAGGAAAGTGTAGCTG
CACCCATTTAGAATGATAGAAAACATCAATCTGTCTGATTCCAAAGCCAA
GTTCTTGCTACAACGAGAAATGAAACAACTGGATCCCTACAGATGCAGAG
ACCTGGGCCCCACAAATGTGAATTCTGTTCCCCTACCGAATAGAGTTACA
GTTCCATAATACAGTACTCCCTCACTTTTCCACAGTCTCACATTCCACAG
TTTCAGTTACCCACAGTCAACTGCAATCCAAAAATATTAATGAAAAATTC
CAAAAATAAACAATTCAGAAGTTTTAAATTGTGCTCCATTCTGAGTAGCG
TGATAAAATCTTGTGCCACCATCCCACCTGTCCAGCTTATCGTTAGTCAT
TGACATCGTCTGCTCCTGACATCCAACCATTGACATCATCATGACTCTAT
GATCCAGGATCACCGAAGCAGATGACCCTCCTTCTGACATATCATCAGGC
CAATATCAGCCTAAACACTGCATCACTATGCCCACATCAGTCACCTCACT
TCATCTCATCAAGGAGGCAATGGATCACCTCACATCATCACAAGAAGAAG
AGTGGGTATAGAACAATAAGATAATTTTGGGGCAGGCATGGTGGCTCACG
CTTGTAATCCCAATACTTTGGGAGGCCAAGGCAGGAGGATCCCTTGGGCC
CAGGCATTCAAAACCAGCCTGGGAAACATAGTGAGACCTCCTCTCTCTGC
AAAAAAAAATAAACAAAATTATCCAGATACAGTGGTGCATGCCTGTGGTC
CCAGCTACTCAGGAGGCTAAAGTGGGAGGATCACTTGGTCCCAGGAGGTC
GAGGCAGCAGTAAGCTGTGATCGTGCCACTGCACTCCAGCCTGGGCAATA
AAGTGAGACCCTGTCTCAAAAAAAAAAAGGTAATTTTGAGAAAGAGACCAC
ATTCATACAACTTTTATTATAGTATATTGTTAGAATTGTTCTATTTCATT
ACTTATTGTTGTTAATTTCTTTCTTTGCCTAATTTTTTTTTTTTTTTTTG
AGTCGGAGTTTCACTCTTGTTGCCCAGGCTGTAGTGCAATGAGACGATCT
CAGCTCACCGCAAATCCCGCCTCCCGGGTTCAAGTGATTCTCCTGCCTCA
GCCTCCCGAGTAGCTGGGATTACAGGCGCCTGCCACCATGCCCAGCTAAT
TTTGTATTTTTAGTAGAGGCGGGGTTTCTCCATGTTGGTCAGGCTGGTCT
CGAACTCCTGACCTCAGGTGAGGCCTCAGCCTCCTAAAGTGCTGGGATTA
CAGGCTTGAGCCACTGCGCCTGGCCTCTTTGCCTAATTTATAAATTAAAC
ATTGTCACAGGCATGTATTAATTTATAGGAAAATCATAGACATATAGAGT
TGGGTACTATCCACAGTTTCAGGCATTCACTGAGGGGCTTGGAACACGCC
CTCCTCAGATGAGGGGGGACTACTGTCATCTCCTCAATCATTCTTGATTC
AATCCTCAACACAAATGGTTTGGCCAGGTCTTGCCTCTGGAGACAAAATT
GCTAAGGATTTAGAGGGGAAAAAATGTAGTTCACTGGAAAGTCACCTCT
GCTCCACTGGACAGCAACTTAAAACCCAGGCCATGACAAGTAGAAAGGCC
ACCCCCACTCTCCTTCACACCTGGAGTATTCAGGAGTCAATCATATTTCA
GGACCACCAGGAGCAAACTGGGAAAAACTGAGCTGCCTTGAGGAAAGCAA
TCAGCTCCACAAGGGGCTTAAGAAACAAGCTCTGGGAGGAGTGGTTGGAG
AAGAGTTGGGGACACATCAGAAATGCCATCAAATTTCTAAGGGCTACCTC
GTGGTGTCAGACCTGTGCATCTTCAAGGACATAAACAGATGGGATAAGCA
GATGAGATTCACAGAGGACATCAAAATATTGGCTCCCCAGAAGGGAGAAC
ATTCTAGTAACAGAGCTGCCCAGCTGCAGAGTGGACTGTTTCACAAAGCA
ACAGGTGCCCTGCCTCTTGAATCACCATCTTCACAGGAATGCAGTAGAAG
GGACTTAACTCCTGCCCTGAAGAAAAGGTTAGGCTAGGGAAACAGCTCCA
AAATTTTTTAAAAGGAAGCAACATAGGCATCTACTGGGAGTTTTCTAAAG
CCTTTGTTTAATGAAACTAAAGAGCTGGGACAGGAAATGCCAAATTAAAT
TAATAGAGCCTTGCTTTAAGACAATGCAAGTGGATGGTAATGAAGGAATG
AGTCTTAGGCCTTGGATCAACCGTATTAAGCAATGCTGAGCATGGAGCCA
ATTCTGTTCACTAGATTTGCTCAGAAAGGGCCAGACGAGAAGGATTTTTC
TAAAGGCACCTACTACCAAAAAGCTGCCAAGGCGTCCAATGGAGCCCAGA
GAGAATATGCTAACAATAAAAAGTTGAACACCCTCAATAAAAAAGGGTAA
AAGTAATTAATAGAAAATTACTGAAAGCTTTTTTGAAACCAAAAGTAGTC
AGCATTGGTAAAAGTCTACAAAAGTGGACACTTTCATATAATGTTGGCAG
GAGGGTAAAAAGACATAACCTTTTTGGAGGACAATTTGGCAACAGAGTAC
CAAAAACCTTACAATTGAAGAGAACTTTGGCCTGAGTGCAGTGGCTCACA
CCTGTAATGCCAACACTTTGGAAGGCCAAGGTGGGAGGATTGCTTGAGCC

FIG. 3X'

CAAAAGTTTGAGACCAGCCTGGGGTAACACAGTAAGACCTCGTCTCTATG
AAAAATAAGAAAAGTTAGCTGGGCATGGTGGCATGTGCCTGTGGTCCCAA
CTACTTGAGAGACTGAGGCAGGAGGATCGCTTGAGCCTCGGAGGTCAAGG
CTGCTGTGAGCCATGTTCATGCGACTGTTCTCCAGTCTGGGTGACAGAAT
GAGACCCTGTCTCACCAGAAAAACAAGGCAAGAGAGAGAGAGAGAGAGAA
GGAGAGAAAGAAAAGAAAGAAAGAAAGAAAGAAAGATGGAAGGAAGGAAA
GAGAAGAAAGAAAGAAGAAAGAAAGAAAGAAAGAAAGAAAGAAAGAAAGA
AAGAAAGAAAGAAAGAGAAAGAAAGAGAAAGAAAGGGAGAGAAAGAAGGA
AGGAAGGAAAGAAAGAAAGCAAGCAAGCAGGAAAGGAAGGAAGGAAGGAA
GGAAGGAAGGAAGAAAGAAAAAGAAAGAAAGAAAGAAAGAAAGAAAGAAA
GAAAGAAAGAAAGAAAGAGAAAGAAAGAAAAAGGGAGAGGGAAAGGGAAA
AGAAAAGGACAAAGAAAAGACCTTTGAACCCTGAATTTCACTTTTAGAGA
TTCATCTTAAGGAAATTCATTCCAATAGAAATTTATCCCCAGGATTATCT
AAATATTTGCTTTTATTTTCTTCTAGTAATTTTATGGTTTAACTTTCTCA
TGTTTAAGCCTTTAATTTATTTGGAATTTATTTTGGTATGAGAAAGTGTG
ACCTTTTTTTGTTTTACTTTAAAAAAAATGTATTACGATTATTATTTTAG
AGACAGGGTCTTGCTCTGTCACCCAGGCTAGAGTGCAGTGGTGTGATCAT
AGCTCACTGCAGCCTTGAACTCCTGGCCTCAAGCAATTCTCCCTCTTCAA
CTTAGGAGTAGCTGGGACCACAGGCATGTACCACCATGCCCAACTAATTT
TTTTTATTTTTTGTAGAGACAGAGTCTTGCTTGTTGCCCAGTCTTGCAAT
GTTGTCTCAAACTCCTGGGCTCAAGTGATCCTGTCGCCCCAGCCTCCCAA
AGCACTGGGATTACACGTGTGAGCCACTGCGCCCAGCTGCCTTTTTATTT
TTTAATTTTTCAGATGCTTTGTTGGTTCCAAAATAGCACTTATTAACCCA
CGCTTTCCCCCTCTGGTTTTAAATACTGCAAGTTTGGCTTTGAAATACAA
CCCACTGCCTTATTCAGGCTACATTCAAGGAAATCTGAGACCAAGAGTCT
GAAGGCCCAGTTTCCTTCCTCAAACCCAGGAGGTGGTAAATGTGTCACTT
CCACACTTTCTATCTATTTCTAAGAACTCCTTCTTTCCAAACTCTGACAT
GCCCCTGGCTCAGGTCTATAGAAATTCCCAGGGTCCACAGACAAAGCAGA
ACTCACTTATGGGGAAATCTGGGAAATACTTATCTGTTAAACCTGCCCCA
TATGGTGACTCAGATTGTCTAAAGCCCAAAGCATCATTTTCCACCCCAAA
CCATTTCCTCCTCCAGACTTCTCTATTTCTGTGGTCCAGAGTCAAGATCT
TGATATTACCCTAGAGTCCCCCTTCTGCTCTCCTGCATACCCAGATGCCC
CTCCCTCCCCAGATCCATTCTCCCACCCTCCCTCCCATCAGTTTGGTGGG
CCCATCACCGCTTCCCCTGGCCCAGGCTCTCCTTTTGTGCGCTTGGAGCA
GCAGACTGATCTCCCAGCCTTCACTCACTTCATGTGGTAATCTGTTGTGT
TCATCACTGTCAGAATCTTCTGCATCCCCTCACTACTCTGCTGAAAACAC
TCTAGTGGTTCCTCATTGCTCATTAATGAAAGTCTAGATATTAAACGTAG
AAGGCCCAGCACAATTTGCCCCTATGCCACCTACCTCTCTAATCTTTTCT
CCTTACTCTGACAGACTCTCCGTCTGTCATTTATGTATTCTTTTATTGCT
CTCTTCTACTTTTAGTATGAACTGGATTTATGGATTTTTTTAACATTGCT
TTCAAGTATGGAATAAAGAATTTTATTTATTTATTTATTTATTTATTTGA
GACTGGGTCTCACTCTGTTGCCCAGGCCAGAATGCAATGGTGCAGTCATA
TCTCACTGTAACCTCGAATTCCTAGGCTCAAGCCATCCTCCTGCCTCAGC
CTCCTAAGTAGCTATGACTACGGGTGTGCATCACCACATCTGGCTAATGG
AATAAAATATTACAATGCCTAATCTTAATTTTCAAAATTTTAAATTACAT
TGTACCTAATGCCCATGCATTTACTTTTTTCAGTGGGTCAATAGCCCTCA
CTTTGGCAAAGGTCCCAGGCCCAAGGTAAGGCCTTACTTTTTCCAAACTC
ATCTTTTGAAAGACATAAGTGCCTGTAAGTTGTACCACATTAGGTTCTAG
GAATTTTTCATCAAAGACTTTATCAGACTATTTTCCTCTAAGTTGAGAAA
GAGCTGGGGGCAGAATATGGCACTGAATGACTGAAGAGAAGGCACTGAAA
TCAGGCCAGAGGTTGCTGGAAAGAGCAATGAGGAACACCAGCAGCAATGA
GGAGCCGGTGATGATTTTGGCTTCACAGGGAGGTGTGTACCACACCGATT
TTATCTCTACGTGGATGAACCACAGCTGTCGGCTCCCTTGTCTCCAGGAC
ATCACACTCTCCACATTCCCTCCCATCTTCCGGCTTCTGCTTCCCGGGGC
CCTCATCTGCCCCATCCTGGGTGAACACTGGTCGGTCAACTGCTGGGCGT
ACCTTCCCGCTCTGCACACCCTCCCTGGCCACCCCACCCACTCTCACGGC
TCGCACTGCAGAGGAGCCGCATCTCTAGCTCCAGCCCATCTGCCTCTTCT
GAGCTCTAACTTCATGTAGGCGACTCCTGCCGGTGTTGCCTCACAGGCCC
ATCATACTTCAAAGCATTTTCCCCTCAGAACACCATGTCCTGGCTGCTCC
CTCCAGAAGATACATCTCTCAAGCACATCCCCGCGGCTCTCACCTGGATG

FIG. 3Y'

ACTGCATTCACCTTCTCCCACATTTGCCCTCCTTTGGATGTATATAGATT
GTTTTAAAATACAAATCTGATGTGCTTGCTCTCCTGCTTGAAACACCTCA
AAACTGCCTTCAGGATAAACCACTGCCCTTGACATGTTCACAGGTTGCCC
ATGGCCTGGCCCTGCCCATCTCTTCAGCCTCATCTCATGCCCCTTGCCCC
TCGCTCTCTGGGCTTCTGCCTCCCTAGCCCTCCTTTAGGTTCTCTAACAC
ACCATAGTCCTTCTAGTGTTGGGGCCTCTGCAAGTGCTGTTCCCATTGCC
TGAGACATGAATCCCTCTCCCTATCTCTACCTGCACCTTCATCTGATTAA
TCCCTACCCTTCCTACTCATGATGTTGCTTTCTCAGGGACTCTCTCTGAC
TTTTTAAACTAATCAGGGTCTCCCCAGTATATATCTTCATAGCACTCTGT
ATTACTCCTTTCTTAATGACCACCTGCTGTAGACTGAATGTTTGTCTTCC
TCCAAAATTCATATGTTAAAACCTAGCCCCAAATGTGATAATATTTGGAG
GAAGGCTCTTTGGGAGGCAGAGCCCTCATGAATGGGATTAGTAGCCTTAT
AAAAGAGACCCCTGAGGGCTCCCTTGTCCCCTCCACCGTGTAAGGATGCA
ACAAGAAAGTATGGTCTATGATCCAAAAAGCAGACCCTTGCCAGGTACCC
AATATGCTGGCACTTGAACTTCCCAGCCTCCAGAACTGTGAGAAATAAAT
TTCTATTTTTCATAAGCCACCGAGTCTATGGTATTTTGTTATAGGAGCAC
AAACAGACTGATGTGCCACCCAACCATGATTATACGTGTAATTTATGGTT
TCTCTGCTAGTAGGGATGCACCATGGGGTTAGGAACCACGCTTTTCTTAT
TTCCCACACAGTCCTTAGCTCTAAGCATGTTCCTGAATCAAAGATCCCCA
TCTTTTATGAATGAAGGAGTCAGTGAATGAATTAATGAAAGAACTGATAA
CCCTCAATAATTATTCCAGCCTTTTATACCTACTATTAACAAGCTTGCAT
TCTACTCCAAATTTATTGGGCTTTAACTCTATTTTTGGCCAGCCACATTT
GACATTCCCTGAAGTAAATCTATGCTTTCCATCCTAAGTCAAGGAAGGAC
CTGGACTAGTAGGGCCAAGAAAGGTCTAAATTCCATGGGTGGGAGAGAGA
GACTAAATCTGAAAGGAAGAATAGATTGAGCAAAGGTGTAGAGATTGGGG
AAGGCTGGACATTTGGAGAGAAGGAAAAGGAAACTGACACTAAACCAAAC
AGTCTCACAAACACAATCTCATCCTTCCAAAACTCTGTGAAGTAAGAATT
ACTATCCCAGGGCCAGGCACAGTGGCCCATGCCTGTAATCCCAGCACTTT
GGGAGGCCAAGGTGGGTGGATCACCTGAAGTCAGGAGTTCAAGACCAACC
TGATCAACATGGTGAAACCCCATCTCTACTAAAAATACAAAATTAGCTGG
GCATGGTGGTGCACACCTGTAATCCCAGCTACTTGGGAGGCTGAGGCAGG
AGAATCATTTGAACCTGGGAGGTGGAGGTTGCAGTGAGCAGAGATCGTGC
CACTGCACTCCAGCCTGGGTGACAGGGAGACTCCGTCTCAAAAAAAAAAA
AACAAAAAAAAAACCAAAAAAAAAACAAAAAACAAGAATTACTATCCCAG
TTTTGCAGATGAGGCAATGGAAGCTCTAAAAAGTTAAGTAGGAGAAACAA
ACATGAAATGTATGTCTTATGCTTTTCCTCATCCTATTTCCTCAGCCTGG
AATGTCCATTCTCCCTCCACTATGCAAATCTAACTCTTCAAGCTAACACA
TAGCAATGTCTGAGAAACCGTCCCTGTGTTCACTCTGTTAGCCTCACTTG
CTCCCTCCCCATCCCTCTGTTTCCTTTCTGTTATAACACTTCTCTATTCT
GCTGGCATCACAGTCATCTCCACCTGCCTTCCTCACAAGTTAAAAGCTTG
TTAAGGGCAAGTGGTGTTCTTTGCCACCTCATTCCCCAGGGCTTCTAACA
CAGTGCCTCATGCATGACAGAGTTGTAAAACAGGTTACCAAGCTGGCTTC
AGGCAGGTTTGCATGGAACTGTGCTTTACAGGAATACCTGCTCCCCCCAG
GCCCTGGGTCTTCCTCCTGAGTCCAGGCTCAGACTCTCTCATCCTGCTCG
TTCTCTCTTGGGGAGCCACAGTAACTTTGAGCAACTTTGCATGGGATAGA
ATGGCCTATTAGGGGCAGCACAAAGACCCCATGGAGGGAAGAGTACAGAA
AGGGAAAACGATAATCATATTTTTTAAGATGTGCATTTTCTTAACAAAA
TGCTCTAGTACTTGTCCAGACTTTCAAACTCAAAAACCTAAGCGTCCTTT
TCTTGAAGATCATCAAAGGCCCCAGTGGTCCTTCAGGTATGTCAAGCTTT
CTAGAAAATAAAGGTAAGTCATAATCACTTAACACACATGGCTAAATGGC
CATTTCCTTCTAATTTATCAGCAACTGTTACATATTTCTATACTAGAAAA
AATTTATATTTATACTCAGGGTGGTAAGTTAAATTTGCCATCGAAGTAAA
GCAGAAAGAGCGTAGCATGTATGTATATGTAACTCAACTGTGCATGAGAC
AAAGATGTCTTGAGGAGAATGAGTCTAAGATGCGCCTGAGCAATAGTACC
C

FIG. 3Z'

>Contig1
GCACCCATGTTTCTAAAGGGCATACCAGCCATAATAACAGGATGGGTGAG
GATATAGACAGCAGATGACAGAGAGGAGAGTGAAAGCTGGGAATCCCAGC
TAAAGGCATCAGGTTTATGGAATGAGTAGGGGACAATACTGTGTGTGTTT
ATACACACATGTATATGTGTGTATATGTATACATGTTTATGTATATATAT
AATTATATGGTACCATTTCTAATTGACAAAATAATCTATCACATTTTACA
TTATCAGATTTTACATCTATTGTTCTAAATACACTCAGTCATCAGCCCTG
TGTGTGGGCTCTTACCCATCCCCATGCACACCTCAGCTCAACCACTGATG
GATGGATCATCTGCCTATCAGAGGTGGCATATTCAGGTGAATCCATGGCC
ACAGCTGCAGCACTTCCTACCCACGCAGAAAGGCTCCACAAGAGGAGGCA
CACCCGCTCTGACTGTCCCTAAGCTCCTGACATCTTCACCCCATGAAACT
GCTGCTCCTGGGTGCTTCCTGCCTTGCCCTGCCCACCCTTGTACTGTTCT
CACCATTGACACAGCTGGTGCCCGATGCAC
>Contig2
NAAAACGAATCGTCACTATTGAAGCCTGTCTCTCANCGGATCGTGACTAA
GAACCCCCTCCTTGCTTCAAGTTGTCCTGCCTTTCTAGGCAGAGCCACCC
TACATCTTAAATATATTGATTGATGACTTACGTCTCCCTAAAATATATAA
AACCAAGCTGTGCTCTTACCAACTTGGGCACATGTGGTCAAGACCTCCTG
ATGCTCTTGTCATGAGTGGGTGGGTGTTCTCAACCTTGGAAAAATAAACT
TTCTAAATTAACTGAGACCTGGGTCAGATTTTTGGGGTTCACAGCAACAA
TTTAAAAAACTCACCATTGACCTGAAATTTTGACCTTATGCTGTTCCTCA
CACTCCTCCATGAAAATAGACGCCATCCTATGAGTTCCCTCAGCCATGTC
ATGCCACACTTCCAACATGTGTCCCCATCCACCATCTGTCTTCTTATTGC
TGCATCCTACCCAGGCCCTGATCTCTGGACCCATTGTTGTATAATTAAGA
ATTTGGGGCTGGGCATCGTGGCTGTGGCTCACTCCTGTGATCTCAACATT
TTGGGAAGGTGTATTAGTCAGGATTCCTCCGAAGGATGCAACCCTAGGGA
TCCTCTCTATGACCCTATGTCTA
>Contig3
CGCGCTCAACCGACCGATTTGCGCGAACCTGCCCATGCCCGAGGACAGTG
TAATCCTAAAACGTCCCCTGAATCATAAGGATATGAGTGCGAAAGTACGG
TTCCCTCTGTCACCACTTTCTAACAACGCTATGTCCGATCCGTGCACTAA
CCCCGCCCAAGTCACTGAAACACTGATGGGCGCTTCCTCTACAGGTATCC
AGGGCCAATACCACTACTCCCCTCCTCCCTGTCCCCCTTCCACTCTCTAG
AGGCCGCGGATGCCATCCTCTATTAGCACAACCGAAAACGACGGTGAAAG
TACCACGAAGCTCACGATCTGATCGGTCGCCCAATGCGGTTACAACGGCT
GTCATCCCAACCCCCGTCCCATCCTCCATATTGCCCCCCCCTATGAGGAT
GGCCCTATCATCATGACCTCCAAAATTCTGTCATCTCCCGACGTAATGCC
GCCCCTCGAACGCCTGACACCATCAAGTCNGTCACCTCCCAAAATACTCC
TCCTAATCACCAGGCCGAGTATCCCCGGTTCCACAATACCTCCTTGAGAC
GGGCCGATATCACACAC
>Contig4
NGGAGTTTAGGTCAACTAGTAACAAGTGGGATTTGCGACTCAGGTCTATC
TAATCCTCAAACCCACGTCCTGGACCCCTACACAGACTGCCCTCCCTCAG
TCCTCTGTGTGGCCTCAAGAAGGGTCTGGACATTCAAGTTTAAAAATCCA
TCCAAAGAATCTATGGACCCAGTGGTCTCTGGAGTCAATGTTCTGAGGCT
CAGAAGGGCCAGGCAGGAGGGAGCCGCCTCTACACAGTCCTGAGCAGAGT
GGGCTGTGTCCCGGCACAGCAGGGGAGATCATAAACAGAATTCTGCCCTG
GGCCCTATTTAAGTAGGACCTTTAGGCTGCCGGTGTCATGACCACAGGTC
CCANGTCTGCACGATTGGCTGTGTGTGGAAAATCTTCACTCCTTGCGGCC
TTGTCCTTGGCAGAGAGCACCGCTGCTTCCTCTGATGGCCACCAGGGGGA
GGCGCTCCCCTGGGAACGGTTTGAANGGGAGCCTCACCCCACACGTGCCT
TCCGTGGTACCCAGCACCAGCTGCTACCCATGGTTACCCACAGGCCCAGC
TCTGCTCTGAAGAAGGAGGAGTGGTGGCGATCANGCCTTGTCTGCATCCC
GTGGCTGCCCCTTTCTTTTCTTT
>Contig5
GGGAGCTAACCGCTCACTGGGATTACAGGTACGCACCACCACGCCTGGCT
AATTTTGTATTTTTAGTAGAGACGGGGTTTCTCCGTGTTGGTAAGGCTGG
TCTCGAACTCCCAACCTCAGTTGATCTGCCCGCCTCAGCCTCCCAAAGTG
CTGGGATAACAGGTGTGAGCTACCATGCCTGGGCTTATATGTTTCTAGTC
CAAACATTTAGCTACCTTTTTTTTTTTTTGAGACGAAGTCTCACTCTGT

FIG. 4A

TGCCCAAGCTGGAGCACAGTGGCACAATCGTGGCTCGCTGCAGCCTCAAC
CTCCTCAGGCTCAGGTGATTCTCCCACCTCGGCCTCCCTAGTAGCTGGGA
CTACAGGTACGCACCACTACACCCTGCTAATTTTTTTGTTTTTGTATTTT
TTGTACAGATGGGGTTTCTTCATGTTACCCANGCTGGTCTTGAACTCCTG
GGCTCAAGCAATCTGCCTACTTCAGCCTCCCAAAGTGCTAGGATTACAAG
CATAAGCCACCATACCCGGCCTACCTACTTTTAACTTGTGGAATTTTCTA
TAAGGTCANGGATGCCTGNGGGAACAAAAGTTTCTCCCTTGGTATATGCA
AGTAAAATCCACATGCTGCCTCCC
>Contig6
AGGACTGTAGCTGTTGTCTAGTCACCAGGCTGGACTGCTTGGCATGATCT
CAGCTCACTACAACCTCCACCTCCTGGGTTCAAGGGATTCTCCTGCTTCA
GCCTTCCAAGTAGCTGGGATTACAGGCATGCACTACCATGCCCGGCTAAT
TTTGTATTCTTAGTAGAGACGGGGTTTCGCCATGTTGGCCAGGCTGCTCT
CAAACTCCTGCCCTCAAGTGATCTGCCTGCCTCGGCCTCCCAAAGTGCTG
GGATTACAGGCGTGAGCCCCCGGCCCACATGTAAAAGTTTATATCTCTGT
TGTTTCACCTTGTTTTTGACCTAGTCTTTCAGTGATTTGAATCTTGATTC
AGTCTTTTGTTATTTTAGTGGTACTTCCCAGCTTTGTGTCATCTGTGGAT
GACATATGAGTCTTGCTTCTTCATGCCAATTTAAGAAGACTGAACGGGAA
TAGGTCAAAGGCATGGCCATGAGCGATTTCTCTCCAGCTTTTCATGGTGT
TCAGCTTCAAATCTATTCACATATTGGACCTGCAAGCCATCATCTTATCC
ACAGGCTATCATCATAGGTGAATGTAAATTGGGTTTAGGTGGCCAAGCTG
AACGTGAGATATNTTC
>Contig7
AGCATGTTCTCTAAAGGCCTATCAAAGCTGACATCAAAGGGATAAGTTCC
AGTTACCCAGCTGAAGGGAAGGAGGGTGTTTCAGATAGAGGAAGGATAAG
CATGACCTATTCAAGGCCAGTGAAAGAAGCGTGCAACGGCCAAGTCAGGA
GAACCTGAAATTGTGTCAAAGAGCTTGGATGCAAAGAGCCGTGGGAGACT
ATTGGGGGTTTTAAGCAGGGATATAATATTCATTCAAGCATGCAGTAAAA
GGTCACTGGCACCTGCCATGGGCCAGGACTCGGGCTCTACATGATTGCGT
CTGTTTTGGAAATATCACCCTGGCTGTGAGATGAAGAACAGGTAGGAGGG
TCACAAAACTTGAAGCAGAGAGACTGTTGAGGAAGTAAGCTGTTTTTGTG
TGGACTGTGGCAATCACAGAGGCAGAGGATATAAATGCACAGAGACACAA
GGCATGTGGGAGGCAGAAGGAATCAAATACAATGAGTGATCAGATGTGGG
GTTAGAATGGTGAGTGANAAAGACATACTCAAGGTGACACGCCCAGGTAT
CTGGGTGGATGGTAAGACATTCATGGACTAGAATCGAAGAGGAGGTGGGG
ATGGACATTCCTTCCGTTTAGAGGGGTTCACCAGGAGGATTTGCCGGAAC
ATGGAGAGGATTAACCAGGAATCCGGTGCCTTTTTCCAAACTGGGTTGGA
GGGG
>Contig8
GGTGAATGCTTTGGCACGCTGTGTAGATTTTAGGTGACGGGTGGTGACAA
TGAGTCCGTGTCGAGCGCTGATTTTTTCGGCCTTTAGAGCGAGATTTATA
CAATAGAATTTGGCATGAGATTGGATTGCTTTTAGTCAGCCTCTTATAGC
CTAAAGTCTTTGAGTGACTAGATGACATATCATGTAAGTTGCTGATAGGT
TTCCAGTTTTCCGCTCCTAGGTCTGCATATTGTACTTTTCCTCTTACTCG
ACTTAACCAGTACCAACCCAGCTTCTCAACGGATTTATACCATGGCACTT
TAAAGCCAGCATCACTGACAATGAGCGGTGTGGTGTTACTCGGTAGAATG
CTCGCAAGGTCGGCTAAAATTGGTCATGAGCTTTCTTTGAACATTGCTCT
GAAAACGGGAACGCTTTCTCATAAAGAGTAACAGAACGACCGTGTAGTGC
GAATGAAGCTCGCCATACCATAAGTCGTTTTTGCTCCCGAATATCAGACC
AGTCAACAAGTGTCAATGGGCTCGTATTGCCCGAACAGATTAAGCTAGCA
TGCCAACGGGATAAACGAGTCGCTCTTGGTGGAGGG
>Contig9
GGGGTGGGGCGCCTGGTGTTTCTAAAGAGGATCTCCTGCCAGAAATGGTG
TGCTGACACTGTTGTCCTCCTTGGTGTGGAACTTTGGTGGGAAGAAAGGT
TGGAAAGGGAAATTTTGATCCTTGGATTTAACCCGAGTTTGTTACTGATG
CTCACAAGACTAGGGGAAGGATAAAGGCAGGTGAGTCACTCTAGGATGGC
TCANTGAGCTCCACAGAGCTGGAACCACAGGCACCAGGAGGGATTCAGAG
CAGGCCTCAGTGCACGTCAGCTGAGTGAACCAATGAGCAGGTGATGGGTC
CAGGCAGAGCCCTGTCCTCTTTAGGCAAAAACCCTTGAAACACCGTTCCC
ATCCTAGCCTGTGTTCCACCCAAAGCTGGCCAGTCTCCAGGCCCTGCCTG

FIG. 4B

AGCCCCAAGGAAGTGGTATGGTGAAACAGAAGGGCCATTCCTGTCCAATG
TGTGAGGAACTTCATTTCAGACTTGTTGGAAGCCCTGATGTTCAAAAACC
TCAATGATATCATTCATTTTCCCCATCCATTCAATGCCCATCCAATGCCC
ATCCGTTCAATGCCCCTTCCATTCCTCTTCAGGGAAATGAAAATTGTTCA
GAAATCCTTTCTCTTTCGAGAAACCAACCAAACCAAAACCGCGAAATTCA
CTAAACTAGCCAAGACACAATCCTGGGTTATTTTCCTTTTCCCAAACCTC
CTCTGTTTAAATTAATTCTACCCTGGTTCTCGGCCCTTACTGCGAAGGTG
AACTCACCTAACCTCTCCCAAACAGAGAAGAAACTTCTCTTGGTAAAATG
GGTTTTAACACTTCTAAAAAACCCCC
>Contig10
GCTATGGTTCTAAAGGTAATGGACTATGGCGTACACAACGTCTCGCTCAT
CGTCTGCCAGGAGGCTAAGGTATCCACGGACAATCGCTGAGCAACAGTGT
CGTTGATCCATCTCTGTACGCACTTGTCAACATGGCAGGAGTACGGGAGC
TGCGAGAATCCTCTCTGCTGATGTCCCACGGAGCATGCCGTGAGACAACG
CCACGAACGGCCCTCGGAGANANCTACTCTGCAATGAAGACGTACGATAC
ACACGTAGGAGTCCTAGCTCACCAGCCGTATCTAGGTATACTGTACTCGC
GGATACTCACTCGTGCATGCGGCAATAGATCGATACGCAGTCGTCACGCC
CATGCTCTCAGTGTGTGACCTTCTGGCGGTAGCGTNGTGGGCGCTATTAC
TGTGCGCAGCAGGCGCNTCGTACATGTGTCGGGTAGCGATGCCAGGAGCT
GTAACATAGCAAGTCGCCCCCCTACTCCTATCACTATCCCTACGCTGGAC
CGCACTCGAGATCTGAACGCACGTCTTAACCTGCCAGTACTCGTGAGACC
TATACTGCGCAAGCCTTGGCTAGGAGATCCTGCAGCGCCGGCAAAGAATC
AGCTATGATCCCCTTGCGATTATCGCACACGCACCATAGAGTATGTGCAT
ATTAACCTCTGAATGTGCTGCAAGCAGACGGTTGCTCAACATATATATGG
ATGTGGGGAAATCGCCCTGGTCACCGCCACTTGGCGTCAGGAGGCACCAG
CACGTCTGAGTGTCACGCACGTTACTC
>Contig11
GGCCGAATGGTGAATTCATCCGTCGTCTCGAGGGGGTGAAAGACGGGGAG
TTATGCTGTAATGGCACCGCTCACCCTGGGCTTATGAGCAGACCTAACCC
TCCCANAGTGCTGGGATTACAGGCATGAGCCACCGTGCCCGGCCCAGTAT
CTGAACTTCTGTGGCCAGGCAGAAAAGGTCCTGTGTTACTCGTCTCCTTT
ATCATTCATGTCCATATTCTCCCATTTGCTAACATTTATGTTTCTGCTCC
ACTGGATTCTTTGGATTTTTCTAGAACATACCCATGCTTTGCATTGCCTT
GGTCTTTGAATATTTGGTCCACTTTTCCTGCAAAGTCCCCTCTCACCTTA
TCTTCCTGGTAAACTTCCAGCCAACACCTCTTTACTAACCAGAGAAACAT
GGTTCAACTGTGCACAGGCTTGCACAGAAACTGTTCTCATATTGTCTTGT
CATTGTCAATGTGGCAGAGATGCACCTTAGATACCTCTTTGAGAAAGGAC
TCACTGCCCAGCTGCCTGGCACGTGATGAGCTGATAGCTCCAGCTATAGA
CTCCTTTAGGGTCAACCTCTGCTTTCCAGTTGAGATCATATCCTTTGCAG
GGTGGCCTCCCCAGTGATGACTAAGGCAGTGTTACAATGGCCTAGTCATT
TCCTCCCAATGCTGGACTCCCAATGAACCATCTGCTCCGGAGCTTCCCAC
TGGGCAGTCAGAGACCTTAGCTAGTCTGCCTCCGAATCAGAAGGCTCTCT
CTTGCCACTCTGGCC
>Contig12
GCTGTGTCTAAAGATTCACGGCTGTAGTTCCAACTCCCGCCGCCCTCTAC
TGTGTCCTCTTAATGGCAGTCATTCACCATCTTCCTGTCCCTCCCCTTCA
TTTCTTGGATGGTGACTGTCACTTTGCTGCAACAGAACCCTGTCCCAATC
CTTGATGGTTCAATACACACATAGACATTCTTTTTAACAGGGCGGCCTCT
CAGGTCTTTAATTTTCTTCCCTCCAATAACCTTGTGATGATCCCCCAGCT
TAGCCACTTACTGCCAGATCATTACCAGTAACTCCAGCCCCTCCTTAATT
CTAGTTTCTAATATCCTAATCTGTGACCTCACATTCCAACTTCTTCATTC
TTATCCCCTGAGTCAAAAAATCCTTTGATCCATGCAATCCATTAAGTCAT
CTACCTTTTCACCATTCTTCGCCCCACTAGGGTTCTCATTCCTTTATTAC
CCATATGAAATTCCAAGGCCTGTTGGAATCACTCCCTTGCAGCCACTGTC
AATACTTCTGCCCCTTTTACTTCATCACCCTTATGTGGCAAAACCACAGC
CCTGGTGGAGTCGATCCTTACCCCTGCTCTGTGCCAACAGCCGCACACGC
ATGGCTGATGGAGGTTGGAAAAATCCACACATGCAGTGGGCCCTGTATGT
CCATATACGTATCCAACCTCCAGCCTTGCATATGCCTCAGTGCTGCCTGA
CAACACATTATATGTTTTCCTTAGTTCCTTCAGTCTCCTGGGTGCCTAGG
TGAGTATCTCAGACATCCTTCTCTCTCTGCAAAGCTCCAACACCTCCACG

FIG. 4C

TCACATTCAACTGATGACTGTGTCTCCTATGTCACTTAGATCACAGAGGC
ATACATAAACAAATCCCAGCCACTGCCAGCACTCTGCACATCTGCGAGCA
TGGCACCCCCAATCTAGGCCTTTCCTGCTGTCACTTGGGGTGAGCTGATT
ATACTCGATCCTAGTCATTTCTACTTATGCAC
>Contig13
CTTAAGGCCTCCCTCTAACATTTTAATTTAAGATTGAAAAAGCAAAGATT
ATTCTGTTTTGGCTGCGCCTATAGTAAAGTAACCCCTATGNCAAATTTTG
ACACCTTATAGTATTTGACAGGGATAAGTATAAAATTGCTTGATTGATAC
ATCCACACCCAAATGTATGCTGGGAATGATTTTGTTTCACGGCACTCATT
ACTTAATTTTTAAAACTCTTATTTAAATTTGCAATGTTTTAAATGACCAT
CACTTAAAGTAGTAATCAACAGAGGTTAGGAGAACATAACAATACTCTTT
CTCTTAGAAAATACAACAGAAATATAATTTTTTACAGTTTTGCTCCCAAA
CTTTTCTCTGTAATAACATGCCTTACTCACCTTTACAATAGGTTTGTTGT
GAGAATCTTGTAATGTAAACCCTGGGTGTTCTGTGAAGCATTTTTAAACT
TCTAGTTTACACTGACTCTTATTCAAGTGTTTTTAAAAATATATTTAAAA
AACTGGCCAGGTGCAGTGGCTCACACCTGTAATCCCAGCACTTTGGGAGG
CCAAGGCGGGCAGATCACAAGGTCAGGAGTTTGAGACCAGCCTAGCCAAC
ATAGTAAAACCTCGTCTCTACTAAAAATACAAAAATTAGCTGGGCGTGGT
GGCGGGCGCCTGTAGTCCCAGCTACTCAGGAGGCTGAGGCAGAAGAATCG
CTTGAACCCGGGAGGCAGAGGTTGTGGTGAACCAAGTTTGCGCCAATGCA
CTGCCAGCCTCTGCAGNGACAGCC
>Contig14
GGGGGCGGGCCGAGTGATCCTAAAGCCCGCTCGCTTCACAACAAAGCCTA
ACAGTCCAATCACTTAATGCTGCATTTATTCCTGGGGAAGCAAGTCTCCT
TTGCACTTTACACAGTGAGATAATCAGTTTCTCATGTGGACCACTGGGCC
AGGAGGGCCTGACAAAGGGCAGTCTACATTTCAGACTGGAAACTGCTCCC
AGAACTATTTCTTTCTAGTTCCCACCTCGGTCTGAGGTGCCTGAGGAGAG
GGACTCAACAGAGGAAGCAGGAGCATAGCTCAAAGTCTCAGAACATGGAA
GAGGAAAAGAATCCTCACAAGATTACGTAACTTACAGGCGTGTTGCTGCT
TCAGTAGAAGTTTCATCTCCCTCAATCCTGTACACTTTTCCATACATTAC
ATACTCAAACTGGTCAGCCCTATGGAGCAATAGCAGCAAAGTTATTCTTA
ACAGTAATTAACAATATAAAAGATCCCATTTAAAAATGGTTACTGGTCAG
CCGGGCGTGGTNNNTCNANCCTNTAACCCCANCACTTTGGAAAGCATGCG
GGCGATCCCAAGTCTGATATCGAAACATCTGCCTAACATGTGCAACCCCT
CTCTACAAAATACAAAAAATATCCGGGCTTGTGTTGGCGCCGTTATCTCA
CTACCCGGAGCTAAGTAAGAAATGCTTTACCTGGAAGCGATTTTTTTACT
TATATCCCCTCTCTTCACCGGGCGCGACCAAATTCTTTAGTATAGGAAAG
TTTATTGTTTTATGCCTTTGTCAAGGCTCTACTGTATCTTTTCTGTCCAC
TCAC
>Contig15
GGTTCTGAACAACAGCAGGCGATTCCTAGCCCTGTACCCGGGGCATTGTC
CAACACTCGACAGGGCTGAATTCGTCCATAACGGTGTGCCCCTCTGGGAT
ATAGGATGAAATGAATTGATCTGAGTACCTGGGATGTAAAGTTACTAAAA
CGCCAGCTAGGTTCACGCCCCGATGCTTAAATATGATCGTGGCCTACACC
TCGTCCAGCAGAAAAAGTACCCTTTCTTCAACACCACCTCACGATCCTCC
AATTTAGGAGCTATAAAACTCATGACTCTTTATTTACCCCCTGCAGATTC
TCAATCCAATAGTGTGTGTCTCCCTGTGAACTCACGGATATACCGATTTT
CCCCACGTCATTTCCACACGTCGCAATCGCTTAGTCATCCCTATGTATGA
GAATCATGGATGACTATGTTGAAGTCCATCTATAAAGTTCAACCCCCATC
TCCGTCCCTGATTCCCCCTCCCCAAGATCACCAACGCGACTCGACATATT
GTTATCGCCCAAGGGACCTCTTGCATCCCCCATATCCACTGGTCACCTCC
CCTCTTGGCTGGAAGTCACCGGGAAGTTCTCCACATGTTGT
>Contig16
TGCGAGCGATGTTCCTAAACTTTAGCGCCATTGACTCGAGCATGGTCATG
GCTGTTTCCTG
>Contig17
AGGGTGTTCCTAAAGGATACTACGTTCCCTAAAGTCCAGAGAAAAAAAAA
AAAGTAACATAATGTGGCTTATTTGGTATAAAAATTTTACAGGAAGCATT
GTCAAATATGAAATAGTGTTTGGTTTTGTTTGGGCTGTATTTGTATAAAT
ATGTTATTGGTATGTGTTCCAAAATTATAGGAAACTCCTATAATTCTGAT

FIG. 4D

ATGACTTGGTGTACATTATCAGTAATAATTATAATTGTTATGGTAAATTA
TTGTGTGCCATGGAGGTAACAAATTTCCTCATCAAGTGTGTCTTTGACTA
TGGTTGCCCTAAAACTTTTTGCCATTCACAGACAATTGTCTTGCTTTGGT
CCTCTTTAGAAGGTGGTTTTATAATCAGCTATAAAACTCTAACGGGTGCT
CTTGAATGCAGGCTTAAGATAGCTTTGGAGACTGTGACATCAGAATAGAG
GAAAAACTTTCAGTATTCATGGAGTGCTGAAATATTCATGAATATCAAGC
AAAACAGGAATTAACTTCATAGATGGAACTAAAAGAATGCTGAAGTAATC
TTTTTGACTTTTTTTCTTAAAATGTTGATCCTTCGTTTTGTTTTTCAGAG
TCAAGGAAATTTTTCTGTTGAGATATTGACAGCTTTTAACAATTAAGTAT
ACTCCAGTGAACACAATTTGGAGCATATTTGTGTCTCTCTATATATATTT
GGAAACAATNTTTGAGTATTCTTAACTTATTGCAATATT
>Contig18
GGTTGTCTGCTATACCAGTAATGGGATTGCTGGGTCAAATGGTATTTCTG
GTTCCAGATCCTTGAGGAATTGCCACACTGTCTTCCACAATGGTTGAACT
AACTGACACTCCCACCAACAGTGTAAAAGCATTCCTATTTCTCCACATCC
TCTCCAGCATCTGTTGTTTCCTGACTTTTTAATAATCGCCATTCTAACTG
GCATGAGATGGTATCTCATTGTGGTTTCAATTTGCATTTCTCTAATGACC
AGTGATGATGAGCTTTTTTTCATGTTTGTTGGCCACATAAATGTCTTCTT
CTGAGATGTGTCTGTTCATATCTTTTGCCCACTTTTTGATGGGTTTTTTT
TTCTTGCAAATTTGTTTAAATTCCTTGTAGATTCTGGATATTAGCCCTTT
GTCAGATGGATAGATTGAAAAAATTTTCTCCTATTCTGTAGGTTGCCTGT
TCACTCTGACAATAGTTTCTTTTGCTGTGCAGAAGCTTTTCAGTTTAATT
AGATCCCATTTGTCAATTGGCTTTTGTTGCAATTGCTTTTGGTGTTCTAA
TCATGAAGTCTTTGCTCATGCCTATGTCCTGAATGGTATTGCCTAGGTTT
TCTTCTATGGTTTTTATGGTTTTAGGTCTTATGTTTAAATCCTTCTTTTT
TTTTTTTTTTTTTTTTGAGATGGAGTCTTAGTCTGTTGCCCAGGCTGGA
GAGCGAGTGGCGTGTCTNTAGGACGC
>Contig19
GCATGTTGTCTAAAGGTTTGTCTTCCTCCAAAATTCATATGTTAAAACCT
AGCCCCAAATGTGATAATATTTGGAGGAAGGCTCTTTGGGAGGCAGAGCC
CTCATGAATGGGATTAGTAGCCTTATAAAAGAGACCCCTGAGGGCTCCCT
TGTCCCCTCCACCGTGTAAGGATGCAACAAGAAAGTATGGTCTATGATCC
AAAAAGCAGACCCTTGCCAGGTACCCAATATGCTGGCACTTGAACTTCCC
AGCCTCCAGAACTGTGAGAAATAAATTTCTATTTTTCATAAGCCACCGAG
TCTATGGTATTTTGTTATAGGAGCACAAACAGACTGATGTGCCACCCAAC
CATGATTATACGTGTAATTTATGGTTTCTCTGCTAGTAGGGATGCACCAT
GGGGTTAGGAACCACGCTTTTCTTATTTCCCACACAGTCCTTAGCTCTAA
GCATGTTCCTGAATCAAAGATCCCCATCTTTTATGAATGAAGGAGTCAGT
GAATGAATTAATGAAAGAACTGATAACCCTCAATAATTATTCCAGCCTTT
TATACCTACTATTAA
>Contig20
ACGGTTCTCTAAAGACTTTCAAGAGCTGGATTTTATGCTTTAGGTGAAGG
TGATAAAGTAAAGTGCTTTCACTGTGGAGGGGGGCTAACTGATTGGAAGC
CCAGCGAAGACCCTTGGGAACAACATGATAAATGGCATCCAGGGTGTAAA
TATCTGTTAGAACAGAAGACACGAAAATATATAAACAATATTCATTTATC
CCATTCACTTGAGGAGTGTCTGGTAAGAACTGCTGAAAAAACGCCATCAC
TAACTAGAAAAATTGATACCATCTTCCATAATCCTATGGTACAAGAAGCT
ATATGAATGGGGTTCAGTTTCAAAGACATTAAGAAAATAATGGAGGAAAA
AATTCAGACATCTGGGAGCAACTGTAAATCACTTGAGGTTCTGATTGCAG
ATCCAGTGAAGGCTCAGAAAGACAGTACACAAGACGAATCAAGTCAGACT
TCATTGCAGAAAGAGATTAGTACTGAAGAGCAGCTAAGACACCTGCAAGA
GGAGAAGCTTTGCAAAATCTGTATGGATAGAAATATTGCTGTCGTTTTTA
TTCCTTGTGGACATCCAGTCACTCGTAAACAATGTGCTGAAGTGGTTGAC
AAATGTCTCAAGTGGTACGCAGTCATTACTTTCAAGCAAAAAAATTTTAT
GTCTTAATCTAACGCTATAGTAGGCATATTATGTTCGTATTATCCTGATT
GAATGTGTGATGTGAACTGACTTTAAGTAATCAGGATTGAATTCCATTAG
CATTTGGTACCAAGTAGGAAAAAAAAATGTAAAGCCAGTGCTTAGACACA
GC
>Contig21
CGCTGTCTTAAGAACTGGGCTAGGAGTGAGCAGTGAGCCAAGATCGCACC

FIG. 4E

ATTGCACTTCAGCCTGGGCAACAAGAGCAAAACTCCATCTCAAAAAAATA
CATATATATATATGACCCATAAAAAGGAGATAAATCAACACTTCAGAACT
GACCCAAACTTGCAAAGATACTATAATTAACAGAAAAGGACAGTTTACTA
AGTACTCCGTATGTTCAACAAGTGAAAGATTAAACATATTAAGTAGAGAT
GTAGAAGATATAAGAAGATCCAAAATGAACTTTTAGAGTTGAAAACTACA
ATATTTAAGATAAAAATACACTAGGTGGGATTAAAAGTAGATTACACATT
GCATAAGATAAAAAAAAATGAGCCTGAATACAGCACAGTATAAACTATCT
TAAACAAAAACACAGAGAGAAAAAATAACTTTAGAGACTTAGCTCTTATC
CTCTATTTGTTTCTAAACAGAGGATAAGGGGCAGAAAAAATGTTTGAAGA
AATCATGATTTTTAAATTTCCAACTGAGATAGGAATAGCACTGGGTAGTC
ACAGGAGGCTGGAAAGACCCAAACAGCAGTTAAAACAGGAACTAGGCAAA
GAAACCAAAGGATAACAGTAAACCTAAACTAAGGGAGAGAAAACTGACAA
AAGCTGACTTAGGATAACTGAC
>Contig22
CCTGAATATAAGCCGCAAGTAACCAATTAAATTTGTTTTCCAAAATTGTA
TTAACAATCTATGAAATTTTTATCTTGACCATAGCTATAACTTCCAGAAG
CCTTTTATAACCTCTATAACCTTTATTAAGGAGTAGGTTAATGCTTCAAG
AAAACCTTGTTAATCTGACACAGGACCCATATGCTGATCTTGCATCAGTG
TGGCTTGGACATCAATGATTATGATTAATTTATAGAGAAATTGAACTTAT
TTTATCTCTCAAAATTGGCCCTTACAATCTCACACACCCACCTCTTCCAC
TATAGTTCCTGGGCCTTGAGTTGAATAGCTTTAATTTCTGGCTCTGTGTT
TCAAGAATGCAGTTTATTTTGATTGGCATTTTCTACCAGTCCTGAAGATG
AACCTTTAATTGCTGTCAGTATTTAAGATTTAGCAGGACTTGTCCTTTTA
AGAACCAGGAGTCAAGCCCTATAACTCAATGTCACAAGGACTTTAAAAGC
ACATACATAAAGATATATGGATGTAATAATCATAATTTTTAAAAAATTGT
ATTAATCTCAGTGTTTTCTAAGCAAACCAAAACTTAATAATAATGGCATA
GAAATTATTTCAATAAAACATAAAATCTGTTAAGCCAGTTACCAAAAGGC
AAAAGAAAAGACCTTCTGCAATGCACAGAATATTATGTTGGAAGAAAACA
TTTCCTTTAGACCTTTAAGAAAACATTGTTAGCATCAGGACACAACAAAC
AGAATCTGAGGGTAAAAAACGTATATGAGCTGAAGGGAGTTGAAGGAGGG
CATTACTATTTCCCACCCTTTTAAAGGGGAGAGAAAACCTAAAACAGCAA
GATGCAATAAAAGCTGAACTTTGGGTTAAAAAAAAATTCTTAAGTCTCTT
ATAATTTATTAAGAGTGAATCAACCCCGTAAGAAAATTTCATTGTTCTAA
CCAATTTTTTAATATATAAGTAGTTTTTTAACATCAACCCAATCTCTAGA
AAGACCATTATAATTTCCCTTTAATTATAGACAACTTTATCATATAAAAG
TTTTTTTAAATAAATCCTCTTATTGTGACTTACACAGACTATTCATGACA
TGCTTGGACTTTCTGGTTTGTCGTGAACATCCTTTTCTTTCTTTCTTTCT
TTTTTAAATTTTACTTTACGTTCTGGGATACATGTGAAGAACATGGAGGT
TTATTACGTAGGTGTACATGTGCCATGGTGGTTTGCTGCACCCATTAACC
CGTCATCTATATTAGGTATTTTTCCTAATGTTATCCCTCCCCTTGCCCCC
CACCTCCTGACAGGCCCTGGTGTGGGACATCCCCTCCCTGTGTCCATGTG
TTCTCAATGTTCACTCCCACTTATGATTGAGAACTGCAGTGTTTGGTTTT
CTGTTC
>Contig23
GCTAAATATAAGCTATGATAAAACAGTTGGCCCTCTGTATCATGGGTTTC
ACAACTGTGGATTCAACTAACTGTGGATGAAAAATACTTGGGAAAAAAAG
AATGGCTGCATCTGTACTGCACAAGTGCGTGCTTTTATTCTCGTCATTAT
TCCCTAAGCAATACAATATAACAACTATTTATATAGCATTTACGCTGTAT
TAGGTATTATAAGTAATCTAGAGATGATTTGAAGTATACAGGAGGATGTG
CTTAGGTTACATGCAAATATTATGCCACTTTATATAAGGCCCTTGAGCCT
CCTCAGATTTTGGTATCCATGGCAGTCCTGGAGTCAATTCTCCTGCAACA
TCTCCATTTGTTCAGATTCTCTTCTATATCATGTTTATATCAGAAAATCT
ACATAAGATTTTTTAATGTGTTCATATAGGTTTTGTGTATTTTTGGTTGT
TAATCCCTAGATATATGCAGTATTTATTGCTATTATGAGTAGTGTTTCTT
TACCATGTATTCTAGTTGGTTATTGCTGACAGAGAAATGTTGCTGGTGTT
TCTAAGTTACCTTGTTTCTAACAACCTTGCTGAACTCTTATTAGTTCTCA
TAGTTTTTAATTAATCTTTCTTAGTTCTGATAACATAATCTGCAAATAAT
GACAATTTTATATCTTTCTTTCCAATGCTTATATCTCTCAGTCCTCTTTA
TCCCAAAGTATTTTCCAGGATCTCCACTATAACATTAAATAGTAATAAGA
ATTTCTGTCTTGTTACTGATCTTAAGGAGAATAAATTTAAATTTCCTCTG

FIG. 4F

TCAGGTTTTATGCTTGATATAGATTTGTGATATATAGCCTTTCACAGGTT
AAAAAAAAATGCTTTCCTAGTAGTCCTAATTTTTAAAAAAATCATCATA
AATAGATGTTGAACATTATCAAATGCTTTTTCTGCATCTATAGAGATAAT
CATATGGTTTTTACTATTTATTAATGTAATGAATTAGACCAATTTTCTA
ATGCCAACTCTTTCTTGTATTTGTAGGGTAAATCCTATGGGATCATAAAA
TACTTTTAATACATTGTTAGATTTGAAGAGTTAACGCCTTATTTAGAACG
TTTTCAGTCACATCCATAAGTGAAATGGCACTATAGTGTCTATTACTATT
ATATTTTTCTGGTTCTGAAACCAAAATTATACTCACCTCATACAGTAAGT
TGGGCAACTTTTGTTCTTTTTTTCTGAAACAATTTGTGTATAGAAGAAAT
TAACTGTTCCTTGAAAGTTTGATAATAATCATCCAGAAAATTATCCCCAT
CTAGGGCTTTTACAAAAAGGAGACTCTAGAATGCCATTTCGGTTTCCTTG
ATGTGTATTGGCCTCTTTCATTTAGGCTTTTGGATTTTTTAGGGCATTTT
TTCACTATAGGCTTTTTACCGG
>Contig24
CATAAACTTCAGGTTGGATGTTCGGTCAAAGTGGTCCGGCGATGCGAAAA
CGAGAGGGCTCGAGGACTGGGCAGAGAACTATTTGAAGGTATCTCTCAGG
GGAAACCAAGCGGAAGGCGGGGAGTAAAATTGGGAGGGAGCGACGGCCTT
CAAAGAAGGGGCTTGCATTAGATCGGCGAGATCCGGGAGGGTCTGGTGGG
GAGAAATGACTAGAGGACAAATCTAATGGAGAGACAGACGGAGATAGATA
TCGTGACAGAGAGAGGGACAGTGACAGCGCACAACAGTGCAGGGTCCATG
AGTACAAGGCCCTTAAGTGTACACCCCAGCCGGAGTCATGGCAATTCGAT
TCCTGTACTGACCACCCAGGATTTGGGTAGACTGTACGAGTTAATGAGCA
TGGTCCCCAACAAGACTGCTTCGACCTCAGATGCAAAGCACACTTCAGGG
GTCCCCAAGCCACTCATGTTTTTTGAATGACTGCCATAAGTTCAAAAATT
CCCACAATTCTCTCAGATTCAATAACTGGGTATAACCACTCATAGAACTC
AAGAAAATGCTATCATTATTATTACAATTTTATTATAAAGGATACAAATC
AGAAGGACTAGCCAAATGAGGAGACACATAGAGAGAGGACTAGTAAAAAA
CAGAGCTTCTGCGTCCTACCTTCAAGGAATCAGGATGCACCACCCTCCCA
GCACATCAAGTGCTCATCAACCAGGAAGTTCCTCTGAGCTCCAATGTCCA
GAGATTTTAGGGAGGATTCATTACATAGGTATCATTGATTAAATCATTGG
CCATGTACTTGAACTCAATCTCCAGTGTCCCTCTTCTCCCTAGAGGTCTG
AAGGGTTGGCTAATATCATGTGGCTCAAAGCCCCAACTCTAATTACCTTT
TTGGTCTTTTCAGGGACTAGACCCCATCCTGAAGCTATCTACAGGCCCTG
CCATGAGTTAGCTCATTAACATAACAAAGACACTTATATTACTCAGAAAA
TTCCAACAGTTTTAGAAGCTCCATGTCAGGAACCTGGGACATAGATCAAA
TTCTTTTTTTTTTTTTTTTTTTGGAGACAGGGTCTTGCTGTGTTGCCCAG
GCTAGAGTGCAACGACAGATCACAGCTCAATGCAGCTTCAACTTCCCAGG
CTTAAGTGACCTTTCCACCTTAACCTTCCAAGTATCTGGGACCACAGAAA
ATGGCTAATTATCCTGGCTGATTTTTAAACTTTTTTTTTTTGTAGGGATG
GGATCGCCCTGTGTTGCCAAGGTTGGTCTCAAACTCCTGGGTTCAAGCAA
TCATTCTGCCCTGGCCTCTGTGATGGTTAATACTGAGTGTCAACTTGATT
GGATTGAAGGATACAAAATAATATTTTTGGGTGTGTCTGTGAAGGTTTCG
CCAAAAGACATTACTTTGAGTCAGTGGACGGGGAAATCCCCCCTTCCCCA
TGGGACGGGGAGACCCCCCTCCATCCAGGTAAAAAAATCTAATCACCTGC
AATGTGGCAGAAATAAAGGAGGGAAAAAACGGGGACCCCTANATGGGTTA
TTCTCCACCTAATTCTTCCCCCAGG
>Contig25
CCATGTATTTCATTTCTACAGACCCTGAGATGAATTTGTCATTGCCACGG
GGTCCTGAAGTTCAAATACTCTATTTGGTATCCTGCCCCTGTGGTTAACT
GTGATCATTTCACTCACCTTGTTTATGATGAGAGGTGCCACCATCTGGCC
TCCTCCACTCTGCAATCCTGTTAATTCCTATCAAAGCTGAAAACCTGCTG
CAGCACCCACACCATCACCTCCAGCCTAGAGAGGGAAGCTACCAGTGAGC
TCTCCTGGATGCCGGTGTGCCCCTCGCCAATACATTTCTTCTTAGTCCCT
TGGTCATCCTGAGGTGTGTGATTAATGGACAGCTATGTGGATTGCACATA
ATAGATGTACTCCAGCATCTTCATCCCTGATTTTCCTTTACAGAAATCAC
TCAACCTTAGCAACATGTGAAAATCACCTAAGGACATTCTTTAAATCCCT
CTGTCCACATGGCAACACAAACCACTTAAATAAGAATCTCCAGGGAGTCA
CTCAAGCATCAATGTTTTTTAAAGCTCCAATTTTAAGGATCATTACATTA
TGTCGAAGAAATTATAGTATTTCAGCCTTACTGACTGTAAACCACCACCA
TATCTAAGCATCCATTAGTCAACCTAGCAGACAATAAACTAACATTACCT

FIG. 4G

CCAGGTACTCAAATCAATTCATTGCATCCCAAATCCCAGATGGGCCCACC
CTTATTGACAAATTCAGCCCAATCTTGGTTGAACACATTTAGAATATATT
TCCATGAACAATATCCGGTTGACGAGTTTCTTTAACTTTTTGGAGTTTAA
GCCATTTCCTTTCACAGTAGCCTTGTTAATTCCCTGTCAATGCTCCATGG
GGGTCATGAAGAGACCTCTTATTAACTGTGAAGCAACTTGGCTCAGGTGC
AGACACTCAAATGCTTCACATGCAGTGGGAAAAGAGAGTGATTGTCTAC
>Contig26
TTTAAAAAGAACTGAGTCTTTATTCAGTCGATTCTTCTAATCTATGAACA
TAGCATCTCTCTCAAAGCATTTAGTCCTTCTTTAATTTCTGTCATTAATT
TTTTAAAATTTTCATCCTAAAGATTCTGTATATGTTTTGTTGAATTTATG
CTTAAGCATTTCACTTTCTTGGTAACAATTATAAATGATTTTGTGTTTTT
TATTCCACTAGTTCATTTTCAGTGTGTAGAAAAGCAATGAATTTTTGTGT
GTTGATCTTTGTTCCAACATCTTGCAACATTATTGAACTCATTTATTAGT
TCTAGGAGGTTTTTTCATTTTTCTTGTAGATACCTTGAGATTTTCTATAT
AGACAGTCATGTTGTCTGCAAACAGGCACAGTTTTATTTCTTCCTTTTCA
ATCTATATGCCTTTTTTTTTTTTTTTGCCTTATTGCAGTGGCTAGAACTT
CTAGCACTATGTCAAATAGCATTGGTGAAAGCAGACATCCTTGTTCCTTG
TCTTAGAGGAACATTTGGTCTTTAATCTTGATTTAAAAAATTCCTTGCAC
TAAGTTACCGTGTTTTGCGGGAGGGAGAGGTGGGGTGAGGTGGGGATTTC
CCCTAATGTTTACAAGCTGGGATTTTCTTTTTCCTGTGTCTAATTATTTT
CCTCATTGGCTTGAAAAATCTGATAAAACATTTTAGGACTGTGTATAAAA
TAGAATTAGCCAAGTGCAATGTCTTTATTCAGAAGAAATTTCATGGACGT
TGTGCCTACTCTCTTGGCTTCCTGGCTTCATGGCTTTCCAGATCCCACAG
TAAGCTCTGGATAGTAGAAGTTATAGTAAGACTGACTTCTAAATAAATGA
AGTGACTTTAACCTTACTGATATGGCTTAAAGAAAAGGAGTGGCCTTTAA
GATCCATGAACTTCTCAAACAAAAGTGATAACGTTATCTCCATGCATATA
TAATACTAAATATAATGCAACTGAGAGAAGTAGGCTGTGGTAAGAAAGGA
GACCCAAGTGCCATCTGAAGGCAGCACTTACCACTCTGCTTCATCCCACC
GAGGAAACAAAGCATGAGTATTGCCAGATTTTCTTCTGTTTCAAGAAAAG
CCAGAAATCCAGGTTTTTGCGTGAAATGTCCTGATTTTAATGTTGGGAAC
TAATTTATATTTTGAAATAACATTGTGTGGGACAAGTGAACTTGTATGTG
GAACTGCTTTCTCCCAGTGGCGACCAGTTTGGACCGTTGATACTCAGCAA
GTTCAGCCAAGTGCGCCTTGTCATTGTCAGTCATCAAGGTGATGTGTGAT
TGGTCAAGCAATTAATTTTGCTCAGCATCTCGTGTGTTTTCAAAAGAACT
GAAGGTTCATTTGC
>Contig27
TTTCAGAGCACAATGCGTATTCATAGTATATTGACTTAATTTCTAAGTGT
AAGTGAATTAATCATCTGAATTTTTTATTTTCAGATAGGCTTAACAAATA
GAACATTCTGTATATAAATGTGTAAATTAGAGTTAATCTTTCCAATCACA
TAATTCGTTTTATGTGAAAAAGGAATGAACTGTTCCATGCTGGTGGAAAG
ATAGAGATTATTTTTAGAGGTTTGTCGTTGTGTTTTGGGATTCTGTTTTC
TTTTAAAATTGTAAATATGTACTTGTGTGAATGATTTTTTAAAATGATTT
TACCATTTTTGGAAGGGTATTTAATGATAGAATATCATCGAGCCAACATG
CACTGACATAGAAAGATGTCAAAGATATATTAAGTGTAAAATGCAAGAGG
GAAAACACTATGTACAGTCTGAGCCAAATCAAAGCATGTATGTTTTTTAT
ATGTGTACAACAAAAGGTTTGGAAAGATATGCGCCGAATTGTTAAATGTG
GTTTCACTTGAGGGGGTGGGAGGATGGGGCCCCAGAGGGGTTTTTATGGG
GGCCTTTCACTTGGTATTTTTTTCATTTTGTTCTGTTTGAAATTTTGTTT
TTTCTTTTTAAATGGAGTTTCACTCTTGTCGCCTAGGCTGCAATGTAGTG
GCGTGAACTCAGCTCACTGCAACCTCCGCCTCCCAGGTTCAAGTGATTCT
CCTGCCTCAGCCTCCCATGCCTCCTGTGTAGCTGGGATTACAGGCACCCA
TCACCATGCCTGGCTAATTTTTGTATTTTCAGTAGAGATGGGGTTTCACC
ATGTTGGCCAGGCTGGTCTGTAATTCCTGACCTCAAGTGATCCACCCACC
TTGGCCTCCCAAAGTGCTGGGATTTCAGGTGTGAGCCACCACGCCCAGCC
CTGTTTAAATTTTTTATAAGTATGTACTACTTTTGTAATCAGAATTATTA
GAAAGCATTTTACTGATTTAAAAGCTTAGACATGTTCAAATGCCTGCAAA
ACTACTTAACACTCAGCTTTAGTTTTCTAATCCAAAAAGGCCGGGCAGT
TAATCTTTTTGGTGCCAATGTGAAATTTAAACGGTTTTATGTTTTTCCTG
TGTTGTGAATGAAAAATATTTCTGAGTGGTGGTTTTTTGACAGGTAGACC
ATGTCTTGTCTTGTTTCAAAATAAGTATTTCTGATTTTGTAAAATGAAAT

FIG. 4H

ATACAATATGTCACAGATCTTCCAATTAAGTAGTAAGGGTTTATCCTTAA
TCCTTGCTAATTTAAGCTTGCATAAGTCACTTTACTAAAAGATCTTTGTT
AAGCTAGTATTTTAAACATCTGTCAGCTTATGTAGGTAAAAGTAGAAGCA
TGTTTGTACACTGTTGTAGTTATAGTGACAGCTTTCCATGTTGAGGTTCT
CATATCACCTTGTATCTTGAAGTTTCATGTGAGTTTTTACCATTAGGATG
ATTAAGATGTATATAGGACAAAATATTAAGTCTTTCCTTTACCTAAGTTT
GCTTTCTTGACTAGTAATAGTAGTAGATATTTCTGTAATAAATGTTCTCT
CAAGATCCTTAAAATCTCTTGGAAATTATAAAATTATTGGAAAGACAAGA
ACAGTTTTTATTCATTATATGCATTATTATCG
>Contig28
CTTTCTCAAGAAAAGGGAACTGGAGCAATTAAACATATGTAATTTTTTTT
TAAAAAACCCTAAACCTAAACATCTACCTATATACAAAAATTAATTAACA
ATGGATCATGGACTCCAATGTAAAACATGAAACTCTAAACTTCTAGAAAA
AAAACTGGAGAAAACCTTTGGTACCTATGACAAGGCACAGTTTTTAGACT
TAACACTAGAAGTGTGAACTATACAAGAAAAAATTAATAATTTGAACCTT
ATGAAAATCAAATTATTTGCTCTCCAAAAGACCCTGTTAAGAGGATGAAA
ACTAAATTACAGATTGAGAGAAAATATTTGTAAATCACATATTTGACAAT
GGACTTGTATCTAAAATATCTAAAGAACTCTCAAAACTCAACATTAAAAA
AAATATCTAATTAGAAAATGAGTGAACATTTTACGAAAGGGGCCTTATAG
ATTAGCAAATAAAACACTTGAAAAGATACTCAGCATCACTAGCCATTAGA
AAAATGCATATTAAAACCACAATAATGTATCGCTACACACATATAAGAAT
GGTTTATGAAAAAATAGTGATGACACCAACTGTTAGTGAAGATGTGGAGA
AACACTCATACATTGCTGGTAGAAATGTAAAATGGCATAGCCACTGTGGA
AAATTATTTGGCAGTTCCTTTTAAAACTAAAAATCAATCTACCACACAAC
CCAGCAATTTCATTACAGGGCATATATCCCAGAGAAATGAAGATTTATGA
TCACACAAAAATCTGTACACAAATGTTTTATGGTCACTTTATTCATAATA
GCCAAAACCTGGAAACTATCCAAATGTCCTTCAATGGGCAAAGGATTAAA
CACACTGTGATACATCCATACCATGGAATACTACTCAGCAATAATAAGGA
AAGAATTACTGCTACACACAAGTTGGATTAAACTCAAGGAAATTGTGCTG
AGTGAAAAATTAACAAGCCAATCTCAAAGGACACATACTTCATGATTCCA
TTTGTATAACATTAATTAACACAATTAATTACAGAGATGGAGAACAGAAT
AGTGGTTGCCAGGGATTATACATGGTGGACGCGGTGAGGCGGGCCTCCAC
GCCTTGGAGATGAAGGGGGCTACACCCTTTAAAGCACACCCACGAGAGAG
TTTTGTGCGGAGGGGCCCAATTTAAGTACTCCGCCCCGGGGGGGGAACAC
AGGGGCAAACAAAAAAAAATTGGCCTTGGGGGTGACCAAACACACAAAAAA
AAAACAAACACACACAAAAAAACAACNATGGGTGGAGGATTAATCGCCAAA
TCTGAGTAAGCTATCTGGACAGTACCAATATCGATTTCCCAGTTTTGATG
TTGTACTATAATAATGCAAGATGTTAACATTGGAAGAAGCTGGCTGAAGG
GGGCTCAGGAACTCTCTGGACATTTCTTTGTACCTTCCTGTGAATCCATC
ATTATTACAAAATAGGACATTTTCTAAAGGTTAAATCATTTTAATTTTAA
AATGTCCCTGTTACTGTTGAAACTCACATCTCCATATACTGATCAAGAAC
AGCACTAATGGCCCCCTGGCCTCCAGGAATTCACAATTCCTACTGACTTTT
CTTTGAAACCTTGGCCAAGTCGCTTCTCTTCTCTGGTCCTCAATTTTTCA
TCTTCAAAATGAAGATTGAATGACTATTAAAATCTCTTGCAATTCTTGAG
ATGAAGGGTCCTAAAGGAACTGAAGAGGATGCCATGTAATGTAAATATGG
GTTTTTACTCCATCAGCCAGCCAAGACAGAGGGCAGACACCAAGACATGG
TAACCAAGGAGGCCATGTGTAAACAAAGACCATTTAGACTTATGCTCTGG
CCTTTGCAGCCCAACTGGTGTGGCCAGTTGGTGGGGTATGAAGAAAATGG
GGCCTTCCAGGAACCATGTTGAGTGGAGATAAGCAGGGAGGAATGCAGAA
GACATGGGGGCAGTGCCAGTCTCAGCCCGAGCCAGCTACACCCACACATG
GTTATGAAAGACTGACAGCCTGTAAGNTGAACACAGCCCTGCCTCTCTTA
GATAGGC
>Contig29
GCAAATATGATCTCAGATGTGGATTTACTGTAAAGTTCATCAAATTTAAA
TTTCAGAACACTTAATCTGCAAGAGTCCTTTCCAAGACCCTATACCTAAT
TTTGTGTTTACAATTTTATATTTGTTTTCTTAAAGAAGACCACCAATATA
AACTATATCCAGCCTTCATGATAAGTACATAGGAAACTATGCAAATAAGG
GGGAAAAAAAACAAAGAAAAATACCTAGTTTACTAATGGTTCACTTCTGA
ATAGCACATATTCATAATGATACAAGCACTCATTACTAGTCTAGGAAAAT
GAAGATATAATTGCATTAGGAAGATCAAGAGGTAGGAAATGTGGATGTGT

FIG. 4I

GTGGTATAGACTAGGGCAGGACAAAGAACCTAAATCCTCATTTTCTAAAG
ATAATTGTTAATACGTAAAACTCAAAATTCAAGAAGTAACAGTAAAAGCG
GTCATTAAGAAACAAGCACTAAACACCAGATAGGAAGCGAGAGATGGGGG
AAGAGGGCGACAATCTGATTATTTTTGCAACAAATTTTGTAAAACCATT
TGACTGTTTACATGTAGAACTTGGATCTTTTTTAAAAAACACAAAATAAT
AATACTATTATTTTTTAACTGGATTTTTGAAAAAGAAGATAAAAGTCTCA
TTTTAGTAATTAAAACTCATTCCAGGTTAGTCCACTCAAAACTTATATTC
GAAAATTAAAACTTTGGGAGGCTGAGGCAGGCAGATCACCTGAGGTTGGG
AGTTCGAGACCAGCCTGACCAACACGGAGAAACCCCGTCTCTACTAAAAA
TACAAAATTAGCTGGGCGTTGTGCATGCCTGTAATCCCAGCTACTCGGGA
GGCTGAGGCAGGAGAATTGCTTGAACCCGGGAGGCAGAGGTTGCAGTGAG
CCGAGATCACACCATTGCACTCCAGCCTGGGCAACAAGAGTGAAACTCCA
TCTCAAAAAAAAAAAAAAAAAAAAAATTAAAACCTCTGGAAGTTGAGTTTG
CAAATATTCATTATGCTCATTTTTAACTTGTATGTTTGGAAAATGTCATG
ATGAAAATTGAGGTTGGGGGATGAGAAAAAAAGAAAAACATCAACCCCAC
AGCCCATTCAATTTTCAGCCCGACCCACAGCTCCGGGGAAGGGCAGCAGG
TCCATCCTTCACTCTTTCTTCACCTCTTTCCCCTCCTTCTGGCTCTTCCA
CCTCTAATTTGGAGCCCAAAAAAAAGGCACTGGGAAATGGAAAAGTCTTTT
GTACGTGGTACTTGCCGGGGAAGCTGCCATGAAAACCTGGCCCCACGGTG
GGGAGGGAATGCCCANCTGAGGCCTCGTGCCCATGCTAGGATAGACTCGT
CCAAACATGTCAGGTGGTCTGACAGGGCAAGCANCANGAAATCATGTATG
AGTATGAACTGATCTGTATGCAAGGGCGGGGAGAACACGCGGAGGAATGG
GGCGTGAGAAAACAGCACAGTACGTTTCTTTAGCAGCTGTCTCTGCTCAG
CCATGGGAGGTCACAGAGAAAGAGGCTTGGAGGCGTTATTTTCACTGTGA
GATGTGAGTGTAAAAAAGTGCCCAAGACACAGTGAGTACCAGGGAGATGC
CCTCTTTCCTACCCGAATGCAGAATGGCCACAGGCCTTAAAACACACACA
TGGGTCCTCAGAGGAGAGAGGCCTCCACAGTGGACACCCGCATTCTCCCC
TGGTCAGCAGCAGCAGGGCGAGTGCTGGGCCATCATGAAGCTTCACAGGC
AATGAGCTCTCAGCAATAACAGGAACAGTGCCTGGGGGACTGTAGCTGCA
AGACCGATTTTCATGTAAGATGGCCTCTGAGGACTCCGAGATACACCAGG
CTGAGACTAGCTGGCAGCTCCAAGTTGTTGGTCAGAAGAGAACAGGAACT
AGGGAAATTGGAATTACTGTTACTACAATTCCTTTACATCCGCACAACCA
TGAGGTCCAGCGATTTTCTATTATTTTTTTTTTAAGACAGGGTCTCAGT
ATGTCGCCCAGCATAGAGTGCATTGATGTGATCATGGTTCAGTACAGTAT
TCACGTCCCAGGCTCAAGTGACCCTCCTGCCTCAGCCTCTCAAGTGGCTG
GGACAGCAGTTGCATGCTACCAGGCCAGGCTTTTTTTTTTTTTTTTTTA
GTTTCTGTAGAGCACATAGC
>Contig30
GGTTAACAATGGCACAGGGAAACAAACAGTTCCAGGTGCAGGGGCTCTAA
ATCTATCATAAGATGTTAGGTATGGGGGCTCTGCCGGACACAAACTCAAG
GCTTTATGCTGTTATCTCTTGAGCGAAATCCTGGGAACTTCGTACATTGC
TTGCTTCAGTACCTTATCAGTTAATCGGACTCTTTGATATGTTGGGAGTC
AGCGTACACAAGTTAACTCCTTGAGGAAGGGGGTGGGTAAGGAGTCCTTG
ATGTCTGGTAAATGAAGGAGCGAAATCGAGTTCCTCTGGCTTTCTCAGCT
AAGGGAGAGCTTATTCATGTGGAAACAAGGCTAAGTGATTAAGGGAGAAA
GGGAGAGTCTGAAAACAAGGTTAGGTATTACAATGTCAATAAAATTGGTC
TCCTTATACAGTCCTATGGTAGATTTCTTTCCATCTTTAATCTCCCTCTA
GCACCACCAGACTTTTTCTCTCTGTACCTTGAGATGTAAATTTTGCTATC
TGAATTTTCGTCTAAGAGTTGTTTCCTTTAATATGCAAATTTAGGGTTAT
TTAGCTGACAACTGCCAAAGTAGTGAAACAAGTTATCAAGAACTTGAACG
TCTAAGGTAGGAAAAAAAAAAGTCTTTATGAATCTATAAGATGTACTTCT
ATTGGCATGCCTAATACGTCTATGTATTTACGTGTTGTGTACACAGTTTT
TCACTACTGAAAATATATAGAGGAGTTCTAATTAATTGACTTAAGACAAT
AAAAGCGCTTGAATCAAATACCTTATCAGGAAAAAGGAAAAGACAAGTCA
AATGCTTGTTCAAGTTTATATAACTTAAGTAAAATCTTTAATAAATAAGC
TAGCTTTAACATTATTTGAAATGTCTTAAGAATTGCCAGCAGGTTCTGGG
TTACAGAACTAGTGGGGGTGCAGTGGGGTGAGGGTTGGTGGGGTGGGGGG
TGGTACGGGGGCTTTGTTTTTTCTTGCTGCCCCCTTCTGGGTTGGGGAAG
TGGCAGGACCTTGGCAGCACCCCGAGCCGGCATGGCGTTAATAATGGAGG
GATGCCAGACCCAAGTGGCTAAGGCCCGGCTGCAGAGCCAAGTTGGCATT

FIG. 4J

TCCAGACTGGGGCTCGGGCCGCACCCTCTCCAGGACCCTCCCCTTGTACC
GAGCAGATTGTCGCGGGCAGTTTGGGCCAGCTGTCCTGGCGTGGAATTTC
CCAAATTCAACAAATCCTCCAAGAAATCAATCCATCCATTCATCCATCCA
TCCATCCATCCATCCATCCATCCATCCATCCGTGGCAGATTATGAAGCAT
GGATCATTACTTTTGGGATGTGGATATATTCAGTTAACAAGGAGCAGCTT
TCAAGAGCTGGATTTTATGCTTTGGGTGAAGTTTAGAAACACTAGCTCCC
AC
>Contig31
ACCTCATGTGCTCTAGCGCCTCTTACCTCATGCCCTCCACTCTCAGTCTT
GCACTCACCCTGCCACACTCAAGGGCTTCCCCAGGTTCCTTCTTAGATTC
CACCGATAGCTCAGGGACTTTGCACATGCTACGGTCTCTGCCTGGCTCCT
CCCCAGATCTTCTCATGCCTAGCTGCTTCTCATCAGCACCCCTCAGAGAC
TGTCCCTGCCCCACCTCTCCAGGTTCCATACCTGCCACCCTCCCCCAATC
ACGTAACAGTTTCTTCACAGAGCGAGTTACCATCCCAGTATTTCCCTAAC
TTATTTTTTGTGACTGGTCTGTTGCCTGTCTCCACCACAAGAACATAAGC
TGCATGTGAACAGGAGCCTTGTCTATCTTGTCACCCCAGTGGCTGTGACA
TAACCTGATACACATTAGATGCTCAATGATGTTTGATGAATGAAGTGCTG
GTAGTCCAACTGTGTTTCCTTGTCTGTGTAAGTATGTCTGTTGTGGTTTC
CTAAGAACCTACAGCTCTCCCACTGTGACTCCTGTTCTATGGTCCTGATT
TGCTGGACTAGAATCCTAACCTACATGCTTACTCTTAGTGTCCTCCCCCA
GAGGCTGAATCCCAGTCCCTAAACCTCCACCAAATGGCTAAGACCTAGCT
TCCAACCAGACAGGCCTACGCTGAGACCTCAGCACCGCCCTTCTGCGGTC
TCATCCTTAACGCATCCTTCAGGGCCCAGCTTAAATGTCTCTTCTCCAAG
GAAGGCTATCCTCTTTCTGCCCCTCAGTGCTCTCCATGCCTCCTCTATGC
CTCCATGCCTGCTTTCCAACCCTGCAGAGGTGGAGAAGTTGCTAATCTGC
TGTGTTGACATGTGCTGGGGTGCCTTGGGCCAGGGAGCAGGCTGGTGGTG
TGCTGATAGCCCGTGGCTGTGCCCAGGTCCATGCTCACTTCCTGAGCCCC
AGTGGAGTAGGCTCCCTTTCCCTTATTGCAGCACTCAGAGGAAGGACGTG
CTTCTTAGGACAGATCTGGCCAACCTCTCCCTCGTGAGAGAAGGCCCAGC
CATCCTCTTGCCCTCTTTCTTTCTCCTGCCCCCGAGTAATAAAGGTGCCT
GGTCAGAGCCTTCTAGAAGGAGACCCAAACATCCACCACACATTCCCAGT
TCCAACCGTCATCCACATGGCTGGCTGTGCAGGTAAACGCAGAGTCTGTT
TCACACACCCAACCATCTAGTATTGGATGGGAGGACAGTAGCGTGACACT
CTTCTCCAGCCTTGAGCCCTACTGTGGGCCCCACCCAACCCAGATACCAG
AGGAGCCCTGTACTGGGATGCTATTGGATGCTTGTCCAGTCATGTACAAA
GTTAGCCCTTTGTTATATAGAGTTAGCTACGTACATCTTCCTCTGTAGGG
AACCCAAGAGGGGAGAAGAGATATGTAGTAGGATTTAACCTGCAAATCCT
CTGCTGAGCACCGTGCACTACATACAGTGGGTAGCATGTGGTAGGTGCTC
AATAACTATTGACCGATCTATTGAATACACGTAAGATCGTGACACTATCT
AAAACGNGGGGTGTGGGGGAAAAACCCCCCCCTTGTTTAGGAAACCCAAA
TTGGACCGTGTTGGC
>Contig32
GCGCGATTGTGCTAAAGATCATGCATGCCTGATCAAACGTCCCCATATGG
CGTCTCAGAGTCAACTCCTTCCCCATCAGTGCCCTGACTTCGGCATAACA
AACCTGGCAGGTTAAGTGATTAATCGGTCCTGTACAACTGTAGCCCTTAG
CAGGAAGCACTAAGCTTCGTTTCATTTATTTCTTCCCTGGAACTGCAAG
AAATGAGGGATGCCTTCCGCCATGAAGTTTTGCTGATTGTCCACTTTGTT
CTCAAGGAGATATTCACAGTTTTTAATTTGTCTTTCTCTCCTGCATGGTC
TCCAAACCTGTCCAAAGAAGCCAGCTGGCTCCATCATCTGTAAAATCACC
ATTGTCACCAGAGCACTTGACTTCCTGTTGCCCTACAATCCACCTGCACT
TTATTTCCTGCCACCATGATAATGTAGTGTTACTACATTTTACATTCAGC
TGTAAGAAATGTTACATTCATTTACTTAAATCAAATTAAGTCTGCTCACT
CAGTCCCCCACAGTGACCAACTTATAAAAGAGAAGGTACATTTCAGTCAT
CACTGAGGTTCTCTCTACCACTGGAAAACTGAGGAAGGGTCTGGAGTCCA
CAGTGGTTAACATCATTGCCTCTGTTTTTTCTCCTACTCAATGTAACCAT
CCAAGGTTACTCACAAATTCACAAAAAGAGGTCTTCACCTCTGCTCTCAA
GACCCAGAGGGCTGGGTTCTAAACTCAAAGGCCAATGTTCCCCAACTTTT
TGCATTGTTTCAACATTGGGGAAAACTCGAGGGGATTCAAGAATGGTTAT
ATAAGTTTTGTGGAAAAAATGTATAATTTTTTAAAATTAAAATACAAAGTA
TTATGGAAAGCACTAAATATTGAATTTATATAAATATTCCAAATATTTTT

FIG. 4K

CTAAATTTTTAGTGAGAAACTTGAGCTTGCTTCTGTGAGATATTTATTTT
AAAACAGATTTGACACTTAAAATGTCTAATCAAGCCTTTTAAACCATGAT
CTATCTCTTCAAATTCTTCAGATGCCACCATCAATAAAGAAACTTTGTTC
ACACAAGTAAGTGGTAGCAAATGGCAGGGTGTTTATCATTTTTTTTTTTT
CTTTTTTTGAGACGGAGTCTCGCTCTGTCGCCCAGGCTGGAGTGCAGTGG
CGCGATCTCAGCTCACTGCAAGTTCCACCTGCTGGGTTCACGCCCTTCTC
CTGCCTCAGCCTCCCGAGTAGCTGGGACTACAGGCACCTGCCACCACGCC
CGGCTAATTTTTTGTATTTTTAGTAGAGACGGGGTTTCACCGTGTTAGCC
AGGATGGTCTCGATCTCCTGACCTCGTGATCCGCCCGCCTCGGCCTCCCA
AAGTGCTGGGATGACAGGCGTGAGCCACCGCGCCCCCGCCGTGTTTATCA
TTTTTTGCCTGATGAAATTTTCCTTGCCACTACTCTGGATGGTTTGATAC
ATTTAAATTGTGCTTCCAGGGTACAATTATCCTTTAAATCTATACCTCTT
TCCTTTCTTTTATTGACAAATATAATGTTACACTTTTCTGTCATTGCAGC
CACACCACCAGTACACAGATCCCAACAGAGTTGTAATATTTTATTAGTTT
CAGAGTTTCAATATTTTATCACTTTCAATACTTCATGTGCAGGAGTTTTA
TTTGGTACTTCTTTACAAAATAAATGATGTGCTTCCAAGCATTTCTTTTC
AATAATTCCAATCAATGTTATTAACTGAGTAATACTAGTATCTGTTTATT
CATAAATTCACAGGAAATGCTTTTTTACTTATTAGTCTTTGGAATTCTGT
TGTTTGTATAAACATCTTTCATGATGGCTTTGTGTCTACCAATAGCACTA
TTGCCAAAAGGCACCTTTTTCTTGTTCCTTTACTTCACTGGTCCGAAGCC
TGGTACCAACAACTACCACACAGACTGGGAAATGAGCAATTTTGCCACGT
GCCCTTAGCTATTAATGGTGGCACTCCATAACTAGCATCTTAAGCTCAAT
TTCATGAAAGAAATGTGTTTCTTATTTTGTACTTGCAGGCACTTTTTAAA
CTTGTAATCTTTTATTCATACTTTAAAATTAAAACAGAGTAATAGAACCC
ATAGAAGGAAATCAATACCCACGAGTCCATACTGATATAAATAAATAGTT
ACATAAATAAATGGGGGGAGAAATAACAGCTCTTCCTTACAGAAAAATTT
CAATTAATAAATGAAGAAGGAATTAGGGAAATACAACGTTACCATTAAGC
AACCACAGTAATAATCATTACAGGCAATATCCAAAAATAAATTCCAAAGC
CAGTGGGCAAAAGTTTGAGGAGATACAGGATATTAACATAGTCTCCAAAT
AGCTCATGCTATTTATAAATTACAAAAGGAAACATAACAACTGTATAGTG
AAGAAACTCAGCAGACACCACCTTAGCCAAGTGATCAAGGTTAACGTCAC
TAGTAATAGGGCTTGTTGACATACTGGACTCCAATCTGATACACTGATAA
GGACACATGACTTCTGCAGTATTCTTACCAAAAACAGAATTCTAATGTAA
TTAAGGAAAATGTCAGACAAACCTATTCTGAGAAACATTCTATAAAACAA
CTAACCAATACTTTCAAAATTGTCAAGGTCATAAAGACCAGGCGATGGTC
ACAGATTTGAGGAGACTAAGGAGATACAACAACTAAATACACAAATGGAA
CCATGGCATTCTTGATTGGATCTTGAAACAGAAAAAGGATATTAGGAAGA
AAAGCTGATGAAATTCTAATACATTCTGTAGTTTAATTAATAGTATTGTA
CCAATATTAATTTCCTAGATTTGATCATTATACTATGGTTAAGTTTTTAA
CATTAGAGGAATCTGGGAGAATGGTATATATGAACTCCACTGTTCATTCA
ACTTTTTCAGTAACTATTATTTCAAAATAAAGTT
>Contig33
GGGAGCGGCGGCCCACGCTGATCTCTAAAGCTTTAGACCACATTGGCTCG
AGCATGGTCATGGCCGTTTCCTG
>Contig34
GACGTCTTAGCGCTATATTATAAAGAAATATTCACCTCCCTGCTGAGCTT
ACAGGGTGTACCTAATGTCCAACAATATGAAATCTCTTCAATGAATTGCA
GCACGTCCATATATAACCCACATGGAAGCTGTCCTCTTTCCTCACCTTCG
AACTTCCCATGCCAAAGAGGGACCTCTTGGACTCAAATACATCTTAGCAA
TATAGAAGATGCTGGAGACTTGTAGGAGAAGTGGAGAGGGTTTACAGTGT
AGCCCCACAGAAAACAACTTATGACCCCATCAGTCACTTGTCCCTTTTTT
CCATGCCTCAGTCTAGTCAGGAAACCACTAGATCCTGGATGGCTTCTTCT
CCCTTCCCCTCCTTTCTCTTCTCCTCTCCCTCCCTTGCTCCTCCTTCCTC
CATCACCCACTCCTTACTTCCAACCAAAACTTGACTAGCTCCAGTCTCAT
CCCTCCTTATTGAAAACTATTTTACTCAGCCCTCCTCCCCCACTCCTGCC
CAATCTTTATTCCTTACCTACATCAGACTTCACCAAAACAAAGGCCAGGA
TAATAAACAGGACAAACTCTTTCAAACACATTTTAATGACCATATTTTGT
TATTTTGGTACAATTTGAGGAGTCCCAATCCCCAGGGAAGACTAACAAGA
AGTTCTCCTAACAAAGGTGGGTCTCCCCTTACTAAAAACTCCTGTAATGG
CTGAAAAGAGCATGAGGTTTTCTGCATATCATTACACATTCAATAGAACG

FIG. 4L

TCATGCAGCTGTTAAAAATGATCTGTAGAAGGCTATCTTGTGACAGAAAG
GCATTGGAGATATACTGTTAGTGACAAAAATAGGTTATAAATGAATTTTT
CCATGCATGCCTCTATATTTATAAATACACACACATAAAAGACAGGAAGG
ACAGACATTAAACATTCATAGTGCTTAAGATGATGCATAGTATAATAGTT
AGGACCATGGCCTTTGGGACAGAAAACTACAGCCTCTCTCCCACTTATCA
GCCATGGGACCTTGGGCAATTTGCTCAGCCTCAAAGCCCCTGTTCCTTTA
TCTGTGTGCTGGGGTTGTTGTAAGAGTTAAGTGCAATACACAGAGAGAGA
GAGAGTACCTAACATGTATTATGTGCTCAGTCAATATGCATCATAGTACT
CATTGTTACATATGTTCCTAAGTGCTTTATACGTTTTTTCCCTAAGTTGA
CCATCTGTTTTTGGCATTATGAAACATAATGATCCTAACAAATTAAAATT
AAAAACATAAAGAATATTTGCCCCAAAAAAATAAAGAACATGAATTCTTC
AAGTAGCCAAGGGGCCATAGACAGAAGTAAGCCCTTGGTGGGGCTTAGTT
GAGAGAAGTCTCCAGAAGGTCTTTCGTGTGTTAAAGAAGAGGGTAACAGG
GAGGAGGTGGGGAGAGATGTTAACTGAGTCTAAATGAGCACCTGGAAGAA
GAGATGGGACAGGCCACTTCTGCCTGGACTCCCTGATTGTTAAGAAGAAT
GAAAAAGAGCAGAAGTCTTCCCTGAGCCCAACTTCACTCCCTGACTTAAC
CTAGTCTTTGCCCCTTCCCTCTCACTCATGGCTACTTTCTGTGGTCACCT
TGTTGTAGAAATGGATGTGCAGCCACCTCATCTTTTTCTACCTCCTTCAC
ATGTTTTAGATAATTTAATGTAGTAGAAGACGGTTACAGCAAAAAATTAC
AAAAATCAAAATATCTCTGCTATCTACTGTTGCATTTCTAACCATCCCAA
AACAGTAGCTGAAAACAGCACTCGTGGTCGAGCGCGGTGACTCATGCCTT
TAATTCCAGATACTCCGGAGGCTGAGGCAAGAGAATCACTTGAACCCGGA
AGGTGGAGGTTGCAGTGACTCAAGATCATGCCACTGCACTCCAGCCTGGG
TGACACAGTGAGACTCCGTCTCAAAAAAAAAAAAAAAAAAAAGCACTCGTG
TATTTTGTTCAAGATCTGTGGTTTGGGCAGGGCAGGGCTCAATGAGGACA
TCTCGTCTCCGTTCCCGCAGTGTCAGGAAGTGTAACTGAGACTGGAGGGT
CACACAGAAGATGGCTCCCTCAAGTGGCCAGCAAATTGGTGCTTACAATT
GACAGGGAGCTGTTGACCAAGGGCCCCAATTCCTCTTCCTATGGCCCCTT
CTCGGGCTGCATGGGCTTCTTTACAGAATGGCAGCTGGATTCCAAGAGCA
AGTATCACAACCTACAGAAGAGTGGAGGAATATTGAAAGTTCACAGTCTC
TTAAGACGTTGGCCCAGAAACTGGCAAAAGCTTCATTTCTGCCATGTTCT
ATTGATCAGTCACAGAACCTGCACCAATTCAAGAGGAGAACATATAGAGG
ACATCTCTCAATGGGATAAGTGTCAACAAATTTGCATCTATCACAATCTG
TCTTTTGGGTACAAACTATTTCTATTCCTCCATTATGCAAAATATACTCA
CAACCTCCCAGGGGTCGCAAAAGCCTCATCCATTTATGGCAAATGTGGCC
CTTTTAATTTATATAAAATAATTTGCGGGGGCTTCCTTTATATTTTTAAC
TCCCCTGC
>Contig35
GTGCAGAGAAGTGATTTAAAGCCCTTCAGAAAGAATGCTTTATTCCCGTG
GAATTTGGTAACTTGCTTGGGTGTGGGGAGGTTTGTCAGCTTTCTCCACT
CAAATTATCAGACCCTTTCCATTTAGTGGTAGACCATTTCCCTCGTCCAG
GCCAAGGGCACATAGTACAGAGAAATAGGGAGTTGTTACCCAGGGAGAGA
ACTTGGCTCTAAACCTGTAATAGAAAGGTCAGTTCTGGTCTGGAGGGTCA
ATTTTGATCTTTGGCTCAGATCCAGGAATTGGAACCAAGGCTTTTGAACA
TTTTAATGCAGGGGATTAAAAAAATGATACGAGTCATTCACGAATATATT
TGCTTAACATCTAAAGAGATCCCTCAAAACACTAGAAAAAATAAGAACAA
AAATCTAATAAAACAAAATTTGTTAAACACATTTACCAAATTTTTTTTTT
TGGTAAAAATTCAAATGTCATAAATAAAGCTAAAGTTCCTCTTGATGACT
CGCTCCTCTGCCCTATTCCACTCCAAGTAACCACTATTATCAGTCTTGCC
AATACCCTTCCAGACCTCTCTACCTCTATATACCATTAGAAGCACATGGT
TTTGCATTGAGGATGTGCAGTGTTTTGTTTTACGTAAATGTTATCACTCT
GTTCTTGTTCCATAATTTGCCTTTTTCTCTCAATGATTTGCTTGGCTATC
TTTCTATTTCAGTAGCATCTCCTTTCTTTTTAACTTACCATTGTTTATTT
AACCTTGCCTCTATCAACAGATATGTAGGTTGTTTCTAGTTGATTTCATT
AAGTATTTATAAACAACGCATCAGTAGATGTCCATAAATTTCTTTACGGA
AGATGGCAAGTAGTGGAATTGCTGAGCCAAAGAACATGTTTAAAAAACCC
AAAAAAACTAGACGCTACCAATTTTCTCTCCAAAATGGCCATACCCACTT
ACCCATACAGAGATGATTTGGAATCTGGCTTCCTCACAAGGTGAGATGCC
TTCACAGTTTCATTCTTCCTGGCATGTCTTCCCTTTTGTATCTGAGAGAG
CTGGCAGAATTGTGTCACTAAATCAAGGATAGAGGGTCAAATGACAGCTC

FIG. 4M

AAGCTCACAGGCACCTCTGCTTTCTTCCCAGACCACCTGCTTTCCTGCCA
CCAGCTCTGTTCCATCTTATAGAATGGTTGCCACTTGGGTGTCTGCTCCG
ACAGCCATGTCATCCTTTGCACTGCAGTTATGAAGCAGACAGAGCTAGGA
GAGGGGCTTTGCCAGCCTCTGCCCTAGCTTGGAGAACTTCAAAAAAGGAG
GGTATTGAAGTTGAACTCCCCCAAAAAGGGGTGGTCCCCACACCTCAAAA
AGTGGTGCCTCCGAAAGAAATGTAAAATTCGTGTGGGGGGGGAAAAAGGT
TATTTAGAAATTGTTGGCTTGTCGTGCCGAAAGTATGTGTGGTTACGGGG
AGTACGGAAATTTCGAGGGGTGGGGGCGAGGCCGTGTGTCCTTTAGCCCG
GGGTTTTCCCGTCGCATGTTTAAGGGGGGGGAAGAGGGGGGATGTTTTCT
TTCCGCGAAGGTTTTTGAAGAACGGCGTGG
>Contig36
CCCCCCACCGCCACTACTCAACCGGCCGTTCACGAAACAACTCGCCACAT
CCACTAACCCGCTGGCTCACCACCCACCGCCCTCCCGATCCCCCCAATCC
AAACTCAACCCCCACCACCAAGCGCCTCCCCCCTCCCCCACCCTCCAGCT
CAGCCCCAACCTACCACCAACCCCGACTCGCCCACCGAAAACCAACAGCA
AACCCAAATGCCCACAAAACCAGTGTCCAAACCCTCCTTCCCATCAGTTT
GGTGGGCCCATCACCGCTTCCCCTGGCCCAGGCTCTCCTTTTGTGCGCTT
GGAGCAGCAGACTGATCTCCCAGCCTTCACTCACTTCATGTGGTAATCTG
TTGTGTTCATCACTGTCAGAATCTTCTGCATCCCCTCACTACTCTGCTGA
AAACACTCTAGTGGTTCCTCATTGCTCATTAATGAAAGTCTAGATATTAA
ACGTAGAAGGCCCAGCACAATTTGCCCCTATGCCACCTACCTCTCTAATC
TTTTCTCCTTACTCTGACAGACTCTCCGTCTGTCATTTATGTATTCTTTT
ATTGCTCTCTTCTACTTTTAGTATGAACTGGATTTATGGATTTTTTTAAC
ATTGCTTTCAAGTATGGAATAAAGAATTTTATTTATTTATTTATTTATTT
ATTTGAGACTGGGTCTCACTCTGTTGCCCAGGCCAGAATGCAATGGTGCA
GTCATATCTCACTGTAACCTCGAATTCCTAGGCTCAAGCCATCCTCCTGC
CTCAGCCTCCTAAGTAGCTATGACTACGGGTGTGCATCACCACATCTGGC
TAATGGAATAAAATATTACAATGCCTAATCTTAATTTCAAAATTTTAAA
TTACATTGTACCTAATGCCCATGCATTTACTTTTTTCAGTGGGTCAATAG
CCCTCACTTTGGCAAAGGTCCCAGGCCCAAGGTAAGGCCTTACTTTTTCC
AAACTCATCTTTTGAAAGACATAAGTGCCTGTAAGTTGTACCACATTAGG
TTCTAGGAATTTTTCATCAAAGACTTTATCAGACTATTTTCCTCTAAGTT
GAGAAAGAGCTGGGGGCAGAATATGGCACTGAATGACTGAAGAGAAGGCA
CTGAAATCAGGCCAGAGGTTGCTGGAAAGAGCAATGAGGAACACCAGCAG
CAATGAGGAGCCGGTGATGATTTTGGCTTCACAGGGAGGTGTGTACCACA
CCGATTTTATCTCTACGTGGATGAACCACAGCTGTCGGCTCCCTTGTCTC
CAGGACATCACACTCTCCACATTCCCTCCCATCTTCCGGCTTCTGCTTCC
CGGGGCCCTCATCTGCCCCATCCTGGGTGAACACTGGTCGGTCAACTGCT
GGGCGTACCTTCCCGCTCTGCACACCCTCCCTGGCCACCCCACCCACTCT
CACGGCTCGCACTGCAGAGGAGCCGCATCTCTAGCTCCAGCCCATCTGCC
TCTTCTGAGCTCTAACTTCATGTAGGCGACTCCTGCCGGTGTTGCCTCAC
AGGCCCATCATACTTCAAAGCATTTTCCCCTCAGAACACCATGTCCTGGC
TGCTCCCTCCAGAAGATACATCTCTCAAGCACATCCCCGCGGCTCTCACC
TGGATGACTGCATTCACCTTCTCCCACATTTGCCCCCTCCTTTGGATGTA
TATAGATTGTTTTAAAATACAAATCTGATGTGCTTGCTCTCCTGCTTGAA
ACACCTCAAAACTGCCTTCAGGATAAACCACTGCCCTTGACATGTTCACA
GGTTGCCCATGGCCTGGCCCTGCCCATCTCTTCAGCCTCATCTCATGCCC
CTTGCCCCTCGCTCTCTGGGCTTCTGCCTCCCTAGCCCTCCTTTAGGTTC
TCTAACACACCATAGTCCTTCTAGTGTTGGGGCCTCTGCAAGTGCTGTTC
CCATTGCCTGAGACATGAATCCCTCTCCCTATCTCTACCTGCACCTTCAT
CTGATTAATCCCTACCCTTCCTACTCATGATGTTGCTTTCTCAGGGACTC
TCTCTGACTTTTTAAACTAATCAGGGTCTCCCCAGTATATATCTTCATAG
CACTCTGTATTACTCCTTTCTTAATGACCACCTGCTGTAGACAGAATGTT
TGTCTTCCTCCAAAATCATATGTAAAACCTTCCACCAGAGCGATGATTAG
AGAAGCCTCCC
>Contig37
GACTGACATTCAGAAGATATTAATAAGAGCACTAATGATGGGGATTGCAA
CCATGTCTTTACTGACTTCCAGAAGCTTCTTACAGTAAACATGAAATCAC
ATAATTTCTTCCACTTTCCTACTGTTTCTTGTTCTGGGCTCTGTCCTGCT
TACTGTCTAATATCTTGGCCCCTTAAAAGTTGCTAATCTTCCAAACCTCA

FIG. 4N

TTCCTGTGACTGGGCCGCTGGTCCTTGTTCATGGGCCTTGAAGATACTGA
CTGTACACTTATCTGGAGCATCCAGTGCCTACCACCTGACCCAGATTCCT
CATTGCGCTCCTCCCTCCTCCACCTAATGGGATTTGCTCATACCCGTGTG
GGACCCCTCCCATTTTCCCCAACTGAATACTTATCAAGACAACGCATTGC
CATACTCCCTCGTACCCTGCTCTGGGCATCAGACTGAATGTTTGTTTCCA
TTGAGGATCTGCAGCTGCATCAGTTTCCCCAGCACCGTCCAACCCCTTGA
GCATGGCTAGTCCTAAAGCAGAGAATTAGCCTTTCTATCCCTGCTGCTAT
ACATGCTGGGACAAATAATAAGAAATGACAGCATTTTATGATAATGCAGG
CTGCAGGAGGCAGGAGGCAGGAATCAAATTCGTGCTTATCAAATAGTGCT
CCAATTCTTTGAATATTGGACTATAGAATATGTCATGGATCTATGCTCAG
GTGGGTTCCCTATTACTCACTCCACTGAGGCCAGGTTGTGGGATTAGCTG
TCCAAGAGGGAGTTTCAGTCTCACAGCATAGGGTCATTCTGAGAATTACT
GGCCCACACTTGTGTGGAGACCTCCAGAGAACAGAATCTGGGTTGGTGCC
ATGTACTTCCAGGAGGAGAGAAGTGGCAGGATGCCCAGCCCCACAATCAG
AGGGGAAGGGGCAGAGCCACATGTATGAAGATCCTCTCCCCAGTACGTGC
CAATCACAGGGCTTCCTAGCTTTTGGGCCAAGGAAACAATGTGGGAAGCA
AAAAAGGACAATTTTCTCCTCCCTTTGCATGAAGACTGAGCAGTTTTACC
AGATTCCCAGGGAAACACCCTTCCACTCTGGGTTGAATGTGAGTGAGAGA
CATTCAGCTGGAACACTAGAAAAACTATTTCCTGAGCCACTCACCTTTAG
CCCTAGAAAGTGTTGGATTTGTCCTTCATCTTTGCCACAGTAGAGACTGC
TGATAGCATCAGAACTTGGGCTCTGGAATTAGACAGATATGGGTACAAAT
CTGAGCTCTCTCACTTATTAGTGTGGGATGTAGAGCAACTTTTAAAATCC
TTCCAAACCTCAGACTTCTCATGCATGATGTGAGGATTGTAATAGGGCCC
ACCTAATAGGGGTTTTTGAGAATTAAAAAAGTTATTCAATGAACAGCATT
TAGCAAGATGCCTGACCATTGAGAAAATAACAAATTGTTTATTATTATTG
TTATTATTAAACATCTTTCCTGCACCTTCTGACTGGGGGCATCGTATCAT
CAGAAATACTTAGGATGGGATGGATTCCTGCATGGGCTGAGTCAAGGGTG
CAATAATGGAGGAGTGAAGAAGGAAGAAATGGAGGCAGAAATCCCCAGGA
GCCCAGCATGGTACAAGGCTGAGCTAGTGCTGCAGAGCCTCCTTGGAACA
GCCACAGAGCTTGCATCTGGCCCTGGAGGAACCTCTTCTAGCTGGCAGGA
CCAGCCACAACAGTGGCCAGGGGATTTCCCAGGGCGTGGGCTCCTCAGGA
GTTCATTTGGACCAAGCCTGCCTGGAGAGGGGTTATAACAGGGATCCTTC
CCTACTGGCAGGTGATTTACCCCTCGGTGAGAAGCTCAGGCATTTGTTTG
ATGGAAGGTGGAAGGCCCTGTGCTGGGCCAGTGACTATCAGGGATGGGCG
GGTGGCTGGAAAATAGCAAATAAGACAATATGATAACACAGTTAACCACC
ACACTATGTGAAGCTACAATATGGGTATCTGTAATAGACAATTCCAATGT
AGAGAATAATTTTAAGGTGTCATTCTCCCCGCCAATGCCATAAGCACACG
GCCTCTGCCTGGGTTTCTCACTGTGGAATGTCCTCCTGGTCTCCTCATGC
CCAGAGAGTGGGAAGTACTCCTACTTTAACACCGGCTTTCCTGTCATTTC
CNTGCAGCCCTCCTCAGCCCCCTCTGCACAGGGAGGTTTCCTCCCTGCTG
CTGCAGTGCTTTGTACTTGTTAGTGGTACCTGCACACAGGTATTGGTGTC
CTTGTCTCACCACCCTACATCACTGTAAGCTCCCCAGGAGCAGGCTTCCT
GTTTGACTCACCTGTGATCCTCCACCTCCCACCCTGTAGTGCCTCAAGCA
TTCTGTAGAGCACATGGACGCC
>Contig38
GACTAATAAGTACTTCATTATTTGGGTATTTTCCAAGAACAACATATTGT
AGGAAACCATTCTTTCTAAAAAAAAAAGTGTCCTTTTAAAAAGGTGAATA
ATTTTTGTCTAATTCAAAGTTTATTGAAAAGTTATGTATAAAACAAGGTA
AAAGGAACAAGGAAATAAGGGAAATGTAAAGAAAATTATAGAAATAAAGT
GGTATTTTTTGGTAAGAAAGCTTAAAGAGAAATAATTTTAGGTAAGAAAG
AATCTTACCTAAAATTTTGTGCTAGAATAAAGTGACTGGCTAAGAAAGGG
ATGTTCAAAGCTATTTATGACAAACCCACAGCCAATATCATACTGAATGG
GCAAAAGCTGGAAACATTCCCTTTGAGAACTGGCACAAGACAAGGATGTC
CTCTCTCACCACTCCTATTCAACATAGTATCGGAAGTTCTGGCCAGGGCA
ATCAAGCAAGAGAAAGAAATAAAGGGTATTCAAATAGGAAGAGAGGAAGT
CAAATTTTCTCCGTTTGCAGATGCATGATTGCATATTTAGAAAACCCCAT
CATTTCAGCCCCAAAACTCCTTAAGCTGATAAGCAACTTCAGCAAAGTCT
CAGGATACAAAATCAATGTGCAAAAATCACAGGCATTCCTATACACCAAT
AATAGACTAACAGAGAGCCAAATCATGAGTGAACTCCCATTCACAATTGC
TACAAAGAGAATAAAATACCTGGGAATACAACTTACAATGGACATGAAAG

FIG. 4O

ACCTTTTCAGGGTGAACTGCAAACCACTGCTCAAGGAAATAAGAGAGGAA
ACAAACAAATGGAAAAACATTCCATGCTTATGGATAGGAAGAATCAATAT
CGTGAAAATGGCCATACTGCCCAAGTAATTTATAGATTCAATGCTATCCC
CATCAAGCTACCATTGACTTTCTTCACAGAATTAGAAAAAACTAATAGCC
AAGACAATCCTAAGCAAAAAGAACAAAGCTGGAGGCATTGTGCTACCTGA
CTTCAAACTATACTACAAGGCTGCAGTAACCAAAACAGCATGGTACTGGT
ACCAAAACAGATATATAGACCAAAAGAACAGAACAGAGGCCTCAGATATA
ACACCACACATCTACAACCATCTGATCTTTGACAAACCTAACAAAAATAA
GCAATGGGGAAAATAATTCCCTATTTAATAAATGATGTTGGGAAAACTGG
TTAGCCATATGCTGAAAACTGAAACTGGACCCCTTCCTTACAACTTATAC
AAAAATCAACTCAAGATGGATTAAAGATTTAAACATGGCTGGGCATGGTG
GCTCACGCCTGTAATCCCAGCACTTTGGGAGGCCGAGATGGGTGGATCAT
GAGGTCAGGAGATGGAGACCATCCTGACTAACACAGTGAAACCCTGTCTC
TACTAAAAAATACAAAAAATTAGCTGGGCATGGTGGTGGGCGCCTGTAAT
CCCAGCTACTTGGGAAGCTAAGGCAGGAGAATGGTGTGAACCCAGGAAGT
GGAGGTTGCAGTGAGCCAAGATCACGCCACTGCACTCTAGCCTGGGCAAC
AGAGTGAGACTCCATCTCAATAAATAAATAAATATGGAACTCTCCCAACA
CAATAATAAGACAAACCCCCAAATGTTTTAAATGGGCAAAAATATTTGAA
CAGACACTTCACAAAAGAGGATATGTAAATGGTCAAAAAGCACATGAAAA
GATGTTCAACACCATTGGTCATCAGGGCAAAGAAAACTAGAACCACAATG
AGATGCCTCTGTACACCACTTAAATGTCCAAATTAAAGAAAACAAGTTTT
GGCAAAGTTGTGGAGCAACTGAAATGCTCGTGTATTGCTGGTAGAAAAAC
AAAATGGCATAACCATCGCAGATAATTTGTTGTCAGTTTCTTACAAAGTT
AAACATATACTTATTGATATGACAGTTCCATTCCAAGAGAAATGAAAACA
TAAGTCCACACAAAGACTTGTACCTGGGTGTTCATGGTAGCTCTATTCAT
AATTGCCAAAATCTGGAAACAAATCAAATGTCCATCAGCAATGGAATGGA
TATACAAATTGTGGTACACATGTACAATAGAAAACTACTCTGCAATGGAG
AGAAATTAACCATTGACAAACACAAAAACATGGACAAACCTCAAAAACAT
TATGCTGAGCAAAAGAAGCCAGACACAAAAGACTGCTCAGCGCATGATTC
CATTCATATGAAATCACAGAAAGGGTCAGTTGAAGGTGCAGAGACAAAAA
GTAGATCTGCAGTTGCCTGGGGATGGGGTGGGAGGTTGACTGCTCTGACG
CGTAAGGAAATTTGGGGGTAGGTGGGGGATGGTGGGAATATTTTTTGAAT
TGAATTGGGTAATAGTTTTAATAGGTAAAATATTGGACCCCACAGTATTT
GAGATAGGTTTCAGTCAATTTAGACAGTTTATTTTGCCAAGGTTAAGGAT
GCATCCGTGACCCAGCCTCAGGAGGTCCTGACAACCTGTGCTGAAGGCAG
TCAACATACAGCTTGCTTTTATTCATCTTAGGGAGACATAATACATCAAT
CAATGCATGTAAGGTTTACATTGGTTCAATCTGGAAAGGTGAGGGAACTT
GAAGCAGGGAGCTTCCAGGTTACAAGGTAGATTATTCTCAACAGAAAGGA
ATGTCTGGGTTATGATAAGCGGTTGTGGAGACCAAGGTTTTATCTTGTAG
ATGAAGCCTCCGGGTAGCAAGCTTCAGAGGGAATAGATTGTCAAAGTTTC
CTATCAGACATAAGGTCTGTGTTGATGTTAATGCTGGTCAGCTTTTCCTG
AATTCCAAAAGGGAGAAGGGTATACTGGGGCATGTCCAACCTTCCCTTCC
ATCATGACCTGAACTAGTTTTTCAGGTTAACTTTGGAATGCTCTTGGCC
AAGAAGAGGGGTCCATTCAGATGGTTGGGGGGCTTAGAATTTTATTTTT
GGTTTACAGTGAAGACTTTTCAAGCTAGACACTTAAATGAGTATGTTGCA
AAATGGCAATTTCTTAGCACGGC
>Contig39
GACGTCCTAAAGAAATGCTAAGGTAACTCAATTAACTATGCTAGAAAAGA
GAGTTAAGTATTTAGGAGGATTTAATATGGTGTTAAAGTTGTGAAAATCA
AAATGGAGACACTAATGTTAAGAAAACCCTGATAAATGGAGCCAGGGAAG
GCCATGAAGAAAGAGTTCTCACACTTGTATCCCTGATCATGAAAAAGACT
CTGCAAAAAACAAAACCTTGCACAAAGGCCATTGCAACCTTACACAAAAA
ATACTACTTTAAAAGGACATGTGCCCAGCAACTGCCTGTCCAACCTCAGA
CTGGCAATATCTTTGTTATTGATCTTAGTAGCCCAGCATAACTATTTCAA
AACAGTGATGTAATGCTCATTTTTTTCTTTTGAAAACTTTTGTCTTCCT
GTAAAAACCTTTGTCTTCTTTACTTACCCTGAATATGCACAGAGTTTACT
ATGGAGTGCATATTCCTGTTGCAATGCTCTATTCCCAAACAAACATCATT
TTCTTTTAGAGAGCCTCTCTCTGTTTGTGATTTAGGTTGGTGATGTAAAG
CAATGGCATAACTGAACACTGATTCAAAGAAAAGTGGCTTTTCTCTTTGT
TGTATTAAAAAGAGGCCTTATAAATAGGATAGTAAGATTTGTAAGTTGAA

FIG. 4P

CTTAAAGCATGAAGAAAATTTAGGGGCCAGGCAGGGTGGCTCACACCTGT
AATCCCAGCACTTTGGGAGGCCAAGACAGGAGGATTGCTTGAGCCCAGGA
GTTCAAGACCAGTCTGGTCAACACAGACCTCATCTTTACTAAAAATAAAA
AAATTAGGCCAGGTGCAGTGGCTCATGCCTGTAATCCCAGCACTTTGGGA
GGCCAAGGCGGGAGGATCACTTGAGGTCAGGAGTTCGTGACCAGCCTGGT
CAACACGATGAAACCCCATCTCTACTAAAAATACAAAAAAATTAGCTGGG
TGTGGTGGCGGGCACCTGCAATCCCAGCTACTCGGGAGGCTTCAGGCAGG
GGAATCACTTGAACCTGGGAGGCGGACATTGCAGTGAGCTGAGATAGTCC
CACTGCACTCCAGCCTGGGCGACTCAGCAAGACTCTGCCTCAAAAAAAAA
AAAAAAAATTAGTCAGGTGTGGTAGCACACAGCTGTGGTCCCAGCTACTC
GGGAGGCTGAGGTGGGAGGATCATCTGAGCCCAGGAGGTCAAGGCTGCGG
TAAGAGCTGAGATTGTACTACTGCATTCCAGCAGGGGCTACAAAGTGAGA
CCCTGTCTCAAAAAAAGAAAAAGAAAAAGAAAATTATGTTTTTAAATTTA
TAATTATAATAAATTTAATTACATAAATTTAAGCTCAAGTAATTGTAAAT
ATTCTTTCTGTGCACATAAGTTATTCTTGTATTGACCCCACAGGAGCTGG
CCATTCTTCAAGTCAGAAGGCCTGAGAGAGGAGCTGCCCAGGTGGTCTTC
ATGGGGCTGTGCGGCCAGTCATCCCCCACAGGTTGACAATCCTTGTGTAC
TTCATCCTCGTTGGATCCTCTGTATCCCTGACGATGAGCAACTGTGAGGC
CCGTTTCAGCACTGAGTTCCAGTCAGGAAAACATCCACCCACCCACCACA
CGCTCACACTTACACACACATTCACACATGCACACACGTTCTGGCTCCGA
AAAAGAAAAAAAAAAAGCAATTTAAAATAATTCTGATCCTTTGCTTATTT
CCACAAACTCCATGAAAATTGTACATTGTCCAAGCAACATTTCTTAATAT
TCTCTTTTTCTCTCATATCCATTTTCCTTACTGCTGTCTCCACCTTTCTC
TTCCAAACTCCCTGTTAAAATCCCTGCCCCAGCGAACTTTTATTCAATTT
TGTGGAATGGAGGCTGCTCTGATTTAAATTAAAAAAAAAAAAAAAAATCCC
TACTCCATGTCCCAGATCCCTAGTTGTTTTTTGTTTTTTGTTTTCCTGAG
ACAGGGTCTTGTGTCTTCCATGCTGGAGTGCAGTGGCATGATCATGGCTC
ACTGCAGCCTCAACCTCCTGGGCTCAAGTAAATCTCTTGCGTCAGCCCTC
CCCAGTAGCTGGGAGTTCAGGTATGTGCTACCATGCCTAGCTAATTTTTT
TCTTTTATTTTGTAGAGACACGGTCTTGCCAGGTTGCCCAGGCTGGTATA
GAACCCCTGGGCTTAAGTGATCCTCCTGCCTCGGCTTCCCAAAGTGCTGG
GATTACAAGTGTGAGGCACTGCACCCAGGCTGGATCCCTGCATTTTTACA
GATTTAGCATCACAAAAGTCTAAACAATTAGACTGACTAAGGCAGAACTG
CCCTTATGACAGCAGACATAAGAAGGAAAAGGCCAAAACACTGTGTTAAA
AATTATCCAAATGTGAGGAAAAGGCAAAGAGAGTAGGTGTGCCTTTTTAG
TGTCTAAGCTGCCTGCCCAAGGGGCATCTGATGCTCTCAGGCAGGAGTCC
ACAAATTTTTTTTTGTAAAAGATCAGATAGTAAATCTTTTCAGCGTGAAG
AGCATGAGGTCTCTGTCACAAATACTCAACCACCATTACAACATGAAAGC
AGCCAACAGACAACACATGACAAATGAGTGTGGCTGTGTTCCAGTAAATC
TTGATTACAAAAACAGGCAAGAGGCCAGAGCTGACCCATGGGCCATAGTT
TGCTGACCCCTTCTGTAAAGGAAAGTATTTTTGTTTGACTTGCTGTTTAC
CATTGATTGAACACAAGGCTCTGTAGAGTTACTTGTTAACTTGCAGAAGA
TTGATGAGTGGCAAGTAATTTTTATTCACCAGAATATANNATTATTCTGT
TCAGTAGATAAGATAAACCCACTGTTATATTACTGTCTTGTTTAGAATGT
GACTTTGATTCATTTTTTCACAAATTCATATTATTGCCCTAATTTGTATA
TAAGTATGCTTCTTTTAAAAATATATATTTTTTAATAAATTTGAGACAGG
GTCTCACTAGGTTGCCCAGCCTTTTGCTATAATGAGAGCATAAAGTGAAT
TTCACACTTTAGCCTAGTGCATAGATGGGATTACAGGCACAAACCACTGC
ATGCAGCTAACTTTGCTTCTCATTCCAGCACGTTCTATTCCNNNGNTTTT
CATATACGCGTCTCTTAATGC
>Contig40
CGCATTCAGCCCAAGTTTTCTTCAGTGTTAAGGTTTTTGTTACTCTGTGC
CCAAATGTCCTTCCAAAAAGGTTAAGTTTTTTTACCTTCCTGCCAACATT
ATATGAAAGTGTCCACTTTTGTAGACTTTTACCAATGCTGACTACTTTTG
GTTTCAAAAAAGCTCTCAGTAATTTTCTATTAATTACTTTTACCCTTTTT
TATTGAGGGTGTTCAACTTTTTATTGTTAGCATATTCTCTCTGGGCTCCA
TTGGACGCCTTGGCAGCTTTTTGGTAGTAGGTGCCTTTAGAAAAGTCCTT
CTCGTCTGGCCCTTTCTGAGCAAATCTAGTGAACAGAATTGGCTCCATGC
TCAGCATTGCTTAATACGGTTGATCCAGGGCCTAGGACTCATTCCTTCAT
TACCATCCACTTGCATTGTCTTAAAGCAAGGCTCTATTAATTTAATTTGG

FIG. 4Q

CATTTCCTGTCCCAGCTCTTTAGTTTCATTAAACAAAGGCTTTAGAAAAC
TCCCAGTAGATGCCTATGTTGCTTCCTTTTAAAAAATTTTGGAGCTGTTT
CCCTAGCCTAACCTTTTCTTCAGGGCAGGAGTTAAGTCCCTTCTACTGCA
TTCCTGTGAAGATGGTGATTCAAGAGGCAGGGCACCTGTTGCTTTGTGAA
ACAGTCCACTCTGCAGCTGGGCAGCTCTGTTACTAGAATGTTCTCCCTTC
TGGGGAGCCAATATTTTGATGTCCTCTGTGAATCTCATCTGCTTATCCCA
TCTGTTTATGTCCTTGAAGATGCACAGGTCTGACACCACGAGGTAGCCCT
TAGAAATTTGATGGCATTTCTGATGTGTCCCCAACTCTTCTCCAACCACT
CCTCCCAGAGCTTGTTTCTTAAGCCCCTTGTGGAGCTGATTGCTTTCCTC
AAGGCAGCTCAGTTTTTCCCAGTTTGCTCCTGGTGGTCCTGAAATATGAT
TGACTCCTGAATACTCCAGGTGTGAAGGAGAGTGGGGGTGGCCTTTCTAC
TTGTCATGGCCTGGGTTTTAAGTTGCTGTCCAGTGGAGCAGAGGTGACTT
TCCCAGTGAACTACATTTTTTCCCCTCTAAATCCTTAGCAATTTTGTCTC
CAGAGGCAAGACCTGGCCAAACCATTTGTGTTGAGGATTGAATCAAGAAT
GATTGAGGAGATGACAGTAGTCCCCCCTCATCTGAGGAGGGCGTGTTCCA
AGCCCCTCAGTGAATGCCTGAAACTGTGGATAGTACCCAACTCTATATGT
CTATGATTTTCCTATAAATTAATACATGCCTGTGACAATGTTTAATTTAT
AAATTAGGCAAAGAGGCCAGGCGCAGTGGCTCAAGCCTGTAATCCCAGCA
CTTTAGGAGGCTGAGGCCTCACCTGAGGTCAGGAGTTCGAGACCAGCCTG
ACCAACATGGAGAAACCCCGCCTCTACTAAAAATACAAAATTAGCTGGGC
ATGGTGGCAGGCGCCTGTAATCCCAGCTACTCGGGAGGCTGAGGCAGGAG
AATCACTTGAACCCGGGAGGCGGGATTTGCGGTGAGCTGAGATCGTCTCA
TTGCACTACAGCCTGGGCAACAAGAGTGAAACTCCGACTCAAAAAAAAAA
AAAAAAATTAGGCAAAGAAAGAAATTAACAACAATAAGTAATGAAATAGA
ACAATTCTAACAATATACTATAATAAAAGTTGTATGAATGTGGTCTCTTT
CTCAAAATTACCTTTTTTTTTTGAGACAGGGTCTCACTTTATTGCCCAGG
CTGGAGTGCAGTGGCACGATCACAGCTTACTGCTGCCTCGACCTCCTGGG
ACCAAGTGATCCTCCCACTTTAGCCTCCTGAGTAGCTGGGACCACAGGCA
TGCACCACTGTATCTGGATAATTTTGTTTATTTTTTTTTGCAGAGAGAGG
AGGTCTCACTATGTTTCCCAGGCTGGTTTTGAATGCCTGGGCCCAAGGGA
TCCTCCTGCCTTGGCCTCCCAAAGTATTGGGATTACAAGCGTGAGCCACC
ATGCCTGCCCCAAAATTATCTTATTGTTCTATACCCACTCTTCTTCTTGT
GATGATGTGAGGTGATCCATTGCCTCCTTGATGAGATGAAGTGAGGTGAC
TGATGTGGGCATAGTGATGCAGTGTTTAGGCTGATATTGGCCTGATGATA
TGTCAGAAGGAGGGTCATCTGCTTCGGTGATCCTGGATCATAGAGTCATG
ATGATGTCAATGGTTGGATGTCAGGAGCAGACGATGTCAATGACTAACGA
TAAGCTGGACAGGTGGGATGGTGGCACAAGATTTTATCACGCTACTCAGA
ATGGAGCACAATTTAAAACTTCTGAATTGTTTATTTTTGGAATTTTTCAT
TAATATTTTTGGATTGCAGTTGACTGTGGGTAACTGAAACTGTGGAATGT
GAGACTGTGGAAAAGTGAGGGAGTACTGTATTATGGAACTGTAACTCTAT
TCGGTAGGGGAACAGAATTCACATTTGTGGGGCCCAGGTCTCTGCATCTG
TAGGGATCCAATTGTTTCATTTCTCGTTGTAGCAAAAACTTGGCTTTGGA
ATCAGACAGATTGATGTTTGCTATCATTCTAAATGGGTGCAGCTACACTT
TCCTCAAGAGGTAGTTCTGAAAATTTAACAAAATGTGAATTTCTTGGTAA
AAAAAAAAAACCTCAAAAATATTCAGTTTCCTTTCCTTTGTGTCTGATGT
ACTCCATCAAATACTGGGAAATATGTGTCTCTCATAGAAATGTCATGGAT
CTTTGTAATTCTGATTATCCACAAACCTTGGGGATTAGCTGTTTCAATGT
TCCTATTTTACAGATAAGAAAATGGAGCCTGTGGTAAGTTAAGTGAGTTA
CTCATGGCTACTTAACTAATATTTTACTAGGTGATAGGCCAGAGCTAGAG
CCCAGGTCACCTTCTTATCAATGCTCTGCCTTGTCTCTGTGCCTTCCTGT
CTGTCTGTATGTGTATGTGCCTGTTGACAGTAAGGCATAGTTTAACCCAG
TAGAACTACCGGTTTGTAATGAATTCCACTTGTAAATGACTGACCATTCA
AGGAACAAGTGTTTTTTCTATGCTTGACACCTGTTTTGGATGCCAAAAAG
GATACAAATGTAACTTCAGACACTCTGGGCCTCATTTTGCACTCATTAGC
ATGTCCAAAATTAAAAAGACTGACCACACCAAATATTGGTGAGGATGTGG
AAGAACGGGAACTTTCATACACTGCTGGTGGGGATGTAAAATGGTACAAT
CCCTTTGGGTAACAGTTTGACAGTTTCTTAAAAAGTTAGACATATATATT
TACCATATGACTCAGCCCTTCCACTTCTAGGTCTTTACCCAAGAGAAATG
AAATGCTGTGCTTTTACAAATGTCTATACAGGAATGTACATAGCAACCTT
ATTTGTCATTGCAAAAAACAGAGACAATTCAACGTTGTCAAGAGTGAATG

FIG. 4R

GATGAGCAAGCTGTGGTCTGTCTATGCAATGGTATCCTACTCAGCCAGAC
AAAGATATGGCTAAT
>Contig41
GACAACAATGTCATGCATAAGATGACGATGGCCTGGGTGATTGATGCAAA
CAAGGATAAAGAAAATAATCAATTTTGTCCCCATTTTCAAAGACAGATAG
CAGCAGCAAGAGTGTAAGTCTGAGGAAAGTCATATTCCTTCCTCCTACAA
CATAGCACACACACTTACAAAAACAATACACAGACTCCTGGCCAATGGAC
TTCAAAACTGAGGAGGATCATTAAATTTAAATGTTCACCGCTGCATGAAA
TCTCCCTGGGTCCTGCCCTCCCTTCCCCACCCTCCTCCACTTGGGCCGGG
GCACAGCAGTGATTCTCTCACCTCTCAGAGTGAGCCAGTGTTGGCTGCAT
TGAAGGCTCCAGATATGCAAACAGGGCAGATATTCCTGGACCAGGGTGCA
CAGAGTGAGGCTCCAACGCACCCTATTAACTGCATGAAGGATGAATGAGC
CTCTGGTATGGGCTGGGACAGAAAAAAGGATTCAAGGGGCCCAAAAGGGT
TTGGGTGGAACCTACCAGGAGCGGCAGTACAGACTCCTTGGGAAGGTGGC
CATGATTTAGCCACATTCACCAATAGGATAATCTGGAGAATTTCCTAGCT
TGAGTTTCTGGGAGAAAGCAGATTTCTGGATTATCTGGTGACAGGTAACA
GGGCCGAGTTCATCCACAGCCACCTGCAGTGTTAGCACCTTAAGCTGAGT
TCCTTGCACCAGGATGCTGTCACGCCCAGTCAGTGTGAGACGGTTCTTGG
CTGAAGGACTGAAAAGCTTGGGTAAGTGACTTCACCTAAGCCTCTATCTC
TTGCTCCCGTAAGTCAGGGCTCATTGTGGCTCCTTGCAGGCTTGACTTCA
GGGTTAACAGAGAAAATGAAGGTACAAGTGCCTTGTGAACTCTGAAACTC
CAAACCAGTCATTCTCAAAGTGCCGTCCACCAGTCTAGCACATCAGCATC
ACTGGAAGCTTGTTTGAAATGTAAATTATCAGGTCCTCCAGAGCTATGTA
TGAATTAGAAACTCTGGGAATGGGGCCCTGCAATCTATTTCAACAGGTCC
TCCAGGTGATTCTGATGCAAGTTAAAGCCTGAGAAACTCTGTCCTATACA
AATGGATGTCAACTCAAGCTGCTCTTCAGAATCACCTATAGCACTTGTTC
ACCCGAATCCCTGAGAATGGAGCTTCAGGACTGCTATTTCTCAAAGTTTG
CCTGGTGATCCTGAGATGGGGTTTGGGGGACAGAGATCCAAGGTGCTACC
AGGTGTGAGGAATTGTTAGAAGGCAAACCTGGCTGTCATCTAGGGTGCTT
AAAGGGTACAGATCCTAGGATTCTGCCTCTTACAGCTGAATCAGACTTTC
CTAGAATGGGATTGCTGTCCAATGGCATGCCTCCTGGGTGACTCTGATGT
ATAGCCTGGGCTGGGAACCACCAGAGGATTATCTTCCATTGACCAAGCTG
ACAAACTCGCTTAAGGCTCTGAGTTTCACACTTGATTTTCTAGCCCCTGT
CCTTCCATGGATCACCTGCCCCCTTCCCTCCTAATCAGGAGCACAGTCAG
TGGATGCACTAATGTGGCCTCTCCTTGGCTGCAGGGAACAGGTGGAAATG
TGGCCATAGGTGTGCAGGGCTGCCTGCCATGTATTAATAGCTACAGATTT
GAAAGATCCAAGGACAAGAGACTAGAAAAAAATTTAAAACAGCCAAGCAT
TGGCCCAGTAATGGCATTTCAGAAATCCACCAAAATATTAAGATGCTTTT
TGAAAAATATCCAGAGCACTCATGTAAAAGTGCTTAATTATTAATAAAAG
CTGACATGTGTTGGGTACTTCCTGTGGGTCTGGCACTAGGCTAATTATGT
TTTTAGGAGTTGACTCAAATGCTCCCTGTCATAATTATGTGAAAAAATAT
AATTATTAGCTCCATGGTACAAATTAAGGAGAGGTTACATAAATAAAAAG
GAATGATACTCAAATTAGTAACCAGAGCCCATGCTCTTAAACACTATGCT
ATTATTTGTGGACTCTTACATAGGTGGCAAAAGTCAAAGGCTAGATTGAC
TTCTGTCCACTTCCAGCCAAGATGAAGTACAAGATTCAGATACACCCTTC
CGCATTAAACAACTTAGGAATCAGACAAAATATACAAAGCATTGTTTGTT
ACACATTGGATAACAGACAGCACTAGATAGTCGTGTCTGAGAAAAGCGGT
GAAATGAGCTGAGTCTTAGAATTGCCCCAGTTTACTAAGGGGCATAGTAA
GGGCATAGCTGCAGCACAAAGAAGCAGAACCCAACAGAGACTGGCGTTCA
CCTGAGTTGAGAAAACCAAGTTGAAAATTTAGGAACACTAACACAGATAT
GTAGGCAAGAGTATCAGAGAGGAGACAGTTGTAGGGAAAAAGAGAGCTTT
ACAGAGAGACAGCGAGAGCTCCAGAGACCCGCAGAAGATTGCCCTGACGT
CACTAGCTGAGTACCGATCAGTGCATACATGTAAGGATATTACTCAATAT
GTGGAAAAGAACAGAAGGAATGATGTCCAAAGCTCACCCAAAGACAGGAA
TCATTTATGTTTCCACCAGCCAGAGTGGAACAACCTTGTAACGCATATGG
AGTACTCAAACGAATATTTCCTCAATAATAAGTTCAAATTAACTGAGACT
AAAGCCTGCCCGCTTTGTCTGGACATGCCTAACAAAGCTTTGAGGGAAGC
CTCAAAAGAATGAAACCGTGTCCAAGTAATTTAACTGTGTCCCAGAAAAA
AATTCAAGAACATTTAAATAAATATTAAAATATGATCAAACCCAGCAAGG
TTAAATTCAAAATGTCTGGCATCCATTAAAAAATTACCAGCCTTGAAAAT

FIG. 4S

TGGCGGGAAAATATTATTCATAATGAAAAGAAAAAGCAATCAACAGAAAC
AGGCCTAGAAAGTATACATATGATAAAATTAGCAGACATTAAATGGTTAT
GATTAATTTATTTTATATGTTAAAGAAGGTAGAGAAGAGCATAAGCACAT
TAAAGAGAGACAGGAAAGTCCCAGTACTCACACAGGGCCAGGAGCAGTTT
TCACCAGTCAGGTGGGAAAACTTCATATTTCATGGAGCATTGGTAGAGTA
CACAGTGTCTTGCCTTAGTAGAGGGATAAATGCTGTTCTGTTCCCGCCTA
ACCCATCTTGAAAGAAAATCTGAAAGGATCAAACTGTATTCAAGTAACCT
AATCACATCCCAGCACACAGCTCGACTAGTTATAAAAACACAAAATATTA
ATATCTAGAAACACAAAAATAATATCTAGCACCCAACAAGGTAAAATTCA
CAATGTCTAGCATTCAATTGAAATTTTCTAGGCCATCAAAGAAGCAGTAA
AATATGACCTATAAGGCCGGGCACATTGGCTCATGCCTGTAATCCCAGCA
CTCTGGGAGGCCAAGGTGGGTGGCTCACCCGGAGGTCAGGAGTTCAAGAC
CAGCCTGGTCAACATGGTGAGACCTCATCTCTACTAAAAATATAAAAATT
AGCCCAGCATGGTGGTGGGCGCCTGTAATCCCAGCTACTCAGGAGGTTGA
GGCAGGAGAATCGCTTGAACCTGGGAGAAGGAGACCGCAGTGAGCCAAGA
TGGCACCAATGCACTGCAGCCTCATTAGAGAACATCGGGAAG
>Contig42
GAAACTAAAGGCTTATTTAAAGCGCGAGACCGTGGCGCCTTTGGACTGGA
CCCTTTCTAATGATCATTTAGTATCAGGCTATGTGGGAGTTGACCGTTTT
GCATAGCCTGAAAGCCAACAGTATCACTCCTCCTCTAGGTGTGGCAGAGA
TGTGAGAGAAGGAGACTGACAGTCTGTGGGTGTGTATGCAGTGTTGGGGG
AAGCGAGGCACAGGGGACAATACTGTGGTGTAGAAAACTAGTCTAAGGTA
GCATCAGGAAATTCATGAAACCAAAATGAATTTCATAACAGCACAAGACA
TTATTTGTTTTTGCCTCCCTCTCATTTTTTTTTTTTTTTGAAACAGAGTC
TTGCTCTGTCATCCATGCTCGTGTGCAGTGGTGCAATCTCGGCTCACTGC
AACCTCCACCTCCAGGGTTCAAGCAATTCTCATGCCTCAGCCTCCTGAGT
AGCTGATTACAGGTCTGCACCACCCCGCCGGCTAGTTTTTGTATTTTTAG
TAGAGATGGGGTTTTGTAATGTTGGCCAGGCTGCCCTGTCATTTTTTTTT
TACTAGTGTCCAGTGGAGTTTTTTAGGGGCTACATAACATGATACTGTCA
TTAATCTAATGGCTAATGAAAGGGATATGTATATGTTTTTGTGTTTAAAA
CAAACTTCTTTGGGGTCCTCAATAATTTTTAAGAGTATAAAGGGGTCCTG
AGATCAAAGAGTTTGAGTTCTGCTGGACTGGGACAGTGGTTGTCAACCCA
GATTGTACATTAGGGTCATCTGGGAAGCTTTAAAATAGTACTGATGCCCA
ACCTTACCGCAAACCAATTAAGCCAGAATCTCTGTGGATGAGAAGTCTTC
ATTGTCATCATCACCATGACCATCATCATTGTCACCGTCACTACACCATT
ATCATCATCATCATATCATCTTCATTATCATTGTTAGTATCTCCATCACC
ATCATCAGCATCACCATTATTATCATCATCATCATCCCCACCATCATCCT
CATCGGAACTTCACCTGCATGGAGGACAATCCACTATGCATTAGGTGCTA
TGCTATTTGCTATACTCCTTATTCTCACAACTGCCCAGAGAGGCTGATAT
TATCTCACTTTATAACAGGAGGAATCTGGATCGGAAAAGTTAAGGTAAGC
TAATTCACAGAGCGAGAAGAGATAGAGCCAGGATTCGAAACCAGTTCTCT
GCTACATCAATGTTCCCAGTCCTTGCACTATTGAGAACCTCTTTAGTTAT
GCTTTCACCCCTCCAACACCACAGTAAATTTTTTCTTTTTTTAAAAAAAT
TATACTTTAAGTTATAGGGTATATGTGCATAATGTGCAGGTTTGTTACAT
ATGTATACATGTGCCATGTTGGTGTGCTGCACTCATTAACTCGTCATTTA
CATTAGGTATATCTTCTAATGCTATCCCTCCCCGCTCTCCCCACCCCATG
ACAGGCCCTGGTGTGTGATGTTCCCCACCCTGTGTCCAAGTGTTCTCATT
GTTCAGTTCCCACCTATGAGTGAGAACATGTGGTGTTTGGTTTTCTGTCC
TTGTGATAGTTTGCTCAGAATGATGGTTTCCAGCTTCATCCACGTCCCTA
CAAAGGATATGAACTCATCCTTTTTTATGGCTGCATAGTATTCCATGGTG
TATGTGTGCCACATTTTCTTAATCCAGTCTATCATTGCTGGACATTTGGG
TTGGTTCCAAGTCTTTGCTATTGTGAATAGTGCCACAGTGAACATTCATG
TGCATGTGTCTTTATAGCAGCATGATTTATAATCCTTTGGGTATATACCC
AGTAATGGGATGGCTGGGTCAAATGGTATTTCTAGTTCTAGATCCTTGAG
GAATTGCCACACTGTCTACCACAATGGTTGAATTAGTTTATAGCCCCACC
AACAGTGTAAAAGCATTCCTATTTCTCCACATCCTCTCCAGCACCTGTTG
TTTCGTGACTTTTTAGTGATTGCCATTCTAACTGGCACCACAGTAAATTT
TTATAGATTTTATAAGCAAATTGTATTTACTGTGCAAGAATTGGTTTATT
TTTTAAACCATGTGTTGCAAACATACAATGGTTAATTGTGATATTTGCTC
AGTACAAGATCATCAGATCACTACACAGACTTGAGGTAATTCCACCTAAA

FIG. 4T

AGCAAAGAGAACTGACCCCACATTAACTGAGAAGTCTTTACTTATTTATT
CCCTATAAACGAGCCAATATGAAGAGAAGGCCTTAATGTGGTTAACTATG
TAATTTTTTTCTGACTTTTTGAAATACTGAGAAGAGCTCATGACTCTCCC
ATCTCCTAATTCTACCTTGGTGGATTTTAGACTGACCACAACTCATGGGT
AAATGAGGGAAGACGAATAAGAAACCTTGCTTTTTTTTCCTCCTTGTTTT
TGGCTGGCTGCAGTGGCTCACACCTGTAATCTCATCACTTTGGGAGGCCA
AGGTGGGAAGATCACTTGAGCTCAGGATTTCAAAACTGGCCTGGGCAACA
TAGTGAGACCCCATCTCTAAAAAAAAAAAAAAAAAAAAAAAAGGCGACGG
GCGGTGCGTGCCTGTAATCCTACCTACTCAAAAAGCCGAGGTGGAAAGAT
CACTTGAGCATGGGAGGTCAAAGCTGCAGTGAACCTTGATTGCACCACTT
CATTCCAGCCTGGGTGACAAAGCAGGACGCTGCCTCAAAAAAACAAAAAC
AAAACCTTAATTTTTTGGCTATTCTTTTCTGGTAAGAATGGTATAGAGAT
GGGGATGAGGATGGCTATTGTATGAGAGAGCAAACAGGGTCCAAGCAGTG
CTCTGGGCTGTCTAAGGACCAGTAGTCAGCTTAACTTCTCAAATTTCCAG
GGAAGGAGTTCGGAGTGGTAGAATATCCTGGGTATGCCCAAAGCATCACC
TTGCAAATAGCCTGTCATGAATAATTTGTTTCATTTGTTATGACTGGAAA
CTGGCTTTGTGTATGCCAGAGAATGGGGGCAGGAAAGAGAGATTGGTGTC
TTGAGCTCTCTGTGCCTCTGGGGCAGTGATGCTTTTCCTCTCATGTGGAA
GGAGAGCATGACTGAAAAGGTGCACAAATAAGGTGTCTGTGAGAGAAATT
AACCTTCCAGATACAGAGACACAACCTTCCCCAAGAGGTCCTCATTGCTC
TGCCTTTTTTCCTTTTTTTTGCTTGTTCTACCATTAATAACAGAAACTGA
TTATGACCTCAAAAGAGAGGAGAAAGCGACTCTCCCCACCCTAGAGCTAG
TTAACCACCATATCTTCCTAGATCTCAGTTCAAGAGTCACTTCCATCCCC
AATAAAAGCCCTTGAGTGCTGAGCACCTCTCCGTCATAGCATTTGTCCTA
GGGGTTTTTGTACATTTTCTTGTGTGAAACTTGGGTTGACATCTGTATTT
CCGACTAGATTACAGTTTCCTCAAGGGTAGGGATGTCTTGCTTGCCATTT
TCAGTTCCAGCATCTAGACAGTACCTCAAGCAAACAAGGCCGAGGGGGGT
GCGGATCACGAGGTCAGGAGTTCGAGACCAGCCTGATGAACATGGTGAAA
CCCCGTCTCTACTAAAAATATAAAAATTAGCCAGGCGTGGTGGCAGGTGC
CTGTAATTCCAGCTACTCAGGAGTCTGAGGTAGGAGAATCGCTTGAACCC
GGGAGGTGGAGGTTGCAGTGACCTGAGATCCACTGCACTCCAGCTTGGGT
GACAGAGCAAGACTTCGTCTCAAAAAAAAAAAAAAAAAAAAGAAAGAGAAA
AGAACATCAAATGAATGAATGAGTGAGATGAATGAGTTAGCAGTGTTGGA
TTTAAGTGTCAGATTCTTCCCAGCTTGACTTTTTTCTTTGGCTTAGTGAT
TTTGAGGTCNCAAGATTTATTTTCCTTTCACAAAGGTGATCACTACCATA
AGATCTTCAGAAAAAGAATGTGGCAAGCCANGTCTCACTAATGCAAATCT
CTATAACAACTGTATCAGTACT
>Contig43
GAGGTGTCATAAATATGGACCGATAGATGAATACAGGTAGGATGGGACAC
AATCTAAGATCCCAGGGGGGGGAGACCACACGCTTGGTTAGGGAGACCCA
AAGTGGACCGTGTGGCCAGAAGAGTCCCGCACTGCACTCTAGTGACAGTG
CAGAAAGTCACTGTGGGAAATCTAGAAGTTTCTACAGGTTGCTATTTCAT
CATAGCACTGTGCAGGCCAACCCTTCCTGCTCCACTGGCTGTTGGGAAAA
GCTTTCTCTTTTCTTCCTAGCCAGGGAGCTCTCAAAGTGTTCCACTCTCT
CACCTCCACCCAGGCGTCCAGGTGTGGAGGACACTTGCCGGCTGCTTGTC
TGCTGACTCATCCCTTGGTTTCACTTGGAAAACCTACCACCAGCTGGCCT
CTTTCCAAGCATCAGCCTCCTCATTTTCTTAATCCCTTAGGTGTGATCTC
ACCTCCACACAGTAGATTGCCTCAAGGCCCAATTCCAATATGAATAAAAA
TGATTATTTTGTCATCTTCCAATCTTCCTTTTAAAATATTATTTTATAAT
TCCCTTTAGGAGGATCACCTAAGTGAAGACTATTTTTACCTAAGAAATGT
TAAAATGTAAAGACATGGTTGTAATCTGGGGATTCCTGTTAAAATGGCTA
GCAGACAGAAGTCAGACGACAGGCTAGAAATGTGTGAAGAGTGGTTGCCT
TTGAAAGGCGGAGTTGGTAATGATTTTCTTCCATTTTTCCATGCTTTCCA
ATTCTCTACAAAGGCCTTAATATTACTTCGATAACCAGGACCTCTGATAA
CCTGCCCCCACCGAGTAAAGACTTAGCTGGGAAAGTCAGCTTCATGTGAG
GTAAAAGGAACCAGGTAATACACAATTCCCACTGCCAACTGTCGGGTGTG
CAGGCCTGAGCTTCCTGCATGTGGGAGGAAAGAGAAAGAAGAGAGAAACT
CCAAGATCCAAGAGATCCAGCAAGAAGGCTGGAGTCTGAGGACGCAGAAA
GCTGAATGGCACAGTTACCACTATTGTGCTGAGGTTCTGTGGCCTCTGGG
TCTCTTGACAACTGGGCAAAGACCCACAGAAAACTATCTCTAGACCCTAC

FIG. 4U

CTGTGGGAGGGGAAAGTGCTTCAGATCATCTACAGGACAGCCACCTGGAC
CTCAAATGGCTTACAGTTCCTTCATCCAGAGGGTCTTCATCTAGTACATA
CCAGGTGCTAAGCCTGGGTGCTGGAGACATGACGGGGAACCCATTTACCA
TGGCTTTGTTACTGTGACATTCACATCTAGGGAAAGCCAGCAAAGGGGAG
GGATCGAGGAGAGCTTGTTAGGCAGAGAAAATACCCAAGGGCAAGGGAGA
AGCCAGCCTGTTCTGAGCACACACAGTGGTTCCATCTAACTGGGCCTCAG
TGCCAGGTTGGACTGGAGATGGGGCTGAGGAGCTGTCACAGAGCATTCTG
GACACAGATGTCACATAGTCCCTTGAGGTTAGGGTCCTTAGGCATGGCAG
CATTGCTTTGAGTTTTTCCTTTTGTAATGTTGCCATTCATGACAATGTGG
AAGATGGGTCCTTGCAGAGAAGGGCAGGGCTGTGAGACCAGTTAGGAGAC
TAAGATGTGAGCCAAGGAAAATGAGGAACACCTGAACACTGGGGCAGGTG
CAGGGCCCAGAGAGAAGCAGATGGCTTCCTGAGGTTTTAAGTAGGTAGAA
TCAAGGCAGCTGGTAAAGATCTTTTATTACATATAAACTGGAATAAGCCA
TCTGCTCCAAGACAAAAGAGTAGGCGGAAAACAATACAAGACAGAAATGG
AATTAGAACAAACCTGGGAGGAATGTGGAATTAGAGTAGAGAGTCCAACA
CTGGCTGCAATCATAAAAATGTAAAACAAACAAAAATTTGCTAGGTGTGC
TTACTTAGAAATAATTAGCTGTCATATTAAGTTCACTTGTGTTATGGCTT
AAATGTGTCCCCCAAAATGTGATGTGTTGGAAACTTGATCCCCAATGCAA
CAGAGTTGAGAGATGGGACCTTTAAAAGGTGATTAGGTCATAAGGGTTCT
GCCCTCATAAATGAATTAATACTGTTATCATGAGAGTAGATTCCTGATAA
AAGGATGATCTCTGCCTCCTCCCCACAGCCCTCTTGTGCATGCTTTCCTG
CCTTTCCACCTTCTGCTATGGGATGACACAGCAAGAAGGCCCTCACCAGA
TGCAGCTCCTTGATCTTGGACTTTCCAGCCTCCAGAACTGTAAGCCAAAC
AAATTTCTGTTTATTATAAATTACCCAGTCTCAGGTATTCTGTTCTAGAA
GCACAAAATGGACTAAGATCATTAGATTATCATTTTTTATCAGACTGTTG
AAGTGAAAAATAAAAATCAAATAAAGAAATTAAGAGAGCTGCATGCAGCA
GCTCATGCCTATAATCCCAGCACTTTGGGAGGCCAAGGCAGGTGGATTGC
CTGAGCTCAGGAGTTTCAGACCAGCCTGGGCAACACGGTGAAACCCTGTT
TCTACTAAAATACAAAAAACTAGGCCGGGCGCGGTGGCTCACGTCTGTAA
TCCCAGCACTTTGGGAGGCCGAGGCGGGTGGATCATGAGGTCAGGAGATC
GAGACCATCCTGGCTAACAAGGTGAAACCCCGTCTCTACTAAAAATACAA
AAAAAATTAGCCGGGCGCGGTGGCGGGCGCCTGTAGTCCCAGCTACTCGG
GAGGCTGAGGCAGGAGAATGGCGTGAAACCCGGGAAGCGGAGCTTGCAGT
GAGCCGAGATTGCGCCACTGCAGTCCGCAGTCCCGCCTGGGCGACAGAGC
GAGACTCCGTCTCAAAAAAAAAAAAAAAAACTAGCCAGGCATGGTGGTGT
GTGCCTATAGTCCCAGCTACTTGGGAGGCTGAGGCAGGAGAATTGCTTGA
ACCCAGGAGGTGGAGGTTGCAGTGAGCTGAGATCATACCACTGCACTCCA
ATCCAGCCTGGGTGACAAAGCAAGACTACATTTCAAAAAAAAAAAGAAAG
AAAAAGAAAAAAAGAAAAGAAAAAGAAATTAAGAGAAGGGCAGGTATTAA
CCCCAAATATCCCACCATAGGGACACATTAAAGTTTGCTTGGCCACTCCC
CTAGCATAATATATGGAATGTCTTCAAGGACCCTCTGTTGTAAATACAAG
GCCCTGCTGGACTTAATACAACCTGCAGGCTTTGAGATCCCTACTCTGTT
GCCATCTCTCATAGGATTTGCAGACCAAATCCAAATACTTAAAATAGCAA
CACTCACAAACATGCAAATCAGAGCAGAAAAGAAACTTCTAAAAGGCCCT
GAAACTACACTTTATGAGAGAAGACAATAGGGACCTGAGGGTGGTAGAAT
TTTCTCTCTATGCATCTATGTTTCCAGGGCTCACTTTCTCAATAAACTCT
TAAATTGCTTTTAAAGTAAGGGAACAAGCAAACATTACATTTAAGAGAAA
TCAATTTCATAAAGAAGGGGGGATGTCCAGGGTACTTTGCTTCCATGTTT
TGCTTCCATGAATTTGTGTTTAACAGAAGATGCAGAAAAACACACAATTA
TTGCAAAATCAAGGAAATCCACTCTAAACATCCCTTGGTTTCCCAGGCCA
GTGTCACAACTGAAAACACATATTGTGGCTAATTATGTGTCACAAATTAG
AATGACAAGGCAAGAAAAAAAAAACTCTCTGATTAACTAATAGCAGCCAA
CACAGACAGCCTGTGTAGCTCGACTCTGCTGGTTTATAAAAGGCAGAAGA
AGCAAACGGCTTCTGTGACCGCAACAGGAAGGGCCTCTGCTCTTAATAAA
TAAATAACATTTAAATTATTCTCCCCCATTTGCAAAGCATTTTCCAACTC
ATTATCTCATCTGACCAGGTATTATTGTATCTGACCAAGAACTTGTATAC
NAAATAAAGAATAAAAAATAAATATGGGCCANGCACAGTGGCTCATGCTT
GTAATCCCANCACTTTGGGAGGCCCAGGCGGGTGGATCACTTGAGGTCAG
TAGTTTGAGACCAGTCTGGCCGACATGGCGAAACCCCGTCTCTACTAAAA
ATACAAAAATTAGCCCGGCATGGTGGCACATGCCTGTAATCCCAACTACT

FIG. 4V

TGGGAGGCTGAGGCACGAGAATTGCTTGAACTCGAGAGGCGGAGGTTGCA
GTGAGCCGAGACTGCGGCCATTGCCCTCCAGCCTGGGCGATGAGAGCGAA
ACTTCATCGAAAAAACAAAAACAAAACAAAACAAAAAACACCTTAGAAGA
AGCGTTCCTCCTCTTGCTTTCTGAAGACACTCTACGCTGAAACAGTAACT
TTCAATAAACCATCTCTTCTCACCGCACTCTGCGACTTGCCTTGAATTCC
TTTGTGTGCAAGATCCAATAAGCCTCTCTTGCGGTCTGGATGAGAACCCT
TTTTTTGGAATACTCTGACACAACAAATTGCAGAAAGAAAGTCTCACATG
TATAAAATAAGCAAAAAGATTCTCTGGCATCTGAAGAAACAATTTCCTTG
TCAATATTAGTATCACTATAAGTGTAGAACAACCTGTTGTATGATGCTAC
ATAAAGTATATGAATCTGAATACTGTTGGATACAAAGGGAGACTATNNAA
TGTAATACGTCGCCCGAAATGACTACACTGTTGGTGATCTTTCTTTCAAG
AAGCANAATATTGCCTCNAACATCCTGTACATGGTATAAAATTTTA
>Contig44
CCCAGCAAGAACACCAATACAACGGGGGGGGCGTTCTTTGTGAGGGGTGG
GGAGGTCAATTTTTTGGAACCTGCAGCAGGTAACACACAAAACTTCCACA
GCTGCTACCAGCTTTCCAGGAGAGCCTGTGTACCTGGAGAGGAGAAGGCA
AGTGCTTCCGAACTTGACTTGATGTCTTAGATTCTGCAATGCGTAGTCTG
TAGGGACAGGCTGTAGCTTATCCTATAGGCTTGGGCTGGAGTCAGCAAGC
ATCTGGGCTGGCAGAAGATAAAAGATGCAAAGGTGGAGGAAAGCATACGT
GGTCTGGAAGACAGACTTGGTGGGTGGGTGGCTGCTACAACACCCTAGTT
AGAGGTAGAGGGGTAAGTCAGTGTGTCTTCTGCACAGGCCTCTTCCCCAC
CTCATTCTTCATTTCCCATACAGCCTTGCTGAGTTATTCACAAACATCTG
ATTCAACTGGAAGCTGGGTTGAGGATGACCTAAAGGACTAGTGTGATGCC
TGCCCAGGGGTGTGGGCCCATAGTCAGAGTCCAGAGCCTCCTCTCAGCTT
TTAGCACATCTCACCCACATCCTGGGTCCTTAATTAGCAATATGAAAGCA
AGCCAAGTGACAAGATTTTGTCCCTGGGAAGTCCAGAAGCACTCCTTTTC
TCATTTGTATAAGCATAATGATTTGCTTACATAAATAATCATGAAAATTC
AAATCCCTCTCAGAAATCAGGTCATAAAACCATGAAATGCAGCATGTGGG
CAAGAATCACAGGGAAAGGTAGGTCTTGGAAAAGAAAGGATGGCAGGGAG
GAAGAAAGCAGGGTGCCAGGGGCCCTGGGCTGCTGTCCAAGTCAGGTGGC
TCACCGTCTCTGAGAACATTTCACTTTCTGGTAAATGGGGCAGTTGGAGA
TAGAAGGGTTGGGTGAATGCCAAGAGTGAGCACAGCTGAGGTCAGTGCTG
TGCCTGCAGTCCAGGCGGGAGTAGAAATCCTGGGCCCATCTTACCTCCGA
CCTCATTTCCTCCTCTGTAATAATGTGGGGGTGGGGGAAAGTTCTGGTCA
TCAGCCCTAGCATTCCATGGTTCATTTCCTCATCAGTGATGGAAAATCAC
CAAGCAAGAGAACAGGATGGAGAATAACCGGATGGGTGCAATCGGAGGTG
CTATTTCAGGTGAGGTGGCCAGGGAAGGCCCTCTGAAAGGGTGGCTTGAG
CAGGTGGCTGAATGTACAGAAGCTGCCAATCATGAAAGATCTGGGGTACA
GCATGCCAAGCAGAGGAAATGCGAGTGCAAAGGCCCCGAGATTGGATGTG
GGCTTAGCACAAATGTGGCATGGCAAGAAGGCCAGTGTGGCTGAAGCAGC
ATGAACAATGGGTGGAGGGGCTGAGAGGACAGAGGAGCAGGAAAGAGCCA
GGCTTGGGTAGGAGAGGTGTCAACTTGATATATGATGCAAAGCCCTTGGA
GGTTCCCAAACACAAAAGCAATGATCTAATATATGGTTTTAAAAATGCCA
CTCTTGGCCGGGCGCGGTGGCTCACGCCTGTAATCCCAGCACTTTGGGAG
GCCGAGGCGGGTGGATCATGAGGTCAGGAGATCGAGACCATCCTGGCTAA
CAAGGTGAAACCCCGTCTCTACTAAAAATACAAAAAATTAGCCGGGCGCG
GTGGCGGGCGCCTGTAGTCCCAGCTACTCGGGAGGCTGAGGCAGGAGAAT
GGCGTGAACCCGGGAGGCGGAGCTTGCAGTGAGCCGAGATTGCGCCACTG
CAGTCCGCAGTCCGGCCTGGGCGACAGAGCGAGACTCCGTCTCAAAAAAA
AAAAAAAAAAAAAATGCCACTCTTGCTGTGAAAAATTGACCCTGGGGA
AGGAGGAGTAGAAATGTCAAAAGTGGAAGCAGACCACTCAGGAGGTCAGG
GCAATGGACTGTGCAGGAGAGACTGACATCTTAGACTCGGGCAATAGGAG
AGAAGGTGGTGAGGATTATATTCTGGGCATAAAGGCAACAGAACTAGCTG
ATGGCGTCAACGTAGGAGATGAGGGAAAGAAAGAAATCAAAGGGCATTCA
TAGGTTTGAGGGTTGAGTAACTGGGGATATTTAACAGAAATGGAGAAGTC
TGGGGAAGGGGCAAGTATTGTGGGGGCAGGGGTCAAAAGTTCTGTATTTT
GGCCAAGTTAATTAATATTTGAGATACCTCTTAGGTGTCCAAGTGAAGAT
GTCAAACAGTCAATTGAATACAAAATCTGAATCTTAGCCCAGGATGGTCT
CACACCTGTAATCCCAGCACTTTGGGAGGCTGAGGTGAGAGGATCACTTG
AGGCCAGGAGTTTGTGATCAGCCTGGGCAATAGAGCAAGACCCTGTCTCC

FIG. 4W

ACACACACACACACACACACAAAAAGTCATCCAGGCATGGTGGCACATGCCT
GTAGTCCCAGCTACTCAGGAAGCTGAGGCAGGAGGATCACTTGAGCCCAT
GGTTCAAGGCTGCAGTGAGCTATAATCACATCACTCAATACTACACTCCA
GCCTGGATGACAGAGAGAGACCTCATTTATTAAAATAAAATTTAAAAAAA
TTAATTAAAAATAAATCCAAATCTTTCCTGAGATTCATATTCAGGAGTAA
CTGTCATGTAGAAGGCATATAATGCCATGGGTCACATGATACCATCTAAT
GAATGCCACTGGAAAAGAGAGAATAGCTAAAAACTGAGCACTGGGCACAC
CAGCACAGTGAGGTTGGAAGGAAGAAATGGAGCTAACAAAGGAGACAAAA
GAGGAGTAGCCAGTGAGAAGAGAGAAACATCTGGAGAGAAGAGAGAGCAG
CAAAAGGTGGGTGAAGGAGAATGTGGTCCACCAGGCCCAACAATGCTGAG
CAGTTGAGTAAGTGAGGACCTGGCCACTGAATTTGGCAAGAAAGAGGATG
TCAGCGGCCCTAGAACAAAAGTGAAGAAGAGCTTGAGGACGGAAGCCTGA
CAGGAGTGAACTGAGGAGAGAATGAAAGGTGGAGACATGGAGCCAAGGAG
CACTGAGACTCCCTTGAGTAGTTTTGCTGTAAAATAAAAGTGAGTGCAGA
GACGGGGCAGGGGGACAGAGAAATGCAGGGGTAGCTGGAGGGAGCCACAG
AATCAAAAGAGGGTTTTTGTGTTTAAGATGGTAGTTGTCACATAGCACAT
TAGTAAGTTCATGTGAATCACAACGTAGGTGAGACAGATCACTAATGCAG
GAGTCAAATCCTTGCAGAGCCCCCAGAGGAGGTGATGAAGGGAAGTGATG
GACATCATTCAGATGCAAGTAGGTTAGCAATTCCTGGGGTACAAATAGGA
GGTGACTCCTTTCTGATTGCTCCTGTTTTCTGAATGAGATAGCACATAAA
GTCCACTCAGCCATGTTAGCTGTTGAAGTCCTTGTGGCTGTCATGCCTGT
ACAGACTGGGCTCTCCTCTCCAGCATTTCCTCTCAGACTAAGCTGAGCTG
CACTAGCCGCTGCCACATCCTCTTGGGGCCATCCTCTGCCACACTCCACA
TATTGCTGTGGTTTGCTTGCAACCCCTGGAAGGTCCTACTGGCTGCTCCT
AGAAGAGTCTGGGCGGCATCTCTCCCTTACTCGTTATCACATGGTGCTGT
AAGCAGTGGCCACACACTTTAGCTGGTGGGATGGGCCATCACAGGCAGTA
AATGCGAAAGACTGCTCAGATTTTAAAGCACCCATGAATCAGTAGAATGA
GTTTAGAATTGTAGTCATCAACACACATTAAAAAAAAAAAAAACAGGCAC
TAAAAAAATTAGTTGAGTAGGATAAAGCCATAAAAGATATTAACTACAAC
CCAGATAGGAGGTGCAAAATTGTCCTTACATAAATCAGATGGAAAAAGTT
GAAAGCAGATAAGATAAAATAGGTAAGCATGACATTTAAAAGGTATTCAT
GGGACGTGGTTACAAAACCAACTCACAACTAAAAAGTCTTAGGACCTCTC
GCTGACTTAGGAGCCTGATCCCAACTTTGAGAATGACTCAGTGTGTTACC
CTGTGGCTAGTGTAGACCAATGATCCTGTCTCAGAGTCACTAGCCAACAG
CCCATATCAAGTAATTGAAACTTTGACTCAGAAACCTCAGTGTCAGAACC
TTTGACTTAGGAACCACCTGTAGTGGTTAACTGCAATTTGCACCCCTTAG
TTCAGGGCTTTACAACACCGGGGGCGGGGAGGGGGAAGGCATAGAGCTGA
TGACCTAAAGGAAACCCATTGCAGCAACGCTTTTGTGTTAAGTTTACAAA
TAAGTGTTGTTTTAGAATCCTCCAGGTAATGCCTTTGTTATTTAATGTGT
CTGAGACAATTCTGCACATTAAAGAATATAAAATATTACCTTGTAATTCC
AATTTGAAATGTGTAATTGACATTAGACTTCTATTTTAATTTGAAATGTC
TAAAACAATGTGGTTAAGTTTGTAAAAGGTGTGTGAATTTTGAGTCTGAT
TTACTACATTTTTTTTAATTTTCTTTTTTTTTGGAGTTTTAGGGATTGC
TTAGATGGCTAGAAAGATCGCTAGGCACATGTCC
>Contig45
GATGTGTGTACGTGTGTGCAAATACCGTGCCTTTTTTGTTTTCTTTTGTT
GAAACAGAGTCTCACTCTGTCGCCCAGGCTAGAATGTAGTGGCGTGATGT
CAGCTCACTGCAACCTCCGCCTCCCAGGTTCCAGTGATTCTCCCGCCTCA
GCCTCCCAAGTAACTGGGATTACAGGCGCCCACCAACACGCCCAGCTAAT
TTTTGTATTTTTAGTAGAGACGGGGTTTCACCATGTTGGCCAGGCTGGTC
TCTAACTCCTGACCTCGAGATCCACCCACCTCGACCTCCCAAAGTGCTGG
GATTACAGGCATGAGCCACCATGCCTGGCCAATACTGTGCCATTTTATTA
TCAGGGACTTGAGCATCCATGGATTTTGGCATCCATAGGGGTCCTGTAAC
CAATACTGCACAAATACCAAGGGACAACTGTATTCTAAAAAGACCAAAAA
TTAATAAGCAGGACGCTGAAGGTAATTGCCCCAATAAAGTCATGATCCCT
TGCCCAGTGTCTGAACCTCAGCCAGTTTTCATACTCAGGACCTATTGGCT
GCAGAGGTGGTAGGAACCATATGAGAATCCTGCAATATCATGGCAAGTAT
GCACTTTAATGATATCTGCAGTCCTTCCCCAAAAGGACCTTACATTTACC
ATACTGCTATGTCCTGCGTGAGAGGGTAATACTCAGATTTTTTTTTTTTT
TTTTTTTACACAACGTCTTACTGTGTTGCCCACACTGGAGTGCACTGGCT

FIG. 4X

CGATCTTAGCTCACTGCAACTTCTGTTTTCTGGGCTCAAGTGATTCTCCT
GCCTCAGTTTCCTGAGTAGCTGGGATTACAGGCGCCCGCCACCATGCCTG
GCTAATTTTTGTATTTTTAGTAGAGACGGAGTTTTGCCATGTTGGCCAGG
CTGGTCTTGAACTCCTGACCTCATGTGATCCGCTGGCCTCCCAAAGTGCT
GAGATTCCAGCGTGCGCGGCCATACCCGGCCGGGAATTCTTTATATATTC
TGAAAACTAATCCTTTGTGAGACATAAGTGTTGTAAATATTGTATCCCAG
TTTGTGGCATGTATTTTTAATTTTTAATGGTGTCTCTCAATGAAAAAAGC
TTAACACTTAAATGAGGTCAAATTGATCACCTTTTTATTTATGGTTGATT
CCTTTGGTGTCATGTGTAAGGAATGTTGTTCCTTCCTGTCCCAAAGTTGC
AAAGATTTCTTGTGTATTTTGTCCTAAAAGTTTTAAAGTTTTGCTTTTCC
CATCTGTGCACATTTCACATTTGCTACATCTCACTGACTGCTTCCTCTGC
TGCAGAGCAAGCTCCATGAGAGCAGGAGGCATGGGTCCTGCTTCTTGTTG
GTCCCCAGAGCCCTATGTCATGACTAGGACCTGGCAGGGGACTAGTGAGT
AGCTCCTGACTAACTGACTCAATGAATGAATGATTGGATGATTGAACAAA
GTGGTATGGGAGTTCACAGCGAGTAAGAGATGCCTTAGAAGAGATGAAGA
AGGAGATGGTATAGGGTAGTGGTTCTCAATTCTGGGTCCATGGTGGACTC
ACCTGGGGACCCTTAAAATGTACCGTGGAGGATCCCAGCCCAAGAGATTC
TGTATGACTGGTCTAAGATGTGGTCTGGGCACCAGGTGATCCCAGTGTGC
AGCCAGGCCTGAGGCCACTGGATTTGGTGGTAAATGAGGTAACTATCAAG
GGTACAGACGTTGGTTGCCAACAGGCTTGGGCTTGAATTTAAGCTTTGTC
ACTGACTTGCTGTGTCCTCCTGCACTCGTTGAGCCTGTTTTCTCACCTGA
GAGATGGGTGTGATAACACCTACCTGCTGTAGTTGTTGTGAGAGTTAGAG
GAGATAAGCATGTTCCTGGAATGAAGTGTGTTCTTAATCCATCATAGGTT
TTTTGCTTGTTTGTTTGTTTGTTTGTTTGTTTTTTCCTTTTCAAGAATGA
GGTTGAGCCAGACTTTGACAGCTGGGTGGGAAGTGAACATGTGGTGATTG
GGAGAGAAGGGCAGTTTATGTGAAGGGAATGTAATAATTAGAGAGTGGGC
GTGGGAAGACATGCTGGGGAGAGTGAGCAGGCCGGTTAGCCCTGGTAGAG
GGTGCAAGAGAGCAGTGCGGAATCTGCCAGGGAGACAGGTGGGTGACCAG
GGTGCCAAGGGTGTGGCTTTTCCCAGGTTCCCATGGACACAGCCATCCTC
CCAGATGCCCAGCCTAGCTGTGAGTGAGCAAGAGTTCTGGATTGTCTCTC
TCACTCTGTCTTTTTCTCTCATTCCAGAAACAAAGCAGTGACTGGTACTT
AGGAGGAGAATCAGGTCAAGTTGGGAGAAACTTGCTTCTGCTCAGGGGAG
CAGAAGCAAGAATGGAGGCCCCACCCATGCTGGAAGATGATGAGGGTTTT
GGTTCAGGGAGGAGGAATATTGGGGATCTAAAGGGGCCTGGGAGTGGGGC
AGGACCCTGCCTTAGGACAGGTAGAAACATTTTCTATAAAAAATGGGGTG
GAGGTTGATGGTAGGACCAGGCATCTTTAGTTGGCTCCCTGGAGTGTCAA
GCCCTTGAGATGGTCTTTAAAAGCCATGCAGTGGGGTTTGAATCTGGTGT
TCAAGCTCATAGGTTATTAACATAATGACACTTGGAAACTATTTGGGAGA
GCTCAAGTGAGTGGCCTGGAAGTTCTGTGTTGGTGCAGGAGGTGACTTAG
GATGTGCTGCTCCAGACTCATATCTTTGACTGCACACCTGATGCTTCATC
TGGCTATCCTGTAAGCACCTTCAACTTAACATGTCCTACACAGAACTCTT
GATATTCCTGTTCCTCCCCCAGTTCCTCAGTTCTTACCAAATGTTCTTCC
AGTTACCCAATTGCTCAAGTAAAAAATCTAAGTCCTTCTCTTGGATTTCT
GCCTGTTCCCTCAACATCCCACCTATCCATGAGTGTTCTGTGGGCCCTGC
CTCTGAAATAAATCCTGCCTTTGTCTCCCAGTTCACTCCAGCCACCCATC
CTGGGGCTGCACCCTCCTCCTTCCAAGCCCTCTCCCTTTCCTTCCTGGTG
CTGCCTGTCATGTCAAGCATATGCATCAGTGCGACCAGGACATTTGAAAT
GCAACCAGTACAATTGGGCGCGGTTATGCCTACCAGTTTTTCTTCCTTAA
ACATTTTATATTTATGTTTGAAAGCATGCCACCTTTCTTCACTTGCCAAC
TTGACAGATTTATTAGTTGACAACATCCGCTGATAGCATCAGTAATAAGT
TAATTGTTTTTGCACATGTAGCTTTAATTATTCTCATTATCATTTATAGG
AGTTATTCTTTGTAAAGGGTAACTGAGTTTTCCAAAACAAACAGAAATTT
GGGGTGGGCCCATGGAGCGTGACTCATGAAATCAGATTCTTAGAAGGACC
TCGGCAAGTCTCTGGGTTGCTGTTAATGAGCCTGGCTGGCTGCCAGGGGT
GTGTCTGCCCTTTATGAGGCCACCACTGTTCAAATGCTTGCCTGCAGCAT
TACTTGCCTAGGTAGTGCTTGTTTCTACTGAACTGTCAGGGATCCAATTC
TTTGTGGTCTAAGTAACAATACTCAGATTCACAAGGAATTGATTAATAAG
CCAGAATGCCAATGTATTACATTTTTGATGAAGACCATATTTACAGTGAT
TGTATCTGCTCAAGCTCAAATTAGGATTAGAGTTCTGACAAATACATATG
TGAGAAGTATGAGGTTAAATACTTGAAATTTGGACTTTTCTAGAAAATCT

FIG. 4Y

GAATGTGATTGCCATTCACATACCTTTCTGGGGATGATGATTCTTGTACT
TTTATTTTAAAAGACATAGAAAACTAACTTAAGAATCAGATTGCTTGGCT
GGGCACAGTGGCTCATGCCTGTAATGCCAGCACTTTGGGAGGCCAAGGTG
AGTGGATTGCTTGAGCTCAGGAGTTTGAGATCAGCCTGGGCAACATGGTG
AAATCCCATCTCTACCAAAAATACAAAAAAAAAAAAAAAAACAACCAAAA
AGAATAAATTAGCTAGGTGTGATGGTGCGTGCTTGTAGTTCCAGCTACTT
GGGAGGATGAGGTGGAAGAATTGCTTGAGCCCAGGAGGTGGAGGTTTCAG
TGAGCTGGGGTTGCAACAGTGTACTCCAGCCTGGGCGATAGAGTGAGACT
CCGTCTCAAAAAAAAAAAAATCAGATTGCTTTATTGCTGGTTTTCTTTCT
AAAACTGAGATTGGGTCCCATCATCCCCTGGCCCCCATTGGTTAATGGTT
CCTCCTTTGTCTATTGAATAAAATACAGATGTCTGCTTTTGGCAACATGG
TTGAATGTAGACACTGCAGGGTCTTCCTGACTCAAAATGATTTAGGCTTA
GATAAAACACATTTGGAAATGCATTTCTGGATTAACACCAAGGAAAGGAG
ATCTCTTTAAATCCCCTTTCTGTTCCCCCCTCCCTACCCCCTCCAATTGG
GCTTAAGTAAGAAGGGTGGTTACCCGCTAGTAAACCCCCTTCGAAGGGGG
TCTTCTCCTCTAAGGGAAAACCCTTGTTTTGACATTTGCTTCAATGGGCC
CTTGTATTTTGTTCCTTGCTAAACGGGTGCTAAACCAGGGGCCTCCTCTT

>Contig46
AAGGCTTTTAGAATATTTGCACACTTTAGAAATGGAAATGTTTTTGGGGG
GCGAGTTGTCTTAATATTTCATTTTTCTAGCTTGTGTGACATCCTTTTGA
AAGCAGCAATTCTGGCCTTTGTGAGAGATGGTGAATGCCTGCAGGTGTGT
GGACCAGTGCGTCCCTTCCTTCCTACATGCACGGCCCCCAGCTGGGCCCA
GCAGAGTGCTGTTACAGAATAATTTCCAAGGGCTGTGTCTCTAACCTTTG
GTCTTGTCCCCCATTGCTGTAGATTTGGCCAATTGACTTCATAAGTGCCT
CTTATGAACATAGATGTTGGCAATGGAAGTTGAGGACCAGTCAGTGGTTG
TTTTATTGAACACACAGCGTAAATCCCAACACAATGCTGACCTAAGAGAA
TTCCAGCCACTCTGATTCTCAGTCTCTTTATATCTGAAAGGGTTCTGTTC
CACTTTTTCCCAGATCAAAATGTCCCTGCAGCTACTCAGCAGAGCTGTCG
CAACTTATACGTAGAAGAGGTAACAGTCCACAAACAGAAAGGCACAGGAC
GAGAGTGGTCTGGGTGATGCTTCCTGTGGGGGAAAAGGTGATGAGGGTGC
ATCTGCACACCTATGTTCATAGGTAAGTCTGGGAGGAGGTGACCTCCCCT
TTGGTTGAGGTGCTGAGGCGTCTTGTTAGAATGGCACTATTCCATTTATC
TGATGCAGTCTGTGGGAATTTTGTGGTATGGCCACCACAGGTACCATGCT
GGGAACAATGCCAGATACTGCCTGCTAAGCCACAGCATGAGTCACATGAG
CATTTGTGGGCTTTGGGAACTAAAGTTATTGAACGATAGTTATCTGAAAA
GGAATTTAGGGAAAGGGGACTTTAGTCCAGCGAACAGTTTGCAAACCAGG
GGGAAGGCAGCCTTCAGCGTAAAATGAAGACGTGTGTGCCCCAAATAACA
AAGGGAGAGTTTGTCTTTTAGAGAGTAAATGTCCACGCAAGGTTCCACTT
AGGCAAATGAAAGATGCAAACTTGCTTAGTTCTGATTTGTTTACATTTGC
TGAATTCGGATTGGTCCGTGCAGGCTTTTCTGGGAACTCCAAATACATGT
ATGACCTCTAGTCATACATGGCAAATGGCCGCTTGGCTCTAATTTGAATT
TAGGCCCAGTTAGTCACTCAGGATTAACCTTTTTCAGGGTTCACAGCTCT
GAACAATGGACTTAGACCTGCAGGACATAATCTGTTCCTAACTCTGGGAC
TACCTGTGCCTTTTGACTGTGCCCAGTGAGCAGCTGTGGCTCTGGGCCCA
GACCCACAGGGCGATAAGGCACAGAGGTACGCATGGAGCAGGCTGTCCTT
GCTGAGTGATCATGAAGATACACTTACATAGAGCAGCACTTTTCCTTCCA
GTCTTTGTGATTTAACTCATTAGATCCTTATAACAAGAGTCAGTCCTCTA
TTTAACCCATGAAGCACAGGTGGAGTCCAAGCTTAGTTTGTGAAGGATGA
GCCAAAAGGATTCTTCTCTTGTAGACCTCAAGCTCAGCTCTCTCCATGGG
CCCTGGAGTAGGTGAGAAGGCCTCTGTCTTCCAGAGCCCACTGCCAATCA
TCTACATTTTCTGTTAGCCCAATTCTAGGACATTGCTTTACCAACTGAAG
GGTGAGAACTATCATAAGTTATAAAAATCAATTGAAAAACAAAAAGGTAC
AGAACAGAAAATAAAAGATGAGAATCTATTAAACATAGTGATGTTACTGG
AAAAGGGGGTCTCAAACCAGACCCCAAGAGAGAGTCCTTGGATTTCACAC
AGGAAAGAACTCAAGGTGAGTTGCAGGGTGCGGTGAATTGAGAGAGTTTA
TTGAAAGCTATTCCATTACAAAGTAGAGCATCCTCAGACAGCAAGTGGAG
GAACATGCCATCATTAAATTTTTCTTATATAGGAATCTTGTCTATATAAA
GACTAAACTAAGCTGTGGCTATGTGTGGGTGGGCCGACAGCATGAAAACA
TTTATTCTCCTATTGATTTAAAGAGAACTATCCTTGACATTTTAGTGTGT

FIG. 4Z

TTAAGTACATCAAAGCATAACTATAATTATCTTGAAAGCATATATTTTTA
TAGGGATTGGGACATCTGGGCTTTCTGTTGTTGTAGAAGTTTGTCCTTGC
AGGGATTACCAAGCCACTTCCTTAGCTGTAAACATCTTAGGGCCATGGGT
CCTGACTGGCAAGGAATGTGTCTTGCTAGTTTTAAGATGGGCTTGATTTG
AAAATGGTGTCCATCTGGCTCTCCTAGGCTCCTGCTTTCCTAACAGTAAG
GGTAAATGCTATGTTATGAAATGTCATTTCTGCCTTTAGCTTGCAAACTC
TTGATGGTGAAATTCTCCTGTCCGTTTTCAGTGGGGTATTTATTCTGCAT
CCACGTCTTCACAAGGAGCTGAAAACAAATTGGATGGAAGCAACTGGGTT
TTATGGGACACGTTAATGTTTTAATGTCATTTGGTGTGGAATTCAGATGT
CCAAGCAACATTTTACACTACAAATCTGCAACTTTAATAATCACTCAAAG
TACCTGAACCTCAATGCTTTCAGACAGACTTGGTATAAAGCCACCACCTC
TTTCTATTATGGCAGCCCTATCCTGAGGACACAAATTTCTGCAGGGCTTC
TGGCATATCTCTGATTAAACAAATGTCAACAAGGTTAAAACAAATGTCAT
CTCTGATTTGTTTGTTTTAAAGCCTGGATTTACTCATTGAATATTTCACT
CCTACTAGCATGTCTTGTAGTAGTTTCTTCAGGGACCCTAATTATTGCT
ATTAAAAATATGTGTGCAGCTACATGTTTTTTTTTATCAATTTGCAATG
AAAACTTTAATTGAATAATCTATTAGTGTTATTATTTGAAAGTGAAATCT
TTTCCTTTTGCTTTCTTGTTCTCACACATAGTGCAGACAGTTTCCACACG
GGCTCATAAAAGGAATGATTCTGCCTTGTGTGAACTTTTTGCCTTTATTG
TTAATTGCACCATTTTGTGACTGGCTTCTTGACCCTGTTGTAACCAAGCT
CATAATGTACATTATTTCTTATTTTGCAGTTGTAGACACTTGAGGAAGTT
CCCATTCTTTGTTTCTTCTTGCTTTTGTTCCCTGTGATAACTTTTTCATG
CAGACATTTTTTTTTTTTTTTTTTTTGAGACCGAGTCTTGCTCTGTCATC
CAGGCTGGAGTGCAGTGGCATGATCTTGGCTCACTGCAACCTCTGCCTCC
CAGGTTCAAGAGATTCTCCTGCTTCAGCCTTTCTAGTAGCTAGGATTGCA
GGCGTGCACTACCACACCCAGCTAAATTTTTCAAATTAGCCACCCCACCT
GGCTAATTTTTGTATTTTTAGTAGAGACAGGGTTTCAACCATGTTGGCCA
GGCTGGTCTCGACCAGGTGATCCACCCGCCTTAGCCTCGCATAGTTGCAG
GTGCTATTCTGAGCTCAGGGCTCTGGCAGCTACAAGCCCAAGATGCGGTC
TCCAACATGTGGCCATTCAATGTCATGGCGCCCTCTACTGGTCCTGGGAA
GCGCAGCTCTGCCAGTAGCTCCAGCAGGGCACAGCTGTTAAGTCGTGATG
TTCTACAGGTGACCAAAGGGCAATCTCTGGACTCCTTAGCCGCTAGGTCC
TCTCTGTAGCAGGACCCAGGAGAAGGCAGGGGCTGAGGATGGCTCTCTTA
GACATTTGTGATGAACCAAACGTGTGCATTCATGAAACTTCTGTGAGCAA
GCAGGTGAGTAGAGTTGGGTTATAAAAAGTCTTAGGGTCTCACTACAGAG
ATGGACTTGCTGTGTAGATGGTGCAGAGCCGCTGAAGAGTTCTACTTGGG
GTAATGGTGTGATTGGGTTTGCGTTTTAGGAAGATTTCTTGGCCAGAATG
AGGCGGGCAACCCAGAGCAGGGAGTGGCCACATGTGGGTGTGCAGTTATG
GGCCACTAATCCAGGTGATAAATGGTGTCTCTGAACTTCAGGTGGGGGTG
CCACATGTCTCCATCTGCTCTGTACCCTTGAGACTGGCCTTATGGGCTGC
CTTAGTGGTCTGTTGTCCTCTATCTCCTGGTTGGGCTCAGGCAATGGGAG
ATCAGAGGGAGGAAAGAGAGCTTGGTTAGAGTGCACCCGCGCCCCTTCAG
GTTGGCAGTGGCCACATTCCCCTATACAGAAGGCCACAGTTTCTGTCAGT
GGCCCTCCCACAGCCCCAGCTTTCTCAGTGGGCCAGCCACCTCCCCATCC
CTTGCTCCTCCTCCTCCAGAGAGGGTTGTGGATTTCCACTGTCAGCAGTG
CCTGGAGCTCCACCATCTCCTGCTGCTTCCTCTGGACCTGCCTGCAGTTT
TATAAATAACCTTTCCTTACATTACCTCTAGCATGCACCTTTTGTGTGTA
TACTCTGCCCCCTGTCAGCACATGACTCATGCCAAAGAGTTTGAATTTTT
TTCTCCAGGCAACGGGAGGTCATTGGAGGATTTTAGACATTGAGAACAGA
TGTGTATTGTGGAAATATCTGTCTGACTGAAGTGACCAGGATGGTCCAAA
AGAGCGAGAATTTGAGGCAAGCAAACCATCAGCAGGCCAGCAGCAGAAAT
CCAGGTCATAAACAGGGAAGCTGAGGCTCACAGGGTTGGATCAGGGAATG
GGAGAGGGAAGCCAAACAATTCCATGAGCATGTCAGTTGCACATATGACT
TGGTAACTATTTTTATTTTTATTTTTATGTTTTGAGACAGAGTCTCGCTC
TGTCACACAGGCCAGAGTGTAGTGGCATGATCACAGCTCTCTGCAACCTC
TGCCTCCTAGGTTCAAACAATTCTCCTGCCTCAACCTTCCAGGTAGCTGG
GACTACAGGTGCGCACCACTACACCCAACTAAGTTGTGTATTTTTAGTAG
AGATGAGCATTCACGCTGTTGCCTTAGACACGG
>Contig47
AATATTGATTATTTGACCAGAAATTCATGCAGCTAACCGTGACCCCTGGC

FIG. 4A'

AAAATAAAATAGTGTATATGTACGTGCATATACATGCAAAGAAATGAGTT
GAAACTAGAAGGATGTCAATCAAATGATAACATGGTCATCTTGGGGTCGG
AGTACATTTGGGGATGAGGGGAGCTGTAAAGCAGACTTGGACCTTTTCT
TCTACCAGTACCGTGTCATTTGAATTTTGGAAAGAAAAAAAAAAACTCAG
AAGGAGGAGAAGGAGCAGGAGGAGAAGAAGATGGATCTTAAGTGATTTGC
CCGGGAGCACCTTGAGAAGGTGAGATTCAAGTCTAGGTCTAAGCTTTCTA
ATTCCATGAGTGGGAGTGACCCACGTCCAAGAGGAAGCTCAAAAGGAAGA
TGTTCTCCATCATCTCTTGCTCATCCTAACAGCATGCAAAACCACATCCA
ATGCAGCTCAGAAAACTCCCAAATTGCCAAATTTCATTGGAAACACTTAA
TGCTGTGGTTTCCAATTTCAACTGTAAAGTAGGTATGTATGCCATTGTTA
CCATTAACTTCTCAGAAATGGAGAGAGCTCTCTTTCCGCCTCCTCCCCCT
CTGCTGTGGCTTTGGTGAGACGTGCACTCAGGCTCACCTGTCTCCATGAT
CTCCAGTAAGTACACATGAGCAGAGAGGCCTCAGCTCAGCTCTTCCTGGT
CCCACCAGGGTTGATTCTTTGAGAATTCTAGAATGCCACATCCTAGGCCC
CCCAAAGAAATCCTGCATCTTACCCCCAGAAATATGAATCATAGCAAATT
TCAAATCAACCATCGTTTAATACTCACAGACTGGGCACATCCAAAAACAT
ATTTTCAGTTTTACAACAGTGCCTGGTGCATATCGGCACTATTTGTGGAA
GCAATAAATCGACACGGAGCTGAAACACAAACAAATGCCAAATTGTTTTT
ATAACACCTGATTTTCTTTCTGTTTCTTTATGCAGTTTAGTTTTGTTTTG
CTTAACTCTACCTCAGACCATAGTCTGGTAAACTCACCACCCAGAAGCTC
CCTTGAAATGTGGGTATGCAGCCACTAGGTGGCAGGAGAGAGTTTCCTGC
CTGGAGGGAGGACAGCCACTCTGTCCCCGGGTCAGGCCAGGGCCACCCTG
CTACCTGCAAAATTAGCATGGGGCTTTATGAACCACAGCTTCCTAATAAA
CACAGGATCTGTTTGATAGAGACTCCAAAACACGCCTACCTAGTGATGAA
AGACTCAACTTCAGAAGAAAACCTTCATGGCAAACATCTTCAGAGATGTT
TCCAACTTAAGGTTCTGAACACAGACGCTTCCCCAGAAAGCCATTGTTTC
TCAGCACCTGGGAGCCTTGCTTTGCTTTGCTTACAGACTCGCTGTTCTTA
AATCACTGCCAAGATAACATCTGTCTCTTCTCTTACCCTCTATTTCGATA
TAAGGACTCCTCACTCTTGTTGCTTCCTATTGGCTACCTCTCCACAGGGA
GAAATCGCTGATTTAACAGCAGTCAATATCCCAAATCTGGAACAGGGAAC
AGGGAAGCATTTAAAAATTGGAGAATTTAGGCCGGGCACAGTGGCTCATG
CCTGTAATCTCAGCACTTTGGGAGGTCGACGTGGATGGATCACTTAGGAG
TTCGAGACCAAGCCTGGGCAACATGGCGAAACCTCATCTCTACAAAAAAA
AAAAAAAAAAAAAAAAAAAAAAAAAACCCAAAAATTAGCCGGGCATGGTA
GTGCACACCTGTGAGCCCCAGCTACTCAGGAGGCTGAGGTGGCAAGACTG
CTTGAGCCCTGAGGTCGAGGCTGCAGTGAGCCGAGATCACACCACTGCAC
TTCAGCCTGGGCAACAGAGTGAGACCTTGTCCCAGATAAATAAATTAAAT
TAATTTAATTAGAGGATTTAAGGATTTTCCCTACAGACACCTCCTTATTT
TCTCTGGCCTTTTCTGACTACTCTCCCTAACTCCCTGCTCCTCTGGTCTC
CCAAAACTACTCCAGAAAAAAAAAAGGGGGGGAGGGACTAAAGGAAAGCC
AGGTGACAGTGCCAGTGTGACAGATGACAAAGCATCTGCCCGAACAAACC
GTAGGTCCCTGAACTTTCTCCAAGACCTGTCTGTGGACTTACCTATGAAA
ACCAGTTTTAGCAAAAACCCTCCTAAGCCAGTTTATCAAGATCCCCTTAT
CCTCAATATCCATCTGATTGGATTCTTCATCCCCCACCATTCCCCAGTGA
TGTCACCAGGCCTTTCTTCAGCAACAGTAGTTAGTGGGTGTAGCCAGGAC
GCCCCCTCACCCCTGATATGCCCTTTTAGTAATTCTTCATCCACAGGTTC
CCACCCTGCTCCTAGGCTATACATTCCCATTTGCCCATGCTGCATTCGGA
ATTGAGCCCAGTTCTATACTGAGGTCTTACTTCACCTCTCGCCATAGTCC
TGAATAAAATTGGTTTTCACATTTAAAAACTGTCCAGCTCTGGTTGTTCC
TTGACACAGGGTAATTTTTATTCCATGTGATAGTTTGCCTTACCTCAGCC
TACACCCCTCAAACCTGCAACTCTATATTCAAGAACCAGACAGCCCTTTC
CAACAGATAGGAAGAGGCTGCCCTGGTGCAAAGGAAGAGGCTCTGGGAGG
AAGGAGAGAACCCGAAGGCTGCCCCCTCCTCTAGACTGAGCTCTGGGATG
GGTGGACGATAAAACCCAGATACGTTTAGACATCTGAGCGTGGAGAGGAC
TTTGCTTTGCTTCCACAGGGACCCCAAGGAAACTGCAAGCCCTCCAGAGA
CTAAAAACAGCAGAACAGCAAGAAATGGCAGCAAAGGTCTGGGCAGAATC
ATCCTATGTGGGCACAGACACAAACAGAGTCCCCTGTGGCCCCAGGAGAG
TTTAAAGAAGATCCAGAGGCTGTCCTATTCCATATCTCAGCAGAGACAGG
CCCGTGAGCCTAAAAGCTGATCATTAGGACAAGAAGGACACGAACTGTCC
TGCAGCGTGAACCGCGTGGAACAAGGCCAATCACCAGACACCAGACCAGC

FIG. 4B'

CAGACACAGCCCCGCAGTTCCCCAAGACCACCACGGACCCATCGCCCCTC
ACCAATAGCTCCAGGCTACATAGACCCCCTCCACTTCATGGATGTCCTCA
GAGCAGAAAGGGGAGGCAGGAGTGGAACCCTGACTTGGTTCAGTTGAAAC
ATAAAATGACTGTACTATTATTGAATTGCTGAAGTTTACGTGAAAGAAAT
GAGATTTAGTTTTTGGCCACAGTGCAAAATAAGAAACGAGGCTTCAACTG
AGATTAAGGTGAGTTATAGGAAAATGTACTCCCTTGAAGGACCTGTGAAG
TGTGTTCGCTATGAGAAAATGACCAGAATCCACGTTCTTAGCTGCGGGAC
TCAGGCTGACTCCTGTTTCTGGAGCTTGCACAAAGGGCAGGGAAATCCCT
GTTTCAGGCACAGTGATTTCAATGTTTAAAAGAAAACAGGTGGGCCCTGG
CAATCATGATAACATGTCATAAGTTTACATCTCTGTGAGGCAGGTAGTGT
AATCCCCATTTTGCAAAGGAGGAAACCGAGGCTGAAAGCAGCTACATGGT
CTCTTCAATGTGGCCCAAATGTTGGAGAACAGAGCTTAACTGAATCAGCA
ATTCTATACTTAGAACTGACTCTCTCTTTATTATATCTCACTACTACCTT
GATATTTGAAATATTCAACTTTTTTCAATCAAAAAATAACAATAATTTAG
GCATAATGACTACTATGTCATTTAATTTCTTGCTGATATTTCAATATCCC
ATGCCAGGAATATTGAAAGCTCAGCTCCTTAAGAGCTGACTATGGCATCA
ACTCCCAACAACCATCCTTCCAGAAATATTTTCCCCTTTCTTTTGTTATA
GAGTGGCACTGCCCTATATGGTGACCACTTGCCACATGTGGCTGTTGAAC
ACTTGAAATTGGCTTGTCAGAATTGCAGTGTAAAGTGTAAAACACATACC
AAATTTCAAAGACATGGCACATAATAAAAAATGTAAAATATCTCATTAAC
AATTTTTATATTGACTGTGTAAGTAACATTTTGAATATATTGGATTAAAT
ACATGGATGATGCCCCAACACCCACAGTCCCTTATCAAGTCTCTACTTCA
CATTTTTGTACTTCTGACTTAGAAATAGCACTGGCGTCTAAGAGCCTATT
AATGTCGTCAATAGGTTCTTGGGAACCACAATTTTAAACAAAATGACATA
TAAGAAAACGAATAACATTGAACAAAATGACATTATTCGAGGACCTGCTG
CATGTTGTTTCACTTAAAGTCAGTGTCCAAGAACCTATCAGTGACATTTA
GTGAGGACTTGCTGTCCTTCCTGTTTACAGGAACCTGGGCAAGTTACTTA
ATTCCTCTAAGCCTGGTTTATATCCCTGCAAAGAGAGAAGGATAATAATC
ACCAGTACTTAGTGATGTCGTAAGGAGAAAATAAAATAATAAATATGAAA
TGGCTGACAGTGTCCTTGTCACACAGAAGATGTGTGATCCACAGTAGCTG
CTATTGTCTGCCTCACTTCACTAGTAATGGTCCAGGGAGGCCTTTAATGT
GCATGGTGCAGTACATTCACATGTTGGACATGGGTGAAGGGAAAGACCAG
GCTCATCTAAACACAATAGGATGCTTGTGGTGTTTTGAGGAGGAATCAAG
GACTAGTTATCCACAGCTGTAACATGCATGGATCAAAAGAGATAAGGCAC
ACAAAAGACTTTGTCAGTAGCAAAGCATTACAAAATGCAGAGACCAGCTG
TGGGTGGTGGTGAGTCAGACCCAGCTTCCCTCTGTGCCTGGCTGAGTGGT
TCTGGGCAAGTCACGCCATCTGTCTTGATGCCCTTCCCCATCTATAGAGA
GGGAGCAACTGAGGCCCCTTCCAATACTGAAGTCCTTTATTTCTGCTACT
TTAGAAATATCCACATTTTTGGTAAATTCAAATGATCCAATGATTCCATT
TCCTAATGTTCAAAACTAGCCCCAGAAACATCTAAATGAATCAAACAAAT
AAAATATTTATTGTGTATGTTTTGATTGCTGAAACTTCTATTTTAGCAAC
ACACACACACACACACACAGAACCCATAAGCCTTCATCTTTCCTTGGATAAA
CGAGCCTTCCTGTCTGGCCATTTAAGTCACGATTAAGTAAATGATTTCCA
ACTCGCCTTTTGCAGCAGTTCAGATGGGTCTTTCCTGCGTGGCAGTGGCC
CTCCTGACTTATGATTTCCTGTGTGTCGGCCTGTTACCACTGCAGCTTAA
CTGAGGAAACAAGAACAAAACAGCTTCTGACCCCAAGAGACTGTTGGAGG
CAAAGGCTTCAGTCCCAAGAACCTCACACGTGGGGAGCCCGAGAGCCCAG
CCCTGACCTTTTCTCCAGTAATAACATAAGAAACAACAGGCACTGGCCTT
ATTTTGGATACAAAGAGTGGTGCTTTTCCTTAAATCTTCCTTTAGTCAGG
GCTACCCCTTCATGGACGCCCCAACATCCATGGTTCCTGCTTGAGTCCCT
GCTTCCATATTCCTGCACTTCTCACTTGAAATATCCCTGGAGTACGTTAA
GCAGCCAGGTTTGGAAGTTCTTGCTGTGCAGGCGGGTGTGTGCATGTCCT
CTCTCTCAACAGGACACAAGCTCCCCAAATCAGACGGTATGCCTCCACGC
CCCTTCCCAAGCCTCCCCAGCAGCACCGAGCATGTGAGGGGAGCTGGGGC
CCAGGCCATGATGGGAAGCACTCTCTGCCTAAAGACTAGGGTGATGCGCC
CTCAACTGTGGGAATGAGCCCCAGCTCTGGTGTCTGCCTCGGTTTTTCCT
CCTGGACAATCAACATGAACTCCTCACCCCTCTTATCCACTTTGCATAAA
CTGAAAATAACAAACCCAGGGCTCTTTCTGTCACAGGAAAGGGTTTTTTT
TTATAAAATTAAACAGAGATGATTCAACACACCCAGGATATAACACATGG
GCCATGAATCAAGGGCAGCATTGCTCTGGTCAGCCTGTTGTTTGGGCCCC

FIG. 4C'

CTTGGCAGGGCTCTCCCCTGAATCTTCCCCTCTTGACTCCCATCANCACA
GCACTCCANCTTTGTGTTACAGGCGATAAATGGGAAAGGGGTAAAT
>Contig48
CATTCTTAATTAGAGAAACGCTCATTAAACTAGACACCCAAATTCTCTGG
GGGGGGATCATTCTTACAAGCATGCCCTTCTCTCTTAAAGAGAGAGCACT
TTTTTCGCAAATAATGCTGCCATGAACATACGGGGTGCATGTATCTTCGT
AATAGAATGATTTCTATTTTGGGGGGTATGTACCCAGCAATAGGATTGCT
GGGTCAAATGGTATTTCTGGTTCTAGATCTTCGAGATCTTCCACACCGTC
TTCCACAATGGTTGAACTAATTCACATTCCTACCAACAGTGTGAAAGCAT
TCCTATTTCTCTGCAACCTCGCCAGCACCTGTTATTCTTGACTTTTTAA
TAATCGTCATTCTGACTAGCATGAGAGACAGTATCTCGTTGAGGATTTGA
TGTGCATTTTGCTAATGATCAGTGATGTTGAGCTTTTTTTCATATGTTTT
TTGGCTGCAAGAATGTCTTCTTTTGAGAAGTGTCTGTTCATGTCCTTTGC
CCACTTTTTAATGGGGGTTTGTTTTTTCTTGTAAATTTGTTTAAGCTCCT
TATAGACTCACAATAACAAAGACATGGGATCAACCTAAATGTCCATCAAT
GATATAACGGATAAAGAAAATGTGGTACATATATACCATGGAATAGTATG
CAGCCATAAAAAAGAATGGGATCATATCCTTTGAAAGGACATGGATGAGC
TGGAAACCATGATCCTCAGCAAACTATGCAAGAACAGAAAACAATTGTTG
CATGCTCTCACTTATAAGTGGGAGCTGAACACTGAGAACACAGGGACACA
GAGAGGGGAACAACACACATTTGGGGCCTGTCAGGGGTGAGGTGGGGGAG
GGAGAGCATTAGGAAAAATAGCTAATGCATGCTGGGCTTAATACCTAGGT
GATGGGTTGACAGGTGCAGCAAATCACTGTGGCACACATTTACCTATGTA
ACAAACCTGCACATCCTGCACACGTACCCCAGGACTTCAAAATAAAGAGA
GACAATACTTCTCCCTTAAGTGTCTACTGTTGCTTTGCAATAAAAACTTC
CTGCCTTTCACTTCACTCTGACTTGTCCCTGAATTCTTTCTCGTGATGGT
GTCAAGAACGTGGACACTGGCTGGGGCTGGAGACTCACCAGCATCCGGAG
ACCCTCCTGAGCCCTCCAGCAATACAACTTTGACACAAACTATGAAATCA
CAGATCCAAGAAGCTCAAAGAACCCAAGCACAGGAAACATGATGAAACTA
CATGAAGGAACATCAGAATTGAATTGTTCAAAATCAGTGATAAAGAGTAA
ATCTTAAAAGCAACCAGAACAAAATATCCATCATATACGCAGAAATAAAG
ATAAGTATGACAGCAGATTTACAAATAGAAAAAAAAACAAGTGCAGCAAC
AGAAACAAACTATCAATCCATAATTCTATACCTAGTGAAAATTTCTTTCA
AAACAAAGGTGAAATAAAAAAATTATTTTCAGGAATACAAAAGCGAAAAA
ATTAATCACTAGCATTCATCACTGCAAGAAATGTTAAAGGAAGTCCTTTA
GGCAGAAAGAAAATGATACAAGGTGAATATTTGGATCCCTGCAAGGAACT
AAAAAGATCCAGAACTGATAACTTAATGGGTAAACATGTAATTTTCATCA
ACAAGTGAATGAATAAACAAATCATGATATATCCATATGATAGACTACTA
CTTAGAATACAAAAGAAGAACTACTTATGCATGTGATAACATGAATGATA
TTCAAAATTATTATTGAGTGAAAGACACCAGATCAAAACAAAGTACATAC
TGTATGATTCTGTTTATATAAAACTCTATAAATTGCATGCTCTTCTATAG
TGACAGAAAGAAGATCAGTGGCTGCCTGCAGACAGGAAGAGATTACAAAC
GGAAATGAGAATTCCTTAAGAGATGATGGACATGCTCATTACCCATCATA
TGTATACAGCCATAATGGTTTTACAGATACATATATATGTACACGCCAAC
ATAAATATAAGTTATCAAATTACAGTAAGTTCTGACTTAATGTCACTAGG
TTCCTGGAAACTTTGACTTTAAGCAAAATGATGTACAGTGAAACCAATTT
TACCATAGGCTAATTGATATAAAGATGAGTTAGGTTTTTGGTTTTTTTTT
TTTTGACATGAAGTCTCGCTCTATCGCCCAGGCAGGAGAAGAAGAGTTAG
GTTTTACAGCATGTTTCTGGTCACAAGAACATCATCAAACTTGTAAATAA
AGGCACAAAACACTTCTAATATTAAATATCAAAATAAATATGAGTTATAC
AGAATTTAAGAAAGATTAATAAAAACAAGTAAAATCATTATTTATGGGAT
TTTTGGTAATCAGTGAGTTATGTGGTCATAGTGGAAGTGGGTTAAGTCAA
GAAATAAATGTTTGCAAAACAAAAATTTTAAAGATCCTCTCCTACCACCA
CACAAAAAACAAGAAAACACGGTGGGCTCGCTAAGCACTTTTGTACCACT
CGTATCTTATGCGTTTGTATGATTATTGTAAATGCTTTATGATAATTTTT
AGAGACAGGGTCTCACTCTGTGTCTCAGGCTGGAGTGAAGTGGTGCAATC
ATAGCTCACTGCAGTCTCAACCTCCCGGATTCAAGAGATCCTCCCACCTC
AGCCTCCAGTGTAGCTAGGACTACAGTTGTGTGCCACCATGCCCATCTAT
CTTCTTTTTTATTTTTTGTAGAGACAGGGGTTGTGCTTTGTTGCCCAGGC
TAGTCTTCAACTCCTGGGCTCAAGCAATCCTCCTGCCTCAGCCTCCCAAA
ATGCTGGGATTTCGGACATGAGCCAGCAGCACCTTGCCCAGCATTTTATT

FIG. 4D'

TCATAATAATTATAAGTCATTCCTTCATTCATCTTACAACCCACTTGTTC
CAGTTCAGGATCTCGGGTGACCAGAACCTATTAACGTTCACGCACAAGTC
AGAAACCAGCCCTGGACAGGACACCATCCTACCGCAGGGAGAACTTACAC
ACCCACACTCACTCAGACTGGGACCATGCAAAGAACCTAACGTGCACTTT
GGAATGTGTGTTCCATACCCACTAGAACAGCTAAAATTTAAAAGACTGAC
CATACTTGAGTGTTGAACAGGATGTGACACAACTAAATCTTTTAAGCGCT
TCTGCGTAAATGGCACAGCCGCTTTGGAAAACAGTTGGCAGTTTTTCAAG
TTAAATATACCCAAACTCTATGATCCACTTCTCAACAATCAAACAAGAGA
AATAAAAGCAATGTCTACACAAAGATGTATACACAAATGTTCATTGCAGC
CTTAATTATACTAGCCCCAAGTTGAAACAAGCCAAATGTCCATTACCAGA
TGACTGGAACATACAAATTGTGGTATATTGATACAATGAAATACTACTTA
GTAATAAAAAAGAAAGAGCTATTAACATAAGCAACAACATGGATGAATCT
GAAAACAATTATGCTAAGTGAAAACAGCCACACAAAAGTTACATACTGTA
TGATCACATCTACATAAAATTACAGAAAAGGCAAACTAATCTATAGACAG
AAAAGCAGATGAGTGGTTACCTAGGGATGGGGCAGAAGGGACGAAAGGAT
GGATTGCAAAATAGCACAAAAATATTGGAGGGATGACAAATATATTCATT
ATCTTGATTGTGGGGATAGTTTAATGGGTATATATAGAGATCAAAGCTCA
TCTAATTATACACTTTAAATATATGTATTTCATTGTGCATCAGTTATTCA
TCAACAAGACTATAAAATAATATATGCCTACATACATTTTTAAATATTCA
AAATCTCACAGTTATATACATAAATGCAACTGAATATGTATTCAGATGTT
TTAACAAGCAGAAAGGACTGATTAAACTCATGACAGCGGCTGTTTCTGGG
AAGGGTGTAGGAGACAAGAGATGGAAAAGAGGATGAGAGCCAGAAGAGAC
CCTTGTAATGTTTCCTTTCTTTTAGTAAAAATATATTGACAGTTAAAGCT
GAGAGGTGAGAATAATAGTCTCATGGCTTTTGTGTCCTTAAAATTTCACA
AACTAAGTGAAATGGGAGAAAGCAAAAAAATAAACTTAAATAAATGTTAT
ATTGCCCAAAAAGAGATTTAAAATGGAGGTTAGACACATGAGACTTACGT
TCTCAAAAAAGTAGAATCTGCAGGGAAGTTTAACAACTATAAAGAATTAA
AATCTAGCTTCTACCAGCCCAAAGCCTAAAATGTTCTGCTTTATTCTTCC
TTATTATAATTCATAGGTAATATATTTTATGTTTGCAAATGAATGCAGTG
ATATTAGATCTCTAAGAGGTGCTAAAAATGAAAAGTACATATTCCAATTT
TTCCCAATTTTCCTTCTCTTTCCATGAATGAAAAATATACATATTTGATG
ATTTCCAAGTTTATACAACCGATCTTTCTCTTAGTTTTCTCTTACCAAAT
TCCCTCCCTCACTCAGCCACCAGCCAGTCCAACTGTGCTACCTGCACAGC
AGCCCTCATACCATCCACACTCTCATCAGGATCCTGCCTGACCTGCGAGG
AGCAGCAGCAAGAAGGAGACAGAACCTCCACGCTGAGCATCTCAGGGCTT
TCTCAGAGACTCCAGAGGACCCTGATAGGGACAGAGCCTGGCCAGCAATC
CATGCTGCCAGCTGTATGATTGTGGGCATGTAAATTCTCAACTGAAAATG
GGTGTAATAATAACATGTTCTTCCCAGAATGAGCTTTATGAAGATCATAT
AGCTGTTTGGAACTCAGACAAGCACTGGTAGGAATACAAACAGGGGAGCC
AACAGCCTATAAATAATACTTTAAGAAAGGGCATGAATGTAATTACTTAG
GAACAAAAGGCAAAGTGGAGAGATGCCTAGGACTGAGCTGGACAAGCTGC
ACCCTTTAGTGGCTCAGCCCATGGGCTGACAAGGAAAATGGAGGAGCTAC
CAAAGAAGGTGGAAGGATTCTGGGAGAGTGGCCCTCACCCTGCCCAGGGC
AGGGCTCAGTGGGAGAGAGGGAGATCTGTTATAAATGCTGCCAGGAGGTC
GAGTCATGTGAGAATGTCCATGTGAAAACATCCACTGTGTGTATCTAAAG
AGAGTGGCTGTAAAACAGGTCAGGGTCAAAGGTCTTATTGTCTCAGATGT
TATCTGCATGCATTGTCTCACGACCAAGAAAACTAAGGAGCATGGACACA
AAGGGTTAGGTTGAAGCAAAAATTTAATAAGTGAAAGAAGAAGGCTCTCT
GCAGTGGAGAGGGGAGTCTGAGTGGGTTGCCACTTTGACAGCTGAATCCA
AAAGCTTTTATAAGAAACTCTTCTCATATCTGCAGCTGTTTGAGTAACTT
CTCTTACCTATAAAACTGTCTGTATAACTCTCCCTTATCTATGCAGCTGT
GGGATGTCTCCAGGTAAGCATAAAGTGTAGCTTCTCTTGTTTGTATAACT
GTGGGTTTGTTTTAGGCAAGCCCCCATCCCCTCCCTGTGTAAGCTCCCAT
GGAGCCCACCATGTGCATATCTGAGAAGTGGAGGAAGCTTTCTCTGGGAG
CTCACTGATCGTACAAAGAACAAGAGGCTTCTGTGCCGCTTATCTATTCA
GGTGCAGCCTGAGTTTTCCCCAGGCTGCTCTATTTTTGCCTGTAGCTATG
ATTTTTCAGGCAGGCTGCTTCTCTGAAGACTAGCCTTAACTGTCTACCTA
TCAGATTTTTCCTTTTCTTCTCCCTCAGCTGGTTCCCCTCACCAAGGCTG
AGCAAGTGAAAAGGAGGGCACAGGGCAGGCCAGTAGTGAGCAGCAACAAG
GAACTAAGACAGCAGAAACCACTCTTCACACCTGGGTTGAAAGGGGTGGG

FIG. 4E'

GAGCCAGGACTACAGCTCAGGTAAGAACATAGGTAAAGAGATACTGTTGT
TGTGTTGTTTTTAACTATGAGAAGCATTGAGCTTTAAATTTCTACAGGAA
GGATCCAGTTCAGACAGGAGCACCCAATATTCAGAAGAGAAGAACATGGT
GTAAAGGTCCTGGGAAGGCTGAGAGGATTGGGACTCAGAATCCAGAGCAG
AAGCCGTCTGTGAACAGAAGAAGGACCTCCCCCAGTGTAGCAAGAGGGAG
GGAGGAGGGACAGATGCCAAGATGGTTCAGGAAGAAGGTTTGGTGGTAAA
TGTGAGGCTGTGCTCACCTGCTGGCTTCAATTTTCTCTTTAAAATGTCAG
ATGGAATCATTTGATGAAGGCCATGCCATGCAATGAAATGGCAGTCTGAG
GCATGGAGCAGCTCCAGCTTAGCCCGTGTTTAGGGTAATTATGGCTCCAA
CCCAGGAGATGAATATGACTAGGGAAAGTGAAGTCCAAAAACAAATGGTC
TCAAGTTGACTGTGAGTCTTCTGGGAGGCTGAGACGACAGGTGGGGTTGA
CAAGGGAAGGGGAACCCACCTGCTGAAAAACATCAGGCTGTTGGCTGGGG
GAGGGGTGAGGCCTGTGTTGTAGAGATGGATGGATGCCTAAAGTTGGGTA
AAGGTTTCAACTCTACCCTCTGCTGGGTGTGGAAATAAACAAAGACCACC
CAAATGAGAACAAACAAAGACTATTTATCCAGAGCTTGCTCTGACAAGGG
AGTCGGCAACCATCACTTGCTTGGCAGAGACTCAGAAGTAAGCAGGGGAG
AAAGCCTCATAGCAGAAAGAAGGGAAGTCTTCATGTATGCCCTGAGTGGC
AGCTGTAGATGTGGGTGAGTTGCAGGTGGCTAACTAGAAATGGGGGACTC
CTGTGTGATTGATTAGGAGCATGTTTGGCTTTCTCTGGTTGGTCCTACAT
TGGAAGAGGGAACAAAAAATTTAGGGCAGTTGTCAGTTATTAATCAAGTG
TTGGCCATTTTTGACTGACTGTTACAGGAGTGACTGGCTCCCTGGATTGT
TTGCTAGAAATAGTGGTCTTCACTTCCTGCAAGTCTGACTTTCTGGTAAT
AGGCTTCCTGGGTTGGCTATTGTGGATAATAAGTGGGTTTCCTGAGCTGA
TTTCTGCAGATTGTGGATCAGAGTTATTTTATATAAACAGTCTGACCATT
TTCCACTGGCATATTCCATCTTCCAAGAGCTGGCCAAGCTGCTGTCTTAT
CTGTCTCCCCCAGCCCCTCCACTCTGGCTGTGAAAATACAAGCCACTAGG
TGAGGAATGGGGACAATTGAAGACTGAAAGCTTTTCTTTGCTGGGTTCGC
AGAGCTGAGGAAAGAAATGACAACATCCAAGTGTCTGCCCTGGGCCAGTT
TTAGGACTGTAGTGGTAATGCAAGGACTGTGTGAGTTTATATTTTCATTT
GTCTCTCTAACTAAGGTGGAAAAAAAAAAACAGAAAATTGTCTGTCTGCA
GTCTCTGCAAAAGTCTAACACTGTGCTTCCCAACATTGCAGCCATTAGCC
ACAGGTGAGTATCAAGCACTTTAAATGAGACTGGTCCAAACTGAGATGTG
CTCTGAGAATAAAACACACAGCAGATTTCAAAGACCTAGTACATGCCCTG
ATTTCAAGCTATATTACAAAGCTGTGGTAATCAAAACAGTATGGCATTGG
GAAAAAAATAGACACATTGGTCAATGTGACAGAATAGAGAGCCCAGAAAT
AAACCCGTGCATGTATAGTCAACTAATCTTTGACAAGAGTACCAAGAATA
CACAATGGGGAAAGTCTCTTCAATAAGTGGTGTTGGGAAAACTAGATATC
CACATGCAAAAGAAAGAAATTAGACCCTTGTATTACACAAAATCTAAAAT
TAATTCAAAATAGAAAAAGACTTACATGTAAGATCTAAAACCATAAAACT
CCTAGAAGAAAACATAGGGAAAGAGCTCCTTGACACTGGCATTAGCAGTA
ATTTTTCAGATATAACATCAAAAGTACAGGCAATGAAAGCAAAAACAAGT
GAGAGTATATCAAACTAAAAAGTTTCTGCACAGCATAAACAATCAACAGA
GTAAAGACATGACGTATGGAATGAGAGAAAATATTGACATCTGACAAAGG
GTTAATATCCAAAATATATAAGTAATTCACACAACTCAGTAACAAAAGCC
AAATAACCTGACTTTTTTTAAAATGGGCAAAGTACCTGAATAGGTATTC
CTCAAAAGAAGACATACAAATGGCCAAGAGATGTATGAAAAGCTGCTTAA
CATAACTAATCATCAGAGAAATACACAAATCAAAACAAGATATCATCTCA
CACCTGTTAGAATGGCTATTATTAAAAAATGAGATAAGTGTTGGCCAGGT
GTGGAGGAAAGGAAACCCTTGTACATTATTCATAGGAATGTAAATTAGTA
CAGCCATTATGGAGAACAGTATGGAGATTCCCTAACAAAATTAAAAATAG
AATTACCATATGACCCAGCAATTCCACTTCAAGGAATACATTCAAATACT
ATCAGTATCTCAATAAGATACTTGCACTCCTATGTTCGTTGCAGCGTTAT
TCACCATAGCCAAGATACAGAAACAAGTTAAATGTCCATCAACAGATAAA
TGGATAAAGAAAATCAGGTACATATATATATACAATGGAATATTATTCAG
CAAAATCCTGACATCTGAGATAACCTGGATAAACCTGGAGGACATTATGC
TAAGTAAAATCAAAGCCTGACACAGAAAGACAAATACCACATAATCTCAC
TTACATATGAAATATGAAAATGTTAATTTTATGGAAACAGAGTAGAATGG
TAGTTGCCAGAGCCTGAGAGTAGAGAAAATGAGATGCTTGTCAAATCAAA
TCATCACATTGAATATATATAATCTATTTGTCAATTAAATATTTTAAGAA
TAAAAAATACCTGGCACCAAAAAAAGAATGCAAAATGTCTCAACAATGTT

FIG. 4F'

ATATGTATTGCATTTTGAAGTGATAATAATTTGAATATTAGGTTAAATAA
AATATATTTGAAAAATTAACTTCACCTATTTCTTTCCATTTTTGTTAACA
TAGGTACAAAAAAAAATTAAAATTACCTATGTGGCTCATGTAGGTGGCTC
ACATTATACTTTGATGACACTATACAGGCTGGTGACCATATATCTCTTAG
ACTAGTCTAAGTGATTTAACAGTGGTTCCAGAAAGATCCAGGTTTAACAC
CAATGAAAGGGCCAGCTGGCTTAGCCCAGCTTGTGTGGGAAATGTTGGGG
AGTGGTTTAAGACAGGGAAAAGCAAAACTTTTGATGCTATTGACTTTTTG
AAAAATCTTTTGTGGCTGAAAAAACCAAAACATTATT
>Contig49
GCTCGAGTGTGTCTCTAAAGCCTTTCCCCCATTGGCTCCACTATACGCAC
TCTCCTGGTTTCCTCCCCTCTAGCCGCTGTCTTTGGTCTCCTTTCTGATT
TTGCTGCGTCCTCTGTCCCCTGAATGATTGCTTCTCCACTACGGGGTGAT
TTTGCTCCCCAGGGGACATTTGGCAATATCTGGAGAGGTCTATGGTTGTG
TTTGAGGGTGTTGCTACTGCCATCTAGTGGGGAGAGGCTAAAGATGCTGT
TAATGCCCAGGACAGTCCCCATAACACAGAATTATTCAGCTCAAAATATC
CATGGTGCCAAGATCAAGAAACCCTGCTCAAATATTAGCATGTGCTGAAG
GCCCTTCTCTTTCCTTTAGCAATATCTGCCTCCTTAGGGATCTTTTCTAG
TCTCAGTGGTTTAACATTTAAAATCCCAAATTAGGCAATAAATTGGGCCC
CAAACTTCGTTAGTATAAAATGTAGAACTGTGTTATTAGAAGGCTAATAA
AATGACCTGGTGAGCATCTGCAGCTAGCCTCTGAGCAATTCTGGGGACCA
CGTGCAAGATAAATCCATCTGTTCCCTCTCTGTAATGTGGCGCTACCTTG
TGGCCGATTTTTCCTCGGGTTAAATATCTCTGGGGATGCAACTTGTCGTG
GTTAATGGCTGTGTGAGGCCAGCGCGTGGTGATAAAGGAATCAATCAAGA
CAATATTGAATTTAGAAAGGCAGATTTATTTAGAGAAAAGGAGAGATACG
TTGCAAGGGAGCAATGGGCAATACAGCAGAGGGAAGGCTGTCTGCAAAGA
GGCAAGGGCTACGTATGACGTAGGGCTGCTTAGGCTGAATGCTTGCAGAC
AAGATGCTTGCGTGCAGGTGGGCTGTGAGCTGAGTGCTTGGGTGCTAGTG
AGCCATTGGCAGCTGACCCTATTTCTTGGAACATTCGCTCCCTGCAAGCA
TTTTAATGTTAAACCGCCAGGTCAGTTTGAATTTTCTTTTTTCTTTTTTT
TTTTTTTTTTTTGCCTTTAGTAGGACCTGCCGTTGTGAGACTATCTGAGG
TAAATTAGACACCCTCCTGGTTTAAGTCACCGCTCCAGTGACTAGGCAGG
GAGCTCTTCCTTGAAGAGGGTGTGGGCAGTGGGTACTTTGCATGTTGTCC
ACACCAGGCGAGCTGCTGCTTCAGGGCCTTTGCATTTGCTCTTTTCTTTG
CCCAAAATGCACTTCTCTCACTGTTCACATGATTTTTCTCCCTCTTTTCC
TTTTAGTCTTTGCTTAAATATCACCTTCTAGGGAGGCCTTCCCACACCAC
CTCTTCAAGATTTGAGGGTATGCACCCCCACCCCTAGCCTTCTTATCCCT
CTCCACTGCTTTCTTCTCAAAGCACTTGTTACGTTCAAATAAAATAGATT
AGTTACTTTATAGTTCTAATTTTACTATTTTTTGTTTACTTCATCAATAC
CCATGTAATCTCTGGAAGGAACGTTTCTTTTTGTAGTGTATTTCTAGCAC
CTAGAACAGTACTTGGCACATGGCAGGTGTTCAAAAGTATTTGTTGATTA
TTTTCTCAAAGGGCATGGAGTCTTAGAAGTTTGAGAACACAGTTCTAAGC
ACAGCTGTTTAGAGACTATGGATGATGCTAATGGCTGTATTCCCAGTAGG
TGGGGCAATTCTCAAATTGACCTGGAATCCTTGAGATCTGGGGACAGTCA
CCAAGCACTGGGCTCTGTGGGGAGAGATGTGCTGGTTTTTAGAGAGGAGA
ATAGCATCCTGGGGGACTTGGCCCCAGGGCTTTCCTGTCCCAATCTCTTC
CCAACTGAGTCCCAGAGGCAGGAGGCCTTGTCTGTAGCTGGTCAGTCCTG
TAACTGTTTCCCTCCCATCTACACAGATGCAAAGAAGGCTGAGAAAAGCA
AGCTGTCAGGTGAGCAGGGGCCCTGACTCCTCCCCAGAAGGCACTCAGAA
CTTCCATAGGGCAACTGGAAAGAAGGTTCTACTTCCTCACCGGCAGCTGT
TGCTGGGGAAAAAACCAGCCTCAGGCCCTACCCTGTGCTGAGAACCTGAA
TCCAGTATCAGGTTCTCCAACAAACTTGGATCCAGCTGACCCTCACAAGG
GGTCAGATGCAACCTTGTAGCATATGGAAAATGGCAGCAAGGTCCTTGTG
TGGACTATGCCTAGAATCTAAATTAAGACAAGGCCTCAGAGGGGCTAAGT
GACATCTGTCTCCAAAGTTTCACAGCTAGTGTGTGACTAAATCTTGATTC
CACCCTCTCAGGTTTTACCATAATCCCAAAAAAGGTTGAAACAAGAAAAG
TTATCTTTGGGCAATTACCTCTTTCTGTTCCTTGCTTTACCTACTAATGT
TCTAGGCTCACCCTCTGGTCTGCAATCTCACTGAACTGACAGATCCCTCA
TGGCCTAAAGGGTTTTCACACTGGGTTGACTAGGCTCTCCCATTGCCTGT
CCTACTGTCTAAGGCACCTCCTGGGTAGGGTGCCCAGCGTCATTCTGATG
CTGCCTGACTTTCCTTCCAGCTACTTTTGAAACTTGGTATCCATGGCAGA

FIG. 4G'

GGCTTAAAGGGCATGTTCCAGGTACTTTTATTTCCAAATTCCCCAGTGGC
ATCAAGGAAATCAGCATCTCTGGATAGCTCTACTAAGGCTTAGTTCTCAT
TGTCCAATCTAGCTCCTGGGTCATGGGAGGCATTCAGGAAATATTTGAGT
GTAAGAGTGAGTTGCTTTACCTCCAGAATATCCTTCCAATGGCTCTGAAG
CAGGCTGTGGAGTCCTGCTGGCTGATCACAGTTCACAGGTGGCTCCCAAA
CCTGTGGTCTACATCCATCCTTTGTCAGTGTCACTGCCATTGTCCCACAA
ATGTCATTTGGGCCTAGCCCCTGGGATAGTAATCAGTCTTTACATAGATA
TACATTGTGCTTTACATCCACAGTAATTCTGAGTGGACCTTAAAATAAAT
TCCATGTCAGGTCTCACCAGCCCATGGGTTACAGATGGGGTTACCTTTCA
GCCTTGTAAGGTGCCCCGTCTTTGAGTGTAGACATGGACTCACAACGAGT
CCACTCCTGCTGTTCCTCTGCTCTTGCTGAGGCTTCTGCTGCTGCTGCTG
CTGCTTTGCAGAGGCTGGCCAGCTGTGGTGCCTGAGGCACCTGTGTCTTC
ACAGCACCAACTTGCATGGTGGCCACGGTGTAGTTGGAAAGGGATGCTTA
GATGGGAGGCCAATGGGAGCTGCTTCAGGAGGCAAATCCAAGTCACAGAG
ATCGAGTCACCGAGAGCATAGTAAACTCAAAATCCCTTCTTCTGCTTAAT
AACTGAGATGCTGTCACTGGGTTAACCTCACCAAGCCTTGTTTTGTCTTC
ACTTAGAGTGATTTCTGTCTTAGAAGGCTCCTCATATCCTTCTGGGGAAG
GCTTCTAGTGAGTCCACAGATAGCTGGACCAGGCATGTCCAGAAATAATC
TGATTCTCACATTTGAGTTAGCCAGCGTTCCCAGCTATATCCCCATTTTG
TGTCTATATAAGTTACCAAAGCCCACAAGGATATTAGGTGGCTCCTTAGT
TTGCTTTATGATTATGCCTTGTGTGTGTGTGTGTGTGAGTGTGTACGCCT
ATGAGGATTCCTTCTCTCCCGTTCTTGCTATGGCTTCTCTTCCCCACTGA
TGGGCTGTAGTTCCCTGTCCTTTTGACTTTGGGCTTAGTCATGTGACTTT
TTTGCCAAGGGAATGTGGGCAGAAGTAACTGGGAGCCAGTCCCAAGCTAA
GGCCTTGGGAAGCATGGTGAGCCTATGCCAGCTCCCTCAGAACTCCTTCC
CTTGGCCATGAAGAGAGAATAACCTGGATTGTACCTTCAGCCCATGTCCT
AGAATACAAACATGGAGAATAATGAACTTGACTCAAAGGCTGAAGGGCAG
CTGAGCCCACATGAGGTCAATTGAACTGCAGCTACCTACAGACCTGAAAG
TGAAATAAACATGTATAAGTCTCTGACGTTTGGGGTTTGTTTACATAGCA
TTATTGTAGCAGAAACTTAAATAATACTGGGGGCTAAATATAGTGGACCA
GTGACAGCACAGAATGGTAAAATGGAGTGATTGTTACTTACATCACAACC
CTTCATCTCTGTTGATGGACACTAAAATCAAAGTGGCAATTACTCAGAGT
TGGGAGTCATTGAGTTGCATCATTGTTGTTTAGAATCATTGACAGTTTGA
GCTCTAAGTGATTACAGAGATGGTTTCCTCAGCTACAGGTAAATAAACAA
AGGCACAGAGAAGTAAAGTGACTTCTAGAGGGCTTCATTGATATTTAGCA
GCAGAATCAGAGCTAAACAATGAGTCTCTCATCTCCAGCCTTTCTATTCT
TGTTTCCTAGGTTGGGATTTTGGGAAATAGTGCAGAGAGATTAGCAGTAG
TGACATGGAACAATGTGAGCCTCAGCTTCCATCCCTGAGGCTGCCTTCAT
CTGCCAGGGAAATGTCTCTGTGTGCAGCCTTGCCCTCTGCACACAGTGTG
TATGGCCACCTGAATAAGTGTCCTTTCATAGCGACTAATGGATTGAAATG
GGTGCTAGAGCAGTGCTTCTAAAAACTCCATGTATTAATCATCTAGGGGT
CTTACCAAAAACGCATGCAGATTCTGATTCAGTAGGTCTGGAGTGGGGCT
TGACATTCTGCACTTGTAACACATGGACCACACTTTGAGTAGCAATGTAT
TAGATCATTCCAGTGGAAACATGTATGAGTGATGGAATGAACAGATATAA
TTAATCCAGGTCTGGTAAGTGAGGTACTGATACATATTAAGTTGAAGTGA
ATTTCACATCAAAAATAATGGTTACACAGTGACTTTTACTGCCCCCAAAT
TCTTTCCTTTTGAGTGGTTTCAAAGTGAACTGAGCCAGCCAGGTTAAGTC
CCTGGTTTAGTGTGTGATTAGAAGATTTGATCCAGCTTTCTCCTCCTTCT
AATTCTTTAAATATGCAATGGCCTTCTAGAAACTTGTCTCTCAGGCTCCC
CATGAGCCACCTGTCTTAATATCTTCCCCCCCAGGACATTTCCTGGGTCA
AGGAAGGAATCAGGGACTAGGAAAAGTAGAAAGGTTGCCTGACAGTGAGA
AACTTTTTGCACTCCTATTTGTTCAATTCTAAAATGTGGGTATTGTTGGG
GCTTCTAATTGGAATCTAACCTGAAATTCAGGCATGTCTAGCTATATATG
ACCAAGAATTAGGATGAGTTCACTAGAAGCCTATTTTCAGGAGAGCGGTC
AGTTAAATTGAAGTTTATGGGTTTATGGTAATGGGTTGGGGAGTTTACTT
CATTAGCAATAGCAACGTTTTTGAATCAGAGAAGTGATTTTGAACACACT
GTACATAGTTTTCTCACTTAGATTTATCTCTGGGTCAACCCTTGTTGGAC
CTATATTAGAATCATTTAGTGAAGAAAAGGTGGGTGTCATTAGGAAAAGA
GCCATTTATTCAAATGTTCTGTTTGACATTAGGGCACTGGCAAGACTACA
GAATCAATAGATATTTAAAAACAGCCAGGTGCGGTGGCTCACGCCTGTAA

FIG. 4H'

TCCCAGCGTGATTTGGGATTACTTTGGGAGGCTGAAGCGGGTGGATTGCC
TGAGCTCAGGAATTCAAGACCAGCCTGGTCAACACGGTGAAACCCTATCT
CTACTAAAATACAAAAAATTAGCCGGGCATGGTGGCAGGCGCCTATAATC
CCAGCTACTTGGGAGGCTGAGGCAGGAGAATCGCTTGAACCCAGGAGGCG
GATGTTGTCATGAGCTGAGATCGCGCCATTGCACTCAAGCCAGGGCAAGA
ATAACAAGACTCTGTCTCACAACAAACAAGCGAACATACGAAACAAACGT
AACATCCAAACTAGCAGGTACATGCCGTGCCAGTCATGACCCATGGTCAT
AAGATGTCTACAGCTCAGGAAGCAGCTGCACAATGCCTGCATAGACAAAC
TCTTATGAAAGCAGAATGTCCTGATGTCTCCATAACACATAACAGTGTAT
GCTTTTATTATGGTCATACTCTAGCTGTGATGTACCTACGCTCTAATATG
CCAACGATAGTTTTCTTTAAATCATCAACATAATAAATGTCATGCTGTCA
GTCCCCCACATGTAGACATAACTTAGCTGGTACATGGATAAGAAACCTAT
ATTAGATAACCTTAGGCCAGGTGTGGTGGCTCATGCCTGTAATCCCAGCA
CTTTGGGGAGGCCGAAGCGGGTGGATCACGAGGTCAGGAGATCGAGACCA
CCCTGGCTAACACAGTGAAACCCCGTCTCTACTAAAAATACAAAAAAAAA
TTAACCGGGCATGGTGGCAGGCACCTGTGGTCCCAGCTACTCAGGAAGCT
GAGGCGGGAGAATGGCGTGAACCCAGGAGGCGGAGGTTGCAGTAAGCCGA
GATCACACCACTGCACTCCAGCCTGGGGGACAGAGCGCAAGATTTCGTCT
CCCAACCCAAAAANCNANNNNAAATTTGCACCCAAATCTGACTAATTCCA
GAGCCAATTCCAATTTAGAATCGTTATATCTCCCTGGTGAACTGAAGCTT
TTATCTTTAAGGAGACACACTCTTTATGTCTACCAATGCTTATTGCCTTA
AAGTCCACTTTGTCAGATACAGCTGCTTTCTTTTAATTAGTTTTTGTGTG
GTATATCTCTTTCCATCCTTTTTCTTTCAGCCTTCTCCATTCTTACATTT
TAGATATATTTCTTTTTTCTTTTTTTTTTGAGAGAGAGTCTCACTCTCTC
GCCCAGGCTGGAGTAGTGCAATGGCGCGATCTTAGCTCACTGCAACCTCC
ACCTCCTGGGTTCAAGCAATTCTCCTGCCTCAGCCTCCCAAGTAGCTGGG
ATTACAGGAGCCCACCACCAAGCCCAGCTAATTTGTTGTATTTTTAGAAG
AGATGAGGTTTCGCCATGTTGGCCAGGCTGGTCTCGAACTCCTGACCTCA
GGTCATCCACCCACCTCGGCTTTCCCAAAGTGTTGGTATTACAGGCGCGA
GCCACCATGCCCAGCTGATTTTAGCTGTATCTCAAAAACAGCATGGGTTC
TGTTTGCTTTCCTTATTCAGCTTTATAATGTAAATCATTTACATCAAACA
TCTAATACACCATGGACTGTAAAACACAGCCATATTTTATGTATGAATTA
AAAAAAAAAACACCACCAATTAGTTCCTGAGACACACACCTTAACAATAT
CTCTGTGATGTGCATAAATCAATCACATCAGTTTCTCTGCACCTCAAAAT
TTCTTTCCTCAATTCTCAGAGATATGGCAATTTCTCTGGTTTTACATTCC
CAGAAGCAAAGAAAAAGTACACAGCTTCTTCAAGTCATGAGTAGCTTCTT
TTTTATAGCTCTTGGTGTTTGCAAAAAAGATTGGAATTGCTTCACTAATA
CTAAATTTTCATTCTGCTGCTCTGTTTCTATGACAAGTCAGAGGGCATCT
TTTTGAAGACATTCTAAACAGCAATTAAACTCAAAACATGTAATGACAAT
GACACACAAAACTCAACTGATGACCAAATGAAGAGTTCCAGCCAAGTTGA
CACAAGCTGGCTGACAGAGCTTGTAATACACACAGCTTGGCATATGCCTC
GCCATTTCAGAGATGTAAAAATAGGAATAAATGTTTTCCCTTAAATCAAT
GAAATAGAGCATTTGGACTGAAAATCTACGACAGTTATAGTGTTTTCTAT
TCATTATTCTCATTCTGTTCTTCTCCCCCTTGCTTTCTTTTAGTTTGAA
TATTTTCTATCATTTCATTTTTCTTCCTACTAGTTTGAAACTTATGCATT
TATTTTCTATTTTTTAGCACTTACCTAAAATTACTCTGTAATCCATGGAT
CCTTAATTTATTTAAAAAACTAATGTTAATGAGTAGCTTTATTTTCCTCC
CATCTAATTTAAGGCCCACAGAACACCTTCACTTACCTCAATCCTCTCCC
AACTTACATGCTTTTAATGTCATATATGTTAATACCGTATACTTTTAAAA
CTTTCTAAAATAGCATTATTTTATAGCATGAGTGTTCATTTACATTTTTG
CATATATTTAGAATTTTCTTTGCTCTTCGTTTCTTCTTCTATTTATGACT
CCCCTCTGGGATCATTTTCCTTCTACTTGAAGTACATAGTTTAGAACTGC
ACTATTCAATACAGTAGCCACTAGCCATGTGTAGCTATTGAAGTTTAAAC
TAAGTAAAATTGAGTAATATTAAAAACTCAGTTCCTTCATCTCACTAGCC
ACATTTCAAGTGCTCAGCAGCCACATGTGACTAATGACTACTGTACAGCA
AACATATAGAACATTTCCATCATGGCAAAGAGCTCTATTGATAGTGTTCA
TCCAGAGTTTCTGTTCCAGGACCAAACTGAGGGTTGGGCTGCTATTTCTC
ATGGCCCAATAACAAGATGCAGATGAGCTGGGGAGGAAGAGAGTTTTTAT
TTCTGCAACCAGTTACAGGGAGAAGGCCTGGAAATCATCACCAGGCCAAC
TCAAAATTATGACGTTTTCCAGAGCTTATATACCTTCTAAGCTATATGTC

FIG. 4I'

TACGTGTAAGTGTGCATTCACCTGAAGACGTAAGTGATTAACTTCTTTTA
ATCTGTAACTAAGGTCTGAGTCCGGAAGATCTTCCCCTGGAGCCTCAGTA
AATTTACTTAATCTAAATGGGTCCAGGTGCTGGGGTAATTACCCTTATCT
TGTCCCCTGCTAAATCATGGAGGTTTGGGGAATTCCCTTTAGAGCACCAT
TAACCTGTTTGTTGAAGGCCTGGGAATTTCCTCCAAACCCCCATTAAACC
TGTTTAATCCCAAATTGGTTCCGTTAAAAATTCCCTCCTTAATTTGTCCA
ATTTTAAAGGCCCAAAAAAGGCTGGGGCAAACTCCTGAATGGCCTTTGTT
ACATTCCAACCTTTGTTTAAAAACACCGGTTTTTAATATTTAACTTAACC
ATTTAATCTCTACTGAAACACTTGTTATATAAATCTGCATTAATGAGAAC
TGGCCTGCGCCATATCTCCTTCTCAGAATATCTTAGGGTTGTGATCCCCT
GTGTGAAGAGAATATATCTCTGGAGATCTCAATCTCTCTACCCCAAAAAA
AATCTCACTCGGAGAAAACTCAGACTCTTATCTCCACAGCGCTATCTCTC
TCCTCTCC
>Contig50
GCTTGTCTAAGATGGTGCTCCTTGTTGCTGTGCCTGCTTTCATCCTGGGA
TCTCCCTTCACCATCAGGATTGCCTTCACCTCATTCCAGTCTTGGATCTT
TCTTCTTGTTTCTTGAGTATTTTTTTTTTTTTTTTGCTGCATTCCCTTCA
GTGGCCTCTTGGGAAAAGATGTGTAGGGAGAAAAATTTTCTTTAGAAACT
TGCATATCTGACAATATATTTATCCTATCCTGACATTTGGTAGATAGTTC
AGCTGGGTACAGAATTCTAATTAATTTTCCTTCCTGATTTATAAGACATT
GCTCCATTTTCTTCTGGCTTCCAATATTGCTGCTGAGAAGTCTGACACCA
TTCAAATGCCTGATTTTTTCCATGTGATTGTTGTTTTCTGTCTGGAGTGT
TGTAGGATTGCCTCTTTATCTACAGTGTTCTGAAATTTCATGACGTAGGT
CTTTCTTCATTCATTATGGTAGACACTCAGTGGGCCATTTAATCGGGAAA
AACATGTGTTCTTCAAGTTCTACAAACTTTATTACTTCCTTTTTCTTGTG
TCTTTCTCTGGTCTGTTTTCAGCCCCGAGTCTCTTAGATCTGTCCTCTAA
TATTCCTATTGACTTTACTTCATTTTCTAAGTCTTTATCCTTTTGCTTTA
CTTTCCGAGAGACCTGCTTAACCTTATCTCCCAACTCTTTTATTGAATTT
CATTTCTTTTACTATATATTTTTTACTTTGAATACACCTCTCTCTTCCTC
ACATTTTCCCCCATAGTATTTTGTCTTCAATTGACAGTTCTACTATCTTA
TTACTCTGGAGATATTAATAATAGTTTTTAAATTTTTATTTATTTTTATT
TTCAAAACAGTGTCTTACTCTGTCACTCAGGCTGGAGTGCAGTGGTGTGA
TCATGGATCACTGCAGCCTTGATCTCTGAGCTCAAGCTATCCTCCTGCTT
CAGCCTCCCAAGTAGCTGGAACCACAGGCATGTGTCACCATACCCAGCTA
ATTTTTTTGTTTTTGAGGTGGAGTCTCACTCTGTAGCCCGGTCTGGAGTG
CAGTGGTGCAATCTGGGCTCACAGCAACCTCTGCCTCCTGGGTCCTGGTT
CAAGCAATTCTCCTGCCTCAGCCTCCTGAGTAGCTGGGATTACAGAAACA
CACTACCATGCCCAGCTAATTTTTGTATTTTTGTAGAGACAGGTTTCACC
ATGTTGGGCAGCCTGGGTCTGAACTCCTGACTTGTGATCTGCCCACTTGG
GCTCCCCAAAGTGTTGGGATTACAGGCGTGAGCCACTGCACCCGGCCACT
AATTTTTAAATTGTTAATAAAGACGAGGTCTTGCTATGTTGCCCAGTATG
GTCTTGAACTCGTGGGCTTAAGTAATCTTCTGCCTCAGCCTCCCAAAGTG
TTGGGATTACAGGTGTGAGCCACTGAATCTGACATTTTTAAAAGTTTTC
TTCTCTTTACCAAGTCTTTTTTCCCCTTTCTGCTTTTTTGGGTTGTTTTA
TTTTGATCTCTATCTTGCTAGAAACTTTCTGCAGACGTTTAGTAATACTA
GATTTTTGAGAGTGGGCAACTGGAAAGCTGATTGGAAACTCTGAATACAT
GGGTGAGGCTTGTTGGCTGTGAGTGTCATTGCTTGATGTCCTGGCAAGGC
CAATGGGTTTGGGACCCCTACTATTAGTATAGGCCTGATTCCCTGGGAAA
GGCTCTTTTGATCTCCTGCCTGGAGGATAAAGGCCTGGCTACCAGCCTTC
TGTGTGTAATGTGAGGGAGAAGGGCTGGAGTATTCAACATCATGCTGAAT
CCTTTCAATGATCATCTTGTTTTTAGTAATCTCCTACCTTAACTCTCTGT
CTTCTGCTAGTATGGGAAAGATGACCTGAAAATCTAACCATTTATTTTTC
CCCCATTAATATCATTTTATGATTATTCAGAAGTTAAATAATTGTCATGC
TGTCCTCCAAAAAGACTGAATCAACTAGCAACAAATAAGAATTTTCTCAC
AGCTCTGCCAGCATTTTAAAAGAATAGCTTTATTGAGCCCAGGAGGTCAA
GGCTGCAGTGAGCTGTGATTACACCACTCTACCCCAGCCTGGGTGACAGA
GCAAAACCCTGTCTCAAAAAAGAAATTTAAGGAACAGCTTTATTGTTGTA
AAATAGACATACAATAAACAGAGCACATATTTAAATTGTGCAACTTATAC
TTTGATATAACCCTGTGAAAACATCACCACAATCAAGATAGTGAATATAT
TTATCACCTCCTGATACAGTTTAGCTCTGTGTCCCCACCTAAGTCTCATG

FIG. 4J'

TTGAATTGTAATCCCCAATGCTGGGGGAGGGGCTTTGTGGGAGGTGATTG
AATTGTGGGGGTGCACTTCCCCCTTGCTGTTCTTGAGATAGTGAATGAGC
TCTCATGAGCTCCCCTTCACTCACTCTCTTTCCTGCTGCCATGTGAGGAT
GTGCTTGCCTCTTCTTTGCCCTTCTGCCATGATGTGTTTCCTGAGTCCTC
CCTAACCATGCCTCCTGTACAGCTTGCAGAACTGTGAGTCAGTTAAATCT
CTTTTCTTCATAAATTACCCAGTCTCAGGTGGCTCTTTATAGCAGTGTGA
AAAGGAACTAATATACCTCCTAAGTTACCTCAAGCTTCTTCTTAATTCCT
TCTCCTCCCTTCCTTCATTGCCAAGCAAACAACCACCTGTTTTCTGTCAC
TATAGATTAGTTTACATTTTGTGGGTTTTTTTTTTTTTGAGACAAGGTC
TCACTCTGTTGCCCAGGATGGAGTGCAGTGGTGCGATCATAGCTCATTGC
AGCCTTGAACTCCTAGTTTCAAGTGGTCCTCCCACTTCAGCCTCCTGAGT
ACCTGGGACTACAGGGGTACACCACCACAACTGGCTTAAAAAATTTTTTA
AATAAAAATGGGGTCTTGTTATGTTTCTCAGGCTGGTCTCGAACTCCTCG
CCTCAAGCAGCCCTCCCTCCTTGGCCTCCCAAATTGTTGGGATTACAGGC
ATGAGTCATGACTCCTGGCCTAGTTTACATTTTCTAGAGTTTTGTATAAA
TGGAAACATACAGAATGTATTTTTTTGCGGAGTGGGGGAGTGTTTCTATT
TCTTTCTTTCTTTTTTCTTTTTTTTTTTTTTTTTTTTTGAGACGGAGTCTCG
CTCTGTCTGTTGCCCAGGCTGGAGTGCAGTGGTGCGATCTCGGCTCACCG
CAAGCTCCACCTCCCGGGTTCAAGCAATTCTCCTGCCTCAGCCTCCTGAG
TAGCTGGGACTACAGGCGCCCGCCACCACACCTGGCTAATTTTTTTTGTA
TTTTTGGTAGAGACGGGGTTTCACCATGTTAGCCAGGATGGTCTCGATCT
CCTGACCTCGTGATCTGCCCGCTTCGGCCTCCCTAAGTGCTGGGATTACA
GGCGTGAGCCACCGTGCCCGGCCCAAGTGTTTCTATTTCTTAACCAGCTT
TCATGCAATCTTTTTTTATTTTACCATCTCTGTGATCCCACTCCCAAAGG
TACTAGATGTCGATTGGTCCTTAGGATCAGCTACCATTTGCCCAACTGCT
TTCCAGCCTTCCAAAAATTTTTTTCTTTTTTTCTTAAAGATACTCCTGTG
TGAGGCTCAGAACTCTTGAATTGCTACTGCAAATATGAACTCGGTGATGT
GAATGCCAGGGAATTGCCTGATTGATCAAAGAAATGTATCCCCTTCTCCC
TCACTCTTGCTGTCTTCTCATTTGTTTTCCCCATCCTTGTGGATTCGTGA
ATTTAAATATCCCTTTAATGTTATAATATTTTAATGGCGTTTGGCGAAAA
GTACAGAATTAGGTGCAAGAGTGCATAGCTGTTATTTTTTTTTTGGCCTC
TGAGACTGTTCATATATGCAAGTTATTTAACAGAAAGTTCTGCAGTGACC
TGAGATGTCAGGGGGGTCTGATAGAGTACGTTTGAAGGCAGTTACTGGAA
AAAAATAATGCCATTTCTGGTTTGTACTTCGGTAAGTTCAGATGACCCAA
TATATTGTTTACATGTGGCATTCAGTAAAAAAGTAGCTTCCCCTCCCTTT
CTTCTTCCTTTTCTCCTTTCCTGCTTCTATAAAGCATCTGCTTTGGGAAA
CTTCTTAGGAGGAGAGCTTGCCAGCCCGTGGGTAATGGAGAGGTCTTGCA
GAGATAAAAGAGATGCTCCCACTCAATGCAGGATGGTGTGGAGGTAAATG
GGGATACGTCTGGCATCACTCAGGAATGGGCCTTCCTGGCAGGGAAGAGA
AGGGAGGGGAAAGAGGAAGGGAGTCAAAGATGAATTGCTGAATACGGGGA
TTCCAGGGCCTGGAGCCAGGAAGAGAACTTTGGGAGGTGTGAACCTGGAG
GGCATCAGCTGATGAGGAGCAGCCTGAAGTCCGGGGAGGACCTGTTTTTG
GTGGCCAGGAAGAAAGTGCCTTCCACACACAGGGAGGCCACAAGGCTGAT
GGGCTGGGGGTTGGAAGGACAGCCCTAGGACAGGCTTGGGAAGCAGGCTC
AGGTAGGGACTGCGAGGTTCTTGTTGAGTCTTTTTCATTCCTGGTCTTAG
AAAATAGAATCCAAGGCCTCTTGAGAGTGGAAGGTGGGTTGGGAGGAGGG
CAGATGGGGCTTAGGCCCAGGACACCCGTAGAGCTACTGCCCAGCTGTCT
CTCAGGGACTCTGCTGAGGTCACTCCAAGGATCATTCTTAGCCTTGCTAG
ACAGTACTGACAGAGGGAACCGTAGTATCGCACCCACTTCCTTCTCTTTC
AATGAAAGTTTAAAGGTCACCATTTCCTCTGGCAAAGGAAGTTCCACAAA
TATTCCATTTCCGGTCTTAGAAACAGCAAGGTATCAAGCAATTGCAAACT
TCCTGTGCTGGGGAATTCCCAAGGAAGTAGGGGCAGAGTTCTGGTGGAGA
CAAAGTGAATTCCGAGTGATTAGTCAGTAGCAGTAGCAGTAGCAGTAGCA
GTAGCAGTAGCAGTAGCAGTAGCAGTAGCAGTAGCAGTAGCAGTAGCAGC
AGCAGAACCAGAATTTCCCCGCACGTGTCTCAGGCTCTCATTTGCCAACT
CAGTCTCTAAGTATTTTTATTGGCAGGAAAAATAAAATAGCTATGAGTGA
AATAATTCATTAGACCTGAGCCTCCATCAATTTTGTGTTTAAAGGCCTGA
CTCTCTTTACCTTTCCCTGGGATGGAAGATGCAAATGTTCCTGATGTCAC
TGTCAAAAAAGAAGAACCAGTGGGTATATTGTATGCTTGAGTTCCAGCCA
TTTGTCACAATAGATAGAGATGACTGCCATGTGTGTAGACTTTCTATAGA

FIG. 4K'

CTGTGTGCTAAACCCGACCTGCCACTTCCAAGGAGTAGATGAGGAATGTC
CATGGTTCTGGGGAGCCCTACCCCAATTTGGGGCAGACATTCCAAAGCTC
ATTTTCTGTGGAGGGGGTTGATGGTTAAAGGACGGCCTGGGAGTAACTCG
TCTGTACTAGGGCCCAGGAGAGTTACATGCTGCTTCCCATGTTATTCATC
ATTCCCCCATGTGAATAGCTATGGCGTGAGGTCCAAGGTTAGGGCCTTTC
TACCATAAATGGGGGAATAAAATTCCCCTACCAGCCTGAGAAGTTTCTGT
TATAAAGAGGCTTTTTTTTTGCGGGGGTGGGGGAGCAAGCCGACTAATGT
GTTATTTCCATACGGTTTGTTTTAAAATGTAGATGTCATATGCAGGAGAG
GTGGTGTAGTGAGTCACAACGGGATTAGAAGGACCAGTCCGAAAAGCAGA
AGAGGGTCAAGTTCAGGGCACTGAGGACTACTGCATTCAGTGGCGTGAAA
GGCAGATGGCTGAACAGGAGGGGGACATTACATTGCTTGTTCTCCTTGAG
CCTCGATTTCCTCATCTAAAAAGAGGGTCATTTATTCACAGAACATTTAT
TAAACTTGTGCCAGGCACCGTGCCAGGAGCTGGACTAAAAATTAAATCCA
CCCCTGTGAGCTGCTCTGAAGGCTAAAATATGAAGTATGTAAAAGTAACC
AAGTGCTGTACACATGCAGCTATTCAATGACTGTGTGGGCATTGCGGCAG
ATTTTAATTTTCTTTTTTATTTCTTTCTCTTTAGTGAGAGGTGTTGGTTG
TTATTATTGTCGTCGCTGTAACTGTCTATTTCACTTGCTTTTTTGTTGCC
TCCAGCCCATTCCAGGGCTGTCATCTAAGACACTTCTTATCACCTAAATA
ACCGGGGAGGCAAAGCGCTTTCTTAAGAGATGGATCCAGAAGAACAATGC
TGGTTTTCTGTAGAAAAAGGGGCTGTGGGAAGTAGAGATAAGAAGGGAAT
TGGCCAAGATGAATGTACAGAGCCTTATTTTTTTTTTATAACACAGCAAG
ATTAGATACAAAACAGGACAATAGCATCATCTGTTTTTATAACTGGAAAG
GACCTCACTTTACAGGTGGGGAAGAATAGAGTGGAGAAGTGAAGAGAATG
GTCACAGAGTCAATCAGCATGTCTGCGTCAAAGCTGGGATTCCCAATTCA
GGGCTCTTACTACAGTGACGTATGGCTAATATTTTGGCATTGTTTCGGGG
AAAAGCTGAAGCCCTGATGGTGTACGTCACTCTTGAGATAGTCTGTAGTC
CAGCAGGGAGGAAAGCAAGGAAGGGAGGTGGAGGCAGCATTTTTGGGTGT
AACATTTCGTTCTTGTTTTGTGGCCAAATCATAGTGTGATTGGGACAAGC
CACTGCCTTTCTCTGAGCCTCCACTTTCTTTTTCTTCTTAAGAGGGAGGG
AATAGTAGAGTAAAAGTAGTCATTTTATCAAACACCTGCTATTTTGGAGC
CATATTGCAAGTGGGTTGGGGGTTGAACACTTGGCTTTATTACCCATAGG
ATTAAATCCAACCTCGATACTGTGGCATTCCCAAACTCCAGTCTAATCTT
CTTCTCCATCAGCCATGCCCCACGACACCCTGGTCATATCTGATGTTGCC
CCTTGCACTTGCCCCCTCCTTATCTTTGCTTTCTGACCTACCATATGGCT
ATTGGTTGAAATTCTCATTTTCCAGGGCCTTGCTTAAATATCATCTCATC
CATTAAAACTTTCTTGAACCTCCCCTTGCCCTGTTCCTCCCTAATGTCTC
AAGCCAGAATTTATTTCCTTTTGTGGCCAAGGGACTGGGTTTGTGACCTC
TCTCACGAGACTTAATATTGAGACCAAACGTCTTTAGACCTCACCAGCCA
GAGAGATGAGCATCTATGGAATGCAGGCTTTTGCCTGGACTTGCTGATGC
AGGGCCTCTGCCTTCCTCCAGGGCCTCTCCTGCTGTTTTAGGAATTTCCC
TCATGGCACAGTCCATGAGCTCAGGGTCAAGTTCATACATGTTTTTACTT
CTTCTACTCTGCAAATGGTCTTCTTGAACTCTGAGGGTCCTAAAGCTGCT
CTGCAGTTTGTGGGGTGAGTAGAAAGGGGCTTTCAAAAGTTGTGCTGTTG
TTTCCCACCCCAATAGCATGAAACACAAAGATGCTTACAAATAGCTGCCT
TGCTTTCTAGTCCCAACTTCTCTCTCCTGAGGCTTTAAAACAAGTCCCCT
AGGTTGAGCTGGACTGGAGTTGTATCCTATCTTCATTATCTGTCTACTCT
CTTTCTGCTCTCTAGAGAAGATATTATATATGTGTGTATGTATGTGTAAA
TATATAATATCCATATATAGAACATATATTGTTATATTTACATATACATA
CATAACATATGCATGTATTCATATATACATATGTAGTATCAAAGTTGGAA
TTAAACTGTATATTTTGTAATTTGCTTTTATTTGCATCTATCACTGTAAA
ATGAATATTTATCCATACCGTAAGATATTCTTCAATGTATTTTTTTTTTT
TTTGAAACAGGGTCTTGCTTTGTTGCCCAGGCTGGAGTGCAATGACCCGA
TCTTGGGTCACTGCAGCCTTGACCTCCCCGGCTCAAGTGATCTTCCCACC
TTAGCCCTCTGAGTAGCTGGGACTAAAGGTGTGTGCCTCCACACCCAGCT
TTTTAATTTTTTTTGTATTTTTTTTTTAAAGACAGGGTTTTGCCACATTG
CCCAAGCTGGTCTTGAGCTCCTGGGTCCAAGCAATCCTCCCACTTTGGCC
TCCCAAAGTGCTAAGATTACAAGCATGAGCCACCACACCTGGCCTCAATG
TAATTTTTAATGGCTGTATAGTATTCCATCATGTGGTTGTACCCAAAATT
ATTTAACCAGTCCCCAGTTTATTTCAATTTTTTTTTACTATTTTGAATAA
TGTTTTAGTAAATACCCACAAAATATGTACAATGGCTGGGCTTAGTGGCT

FIG. 4L'

CACCCCTGTAATCCCAACACTTTGGGAGTCTGAGGCAGGTGGGTCACCTG
AGGTCAGGAGTTCGAGACCATCTTGGTTAACATGGTGAAACCCCGTCTCT
ACCAAAAATACAAAAATTAGCCGGGTGTGGTGGCACACACCTGTAATCGC
AGCTACTTGGGAGGCTGAAGTAGGAAAATCACTTGAACCTAGGAGGCGGA
GGTTGCAGTGAGCCGAGATCACACTACTGTACTCCAGCATGGCAACAGT
GAGACTCCATCTCAAAAAAAAAAAAAAAAAAAAAAAAAGTACAATTTGTTG
TACCTCCCTGATTATTTCTTTTAAGTAGAATTTTCTTATAATTTTTTTTA
TAAGTAAAATTTTGAATCAAGGGAGAAGCACCTGGAGTCCTTCAGATACC
TATTGCCAAACTGAACTTTTCTGTTCCAGGTTTACTACATTCAGCCTGAC
TCAGGGTTTGGGGAGTAGAGGAGGGGGTGGAGGCAGAGGGCCTCTCCCTG
TCCCCACAGACCTCCCTTGGTGAGGTCCAAGTCTGGACAGGTGGAGTGTG
GCATTGCACCGTCAGGTCCTGCTTCCTGTAATTCCCCTAAATCCATCCAG
TGGAGCCTCATTGTTCAAGTCTTTTTTTTTTTTTTTTTTTTTAACTCCC
CTGAAGACGGAGTCTCACTCTGTCGCCCAGGCTGGAGTGCAGTGGCACGA
TCTTGACTCATTTCAACCTCTGCCTCCCAGGTTCAAGTAATTCTCCTGCC
TCAGCCTCCTGAGTAGCTGGCACTACAGGCGTGTACCATCACGCCCGGCT
AATTTTTTTTTGTATTTTTAGTAGAGACGGGGTTTCACCATGTTGGCCAG
GCTGGTCTCGAACTCCTAACCTTGTGATCTACCCGCCTCTGCCTCCCAAA
GTGCTGGGCTTACAGGTGTGAGCCACCAGGCCTGGCCTCAAGTCTATTTT
TTAACTCCAGGAGGCCTGGTATTCAGAGGGATTAGGGCTGGCAGAAGGGC
CTCAAAGCTTTCAAGGCCTGGGGAATAGGCTGCAGCCTGGTTCAGGGTAA
CCCAAGTGATTTTGGTTCCAAAGGGACAGGAAAAAAAGTGATTGATATGG
AAGTTGTCAAAGTGCAACTGTCAAGACATTAAAAAATGTAACCCTTTTAC
TAATATACAGTAGACTTGTGTTAAATATTTAACTGATTGTAAAAGGAAAA
AACCAGACGCAGTTTTCCCTACCATACTGTCACAACACCTCAACACTGAG
TTCTTCTGTGACCTCTAGTCACCGAAATGCTTGGGGATTTCTCCCACCAC
TAGTCCTCCAGCAGCCGACACCAGTTGGGTGTCCTAATTCACTCCAACAC
TATCTACCTGGAGTTAGCGTTAGATCCCACAGGTTGAGGGCTCAGTCTCA
CAAGACTGCCTCCCACTTCAGGTGCCAGTTACAAGTGGTAGGTTGTCACC
TATGCTTCTGACTGATGGCTATAAATCTGGGTTTGCTTCCCTCGGGTTCC
GTGAATTTGCTAGAGCAGCTCACAGAACTCAGGAAAACACTTAAGTTTAC
CAGTTTATTCTAAAAGATATTACAAAGGATACAGATGAACACCAGATGAA
GAGATGCGCAGAGCAAAGCATGTGAGAAGGGGTGTGGAGCTTCCATGCCC
CTCTGGGGCACCACCCTCCAGGAACCTTCATGTGTCCAGCTATCTGGGAG
CCCTTCCAAACCCTGTCCTTTTTGGGTTTTTAAGAGTGGCTTTATTACAT
ACACATGATTGACCGAACCATTGGCCATTGGTGACTGACACAACCTTCAG
CCCCTCCACTCCCTCCAGTGGTTGGGGAGTGGGGCTAACAGTCTCAAGTC
TCCAATCCTGCCTTGGTCTTTCCTGTGACAAACCCCATCATGAAGCTACT
GCATTGGGGCTGCCAGCCAGCAGTCATCTATTAGCATGCAAAAGACACTC
TTATTATTCCAGAGATTCCAAGGGTTTTTAAAAGCTGTATGTCAGGAAAC
AGGAGATGAAGAACAAATATATATTTCACAACATCACACTCGTTGGGGGA
ATTGACAGGATAGCAAAACTGATTAAAGGAGGATAGGAGAGACTGAGATA
TATATTTCCATATATATATATAGAGAGAGAGAGAGATATTTCCATATATA
TATATAGATCTAGAGAGAGAGAGAGATAGAGAGAGAAGAGTCTTTCC
>Contig51
ACACATTTGGGGGAGCAGTTCCGGAGGTACAGCCCGGACAGGAGATGTGA
GAAGATCGTGGTTANTGTTCCCCTGGTCCAGAACCCCTCCAAGTGGGCTT
AAGTAGGAAGGGTGGTGAGCGGCAGGTAAACACACGTCAAAGGCAGTCTT
CCTCTCTGAGGGAAAACACTTGTATAAGCATTGCAATCAATGGGCCTCTT
TAATTATGTGCCAGTGGCAAGAGCGGGTGCTGAACCCAGGGGCCTGCCTC
AATCCGGGGCCTTTGAGGCAGAATAAAGTGGTCTCAGGTTGTTGGCATTT
CCTTGCCCTTCCACCCGAAGCAGACACAAATCCTCTCTGGAGGCAAGTTC
CCCAATTCAGCCAGTACAACTCCCACAGACTAAGATCAATCATGTACAAG
CTCACAGACAAAGGTCACCAAACACACAGAGCAATAAACAAATTCATGAG
TGACGTGAATGAGAATAAACAGAAACAATAACCACCAGCTGGGATGCTCT
AAGTCTTCAGCTGTTAGAATTCCTGAATATAGAATAAAACTGCCACAATG
GCAAACATGCATCTAGTACTTACTGTGTGCTGGGTTCTAAGAATTTTGCA
CATTGTGCCAGATACCGACTCAGCTTCACACTCACCCTCCTACTGTGCCC
TCTTAATTTGCACTAGATTAAAAGGTAGAAAGGAAGAGGCAGCTATTCTG
TTCTTGGCTGTGCCTCTGGCAGCACATGCAAAATGGGCAGTAACAGTGGC

FIG. 4M'

AGTCACAGGTAAGTAGCCTTCTCACAGTGTGGAGTTAAAGGCATGGGACT
GAGACGAGCAAGGTTCCTAAAGGGACAGTGGCCAGTAAATGACCAGGGGC
TACTGGAGTGGCTGCATGGCTCTGTGGAAGCTCAGAGGAGCCTTGGGTCC
TGCAGGTGCAGTAGCAGCTTTCTGTAGTTCCTGATCTCTGGGTCCCACAA
TCTTCCCCGTTTTTGCTCCTCCACTTCTAATTTGTAACTGACTTCCCTG
TGTGTACTTCTCTCTCTGATTGAAATAGCCAGACTGGTTTCTGTTTCCTG
ATAAGACATTGTCTGGTACGAACACAGTAACTCATTTAATCCGATATCTC
TATGAAGGAGGTACAATAATTATTCCTATTTTACAGATGAGGAAACACAG
CAGAAAAATAAAGTCAATTGTCTAAGGTTGCACATTTAGTCAAGGGAAGG
GTTGATATAACATATAATTATTTAGAAAACATCTAAGGAAATAAAAGGCA
TAATTTAAAAATAAAACTAGGCAGGTTTAAAAAAATGAAGTAATCTATAA
GTAAAAAAGTATAATTGTTGAAATACATATCTTAGTGGATGGGTTAAATA
GCTGAAGAAATGATTAATGAACTGGAAGGTAGTTCTGAGGAAATCAGAAT
TCAGCATAGATAGAAAAAAATGGGAATTTACAAAAGTACACAGGAATTATA
AAAGAGGTTAAATTATAGGGAGGGTAGAATGAGAATTAACATTGGTCTAA
CTGGAATTTTGGAAGAAGAGAATAGAGAGAATGAACAAGGCAATATTTAA
AGAGGTGGCTGAGAATTTTTCAGAACCAACACAAACTATGACTTTACCAG
TAGAGAAAACAATGTACACTGAGGAGGATAAATAAATATACTATGAACAA
ATTGTAATAATAATACTCAACAAAGACAAAGAGAAGATCTTAAAATCAGC
AAAAAAAGAAAGTCAGACTTAGAAAGAAATGACAATGGCAGACTACTCAA
CAACAACAATGGAAACCAAATTCAGTGAAACAGTATTTTCAAAATGCATA
TTTAATCTATCTTTGAAGAATAAGGGTGAAAAGGGTGAAAATTGCTGCCT
TATACAAAATATCAACATTAACAAAAAGTAATGAAGGTAATATAAAAATG
TTTTCAAATAAACAAAACTGAGAGAGTTTACCACCAACAAGCATTCATTA
AATGGACTTTTAAATGCAGTTTTTAGGAAGAAGGAAAACAATTCCTAAGG
AAGGTCTGAGATGCAAAAAGGAATTATGAACAAAGAAATTGTTAAAATTA
TAGGTGAATTAAAAAAACTGCCTGCATAAATGATAATAATGACAATGATG
CTATTAATAATGAGTTGATAAGGATAAAGAAAAGGACAGAATTAAAATAC
TAGAAAACAAGCATGCTGGAAAGGATTCAGGAATTACTTGAAGGTTAAAG
TTCTAGGGTCCTTCTATCCTTCTAGAGGGGAGTCAATATATTAATTTTTG
ACCGTCACTTACACAGTGAAAAACTTTAAGGATAACCATAAAAAAATAGA
AATAGAGAGTATAACTTCTGAAACAGTCAAGGGAAAAATATGGAATAAGA
AAACTGACCAAAAAACATCTCAGTCAATCAAAAAAAAAAAAAAAAAGAAA
GAAAAGGTTCGGAAGGAGAAAATCAAAGCATAGAAAAAGCGGGACAAATA
GAAGTGGAAAAGAAAAAGGTAGAAGAAACAGGTCCAGAAATATCACTGAT
GCACTAAATCACCATTAAAAGATGAAAACAAATGAACAACATCAAAAAAT
TCTAGTGACTGTAGTAGTGCTGATCAGAATAGGCTCTAAGATAAGATGCA
TTATTGTGAGTCAACTTGTGATGATGAAAGGTTTAATTCACCAGAAAGAC
ACAATTATAAACTTGTAATCAAATAGTTTTATTTTATTTACTTTATTTAT
TTATTTTTTTGAGACAGGATCTTGTTCTGTTGCTCAGGCTGGAGTGCAG
TGGCTTGATCTCAGCTCACTGCAGCCTCCACCTCTTGAGGCTCAAGCTTT
CTTCCTGCCTTAGCCTCATGAGTAGCTGGGTCCACAGGCACACACCACCA
AGCCCTGCTAATTTTTGTATTTTTTGTAGAGATGGGGTTTCACCATGTTA
CCAGGCTGGTCTCAAACTCCTGGGCTCAAGCGATCTGCCCCCCTCGGCTT
CCCAAAGTGTTGGGATTATAGGCGTGAGCCACGGTGCCTGGCCTCAAATA
ACTATTTAAGTGAAACAAAACTAGTATGGCACTAATGAAAAATGTATAAA
TCCATAATCGCAGAGGGATTTCAACTTACTTCTTTCGATTATGTAAAGGT
CAAACAGACAAAAGACAATGACAAAACTTAATGCAATGAACACTTTTGAT
TTAATGAACATATATTGGATATGTACCCAAGAATTAGAGAATACATACTA
GTTTTGAGTTTATGCAGAACATTTACAAAAATTTAGTGGAAGCCTAAATT
ATAAAAAGTTGCTGTCACGTAGAATAACACACAAACCCCTGAGTCCGGAA
TTCAAAGCCCTCCACACTCTCCTCTACCTTTGCATCTTTATCCTCCACCA
CACTGCAGTGCATACTCTGGGCTACTACTCACTGTTCTTGATTCAAATTC
CATGTTCTGTCAGCTCAAATCATTCTCTCTGCCTGGAATAACTACTTCAT
ACATATTCTGCTATTGAATTCTTGTCTTAGCACCCCATCTACTCCAAGAC
GATGTCCAGTTGGGGTTACTCCCTGTCCCATTTTCTTTGATTACACTTTT
TTTTTCTACTTCCATTATATTATTGATCACATCTGTGCCACAGTTTTTGA
CTTTGTGTCTGCTTTTACTCTTTTCTAGACCCTGAGAGCTCCTGAAGGGT
TGGGTCATTTCTTTTTTATTTGCTCATTCCTCATGGCACAGTGAGTGCTT
AATAAATGGCTATTGACTGAAATTAAACTGTATCTAAATGGACATATTCC

FIG. 4N'

```
ACTTCTGGGCCATTCATTCTTTCTTTCTATTGGAACCAGGAGATGGGGAA
CCATAACAAAGGTAAGGTTGTGCCATGTGAAAGAACATGGAACCTTCCCC
TGAGGGCCAAAAAAGAGCAGGGAAAGGTGCAAAGACAAAATCTTCCATTT
TTAAACAATGTAAGAATGTGGTCCACCTCATGCTCAGGTGGGACTTTATC
ATGACGTTATTTTTGGGGACTTATAGCTGCATCATTTACCCCATATACAT
TTACCTTTAGTGTAGGGAACTGAGGACAGGAATTTTGTTGATGCAGACTC
TTGCTAATGAGGCTAACACTTGGAGAATTTTTATCATGCATTCAAGAAGC
TTGTTTTACATTTCTTCATTAATACTTTAGTTGGTGGTTTAGCTTTAGTT
GTAGGCTTATCAGATATTTGGAGATATCTTCATAAACGATGGCTTTGGTT
TTAGAAGAGTTATTCTGAAGCTACTATTTCTGGCAATAATCAAACAGCAT
GGCCATTTGTTTTGTAAGGCCTTTCCTAAAATATGACGGTAAAATCTACG
TGTGGAAAAATGCTTATTCTTCTGTCCTCTATAAATGTGAATCTAGTTTG
TCTTCAAAATGAAATCAAGTGATTAAAATGTAGTTTTCTAAGAAGATAAA
TGGAGCAAAGCACTCTGTGTTTCACAGTGTTGGAAATCACTCATCCCTCA
TAAAACTGTCCCAACTGATCCTGACTCACATGAATGAATTAAAATAAGAG
TTAATAACATCAATTTACATTTTTAAAGACACTTTCCCATGTTTTAGACT
ATTGGTTGGAAAAGCTGGTAGGTGTACAATTTGTGGAGAGTTGGCTGTTT
TTGTCTGTCGTTGTTTGACGTATTTCAAAGCCATATCTAATTTTGTTGCA
GAATGGTCTGAATTCTACAAAAATGTTGAGTTGTGTAGTGTGGAGAAGTA
CGGAGCCATTTACTGAAAGGCTGGGGGGAAATGACGAGACCCTGAGATAA
GGCAGTAGTGGTGCGAACAGAGTGGAAGGGAGGTAGTTGAGATATGTTCA
GAGTAGAATCAGAATGGACATAGTGAACAACTGGATGCAGGTGGGGCTG
AGGAAGCAAAGTTGAGGATAATTCTGAGACTTCTAGGTTGATCCACTGAA
GTTACATTATTCAACACCACAAGGAAACTAGGGGAATGAGAAGGCATACT
GGTTTGCTTTGGAGTGGAAGGGCAGTGATGTAAGAGGAGTTAATGAGTTA
AAGTTTGGATATGCCTGAACTTCAATTTGATATGTGCATCTGATATACCC
TTGGGGTGACCCTCCAGGCAATGGTTGAACATGTGTATTTCTTAGTAACT
GATAGGCATCACAGACTCACATCAGTAAGGAAGCAACAGCAAACTTGATT
GGACGATATACCTGGAACTCAGTACCCTATGACTGGAGCAAGTCTCTGTC
AGTGAAATGAGGATAAGAAGAATCTTGACCTTGTGGAATATGTTGTTAGG
AATATATGTGATGAACAACATAGGATACTTCCTACAGGGCTCCACATGTA
GTAAGGGCTTTATAAATGCTTGATAAATATTATTGTTGTAATTTATTTCC
AAAGTAAGATGCCACTGGAGGAATCTTTGGAACCCAAATTAATAACAAAT
AGGACTGGATGCAATGGCTCACACCTGTAATCCCAGCACTTTGGAAGGCC
AAGGCAGGAGGATCTCTTGAGCCCAGAAATTCAAGACCAGCCTGGGTGAC
ACAGGGAGACCTTGTATCTATGAAGAATTAAAAAAAATTAACCAGATGTG
GTGGTGCACGCCTATAGTCCCTGCTGCTTGAGAGGCTGAGGTGGGAGGAT
TGCTTGAGCCCATGAGGTTGAGGCTGCAGTGAGCCATAATTGTGCCACCA
CACTCCAGACTGGGTGACAGAGTGAGACCCTATCTCAAATAAATAAATAA
ATAAATAAATAAATAAGTACAAACCAGCAAACACTAATCCTTTCTAGAGA
TTATTGAACTCTGGAGGGCAGATCTGAATGGAGCCAGCAGAGGGACCTAT
GGAGATCAGCCTGGCCCTGGACAGCACCAGGCAATGGGGTTGCTAGAGAG
GTAATGGGGTTGAACAGGGTTTAAGCCATGAGGTCTCAAGAATCCGTGAA
GACTCAGACTAATTTTTTTTTTTTTGCATGAGGATTAGGTGTTCCTAGGA
ATTTCAATGAGAGCAGGGTTAATGAAGGAATGCAGGGTAGGAGAGCTGAG
GGAAGGCATCTGAGAGAGCCTGGCTTATGAATGGCTGCGTCAGTATGGCT
CACCTGCTTTCCTTGTATCTACTTAGCAGATGATCCCACCCCAGGCCTCC
AGGGCCAAGGTCATTTCCACATAGTCATGGGCCCTTGAGGGCCTGGAGCA
GTGTAAGGAAGACAGAGTCTTAAGAAATTGCATTAACAGTCATGGTGCTT
GGCAAGTGTCGTCATCCTATGCCAAGCCTGATCTGAAGGGGTGCATGCTC
ATAGGTAGCTGCTGCCCAAGATTACAGCAGCTTCTTCAATCCCAGATCCA
TGCTCTCCTATATTCATTTTTCCAGGGGTTCCTGTCCTTCGACAGTGATG
AGATGCAGAATGACTTATTGAGTTATTCTCCTGATAGTTGCCAACTTTTC
CAAATGACAATGGGGCATGGAGCTTGAGAGTGGAAATGAGGCCCTAGGGA
TAGCGTGCTTAGGAAAACACTCCCAGCCTGATGTAATTCTGGGGGTACAA
TGGCATTTTCATCATCAAGACTGATGTAAAGGGTGACTAGCAGTGAGTTG
GGGGTGACTCGCACTGGGGCTAGGTTTCTGATTCTGCCTAATCCAGACAG
AGCAGAAGCACTAGTGGGCTGGTAGAGGGCCTCCAGGGCCTCACTTAATG
TCCTGGAAAAACAGCTCCAGATTGTTGGTTCACGTTCTGAGGACAAGCTT
GGGTACTACAGGATAGAGAGAGTGGTGGGAGATGCCGTGGCCTGCCCTGC
```

FIG. 40'

TGATGCCTGCCCTGCCATTCCTGCGTGTGATGTCTCTGGGGCATCTTGCC
TTCCCTGCCCAGACCTGTAGTTCAGCTGAGGGCATGTGGAGGCCAAATGG
CTTCTTAGAGTGTTACTTTCCTTGAACAGCTCTGCTGGGAGAACTGGAGG
AGCTAGCTAGTCACGGTAACTGCAGCAGTCAAAGGATCGTCCCGGTGGAG
GTGGGGTGGAAAGGTAGAGAAAGAGAACATATAGCGTTTTCCTTGGAGAT
GTGTGGGCATGTCATAGAGGAAATACCCAATTCCTGAGCCTTGAGCCCTC
CAGGAAACCTTGGAATATTAGGTTAGTCATCCCCAAGGAAGTCTAAGAAT
TCTGGTCTCACCCATCTCCTTTAATTCCCACAATGATCCTACATGATATT
AAGGAACACGGGCCAGTAACCCTCCAAGCAATGGATGTGGTGGTGAAGTT
TGACCTCATGATGGAGCGGAGGTTGGTTTGAAACCTAAGAATTTAATTTA
TTGTTTCAAACTGTTCTCCACTCAGCGTTATTAAAGCATACATAATTGAC
ACATAAAAATTGTATATGTCTACGGTGTACAATGTGATGTTTCGATCTAT
GTATACATTGTGAAATGATTACAACAAGCTAAATAACATACCCATTCATC
GTGTTTCAAAGGAATTAAACTCAAGCACAAAAGAGAGGTGCTGTTGAAGA
GTAGGGCTGCTCTATCTAAGTAGTATGTCTGGGGTTGTCCTGGATCAGGG
TCCTTTTGTGCTAGTAATAAACCAGCCCTTCTGGGGCTGCTCCACTTTCC
CCACATTTTCTTCTGGAGCCTCCCTAAGAATTAGGACATGGCCACTTTCT
CTGCATAGGCTTCCTACTTCAACAAGGACAGGGCTTGTGCTGCCCCATGC
CACTTGAGTGTCCCTACAGCACAGAGCTGAGTGCACACTGGCTGAGTGAG
GAAATCCCCCAGATTAATCTTGGTTCTAAGCATCATGGCTGTATTTCACA
CGTATATGAATTACAAATTACAGCATAGTCGAATAAGGATTTTTGTGCTA
CAACTGGAATCCCAGATTATGCAAATTGGATAGTATAATATTGAAATTCC
TAGGACTTTTTATTAGTTTTAAAAAATTATACAAGCTTAGAGTAAGAAAT
TAAACAGTGCAAAAGAATTCACTGTGAAAAGTAAAATGCTCTGTCTCTGC
TGAGAGACAGATATTGCAGCCCAGATACTACTGGGGTCAATAGTTTCCTT
TAAGCATGCCATTTTGATGGTTTATGGGACTTACAGCTCAAGAAGCTTGA
CACTAGGGTTGATCTCAGAAAATCATTGTTGCAGGTATTAGATATGACCG
TCTCATAAAGATACACACACAGACACAGCGATTGGAGATATTCACTGGGG
CTTATGGGCTGCTTGTCCTTTCTGCTCTGTGCCTAAGTTGGGCTCAGAGT
AGCCTGGCATCGGCTGTGGGGAGAATGCTGGCATGGGGTTAGCAGGAGCC
CACTTAACATGTCCTAAGCCACCTGGAAGAGTCCTTCAAGGAGACCAGAC
TCCAGAGGCCCTAAGGAAGGAAGGACTTTTGCCCGTTTTTAGGTATTCTA
GTCCCAGAGTTTAGGGAGGAATGGTTTGGCTTTGGGTCGTGTGCCCCTTT
ACCGAGTGGGATGGGATGTGCCCATGAGCTGTTGAGCTGGCTCTTGGAGA
AGACAGCAAAAGCGGGAATAAGAGGTCAGGAAGCTGTGTGGTTGTAGGAA
ATCCCAGCAGAGGGCCTGGGGGTCAAAAGTGGTCATGGTAGTGACGGTGG
AGGCTGAGGTGGTAGAAAATCAGAGGACAAACCCCATGGGCTGCTGGTGA
TCTGACCGAGCTCCTATGCTCTCCTGGTTCATTTTAGGCTCTGTAGCAGC
AGATGATTGGCTGGTGTGAGAGCAGTGCACCTGCCATATCAGGCAATCCA
AGACAAGTCCAAGCTACGCTGGGAGGAAACCTGAAGGCAGCAGCAGGTAG
ACTGGCTGAAGACAGACAGGCAGGCAACTTGTCAATCAGATTTGTGTTTT
TAAGGACTTTTAACTGGGGAGCCCTCCATGACAGATCAGATGAGAGAGGA
ATCTGGGTCCGCCCATGTGTCAAGCTACCAGAGGGTCCCATCGGTGCTTG
GATCTTCTTTGAAGCTGGGTCTGAGGTTTGCAGGTAGAGGGTGAGCTGGT
CAGAGGGACCTATTGCAGAGCTAACCAACACCTTCCCAGGAATGCAAGCA
CAAGCACCCCACCGCGGGCAGGCGGGCAGGCACTTCTCCTTTTGCCACCA
GGACCTCACAGAGGCTGATCTGGCTCTGTGAGGTGGGAAAATGGGTTGTA
CTTAGTACATAGAGATAAAAGGCTTAGGAGGCCCCTCCATCCTGTGACCC
TGTCCCCAGACCACAGGTGCCGGCAGGTGCTGCTATTTCAAGGCTGGGCC
TCAGTGCAAGCTTGTGGTTTCTTGCCCACCTGTGATGTCCTCCCACTAAT
GAAGGGGCTCTCCATCCTCTGTCTGCCTCTAGCAAGTGGAGGCTCTGGGC
CCTGGGCAAGACACAGGGGGAAATGCCATCTGTTATCCAAATATATTTCA
ATGTGACAGGAAAGCTGTCTTTAGAGCACAGC
>Contig52
GCATGTGCTCTACATTGATCCCAGGAGTTTGAGACAACATTGCAAGACTG
GGCAACAAGCAAGACTCTGTCTCTACAAAAAATAAAAAAAATTAGTTGGG
CATGGTGGTACATGCCTGTGGTCCCAGCTACTCCTAAGTTGAAGAGGGAG
AATTGCTTGAGGCCAGGAGTTCAAGGCTGCAGTGAGCTATGATCACACCA
CTGCACTCTANCCTGGGTGACAGAGCAAGACCCTGTCTCTAAAATAATAA
TCGTAATACATTTTTTTTAAAGTAAAACAAAAAAAGGTCACACTTTCTCA

FIG. 4P'

TACCAAAATAAATTCCAAATAAATTAAAGGCTTAAACATGAGAAAGTTAA
ACCATAAAATTACTAGAAGAAAATAAAAGCAAATATTTAGATAATCCTGG
GGATAAATTTCTTTGGAATGAATTTCCTTAAGATGAATCTCTAAAAGTGA
AATTCAGGGTTCAAAGGTCTTTTCTTTGTCCTTTTCTTTTCCCTTTCCCT
CTCCCTTTTTCTTTCTTTCTCTTTCTTTCTTTCTTTCTTTCTTTCTTTCT
TTCTTTCTTTATCTTTCTTCCTTCCTTCCTTCCTTCCTTCCTTCCTTTCC
TGCTTGCTTGCTTTCTTTCTTTCCTTCCTTCCTTCTTTCTCTCCCTTTCT
TTCTCTTTCTTTCTCTTTCTTTCTTTCTTTCTTTCTTTCTTTCTTTCTTT
CTTTCTTTCTTTCTACTTTCTTTCTTCTCTTTCCTTCCTTCCATCTTTCT
TTCTTTCTTTCTTTCTTTTCTTTCTCTCTTTCTCTCTCTCTCTCTCTCTT
TCTTTTTTTTTCTGGTGAGACAGGGTCTCATTCTGTCACTCAGACTGGAG
AACAGTCGCATGAACATGGCTCACAGCAGCCTTGACCTCCTGGGTTCAAG
CAATTCTCCTGCCTCAGTCTCTCAAGTAGCTGAGACCACAGGCACCCACC
ACCAAACCTGGCTAATTTTTGTATTTTTAGTAGAGATGGGGTTTCACCAC
ATTGGCCAGGCTGGTCTTGAACTCCTGACCTCAGGTGATCTGCCTGCCTT
GGCCTTCTGAAGTGCTGGGATTACAGGCTGGGCCTCTACGCCCGGCCGAG
ACTACCTCTCTTTTAACTGGATCTCTGAGCTCTGGGCAGAGCCCACCCTG
AATCCTGGTCTCCAAAAAGGGAAAATTATTAGGAGGCTAGACCATATGAT
GCTTTTACAGTGCACTTAAAAAAAAGTTTGTTTTTTTTTAAAAGACATT
TCTACATGTCTAAACTACAATCTTCCTTGAAAACCCAAGAGTAGCTTCTG
TTGCAATAGCTAGTCAAAAATATAATAGTCAAAAAAATCAGGTAACACAA
CACAAACGCAAGCAGTTTAAGAGCTGAAATGAACTTGTCTGTTTACACTC
TAGGGATTCCATAAGGAAAAATAGAAGTTTCTCCCTAAAAGGGAGCCTGG
CACCTTCTCCATTTTCTTTAAGGAACCCCAGGCTATTATAAACTATTTTA
GGGCTCTCATGCAGCAGACGGTGCAAGAGAAAGGAGAGACAGCAGAAGTA
AATGAAGAAAACAGAATCCAGTCAACAGAGAAGAAAAAAACTTTTGCTCA
AAAAAAGGCAAGTTCCTAGGAAAGAAAAAAAAAACATGAGGGCTATTTAA
ATACAAAGACGCATACATACACATGCACACATCTTGGATGTTAGCTTTTA
ATTAAGCTGACTTTTAACTATTGAGGTCCTTTAAAATAAATCTTTTAAAA
TCTTATTACGATATTTCAGCTAGGACAAATTGCTGCTATTTCAGCATTAC
CAAGTATCAAACCAGAAAAGGCTTGATTTAGGAACCAAACCCAGGCTGTC
GTGGTAGGAAAAAAGGCAGAACGTTAGCTATGGAACCCACAGCATGGGGC
AACAGCCATTGCTCTTTCAGTATGGCCTGGCTAGCAAAAAGGTGGCCTTG
TTATGTAAATAAAGCCCGTTTGGTGGTCAAAATGAAACATCTTTTCCTTT
TTTTTTTTCTTTTGCTGGCCGTTTTTTCCCCCACCATACCACGTTTGTGT
GTGTGGGAGGGTGGGAATTTAGCCACTTCAGAGGCCTCATTCCCCATAAT
TTGGAAATTTCCTTTGGATTTGATCAAGTCAGATAGAGTAGGTCAAACCC
AATGGGAAAAAGACTGAAACAGCAATAAAAACAGAAACAAACAGTTAAGC
AAAATGAATGATCACACAACTTATATGATTACTGAGTGCTCTAATGGTAA
GGAGAAATTAAGACCAGCTGGTTGTTAAACTTTAGCCAAGACAAAACCCC
AATTCAGCTACTTACCTAGGGTTGGGTCTCAGGCTGAAGACCGCTCACTA
CCGTTCTAGAAGCAAGAAATAAAACTTGAACTCGTCTTACCTGTGTAGCA
GGACAAGCCGCAGACAAAATCCCTCAGACACCAAATTAAAGAAGGAAGGG
CTTTATTGGGCCTGGAGCTGCGGCAAGACTCACGTCTCCAACAACCGAGC
TCCCCGAGTGTGCAATTCCTGTCCCTTTTAAGGGCTCACAACTCTAAGGC
GGTCCACATGAGAGAGTCGTGATAGATTGAGCAAGCAGGGGGTATGTGAC
TGGGGGCTGCATGCACCTGTAGTTAGAATGGAACAGAACATGACAGGGAT
CTTCACAGTGCTTTTCTTATGCAAATAACCGATTAGATCAGGGGTCGATC
TTTACCAGGCCCAGGGTGTGTCACCGGGCTGTCTGCTTGTGGATTTCATT
TCTGCCTTTTAGTTATTACTTCTTTCTTTGGAGGCAGAAATTGGGCATAA
GACAATATGAGGGGTGGTCTCCTCTCTTACCTGCGGGGAGTGAGCTCAAA
CTCCTTAAAGGAGTTACCTGCCTTCCATCATCAGGGAAGCAGGAAATCTT
GCCTTCCTTGTTGGAAGCAAGTAAAACTCAAAACAAACAAAGAAAAAAAC
AGGGAGTTGTACAGCAAAATAAACTTTTGATTTTGACCAAATTTTGGGAG
ATCAGGAATTCTCTGAAGGAGATGCTTTCAGACCTCAGCAAATTGTCCTG
TTGGTTTGAGCCATAAAGTTAGCTCATGCTGGTACCAAACACCAGTAGGA
GATTTGTCAAAGGTAAGAGGCATCTCCACTCAGAATCCCTTCGTGGTTAC
CAACATGTGAACCTTGGAAATCTGAGACAGGTCTCAGTTAATTTAGAAAG
TTTATTTTGCCACGGTTGAGGACACCCACCCATGACAGAGCATCAGGAGG
TCCTGACCACATGTGCTCAGGGTGGTCTGAGCACAGCTTGGTTTTACACA

FIG. 4Q'

TTTTAGGGAGACATGAGACATCAGTGAATATATGTAAGATGTACACTGGT
TCCCTCCAGAAAGGCAGAACAACTTGAAGCAGGGAGGGAGCTTCCAGGTC
ACAGGTAGGTGAGAGACAAACAATTGCATTCTTCTGAGTGTCTGATTAGC
CTTTCCAAAGGAGGCAATCAGATATGCATTTATCACAGTGAGCAGAGGGG
TGACTTTGAATAGAATGGGAGGCAGGTTTGCCCTAAGCAGTTCCCAGCTT
GACTTTTCCCTTTAGCTTAGTGATTTGGAGGCCCCAAGATTTATTTTCCT
TCTACATCACTGTGGGCAGCTGACTAGGAAAGCTTTGTAGGACTGGTGGG
CAGTGTGAGAGCCCAGTGGGGGGTGGTGGTCCTGTGCCAATGGTAGCAAC
CACCTGTGAGGCTGAGTAAACTCATTTCCCAACCTCCTCTAGCAGCCCCA
GTGGAGATACAGATGAAGCAGACTAGCGATACAACCCAGCCTGAAGTTTT
GTCTGGTGAGTGTAATGGAATAAAAATGGGAAGGGTGCTGAAGAGACCAG
CAAGAAAATGGTTGAAGAGATGGGGCACAGAAATTAAGCTGGATCAAAAA
GGACGGAAAAGCAGAAAGGGCCGATAGAGAGAGGGGATATCTATGGGTTC
GCGATTCTGAAAAGGACAAATCACTGGTGCTTTGAGAAGAGAGAGGGTGA
GAAAGCAGGAAGGCTGGAGGCTGTCATCCAAGAGGCGGACATCTGTGAAC
ATGATTCCAAGAGTCACCAGACCATGGGGGTGGCCAAAGGGAGTGCCTCT
TCTCACCTCCTACTCTTAATTCCTTGTACTCAAGATAATAAGTTCCCAGA
AGAGAAGTACCCATATTTAATTCATCTGTGTCTTCCTAGCAGTACTAAAA
ATATTATATGAAAGGTATCAAACCTTTGAGAATGTGTGCTGCTAAATTGT
TAAGGATGCTGGAAAACTCAAGACGTCCCTGATCCTGAGCCTGAGTATGA
GCCTGTGGTGAGCCCAATGCAGGTCTCCATTCAGACAAAGGCCTCAGGGA
ACGGATGAGACCTAGGGACAGAGATGCATGCTGGAGCAGCATTCCCCATC
CCTACTGCAGCTCAGGCCAGCTGACTGCTTTATGAGTAAACGTTACCAGG
GAACACTTTGCAGTCTTAACACACATGCCCACCTGTGACCACTGATCCCT
GTTGGGTGACCACTGACATCAGAGATTCGATGGCAGCAATGAAGACAAGG
CTATCCTCATTAGGAAGGAAAGGAAGGAGGAGGGAGGAGGGCAAACGAAT
CTTTCCTGCTTGTCAACCACGTCCATCTCTGTTAGGTGATTTCCCATGTG
TGACTTTGTTTATCTTTATAATAACTCTGAGAGGTAGGTCTTGATGTCCA
CATTTTGAACATGAGGACATCCAGCCAGGAAGTTGAGTTCTGGGGACATA
GCTGAGAGGGCAAAGCTACATATAAACCCCTCTTTGTTTTTTCTGGCTTA
TCCACTGAGTGCCCCCTGCAATCCACCAGCCCATTTGTGAAGTGCATACT
ATAGGTAAGTTGGCACAGGAGGAGTGGATGTGGGCGATTTTGTCACAGCT
CTCCAGGAACTTACACACTGGTGAGGAGGGCCAGGTATGTTCCTGACCAG
TCACAATCAAAGCAACCTCCTACTAATCAGGGAGGCTTGGTACCTGGGGA
ATGCTATGTTGAAAGGTTCTTTTCTGGGTTTTAAAATGATGGGTCTATTT
CCTTATTCTTAAGATTGCTTTTTTTCTGGCTAGAACTTAAAAGAAATTTT
CAGTAAAATTTCCCTTCCCTGGCACAAAGTGAGCTTGAAATGAATTCCCA
GGTGGCCTTGATACTTTAAAATATTGCCTCCTATAAAATCAACCTTTAGA
AGAAGGAAGTCAAAGAACATGCTAGATTTCACAAAGGTTAATTCCTTGAA
ATCCAGTTATCTACAGGACAATGTTGTCAAAGAAAAAATTATTTGGCCAG
GCACGGCGGCTCATGCCTATAATCCCAGCACTTTGGGAGGCTGAGGCAGG
TGGATCACCTGAGGTCAGGAGTTCGAGACCAGCCTGGCCAACATGGTGAA
ACCCCATCTCTACTAAAAATACAAAAAAAATTAGCCAGGTGTGGTGGTGG
GCACCTGTAATCCCAGCTACACGGGAGGCTGAGGCAGGAGAATCGCTTGA
ACCCGGGAGGAGGAAGTTGCAGTGAGCCAAGTTCAAGCCACTGCACCCCA
GCCTGGGCAACAGAGCAAGACTTTGTCTCCAAAAAAAAAAAAAATTCAAT
GATATTTTTAAATTCATGGTAAGGAAGATTTCATTCAGAACCAGCACAGA
AGATATAGGAAACACTGCAATGGGACTTTGCGGTGGGGAGAGAGATTGA
ACACAACTACATATACAGCACGGGCAAGGACATATTCATAGCCAGGAAGC
AGAGCAAAGATCAGTGGATGCGAAATTACTAAGAGGAAACATGAAAAATA
AGGGAGCTTCTGCCTAAACCCACCTAACCGGATCCTTGCTGAAGACAGGA
CAGGGTGATTGGACACCACTTTGGGGATGGTGGAGGATGGGGAATCCAGT
GAGATTTCAAGGGTGATCAGATATTGAACATAGAAGGTTCTTGCTAAAAA
AGGAGTTTACAAGAAAGTGTACAAATGTGCCTGGGAGAAGGTTCAGGAGC
CTGACTAAAATTTGGTCAAGCAGAGAATATTTGCCAAGATAATAGCTAAG
TCTTCTGACAAACAATAGATGCTAAGCCAGCAAGGGTGATGTGCTCAGAG
AAAGCACTGAGGGCTTATTTCCTTTTCCCCCAATCTCCACTCAGTCAAGT
CTAGTCCCCTTGTCAATGTAGCCATTTGTAAGAATGCAATCAGGCAGGGT
CCCATCTCCTAGTGACAGGACTGACTGAAGTTCTGCTGAAGAGAGTGGCC
TGGGGCTGACACCGAGATTTCAGAGTCCTGGGTTTCGCCGAGAGCTCAGT

FIG. 4R'

GTAGTGCCATGCCCTCTCTCCACCTGAACGCCCAGTGTGGGCAGGAACAA
CTGCAGCTAGAAGTCTGGCACTTACGCTGGGGTCTAAGACCTGCCTGATC
TGCTAACTAGTCTTGTCCCTTGGCTATAAACTGACGTTGGCACCTGGCCA
GAAAGATGAGCAAGAGATCTCTGACACACCTTTAAGTCCCTGTGGAGTAG
GATTATGTTGGGGAAGGTCATTCTCTTGACTGAGCAGCAATTTCAGAAGG
AAGTCCCATGCCGAAGTGAGAGAAGGCAGGGAATCCTGCCTAGTCAGCTA
GAGCAAAACAGTCTGCAGGACGGACCCAGGGATGTGATCCTCCCATCCA
AAGGCACTGAACTAAATGACTAAAATACTTTCCAGGGCTCACGTTCTTTG
AAGAATGGGGACTAAAACTAAGACAGGAGCCAGCAAGTGAGGACTTGGAA
GGAGATGGCTCATCTGATCAGCCTCCACTCAACAATTTTAATCATCCACA
CTGGCATGGGGACACAATATGAATAAGTTGACAGGGACCTACTCTGATTA
AGCAGTGGGCTAGTGCAGAGACCTGTCAGTCAAGAGTGGACAGGAGATGA
TTTCAGACAGTGAGAACAAAATTAACAGAGTCATGTGCTAAAGGGTGGCT
GGAACTACAGAGGAGTTTAAGACTCAAGAGGTCTGGCTGGGCGCGGTGGC
TCATGCCTGTAATCCCAGCACTTTGGGAGGCCGAGGCGGGCGGATCACAA
GGTGAGGAGATCAAGACCATCCTGGCTAACGCAGTGAAACCCCATCTCTA
CTAAAAATACAAAATATTAGCCAGGCGTGGTGGCGGGCACCTGTAGTCCC
AGCTACTCGGGAGGCTGAGGCAAGAGAATGGCGTGAACCCGGGAGGCAGA
GCTTGCAGTGAGCCAAGATTGCGCCACTGCCCTCCAGCCTGGGCGACAGA
GCGAGACTCCGTCTCAAAAAAAAAAAAAAAGACTTGAGGGAGTTGTTTATT
TTTGTTTTCTTTTTAAGACAGGGTCTTTGTTGGGCGCGGTAGCTCACGCC
TGTAGTCCCAGCACTTTGGAAGGCTGAGGTGGAAAGATCTCTTGAGCCCA
GGAGTTTGAGGCCACTCTGGGCAACATAGCAAGACACCGTCTCTACAAAA
AATGTGCAGGTTGAGGCTGCAGTGAGCAGAAAAACACCGCTGCACTCTAG
CCTGGATGACAGAGCGAGACCCTGTCTCGGAAAAAAAAAGAAAAAAGACA
GGGTCTCGCTGTGTCACACAGGCTGGAATGCAATGGTGCAATCATGGTTC
ACTACAGCCTGGAACTCCTGAGCTCAAGCAATTCTCCTACCTTGGCCTAC
CAAAGTTCTAGGACTACAGGTGTGAGCCACCACACGTGGCCTCAGGAGAG
ATCTTAATAATAAAAGGACAAATTGCCTTGCATCCCTTAGGGGCAGGATT
GACACATCCAAGGATCAGGCAGAAAGCCTGTGCGGAGTGGGATGAGCAAA
GAGAAAGGCTGAGAGTTGTGAAGAGGGAGATGCAGTGCCAGCTAGGACAG
GCCTTTTTGGGCTATGGGAGGTTTTCAGAGGAGACCCCACCTAAACTAAC
CCATAACATTGCAGTGGGGACCTGTTGAAGTCATGGACTACTACCTGAAA
GCCAGAGAAATGGGAGGAGCCTTTCCTCTGAGGAGGGACTCTAGTCCATA
GGTATCTTGCCACCAAATACATGGACAGGCCCTGGGGGAAGATGGTGGTA
GCCCAGCTGGAGGAAAACCATTTGCCACCTGAACTAGCCCAGGGTAAGCC
ACCCAGGCACTGAGGGTGCACACCCATGCATGCACACACACAGAATCACACT
CCTTCCTATTATTCCTCAATTCAGGGGTCTCAACACCCATTTTTTTTGTT
TTTGGGGTTTTTTTTACATGTTTACATTTTATTTATTTATTATTTTGTGA
CAGGGTCCCACTCTGTTGCCCAGGCTGGAGCACAGTGCAGTCGTGCAATC
ATATTAGATTGGTGCAAAAGTAATCACGGTTTTTGTCATTAAAAGTTTTG
CCATTACTTTTAATGATAAAAACCACGATTACTTTTGACGCAACTTAAAA
GCTCACTGCAGCCTCAAAATTCCTGGTCTCAGGGAATCCTCCTGCCTCAG
CTTCCTGAATAGCTGGGACTACAGGCACATGCAATCCTACCTGGCTAATT
TTTTAAAAATTTTTTTTGTAAAGATAGAAACTCATTTTGTTGTCCAGGCT
GGTTTCAAACTCTTGTCTTTGTGCCTCCCTCTGCCCTGTGCAAGACCTTC
TGGATGCCCACTAATGAAGACTTCCAGGGAGAGGAAAAGTAAACATAGGT
CCCTGATCAAGGGACCAGGGTTTATCGACCACAAACAGCATGCCCAGATT
CCACTGGCAGTCCTAGAGGTCGCATTTGCCCCAAGTGTGTGTGGAAGGCC
TCTCCCTAGCAGTTGGTTTATACACCAGCCACAGCACAGCATATTCTCTT
AAATTGTGAACATTTGCAAAAACTCCTTGAGGACAACTATCATGTCTTGT
GTACTTTTGTTTTGTTTCCCTTCCCCTATGTACACGCGCGCGCATGCACT
CATGCACGCACGCGCGCGCGCACACACACACACACACCCCTCAAACTGAA
TGCCTGGTGTGCTGAATGGATGAATGGCTAATGTAAGTCATTCTAAAAGC
TACTTTCTTTGGCATACCATCACCTTTGATTTCATCTTTCTGGAACTCCT
ATGTTCCCAGATGAATTTGGAAAGCCCTCAGGAAACATTTCAAAATTGCT
ATATGGGAGAAATGGGAGGGTCTCTCTAGAAATTTACCTGCCACAGGTAT
TTCTGGTAAGACACAGCAAAGGTGGCACCACCCATTCCTCGTTACAATGT
CAATGCCAGTCACCTTCCTGTCCCATAAAACTTTATTAAAGGTGCAGAAT
TCCCATGGAAGCAGGTGGACACCATCTGCTTCCAGCCAGCCAGGGGAGCA

FIG. 4S'

AGGTGTCCACTGTGCCTTTGTGGCAGGAACTGCGCTTCTCTACTCTCCCA
CTTTGAGGCCTCTGGGGCTGGCCTGCTGCCTCCTCATTGACAAGGCTGCT
TACTGAGCAGTTCATTCTGAGCTGGACATAGTGCTTCTGGTGAGTCTCTA
CTTCTATTTAACCCAAAGATATTCTTTCCTAAGGAAACGCTTTCCTGTCG
GGGGAGGTTAGCTCCAGATGGAAGTCACAAGTGATGGCATGGTAGCTCTC
ATCCGTTTGGGTGGATGATATTCACGGAGCACCACCATGAGCCAGTCATG
GAGGTGAACAGTATATGCCAGCCCTGAATCAGGTGCATTGACAGCAAGGG
AGACAAGCAAACAAAGCTGAGGTTTGCTGAGGATGTTCAAGACTCACACA
GCACAGAGGAGCATCCACCACCCAGCTTGGGAAAGGACTTGTTATAGAGG
GGGTGAAGCATGAGCTGAGTCTTGAAAGACTAGAAATTAGCCAAACTACA
AGGAGGAGAAGGAGTTTCCAGTCAGGAAGAACAGGTTATGCAAAAGCACA
GAGACTAGAAAGAATATCACATTCAAGGAACTGCAAATAGACAGGAAAGA
TTGATGCGTGGGATAGGAGAGGAGGGCAGGGGATTCCAGGTGGCCCCTGC
TTGCCACACTCAGGAGCTTGAACTTATCCACAAAGGAGGTGTGGAACCAG
TAATGAATGGGTTTTGTGCAAGGGCTTCATGTCACCAGATTTGCTTTTTG
GAGATACTTCTGTGGCTGATATGTGAGGAAGGGATGGAGGAAGTTTCCGT
GGCAATCAGGAAAACCAATTAGCAGATGATTCAAATGGCCTAGGGGAAAA
GGGAGGAGGACTTGGACTACCATGCAGCAGCAGAAATGGAGAGAAATAAC
AGATCCCAGGCACTCAGGAAGCGCTCAGAATGAGCCCTTCAAAGAACTTA
TGGTAGGTGATGGATGGATGGAGTGTGAGTCCTGGGATAGCATTGCCTGG
GAAAATACTTTCTAGTTGAGACAGGGAAGTGGGCCAGCAGAAATGGAGGG
CTTCTTCTTTTTGCTTTAAATACTTTTATAATATTTGGAACTTTGAAAAT
GAGCAGATATATTAGCAAAAAGCCTAAAAGGGATATTTTTGAAATCACTG
CTAGTTCTAACATATAACTTTCAGCTTGCACACATCATCAATTAACTTTG
ATAGCGCCTTTCTGAAACTATCATCCCAAATAGCAATCCTTGTAAAAACC
TATTTTGAAAAACGGGCCTTGTAGGATAGCCTCACAGATGTTTTGTGGTA
GATTTTCTAACATTCTAATGTCAGGGAGTGAAAGGAATCCCGTTAGAAGT
TGGAAAATTCTGGAATCTCTATTCATGGTATTAAAGTTTTGCCGTCACAC
AAAAGTTTAACACCTTTACACAATCAGACTTCCTCATTTTACATTGCTCG
GTAATTAGAGGAAATCAGTCACCCAGAGCCTGGGTCCTAGACTTGACAAA
ATGCACCCAACAAATCCTGAGTGGCCTTGCTGAGGACTTCTCCCAGAAGA
TAGAAAACTCAGTTCCAGCCAACAAGGGGGAAGCAGCTGAAGAAGTGAAA
TTAACAAAGTCCTGGAAGGAAATGACCAAATCATCTTTGATTGTGTAATA
ACCAGAGAGTAGAATACAGCTACGACAGACATTTTGGGAGAGAAGCATTT
TATCATAGCTTTTAGAAGAGAATATTTTTCAGCATCATAAGCACACAATT
CCAAGACAGATACTTTCAAGGGATTGTTTTGACG
>Contig53
ATGTTNNGGTTTTGGGACCCCATTCAAACTTCATGTTGAATTTTAATCTT
CAATGTTGAGCGAGGTCCTGTGGGAGGGTGATTGGATCATGGGGGTGGGT
TCTCCCTTGCTGTTCTCAATGATAGTGAGTGAGTTCTCACAAGACCTGGT
TATTTGAAAGTGTGTAGCACCTCTCCCCTTCATTCTCTCACTCGTCACTG
CTCCGCCATAGTAAGATGTGTGTGTTTCCCCTTTGCCTTCCGCCATGATT
GTAAGTTTCCTGAAGCCTCCCAGCTATGCTTCCTGTACAGCCTGTAGAAC
TGTGAATCAGTTAGACCTCTTTTCTTCATAAATTACCCAGTCTCAGGTCA
TTCTTTATAGCAGTGTGAGAGTGGATGAATATAGTGCCATATGTTTGTAT
TCCCAGCTACCCAGGAGGCTGAGGTAAGAGGATTGCTTGAGCCTGGGAGT
TTAAGGCTGCAGTGAGCCATGACTGTACCACTGCTCTCCAGCCTGGGTGA
CAGCGAGACCTTGTTTCCAAAAAAAAAAAACCCAAACTGTGTAAAATGTG
TTCATAAAAGTGTCTTGCTCCCACACCTGTCCCTATATATCTTATTCCTC
AGCCTCCGACAACTACTTTATTCATTTCTTATGTATCTTCCAGAATCAAA
AAAAAAAAATCAAATACAAGCACAGTGGAATGTATTGCCCTTCTTCCCCT
CCCTTTTGTTACATCAGAGTTAGCATATCATAAATACGGTCTGCATTTTC
TTCTTTTTCAGCTATCAGCATGTTTTGGAGAGGATTTCATATTCGTGCAG
ACAGCATGTATTAGTCAGTCCTTGCATTGCTATAAGGAAATACCTGAGAC
TGCATAATTTATAAAGAAAAGAGGTTTAATTGGCTCACAGCTTCGCAGGC
TGTTCCACAGGAAGCATGGCAGCATCTGCTTCTGGGGAGGCCTTAGGAAG
CTTTTACTCATGCAGAAGACAAAGCGGGAGTGGATGTCTTATATGGCAGG
AGCAGGACTGAGAGAGAGAGAGAGAGAGAGAGAAAGGATGCCACATACTTTT
AAACAACCAGATCTTGTGGGAACTCTGTCACGAGAACAGCACCAAAGGGA
TAGTGCTAAACCATTCATAAGAACTCCACCCCCATGATCCAATCACCCCA

FIG. 4T'

CACCAGGCCCCACCTCCAACATCGGGGATTACAATTTGACATGAGATTTG
GGCTGGGACACAGAACCAAACAATACCAGAGTGCTTTCTCATTCTTTTCT
ATAGCTGCCTAGTATTCTATGTCCTTTACTTCATTTAGGCAGTCTCTTGT
TGATAGACACTTGGGTTACTTCCAATTTTTCCTATTACAAATGATGTGCA
ATGAATAATTTTGATCATTTTCCATTTCACATGGGTTATGTCCATCTGTG
GGATAAATCTCCAGGAGTGAAATTGCTGGATCAAAGGGGAAGTGCACTTG
TGATTTTCATAGTTAGCAAATTTTGTTCTATAAGGGTCATATCAATTTAT
AGTCCCACGCGTAATATTTAACAGTGGGGATTTCCCGACAGTTTGACCAA
CAAGGTCTGTTGTTAAACTTTTGATTTTTGTCAATCTGATGGGAAAATAC
TAGTATCTCAAAGTGCTTTTAATTTGACTTTCTTATTACAATGTTAAGCA
TCATTTTACTCTGCCCAAGATCAAATAGTATTTTCTTTTCTGTGAACAGA
CTGTTAAGATCCCTTGCCTCTTGTTTTGCTGGATTTTTGTTCTTTTTTTT
CAAATGTTTTGAGGCAGTTCTTTACATGTGAAACAAGTTATCTCTTTATC
TGGGGTGTGAGTTACAACTACTTTTCCTCTGGCTTGTTTTGCGCTTTGAC
TTTGCTTCTGGTGATTCCCGCAATTCTGAAAGTGTACTTTTTGCATCATT
CATTCTTATACACCCATGCTCTTGTTCACGCTGGTTCCTCTACCTGAGGG
CTTTTTCTTTTCTTTTCTATCTGGGAACATTTTTTAGAGACAGGGTCTCA
CTCTGTCATCCACGCTGGAGTGCAATGGTGCGATCACAGCTCACTGCAGT
CTTGAACTTCTGGGCTCAAGCAATCCTCCAGTGTCAGCTTCCCAAGTAGC
TAGGACTACAGGTGCATGCCAGCATGCCTGGCTGATTGTTTTATTTATTT
ATTTATTTTTTGTAGAGATGGGAGTCTCACTATGTTGCCCAGGCTGGTCT
TGAACTCCTGGGCTCAAGCGATCTTTCTGCCCCTGCCACCCAAAGTGCTG
GGATTACAGGCGTAAGCCACCATGCCCAGCCCATGTGTGGAAATCTTCTG
TTTATCCCTTTAGGCTTGATTCTTATGTCGTTCTCCTCCCTCCTTCCTGG
CTACTCCTCTTGTTCTTTATCTTACTCTACTTGTCATGTTACCTTGTTTC
TGCTTATAACTAGCTGCCTCTCCTATCTGAGGAGGGACTTGTGACTGTTC
TCATCTCTGTACTCCCAGGTCCTAGTACATAGCGCTTGCTCAACAGATGT
TTGGTGCATTGATAGATAAATCAATGGTAGCTGTTAATACCAGTCCTGAC
TCCCTGCAGTGCTTCAGCTGATCCTGTTCCAGATGTGCACTGAATATCTT
TCTGTTGAACAACAGAAATAAAGGGGATGGGTGAGGAGGATAGTCTTCGG
TGGCCAAGGATATTTGTAGGTACTTTGCAGCACTCAGCAATGAGGAGTGG
GCTTTAGTCCCCCAAGAACTCTCACAGCCCTGTTTGTCTTTACTGTTCAG
TGTCAAATCCAAGACAAGTCAATGATCAGGAAAGACCTTTTTTTTTCTTC
AGTGAAGTTTATTTCAGAACCATTGAACAGTATGATATTTGCTCATTTAT
AAATATTCCCATTTAAATAATCTGAGCTTATATATTTTCAGTCTTAATTA
AAGGACTTGATTTAAAGAGAGCACACCAGTCCAAATTGAATTGATTCCAT
AGCTATTAAAAACTAGGCTCTTTTACAGACACTGCTACTTCTTGCCCCCT
TTGAATAAATTAGACCAATGAATAAAACAAACAAACAAATAAATAAATAA
ATAGGGAAGCGGTTGCTCATCAGAATGTGGGAGCGAATGACAGAGGGTTT
CTTAGAACCAAATGTGGCCGTGGTTTCTGTCAGGCGGGCTTTAAGTGAGT
AGGAGAGGTGAGAGAGGCCTGGCTCAACAAAAGGGCTGGGGATTGGCCCT
GAAAGGAGAGAGAGCTGACTGTCCTGGCTGATGGACAGGAGATCCTCTTAGC
ACTACCCTAAGGCAGGCAGTTGGGCATTGGTGTAGACAACAGGAAAGTCC
AGGCTATAGCCGTACTCAAAAACCTTTCTGTTCCCTTTCTGCCAGCCCTA
GGGATTGAGTCCACATTCAGCACAGGACTCTCTGGGTACAGCTCTCTTTA
GGAAGACACAAATTGCATGGTGAAGTCAGTTATATCCTGGCCGCCTTTGG
TCCCTCCCAGGAAGACGGGCATGTTTTCTGCTTGAGAGGTGCTGATGTAC
CAGTTGGGGAACTGGGCAGACTCAAATTCCAGCTTGTTATTGATTTCTAT
CTTGTTGAAGACAAATCGCTTTTCCATCTTCTTCTTTGGGTAATTTTTGG
GATCTACACTCTGCAGCGAAAGAGAAAGAAGAATTTTTGTGGGGCAAGGG
ACAAAAATGCTATGGGAAAGATGTTCTTTGGGTTGGCCAGAAAGGAAACT
GACGAGCAGGTCACATGATCAGGAGCCACACTCCTGAGTTGTAACTGGGC
CCCCAACTTTCTGTGTGATTATTAAAAGAGCCCTTCTTCTTTTCTAAAAC
TTAGTGCCAAATGCTGAGGAGCATAATGTAGGTGAGAATTTTTTTTTTTT
GGGGGGGTGAAAATTAAGCTAGAGCTTCTTGAAGTACCTAGTTTCCAGGG
GCTTTTTATTGTATTTTTCCTTATGGTCCTAGAATGACATCAACTTGGAA
ATGAAGCTTTTGCTGAGAAAGCTGGAGGTGATAGTGGTGGTGATTTTGGG
AGTGGAGTGGACGTGATAATGGGACCCTTTAAGTCATCTATTTCCCAAGG
TGTCTATCAAATGAGAGCAGCCCTAACAATATATAATCTGTTGGGGTTGT
AACTATGGTAGGACATAATAACATCGGCAAAATGATTTAATTTTCTGCAG

FIG. 4U'

CAGGATTGAAGGTTGCACGCAGTTAAAAATTATGTTAAATTTATTTACAT
TAATGCAAAATTGTCAAATAGACCTGTTCCCAGCTTTTCCTAGGGATGGG
GGCGGGGAGAAGGTGGTTGTCTGGGAATAAGTGGTAGCAGGAGGCTGAGA
AGGGCTTCATTCCATAGCATTCACTTACCTCCAGCTGTAGAGTGGGCTTA
TCATCTTTCAACACGCAGGACAGGTACAGATTCTTTTCCTTGAGGCCCAA
GGCCACAGGTATTTTGTCATTACTTTCTTCTCCTTGTACAAAGGACATGG
AGAACACCACTGAAGAAAGAAGGGGGTCTTGTGGTTAGGGACACAGCAGT
GCAGGGTCACCCCAACCCCTAGGCCCCATGAGTAGGATACATGTAATTTG
GTAGCCTCTGTGGGAACCCACAGTGAGGTTCCTTGGCCTAAGACACAGGA
TAACTTGACTTCTCACAGACAATAGCAGGGTCATTTTGTTGATTTAGGGT
TTCCCCTCAAAGGCCTGAGGGTTTCTCAGAGCCTCATAGCAGTAGGAACG
GAGAATGAAAGAGGGTCTACATTTTAAATGCTGAAGGAAGGAAGGAAGGA
AGCCATTGTGTCACTGGCTGGCAATGTGCCCATCCACAGGAGCGGAACAA
CTTGATCAATGTGGAAGGAAAGGAAAGAGGTGAGGCTGTACTTCTGCCAG
AAATCAGGCACCAGAACTGTTTCAGGAACAGAGAGTAGCCCATGGAAGA
AACTGGGAGAGGAGAGGCTGAGCTGGGAAAGTGGCTCCAAAGAGAGACAC
TCATTTTGATCTTCCTCAGTCACAGCAGTGTCAATTGGAAGGCCCTGGGA
TCACTCTTACTACCCGATTCCAAAGAAACAGGATTTTCTTGGCCTGGCTG
AGAGCAAATAGCTTCCCCCTTGAGTGAGGCTGTCCTTCAAAGTCAGCAGC
CTTAGTTGCCCACACTCCTGTGCAGAGGCTTTGGCTACTGTGGCACGATG
CCAGGCAGATCACCACAGCTAATGATGGGTTCACCGCACTTGAAACTTTT
GCCCGTTACAGCGGAGAGATATAAGTTCCTGCTGGGCGGTAAAATTTCCC
TACAAGGAACCACCTGGCATTGGGTGGACGGATGTTGGGGCAAGGGGGG
AAGACTGGGGAGGGGGATGGACACATTATCGCTCCAGCACTCTTGTTTCA
GCCTCAACAACAGGAAGAGAGAACCCACAGGCAGTTAGGCCATGTCCATC
AAATGACCCCATATTGTGGAAGAATTGACATTGCACTATGCCCAAGAGAC
TTGGGTGGACATGGTCCTGGGAGTGCTTGAGCCGTCTAATTTCTCAGGGT
CACACTCCTGTTAACAAATGCACTGGCCAGTGCAATCAAATGTGCCATTT
CTAGGACCAAAGTTTGTATATTCCTTTTTAATATTTTTTTTCACTTGTGT
TGATCATTTGCCTTAAATTAACTTTCTACTTTGTTTAAAACATGGAGAAT
TAGCAAGCTGCCAGGAAGCCAGGCAGGGAAACCAGGATGTTTCCATTTAC
CTTGTTGCTCCATATCCTGTCCCTGGAGGTGGAGAGCTTTCAGTTCATAT
GGACCAGACATCACCAAGCTTTTTTGCTGTGAGTCCCGGAGCGTGCAGTT
CAGTGATCGTACAGGTGCATCGTGCACATAAGCCTCGTTATCCCATGTGT
CGAAGAAGATAGGTTCTGAAATGTGGAGCACATGTTGTTTAGGTATAAAA
TCAGAAGGGCAGGCCTCGTGAGGCAAGGTGGCAAAATTTGATTTCTTGGA
GGACACCTGAGCATATACGGTCAAAGTCTGATGACAACACCAGTAGGGAT
GAAGCTGGGAGTGGGGTGGCTAAGAACACTGGACCTGACACTATTAGACA
TGGGTTCCAGCTTCAGGTCTATTACTGCTCACTGTGGCCGAGCAACAGAG
CTACTTAGGTAAAATGGTGATGGTCATAACACTAGCCCACAGGGAGGTTA
CGAACCTCTGGTGACAATGTAAGTGAAAGGCCCCTGAGAAAGAGTGAGGG
AGTTGCAAATGTCAGTAGCCATCAAGATCTTCTTTAAGAATAGTTTCCAC
TAAAGAGATGATTGCTTTGGTTTCCAGCCTTCTTTGTTTTGTCTCCCCGC
TGGGCCTTCTACCTTTAAAGGGCTTTGGCTCTGGGGGAATTGAGTTGGCT
GGGGCTTGATGACTTCCAAGAGGACACAAGTGGAGATCTACTGCCTGCTC
TTGGCTAACTACCTTCTTCAAAGATGAAGGGAAAGAAGGTGCTCAGGTCA
TTCTCCTGGAAGGTCTGTGGGCAGGGAACCAGCATCTTCCTCAGCTTGTC
CATGGCCACAACAACTGACGCGGCCTGCCTGAAGCCCTTGCTGTAGTGGT
GGTCGGAGATTCGTAGCTGGATGCCGCCATCCAGAGGGCAGAGGTCCAGG
TCCTGGAAGGAGCACTGCGGAGAGAGCGAGGGAGGGAGCCTGGTGAGGTG
GTCCTGCCAGGAACCATGCTTTGACATCAGAGAGTAGAAAGCTCAGAGAG
GAGGAAAGGGCTTGAAAGAATCCCGAGCTTCTAAAGATCATCCCTCTCTG
GGCCAGGCGTGGTGGCTCATGCCTGTAATCCCAGCACTTTGGGAAGCCGA
GGTGGATGAATCATTTAGGTCAGGACTTCAAAACCAGCCTGGCCAACATG
GCGAAACCCCTTCTCTACTAAAAATACAAAAATTAGCTGGGTGTGGTGGG
GTGCACCTGTAATCCTAGCTATTCAGGAGACTGAGGAAGGAGAATCGCTT
GAACTCAGGAGGTGGAGGATGCAGTAAGCCAAGATTGTACCACTGCACTC
CAGCCTGGGCAACAGAGTGAGACTCTGTCTCATAAAACAAAACAAAACAA
AACAAAACAAAATAAAATAAAATAAAATAAAAAGATTATCCCTCTCTGAA
GCTCAAGGAGGTTAAGGGTGTACTCAAGGGCACACAGCAGGTTAGAGGCA

FIG. 4V'

GACTCAAGACTAGAATGTGGGCTTTCTGACACCTTACAGGCTATTCTTTT
AGAATAAATCCCATTTCTACTTTGTTCATCTTTTTTGTACATGCCCCACC
TACACCATACATGTATACCTTCTCTATATCTTTTTGTATCCCTAATGCTG
TCACACTATGATTTGCTTTTTCATGCAGATGACCATAACATTTTCCATTC
ACCTATGCTCACTCAGCAAGTATTCAATTTTTCTACACTGTTCTTTTTTT
TCCTTTTTCATAACACTGTCTCATAGGCATTCTGCAAATCCTGTGAGAGT
ACTTTTTGTGAAATGTTACCACTTTCCTCTTATTCAGAGAAGCTCCGTAT
TAAGGCTTCACTGAGGTTGCCTTAAGGCATGATAATGGTTCAAAGGCTTG
AAAGACAGTTAAAGAGACCTGTAAGTGCACAAAAGAAAGTTGAGCAGGAG
AGAATTTCTTGCCTGGAGCAGAGCCAAGCTACTGGAAGAGGCAATGGGGG
CAAAGGCCAGGCAGACAAGCCAATGGGCTCCTCCCACAGCTGCAGCCAAC
AAGTTATGCCAGTCTTAAAACTTCTAAAGAAATATGTTTTTAACAAGATT
GAGGACTGGATTATGAGGCTAGGGGAGGCTATCACAAACTGGAATAAAAT
AAAGCCAGAGAAAAGTGGCTGCCTTCCAACCTGCACAACTGACCTAGCTA
GGCTGATGGCTGGGCCACCTAGGAAGGCTACTGAGCATCATATAAAACAG
AAGGGACAGCAGGAATATAACATGGCTCTTTGTAAGGATGAGTCTGAAAA
ATGACCATTTGCTGCCCAAATGCCCTTAGCTACAACTGAAAATATTTCAG
AACTGGAGGTTGCAGGATGCTGGAATCTCAGAGATCATCCAGCTCAGCCC
TTTATTTTTCAGATGAGGTCCAAAGCGGGTAAAATGACTTGTCAAGGTCA
AACAGCAAGTGAATGGTTTTCTTTCAAGTCTCAATTCATCTTTTTGTTTA
TATCATCTATGTCTTGTTGTTATAAGCTTCACCCCAGGTAGCAAAAAACT
ATTCTACTCAAAAGGGGTAGACATATGTTAGTTCTCAAGATCATCTCTTG
GTTTCAGAGTTTAACTCAAGTGATTGGCATAGGCTGAATCCATCTCTTAA
AAGGATAATCAAATTTATGTTGAAGACTTGGTTGTCTTCCTACTATGAAA
TGGGAAACATTATCACTACTCCTCCCCTGTCACCACCAAGTGTGGCCACC
ACCACCAACGTTAGTGAGTGACTGTGGTGATATGATGACCAAGTGGCCAG
GTCAGCAAGTGGTGCAGCCTGTGTCTCACTGGAAGAGGTTAAAGTCTTTC
TAAAACAAAATACCATGGCATCAAAGTGGCCCAGAACTCCCTTCTTTGAG
CTTTCCCTGTGTTAGAGCCCTTCCTTGGGTTGGGAGTTAAACCCATAGTC
TTACCTTCATCTGTTTAGGGCCATCAGCTTCAAAGAACAAGTCATCCTCA
TTGCCACTGTAATAAAAACAGGGACATGTCTCAATTATGTCTTCTAAACA
GGTTTATTTTTCCTTCCCTGTGTACAAGACTTGACTGTTCATAAGAAACT
GCAAACAGCCTGCCTCTCAAAGCTGCCTGAAACACCTGGCAAGTTTCACA
GTGATATGCGCAGAACAGTCCAGAAGGCAGATTCTAGGCCTGGCAGGTGG
GCACCCTGGGTGCTCCCTGTTGGATCTTGAGGCCTAACCTCTAGCCCAGC
AGAGTCAGCTAAAATCTGAGCTCTCCCTCTCCCTCCAAGCCACACTTTGC
AAAGGGATTCCTTGTATTGTGGGCTTGGAATCTTTTCTCCCCATTTGCCT
CTGCAGGAAGCCCTTGCAACAACACATCTGGATAGCCTCCAGGTCCCAAG
GCTGGAGGGACTTGTAATGGGAAAGTAGTCTTTAAATCAGATTTACTTGG
CACCCTGTTTGCCACTGAAAGAGGCAATTTAGGGGAAAAATCTGGTCTCC
AAGCACAGATAACACTCTACTCTTGAAAGAGGAGACCTGCTCATGTTACT
GGTCTCAGCGTCTCCACTGACCTGTAATAAGCCATCATTTCACTGGCGAG
CTCAGGTACTTCTGCCATGGCTGCTTCAGACACCTGTGTAAAAAGGAGAA
AATGAGTGACTTCCCCATGACGGCTACGTTCATGTGTGATTTCTCTCAGC
ATCCAGTGCATGGCAGTCATGCAAAGAAATGATCTCTGAGTAAATGAATG
AATGTGTGAAAGAGAAGTCCTTTGGGTCTAGAGAAAAGCATTTGCTAAAC
CAAACCCCAACTAGCAATGTATTGGCTAGGAGAGCTGGAGCAGAGGCTTT
GACACTAACCTTTAGGGTGTCAGCTGTTAGATAAGCAGTATCCATTCCCA
GAATATTTCCCGAGTCATAAGCATTATATTACACCTGGCATTTTTGCAAA
AAGCTGAGAGAGGGAGGCAGAGAGGGAAGGAGAGGGAGAGACAGAGAAAG
AAAGAGAGAGAGAGAGAGAATATGCATACACACAAAGAGGCAGAGAGACA
GAGAGACTCCCTTAGCACCTAGTTGTAAGGAAGATTAAAGTCATACTTGA
GCAATGAAGATTGGCTGAAGAGAATCCCAGAGCAGCCTGTTGTGCCTTGT
GCCTCGAAGAGGTTTGGTATCTGCCAGTTTCTCCCTCGCTGTTTTTATAG
CTTTCAAAAGCAGAAGTAGGAGGCTGAGAAATTTCTCTGTTGAATACCTG
ATTTCACAATCAAGTTAAAGGAAAGGGGAAAAGAGTATTGGTGGAAGCTT
CTTAGGGGAGGGGACTAATAAACTGAGATAATTCTCTGGTTCATGGAAGG
GCAAGGAGTAGCAAACTATGACACATTTTGCAAATGTATCACCATGCAAA
TATGCATTGTTTTCCTGACAATCGTTGTGCAGTTGATGTCCACATTAAAA
TACTGGATTTTCCCACGTTAGAAGAATGTTTAAATTTAGTATATGTGGA

FIG. 4W'

CAAAGTGGAAGACACACAGATTTATACATGCACATACTTTTCTTCATTCA
CTTCTTTGTACTTAAGTTTAGGAATCTTCCCACTTACAGATGGATAAATG
GGTACAATGAAGGGCCAATAGCCCTCCCTGTCTGTATTGAGGGTGTGGGT
CTCTACCTTGGGTGCTGTTCTCTGCCTCGGGAGCTCTCTGTCAATTGCAG
GAGCCTCTGAGGAGAAAATTGACCTTTCTTGGCTGGGGCAGAGAACATAC
GGTATGCAGGGTTCAGGCTCCTGACGGAGTTGGGGCAACCCTGGAGATAA
GCTCACACAACCCTGCAAGACCAGGTGCTGTTACCCTAGCCAATCTCATG
GATGAACCAGATCAATGCCAGATGAGCTCTGCCTAAAATGATTTTTTGGT
GAACTCTGAAAAGTGGAATATTGTTTCTGTAAGAATATCCATCTGAGACT
CTATCTCTTGGTAATACCAAGAGTTATCAGTTTCTCTTTAACCGAGACAC
CAGCAAAGTGCCTGCTCCAGGGTACTGCCCAGGGGAGCCCTCCATTTGTA
GAATGAATGAGAGTCCAGGTTATGAACAGTGCCTGGAGTGTAGGAACACC
CTCCTTTGCCTCTTTGACAGGTCTGCATCATAACACTTTTTTTTTTTTTT
TGAGACAGAGTCTCACTCTGTCGCCCAGGCTGGAGTGCAGTGGCACGATC
TCGGCCCCCTGCAAGTTCCGCCTCCCGGGTTCACACCATTCTCCTGCCTC
AGCCTCCCCAGCAGCTGGGACTACAGGCACCTGCCGCCACGCCCGGCTAA
TTTTTTGTATTTTTAGTAGAGACAGGGTTTCACCATGTTAGCCAGGATGG
TCTCGATCTCCTGACCTTGTGATCTGCCCGCCTCGGCCTCCCAAAGTGTT
GGGATTACAGGCGTGAGCCACCGTGTCCAGCCTGTAACACTTCTTATAGC
ACTGAGTTGAAACCTTGCTCCTCCTGGTTCCTCCAGGAAACTGAAATCTT
TTTGAGCCAAGTCTAGCACAGTGCCTGGCATGTACATTCAGGTGGTAGAG
TTTGCTGCTTGAATGGGTGAATGGGAATTTGACAGCATTTTTATTCAAAT
TAGTATGTGCCAGGTATCGTGCTCGCTCTGCATTATCCAAGGGAGTGAGC
CTCTGTGCAAGTATTTGAGACACGAGGGAAATAGGTTCTACTGTGGGAAA
AAGAGCATTTCATGGACTTGCTCTCCAAGCAGCCTTCTGATTTTTAATTT
GGCTCCCAGTATCTTGATATCAGGAGTCAGTCACAAGAACTCCATCTTTA
GTAAGTTATATTTTCCACAGGAAATCTAAAAGCTGTTCAACATGTTAGTT
TCCTGTGAATTTGATAAGCCATAATCCATTCCTAACACTGAGCCCTCCTG
AAATTTGGTGTCTGGTCCTGCAGATAGCTAAAAGCCCTGTCTGGGTGGCC
TAGGGGACTCCTCTGTTTTGCCTCCACAGGATCCACTTTGCAAATTAACC
ACTGGTTCTCCCGTTGTAGGAACTGCCACCTTCCTCAGAGCCTGTCTTTC
TTCCTTCCTTCCTTCCTTCCTCTTTCTTTTTCTTTCTCTCTCTCTTTCTT
TCTTTTCTTTTCTTTCTTTCTTTCTTTCTTTCTTTCTTTCTTTCTTTCTT
TCTTTCTTTCTTCCTTTCTTTCTCTTTCTCTCTTTCTCTCTTTCTCTTTC
TTTCTTTCTCTCTCCCTCCCTCCCTCTCTCTCTTTCTTTCTTTTTCTTTC
TTTTCTCTTTTCTTTCTCTCTTTCTTTCTCCCTCCCTCTCTCTCTTTTTC
TTTGTCTCTCCCTCCCTTCTCTCTCTCTTTCTCTTTCTCTCTCTCTCTCT
CCTAGACAGGATCTACCTTTATCCCCCAGGCTGGAGTGCAGTGGTACAAT
CATGCATTCATTGCATGATCACAGCAGCCTCAAACCCTTCCTCAGAGTCT
TTATGCGGCAACCAGCAGGGTCTGGAGGGTTGGTGGCTCTGTGAACTCTC
CTGACAGAACACAGAGATGTCTTTGGTCTGTTGATGTGATTACAAGCTGA
ACGAAGGAGGATCAAAGCCAGTGACAGGAAGGGAGATATGCAAGGGACCC
GAGCATCAGCTCTGAGTTAGTCCATTCTGCTTCTGGGACTTGGGATACAG
GTCAGAAACCTTGAGCTTCTACTTCTCCATCTTCCAATTGTAGCATCCAG
GACCTCAGAATCTGCCAGCTAAGAGGAGCCCTAATGATTGTCTGGTGGGA
TATGGTGGGACCACAGAGATGAAGACATGAATAGCTATTTGAATGTGAAC
AGCAGACGAAGAAATCAAGGCTAGGAGGGTGGAAGTGACTCATCCAATAG
CACAGTGTGGTTGAAGCAGCACTAGTATCCAGGTTGCATGAGCCCCTGAT
GCTTTCGCTCGAGGGAAATTTTGGAGCCATGGGGCAATGCCCCCTGACGT
AACAGTCTCCACAGTTCTGCCATGTCTCATCCTGGCCCTGTAACCTGGAC
CCAAATCTGCTACCATCCCATCCATCTCAGGAAGTGAAACCTCTTATGTC
AAATAGGTTGTGCAACGTATGTATCAGATCCTGTCTTCCCAAGGAGACCG
CTCAGGCCACAGCACTTCCTTCCGATCCCCAATGAGCAGAAAATATCTCG
CTATAAACATAGTTGGCACTAAGGGAGGGAGTGGAAGAGTGATGATGATG
TAGATGGTGATGTAGCCCCAAGGAAGTGGAACAAGCAGAGATGGGGAGCT
GGAAATGCCAGGATGCTCCAGCTTTTGGGGAATTATTCAGCTCTTGAGTC
ACTAAAGCCTTTCTCAGCTGCAAGTTCCTCTTTACCCTGTCAGGTCATTC
TTCCAAGACAGGAGACTGACATTTATTCAAAGCAGCAAGTGCCCTGATAC
CATCTTGTGTCTAATCATGGGCTTCGCAGCCAGTTATCAAGGTTGATCTC
ATCTCATTGGTCTTCAATCATTTTGAACAAGAAGACAAGCAAAATAATCA

FIG. 4X'

TGGGTTAGTTCTTATATTATTGTGTGTACATGCAGTGATGTCTGTTCTTT
GTAGTGAGCTGTTCCTTCCTTGTTCACCCTCTTGCTTAGAACAGAACTAA
GCAATCTGCCCCCAACATTTTCCCCAATTTCCCATCTCATTCTTGGCACT
GGCTTCCTAATATTTGTTCTTATGAGTCATTTTCTTGTATCATTTCCATG
AGTCCCTCTGGGATCTTAAAGTATGAAAAATGTTGTGTGTACCCACACCT
GTCTTTGTGGATATTTCTCTCCTTTCCCTTCTGCTTCTGGGATTATTTGG
GAATGGGCACTATGATTTTTATCATATCGCTTCCACTTCCTTTATGGCAT
CATCTCCAATGGGCTTCTTCTCCCTCTTGGATCCAGGTTCTCAGATTGGG
GACATGCAGAGTCCAAGGAACATTCCATTCTCCTCCCTGGTCTAGAACAA
GGAGGGCTTAGATATATGAGCAGGTGGCTGGGGCTGGCGAGCTATGTAGT
CTCCAATGGCTTTTCCCTGATGTCGGAGTTGTTATGTCAGTTCTGGGAGA
CCAATAAGACCTTGTCCTTCCTTTGGATCCATCAGAAAAAGCCCCTGGGT
GGGTAAGATGGATGGCAGGGCTCTCCTACTCTATGTCTTTTCTCACACCT
AGTGGGTATAAGAGAGGGGACCACAAACAGAGGGGGCTCTGGTACCACTT
ATCCAGGGTCTGGAAACATTTTCTGTAAAGGGCCAGATAATAAATGTTTC
AGGTACAACTACTCAACCTTGCATCATTTCAGAAAAGCAGTCAGATAATA
CATAAATGAATGGGTGTGGCTGGACTTGTCCTGCGGTCCCCTGTCTTATA
TCATTGTATTATATCATTTTTTCTTACATACAAATTTAGAAGCAATACTT
AAAAAAAAAAAGCCGTCCTTTATTGAGCACCTACTAAGTGCCAGGTACCT
TTTTTTCCCTCATTATCTTATTAACTCTTCATAATAACCTTTAAAGTAGA
TAATATTGAACCATTTGACCTATGCAGAAACTGAGGTTGAGACAATAAAT
TATTTAAGACCGCACAAACAGTAAATGCTGGAACTACGACTCAAATATGG
GTTAACTGAACCAAAACCAGATCTTTATTTCTCACTTTTAATTGTTACAT
ATGTTTATTGCCTCATCTCCTGTCCACATGGTGCCCATCGGCAGACTCCT
TTCTCATTCTCAGTGATTGAGTGACATTCTAAACTACATTGGCCTGGCAG
ATTCACCTCTGTCCCCTAAATGTTTCCACATTGTCCTTTTAGGATTGAGA
TCCTCTCTGTTCCCTTGTCTTCCCTCCTTTCTTCTTCTGGCGGTGACGTG
CTGTGTGAATTTGTTTCTTTCTCCTCTCAGGGTAGTACTGGGACTTTCCA
AATCAGGGTTTTTAATGATCTCTCTTCNCTTTTCTGAATTTCTTCCTTAT
TCCCATTCACTTTCTCATCTATAAGTGGCANCTTTGTTGCTGGAAGATAT
CCCTTGTGCAGGGATTNCTCTTTAANAATTTGTCNNNACC
>Contig54
GTGATCGTCAACCTCCCACCCTGTAGGGCCTCAAGCATTGAGGACAATCA
CTGGCTGCCCATTAACCCAGAAATGTTGCCGAGACAGGAGGCCGTGGCCC
AAGTTCCTGGAATGGGGTATTATTATGTCAGCACAAAGGCCTTTGCACAA
ATGAAGGCTTTAAAAATGCAGTCCTAGTCAGGTGGAGGAGGGCTTATAGG
ATTCCCAGGAATCTGGATCATTCTCTTGAGAGCTTTCCCTTGTCTCTGTT
AAAACTCACATCGTACGGCCCAAATAACAACAAAAAATGGATGTAAATTC
TTGAAATAACTTGTGGATGGGGGAACAAGGCCCACCCCCCAGATCTGCCA
GAAGCTTCAGGTGAGGGTCCCAAATGCCAAAAAGTCTGGTATCAGAGAGG
ATGGCCAGTGACNTGGGGACACATGCCCTTTGCTGTGTCACTCAAGGAGC
AGCAGCTTCGGCCCCGCACAGTGACCAGGACCCTGGCTTCCCACGCTGGG
CAGGAGCTGGTGTCTGATGAAGGGAATGCCTGGCAGCACGTGCTGTCTGT
CTCCTCGTGTCAGCTTACCTGGCTTTGCTGCGAAGAGGCCACTTGCATTT
CTTTATTTTTTATATTTTTTTAATTTTTTAAATTTTTTATTTTATTTTTA
TTTTTATTTATTTATTTATTTTAATTTTTTTTTAATTTTTTAAATTATG
CTTTAAGTTTTAGGGTACATGTGCACATTGTGCAGGTTAGTTACATACGC
ATACATGCGCCATGCTGGTGCGCTGCACCCACTAACTCGTCATCTAGCAT
TAGGTATATCTCCCAGGTTAATCCCTCCCCCCCTCCCCCCACCCCACAAC
AGTCCCCAGAATGTGATGTTCCCCTTCCTGTGTCCATGTGATCTCATTGA
ATTTCTTTAAAGGTGGAATCTCTCAGTGGGGTCTAATCTGTTCAGAAATA
TCAAAAGAGTATCCTTGGGAATGACTGGAATTCCAGAGTCATCTGGTAAT
CCTCATAAAACAACTCCTGGATGTCTCTCAGCACATCTCCCACCTTGAAC
GCAGGAGGCTGGTTCAAATGGAGGAGCATCGCTCTACTGCACTTTTTTTT
TTTTTTGGCCTAAAGTGCAAAAGGGGATACGTTTCATGTAAATAAATCAA
CTGCAAATCGCTAGTTATGCTGAGCCCTGTCCCGTGCTGTGGACACAAAG
GAACCAAAGGCTTTTCTCCCCGCCCAACACACACATAACACACACACAAA
ATCATAAAAACATACATACCCCCAACACATAACAACACACAACACACACA
CAAAATATATACACACAACACACACCAAACATGCCCACAAACCTGTGTCC
AAAAATAAATCCTACTGGTGGGTTTGTGGTCTCCCTAACTTCAAAAATGA

FIG. 4Y'

AGCCGTGGACCTTCGCAGTGAGTGTTACAGCTCTTAAAGATGGCATGGAT
CCAAAGAGTGAGCAGTAGCAACGTTTACTGTGAAGAGCAAAAGGACAAAG
CTTCCACAACCCAGAAGGGGACCCCAGCAGGGTTGCTGGTTGGGGTGGCC
AGCTTTTACTTCCTTTTGGCCCCTCCCATGTTCTGTTTCCATCCTATCAG
AGTGCCCTTTTTTCAATCCTCCCTGTGATTGGCTACTTTTAGAATCCTGC
TGATTGGTGCATTTTACAGAGTGCTGATTGGTGCGTTTTACAATCCCCTT
GTAAGACAGAAAAGTTCCTGATTGGTGTGTTTTACAATCCTCTTGTAAGA
CAGAAAAGTTCCCCAAGTCCCCACTGGACCCAGGAAGTCCACCTGGCCTC
ACCTTTCAACTCCATAATGGCATGAAAATACATATGTTGTACAAAACATA
CATACACAAAGTATACATGCATCTCCCCAAATATACACATACCACAGAAA
CATACACACAGGAACTCAGCTACCTGTCAAAAGTCTGCATGGTGATTGCC
TCTGCAGTGAGTAGTTAGAAAAGTGAATTTGTTTTCAATAAATTGGAGT
CCTTAAAAATCGTTGTAAGATAGAAAATTTTTAAAAGTATATAAAATAAA
ATATGTATGTCCTTTGGTCTAGCATTTACACATGTAGGAATTTATCCTAG
TGGAGTAATCAATGATATATGCAAAGATTTGGACAAGCATATTAAGCACA
GAATTATGTATGCATATGTGTGTGTATATATATATATATCTCATACATAT
AATAATGTAAAAGTGAAAATAACTCAGATGTTCAAAATTGAGGATTAGTT
AGACTATGATCTGTCCATATGTGACATACAAGTTAGCTGCCCCTTATTCT
CTCGAGCTTCAACCTCCTATAAACAGTGTCCCTTGTATATCAGTATTGGT
ACAGATAATCGAACTTATTGAGGTTTTACATGGGGCAATAAAGGCAAGAG
TTTATGAATACTCCATACTACACTAGGTAGCACCCCCTATTAAAGACAAA
CTCTTCTCTCTCATTTCCCTTCCTTTCCGGAACCACTTGGTTGAATCTCT
ACAAGTCTCTATTGCAACTGCCTCAACATGGCACCCTCCCTGCATCTCCA
TCTTCCCTGTCCTGAGAGCAATGGCCTGCTGCCCCCACACTCACATCCTC
ATTCATTCCAGAAGTGAGCACCACAGAAGTGCCTACAGTTACCCCAACCA
CCTTCTTAGAAGATAAGTTAGTGTTTGTTTTGACTTTTTAAAATTTTTAC
TTCCTCTTTTCCTTCACAATCTCATCCCATCCCAAGAGGTTTATCAAGAA
GTTCTCTAAAGATATGTGTCTCCTTATGGAATTTAACAGAAATCAGGGAT
TTGTATTCTAGCCATCAAGGGAATAACATTTTTCCAGGTCTTTAGACAAA
TAATGGAATACCTTGCAGTAATTAGATACACTATTGTAGAAAAGTATTGA
TGAAATGGAACGATGTTTGAGATATCATATTGAGTAGAAAAGGCAAGATA
CATTAAGTAGGAAATGTATCTTACAAAATAATTTGTCAGACACACTCCTA
TATTTGTATGTTATATAAATGCGTATGTGAAGAAAGGCTAGAGGATGAGA
CCACAGTCTTCGGTGAAGTTTAAGAGATGAGGCTGCAGCATGCTCAGAAA
GGCCTGGGTTATAGTTCTTCCAGTAATTAAGGATGTGATCTTGGGTAAAT
TGTCCATCCTCTCTAAACTGCACCACCTTTTGTCTGTAAAACAGGAAGGA
TGGTATTTACCCCCAGGGTCATCAAAGGATTTGGTTGGAGAAAAATAAAT
AAATGGGCTGAGCCCAGACCTGGCACAGTGAGAGCACAGTGGTTGACTAT
TGTGCTGGCCTGTTGTTCCTGTGTTATTGACATGCTGCTGGTGGTGGTCC
AGAAGCTATTACCTTAATTGGTTATGTGGATTTCCCCTCATACTGAGCAG
CTGTGTGTGGTGTTGTAAAACATAGCCATACACAGTAACTGACAAGGGCA
AATGTGATGGAAAAATGCAAGGAAGTGCAGATAAATAGCTAATGGGCTGT
AGAAGGAAGCTAGTCCTTGGAGGGCTTGATCAAGGAAGGTCCTTTTGCAT
GTCACCTTTGAAGAAGAGGGGACATAGAAGAGGTATAGTGCATCCCGGAG
TGTACCTGGAAGGGAACATGAAAAGAGGACATTTTTCTCTGGGACATGGG
GACTCCACTTGCATGAACTCTGGAATTGGGGCAAAGAACCATCATGAGAA
CAAGGGCTTCCTTGAACCTCCCAGGCTCATTGGCTGATCTAAACCCTGTG
TCCCCTCTTTCCTTCACTCTCCTCTGTTTTCTATACCTGTATTATTGGAC
TGGACTGGAAGCCACCTGATCTATCACAAGTACCTTGAAATGTGTTGAAT
AGGTGTGGCACAGTCCTTAGCAGAGTGGCACTACCCCCACAGGAATTTGT
TTATACCTTTGGCATGGAAAATAGCAGGAAATGAGTGATCACTGATAACT
GAGGATGCTATTTATTATTGGCCAAAGGAATACTTGTGTTGTATTTGCAT
AACCACTCACAAACTGTTGATTACAAATGAGTACCAGACCTAGCTCCTTC
AAGTAAAGGATCCTGAGAACTGAAGGCAAACAGAGCTCCAGGAGTCCAAG
ACAGAGCCACAGACCACGAGGATCCCTGGCCCAGGTAGGTGGTCCTCCTG
CACTGGCTTTCAAGGCCAACAGGATGGATGGGGAAGTAGAGTAGCATCTG
GCCATCTAGACCCTTGCTTTTTATCCCCACTGGAAGCACATCTGAATTTC
TAAATATGATCTCTGAGACCTGCCCAGAACACCTTGCTCTCAGCCCCAGT
AGCAGCCTGCTCTCTCCCAGGAGGGCTTCCACTAACAAGTAGGGCATTGC
TGGAGGGCCAGGCAGACACTAGCTTAGGAAATCCACCAACCCTGGAAATG

FIG. 4Z'

CTAGTCCCTTCTCTGAAGGCTCAGAAGACTGACTTTAGAGTCTAGAAAAT
ATTGGTCCTTGGGAACAGATTTTGAGTGCAAAGAGATGGACTTCAGATGG
CCAGATGCACTGCTTCTTTAGGGAATTCTGTGAAAGCTCCCTGCATTTAT
CTTAATACAGGCAGCAGATTTCATGAGTACCCCCGAGGGATGGCCCCAGG
TCCTCCAGCCTGTGAGCATCCTTCTGTCCTTCAGCAGCACCACAGTATCT
TTATATGTCTTTGGATACCTACGTTTCTGCCAGACATCTCTTGCTCTGAT
GTTCTGGCTGCCAAATTCTCTGTCAAGCGCCTCCAATTTTTTGTGTCCTT
TGATTTACCCCAACATGACAAAGGCAGTTGTGCTTCATGTATTCAGGGAT
ACTGCCAAACCACAAACAGGTTAAAATCAAATAGCAGATATCCCTGTTCC
TAAAGACCCATCAGCTCTACCCACCTGCTCCTGCTCACCGTCCTTATTGT
TGAGTCCTGAAGCCCTTCCTTGTCATTTTTATTTTTTGCATGAACAATTT
AGTTCCCTTTGTCTCACTCCTAAACCTTTCTCAAAGGATTGGATTTGTAC
ACAAACTGCCTATCTCTGCAATCTTAGAAGTGATATGATTCTGAACAAAT
CACTTAACTTTTGATTTTTTATTGGTAAGATGGGAATACCAATTTTTGCT
CCACTTCTGTCCTATGTTGGCCTGGGCTGATGTTGAAAGCTCTCGGTCAA
CTGAGATAGGGTGTGCAGAATTTATATATATAAATATATCTCCTCCAACC
CCTCCCAATGAAGCAAGTCACGTGAGTCAATCCTACCCTAAGATATTAGG
GATTGAGCCTCCTGGGACATTTGGTGGCTTAGGTTTTCATGAAAAGAGGT
TGCAGAGCAACTGCTTTTTGTTAGGCAAAGATTAGGCTACTGCAGAGACT
CAGCAAACTTCTATAGAAGGTGTCAGATGGTAAGTATTTTAGGCTTTGCT
TGCCAGATGATCTCTCAACTAGTTAACCATGCTATTGTAGCCTCGAAGCA
GCCAGAGACAATATGTAAACAAGAGCATGGCTGTGTTTCAATAAAACTTT
ATTTAAAAAAACAGTCAGGGACCGGATTTGGCCAAAGGCCATAGTGTGCC
AGCCCCAAGACTAGAGCAATGCACTTTTAACTTTTTTATTTTATTTTTGT
AAAATGCCAAGATCCACAAAAATGCTATTGCACCCCGTGTGTTAGCACTG
TGACTCAAGGTTTGGGAAATTCTGCTTTGAAGGCGTGATAGACAGGAGAG
CATGGTCTGGCCCCTTGGTGCCTTTCTGGTTGCAGCGAGCATTTCAAACT
ACAGAGCAAGGCCAGTGGTCTGTTCAGCACTAGAGACATGCAGCAAGGTG
TCCTGGGGTGAGAAGATGCCATAACTGGTCCCCTTTCTATCTCCTTAGGT
CTTGGACTTCATTCCATTTTCTGTTGAGTAATAAACTCAACGTTGAAAAT
GTCCTTTGTGGGGGAGAACTCAGGAGTGAAAATGGGCTCTGAGGACTGGG
AAAAAGATGAACCCCAGTGCTGCTTAGAAGGTAAGGTTCTTGTAGAAATC
TACCTCAGGGCCAAAGTGTAATTCCTAGAGCAGAACTTTGCTAGGTGCTG
TGCACAGACCCAGTTGTTTCCTGCTGACTTGCACAGTAAGTGAGCTTTCA
AATTTCCCTGGACAAATAACTAGACAAGAGAAATTCTGGAAGAGAAAAGG
AAGCTTTGCTTCAGTGTCCAGGCACATCAGGTAGTAGATAAAAGGATCGT
CCTCACCTACAGATTTGGGGCTTTAGCATCCTGTTTGCCAACTGGATGGT
TGCATATGCTTCAAAATGCACCTCTTCCCTCCCAACATTCCCAAGTGGAA
GAGAAGCCTCCGATGAGAAGGAACTCTCTAAGGCTGGGCTGAACAAATGA
CCCAGGCACAGGGCATCTGAGTATTCCATGAGGAACACATTTGGGTGTTG
CCCATGGGGGACAATAGGAGGAGGCTTTTGACCCAAATGATTGTCTACTG
AGGTGTGACGGGAGAGGCCTGTGACATGCCAGAGGCCAAACCCGTGATCC
AGTTCATCTCTATTCTATGTTTCTGAAGAGGGAAGCTATGATTTAATGTC
ATTACTATCATGCTGCTCTAGTATTTCTCAGCACATACACAGAAGAGGGA
ATTAAATGGTCCTTGATACCCCTAAATCCTTGGAAAATCCGAATTGCATA
TGCTAACCTCACTGCGTCTGACTGCAGACCCGGCTGTAAGCCCCCTGGAA
CCAGGCCCAAGCCTCCCCGCCATGAATTTTGTTCACACAAGTAAGGCCTC
GGGGTGAGGTGATGGGGGTGGCTGAGGTGCGAGGGTGGGGATGGGGGATG
GAGCCATTGGGTCCTCTTACAGGGTGAGAGAATTGTAGAATGGGGACACC
TAAGGGTGCTGGATGGGGCTGAAGTCTTTCCTTTGTGGAAGCAAATCCCA
TTAGGAGATAACTCTGGGAAAGATGAGCCCGGGGAGGGGCAGGTGATGCT
CACCTGCTAAGAGGCAAAGGGCAAGGAAGAGTTTGTGCCTGGGAACCTTC
CAGGTGCCTCTTCTGACCATAGCCAAGAGACTGGAGACACAGACCTCCTC
CCAGCACTGAGGACAAACAGCCATGGGGCCAGTGGGGGTGCAGGGACACC
CACACCACTAAGGGCTCAGGGCGGCGCCTTCAGAGCCTGAACCTTCCTCT
CATGCTGCCATTTGAACACCACAACACCCTAATAGGAAACTGTTAACATT
GCCACTGTTCAGGTGTGGAAACCGAGACAGACAGTGGAGATTCCCTGCCC
TAGGTGACACAGGTAATAAGTGACAGATGTGGAAATTTAAAGGTACTATA
ACGTCTGTCTGCCTGACTCAGGCTTAAGGCTCCCATCACCTCCTCTTCTC
AGGACAGAGTCAGGAGGCCTCAGCCTGAGCCCCAGCTCTAGTGCAGGTTC

FIG. 4A"

ATGTGGGAATACTGAGCCTCACTAGTACAATGGCAGAGAGGACCAAATGG
GACCAGGTGTGTAAGGGTGCCTGGCACAGTTGGGGGAGGCTGCTGTCGCT
TCTCCACCGCTGCTGCTGCAGTTACCTTTGATGTTTTAGTTTTGTTGTAG
TTACACCATTGCTGGCTTTGGATCTGCACTGTGTCCACTCCAGGTGGAAC
CACGCACACAAGCCTCTCTGTCGGGCCTGTCCTGACTTCTCCTTGTCAGG
GCTGGGATCTCCTTCAAATCTGGCGGAAGTGGTTCTCCAAGTCTGGTCCT
CAAACGTCAGCAGCATCAGCGCCTAGAAGTGTTAGGAATACACATTCCCA
GGCCCCACCACAGACCTCCTGCCTCAGAAACTCAGGGCGCTGAGGCTCTA
GGGGCTGCTTTAACAAGCCTTCCAGGTTATCGTGACGCACCTTGAAAGTC
TGAGAGCTACTGCCCTACAGAAAGTTACTAGTGCCCTAAAGCTGGCGCTG
GCACTGATGTTACTGCTGCTGTTGGAGTACAACTTCCCTATAGAAAACAA
CTGCCAGCACCTTAAGACCACTCACACCTTCAGAGTGGCCTTGAGAAAGA
TTTGGGGTCAAGGATCATGAGCGAGAACACCACTTAAGAGGATAGTGAAC
TAGTCTGCATGTGAGACGCTGAGATCCTATGTCAGGCTGTGATAGGAGGG
AAACAGAAACCAAAGGAAAGAACAGCTTTAAGAAGCGCTTAAGAGGTACA
AAGTAAAATGATGGTGCTAGAAAAGTAGCTTCTTAAAAAGAGCATTTTCC
AGTCTCACCCTGGACTAACTGAATGAGAATCTCAGGAGTGTGAGGCCCAG
GTATCCATGGTCTTAAAATGCCACCCACCAGGTGATTCCCAGTGTGCACC
AGGGGTGAGAGTCACAGCCTTAGGCCATGCCACTCAAAGGGTGTCTTCAG
ACCAGCAGCACCCACAGCTCTGGGAGTGCATCAGAAAGACAGAGGCTTGG
CACCACCCACACCTACTGAACCATAGTTTGCAGGTGATTTCTTGCACATT
AAAGTGTGGGAAATGGAAAAGCTTAGAGTTCAGCTAGCTCGGTGACTCTC
AGTCAACCTGCACCTGCTCCATGAACTCAGACTGCCTGGGATGGGCCCAG
AAAAGCTCCTGAGGAGATTCTGATGTAAGGCAGGGCTGATAACCATGGAT
CTCATCTGACCCCATATCACTGGGGAGTTACTTAGGATCTTGCCTGGGGC
CAGTCATCTCTTCCATAGACACTGAGAGTGTCCACGATGCTTGGGGCACT
ACAGGGTGGGAGGTGGAGGATCACGGGTGAGTCAGATAGGAAGCCTGCTC
CTGGGGAGCTTACAGTGCTATAGGGCAGCAAGCCAAGGATGCCAATACCT
GTGTGCAGGTACCACTGACGAGTGCAGAGCGCTGCAGCACCAGAGAGGAA
GCTACCCTGTGCAGAGGGGGCTGAGGAGGGCTGCAGGGAGATGACAGGAA
AGCCGGTGTTACAGGAGGAGTCCTCCCCACTCTTTGGGCATGAGGAGACC
AGGAGGACATTCTACAGTGAGAAACCCAGGCAGAGGCCATGTGCTTATGG
CATGGGAAAAGAATGACACCTTAGACTTATTCTCTACATTAGAATTGCCT
ACCACAGATACCCATATTATAGCTTCACATAGTGTGGTGGTTACTGTGTT
TTCATATTGTCACATTTGCCATTTTCCAGCCACCCACCCATTCTTGACAG
TCACTGGCCCAGCCTGGGGGCCCCTGTTCTTTATCAAACAAGTGCCTGAG
CTCTTTGCAGAGGTGAGGGTCACCTGTCCAATCAGAGGCCAGGAGGGAAC
GTTCCCTTTTAAGACCCTACTCTAGGCAGGCCTGGCCCAAATGAGTTGCT
AGGAGCCCACGCCCTAAGAACCCTCTGAGCACTGTTGTGGCTGGTCCTGC
TGCTAGAAGTTGTTCCTCCAGGGCCAGGTGCAAGATTTGTGGCTTTTCAA
AGGAGCCACTAAAGCTCCAGCTCAGCCTTGCACGGTGCTGGGCTCCTGGG
GGCTTCCTGCCTCCAACCCTCCCAACTCTTCCATCACCGCTCCCTTAGCC
TGGCCAGTGCAGGGATCTGTTCCACTCTAGGCACTGCTGAGGGAATGATG
CCTCCAGTCAGAGGGTGCAAAAAAGAGAGTTAAGAAAAACAATGATTATA
AAAAGTCCTTTTTATACGCCAGACATTTTCTTTGCTCAGGCTAAGTGCTA
CTTATTTGAGTAAGCATTTTAGTTCTCATAACTCCTCTCTCAAGTAGGTG
CTGCTATTACTTTCATTTCACAGATGAGGACATTGAGGTTTGGAGAGACT
TAGTAACTTGTCCTCTGTCCTACAGCAGAGCTGGGATTTGAATCTATCTG
TCCAAATCTGGAACCCATTTGCTTGCACAGAAAGCTTAATTGCTTGTCCC
AGCAAGATAGAAAGCCTGGGAGTGGAAGAAATATTCAGTGGCTGTGATGT
CTGAGCCCACAGGCAGGGTGGAGAGCTAGGGCTGGGGCCCTTGGACGTGG
GGAAGAAAGGGCTGAGTCTTCCATTTTCAATGTGAAGTGTTGATATCTGG
TGATATTGATCTAGGTCCAAAGGTGAAGAACTTAAACCCGAAGAAATTCA
GCATTCATGACCAGGATCACAAAGTACTGGTCCTGGACTCTGGGAATCTC
ATAGCAGTTCCAGATAAAAACTACATACGCCCAGGTGACTCTCAGTTTTG
GCTGTGTTTTCTGCCTCCACCTAGCAGGGGTAAGGCCTCCTGCTAGGTGG
GCTCAACTCCATGCTATACCATGCCCCATCTCCAGCAGGTGGTGGAAGCG
AGGAGGAGAGGCCCCAGGGACTAGGGCATCAGATGAAGGGTCTCTAGCAA
TGACCAGATCTGAAAGTAGTCTTTCTGGAAGGGCTGGAGAAAAAGAAGGA
GGCAGACACTTAGACTGGAAGAAGAGGAGGCTTAAACCGGTGTGATGGAG

FIG. 4B"

GGAGAAGTGGACCACAGAGTCAAGGGAGAGGGACTGTGCATCAGGCCTGA
AACCCCAGCAGACAGGAGAGACCTTTCCCTGCTCTCAGAACCCACACATG
TTCTGACTGTCTTTTTCCAGAGATCTTCTTTGCATTAGCCTCATCCTTGA
GCTCAGCCTCTGCGGAGAAAGGAAGTCCGATTCTCCTGGGGGTCTCTAAA
GGGGAGTTTTGTCTCTACTGTGACAAGGATAAAGGACAAAGTCATCCATC
CCTTCAGCTGAAGGTGAGAGTTCTAGCTCAGTTTCCTGGGCCTTTGGCTA
CCCCAAAGTAAAAGGCCAAGATCCTCAATGCCTCTCGCTTTCCTGCAAAT
TCTTATCTTGGCCAATATAACAGGGACATCCACCTTTCTGGAAGCACCAG
GCAGAAGAGCCCCATAACTTCTTCTCTGGTTCCTTGCCCCTTCTAGGGAA
GGAGGAGAGACTCCTCACAGCGGGGAGACAGCAAGGAGCTGAGCACCTGT
TCTCCTCTCCTGGGCTCACTGGTCCTGGCCCTGGGCGGGTGGCGGTCCCC
TCCTGCTGTGGCCCTCCATGTGGCAAGCAACACAATTGGGCCAGGACCCT
GGCGTGCTGCTGTAGGGTAGGAGGGTGTGAGGGAGCACTCGGAGGGCAGT
GTGTCTGCCCTGCAAATTTAGTCCTGGATGGAGCATCCTTTCACTTGAGG
GGAGAAATCTTAGGAAGCTGAATTAGATACAGATCTAAGCCATATTCTCT
AATTTTAAAAACTATAGAGCTGAGATTTTGGTATCCATCTGACTCTTACG
TCTCTCTCTCTCTCTCTCTCTCTCTCAGTTTATTTTTAATCTGGGGGACA
AGAAGGCCTGGAAAAGAGGGCATGATTGCTTATCATCCCTTAAATACCAG
TACCAAGGCTGACACGTCATCTTTCCCAAGGACCATCTGCCTTCTCTCTT
TTCCTCCTCTCCTGTGTAAAGGCCTGGAGGATGAGCACATGTGCTGTGTT
TTCCTCCCTCTCAAAGCCTGTGCTATCTAATTAATCCCTTTTACCTCACA
GAAGGAGAAACTGATGAAGCTGGCTGCCCAAAAGGAATCAGCACGCCGGC
CCTTCATCTTTTATAGGGCTCAGGTGGGCTCCTGGAACATGCTGGAGTCG
GCGGCTCACCCCGGATGGTTCATCTGCACCTCCTGCAATTGTAATGAGCC
TGTTGGGGTGACAGATAAATTTGAGAACAGGAAACACATTGAATTTTCAT
TTCAACCAGTTTGCAAAGCTGAAATGAGCCCCAGTGAGGTCAGCGATTAG
GAAACTGCCCCATTGAACGCCTTCCTCGCTAATTTGAACTAATTGTATAA
AAACACCAAACCTGCTCACTAAACTTTCTGTCATTGGGTTTCATTTCTCA
TTCATGCTTTAAGGATTTGTGTTTTTAGGATATAGCAAGAAGCTTGTTTA
ATTACAAAGTTCTGGGTTGGAAAGAGACCGGCTTCTGCTTGTGTACTGCT
ACCCTGAACCATCAGACATGCATGTGTGTGTCATATGCTATGATGTGGCC
AGTCTGAGTGCAATACTTGCAGCGGGAAGGAGCAGCTGGGTGCATGCTGT
GCTCTAGAATTAGTCTTTCCTACTGGGGTTTGGTAGATTCTGAGGGCATT
GATCCTGGGGCAGAAGTGGCTGAGTCTGTGTCTAGGGTACAGTGTGCAAG
AAAGAAATGTAACAGCAAGTCACAATCCAGCCAAGTGATAGTGGAAAAGG
GGTAGTTAGGTCCCAGATAAGGAGCAGGGTGACTTGACCTGTGGGAAAGG
CACAGAGACAAGGAATCTGGGTCAGATGACAGCCAGGAGACCAGGTGAGG
GAGGAGCCAGGTACTGTCTGGGAGGCTTGTCAACAAGGGCATGGTCCTAT
CACTAAGCAGGGCTCAGATCCTCATAATGGGGGAGTGGAAGGCTGGCCGA
ACAGAAATCAGGGCCTGGAAACAGAGTGAGGGGGTGGAGACAGGAGACTG
AGGCTTGGAAATTAGTTTATTAGTTTTAGCTCTTCAGTTACAAGCAATAA
TAATAGCTTCTAGCTTATTTAAGCAACAAGTATACTACAAAAGGAGCTTT
CTAGAAGGATATTGGGTATATTCATTTCTTACTGCTGCTGTAACAAATTA
CCACCAACTTAGTGGTTTAAACAATGCAATGTATTATCTTGCAGTTATGG
AGGTCAGTCTGGAATGTGTCTCACTGGGCCAAAATCAAAGTATCAGCAGG
ATAGCATTGCTTTGGGAGGCTCTAGGGGAGAGTCAATTTCCTTGCCTTTT
CCAGCTTCCAGAGGCCACCTGCATTCCTTGGCTAGTGGCCCACTCCCATC
TTCGCTGCTTGGGTTTTTCTCACACTGCTTTGCTCTGACCCTCCTGCCTT
CCTCTTTCACATATAAGAACGCTTGCAATTTACATCGGGCTCACGTCAAT
ATCCAGGATACTCTCCCGTCTCAAAGAGGCTTAACTTTAATCACAGATGC
AAAGTCCCTTTTGCTATGTCATGTAACATATACACAGGGTCTGGGGATTA
GAATGTGGACATTTTCGGGGTGCCATTATTCTGCCTATCATGTGAAGTAA
CTTTCAAAATGGAAAGACATGCTGAAGAAAAAGTCAGGGATTTCTGGCAG
GCCAGAAATGACAGAAGGCAGAAAACGTTGGTCCCATCACTCAGATGGGT
AAGAGCCAATCATGCTTTTTGTCAGTTAGCAAAAGATTGAGATTCCAAGC
AAAGCATGCAACTGCCCTAGTTTGGGTCATGTGTCGACTCCTTGGTCAGT
GAAGGGCAGCACACCTTGATCAATACTCCCTCCAAGACTGTATCCAACGA
GGCCAGTGATGTTCCTCAAAGCAGAGCTAGAGAGCTAATCCCAGGAGAGA
GGCGTGTGGGTGGTGGGCAGGAAGACAAAGCTCAGCCGTAAAGGAGTAGT
AGGGACAGCACCCTAGGCATGGAGGCTCAAGTGAGATGATACCCATGGGA

FIG. 4C"

AAAGCTCTGATAAGGTCAGCTCCTTCTGTTTCTGATCCTGATGGTGATGG
TGATCAACACCAGCCCAGTGACAAAAAAGTACATAGTATATTTAGTAGAT
GTTTCCCACACAGAGAAATGGTAAATATTCAAGGCGAGGAATACTCCAAA
CATCCTACCTTGATCATTACACATTCCGTGCATGTAATGAGTACTTGCAT
GTATGCCATAAATATGTGAAATATTATGTATCACTATATAAAAGAAAAAA
AAATGTGGCCAGGTGACATCCATATTTTGGAGAGGAAGGCATGTCTTCTT
CATAATATCACAAAACTATTTTCACAACAAAGACACAGCTGTTCAAATTA
GTCTCTGAGCCGGGGCTGTCTCATGGCAGTGAGGACTCTGGTTCCCTTAC
AGACTAGCAGAAAGGAGATGGGGCTTACTGACCATGGCCTTGAGGAGGCT
GAACATGCAGGCCAAATGGAGACACAGACAGCCTGGGCTTGGTCCTGCTC
CATCCCCTTCCAACCTGATGAGATATAGTGAGTCACTATGACGTGGGTCA
CTCATGCTTCCTGTGAGGCTCCACCAAGACAGCAAGTGCATCAACACCTT
ACGGAAGCACAAGGCCCTGTTTGTTGTTGACTTCATGAAAGGCATGGTTG
TGGTGATCGCATTGAGTAGGCTTTTGGGTGAGAGGTGAAAAACCCCAACT
ATCATGCATTGCAGCCCTCTGGTGGAAACTGTGCTTCAGGCTCTAAATTT
CAGGCTCTAGACTGACTCCAGGATGAGTATTTGGAAGCTGAAGTCAATCT
GTGGTCTCTTCTCCTGTAGAGCAGGAGTCAGCACTTTTCATAGAGTGCCA
GATTCTATATATCCTGCCACATGCTCTGTTGTTACAGAACAAAGAAGGCC
ATAGACAGCATGGCTGTGTTGGCAAATACACAAAACAGGCAATAAGCTGT
ATTTGGCCTTTAGGCTGCAGTTTGCCAACCCCTGCACTAACACAGAGCTT
AAAGGTGGTGGTGGTGTGCTGGAGCTAGCTTATATCAGCTTGCAATAGCC
AATTGCTAACATCTCTTCCAAACTCTGTGTCTGTGCCTTGATGTTGATAG
TTTGAAATTGGCTACCCCATTTAATGCTGCAATCTTTTCTCACCCCAGCA
CTACTGACTCCCCTTTGCCCTGTCTTATTTTTCTCACTCTAACATGCTGT
ATAGTTTTCTTCTTACATTTATTGTTTGTGTCTTCCACTAGCATGTATGT
CCCACAAGTTCTTTGCTCTGTGATGTATCCCAAGAACCCACTGCAGTGCT
TGGCACTTGTAGGAACTCCATAAGATTTTTATAAATGAAGAAAGGAAGAA
AAAAGAGAGGGAGGGAAAAAGGAAAGGAAGCCTTCTATTTAAATGATGGC
CTTCTCCATATTTCTATAGTAATATGACTTCCCTTGCAAAGGGGGATGCA
TTTTGGAAAATGTGTATAAATAAACTCAGGTGGTTTTGAATTTCATTTTC
CTAACTGTAATTGTAATCATTGGTCTTTATGTTTAGTGAAAAAGTTTTGG
CCCTTATGCCTCACACCTGAGAATCCCAAAGTATTGGTTTGTTAGAGCTC
CCATAGAGAACCATAAACTGGGTGGCTTAAAACAACAGAAATGTATCGTC
TCCTGGTTCAGGAGGCCAAAGTCTGAACTCCAGGTGTTGGTTCATTCTGA
GAGCTCTGAGAGAGAATCTGTTCCAGGCTTCCCTTCAGTTTGTGGTAGCT
CCAGGGTTCCTTGGCTGGTGGCAGCAAAACTCCAGTCTCTGCCCCCATCT
TCACATGACTGTCTTCTCTCTGTGTTTCTGTGTCCAGATTGTCCTATAAG
GACAGAGTCATACTGAATTAGGGCTCACTCGAATGACTTCATCTTAAGTT
GAACTGTATCTGTAAAGACCTTATTTCCAAGTAAGGTCACATTCACAGCT
ACTGGGGGATAGGACCTCAACATATCTTTTTGGGGGACATAATTCAACTC
ATAATACCCAACATGATAACTGTTCATCCCATGAAATTTAATGTCTCTCA
AAAGGTGATCTCAGGGCATTTAATCTGTGACAGAAACTCCCATAGGAAAC
ATTCCAACCAGAAGCTCCTTTCACAGCTGGTCACTCCTCCTACCCCATCC
GAGGTCCTGGGGCAGGGTGAGGCAGGTGGGGACAAGAAGAAGGCTGTCTC
GGGTGTAGAAAGAGAAGACCCTTATTCACCCGGCACTCTGTTCATGAATG
AGCTATCCAGCATAGGATATAATAAATCGCTTTAGGAGTGGTAGACTCCA
AACATTTTTTTGGTCCCAGTTATCCTAATCAATTAAACAAACTCTAGAAC
CCATCTTGAAGTGCAGGCATTGGGACATTATGAAACTTACACAGAATTCA
AAAATTTACAAGGGCTAAATAAAACAGGGTCTGACATCTAATATTTTCTT
CCCACATTCCCATGCACTGTCTGGCTCAACCATCCCCAACCCTCACTCTC
ATCCTGGTGGACACATGCCTAGTGATGTGATCAGCTGGTTCACAGGGGGC
TGGTGATGGTGGATATACAGCTTTTGCCAATTTCCATGGCATAACTACTC
CAAATATGGCCAATTTCAAACTACCAACATGAAGGCACAGACACAGAGTT
TGGAAGAGATGTTAGCAATTGGCTATTGCAAGCTGATATAAGCTAGCTCC
AGCACAGCACCACCGCTACCTTTAAGCTCCTTGTGTTAGTGCAAGGGTTG
GCAAACTGCAGCCTAAAGGCCAAATACAGCTTACTGCCTGTTTTGTGTAT
TTGCCAACACAGCCATGCTGTCTATGGCCTTCTTTGTTCTGTAACAACAG
AGCATGTGGCAGGATATATAGAATCTGGCAGTCTTTAATAAGTGCTGACT
CCTGCTCTACAGGAGAACACAGATTGTCTTCAGCTTCCAAACATTCATCT
CTGAGTCAGTCTAGAGCCTGAAATTTAGACTGAAGCACAGTTTCCACCAG

FIG. 4D"

AGGGCTGCAATGCATGATAGTTGGGGTTTTCACCTCTCACCCAAAAGCCT
ACTCAATTTTTTACTGCAAAAACATGTTATCATCATTATTTTTTACTTAG
CCCACCTTTCCTTGGCAATTTTCCATAGGAAAATGCATTCTAAATTTCAA
CTAATCAGGGGACTTGGAGCCTCTGGACACCCCCTTGTTCCTTGCCCACA
GTCCCTTGCAGAAGGTGCCTTATCAGAGCGGCTCCATGCAGGGGCTCAGG
ACAGGATCAGATGTCAGTTGCACCAAGGGGGCAGGGACAGATCCTCTCTG
CTGACCATGCAGAAGGGACTGTTCAGTGCACCGTCATGGTCCTGGTGATT
TCTGGTCCATAAGGGAATTTTCACATGCATCGGGTGATTGTCACATCAGC
ACAACACTGTGAGGAAGGCAGAGTGAGAATTTGTGTGCCCATTTTATAGG
TGAGAAAACAGATGCAGAGACATTAAGTAACTTCACCACAGTCATGCGGG
TTTTAAGTGGCAGACTTTCAGGTGTTGTGACTCCTAGTCCAGAGTTCTTT
GCACTGCCCCTGAGGTGCTAAAACTCTACTGTGCTTTAAGACTCACTTGG
GGAGCTTCCTAAAAAGAGAGATTGCACAACCTGAGATTCTTGTTTAACTG
TTTTGGGATGTAGCTCAGGGATCTAGCTGCCTTAAAAAAAAAAAACTCCCA
AGTAATTCTGATGCAAGCGGTTCTTTTTTGTCCACCTTTGAAGAAACACT
GCCTCCTCCCCATACATTTCATTAGAAAATGGTAACATGTTTTTCAGCCT
GAGAGCCATTTCTGGGTGACCGGACGTCGGCAGCCCGCTGTACTAGCTTT
CAGTCTAGGCTTAAACACACATGATAGGAGATGTCCTACTCCAGATGATA
TGAGTCTGAACCATGGAAAAATTCCATTGTGTGGCACATCTGGTGGGTGT
GCACTGTCCCCAGCAGTGAGGCACCCAGTGAAGACAGCAGCTGGGAGAGG
CTTAGTTACATGCAGTGGGACAGTGTGGGCTAGACTGCTGAGCCCTCTGC
AGTTTACTCTGTGTCAGGCAATGAGGGTGAAAGGCTGATCAGACCCACGT
GCAGACCATACCCTCCAGGGAGACAGATATCAGTCAGGACAACCCCAAGT
GTAGCTGGAGAAGCAGTGCCCAGGTATGACCGGATGTGTATCCAACCAGG
AAATCTGCATATAAATATAAGAGGAGAAAATGAACAGATGTTGCTCTTAT
ATGTAGATATTTATGAAGAGCATATAATTTTGTTTTGTGTGTTTTAAGAA
GTTTATAAGTATGCCTTAAAAATGTATAGTATATACTGTAGGTATTTTTT
CCATTAGATATTTTGTTTTTCATACTTATCCACATTGACATTGTAGCAAC
AGTATAATATAACAACCTCCTCTACAAAAGCAGAAGGAAGTGAAGCTTTG
GAAGGAAGCACCCAGTGAGCTTGCCCCTTTCAGGTGGGTGCAGTGAGCAG
GAGTCAGTGAGGTTGAGATCCTTTGAGAGGAGGCAATCATTAACCAGGAA
ATCTGCACTGCATCCTGGCCACACCTAACCCTTGGACAATGGTGCTTGGA
GCGCCTTCCAGCTCTTAAGGCTTGCGATTTCTTTCTCTCACTCTTCACCC
ACGATGATTAAATCTTCTCCTACAGAGTTGGACAATAAAGCCTTGAGTTC
CTGCCTCCCCTGGTGTGATCACGAGGCATAGACATGGCCAGGAACATGTA
GGTGTCTTTGAAAGCTGAACAAGTTAGTAAATTTCAAACCTCATTTCACC
CACCAGTAAAATGGGAATAATAATAAACCTATTTTACATAGGGTTGACAA
GAGGAGTAAAGAGGGATTCAATGAAAGTTCGTTATTATCATTTGTAGTAG
CAGTGTTGATAATATCAACTGAAAGTTCATTATCATTATTAGTAGCAGTA
TTGATAACCCTCTTTTCTGTGCCTTCTCACTGGTGGGCCCAGGCCATCAG
CAATGCCCAGGGTGTCATGGATCTCTGCTGCATCGGGCACCAGCTGTGTC
AATGGTGAGAACAGTACAAGGGTGGGCAGGGCAAGGCAGGAAGCACCCAG
GAGCAGCAGCTTCATGGGGTGAAGATGTCAGGAGCTTAGGGACAGTCAGA
GCGGGTGTGCCTCCTCTTGTGGAGCCTTTCTGCGTGGGTAGGAACTGCTG
CAGCTGTGGCCATGGATTCACCTGAATATGGGTGGAATTAGGCATTCAGC
TGGGTTAGCTGTGCCTAGAAGGAGGAACTCTAAACTGAGAACTTGTCCCT
ATTGCCACCTCTGATAGGCAGATGATCCATCCATCAGTGGCTGAGCTGAG
GTGTGCATGGGGATGGGTAAGAGCCCACACACAGGGCTGATGACTGAGTC
TATTTAGAACAATAGATGTAAAATCTGATAATGTAAAATGTGATAGATTA
TTTTGTCAATTAGAAATGGTACCATATAATTATATATATACATAAACATG
TATACATATACACACATATACATGTGTGTATAAACACACACAGTATTGTC
CCCTACTCATTCCATAAACCTGATGCCTTTAGCTGGGATTCCCAGCTTTC
ACTCTCCTCTCTGTCATCTGCTGTCTATATCCTCCCCATCCTGTAATTCT
GGCTTATATGCCACTTCCTCCCTAAAGCCCTCCCTCAATCCCTTGCTGGA
AGTGACATTTTCCTCTTTGAGCTGCCCCTGCTTGTGCTTTGGTGAGGTCA
GCTGTATTGCAGTACCTTGTATTGTGGTTGTCACATCATCGTATAGAATT
AATTTCTGACACATTCCGTATTTTTCAAAGGGCCTAGTGTGGGGCTTTAA
CAGTAACTACGCCACCACGCCCAGTTAATTTTTTGTATTTTTGGTGGAGA
CAAGGTTTCACCATGTTGGCCGGGCTGGTTTCGAACTCCTGACTTCAGGT
GATCTGTCTGCCTCAGCCTCCTGGAGTGCTAGGATTGCAGGCATGAGCCA

FIG. 4E"

CTGCACCCAGCCACCTATCAAAATTTTAAGTGCCATTTTTATTTTTTATT
TTTTGTAGAAATGGACAAGCTGATCGCAAAATTCACATGGAATTGCAGGA
GGTTCCAAATAGCCAAAACAATCTTGAAAAAGAAGAACAAAGTTGGAGGA
TTTACACTTTCCAGTTTCAAGACTTAGCTCTTAGCTACAAAGCTACAGTA
ATCAGAACACTATGGTCCTGGCATAAGTGATGCTGGACAGGTGAGCCCCA
AAGTGGGACTTAACCTGTGAAGGTTCTTGGCCTTGCCCAGGAAGGAATTC
AAGGGCAAGCCAATGGGACAAGAAAACAGCTTTATTGAAGGGGCAGTATT
ACAGCTCCAGCCCTGTTACAGCTCCAGCCCTGTTACAACTCTGACTACTC
CTGCACAGAAGGGCTACCCTGTAGGCAGAGAGTAGCAACTCAGGGCAGTT
TTGCAGTCATTTATATCCACTTTTAACACATGCAGATTAAGGGACAATTT
ATGCAGAAATTTCTACGGAATTGGTAATAACTTTTGGGTCATGGAGTCAT
CATGGAAGGGGGGCGGGGAACTCCCTGGTGTTGCCATGATGACGGTAAAC
TGATATGGCGAACTGGTGGGTATGTCACATGAAAAGCTCCTTCCACCCCA
GCCCTGTTTCAATTAGTCCTCGGTTTGGTCCAGTGTCCAAGTCCTGCCTC
CAGAGTCAAGTCCCACCCCCTACCTCTTAAGGAGAGATGTAAATACATGG
AATAGAATTGAGAGTCCAGAAATAATCTCATACATCTATGATCAATTGAT
TTTCAGCAAAGGTGCCAAGACCATTCAATGAGGGAAAGAATCATATTTTT
TTCAACAAATGGTGCTGGATAACCACATGTGAAAGAATGCAACTGGGCCC
TTATCTCACACCATATACAGAAATTAACTCAAAATGGCTCAAACACTTAC
ATGTAAGAGCTAAAACTATAATATTCTTAGAAGAAAACAGGGATATATCT
TTATGACCTTGGATTTGCTGGCTGATTCTTAAATGACACTGAAAGCACAA
GCAACAAAAGAAAAAAAAATAGGTAAATTGGACCTCATCAAAATTTAAAA
CTTTTATGCTGGGTGCACACCTGTAATCCCAGCACTTTGGGAGGCTGAGG
CAGGAGGATCTCTTGAGCCCAAGAAGCTGAGGCTACAGTGAGCCGAAATT
GTGCCACTGCACTCCAGCCTGGGTGACAGAGCAAGACCCTGTCTCGAATA
AATAAATAAACAAATATATAATTATAGATCTCTGGATCTTGCCTTCGGAG
ACTGACTCAACTAACTGGTCTGGGTGGAGCCCAGCCATTTGTATTTTTT
GAAAACTCTCCAAATGATTTTACTGTGCAGCCAAGGTTGAGAATCACTGT
ATCATAGGGTTGGACTCCTAACTGGAAACAGTTTGCACCATCAGGTGTCG
CAGCATTCTGATAATAGTTAAGCTTTCCTCCTAGATTTTCTGATATTAGA
TGAGTCATGTTTACAAGTTTTTACCAAGAGACAAACTATCTTTCTGCCCT
TACTTTCTCTCTTATACTATTCTAATCCCAGAACCCTTTGGAACTTCCAC
TGAGAGATGAATCTAGAAAGTGACTCTCTTGGCTACAACAGAGAGTAATG
TTGGCCTGTTTGTGCCAGATCCAGTTGGTGCTGGTGGTGGGACAGCACCT
CCCTGAAATCCCCTCCTCTCCCGTCAGATTCAGTCCCCCATTTGCATCAC
GTACAATCATCACTATGGGTTTCTATTACCTTGCTAGGGCATTTGGAGGT
ACCATATATACCAACTATTAGTTTTGAGCCATGGTTCCCAAAGTGTGGAC
TGTAGGGCACCTCAGCACACTCACGAGGTGTCATGGGATATTTAAATATT
CTGAAGAAAACACAGTGACATCTGTCAGGCCCGTGAAAACCGTTGGCATT
AAATTGTCTCAACCCAATTGCTTAAGAAGCAGAACTGGCCAGGCACGGTG
GCTCACATCTGTAATCCCAGCACTTTGGGAGGCCGAGGCGGGCAGATCAC
GAGGTCAGGAGTTCGAGACCAGCCTGACCAACATAGTGAAACCCCGTCTC
TACTAAAAATATAAAAATTAGCCATGCATGGTGGCATGCACCTGTAACCC
CAGCTACTCAGGAGGCTGAGGCAGGAGAATTGCTTGAACCTGGGAAGCGG
AGGTTGTAGTGAGCCAAAATCGTGCCACTGCACTCCAGCTTGGGTGATAG
TGAGACTACATCTCAAAAAAAAAAAAAATGAGAGAGAGAGAGAGAAGCAGA
ACCATCAGGTGTTTCTTTTGGCTTAAAGTACTCTGTGAAGAAATTCCTGG
GACACGAAGGATACCATGAACTGAGAGATTTTGGGAACCTCTGCTTTAGA
AGCTGGAGGTAGCATTCCTTGGGCACAGTACTGCCTTGGGATCAGCAAAT
CCTTTTGATGGTGCATTTAGGTGTGGCAAGACAGCTCTTAGAGTGGGACC
GGGATGTGCTTGGAGACAGAGGGAACTAGATTGAGCTGCCCGATAAAGAC
ATGCCAGCCTGGCAGAGTGTAGTGACTCATGTCTGTAATCCTAGTGCTTT
GGGAGGCTGAAGTGGGAGGATTGCTTGAGGCCAGGGGTTTGAGATCAGCC
TGGGAAACAACAAGACCTCTACAAAAAAAAAAGAAAAAAAAAATTAACCA
CATGTGGTGGCATGCACCTGTAGTCCCAGCTACCTGGCAGGCTGAGGTAG
GAGGATCACTTGAGCCCAGGAAGGTAAGGATACATTGAGCCATGACTGTG
CCACTGCACTCTAGCCTGGGTGACAGAAAGAGACTCTGTCTCAGAAATAA
ATTAAATAAATAAATAAATATATAGTGGCCATGACATCCCTAGAAAGACA
AGGTCCTGGGAATAGGTAGAAGCCAAGGGAAATGAGAAATGAGAGGGGGC
CCTGGAGCTGGAACTGGGGGAGCAGGATGGCCTCTGAGAAGTTCCTGATA

FIG. 4F"

GTGGTGTCACTGATGTGTCTGATGTTTAGTTGTAATTATTTGCTGGGCCC
CTGTCATCCCTCATATCTGATAGCTCTTTGCTAGTCAAAGTGTGGTCTGG
GGATCAGCGGCATCAGCATCACTTGAGAACTTGTTAGAGATGCAGAATCT
AGAGCCCCACCCGGGACCCAGAAACAGAGCCTGCATTTTAACAAGCTCCC
CAGGTGATTCTCACACACACTCGCATTTGAGAAGCACTGGGCTAGTTGAC
AGATTCTCAGGCATGGCTGACATTGAAATATCCAGGGAGCAGGCTTGGCA
TTAGGATGTTTAAAAGTCCTCCAGGTGTTTCTAAAGCCAGGTTTGAGGAA
TTACTGGGCTGATACAAATGTTTTGTGATGATGCTTTGTGTGTGTGTGTG
TGTGTGTGTGTGTGTGTGTGTGTGTGTGTGTGTGTGTGTGTAGGGAATTC
TGGGTCACTTGGCACCAACACAGGAAACAATGGAAATATGTGAGCCATGA
CAGAAAGGTCAGGAGATAAAAGAAATTAGTGACATGAGAGGTACTCCTCA
GGTGTTAGGAAAGAGGGTAGAGCAAACCAGGTTTTCCACCATATGTTGGA
TAGGGGGTCAAGTAAATTTCTACTTAAAAATTACAAACAGGGGCTGGGCG
CGGTGGCTCATGCCTGTAATCCCGCACTTTGGGAGGCTGAGGAGGGCGGA
TCACAAGGTCAAGAGATTGAGACCATCCTGGCCAACACGGTGAAACCGTG
TCTCCACTAAAAATACAAAAATTAGCTGGGCATGGTGGTGCGTGCCTTTA
TTCCCAGCTACTCGGGAGGCTGAGGCAGGAGAATCGCTTGAACCTGGGAG
GTGGAGGTTGCAGTGGGCCGAGATCGCACCACTGCAATCCAGAGCGAGAC
TGTGTCAAAAAAAAAAAAAAAAAAGAAAATTCCAAACAGGATGACCCTAAG
CCTGCAGGACTTGGAGACATCTAGGTGACTGATACTCAGTCACAAAACAT
AATTGGTCACAGGCCTGATGAAATGCACAGCAGACCTTCAGATGGTATGC
ACTCAAGTGATATCCACAAGTCCACCTAAAGAAATGCTATATTCAGACAT
TTGGCATCAATCTCTATCAAACAAAGATAGTCCAAAGCAATGGGTTCCAA
AAACACTTTCCTAAGACAAATTCTCTATTTGCTTTTAATATCAGTCATCC
CAGCCCTTGGAATAGAGGAGCAAATGATACCAGTGGTACCCTACCACAAT
GCACCAAGGTATTATACTCTCATGCTCCATTTTCTCCCTCTGTCTACATC
ACTAATAACTCATTGATTTCTGGTGCAAGCCCTGCTGGGAGAAAAAGTCT
ACTCTTGTACCTTGGAGCAAGTTGCTCAGAGTAGGTATCGAGGATAAAAT
TTGGAAAGTTAGAAAAGCTATTAGAAGGAGATCCTAGTAGTTGAAAACAC
AGCCTGGCCAAGTCAATGATGCTATTTCATCTCCCCAGCCTTGCATGTCC
ATAGCTAAGGAAGACAATTTAGGCTTGGGCTAGAGGATGGGAAAGGGCAA
AATTACTGATGCCACAGCCCAGAGAGGTATTCTAGTAATCTGAGGGTGAG
GACCACATACCTGGTTCAGGGACGTACAGTGTTGACAGCTGTGAGTGGAT
GCCTGGAGTTCTGGCGTGTCTTCTAGCACAATGATACCTGAGACTCTTGC
ATCATTGGGAATAATAAAATGGGAGTGGATAGATATGAAATTATGATGGC
AATAAGCAATCAGCTAATAGCTTCATTGATGGGACAGATTAAAGATGGCT
GCAAATCCTTTGGTCCAGGTTTGGGATATAGGCAGCATTTGTATTGGAAT
GCTGATAGTCTGAGGCCATGAAAAGTCCACCTGCAGTAGTGGTAGGAGGA
ACAAGCCTCACTTTCTTCAATGTGTGTGACTGCTGTCTTGATTCCCTGGG
TGGCCAGTTCCATTCGTGTGGTTCTTTGGTCCACTTGACTCTGGGGTGGC
TCTGTGATGGCTTGACCAATACAATGTAGTGGAAATGATGCTGTCATCAT
TTCCAGCCTCTTCCAGCCTTAAGGAACTGGCAACTTTTATTTCTGTCCCT
TGGAATACTTGTTCTTGCAACCCATCCATCATACAGTGAGAAATTCTAAG
CTGCCCCATTAAGAGGCCCACATGGTGATAAATTGGGGTCTTACATACAG
CCCTAGCTGTGCTCCTAGCTGACAAACAGTAGCAACTTGTCACCAGGCGA
GTGAACCACTTAGGACTGTATACTCCAGCCCCAGTTGAGCAATGTGGAAC
AGAGTAAACCATCTCAGCTTAGCCCTGCCCAAACTGCAGAATTATGAGCA
AAATAATCCCCTAGGCTTTGGGCTGATTTGTTCCAGATTACTGGAACAGA
ATTTGGTACCAGGGGTGAGGTGCTACAGCAATGAAAGCTTAAGACACGTG
ACTTTGGTTTTGGGTCTGAGTGGCAGGGGAACTTGGCAGGCCTCAAGGAA
ACTTTTAGGGAGGGTTGAAGCATAGTGAGGAAAACAGTAGGGGAAGCTAG
AGGAAAAAATGATGCTTGGTATGTAGTGGTGGGAAGTTTAGCAAAACTCG
CCTGATGTAATGTGGGAAATTGTAAGAACTCAGAACGATTTAAGGGCATG
TTTTATAGGTCCTTTAAGAAACTTCTAGGCCAGGCGCAGTGGCTCATGTC
TGTAATCCCAGCACTTTGGGAGGCTGAGGTGGGCGGATCACAAGGTCAGG
AGATCGAGACAATCCTGGCTAACATTGTGAAACCCCGTCTCTACTAAAAC
TACAAAAAAAAAATTAGCCGGGCATGGTGGCGGGTGCCTGTAGTCCCAGCT
ACTAGGGAGGCTGAGGCAGAAGAATGGCGTGAACCTGGGATGTGGATCTT
GAAGTGAGCCCAGATTGTGCCACTGCACTCCAGCCTGGGCAACAGAGTGA
GACTCCGTCTCAAACCGAAAAAAAAAAAAAAAAAAAAGAAACTTCTAGGGC

FIG. 4G"

TGGTCCCGTGGAAGCCTCACACATGGTACACAAAGGCTGTCTTGAAAAGA
AACGTAAGTGTGTTTTTTGGTTTAATAAAATTGATTATAAATGGATAATG
CAAAACATTTTAAAGAATTTTACTAGCTTACATTAGCAGATTTGGATCCA
GTGATTGTTACATTCTGGTACTGAGCCCCTGAATTACTTCTTTGAGTAAG
GCATTATACCAAAGCTATTGATAGTTGGGCTTATAGGGTGTATGTTTGAA
GAACTACTAATGTCAAAACCAATATTTCACGGTCGACAAGAGGACATCAG
AACTGGTAATCCTTATTACCATGACTGGCTGGACAGAATACTCAATGTAA
TGGGATTTCCTGCAAATAAAGACGGGGAAGATGTAAAAAAGATGCCTGAA
CATTCAACATTAATGAAAGATTTCAGAAGAAATATGTATACTAACTGCAG
CCTTATCAAGTATATGGAAAAACACAAAGTTAAACCAGATAGTAAAGCAT
TCCACTTGCTTCAGAAGTTTCTTACTATGGACCCAATAAAGTGAATTACC
TGAGAACGGGGTCCCTGTTTCTTCGAAGACCCACTTCCTACATCAGACGT
TTTCAACAGTTGTCAAATCCCCTACCCAAAATGAGAATTTTTAACAGAAG
AAGAACCTGATGACAAAGGAGCCAAAAAGAACCACCACCGGCAGCAGGGC
CATAACCACACGAATGGAACTGGCCACCCAGGAATCAAGACAACGGTCAC
ACACAGGGACCCCCGTTGAAGAAAGTGAGGCTTGTTCCTCCTACCACTAC
CTCAGGTGGACTTTTCACGGCCTCAGACTATCCGCGTTCCAATCCACATG
CTGCCTATATCCCAACCCTGGACCAAGCACATCCCAGCCGAAGAGCAGTG
TAGGATACTCAGCTACCTCCCAGCAGGCTCCACAGGACCCACGTCAGACA
CACGGGTACTGAGCTGCATCGGAATCTTGTCCGTGCACTGTTGTGAATGC
TGCAGGGCTGACTGTGCAGCTCTCCGTGGGAACCTGGTATGGGCCATGAG
AATGTACTGTACAACCACACCTGCCCAGTAGCCAAGTTCCTTCCACCGCT
TTTCACAGATCGGGGTAGTGGCTTCCAGTTTGTACCTATTTTGGAGTTAG
ACCTGAAAAGAAAGCGCTAGCACAGTTTGTGTTGTGGATTTGCTACTTTC
ATAGTTAACTTGACCTGGCTCAGACTGACCAGTACTTTTTTTCCGTGAC
AGTCTATAGCAGTTGAAGCTGAGAATGTGCTAGGGGCAAGCGTTTGTCTT
CATATGTCATGAATTCCTCCAGTGTAACAACATTATCTGACCAATAGTAC
ACACACAGACACAAGGTTTAACTGGTACTTGAAAACATACAGTAGGTGTT
AACTCAGTGAAATAACCAGGACTCAAAGTAAGATTATTTTGGTACACCTT
TCTTGTTAGTGTCTTATCAGTGAGTTGATTCATTTTCTACATTAATCAGT
GTTTTCTGACCAAGAATATTGCTTGGATTTTTCTGAAAGTACAAAAAGCC
ACATAGTTTTTTTCAGAAAGGTTTCAAAACTCCTAAAGATTAATTTCCAA
GTATAAGTTTGTTTTTATTTTCAATCTATGACTTGACTGGTATTAAAGCT
GCTATTTGATAGTAATTAGATATATTCTCATTGATATAAACCTGTTTGGT
TCAGCAAACAAACTAAAATGATTGTCACAGACAATGCTTTATTTTTCCTG
TTGGTGTTGCTTGTGGGAAAAAGAAAGAGAGATCAGATTGTTACTGTGTC
TGTGTAGAAAGAAGTAGACATAGGAGACTCCATTTTGTTCTGTACTAAGA
AAAATTCTTCTGCCTTGAGATGCTGTTAATCTATATAACCTTACCCCCAA
CCCTGTGCTCTCTGAAACATGTGCTGTGTCCACTCAGGGTTAAATGGATT
AAGGGCGGTGCAAGATGTGCTTTGTTAAACAGATGCTTGAAGGCAGCATG
CTCGTAAGAGTCATCACCACTCCCTAATCTCAAGTACCCAGGGACACAAA
CACTGCTGAAGGCCGCAGGGACCTCTGCCTAGGAAAGCCAGGTATTGTCC
AAGGTTTCTCCCCATGTGATAGTCTGAAATATGGCCTCGTGGGAGGGGAA
AGACCTGACCGTCCCCCAGCCCGACACCCGTAAAGGGTCTGTGCTGAGGA
GGATTAGTATACGAGGAAGGAACGCCTCTTTGCAGTTGAGACAAGAGGAA
GGCATCTGTCTTCTGCCCGTCCCTGGGCAATGGAATGTCTCGGTATAAAA
CCCGATTTTATGTTCCATCTACTGAGATAGGGGAAAACCACCTTAGGGCT
GGAGGTGGGACATGCGGCAGCAATACTGCTCTTTAAGACATTGAGATGTT
TATGTGTATGCATATCTAAAGCACAGCACTTAATTCTTTACCTTGTCTAT
GTTGCAGAGACCTTTGTTCACGTGTTTATCTGCTGACCTTCTCTCCACTA
TTATCCTATGACCCTGCCACATCCCCCTCTCCGAGAAACACCCAAGAATG
ATCAATAAATACTAAGGGAACTCAGAGGCCGGCGGGATCCTCCATATACT
GAACGCTTGTCCCCTGGGCCCCCTTATTTCTTTCTCTATACTTGGTCTCT
GTGTCTTTTTCTTTTCCAAGTCTCTCGTTCCACCTAATGAGAAACACCCA
CAGGTGTAAAGGGGCAACCCACCCCTTCATTGCTGATTTGTGAGCGTGCT
TTAAGGTGAAAAAAGCATGAATGTTAACTTCCTTAAAAAGGTACAGCATC
CAATTCAAATATTTTTGTCCTGATTTTAATGCTAGTTGATGTAGTGCTAT
TAAAATTTTGTTCAACATGGACACAGAGAGGGGAACAACACATACCAGGG
CCTGTTGCGGGGTGGGGATGAGGGGAGGGAACTTAGAGGACAGGTGAACA
GGTGCAGCAGATCACCATGGCCCACATATACCTATTTAACAAACCTGCAC

FIG. 4H"

GTTCTGCACACGTATCCCATTTCTTTTTTTTTTTAAGAAATAGAAAAAAA
AATAAAATTTTGTTCACTGATTCTTCCATTTTAAAACTTGTTTGCATGTG
GTTTAGGATGCCCTTACTTCAGCAAAGGAGAAGGAATAGGAGGGCCTTAG
AATTTTTGAGGGAAAAAAACCCTATAACATACATTGTACTGTATCAAACT
ATTTTACATGAATGACACAAGTATTCTGAATAAAAAAATAATTGAACATT
GTTAAGAACAAGGTGTCATGTAATTTATTTTTCATAAATAAAAAAATTAT
AGTGGCTTAGACTGAAAGGAACAGAGAATTTAAAAAATTAAAAAGAAGCC
TTAGTATATTTTTGTATATAGTTTCCATGTGCCATATTTGCCATAATTGG
ATGAGAATTTTTTGACCTCTGGCAGGGTGACCCTATATTTTCANTNTATA
AAGCGTGCATCATACC

FIG. 4I"

MVLKCHPPGDSQCAPGVRVTALGHATQRVSSDQQHPQLWECIRKTEAWHHPHLLNHSLQPGGPCSLSNKCLSSLQRSASA
EKGSPILLGVSKGEFCLYCDKDKGQSHPSLQLKEKLMKLAAQKESARRPFIFYRAQVGSWNMLESAAHPGWFICTSCNCN
EPVGIXNXVDFDLLGKAQKRGTGSE

FIG. 5

NUCLEIC ACID MOLECULES ENCODING TANGO-77-POLYPEPTIDES

RELATED APPLICATION INFORMATION

This application claims priority from provisional application Ser. No. 60/054,646, filed Aug. 4, 1997, and from provisional application Ser. No. 60/091,650, filed Jul. 2, 1998.

BACKGROUND OF THE INVENTION

The polypeptide cytokine interleukin-1 (IL-1) is a critical mediator of inflammatory and overall immune response. To date, three members of the IL-1 family, IL-1α, IL-1β and IL-1ra (Interleukin-1 receptor antagonist) have been isolated and cloned. IL-1α and IL-1β are proinflammatory cytokines which elicit biological responses, whereas IL-1ra is an antagonist of IL-1α and IL-1β activity. Two distinct cell-surface receptors have been identified for these ligands, the type 1 IL-1 receptor (IL-1RtI) and type II IL-1 receptor (IL-1RtII). Recent results suggest that the IL-1RtI is the receptor responsible for transducing a signal and producing biological effects.

As mentioned above, IL-1 is a key mediator of the host inflammatory response. While inflammation is an important homeostatic mechanism, aberrant inflammation has the potential for inducing damage to the host. Elevated IL-1 levels are known to be associated with a number of diseases particularly autoimmune diseases and inflammatory disorders. Since Il-1ra is a naturally occurring inhibitor of IL-1, IL-1ra can be used to limit the aberrant and potentially deleterious effects of IL-1. In experimental animals, pre-treatment with IL-1ra has been shown to prevent death resulting from lipopolysaccharide-induced sepsis. The relative absence of IL-1ra has also been suggested to play a role in human inflammatory bowel disease.

SUMMARY OF THE INVENTION

The present invention is based, at least in part, on the discovery of a gene encoding Tango-77, a secreted protein that is predicted to be a member of the cytokine superfamily. The Tango-77 cDNA described below (SEQ ID NO:1) has three possible open reading frames. The first potential open reading frame encompasses 534 nucleotides extending from nucleotide 356 to nucleotide 889 of SEQ ID NO:1 (SEQ ID NO:3) and encodes a 178 amino acid protein (SEQ ID NO:2). This protein may include a predicted signal sequence of about 63 amino acids (from about amino acid 1 to about amino acid 63 of SEQ ID NO:2 (SEQ ID NO:4) and a predicted mature protein of about 115 amino acids (from about amino acid 64 to amino acid 178 of SEQ ID NO:2 (SEQ ID NO:5)).

The second potential open reading frame encompasses 498 nucleotides extending from nucleotide 389 to nucleotide 889 of SEQ ID NO:1 (SEQ ID NO:6) and encodes a 167 amino acid protein (SEQ ID NO:7). This protein may include a predicted signal sequence of about 52 amino acids (from about amino acid 1 to about amino acid 52 of SEQ ID NO:7 (SEQ ID NO:8)) and a predicted mature protein of about 115 amino acids (from about amino acid 52 to amino acid 167 of SEQ ID NO:7 (SEQ ID NO:9)).

The third potential open reading frame encompasses 408 nucleotides extending from nucleotide 481 to nucleotide 889 of SEQ ID NO:1 (SEQ ID NO:10) and encodes a 136 amino acid protein (SEQ ID NO:11). This protein includes a predicted signal sequence of about 21 amino acids (from about amino acid 1 to about amino acid 21 of SEQ ID NO:11 (SEQ ID NO:12)) and a predicted mature protein of about 115 amino acids (from about amino acid 22 to amino acid 136 of SEQ ID NO:11 (SEQ ID NO:13)).

As used herein, the terms "Tango-77", "Tango-77 protein", "Tango-77 polypeptide" amd the like, can refer and polypeptide produced by the cDNA of SEQ ID NO:1 including any and all of the Tango-77 gene products described above.

Tango-77 is expected to inhibit inflammation and play a functional role similar to that of secreted IL-1ra. For example, it is expected that Tango-77 may bind to the IL-1 receptor, thus blocking receptor activation by inhibiting the binding of IL-1α and IL-1β to the receptor. Alternatively, Tango-77 may inhibit inflammation through another pathway, for example, by binding to a novel receptor. Accordingly, Tango-77 may be useful as a modulating agent in regulating a variety of cellular processes including acute and chronic inflammation, e.g., asthma, chronic myelogenous leukemia, rheumatoid arthritis, psoriasis and inflammatory bowel disease.

In one aspect, the invention provides isolated nucleic acid molecules encoding Tango-77 or biologically active portions thereof, as well as nucleic acid fragments suitable as primers or hybridization probes for the detection of Tango-77.

The invention encompasses methods of diagnosing and treating patients who are suffering from a disorder associated with an abnormal level (undesirably high or undesirably low) of inflammation, abnormal activity of the IL-1 receptor complex, or abnormal activity of IL-1, by administering a compound that modulates the expression of Tango-77 (at the DNA, mRNA or protein level, e.g., by altering mRNA splicing) or by altering the activity of Tango-77. Examples of such compounds include small molecules, antisense nucleic acid molecules, ribozymes, and polypeptides.

The invention features a nucleic acid molecule which is at least 45% (e.g., 55%, 65%, 75%, 85%, 95%, or 98%) identical to the nucleotide sequence shown in SEQ ID NO:1, SEQ ID NO:3, SEQ ID NO:6, SEQ ID NO:10, the nucleotide sequence of the cDNA insert of the plasmid deposited with ATCC® as Accession Number (the "cDNA of ATCC® 98807"), or a complement thereof.

The invention features a nucleic acid molecule which includes a fragment of at least 100 (e.g., 250, 325, 350, 375, 400, 425, 450, 500, 550, 600, 650, 700, 800, 900, or 989) nucleotides of the nucleotide sequence shown in SEQ ID NO:1, SEQ ID NO:3, SEQ ID NO:6, SEQ ID NO:10, the nucleotide sequence of the cDNA ATCC® 98807, or a complement thereof.

The invention also features a nucleic acid molecule which includes a nucleotide sequence encoding a protein having an amino acid sequence that is at least 45% (55%, 65%, 75%, 85%, 95%, or 98%) identical to the amino acid sequence of SEQ ID NO:2, SEQ ID NO:5, SEQ ID NO:7, SEQ ID NO:9, SEQ ID NO:11, SEQ ID NO:13, or the amino acid sequence encoded by the cDNA of ATCC® 98807.

In a preferred embodiment, a Tango-77 nucleic acid molecule has the nucleotide sequence shown in SEQ ID NO:1, SEQ ID NO:3, SEQ ID NO:6, SEQ ID NO:10 or the nucleotide sequence of the cDNA of ATCC® 98807.

Also within the invention is a nucleic acid molecule which encodes a fragment of a polypeptide having the amino acid sequence of SEQ ID NO:2, SEQ ID NO:4, SEQ ID NO:5, SEQ ID NO:7, SEQ ID NO:8, SEQ ID NO:9, SEQ ID NO:11, SEQ ID NO:12, SEQ ID NO:13, wherein the fragment includes at least 15 (e.g., 25, 30, 50, 100, 150, or 178)

contiguous amino acids of SEQ ID NO:2, SEQ ID NO:4, SEQ ID NO:5, SEQ ID NO:7, SEQ ID NO:8, SEQ ID NO:9, SEQ ID NO:11, SEQ ID NO:12, SEQ ID NO:13, or the polypeptide encoded by the cDNA of ATCC® Accession Number 98807.

The invention includes a nucleic acid molecule which encodes a naturally occurring allelic variant of a polypeptide comprising the amino acid sequence of SEQ ID NO:2, SEQ ID NO:4, SEQ ID NO:5, SEQ ID NO:7, SEQ ID NO:8, SEQ ID NO:9, SEQ ID NO:11, SEQ ID NO:12, SEQ ID NO:13, or an amino acid sequence encoded by the cDNA of ATCC® Accession Number 98807, wherein the nucleic acid molecule hybridizes to a nucleic acid molecule comprising SEQ ID NO:1, SEQ ID NO:3, SEQ ID NO:6, SEQ ID NO:10, or a complement thereof under stringent conditions.

Also within the invention are: an isolated Tango-77 protein having an amino acid sequence that is at least about 45%, preferably 65%, 75%, 85%, 95%, or 98% identical to the amino acid sequence of SEQ ID NO:5, SEQ ID NO:9 or SEQ ID NO:13 (mature human Tango-77), or the amino acid sequence of SEQ ID NO:2, SEQ ID NO:7 or SEQ ID NO:11 (immature human Tango-77).

Also within the invention are: an isolated Tango-77 protein which is encoded by a nucleic acid molecule having a nucleotide sequence that is at least about 65%, preferably 75%, 85%, or 95% identical to SEQ ID NO:3, SEQ ID NO:6, SEQ ID NO:10 or the cDNA of ATCC® 98807; and an isolated Tango-77 protein which is encoded by a nucleic acid molecule having a nucleotide sequence which hybridizes under stringent hybridization conditions to a nucleic acid molecule having the nucleotide sequence of SEQ ID NO:3, SEQ ID NO:6, SEQ ID NO:10, the non-coding strand of the cDNA of ATCC® 98807, or the complement thereof.

Also within the invention is a polypeptide which is a naturally occurring allelic variant of a polypeptide that includes the amino acid sequence of SEQ ID NO:2, SEQ ID NO:4, SEQ ID NO:5, SEQ ID NO:7, SEQ ID NO:8, SEQ ID NO:9, SEQ ID NO:11, SEQ ID NO:12, SEQ ID NO:13, or an amino acid sequence encoded by the cDNA insert of the plasmid deposited with ATCC® as Accession Number 98807, wherein the polypeptide is encoded by a nucleic acid molecule which hybridizes to a nucleic acid molecule comprising SEQ ID NO:1, SEQ ID NO:3, SEQ ID NO:6, SEQ ID NO:10 or the complement thereof under stringent conditions.

Another embodiment of the invention features Tango-77 nucleic acid molecules which specifically detect Tango-77 nucleic acid molecules relative to nucleic acid molecules encoding other members of the cytokine superfamily. For example, in one embodiment, a Tango-77 nucleic acid molecule hybridizes under stringent conditions to a nucleic acid molecule comprising the nucleotide sequence of SEQ ID NO:1, SEQ ID NO:3, SEQ ID NO:6, SEQ ID NO:10, the cDNA of ATCC 98807, or a complement thereof. In another embodiment, the Tango-77 nucleic acid molecule is at least 300 (325, 350, 375, 400, 425, 450, 500, 550, 600, 650, 700, 800, 900, or 989) nucleotides in length and hybridizes under stringent conditions to a nucleic acid molecule comprising the nucleotide sequence shown in SEQ ID NO:1, SEQ ID NO:3, SEQ ID NO:6, SEQ ID NO:10, the cDNA of ATCC® 98807, or a complement thereof. In yet another embodiment, the invention provides an isolated nucleic acid molecule which is antisense to the coding strand of a Tango-77 nucleic acid.

Another aspect of the invention provides a vector, e.g., a recombinant expression vector, comprising a Tango-77 nucleic acid molecule of the invention. In another embodiment, the invention provides a host cell containing such a vector. The invention also provides a method for producing Tango-77 protein by culturing, in a suitable medium, a host cell of the invention containing a recombinant expression vector such that a Tango-77 protein is produced.

Another aspect of this invention features isolated or recombinant Tango-77 proteins and polypeptides. Preferred Tango-77 proteins and polypeptides possess at least one biological activity possessed by naturally occurring human Tango-77, e.g., (i) the ability to interact with proteins in the Tango-77 signalling pathway (ii) the ability to interact with a Tango-77 ligand or receptor; or (iii) the ability to interact with an intracellular target protein, (iv) the ability to interact with a protein involved in inflammation and (v) the ability to bind the IL-1 receptor. Other activities include the induction and suppression of polypeptide interleukins, cytokines and growth factors.

The Tango-77 proteins of the present invention, or biologically active portions thereof, can be operably linked to a non-Tango-77 polypeptide (e.g., heterologous amino acid sequences) to form Tango-77 fusion proteins. The invention further features antibodies that specifically bind Tango-77 proteins, such as monoclonal or polyclonal antibodies. In addition, the Tango-77 proteins or biologically active portions thereof can be incorporated into pharmaceutical compositions, which optionally include pharmaceutically acceptable carriers.

In another aspect, the present invention provides a method for detecting the presence of Tango-77 activity or expression in a biological sample by contacting the biological sample with an agent capable of detecting an indicator of Tango-77 activity or expression such that the presence of Tango-77 activity or expression is detected in the biological sample.

In another aspect, the invention provides a method for modulating Tango-77 activity comprising contacting a cell with an agent that modulates (inhibits or stimulates) Tango-77 activity or expression such that Tango-77 activity or expression in the cell is modulated. In one embodiment, the agent is an antibody that specifically binds to Tango-77 protein. In another embodiment, the agent modulates expression of Tango-77 by modulating transcription of a Tango-77 gene, splicing of a Tango-77 mRNA, or translation of a Tango-77 mRNA. In yet another embodiment, the agent is a nucleic acid molecule having a nucleotide sequence that is antisense to the coding strand of the Tango-77 mRNA or the Tango-77 gene.

In one embodiment, the methods of the present invention are used to treat a subject having a disorder characterized by aberrant Tango-77 protein activity or nucleic acid expression by administering an agent which is a Tango-77 modulator to the subject. In one embodiment, the Tango-77 modulator is a Tango-77 protein. In another embodiment, the Tango-77 modulator is a Tango-77 nucleic acid molecule. In other embodiments, the Tango-77 modulator is a peptide, peptidomimetic, or other small molecule. In a preferred embodiment, the disorder characterized by aberrant Tango-77 protein or nucleic acid expression can include chronic and acute inflammation.

The present invention also provides a diagnostic assay for identifying the presence or absence of a genetic lesion or mutation characterized by at least one of: (i) aberrant modification or mutation of a gene encoding a Tango-77 protein; (ii) mis-regulation of a gene encoding a Tango-77 protein; and (iii) aberrant post-translational modification of a Tango- 77 protein, wherein a wild-type form of the gene encodes a protein with a Tango-77 activity.

In another aspect, the invention provides a method for identifying a compound that binds to or modulates the activity of a Tango-77 protein. In general, such methods entail measuring a biological activity of a Tango-77 protein in the presence and absence of a test compound and identifying those compounds which alter the activity of the Tango-77 protein.

The invention also features methods for identifying a compound which modulates the expression of Tango-77 by measuring the expression of Tango-77 in the presence and absence of a compound.

Other features and advantages of the invention will be apparent from the following detailed description and claims.

BRIEF DESCRIPTION OF THE DRAWINGS

FIG. 1 depicts the cDNA sequence (SEQ ID NO:1) of Tango-77. The Tango-77 cDNA has three possible open reading frames which encode the amino acid sequence (SEQ ID NO:2, SEQ ID NO:7 and SEQ ID NO:11) of human Tango-77. The three potential open reading frames of SEQ ID NO:1 extend from: (1) nucleotide 356 to nucleotide 889 (SEQ ID NO:3); (2) nucleotide 389 to nucleotide 889 (SEQ ID NO:6); and (3) nucleotide 481 to nucleotide 889 (SEQ ID NO:10).

FIG. 2 depicts an alignment of an amino acid sequence of Tango-77 (T77; SEQ ID NO:2) with IL-1RA (SEQ ID NO:14), and IL-1β (SEQ ID NO:15).

FIG. 3 depicts the genomic sequence of BAC1 (SEQ ID NO:16).

FIG. 4 depicts the genomic sequence of BAC2 (SEQ ID NO:17).

FIG. 5 depicts an amino acid sequence of an alternatively spliced form of Tango-77 (SEQ ID NO:2) as predicted by Procrustes (T77-procrustes; SEQ ID NO:18).

DETAILED DESCRIPTION OF THE INVENTION

Figure 6:
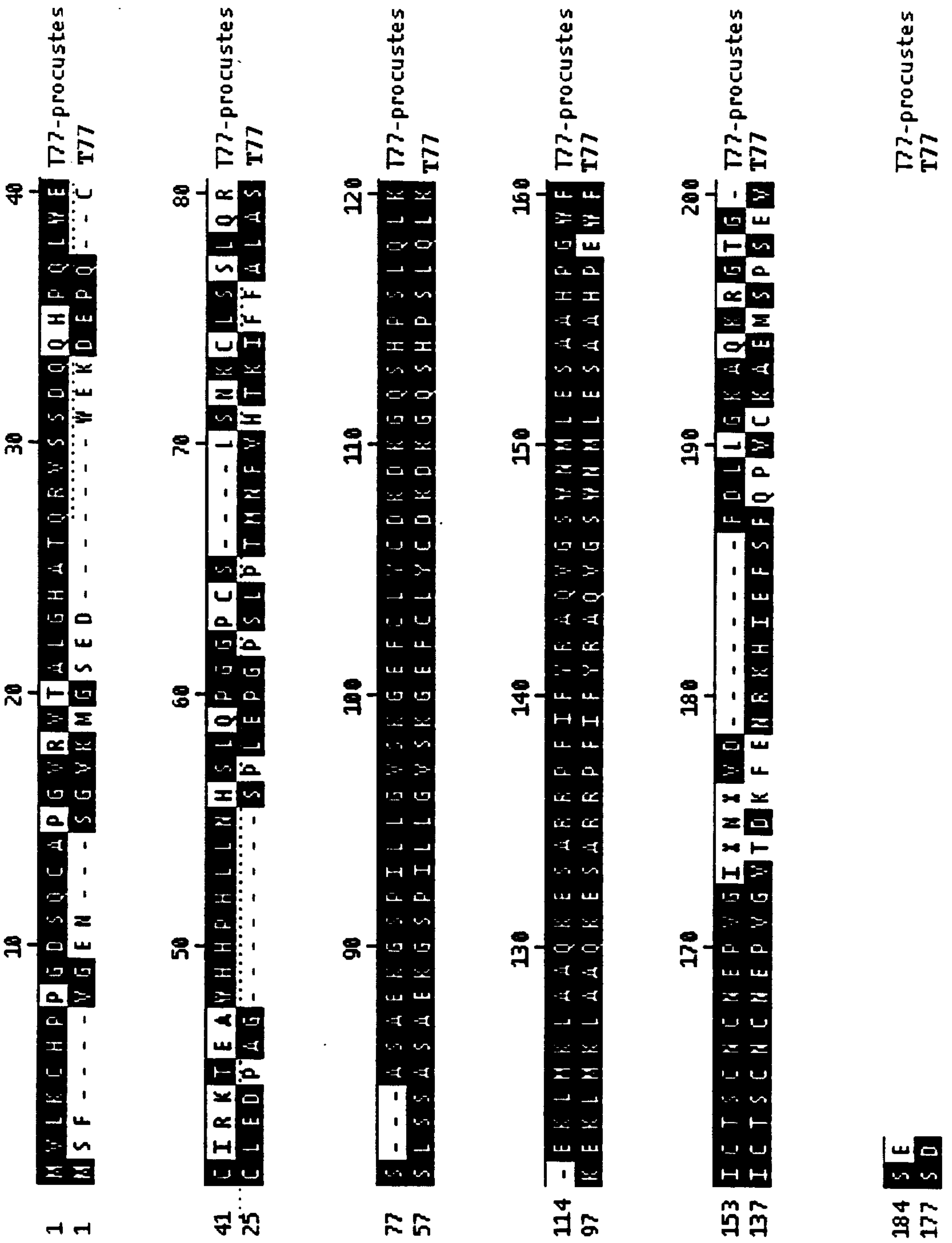
FIG. 6 depicts an alignment of an amino acid sequence of an alternatively spliced form of Tango-77 (T77-procrustes; SEQ ID NO:18) with Tango-77 (SEQ ID NO:2).

The present invention is based on the discovery of a cDNA molecule encoding human Tango-77, a member of the cytokine superfamily. The cDNA molecule encoding human Tango-77 has three possible open reading frames. The three possible nucleotide open reading frames for human Tango-77 protein are shown in FIG. 1 (SEQ ID NO:3, SEQ ID NO:6 and SEQ ID NO:10). The predicted amino acid sequence for the three possible Tango-77 immature proteins are also shown in FIG. 1 (SEQ ID NO:2, SEQ ID NO:7 or SEQ ID NO:11) and three possible mature proteins are also shown in FIG. 1 (SEQ ID NO:5, SEQ ID NO:9 and SEQ ID NO:13).

The Tango-77 cDNA of FIG. 1 (SEQ ID NO:1), which is approximately 989 nucleotides long including untranslated regions, encodes a protein amino acid having a molecular weight of approximately 19 kDa, 18 kDa, or 14.9 KDa (excluding post-translational modifications) and the possible mature form of the protein has a molecular weight of 13 kDa. A plasmid containing a cDNA encoding human Tango-77 (with the cDNA insert name of Of fthxo77) was deposited with American Type Culture Collection (ATCC), 10801 University Boulevard, Manassas, Va. 20110–2209 on Jul. 2, 1998 and assigned Accession Number 98807. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Human Tango-77 is one member of a family of molecules (the "Tango-77 family") having certain conserved structural and functional features. The term "family," when referring to the protein and nucleic acid molecules of the invention, is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

As used interchangeably herein a "Tango-77 activity", "biological activity of Tango-77" or "functional activity of Tango-77", refers to an activity exerted by a Tango-77 protein, polypeptide or nucleic acid molecule on a Tango-77 responsive cell as determined in vivo, or in vitro, according to standard techniques. A Tango-77 activity can be a direct activity, such as an association with a second protein, or an indirect activity, such as a cellular signaling activity mediated by interaction of the Tango-77 protein with a second protein. In a preferred embodiment, a Tango-77 activity includes at least one or more of the following activities: (i) the ability to interact with proteins in the Tango-77 signalling pathway (ii) the ability to interact with a Tango-77 ligand or receptor; or (iii) the ability to interact with an intracellular target protein, (iv) the ability to interact with a protein involved in inflammation, and (v) the ability to bind the IL-1 receptor.

Accordingly, another embodiment of the invention features isolated Tango-77 proteins and polypeptides having a Tango-77 activity.

Yet another embodiment of the invention features Tango-77 molecules which contain a signal sequence. Generally, a signal sequence (or signal peptide) is a peptide containing about 21 to 63 amino acids which occurs at the extreme N-terminal end of a secretory protein. The native Tango-77 signal sequence (SEQ ID NO:4, SEQ ID NO:8, or SEQ ID NO:12) can be removed and replaced with a signal sequence from another protein. In certain host cells (e.g., mammalian host cells), expression and/or secretion of Tango-77 can be increased through use of a heterologous signal sequence. For example, the gp67 secretory sequence of the baculovirus envelope protein can be used as a heterologous signal sequence. Alternatively, the native Tango-77 signal sequence can itself be used as a heterologous signal sequence in expression systems, e.g., to facilitate the secretion of a protein of interest.

Various aspects of the invention are described in further detail in the following subsections.

I. Isolated Nucleic Acid Molecules

One aspect of the invention pertains to isolated nucleic acid molecules that encode Tango-77 proteins or biologically active portions thereof, as well as nucleic acid molecules sufficient for use as hybridization probes to identify Tango-77-encoding nucleic acids (e.g., Tango-77 mRNA) and fragments for use as PCR primers for the amplification or mutation of Tango-77 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated Tango-77 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:6, SEQ ID NO:10, the cDNA of ATCC® 98807, or a complement of any of these nucleotide sequences, can be isolated using standard molecular biology techniques and the sequence information provided herein. Using all or a portion of the nucleic acid sequences of SEQ ID NO:1, SEQ ID NO:3, SEQ ID NO:6, SEQ ID NO:10, the cDNA of ATCC® 98807, or the complement thereof as a hybridization probe, Tango-77 nucleic acid molecules can be isolated using standard hybridization and cloning techniques (e.g., as described in Sambrook et al., eds., *Molecular Cloning: A Laboratory Manual,* 2nd ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to Tango-77 nucleotide sequences can be prepared by standard synthetic techniques, e.g., using an automated DNA synthesizer.

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:6, SEQ ID NO:10 the cDNA of ATCC 98807, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding Tango-77, for example, a fragment which can be used as a probe or primer or a fragment encoding a biologically active portion of Tango-77. The nucleotide sequence determined from the cloning of the human Tango-77 gene allows for the generation of probes and primers designed for use in identifying and/or cloning Tango-77 homologues in other cell types, e.g., from other tissues, as well as Tango-77 homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or antisense sequence of SEQ ID NO:1, SEQ ID NO:3, SEQ ID NO:6, SEQ ID NO:10, or the cDNA of ATCC 98807. Alternatively, the oligonucleotide can typically comprise a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or antisense sequence of a naturally occurring mutant of SEQ ID NO:1, SEQ ID NO:3, SEQ ID NO:6, SEQ ID NO:10, or the cDNA of ATCC 98807.

Probes based on the human Tango-77 nucleotide sequence can be used to detect transcripts or genomic sequences encoding the same or identical proteins. The probe comprises a label group attached thereto, e.g., a radioisotope, a fluorescent compound, an enzyme, or an enzyme co-factor. Such probes can be used as a part of a diagnostic test kit for identifying cells or tissues which mis-express a Tango-77 protein, such as by measuring a level of a Tango-77-encoding nucleic acid in a sample of cells from a subject, e.g., detecting Tango-77 mRNA levels or determining whether a genomic Tango-77 gene has been mutated or deleted.

A nucleic acid fragment encoding a "biologically active portion of Tango-77" can be prepared by isolating a portion of SEQ ID NO:1, SEQ ID NO:3, SEQ ID NO:6, SEQ ID NO:10 or the nucleotide sequence of the cDNA of ATCC® 98807 which encodes a polypeptide having a Tango-77 biological activity, expressing the encoded portion of Tango-77 protein (e.g., by recombinant expression in vitro) and assessing the activity of the encoded portion of Tango-77.

The invention further encompasses nucleic acid molecules that differ from the nucleotide sequence of SEQ ID NO:1, SEQ ID NO:3, SEQ ID NO:6, SEQ ID NO:10, or the cDNA of ATCC® 98807 due to degeneracy of the genetic code and thus encode the same Tango-77 protein as that encoded by the nucleotide sequence shown in SEQ ID NO:1, SEQ ID NO:3, SEQ ID NO:6, SEQ ID NO:10, or the cDNA of ATCC® 98807.

In addition to the human Tango-77 nucleotide sequence shown in SEQ ID NO:1, SEQ ID NO:3, SEQ ID NO:6, SEQ ID NO:10, or the cDNA of ATCC® 98807, it will be appreciated by those skilled in the art that DNA sequence polymorphisms that lead to changes in the amino acid sequences of Tango-77 may exist within a population (e.g., the human population). Such genetic polymorphism in the Tango-77 gene may exist among individuals within a population due to natural allelic variation. An allele is one of a group of genes which occur alternatively at a given genetic locus. As used herein, the term "allelic variant" refers to a nucleotide sequence which occurs at a Tango-77 locus or to a polypeptide encoded by the nucleotide sequence. As used herein, the terms "gene" and "recombinant gene" refer to nucleic acid molecules comprising an open reading frame encoding a Tango-77 protein, preferably a mammalian Tango-77 protein. Such natural allelic variations can typically result in 1–5% variance in the nucleotide sequence of the Tango-77 gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations in Tango-77 that are the result of natural allelic variation and that do not alter the functional activity of Tango-77 are intended to be within the scope of the invention.

Moreover, nucleic acid molecules encoding Tango-77 proteins from other species (Tango-77 homologues), which have a nucleotide sequence which differs from that of a human Tango-77, are intended to be within the scope of the invention. Nucleic acid molecules corresponding to natural allelic variants and homologues of the Tango-77 cDNA of the invention can be isolated based on their identity to the human Tango-77 nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 300 (325, 350, 375, 400, 425, 450, 500, 550, 600, 650, 700, 800, or 989) nucleotides in length and hybridizes under stringent conditions to the nucleic acid molecule comprising the nucleotide sequence, preferably the coding sequence, of SEQ ID NO:1, SEQ ID NO:3, SEQ ID NO:6, SEQ ID NO:10, or the cDNA of ATCC® 98807.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology,* John Wiley & Sons, N.Y. (1989), 6.3.1–6.3.6. A preferred, non-limiting example of stringent hybridization conditions are hybridization in 6× sodium chloride/sodium citrate (SSC) at about 45° C, followed by one or more washes in 0.2× SSC, 0.1% SDS at 50–65° C. Preferably, an isolated nucleic acid molecule of the invention that hybridizes under stringent conditions to the sequence of SEQ ID NO:1, SEQ ID NO:3, SEQ ID NO:6, SEQ ID NO:10, the cDNA of ATCC 98807, or the complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the Tango-77 sequence that may exist in the population, the skilled artisan will further appreciate that changes can be introduced by mutation into the nucleotide sequence of SEQ ID NO:1, SEQ ID NO:3, SEQ ID NO:6, SEQ ID NO:10 or the cDNA of ATCC 98807, thereby leading to changes in the amino acid sequence of the encoded Tango-77 protein, without altering the biological activity of the Tango-77 protein. Amino acid residues that are not conserved or only semiconserved among Tango-77 of various species may be non-essential for activity and thus would likely be targets for alteration. Alternatively, one can make nucleotide substitutions leading to amino acid substitutions at "non-essential" amino acid residues. A "non-essential" amino acid residue is a residue that can be altered from the wild-type sequence of Tango-77 (e.g., the sequence of SEQ ID NO:2, SEQ ID NO:5, SEQ ID NO:7, SEQ ID NO:9, SEQ ID NO:11 or SEQ ID NO:13) without altering the biological activity, whereas an "essential" amino acid residue is required for biological activity. For example, amino acid residues that are conserved among the Tango-77 proteins of various species may be essential for activity and thus would not likely be targets for alteration, unless one wishes to reduce or alter Tango-77 activity.

Accordingly, another aspect of the invention pertains to nucleic acid molecules encoding Tango-77 proteins that contain changes in amino acid residues that are not essential for activity. Such Tango-77 proteins differ in amino acid sequence from SEQ ID NO:2, SEQ ID NO:5, SEQ ID NO:7, SEQ ID NO:9, SEQ ID NO:11, or SEQ ID NO:13 yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2, SEQ ID NO:5, SEQ ID NO:7, SEQ ID NO:9, SEQ ID NO:11, or SEQ ID NO:13.

An isolated nucleic acid molecule encoding a Tango-77 protein having a sequence which differs from that of SEQ ID NO:2, SEQ ID NO:5, SEQ ID NO:7, SEQ ID NO:9, SEQ ID NO:11, or SEQ ID NO:13 can be created by introducing one or more nucleotide substitutions, additions or deletions into the nucleotide sequence of SEQ ID NO:1, SEQ ID NO:3, SEQ ID NO:6, SEQ ID NO:10, or the cDNA of ATCC® 98807 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Tango-77 is preferably replaced with another amino acid residue from the same side chain family. Alternatively, mutations can be introduced randomly along all or part of a Tango-77 coding sequence, such as by saturation mutagenesis, and the resultant mutants can be screened for Tango-77 biological activity to identify mutants that retain activity. Following mutagenesis, the encoded protein can be expressed recombinantly and the activity of the protein can be determined.

In a preferred embodiment, a mutant Tango-77 protein can be assayed for: (1) the ability to form protein:protein interactions with proteins in the Tango-77 signalling pathway; (2) the ability to bind a Tango-77 ligand or receptor; or (3) the ability to bind to an intracellular target protein or (4) the ability to interact with a protein involved in inflammation or (5) the ability to bind the IL-1 receptor. In yet another preferred embodiment, a mutant Tango-77 can be assayed for the ability to modulate inflammation, asthma, autoimmune dieseases, and sepsis.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Tango-77 coding strand, or to only a portion thereof, e.g., all or part of the protein coding region (or open reading frame). An antisense nucleic acid molecule can be antisense to a noncoding region of the coding strand of a nucleotide sequence encoding Tango-77. The noncoding regions ("5' and 3' untranslated regions") are the 5' and 3' sequences which flank the coding region and are not translated into amino acids.

Given the coding strand sequences encoding Tango-77 disclosed herein (e.g.,SEQ ID NO:3, SEQ ID NO:5, or SEQ ID NO:8), antisense nucleic acids of the invention can be designed according to the rules of Watson and Crick base pairing. The antisense nucleic acid molecule can be complementary to the entire coding region of Tango-77 mRNA, but more preferably is an oligonucleotide which is antisense to only a portion of the coding or noncoding region of Tango-77 mRNA. For example, the antisense oligonucleotide can be complementary to the region surrounding the translation start site of Tango-77 mRNA, e.g., an oligonucleotide having the sequence 5'-TGCAACTTTTACAGGAAACAC-3' (SEQ ID NO:19) or 5'-CCTCACTTTTACCCGAGACTC-3' (SEQ ID NO:20) or 5'-GACGGGTGGTACTTAAAACAA-3' (SEQ ID NO:21). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a Tango-77 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave Tango-77 mRNA transcripts to thereby inhibit translation of Tango-77 mRNA. A ribozyme having specificity for a Tango-77-encoding nucleic acid can be designed based upon the nucleotide sequence of a Tango-77 cDNA disclosed herein (e.g., SEQ ID NO:1, SEQ ID NO:3, SEQ ID NO:6, SEQ ID NO:10). For example, a derivative of a Tetrahymena L-19 IVS RNA can be constructed in which the nucleotide sequence of the active site is complementary to the nucleotide sequence to be cleaved in a Tango-77-encoding mRNA. See, e.g., Cech et al. U.S. Pat. No. 4,987,071; and Cech et al. U.S. Pat. No. 5,116,742. Alternatively, Tango-77 mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, Tango-77 gene expression can be inhibited by targeting nucleotide sequences complementary to the regulatory region of the Tango-77 (e.g., the Tango-77 promoter and/or enhancers) to form triple helical structures that prevent transcription of the Tango-77 gene in target cells. See generally, Helene (1991) *Anticancer Drug Des.* 6(6):569–84; Helene (1992) *Ann. N.Y. Acad. Sci.* 660:27–36; and Maher (1992) *Bioassays* 14(12):807–15.

In preferred embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci. USA* 93: 14670–675.

PNAs of Tango-77 can be used in therapeutic and diagnostic applications. For example, PNAs can be used as antisense or antigene agents for sequence-specific modulation of gene expression by, e.g., inducing transcription or translation arrest or inhibiting replication. PNAs of Tango-77 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) *Proc. Natl. Acad. Sci. USA* 93: 14670–675).

In another embodiment, PNAs of Tango-77 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of Tango-77 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al. (1989) *Nucleic Acid Res.* 17:5973–88). PNA monomers are then coupled in a stepwise manner to produce a chimeric molecule with a 5' PNA segment and a 3' DNA segment (Finn et al. (1996) *Nucleic Acids Res.* 24(17) :3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553– 6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated Tango-77 Proteins and Anti-Tango-77 Antibodies

One aspect of the invention pertains to isolated Tango-77 proteins, and biologically active portions thereof, as well as polypeptide fragments suitable for use as immunogens to raise anti-Tango-77 antibodies. In one embodiment, native Tango-77 proteins can be isolated from cells or tissue sources by an appropriate purification scheme using standard protein purification techniques. In another embodiment, Tango-77 proteins are produced by recombinant DNA techniques. Alternative to recombinant expression, a Tango-77 protein or polypeptide can be synthesized chemically using standard peptide synthesis techniques.

An "isolated" or "purified" protein or biologically active portion thereof is substantially free of cellular material or other contaminating proteins from the cell or tissue source from which the Tango-77 protein is derived, or substantially free of chemical precursors or other chemicals when chemically synthesized. The language "substantially free of cellular material" includes preparations of Tango-77 protein in which the protein is separated from cellular components of the cells from which it is isolated or recombinantly produced. Thus, Tango-77 protein that is substantially free of cellular material includes preparations of Tango-77 protein having less than about 30%, 20%, 10%, or 5% (by dry weight) of non-Tango-77 protein (also referred to herein as a "contaminating protein"). When the Tango-77 protein or biologically active portion thereof is recombinantly produced, it is also preferably substantially free of culture medium, i.e., culture medium represents less than about 20%, 10%, or 5% of the volume of the protein preparation. When Tango-77 protein is produced by chemical synthesis, it is preferably substantially free of chemical precursors or other chemicals, i.e., it is separated from chemical precursors or other chemicals which are involved in the synthesis of the protein. Accordingly such preparations of Tango-77 protein have less than about 30%, 20%, 10%, 5% (by dry weight) of chemical precursors or non-Tango-77 chemicals.

Biologically active portions of a Tango-77 protein include peptides comprising amino acid sequences sufficiently identical to or derived from the amino acid sequence of the Tango-77 protein (e.g., the amino acid sequence shown in SEQ ID NO:2, SEQ ID NO:5, SEQ ID NO:7, SEQ ID NO:9, SEQ ID NO:11, or SEQ ID NO:13), which include fewer amino acids than the full length Tango-77 proteins, and exhibit at least one activity of a Tango-77 protein. Typically, biologically active portions comprise a domain or motif with at least one activity of the Tango-77 protein. A biologically active portion of a Tango-77 protein can be a polypeptide which is, for example, 10, 25, 50, 100 or more amino acids in length.

Moreover, other biologically active portions, in which other regions of the protein are deleted, can be prepared by recombinant techniques and evaluated for one or more of the functional activities of a native Tango-77 protein.

Preferred Tango-77 protein has the amino acid sequence shown of SEQ ID NO:2, SEQ ID NO:5, SEQ ID NO:7, SEQ ID NO:9, SEQ ID NO:11, or SEQ ID NO:13. Other useful Tango-77 proteins are substantially identical to SEQ ID NO:2, SEQ ID NO:5, SEQ ID NO:7, SEQ ID NO:9, SEQ ID NO:11, or SEQ ID NO:13 and retain the functional activity of the protein of SEQ ID NO:2, SEQ ID NO:5, SEQ ID NO:7, SEQ ID NO:9, SEQ ID NO:11, or SEQ ID NO:13 yet differ in amino acid sequence due to natural allelic variation or mutagenesis. Accordingly, a useful Tango-77 protein is a protein which includes an amino acid sequence at least about 45%, preferably 55%, 65%, 75%, 85%, 95%, or 99% identical to the amino acid sequence of SEQ ID NO:2, SEQ ID NO:5, SEQ ID NO:7, SEQ ID NO:9, SEQ ID NO:11, or SEQ ID NO:13 and retains the functional activity of the Tango-77 proteins of SEQ ID NO:2, SEQ ID NO:5, SEQ ID NO:7, SEQ ID NO:9, SEQ ID NO:11, or SEQ ID NO:13. In a preferred embodiment, the Tango-77 protein retains a functional activity of the Tango-77 protein of SEQ ID NO:2, SEQ ID NO:5, SEQ ID NO:7, SEQ ID NO:9, SEQ ID NO:11, or SEQ ID NO:13.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions, e.g., overlapping×100). Preferably, the two sequences are the same length.

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to Tango-77 nucleic acid molecules of the invention. BLAST protein searches can be performed with the XBLAST program, score=50, wordlength=3 to obtain amino acid sequences homologous to Tango-77 protein molecules of the invention. To obtain gapped alignments for comparison purposes, Gapped BLAST can be utilized as described in Altschul et al. (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides Tango-77 chimeric or fusion proteins. As used herein, a Tango-77 "chimeric protein" or "fusion protein" comprises a Tango-77 polypeptide operably linked to a non-Tango-77 polypeptide. A "Tango-77 polypeptide" refers to a polypeptide having an amino acid sequence corresponding to Tango-77 polypeptides, whereas a "non-Tango-77 polypeptide" refers to a polypeptide having an amino acid sequence corresponding to a protein which is not substantially identical to the Tango-77 protein, e.g., a protein which is different from the Tango-77 protein and which is derived from the same or a different organism. Within a Tango-77 fusion protein the Tango-77 polypeptide can correspond to all or a portion of a Tango-77 protein, preferably at least one biologically active portion of a Tango-77 protein. Within the fusion protein, the term "operably linked" is intended to indicate that the Tango-77 polypeptide and the non-Tango-77 polypeptide are fused in-frame to each other. The non-Tango-77 polypeptide can be fused to the N-terminus or C-terminus of the Tango-77 polypeptide.

One useful fusion protein is a GST-Tango-77 fusion protein in which the Tango-77 sequences are fused to the C-terminus of the GST sequences. Such fusion proteins can facilitate the purification of recombinant Tango-77.

In another embodiment, the fusion protein is a Tango-77 protein containing a heterologous signal sequence at its N-terminus. For example, the native Tango-77 signal sequence (i.e., about amino acids 1 to 63 of SEQ ID NO:2; SEQ ID NO:4; or about amino acids 1 to 52 of SEQ ID NO:7;SEQ ID NO:8; or about amino acids 1 to 21 of SEQ ID NO:11;SEQ ID NO:12) can be removed and replaced with a signal sequence from another protein. In certain host cells (e.g., mammalian host cells), expression and/or secretion of Tango-77 can be increased through use of a heterologous signal sequence. For example, the gp67 secretory sequence of the baculovirus envelope protein can be used as a heterologous signal sequence (Ausubel et al., supra). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an Tango-77-immunoglobulin fusion protein in which all or part of Tango-77 is fused to sequences derived from a member of the immunoglobulin protein family. The Tango-77-immunoglobulin fusion proteins of the invention can be incorporated into pharmaceutical compositions and administered to a subject to inhibit an interaction between a Tango-77 ligand and a Tango-77 receptor on the surface of a cell, to thereby suppress Tango-77-mediated signal transduction in vivo. The Tango-77-immunoglobulin fusion proteins can be used to affect the bioavailability of a Tango-77 cognate ligand. Inhibition of the Tango-77 ligand/Tango-77 interaction may be useful therapeutically for both the treatment of inflammatory and autoimmune disorders. Moreover, the Tango-77-immunoglobulin fusion proteins of the invention can be used as immunogens to produce anti-Tango-77 antibodies in a subject, to purify Tango-77 ligands and in screening assays to identify molecules which inhibit the interaction of Tango-77 with a Tango-77 receptor.

Preferably, a Tango-77 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology,* Ausubel et al. eds., John Wiley & Sons: 1992). Moreover, many expression vectors are commercially available that already encode a fusion moiety (e.g., a GST polypeptide). An Tango-77-encoding nucleic acid can be cloned into such an expression vector such that the fusion moiety is linked in-frame to the Tango-77 protein.

The present invention also pertains to variants of the Tango-77 proteins (i.e., proteins having a sequence which differs from that of the Tango-77 amino acid sequence). Such variants can function as either Tango-77 agonists (mimetics) or as Tango-77 antagonists. Variants of the Tango-77 protein can be generated by mutagenesis, e.g., discrete point mutation or truncation of the Tango-77 protein. An agonist of the Tango-77 protein can retain substantially the same, or a subset, of the biological activities of the naturally occurring form of the Tango-77 protein. An antagonist of the Tango-77 protein can inhibit one or more of the activities of the naturally occurring form of the Tango-77 protein by, for example, competitively binding to a downstream or upstream member of a cellular signaling cascade which includes the Tango-77 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the Tango-77 proteins.

Variants of the Tango-77 protein which function as either Tango-77 agonists (mimetics) or as Tango-77 antagonists can be identified by screening combinatorial libraries of mutants, e.g., truncation mutants, of the Tango-77 protein for Tango-77 protein agonist or antagonist activity. In one embodiment, a variegated library of Tango-77 variants is generated by combinatorial mutagenesis at the nucleic acid level and is encoded by a variegated gene library. A variegated library of Tango-77 variants can be produced by, for example, enzymatically ligating a mixture of synthetic oligonucleotides into gene sequences such that a degenerate set of potential Tango-77 sequences is expressible as individual polypeptides, or alternatively, as a set of larger fusion proteins (e.g., for phage display) containing the set of Tango-77 sequences therein. There are a variety of methods which can be used to produce libraries of potential Tango-77 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Tango-77 sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the Tango-77 protein coding sequence can be used to generate a variegated population of Tango-77 fragments for screening and subsequent selection of variants of a Tango-77 protein. In one embodiment, a library of coding sequence fragments can be generated by treating a double stranded PCR fragment of a Tango-77 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the Tango-77 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Tango-77 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify Tango-77 variants (Arkin and Yourvan (1992) *Proc. Natl. Acad. Sci. USA* 89:7811–7815; Delgrave et al. (1993) *Protein Engineering* 6(3):327–331).

An isolated Tango-77 protein, or a portion or fragment thereof, can be used as an immunogen to generate antibodies that bind Tango-77 using standard techniques for polyclonal and monoclonal antibody preparation. The full-length Tango-77 protein can be used or, alternatively, the invention provides antigenic peptide fragments of Tango-77 for use as immunogens. The antigenic peptide of Tango-77 comprises at least 8 (preferably 10, 15, 20, or 30) amino acid residues of the amino acid sequence shown in SEQ ID NO:2, SEQ ID NO:5, SEQ ID NO:7, SEQ ID NO:9, SEQ ID NO:11 or SEQ ID NO:13 and encompasses an epitope of Tango-77 such that an antibody raised against the peptide forms a specific immune complex with Tango-77.

A Tango-77 immunogen typically is used to prepare antibodies by immunizing a suitable subject (e.g., rabbit, goat, mouse or other mammal) with the immunogen. An appropriate immunogenic preparation can contain, for example, recombinantly expressed Tango-77 protein or a chemically synthesized Tango-77 polypeptide. The preparation can further include an adjuvant, such as Freund's complete or incomplete adjuvant, or similar immunostimulatory agent. Immunization of a suitable subject with an immunogenic Tango-77 preparation induces a polyclonal anti-Tango-77 antibody response.

Accordingly, another aspect of the invention pertains to anti-Tango-77 antibodies. The term "antibody" as used herein refers to immunoglobulin molecules and immunologically active portions of immunoglobulin molecules, i.e., molecules that contain an antigen binding site which specifically binds an antigen, such as Tango-77. A molecule which specifically binds to Tango-77 is a molecule which binds Tango-77, but does not substantially bind other molecules in a sample, e.g., a biological sample, which naturally contains Tango-77. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind Tango-77. The term "monoclonal antibody" or "monoclonal antibody composition", as used herein, refers to a population of antibody molecules that contain only one species of an antigen binding site capable of immunoreacting with a particular epitope of Tango-77. A monoclonal antibody composition thus typically displays a single binding affinity for a particular Tango-77 protein with which it immunoreacts.

Polyclonal anti-Tango-77 antibodies can be prepared as described above by immunizing a suitable subject with a Tango-77 immunogen. The anti-Tango-77 antibody titer in the immunized subject can be monitored over time by standard techniques, such as with an enzyme linked immunosorbent assay (ELISA) using immobilized Tango-77. If desired, the antibody molecules directed against Tango-77 can be isolated from the mammal (e.g., from the blood) and further purified by well-known techniques, such as protein A chromatography to obtain the IgG fraction. At an appropriate time after immunization, e.g., when the anti-Tango-77 antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol Today* 4:72), the EBV-hybridoma technique (Cole et al. (1985), *Monoclonal Antibodies and Cancer Therapy,* Alan R. Liss, Inc., pp. 77–96) or trioma techniques. The technology for producing hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a Tango-77 immunogen as described above, and the culture supernatants of the resulting hybridoma cells are screened to identify a hybridoma producing a monoclonal antibody that binds Tango-77.

Any of the many well known protocols used for fusing lymphocytes and immortalized cell lines can be applied for the purpose of generating an anti-Tango-77 monoclonal antibody (see, e.g., Current Protocols in Immunology, supra; Galfre et al. (1977) *Nature* 266:55052; R. H. Kenneth, in *Monoclonal Antibodies: A New Dimension In Biological Analyses,* Plenum Publishing Corp., New York, N.Y. (1980); and Lerner (1981) *Yale J. Biol. Med.,* 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Tango-77, e.g., using a standard ELISA assay.

Alternative to preparing monoclonal antibody-secreting hybridomas, a monoclonal anti-Tango-77 antibody can be identified and isolated by screening a recombinant combinatorial immunoglobulin library (e.g., an antibody phage display library) with Tango-77 to thereby isolate immunoglobulin library members that bind Tango-77. Kits for generating and screening phage display libraries are commercially available (e.g., the Pharmacia *Recombinant Phage Antibody System,* Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734.

Additionally, recombinant anti-Tango-77 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heave and light chain genes. The transgenic mice are immunized in the normal fashion with a selected antigen, e.g., all or a portion of Tango-77. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immu-*

*nol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to the described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope.

First, a non-human monoclonal antibody which binds a selected antigen (epitope), e.g., an antibody which inhibits Tango-77 activity, is identified. The heave chain and the light chain of the non-human antibody are cloned and used to create phage display Fab fragments. For example, the heave chain gene can be cloned into a plasmid vector so that the heavy chain can be secreted from bacteria. The light chain gene can be cloned into a phage coat protein gene so that the light chain can be expressed on the surface of phage. A repertoire (random collection) of human light chains fused to phage is used to infect the bacteria which express the non-human heavy chain. The resulting progeny phage display hybrid antibodies (human light chain/non-human heavy chain). The selected antigen is used in a panning screen to select phage which bind the selected antigen. Several rounds of selection may be required to identify such phage. Next, human light chain genes are isolated from the selected phage which bind the selected antigen. These selected human light chain genes are then used to guide the selection of human heavy chain genes as follows. The selected human light chain genes are inserted into vectors for expression by bacteria. Bacteria expressing the selected human light chains are infected with a repertoire of human heavy chains fused to phage. The resulting progeny phage display human antibodies (human light chain/human heavy chain).

Next, the selected antigen is used in a panning screen to select phage which bind the selected antigen. The phage selected in this step display completely human antibody which recognize the same epitope recognized by the original selected, non-human monoclonal antibody. The genes encoding both the heavy and light chains are readily isolated and be further manipulated for production of human antibody. This technology is described by Jespers et al. (1994, *Bio/technology* 12:899–903).

An anti-Tango-77 antibody (e.g., monoclonal antibody) can be used to isolate Tango-77 by standard techniques, such as affinity chromatography or immunoprecipitation. An anti-Tango-77 antibody can facilitate the purification of natural Tango-77 from cells and of recombinantly produced Tango-77 expressed in host cells. Moreover, an anti-Tango-77 antibody can be used to detect Tango-77 protein (e.g., in a cellular lysate or cell supernatant) in order to evaluate the abundance and pattern of expression of the Tango-77 protein. Anti-Tango-77 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid molecule encoding Tango-77 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Tango-77 proteins, mutant forms of Tango-77, fusion proteins, etc.).

The recombinant expression vectors of the invention can be designed for expression of Tango-77 in prokaryotic or eukaryotic cells, e.g., bacterial cells such as *E. coli,* insect cells (using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the Tango-77 expression vector is a yeast expression vector. Examples of vectors for expression in yeast *S. cerivisae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and picZ (InVitrogen Corp, San Diego, Calif.).

Alternatively, Tango-77 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to Tango-77 mRNA. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics,* Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Tango-77 protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Tango-77 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Tango-77 protein. Accordingly, the invention further provides methods for producing Tango-77 protein using the host cells of the invention. In one embodiment, the method comprises culturing the host cell of invention (into which a recombinant expression vector encoding Tango-77 has been introduced) in a suitable medium such that Tango-77 protein is produced. In another embodiment, the method further comprises isolating Tango-77 from the medium or the host cell.

The host cells of the invention can also be used to produce nonhuman transgenic animals. For example, in one embodiment, a host cell of the invention is a fertilized oocyte or an embryonic stem cell into which Tango-77-coding sequences have been introduced. Such host cells can then be used to create non-human transgenic animals in which exogenous Tango-77 sequences have been introduced into their genome or homologous recombinant animals in which endogenous Tango-77 sequences have been altered. Such animals are useful for studying the function and/or activity of Tango-77 and for identifying and/or evaluating modulators of Tango-77 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous Tango-77 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing Tango-77-encoding nucleic acid into the male pronuclei of a fertilized oocyte, e.g., by microinjection, retroviral infection, and allowing the oocyte to develop in a pseudopregnant female foster animal. The Tango-77 cDNA sequence e.g., that of (SEQ ID NO:1, SEQ ID NO:3, SEQ ID NO:6; SEQ ID NO:10 or the cDNA of ATCC 98807) can be introduced as a transgene into the genome of a non-human animal. Alternatively, a nonhuman homologue of the human Tango-77 gene, such as a mouse Tango-77 gene, can be isolated based on hybridization to the human Tango-77 cDNA and used as a transgene. Intronic sequences and polyadenylation signals can also be included in the transgene to increase the efficiency of expression of the transgene. A tissue-specific regulatory sequence(s) can be operably linked to the Tango-77 transgene to direct expression of Tango-77 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the Tango-77 transgene in its genome and/or expression of Tango-77 mRNA in tissues or cells of the animals. A transgenic founder animal can then be used to breed additional animals carrying the transgene. Moreover, transgenic animals carrying a transgene encoding Tango-77 can further be bred to other transgenic animals carrying other transgenes.

To create an homologous recombinant animal, a vector is prepared which contains at least a portion of a Tango-77 gene (e.g., a human or a non-human homolog of the Tango-77 gene, e.g., a murine Tango-77 gene) into which a deletion, addition or substitution has been introduced to thereby alter, e.g., functionally disrupt, the Tango-77 gene. In a preferred embodiment, the vector is designed such that, upon homologous recombination, the endogenous Tango-77 gene is functionally disrupted (i.e., no longer encodes a functional protein; also referred to as a "knock out" vector).

Alternatively, the vector can be designed such that, upon homologous recombination, the endogenous Tango-77 gene is mutated or otherwise altered but still encodes functional protein (e.g., the upstream regulatory region can be altered to thereby alter the expression of the endogenous Tango-77 protein). In the homologous recombination vector, the altered portion of the Tango-77 gene is flanked at its 5' and 3' ends by additional nucleic acid of the Tango-77 gene to allow for homologous recombination to occur between the exogenous Tango-77 gene carried by the vector and an endogenous Tango-77 gene in an embryonic stem cell. The additional flanking Tango-77 nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced Tango-77 gene has homologously recombined with the endogenous Tango-77 gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach,* Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The Tango-77 nucleic acid molecules, Tango-77 proteins, and anti-Tango-77 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, (e.g. intravenous, intradermal, subcutaneous) (e.g., oral inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Tango-77 protein or anti-Tango-77 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). A Tango-77 protein interacts with other cellular proteins and can thus be used for regulation of inflammation. The polypeptides of the invention can be used in assays to determine biological activity. For example, they could be used in a panel of proteins for high-throughput screening.

The isolated nucleic acid molecules of the invention can be used to express Tango-77 protein (e.g., via a recombinant expression vector in a host cell in gene therapy applications), to detect Tango-77 mRNA (e.g., in a biological sample) or a genetic lesion in a Tango-77 gene, and to modulate Tango-77 activity. In addition, the Tango-77 proteins can be used to screen drugs or compounds which modulate the Tango-77 activity or expression as well as to treat disorders characterized by insufficient or excessive production of Tango-77 protein or production of Tango-77 protein forms which have decreased or aberrant activity compared to Tango-77 wild type protein. In addition, the anti-Tango-77 antibodies of the invention can be used to detect and isolate Tango-77 proteins and modulate Tango-77 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to Tango-77 proteins or have a stimulatory or inhibitory effect on, for example, Tango-77 expression or Tango-77 activity.

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993)

*Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In another embodiment, an assay is used to determine the ability of the test compound to modulate the activity of Tango-77 or a biologically active portion thereof, for example, by determining the ability of the Tango-77 protein to bind to or interact with a Tango-77 target molecule. As used herein, a “target molecule” is a molecule with which a Tango-77 protein binds or interacts in nature, for example, a molecule on the surface of a cell. A Tango-77 target molecule can be a non-Tango-77 molecule or a Tango-77 protein or polypeptide of the present invention. In one embodiment, a Tango-77 target molecule is a component of a signal transduction pathway, for example, Tango-77 may bind to a IL-1 receptor or another receptor thereby blocking the receptor and inhibiting future signal transduction. Determining the ability of the Tango-77 protein to bind to or interact with a Tango-77 target molecule can be accomplished by one of the methods described above. In a preferred embodiment, determining the ability of the Tango-77 protein to bind to or interact with a Tango-77 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a Tango-77-responsive regulatory element operably linked to a nucleic acid encoding a detectable marker, e.g. luciferase), or detecting a cellular response, for example, inflammation.

In yet another embodiment, an assay of the present invention is a cell-free assay comprising contacting a Tango-77 protein or biologically active portion thereof with a test compound and determining the ability of the test compound to bind to the Tango-77 protein or biologically active portion thereof. Binding of the test compound to the Tango-77 protein can be determined either directly or indirectly as described above. In a preferred embodiment, the assay includes contacting the Tango-77 protein or biologically active portion thereof with a known compound which binds Tango-77 to form an assay mixture, contacting the assay mixture with a test compound, and determining the ability of the test compound to interact with a Tango-77 protein, wherein determining the ability of the test compound to interact with a Tango-77 protein comprises determining the ability of the test compound to preferentially bind to Tango-77 or biologically active portion thereof as compared to the known compound.

In another embodiment, an assay is a cell-free assay comprising contacting Tango-77 protein or biologically active portion thereof with a test compound and determining the ability of the test compound to modulate (e.g., stimulate or inhibit) the activity of the Tango-77 protein or biologically active portion thereof. Determining the ability of the test compound to modulate the activity of Tango-77 can be accomplished, for example, by determining the ability of the Tango-77 protein to bind to a Tango-77 target molecule by one of the methods described above for determining direct binding. In an alternative embodiment, determining the ability of the test compound to modulate the activity of Tango-77 can be accomplished by determining the ability of the Tango-77 protein to further modulate a Tango-77 target molecule. For example, the catalytic/enzymatic activity of the target molecule on an appropriate substrate can be determined as previously described.

In yet another embodiment, the cell-free assay comprises contacting the Tango-77 protein or biologically active portion thereof with a known compound which binds Tango-77 to form an assay mixture, contacting the assay mixture with a test compound, and determining the ability of the test compound to interact with a Tango-77 protein, wherein determining the ability of the test compound to interact with a Tango-77 protein comprises determining the ability of the Tango-77 protein to preferentially bind to or modulate the activity of a Tango-77 target molecule.

It is possible that membrane-bound forms of Tango-77 exist. The cell-free assays of the present invention are amenable to use of both the forms Tango-77. In the case of cell-free assays comprising a membrane-bound form of Tango-77, it may be desirable to utilize a solubilizing agent such that the membrane-bound form of Tango-77 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either Tango-77 or its target molecule to facilitate separation of complexed from uncomplexed forms of one or both of the proteins, as well as to accommodate automation of the assay. Binding of a test compound to Tango-77, or interaction of Tango-77 with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/Tango-77 fusion proteins or glutathione-S-transferase/target fusion proteins can be adsorbed onto glutathione sepharose beads (Sigma Chemical Co.; St. Louis, Mo.) or glutathione derivatized microtiter plates, which are then combined with the test compound or the test compound and either the non-adsorbed target protein or Tango-77 protein, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of Tango-77 binding or activity determined using standard techniques.

Other techniques for immobilizing proteins on matrices can also be used in the screening assays of the invention. For example, either Tango-77 or its target molecule can be immobilized utilizing conjugation of biotin and streptavidin. Biotinylated Tango-77 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical).

Alternatively, antibodies reactive with Tango-77 or target molecules but which do not interfere with binding of the Tango-77 protein to its target molecule can be derivatized to the wells of the plate, and unbound target or Tango-77 trapped in the wells by antibody conjugation. Methods for detecting such complexes, in addition to those described above for the GST-immobilized complexes, include immunodetection of complexes using antibodies reactive with the Tango-77 or target molecule, as well as enzyme-linked assays which rely on detecting an enzymatic activity associated with the Tango-77 or target molecule.

In another embodiment, modulators of Tango-77 expression are identified in a method in which a cell is contacted with a candidate compound and the expression of Tango-77 mRNA or protein in the cell is determined. The level of expression of Tango-77 mRNA or protein in the presence of the candidate compound is compared to the level of expression of Tango-77 mRNA or protein in the absence of the candidate compound. The candidate compound can then be identified as a modulator of Tango-77 expression based on this comparison. For example, when expression of Tango-77 mRNA or protein is greater (statistically significantly greater) in the presence of the candidate compound than in its absence, the candidate compound is identified as a stimulator of Tango-77 mRNA or protein expression. Alternatively, when expression of Tango-77 mRNA or protein is less (statistically significantly less) in the presence of the candidate compound than in its absence, the candidate compound is identified as an inhibitor of Tango-77 mRNA or protein expression. The level of Tango-77 mRNA or protein expression in the cells can be determined by methods described herein for detecting Tango-77 mRNA or protein.

In yet another aspect of the invention, the Tango-77 proteins can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with Tango-77 ("Tango-77-binding proteins" or "Tango-77-bp") and modulate Tango-77 activity. Such Tango-77-binding proteins are also likely to be involved in the propagation of signals by the Tango-77 proteins as, for example, upstream or downstream elements of the Tango-77 pathway.

The two-hybrid system is based on the modular nature of most transcription factors, which consist of separable DNA-binding and activation domains. Briefly, the assay utilizes two different DNA constructs. In one construct, the gene that codes for Tango-77 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an Tango-77-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with Tango-77.

This invention further pertains to novel agents identified by the above-described screening assays and uses thereof for treatments as described herein.

B. Detection Assays

Portions or fragments of the cDNA sequence identified herein (and the corresponding complete gene sequences) can be used in numerous ways as polynucleotide reagents. For example, the sequence can be used to: (i) map the respective gene on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, Tango-77 nucleic acid molecules described herein or fragments thereof, can be used to map the location of the Tango-77 gene(s) on a chromosome. The mapping of the Tango-77 sequences to chromosomes is an important first step in correlating these sequences with genes associated with disease.

Briefly, a Tango-77 gene can be mapped to chromosomes by preparing PCR primers (preferably 15–25 bp in length) from the Tango-77 sequences. Computer analysis of Tango-77 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the Tango-77 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme) but in which human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the Tango-77 sequences to design oligonucleotide primers, sublocalization can be achieved with panels of fragments from specific chromosomes. Other mapping strategies which can similarly be used to map a Tango-77 sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical, e.g., colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the Tango-77 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The Tango-77 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the Tango-77 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Tango-77 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3, SEQ ID NO:6, or SEQ ID NO:10 are used, a more appropriate number of primers for positive individual identification would be 500–2,000.

If a panel of reagents from Tango-77 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Tango-77 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the Tango-77 sequences or portions thereof, e.g., fragments derived from the noncoding regions of SEQ ID NO:1 having a length of at least 20 or 30 bases.

The Tango-77 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such Tango-77 probes can be used to identify tissue by species and/or by organ type.

In a similar fashion, these reagents, e.g., Tango-77 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining Tango-77 protein and/or nucleic acid expression as well as Tango-77 activity, in the context of a biological sample (e.g., blood, serum, cells, tissue) to thereby determine whether an individual is afflicted with a disease or disorder, or is at risk of developing a disorder, associated with aberrant Tango-77 expression or activity. The invention also provides for prognostic (or predictive) assays for determining whether an individual is at risk of developing a disorder associated with Tango-77 protein, nucleic acid expression or activity. For example, mutations in a Tango-77 gene can be assayed in a biological sample. Such assays can be used for prognostic or predictive purpose to thereby prophylactically treat an individual prior to the onset of a disorder characterized by or associated with Tango-77 protein, nucleic acid expression or activity.

Another aspect of the invention provides methods for determining Tango-77 protein, nucleic acid expression or Tango-77 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of Tango-77 in clinical trials.

These and other agents are described in further detail in the following sections.

1. Diagnostic Assays

An exemplary method for detecting the presence or absence of Tango-77 in a biological sample involves obtaining a biological sample from a test subject and contacting the biological sample with a compound or an agent capable of detecting Tango-77 protein or nucleic acid (e.g., mRNA, genomic DNA) that encodes Tango-77 protein such that the presence of Tango-77 is detected in the biological sample. A preferred agent for detecting Tango-77 mRNA or genomic DNA is a labeled nucleic acid probe capable of hybridizing to Tango-77 mRNA or genomic DNA. The nucleic acid probe can be, for example, a full-length Tango-77 nucleic acid, such as the nucleic acid of SEQ ID NO: 1, SEQ ID NO:3, SEQ ID NO:6, SEQ ID NO:10 or a portion thereof, such as an oligonucleotide of at least 15, 30, 50, 100, 250 or 500 nucleotides in length and sufficient to specifically hybridize under stringent conditions to Tango-77 mRNA or genomic DNA. Other suitable probes for use in the diagnostic assays of the invention are described herein.

A preferred agent for detecting Tango-77 protein is an antibody capable of binding to Tango-77 protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Tango-77 mRNA, protein, or genomic DNA in a biological sample in vitro as well as in vivo. For example, in vitro techniques for detection of Tango-77 mRNA include Northern hybridizations and in situ hybridizations. In vitro techniques for detection of Tango-77 protein include enzyme linked immunosorbent assays (ELISAs), Western blots, immunoprecipitations and immunofluorescence. In vitro techniques for detection of Tango-77 genomic DNA include Southern hybridizations. Furthermore, in vivo techniques for detection of Tango-77 protein include introducing into a subject a labeled anti-Tango-77 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting Tango-77 protein, mRNA, or genomic DNA, such that the presence of Tango-77 protein, mRNA or genomic DNA is detected in the biological sample, and comparing the presence of Tango-77 protein, mRNA or genomic DNA in the control sample with the presence of Tango-77 protein, mRNA or genomic DNA in the test sample.

The invention also encompasses kits for detecting the presence of Tango-77 in a biological sample (a test sample). Such kits can be used to determine if a subject is suffering from or is at increased risk of developing a disorder associated with aberrant expression of Tango-77 (e.g., an immunological disorder). For example, the kit can comprise a labeled compound or agent capable of detecting Tango-77 protein or mRNA in a biological sample and means for determining the amount of Tango-77 in the sample (e.g., an anti-Tango-77 antibody or an oligonucleotide probe which binds to DNA encoding Tango-77, e.g., SEQ ID NO:1 or SEQ ID NO:3 or SEQ ID NO:6, or SEQ ID NO:10). Kits may also include instruction for observing that the tested subject is suffering from or is at risk of developing a disorder associated with aberrant expression of Tango-77 if the amount of Tango-77 protein or mRNA is above or below a normal level.

For antibody-based kits, the kit may comprise, for example: (1) a first antibody (e.g., attached to a solid support) which binds to Tango-77 protein; and, optionally (2) a second, different antibody which binds to Tango-77 protein or the first antibody and is conjugated to a detectable agent.

For oligonucleotide-based kits, the kit may comprise, for example: (1) an oligonucleotide, e.g., a detectably labelled oligonucleotide, which hybridizes to a Tango-77 nucleic acid sequence or (2) a pair of primers useful for amplifying a Tango-77 nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of Tango-77.

2. Prognostic Assays

The methods described herein can furthermore be utilized as diagnostic or prognostic assays to identify subjects having or at risk of developing a disease or disorder associated with aberrant Tango-77 expression or activity. For example, the assays described herein, such as the preceding diagnostic assays or the following assays, can be utilized to identify a subject having or at risk of developing a disorder associated with aberrant expression or activity. Thus, the present invention provides a method in which a test sample is obtained from a subject and Tango-77 protein or nucleic acid (e.g., mRNA, genomic DNA) is detected, wherein the presence of Tango-77 protein or nucleic acid is diagnostic for a subject having or at risk of developing a disease or disorder associated with aberrant Tango-77 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Tango-77 expression or activity. For example, such methods can be used to determine whether a subject can be effectively treated with a specific agent or class of agents (e.g., agents of a type which decrease Tango-77 activity). Thus, the present invention provides methods for determining whether a subject can be effectively treated with an agent for a disorder associated with aberrant Tango-77 expression or activity in which a test sample is obtained and Tango-77 protein or nucleic acid is detected (e.g., wherein the presence of Tango-77 protein or nucleic acid is diagnostic for a subject that can be administered the agent to treat a disorder associated with aberrant Tango-77 expression or activity).

The methods of the invention can also be used to detect genetic lesions or mutations in a Tango-77 gene, thereby determining if a subject with the lesioned gene is at risk for a disorder characterized by aberrant inflammation. In preferred embodiments, the methods include detecting, in a sample of cells from the subject, the presence or absence of a genetic lesion or mutation characterized by at least one of an alteration affecting the integrity of a gene encoding a Tango-77-protein, or the mis-expression of the Tango-77 gene. For example, such genetic lesions or mutations can be detected by ascertaining the existence of at least one of: 1) a deletion of one or more nucleotides from a Tango-77 gene; 2) an addition of one or more nucleotides to a Tango-77 gene; 3) a substitution of one or more nucleotides of a Tango-77 gene; 4) a chromosomal rearrangement of a Tango-77 gene; 5) an alteration in the level of a messenger RNA transcript of a Tango-77 gene; 6) an aberrant modification of a Tango-77 gene, such as of the methylation pattern of the genomic DNA; 7) the presence of a non-wild type splicing pattern of a messenger RNA transcript of a Tango-77 gene; 8) a non-wild type level of a Tango-77-protein; 9) an allelic loss of a Tango-77 gene, and 10) an inappropriate post-translational modification of a Tango-77-protein. As described herein, there are a large number of assay techniques known in the art which can be used for detecting lesions or mutations in a Tango-77 gene. A preferred biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the Tango-77-gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a Tango-77 gene under conditions such that hybridization and amplification of the Tango-77-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Tango-77 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in Tango-77 can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in Tango-77 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Tango-77 gene and detect mutations by comparing the sequence of the sample Tango-77 with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the Tango-77 gene include methods in which protection from cleavage agents is used to detect mismatched bases in RNA/RNA or RNA/DNA heteroduplexes (Myers et al. (1985) *Science* 230:1242). In general, the technique of "mismatch cleavage" entails providing heteroduplexes formed by hybridizing (labeled) RNA or DNA containing the wild-type Tango-77 sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Tango-77 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Tango-77 sequence, e.g., a wild-type Tango-77 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in Tango-77 genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125–144; Hayashi (1992) *Genet Anal Tech Appl* 9:73–79). Single-stranded DNA fragments of sample and control Tango-77 nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Tango-77 gene.

Furthermore, any cell type or tissue, preferably peripheral blood leukocytes, in which Tango-77 is expressed may be utilized in the prognostic assays described herein.

3. Pharmacogenomics

Agents, or modulators which have a stimulatory or inhibitory effect on Tango-77 activity (e.g., Tango-77 gene expression) as identified by a screening assay described herein can be administered to individuals to treat (prophylactically or therapeutically) disorders (e.g., acute or chronic inflammation and asthma) associated with aberrant Tango-77 activity. In conjunction with such treatment, the pharmacogenomics (i.e., the study of the relationship between an individual's genotype and that individuals response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of Tango-77 protein, expression of Tango-77 nucleic acid, or mutation content of Tango-77 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM shows no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of Tango-77 protein, expression of Tango-77 nucleic acid, or mutation content of Tango-77 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a Tango-77 modulator, such as a modulator identified by one of the exemplary screening assays described herein.

4. Monitoring of Effects During Clinical Trials

Monitoring the influence of agents (e.g., drugs, compounds) on the expression or activity of Tango-77 (e.g., the ability to modulate aberrant inflammation) can be applied not only in basic drug screening, but also in clinical trials. For example, the effectiveness of an agent, as determined by a screening assay as described herein, to increase Tango-77 gene expression, increase protein levels, or upregulate Tango-77 activity, can be monitored in clinical trials of subjects exhibiting decreased Tango-77 gene expression, decreased protein levels, or downregulated Tango-77 activity. Alternatively, the effectiveness of an agent, as determined by a screening assay, to decrease Tango-77 gene expression, decrease protein levels, or downregulate Tango-77 activity, can be monitored in clinical trials of subjects exhibiting increased Tango-77 gene expression, increased protein levels, or upregulated Tango-77 activity.

For example, and not by way of limitation, genes, including Tango-77, that are modulated in cells by treatment with an agent (e.g., compound, drug or small molecule) which modulates Tango-77 activity (e.g., as identified in a screening assay described herein) can be identified. Thus, to study the effect of agents on cellular proliferation disorders, for example, in a clinical trial, cells can be isolated and RNA prepared and analyzed for the levels of expression of Tango-77 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Tango-77 or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Tango-77 protein, mRNA, or genomic DNA in the preadministration sample; (iii) obtaining one or more post-administration samples from the subject; (iv) detecting the level of expression or activity of the Tango-77 protein, mRNA, or genomic DNA in the post-administration samples; (v) comparing the level of expression or activity of the Tango-77 protein, mRNA, or genomic DNA in the pre-administration sample with the Tango-77 protein, mRNA, or genomic DNA in the post administration sample or samples; and (vi) altering the administration of the agent to the subject accordingly. For example, increased administration of the agent may be desirable to increase the expression or activity of Tango-77 to higher levels than detected, i.e., to increase the effectiveness of the agent. Alternatively, decreased administration of the agent may be desirable to decrease expression or activity of Tango-77 to lower levels than detected, i.e., to decrease the effectiveness of the agent.

C. Methods of Treatment

The present invention provides for both prophylactic and therapeutic methods of treating a subject at risk of (or susceptible to) developing or having a disorder associated with aberrant Tango-77 expression or activity. Alternatively, disorders associated with aberrant IL-1 production can be treated with Tango-77. Such disorders include acute and chronic inflammation, asthma, some classes of arthritis, autoimmune diabetes, systemic lupus erythematosus and inflammatory bowel disease.

1. Prophylactic Methods

In one aspect, the invention provides a method for preventing in a subject, a disease or condition associated with an aberrant Tango-77 expression or activity (or aberrant IL-1 expression or activity), by administering to the subject an agent which modulates Tango-77 expression or at least one Tango-77 activity. Subjects at risk for a disease which is caused or contributed to by aberrant Tango-77 expression or activity can be identified by, for example, any or a combination of diagnostic or prognostic assays as described herein. Administration of a prophylactic agent can occur prior to the manifestation of symptoms characteristic of the Tango-77 aberrancy, such that a disease or disorder is prevented or, alternatively, delayed in its progression. Depending on the type of Tango-77 aberrancy, for example, a Tango-77 agonist or Tango-77 antagonist agent can be used for treating the subject. The appropriate agent can be determined based on screening assays described herein.

2. Therapeutic Methods

Another aspect of the invention pertains to methods of modulating Tango-77 expression or activity for therapeutic purposes. The modulatory method of the invention involves contacting a cell with an agent that modulates one or more of the activities of Tango-77 protein activity associated with the cell. An agent that modulates Tango-77 protein activity can be an agent as described herein, such as a nucleic acid or a protein, a naturally-occurring cognate ligand of a Tango-77 protein, a peptide, a Tango-77 peptidomimetic, or other small molecule. In one embodiment, the agent stimulates one or more of the biological activities of Tango-77 protein. Examples of such stimulatory agents include active Tango-77 protein and a nucleic acid molecule encoding Tango-77 that has been introduced into the cell. In another embodiment, the agent inhibits one or more of the biological activities of Tango-77 protein. Examples of such inhibitory agents include antisense Tango-77 nucleic acid molecules and anti-Tango-77 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a Tango-77 protein or nucleic acid molecule. In one embodiment, the method involves administering an agent (e.g., an agent identified by a screening assay described herein), or combination of agents that modulates (e.g., upregulates or downregulates) Tango-77 expression or activity. In another embodiment, the method involves administering a Tango-77 protein or nucleic acid molecule as therapy to compensate for reduced or aberrant Tango-77 expression or activity.

Stimulation of Tango-77 activity is desirable in situations in which Tango-77 is abnormally downregulated and/or in which increased Tango-77 activity is likely to have a beneficial effect. Conversely, inhibition of Tango-77 activity is desirable in situations in which Tango-77 is abnormally upregulated and/or in which decreased Tango-77 activity is likely to have a beneficial effect.

This invention is further illustrated by the following examples which should not be construed as limiting. The contents of all references, patents and published patent applications cited throughout this application are hereby incorporated by reference.

EXAMPLES

Example 1

Isolation and Characterization of Human Tango-77 cDNAs

Cytokine genes IL-1α, IL-1β and IL-1ra have been found to be closely clustered on chromosome 2, i.e., IL-1α, IL-1β and IL-1ra are located within 450 kb of each other. BAC clones containing IL-1α and IL-1β were used to identify other proximal unknown cytokine genes. To do this, a BAC clone containing IL-1α and IL-1β was selected from a BAC library (Research Genetics, Huntsville, Alabama) using specific primers designed against IL-1α and IL-1β. The DNA from the BAC was extracted and used to make a random-sheared genomic library. From this BAC library, 4000 clones were selected for sequencing. The resulting genomic sequences were then assembled into contigs and used to screen proprietary and public data bases. One genomic contig was found to contain two segments of sequences which resemble IL-1ra. These two segments are potential exons of Tango-77 gene.

Two PCR primers were then designed from the two potential exons and used to screen a panel of cDNA libraries for the expression of a Tango-77 message. A cDNA library from TNF-α treated human lung epithelia showed a positive band of the predicted size (i.e., if the two exons are spliced together). Using the PCR fragment as a probe, a single cDNA clone was isolated from the same library. This cDNA contains an insert of 989 bp. The cDNA clone contains three possible open reading frames. The first open reading frame encompasses 534 nucleotides (nucleotides 356–889 of SEQ ID NO:1; SEQ ID NO:3) and encodes a 178 amino acid protein (SEQ ID NO:2). This protein may include a predicted signal sequence of about 63 amino acids (from amino acid 1 to about amino acid 63 of SEQ ID NO:2 (SEQ ID NO:4)) and a predicted mature protein of about 115 amino acids (from about amino acid 64 to amino acid 178 of SEQ ID NO:2 (SEQ ID NO:5))

The second putative nucleotide open reading frame encompasses 498 nucleotides (nucleotides 389–889 of SEQ ID NO:1; SEQ ID NO:6) and encodes a 167 amino acid protein (SEQ ID NO:7). This protein includes a predicted signal sequence of about 52 amino acids (from amino acid 1 to about amino acid 52 of SEQ ID NO:7 (SEQ ID NO:8)) and a predicted mature protein of about 115 amino acids (from about amino acid 53 to amino acid 167 of SEQ ID NO:7 (SEQ ID NO:9)).

The third open reading frame (nucleotides 372–889 of SEQ ID NO:1; SEQ ID NO:10) encompasses 408 nucleotides and encodes a 136 amino acid protein (SEQ ID NO:11). This protein includes a predicted signal sequence of about 21 amino acids (from amino acid 1 to about amino acid 21 of SEQ ID NO:11 (SEQ ID NO:12)) and a predicted mature protein of about 115 amino acids (from about amino acid 22 to amino acid 136 of SEQ ID NO:11 (SEQ ID NO:13)).

Tango-77 is predicted to be 35% identical to human IL-1ra at the amino acid level.

Example 2

Expression of Tango-77 mRNA in Human Tissues

The expression of Tango-77 was analyzed using Northern blot hybridization. A PCR generated 989 bp Tango-77 product was radioactively labeled with $^{32}$P-dCTP using the Prime-It kit (Stratagene; La Jolla, Calif.) according to the instructions of the supplier. Filters containing human mRNA (MTNI and MTNII: Clontech; Palo Alto, Calif.) were probed in ExpressHyb hybridization solution (Clontech) and washed at high stringency according to manufacturer's recommendations.

Tango-77 mRNA was not detected in any unstimulated tissues (brain, liver, spleen, skeletal muscle, testis, pancreas, heart, kidney and peripheral blood leukocytes) mRNA on Clontech Northern blots.

Over 96 cDNA libraries were then tested for the presence of Tango-77 using PCR amplification. Only three libraries displayed a positive signal. These libraries were the TNFα-treated bronchoepithelium, TNFα-treated SSC cell line and anti-CD3-treated T cells.

Example 3

Characterization of Tango-77 Proteins

In this example, the predicted amino acid sequence of human Tango-77 protein was compared to the amino acid sequence of known protein IL-1ra. In addition, the molecular weight of the human Tango-77 proteins was predicted.

The human Tango-77 cDNA (FIG. 1; SEQ ID NO:1) isolated as described above encodes a 178 amino acid protein (FIG. 1; SEQ ID NO:2) or a 167 amino acid protein (FIG. 1; SEQ ID NO:7) or a 136 amino acid protein (FIG. 1; SEQ ID NO:11). The signal peptide prediction program SIGNALP Optimized Tool (Nielsen et al. (1997) *Protein Engineering* 10:1–6) predicted that Tango-77 includes a 63 amino acid signal peptide (amino acid 1 to about amino acid 63 of SEQ ID NO:2 (SEQ ID NO:4)) preceding the 115 mature protein; or preceding the 115 mature protein (about amino acid 52 to amino acid 167 of SEQ ID NO:7 (SEQ ID NO:8)); or preceding the 115 mature protein (about amino acid 21 to amino acid 136 of SEQ ID NO:11;SEQ ID NO:12).

As shown in FIG. 2, Tango-77 has a region of homology to IL-1ra (SEQ ID NO:14).

Mature Tango-77 has a predicted MW of about 13 kDa and the predicted MW for the immature Tango-77 is 19.6 kDa, 18.5 kDa or 15.2 kDa, not including post-translational modifications.

Example 4

Preparation of Tango-77 Proteins

Recombinant Tango-77 can be produced in a variety of expression systems. For example, the mature Tango-77 peptide can be expressed as a recombinant glutathione-S-transferase (GST) fusion protein in *E. coli* and the fusion protein can be isolated and characterized. Specifically, as described above, Tango-77 can be fused to GST and this fusion protein can be expressed in *E. coli* strain PEB199. Expression of the GST-Tango-77 fusion protein in PEB199 can be induced with IPTG. The recombinant fusion protein can be purified from crude bacterial lysates of the induced PEB199 strain by affinity chromatography on glutathione beads.

Example 5

Alternatively spliced forms of IL-1ra and Tango-77

Computer program Procrustes (Gelfand et al., 1996, *Proc. Natl. Acad. Sci. USA,* 93:9061–9066) is an alignment algorithm that predicts the presence of alternatively spliced exons for a protein of interest in a stretch of genomic DNA. Using the IL-1ra sequence, Proscustes was used to search for the presence of additional sequences that might encode for alternatively spliced forms of IL-1ra in the two overlapping BAC genomic sequences (see FIG. 3 and FIG. 4). Potential sequences that encode variant exons for IL-1ra were identified. These predicted exons aligned well with the N-terminal region of IL-1ra, but were not present in Tango-77. The results from Procrustes predicts the existence of more spliced forms of IL-1ra.

Figure 7:
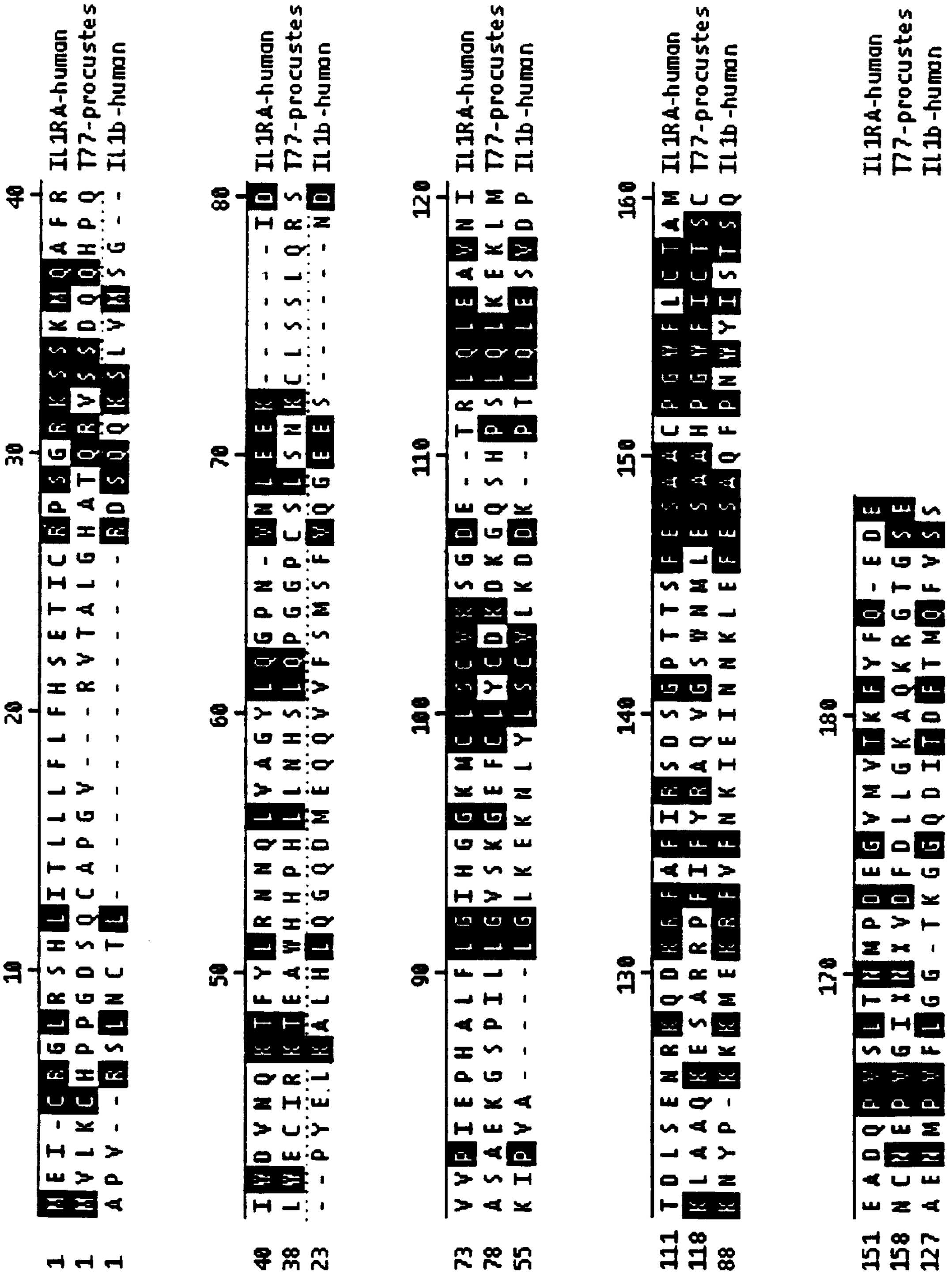
FIG. 7 depicts an alignment of an amino acid sequence of an alternatively spliced form of Tango-77 (T77-procrustes; SEQ ID NO:18) with IL-1ra (SEQ ID NO:14), and IL-1β (SEQ ID NO:15).

Furthermore, Procrustes also predicted an additional sequence in BAC1 and BAC2 that encodes an alternatively spliced exon for Tango-77 (T77-procrustes; FIG. 5). This predicted splice variant form of Tango-77, T77-procrustes, was aligned with Tango-77 (FIG. 6) and with IL-1ra and IL-1β (FIG. 7).

PCR primers within this sequence can be used to generate a product that can be used to screen a panel of cDNA libraries using standard techniques. Suitable cDNA libraries include libraries made from TNFα-treated bronchoepithelium, TNFα-treated SSC cell line and anti-CD3-treated T cells. The resulting cDNA clone(s) can be isolated from the library and sequenced to identify additional Tango-77 cDNAs.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. An isolated nucleic acid molecule comprising a nucleotide sequence which encodes a naturally-occurring polypeptide comprising an amino acid sequence at least 90% identical to the amino acid sequence of SEQ ID NO:2, 5, 7, 9, 11, or 13, or an amino acid sequence encoded by the cDNA insert of the plasmid deposited with the ATCC® as Accession Number 98807, wherein the percent identity is determined using the ALIGN program in the GCG software package. using a PAM120 weight residue table, a gap length penalty of 12, and a gap penalty of 4.

2. An isolated nucleic acid molecule which hybridizes to the complement of the nucleic acid molecule consisting of SEQ ID NO:1 under conditions of incubation at 45° C. in 6.0×SSC followed by washing in 0.2×SSC, 0.1% SDS at 50° C.

3. An isolated nucleic acid molecule which hybridizes to the complement of the nucleic acid molecule consisting of SEQ ID NO:3 under conditions of incubation at 45° C. in 6.0×SSC followed by washing in 0.2×SSC, 0.1% SDS at 50° C.

4. An isolated nucleic acid molecule which hybridizes to the complement of the nucleic acid molecule consisting of SEQ ID NO:6 under conditions of incubation at 45° C. in 6.0×SSC followed by washing in 0.2×SSC, 0.1% SDS at 50° C.

5. An isolated nucleic acid molecule which hybridizes to the complement of the nucleic acid molecule consisting of SEQ ID NO:10 under conditions of incubation at 45° C. in 6.0×SSC followed by washing in 0.2×SSC, 0.1% SDS at 50° C.

6. An isolated nucleic acid molecule which hybridizes to the complement of the nucleic acid molecule consisting of SEQ ID NO:10 under conditions of incubation at 45° C. in 6.0×SSC followed by washing in 0.2×SSC, 0.1% SDS at 50° C.

7. An isolated nucleic acid molecule comprising a nucleotide sequence which encodes a polypeptide comprising the amino acid sequence of SEQ ID NO:2.

8. An isolated nucleic acid molecule comprising a nucleotide sequence which encodes a polypeptide comprising the amino acid sequence of SEQ ID NO:5.

9. An isolated nucleic acid molecule comprising a nucleotide sequence which encodes a polypeptide comprising the amino acid sequence of SEQ ID NO:7.

10. An isolated nucleic acid molecule comprising a nucleotide sequence which encodes a polypeptide comprising the amino acid sequence of SEQ ID NO:9.

11. An isolated nucleic acid molecule comprising a nucleotide sequence which encodes a polypeptide comprising the amino acid sequence of SEQ ID NO:11.

12. An isolated nucleic acid molecule comprising a nucleotide sequence which encodes a polypeptide comprising the amino acid sequence of SEQ ID NO:13.

13. An isolated nucleic acid molecule comprising a nucleotide sequence which encodes a polypeptide comprising the amino acid sequence encoded by the cDNA insert of the plasmid deposited with the ATCC® as Accession Number 98807.

14. An isolated nucleic acid molecule comprising a nucleotide sequence which encodes a mature polypeptide encoded by the cDNA insert of the plasmid deposited with the ATCC® as Accession Number 98807.

15. An isolated nucleic acid molecule comprising a naturally-occurring nucleotide sequence which is at least 90% identical to the nucleotide sequence of SEQ ID NO:1, 3, 6, or 10 or the cDNA insert of the plasmid deposited with the ATCC® as Accession Number 98807, wherein the percent identity is determined using the NBLAST program with a score of 100 and a word length of 12.

16. An isolated nucleic acid molecule comprising the nucleotide sequence of SEQ ID NO:1.

17. An isolated nucleic acid molecule comprising the nucleotide sequence of SEQ ID NO:3.

18. An isolated nucleic acid molecule comprising the nucleotide sequence of SEQ ID NO:6.

19. An isolated nucleic acid molecule comprising the nucleotide sequence of SEQ ID NO:10.

20. An isolated nucleic acid molecule comprising the nucleotide sequence of the cDNA insert of the plasmid deposited with the ATCC® as Accession Number 98807.

21. An isolated nucleic acid molecule comprising a nucleotide sequence encoding a polypeptide consisting of the amino acid sequence of SEQ ID NO:2.

22. An isolated nucleic acid molecule comprising a nucleotide sequence encoding a polypeptide consisting of the amino acid sequence of SEQ ID NO:5.

23. An isolated nucleic acid molecule comprising a nucleotide sequence encoding a polypeptide consisting of the amino acid sequence of SEQ ID NO:7.

24. An isolated nucleic acid molecule comprising a nucleotide sequence encoding a polypeptide consisting of the amino acid sequence of SEQ ID NO:9.

25. An isolated nucleic acid molecule comprising a nucleotide sequence encoding a polypeptide consisting of the amino acid sequence of SEQ ID NO:11.

26. An isolated nucleic acid molecule comprising a nucleotide sequence encoding a polypeptide consisting of the amino acid sequence of SEQ ID NO:13.

27. An isolated nucleic acid molecule comprising a nucleotide sequence encoding a polypeptide consisting of the amino acid sequence encoded by the cDNA insert of the plasmid deposited with the ATCC® as Accession Number 98807.

28. An isolated nucleic acid molecule comprising a nucleotide sequence encoding a polypeptide consisting of an amino acid sequence of a mature polypeptide encoded by the cDNA insert of the plasmid deposited with the ATCC® as Accession Number 98807.

29. An isolated nucleic acid molecule consisting of the nucleotide sequence of SEQ ID NO:1.

30. An isolated nucleic acid molecule consisting of the nucleotide sequence of SEQ ID NO:3.

31. An isolated nucleic acid molecule consisting of the nucleotide sequence of SEQ ID NO:6.

32. An isolated nucleic acid molecule consisting of the nucleotide sequence of SEQ ID NO:10.

33. An isolated nucleic acid molecule consisting of the nucleotide sequence of the cDNA insert of the plasmid deposited with the ATCC® as Accession Number 98807.

34. The nucleic acid molecule as in any one of claims 23 to 56 which further comprises vector nucleic acid sequences.

35. The nucleic acid molecule of claim 34, wherein the vector nucleic acid sequences regulate expression of a polypeptide encoded by the nucleic acid molecule.

36. An isolated host cell comprising the nucleic acid molecule of claim 35.

37. The host cell of claim 36 which is a mammalian host cell.

38. A method for producing a polypeptide comprising culturing the host cell of claim 36 under conditions in which the nucleic acid molecule is expressed and recovering the polypeptide produced.

39. An isolated host cell comprising the nucleic acid molecule as in any one of claims 1 to 33.

40. The host cell of claim 39 which is a mammalian host cell.

41. An isolated nucleic acid molecule comprising a nucleotide sequence which encodes a polypeptide comprising at least 15 contiguous amino acid residues of SEQ ID NO:2, 7, or 11, or the amino acid sequence encoded by the cDNA insert of the plasmid deposited with the ATCC® as Accession Number 98807.

42. The isolated nucleic acid molecule of claim 41 which comprises a nucleotide sequence which encodes a polypeptide comprising at least 25 contiguous amino acid residues of SEQ ID NO:2, 7, or 11, or the amino acid sequence encoded by the cDNA insert of the plasmid deposited with the ATCC® as Accession Number 98807.

43. The isolated nucleic acid molecule of claim 42 which comprises a nucleotide sequence which encodes a polypeptide comprising at least 55 contiguous amino acid residues of SEQ ID NO:2, 7, or 11, or the amino acid sequence encoded by the cDNA insert of the plasmid deposited with the ATCC® as Accession Number 98807.

* * * * *

SEQUENCE LISTING

```
<160> NUMBER OF SEQ ID NOS: 18

<210> SEQ ID NO 1
<211> LENGTH: 989
<212> TYPE: DNA
<213> ORGANISM: Homo sapiens
<220> FEATURE:
<221> NAME/KEY: CDS
<222> LOCATION: (356)...(889)

<400> SEQUENCE: 1

gtcgacccac gcgtccgcag acgtctacct gggggtcccg tctgcgctcc cgggatggaa     60

aacgcccagg ggaaacttag gcaggcgagc ggacgggcac ctcccgcggg acgaactcac    120

tcggtggcct cctacttccc cggccgtgtt ccaacgcctg agaataacgg gaacagcggt    180

cgtactcacc gacagcggca gcagcggcct ctctcaattg ggcaaagcac tccagacctt    240

ttggaagagt gacaccaaag gcaagcacct gcttggcagg cccctcagct tctacgcaag    300

tataagtctt ggacttcatt ccattttctg ttgagtaata aactcaacgt tgaaa atg     358
                                                             Met
                                                              1

tcc ttt gtg ggg gag aac tca gga gtg aaa atg ggc tct gag gac tgg      406
Ser Phe Val Gly Glu Asn Ser Gly Val Lys Met Gly Ser Glu Asp Trp
            5                  10                  15

gaa aaa gat gaa ccc cag tgc tgc tta gaa gac ccg gct gga agc ccc      454
Glu Lys Asp Glu Pro Gln Cys Cys Leu Glu Asp Pro Ala Gly Ser Pro
        20                  25                  30

ctg gaa cca ggc cca agc ctc ccc acc atg aat ttt gtt cac aca aag      502
Leu Glu Pro Gly Pro Ser Leu Pro Thr Met Asn Phe Val His Thr Lys
    35                  40                  45

atc ttc ttt gca tta gcc tca tcc ttg agc tca gcc tct gcg gag aaa      550
Ile Phe Phe Ala Leu Ala Ser Ser Leu Ser Ser Ala Ser Ala Glu Lys
 50                  55                  60                  65

gga agt ccg att ctc ctg ggg gtc tct aaa ggg gag ttt tgt ctc tac      598
Gly Ser Pro Ile Leu Leu Gly Val Ser Lys Gly Glu Phe Cys Leu Tyr
                70                  75                  80

tgt gac aag gat aaa gga caa agt cat cca tcc ctt cag ctg aag aag      646
Cys Asp Lys Asp Lys Gly Gln Ser His Pro Ser Leu Gln Leu Lys Lys
            85                  90                  95

gag aaa ctg atg aag ctg gct gcc caa aag gaa tca gca cgc cgg ccc      694
Glu Lys Leu Met Lys Leu Ala Ala Gln Lys Glu Ser Ala Arg Arg Pro
        100                 105                 110

ttc atc ttt tat agg gct cag gtg ggc tcc tgg aac atg ctg gag tcg      742
Phe Ile Phe Tyr Arg Ala Gln Val Gly Ser Trp Asn Met Leu Glu Ser
    115                 120                 125

gcg gct cac ccc gga tgg ttc atc tgc acc tcc tgc aat tgt aat gag      790
Ala Ala His Pro Gly Trp Phe Ile Cys Thr Ser Cys Asn Cys Asn Glu
130                 135                 140                 145

cct gtt ggg gtg aca gat aaa ttt gag aac agg aaa cac att gaa ttt      838
Pro Val Gly Val Thr Asp Lys Phe Glu Asn Arg Lys His Ile Glu Phe
                150                 155                 160

tca ttt caa cca gtt tgc aaa gct gaa atg agc ccc agt gag gtc agc      886
Ser Phe Gln Pro Val Cys Lys Ala Glu Met Ser Pro Ser Glu Val Ser
            165                 170                 175

gat taggaaactg ccccattgaa cgccttcctc gctaatttga actaattgta           939
Asp

taaaaacacc aaacctgctc actaaaaaaa aaaaaaaaaa gggcggccgc               989
```

-continued

<210> SEQ ID NO 2
<211> LENGTH: 178
<212> TYPE: PRT
<213> ORGANISM: Homo sapiens

<400> SEQUENCE: 2

```
Met Ser Phe Val Gly Glu Asn Ser Gly Val Lys Met Gly Ser Glu Asp
  1               5                  10                  15

Trp Glu Lys Asp Glu Pro Gln Cys Cys Leu Glu Asp Pro Ala Gly Ser
             20                  25                  30

Pro Leu Glu Pro Gly Pro Ser Leu Pro Thr Met Asn Phe Val His Thr
         35                  40                  45

Lys Ile Phe Phe Ala Leu Ala Ser Ser Leu Ser Ser Ala Ser Ala Glu
     50                  55                  60

Lys Gly Ser Pro Ile Leu Leu Gly Val Ser Lys Gly Glu Phe Cys Leu
 65                  70                  75                  80

Tyr Cys Asp Lys Asp Lys Gly Gln Ser His Pro Ser Leu Gln Leu Lys
                 85                  90                  95

Lys Glu Lys Leu Met Lys Leu Ala Ala Gln Lys Glu Ser Ala Arg Arg
            100                 105                 110

Pro Phe Ile Phe Tyr Arg Ala Gln Val Gly Ser Trp Asn Met Leu Glu
        115                 120                 125

Ser Ala Ala His Pro Gly Trp Phe Ile Cys Thr Ser Cys Asn Cys Asn
    130                 135                 140

Glu Pro Val Gly Val Thr Asp Lys Phe Glu Asn Arg Lys His Ile Glu
145                 150                 155                 160

Phe Ser Phe Gln Pro Val Cys Lys Ala Glu Met Ser Pro Ser Glu Val
                165                 170                 175

Ser Asp
```

<210> SEQ ID NO 3
<211> LENGTH: 534
<212> TYPE: DNA
<213> ORGANISM: Homo sapiens

<400> SEQUENCE: 3

```
atgtcctttg tgggggagaa ctcaggagtg aaaatgggct ctgaggactg ggaaaaagat     60

gaaccccagt gctgcttaga agacccggct ggaagccccc tggaaccagg cccaagcctc    120

cccaccatga attttgttca cacaaagatc ttctttgcat tagcctcatc cttgagctca    180

gcctctgcgg agaaaggaag tccgattctc ctgggggtct ctaaagggga gttttgtctc    240

tactgtgaca aggataaagg acaaagtcat ccatcccttc agctgaagaa ggagaaactg    300

atgaagctgg ctgcccaaaa ggaatcagca cgccggccct tcatctttta tagggctcag    360

gtgggctcct ggaacatgct ggagtcggcg gctcaccccg gatggttcat ctgcacctcc    420

tgcaattgta atgagcctgt tggggtgaca gataaatttg agaacaggaa acacattgaa    480

ttttcatttc aaccagtttg caaagctgaa atgagcccca gtgaggtcag cgat          534
```

<210> SEQ ID NO 4
<211> LENGTH: 63
<212> TYPE: PRT
<213> ORGANISM: Homo sapiens

<400> SEQUENCE: 4

```
Met Ser Phe Val Gly Glu Asn Ser Gly Val Lys Met Gly Ser Glu Asp
  1               5                  10                  15
```

-continued

```
Trp Glu Lys Asp Glu Pro Gln Cys Cys Leu Glu Asp Pro Ala Gly Ser
            20                  25                  30

Pro Leu Glu Pro Gly Pro Ser Leu Pro Thr Met Asn Phe Val His Thr
        35                  40                  45

Lys Ile Phe Phe Ala Leu Ala Ser Ser Leu Ser Ser Ala Ser Ala
    50                  55                  60


<210> SEQ ID NO 5
<211> LENGTH: 115
<212> TYPE: PRT
<213> ORGANISM: Homo sapiens

<400> SEQUENCE: 5

Glu Lys Gly Ser Pro Ile Leu Leu Gly Val Ser Lys Gly Glu Phe Cys
  1               5                  10                  15

Leu Tyr Cys Asp Lys Asp Lys Gly Gln Ser His Pro Ser Leu Gln Leu
            20                  25                  30

Lys Lys Glu Lys Leu Met Lys Leu Ala Ala Gln Lys Glu Ser Ala Arg
        35                  40                  45

Arg Pro Phe Ile Phe Tyr Arg Ala Gln Val Gly Ser Trp Asn Met Leu
    50                  55                  60

Glu Ser Ala Ala His Pro Gly Trp Phe Ile Cys Thr Ser Cys Asn Cys
 65                  70                  75                  80

Asn Glu Pro Val Gly Val Thr Asp Lys Phe Glu Asn Arg Lys His Ile
                 85                  90                  95

Glu Phe Ser Phe Gln Pro Val Cys Lys Ala Glu Met Ser Pro Ser Glu
            100                 105                 110

Val Ser Asp
        115


<210> SEQ ID NO 6
<211> LENGTH: 501
<212> TYPE: DNA
<213> ORGANISM: Homo sapiens
<220> FEATURE:
<221> NAME/KEY: CDS
<222> LOCATION: (1)...(501)

<400> SEQUENCE: 6

atg ggc tct gag gac tgg gaa aaa gat gaa ccc cag tgc tgc tta gaa       48
Met Gly Ser Glu Asp Trp Glu Lys Asp Glu Pro Gln Cys Cys Leu Glu
  1               5                  10                  15

gac ccg gct gga agc ccc ctg gaa cca ggc cca agc ctc ccc acc atg       96
Asp Pro Ala Gly Ser Pro Leu Glu Pro Gly Pro Ser Leu Pro Thr Met
            20                  25                  30

aat ttt gtt cac aca aag atc ttc ttt gca tta gcc tca tcc ttg agc      144
Asn Phe Val His Thr Lys Ile Phe Phe Ala Leu Ala Ser Ser Leu Ser
        35                  40                  45

tca gcc tct gcg gag aaa gga agt ccg att ctc ctg ggg gtc tct aaa      192
Ser Ala Ser Ala Glu Lys Gly Ser Pro Ile Leu Leu Gly Val Ser Lys
    50                  55                  60

ggg gag ttt tgt ctc tac tgt gac aag gat aaa gga caa agt cat cca      240
Gly Glu Phe Cys Leu Tyr Cys Asp Lys Asp Lys Gly Gln Ser His Pro
 65                  70                  75                  80

tcc ctt cag ctg aag aag gag aaa ctg atg aag ctg gct gcc caa aag      288
Ser Leu Gln Leu Lys Lys Glu Lys Leu Met Lys Leu Ala Ala Gln Lys
                 85                  90                  95

gaa tca gca cgc cgg ccc ttc atc ttt tat agg gct cag gtg ggc tcc      336
Glu Ser Ala Arg Arg Pro Phe Ile Phe Tyr Arg Ala Gln Val Gly Ser
            100                 105                 110
```

-continued

```
tgg aac atg ctg gag tcg gcg gct cac ccc gga tgg ttc atc tgc acc      384
Trp Asn Met Leu Glu Ser Ala Ala His Pro Gly Trp Phe Ile Cys Thr
        115                 120                 125

tcc tgc aat tgt aat gag cct gtt ggg gtg aca gat aaa ttt gag aac      432
Ser Cys Asn Cys Asn Glu Pro Val Gly Val Thr Asp Lys Phe Glu Asn
    130                 135                 140

agg aaa cac att gaa ttt tca ttt caa cca gtt tgc aaa gct gaa atg      480
Arg Lys His Ile Glu Phe Ser Phe Gln Pro Val Cys Lys Ala Glu Met
145                 150                 155                 160

agc ccc agt gag gtc agc gat                                          501
Ser Pro Ser Glu Val Ser Asp
                165


<210> SEQ ID NO 7
<211> LENGTH: 167
<212> TYPE: PRT
<213> ORGANISM: Homo sapiens

<400> SEQUENCE: 7

Met Gly Ser Glu Asp Trp Glu Lys Asp Glu Pro Gln Cys Cys Leu Glu
  1               5                  10                  15

Asp Pro Ala Gly Ser Pro Leu Glu Pro Gly Pro Ser Leu Pro Thr Met
             20                  25                  30

Asn Phe Val His Thr Lys Ile Phe Phe Ala Leu Ala Ser Ser Leu Ser
         35                  40                  45

Ser Ala Ser Ala Glu Lys Gly Ser Pro Ile Leu Leu Gly Val Ser Lys
     50                  55                  60

Gly Glu Phe Cys Leu Tyr Cys Asp Lys Asp Lys Gly Gln Ser His Pro
 65                  70                  75                  80

Ser Leu Gln Leu Lys Lys Glu Lys Leu Met Lys Leu Ala Ala Gln Lys
                 85                  90                  95

Glu Ser Ala Arg Arg Pro Phe Ile Phe Tyr Arg Ala Gln Val Gly Ser
            100                 105                 110

Trp Asn Met Leu Glu Ser Ala Ala His Pro Gly Trp Phe Ile Cys Thr
        115                 120                 125

Ser Cys Asn Cys Asn Glu Pro Val Gly Val Thr Asp Lys Phe Glu Asn
    130                 135                 140

Arg Lys His Ile Glu Phe Ser Phe Gln Pro Val Cys Lys Ala Glu Met
145                 150                 155                 160

Ser Pro Ser Glu Val Ser Asp
                165


<210> SEQ ID NO 8
<211> LENGTH: 52
<212> TYPE: PRT
<213> ORGANISM: Homo sapiens

<400> SEQUENCE: 8

Met Gly Ser Glu Asp Trp Glu Lys Asp Glu Pro Gln Cys Cys Leu Glu
  1               5                  10                  15

Asp Pro Ala Gly Ser Pro Leu Glu Pro Gly Pro Ser Leu Pro Thr Met
             20                  25                  30

Asn Phe Val His Thr Lys Ile Phe Phe Ala Leu Ala Ser Ser Leu Ser
         35                  40                  45

Ser Ala Ser Ala
    50
```

-continued

```
<210> SEQ ID NO 9
<211> LENGTH: 115
<212> TYPE: PRT
<213> ORGANISM: Homo sapiens

<400> SEQUENCE: 9

Glu Lys Gly Ser Pro Ile Leu Leu Gly Val Ser Lys Gly Glu Phe Cys
  1               5                  10                  15

Leu Tyr Cys Asp Lys Asp Lys Gly Gln Ser His Pro Ser Leu Gln Leu
             20                  25                  30

Lys Lys Glu Lys Leu Met Lys Leu Ala Ala Gln Lys Glu Ser Ala Arg
         35                  40                  45

Arg Pro Phe Ile Phe Tyr Arg Ala Gln Val Gly Ser Trp Asn Met Leu
     50                  55                  60

Glu Ser Ala Ala His Pro Gly Trp Phe Ile Cys Thr Ser Cys Asn Cys
 65                  70                  75                  80

Asn Glu Pro Val Gly Val Thr Asp Lys Phe Glu Asn Arg Lys His Ile
                 85                  90                  95

Glu Phe Ser Phe Gln Pro Val Cys Lys Ala Glu Met Ser Pro Ser Glu
            100                 105                 110

Val Ser Asp
        115


<210> SEQ ID NO 10
<211> LENGTH: 408
<212> TYPE: DNA
<213> ORGANISM: Homo sapiens
<220> FEATURE:
<221> NAME/KEY: CDS
<222> LOCATION: (1)...(408)

<400> SEQUENCE: 10

atg aat ttt gtt cac aca aag atc ttc ttt gca tta gcc tca tcc ttg       48
Met Asn Phe Val His Thr Lys Ile Phe Phe Ala Leu Ala Ser Ser Leu
  1               5                  10                  15

agc tca gcc tct gcg gag aaa gga agt ccg att ctc ctg ggg gtc tct       96
Ser Ser Ala Ser Ala Glu Lys Gly Ser Pro Ile Leu Leu Gly Val Ser
             20                  25                  30

aaa ggg gag ttt tgt ctc tac tgt gac aag gat aaa gga caa agt cat      144
Lys Gly Glu Phe Cys Leu Tyr Cys Asp Lys Asp Lys Gly Gln Ser His
         35                  40                  45

cca tcc ctt cag ctg aag aag gag aaa ctg atg aag ctg gct gcc caa      192
Pro Ser Leu Gln Leu Lys Lys Glu Lys Leu Met Lys Leu Ala Ala Gln
     50                  55                  60

aag gaa tca gca cgc cgg ccc ttc atc ttt tat agg gct cag gtg ggc      240
Lys Glu Ser Ala Arg Arg Pro Phe Ile Phe Tyr Arg Ala Gln Val Gly
 65                  70                  75                  80

tcc tgg aac atg ctg gag tcg gcg gct cac ccc gga tgg ttc atc tgc      288
Ser Trp Asn Met Leu Glu Ser Ala Ala His Pro Gly Trp Phe Ile Cys
                 85                  90                  95

acc tcc tgc aat tgt aat gag cct gtt ggg gtg aca gat aaa ttt gag      336
Thr Ser Cys Asn Cys Asn Glu Pro Val Gly Val Thr Asp Lys Phe Glu
            100                 105                 110

aac agg aaa cac att gaa ttt tca ttt caa cca gtt tgc aaa gct gaa      384
Asn Arg Lys His Ile Glu Phe Ser Phe Gln Pro Val Cys Lys Ala Glu
        115                 120                 125

atg agc ccc agt gag gtc agc gat                                      408
Met Ser Pro Ser Glu Val Ser Asp
    130                 135
```

-continued

```
<210> SEQ ID NO 11
<211> LENGTH: 136
<212> TYPE: PRT
<213> ORGANISM: Homo sapiens

<400> SEQUENCE: 11

Met Asn Phe Val His Thr Lys Ile Phe Phe Ala Leu Ala Ser Ser Leu
  1               5                  10                  15

Ser Ser Ala Ser Ala Glu Lys Gly Ser Pro Ile Leu Leu Gly Val Ser
             20                  25                  30

Lys Gly Glu Phe Cys Leu Tyr Cys Asp Lys Asp Lys Gly Gln Ser His
         35                  40                  45

Pro Ser Leu Gln Leu Lys Lys Glu Lys Leu Met Lys Leu Ala Ala Gln
     50                  55                  60

Lys Glu Ser Ala Arg Arg Pro Phe Ile Phe Tyr Arg Ala Gln Val Gly
 65                  70                  75                  80

Ser Trp Asn Met Leu Glu Ser Ala Ala His Pro Gly Trp Phe Ile Cys
                 85                  90                  95

Thr Ser Cys Asn Cys Asn Glu Pro Val Gly Val Thr Asp Lys Phe Glu
            100                 105                 110

Asn Arg Lys His Ile Glu Phe Ser Phe Gln Pro Val Cys Lys Ala Glu
        115                 120                 125

Met Ser Pro Ser Glu Val Ser Asp
    130                 135


<210> SEQ ID NO 12
<211> LENGTH: 21
<212> TYPE: PRT
<213> ORGANISM: Homo sapiens

<400> SEQUENCE: 12

Met Asn Phe Val His Thr Lys Ile Phe Phe Ala Leu Ala Ser Ser Leu
  1               5                  10                  15

Ser Ser Ala Ser Ala
             20


<210> SEQ ID NO 13
<211> LENGTH: 115
<212> TYPE: PRT
<213> ORGANISM: Homo sapiens

<400> SEQUENCE: 13

Glu Lys Gly Ser Pro Ile Leu Leu Gly Val Ser Lys Gly Glu Phe Cys
  1               5                  10                  15

Leu Tyr Cys Asp Lys Asp Lys Gly Gln Ser His Pro Ser Leu Gln Leu
             20                  25                  30

Lys Lys Glu Lys Leu Met Lys Leu Ala Ala Gln Lys Glu Ser Ala Arg
         35                  40                  45

Arg Pro Phe Ile Phe Tyr Arg Ala Gln Val Gly Ser Trp Asn Met Leu
     50                  55                  60

Glu Ser Ala Ala His Pro Gly Trp Phe Ile Cys Thr Ser Cys Asn Cys
 65                  70                  75                  80

Asn Glu Pro Val Gly Val Thr Asp Lys Phe Glu Asn Arg Lys His Ile
                 85                  90                  95

Glu Phe Ser Phe Gln Pro Val Cys Lys Ala Glu Met Ser Pro Ser Glu
            100                 105                 110

Val Ser Asp
        115
```

-continued

<210> SEQ ID NO 14
<211> LENGTH: 177
<212> TYPE: PRT
<213> ORGANISM: Homo sapiens

<400> SEQUENCE: 14

```
Met Glu Ile Cys Arg Gly Leu Arg Ser His Leu Ile Thr Leu Leu Leu
  1               5                  10                  15

Phe Leu Phe His Ser Glu Thr Ile Cys Arg Pro Ser Gly Arg Lys Ser
             20                  25                  30

Ser Lys Met Gln Ala Phe Arg Ile Trp Asp Val Asn Gln Lys Thr Phe
         35                  40                  45

Tyr Leu Arg Asn Asn Gln Leu Val Ala Gly Tyr Leu Gln Gly Pro Asn
     50                  55                  60

Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                 85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 15
<211> LENGTH: 153
<212> TYPE: PRT
<213> ORGANISM: Homo sapiens

<400> SEQUENCE: 15

```
Ala Pro Val Arg Ser Leu Asn Cys Thr Leu Arg Asp Ser Gln Gln Lys
  1               5                  10                  15

Ser Leu Val Met Ser Gly Pro Tyr Glu Leu Lys Ala Leu His Leu Gln
             20                  25                  30

Gly Gln Asp Met Glu Gln Gln Val Val Phe Ser Met Ser Phe Val Gln
         35                  40                  45

Gly Glu Glu Ser Asn Asp Lys Ile Pro Val Ala Leu Gly Leu Lys Glu
     50                  55                  60

Lys Asn Leu Tyr Leu Ser Cys Val Leu Lys Asp Asp Lys Pro Thr Leu
 65                  70                  75                  80

Gln Leu Glu Ser Val Asp Pro Lys Asn Tyr Pro Lys Lys Lys Met Glu
                 85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140
```

-continued

```
Asp Phe Thr Met Gln Phe Val Ser Ser
145                 150


<210> SEQ ID NO 16
<211> LENGTH: 152331
<212> TYPE: DNA
<213> ORGANISM: Homo sapiens
<220> FEATURE:
<221> NAME/KEY: misc_feature
<222> LOCATION: (1)...(152331)
<223> OTHER INFORMATION: n = A,T,C or G

<400> SEQUENCE: 16

gaagtgaaga tataatgtat agtagtaata tataatgtta ggtgaattaa aggaaataga     60

atatattggg gagtaattat gggtgtaaag aaatatagta gggaagtatt tagatttgag    120

aaaaaaaaaa aggaatttag tgtaggtgaa naataaaagn anaaggttaa aaattaaaaa    180

aaaattaaat ataaataaat aaataaaaat aaaaataaaa taaaaaattt aaaaaattaa    240

aaaaatataa aaaataaaga aatggaagtg gattcttaga aaaaaaagaa agtaaggtga    300

tatgaggaga tagagaggat gtggtgtgag atgattggtt taattagaaa ataggttttg    360

aatagagtgg gaaagtagag ttttggtaaa tgtgggggga agagggtaat gttgtttgag    420

tgaaagaaaa aatggtatat ttttataaaa taatgaggaa agtgtgtgaa aaaaaaatta    480

ttgggatttg ggaaggtgat atataaagtt gtggaaaatt tggggggtgg ggtttattta    540

ggattaaaaa gttatttaaa gaatgaaaat gaatttttgt ttgtaatttg gggataagaa    600

attaatgttt agaaagaaag ggaaaaaatt gaagaaaaaa atttagattt tggaaattta    660

aaaatattgt gggtgtaaat aggaaggatt tttaaaggta attgtggaag ggatttgtgt    720

ggaaaataat agggagaaaa aatgggggca tctaactgga gcctgcatta ttacagattt    780

agcatcacca aagtctaaac aattagactg actaaggcag aactgccctt atgacagcag    840

acataagaag gaaaaggcca aaacactgtg ttaaaaatta tccaaatgtg aggaaaaggc    900

aaagagagta ggtgtgcctt tttagtgtct aagctgcctg cccaaggggc atctgatgct    960

ctcaggcagg agtccacaaa tttttttttg taaaagatca gatagtaaat cttttcagcg   1020

tgaagagcat gaggtctctg tcacaaatac tcaaccacca ttacaacatg aaagcagcca   1080

acagacaaca catgacaaat gagtgtggct gtgttccagt aaatcttgat tacaaaaaca   1140

ggcaagaggc cagagctgac ccatgggcca tagtttgctg acccccttctg taaaggaaag   1200

tatttttgtt tgacttgctg tttaccattg attgaacaca aggctctgta aagttacttg   1260

ttaacttgca gaagattgat gagtggcaag taatttttat tcaccagaat ataaaattat   1320

ttctgttcag tagaaaagat aaaccaactg tgatattatg gtcctggggg tgtctgtcta   1380

ccatgtgctc gcagttctgt aataaatgtt ctctcaagat ccttaaaatc tcttggaaat   1440

tataaaaata ttggaaagag aagaacagtt tttaaaatat atatatatat atatattttt   1500

tttgagatgg agtcttgctc tgtcgtccag gctggagtgc agtggcgcaa acttggttca   1560

ccacaacctc tgcctcccgg gttcaagcga ttcttctgcc tcagcctcct gagtagctgg   1620

gactacaggc gcccgccacc acgcccagct aatttttgta tttttagtag agacgaggtt   1680

ttactatgtt ggctaggctg gtctcaaact cctgaccttg tgatctgccc gccttggcct   1740

cccaaagtgc tgggattaca ggtgtgagcc actgcacctg gccagttttt taaatatatt   1800

tttaaaaaca cttgaataag agtcagtgta aactagaagt ttaaaaatgc ttcacagaac   1860

acccagggtt tacattacaa gattctcaca acaaacctat tgtaaaggtg agtaaggcat   1920
```

-continued

```
gttattacag agaaaagttt gggagcaaaa ctgtaaaaaa ttatattttt gttgtatttt   1980
ctaagagaaa gagtattgtt atgttctcct aacctctgtt gattactact ttaagtgatt   2040
tccttgagag cacatgatga tccgccgttc atagaaaact gaaagcaata agatgactag   2100
gtaagcatga catttaaaag gtattcatgg gacgtggtta caaaaccaac tcacaactaa   2160
aaagtcttag gacctctcgc tgacttagga gcctgatccc aactctgaga atgactcagt   2220
gtgttaccct gtggctagtg tagaccaatg atcctgtctc agagtcacta gccaacagcc   2280
catatcaagt acttgaaact ttgactcaga aacctcagtg tcagaacctt tgacctagga   2340
accacctgta gtggttaact gcaatttgca ccccttagtt cagggcttta caacaccggg   2400
ggcggggagg ggaaaggcat ananctgatg acctaaagga aacccattgc agcaacgctt   2460
ttgtgttaag tgtacaaata agtgttgttt tagaatcctc caggtaatgc ctttgttatt   2520
taatgtgtct gagacaattc tgcacattaa agaatataaa atattacctt gtaattccaa   2580
tttgaaatgt gtaattgaca ttagacttct atttgaattt gaaatgtcta aaacaatgtg   2640
gttaagtttg taaaaggtgt gtgaattttg agtctgattt actacatttt tttttaattt   2700
tctttttttt tggagtttta gggattgctt agatggctag aaagatttta ttcatcagat   2760
ttttaagtct gccttggcag gcacttgcag tgtttgaaag aatcagatat atcaaatttg   2820
tagtttaaaa tatttaaggg aactcaatta actatgctag aaaagagaat taagtattta   2880
ggaggattta atatggtgtg aaagttgtga aaatcaaaat ggagacacta atgttaagaa   2940
aaccctgata aatggaacca gggaaaggca tgaagataga gttctcacac ttgtatccct   3000
gatcatgaaa aagatctgcg ggtttttccg cgtttttacc cgaaatcttc aagggatggg   3060
aaaaagaaaa ttgctaaaaa atctcggttt tttggtttta acagatattt acaccntgga   3120
tcccatttat tatgttgtcc ccaaggtttt cggtgggttc ccaatcagtt agcccccctc   3180
cacagtgaaa gcactttact ttatcacctt cacctaaagc ataaaatcca gctcttgaaa   3240
gctgctcctt gttaactgaa tatatccaca tcccaaaagt aatgatccat gcttcataat   3300
ctgccacgga tggatggatg gatggatgga tggatggatg gatggatgaa tggatggatt   3360
gatttcttgg aggatttgtt gaatttggga aattccacgc caggacagct ggcccaaact   3420
gcccgcgaca atctgctcgg tacaagggga gggtcctgga gagggtgcgg cccgagcccc   3480
agtttggaaa tgccaacttg gctctgcagc cgggccttag ccacttgggt ctggcgtccc   3540
tccattatta gcgccatgcc ggctcggggt gctgccaagt ccctgagagc acaagcccgc   3600
gctcaagaaa agctgaagtg tgaatgttct gtctaccttc acagtaaatg ctaagagaat   3660
gacccaagag cagagggtat cactctgcta cggaggattg attgtaactg gctctcctgc   3720
cttagcaaga aatgccagaa ccatggtcat tcaagttctt gaccaaaaac tgccttcatg   3780
agaatcaact tccccaagaa aaaaaaagca gaaacaggca aagcttccag catggtaggt   3840
aatactgacc cttcttccct ccttcctttg gagattcaca cagtaataat gcataaagct   3900
ttgccaatgg actaagcact gcccaggggt ttttgtcatg cctggactga aatgctcttt   3960
ttgcgttatc atagaatccc agtgcagtct gagtagactc taagcaaaag ggacattttt   4020
caaaaaggct ttaaattgct agtacaaaga aggcaacaaa acttgcgtaa ctgtggacag   4080
attaactcac ttggtgtttt ggctcttcag ttttcccttg gctgcgaagt actcctgaag   4140
ctttctctgc ggctcttcct gcaagcaggc aagcaaaaaa acgactgaac tttatttcga   4200
gatgaagagc cgctaacttg ctgtagtgat aaggaatgaa ctaaggctag ggacatatta   4260
acatccgctg gtggtgactc tttagcctag atcttacccc actcctgctc cttccatatg   4320
```

-continued

```
gttcggtctc aggctcacta ccgatcaatg gcgtactaaa agcactaact atagactcca   4380
acacgtctgt cgtgtgtttc acgacaagcc gtggagttaa tccctctgac agtagctcag   4440
ataaggatgg gctatcatgg gcccggaact ggggcatgac gctcgtcacc aacgcatgag   4500
ctccccaagt atgctatacc tgtccctatg aagggcttcc aactctatgt gcagtcccca   4560
tgtggagagt caggtattga ttgatcaagc caggggtgtg gtgaatgggg agcttcctac   4620
aggggtaatg ataattgaaa tgcacggtga tggggatttt catattggtc tcctaaggag   4680
ataacagatt ggatgcgggg tcgatattcc actgcccagg gtgtgtaccg agggtatctg   4740
caggtggatc tcctccccac gtttgattaa tactcctgtc ttgggaagca tagacgggcg   4800
ggggaaatga tgaagggtga ccactccccg ggaacgcagt gctctgtacg atggccttga   4860
ttgcgaattc ctgcaggggg ggggcaagag atttaatatt cattccatct tcatttggaa   4920
gatgaaaaat tggggaccag agaggggagg ggactgggcc aagttttcaa agaaaagtca   4980
gtaggaattg tgaattcctg ggggccgggg cccattagtg ctgttttgga tcagtaaatg   5040
gagatgtgag tttcaacagt aacagggaca ttttaaaatt aaaatgattt aacctttaga   5100
aaatgtccta ttttgtaata atgatggatt cacaggaagg tacaaagaaa tgtccagaga   5160
gttcntgagc ccccttcagc cagcttcttc caatgttaac atcttgcatt attatagtac   5220
aacatcaaaa ctgggaaatc gatattggta ctgtccagat agcttactca gatttgcca   5280
gttatacttc cactcatttg tgtgtgtgtg tgtgtgtgtg tgtgtgtgtg tgtgtgtgta   5340
gctctatgca attttatgtg tgtagcttca tgtaaccacc acaatcacaa tacttaacta   5400
tgccctcatc acaagactct ctcttgctat gctttacagc tgtatcctct tcatctccaa   5460
accctaagcc cacctcaccg cctccaccat ctctaatccc tggcaaccac tattctgtgc   5520
tccatctctg taattaattg tgttaattaa tgttatacaa atggaatcat gaagtatgtg   5580
tcctttgaga ttgggctgtt aatttttcac tcagcacaat ttccgtgagt ctaatccaac   5640
ttgtgtgtag cagtaattct ttccttatta ttgctgaata atatgccatg gtatggatgt   5700
atcacagtgt gtctaatcct ttgcccattg aaaggaattt ggataatttc caggttttgg   5760
ctattatgaa taaagtgaac ataagacatg tgtgtacaaa ttttggtgtg atcaaaagtc   5820
tcatttctct gggataaatg cccggtaatg aaatggctgg gttgtgtggg gcaagaacac   5880
aggcgcgtat tataacctta ctaccaagac ctgaacccat ataaaggttt atgcgtaaca   5940
atcatcatcc ctgttccaga agattacacg tacgaccacg cctggctcac cgactcacgt   6000
gggccagtac cagaaattct cccaaacaaa cagtcgtgtc tgaaaacaat cgcggtgacc   6060
tccacggtta gaaaagcctg ttttcaagtc ctggaattgc cacatattag ctgggtaact   6120
ttgggcatca catttactct ctccgaattt cagattgcaa aaactcattg gattgttttg   6180
tggattgaaa gaaataatgt aaatttaggc cgagtgcttt gacttacgcc tgtaatccta   6240
tcactttggg aggccaaagc aggagggtca cttgagctca ggaatttgag accacctctg   6300
gcaacatagt gagatcctgt ctctacaaaa aattttttttt aaattatcca gcatggtggt   6360
acacgcctgt attcccagct actcaggaga ctgaggtgtg aggattgcta gaacctggga   6420
gatcaagtca acagtgagcc gtggttgtgc cactgccctc caacctcagt gacagaggaa   6480
gaccctgtct caaaaaaaaa aaaaaaagta gtaagtttaa agaacttagt gtaggcctgg   6540
catataaatg atattgttga tgttgatgtt agcttgaagg cacatttata ggagtaggga   6600
ttttataaca ttatgagcct gagagcacat ataatgttcc cggtctaaca tgctccaact   6660
```

-continued

```
gaagaaaccc cacacttgtc cggcaaggaa actactacag atttcctgac ctactgtgca   6720
attcggggca tgcgacggga ctgtgtttct gggtacgctg tctcaggttc gtctgggatg   6780
taagaattca acttcagtag ttctctcata gacgccgacg agaggggcgt ctcttttctc   6840
tgatgaatct gccagatctt ccacttcata gagtctaaat cctccgattc gatctactgg   6900
agacccccac gttacaaaaa cgtctaacgt cggtgacagc tccccacata gggaaagatc   6960
acctgagtct cactacctca cattagtgct atctccagcc ccatgctatc tacgagatgg   7020
tcacgcgagg tttaaggggt ctccgattcc ggtggtccga ttcagctaat cgtggcccta   7080
cgtgaacgat cactcctgct cgtaacatcg atacagggtc gcgctgacaa atggtactac   7140
gtaggttctc aggtcaatgc cgcgtcacga atgagcctaa ctaccccata agtgcacgta   7200
ctgtgttacc tttcctgttc ggccaaacct gctactgtat gctgtgcttg tttaggctcc   7260
atgtgctcta gcctgattat cttttcaagt gttttatttg ctaatctata aggccccttt   7320
cgtaaaatgt tcactcattt tctaattaga tatttttttt aatgttgagt tttgagagtt   7380
ctttagatat tttagataca agtccattgt caaatatgtg atttacaaat attttctctc   7440
aatctgtaat ttagttttca tcctcttaac agggtctttt ggagagcaaa taatttgatt   7500
ttcataaggt tcaaattatt aatttttttct tgtatagttc acacttctag tgttaagtct   7560
aaaaactgtg ccttgtcata ggtaccaaag gttttctcca gttttttttc tagaagttta   7620
gagtttcatg ttttacattg gagtccatga tccattgtta attaattttt gtatataggt   7680
agatgtttag gtttagggtt tttttaaaaa aaaattacat atgtttaatt gctccagttc   7740
cctttcattg aaaagggtat ccttcctcca ttgaattgcc tttgtcagaa attaattgga   7800
catatttgtg tgagtctatt tctgggctct ttatcatgtt acttttaaaa aatgcatcag   7860
ttcctccacc aatacctcat tgtcttgatt attgcagtta tatagtaagc cttagcatta   7920
ggaaaagtgt ttttcctgct ttattctttn tcaaaaaatt tttggatatt ctagggcctt   7980
tacatataaa ttttaaaata actttgtcta tgtctaaccg aaagccttat gaagattttg   8040
ataagaattg cattatgcct atacattaat ttaaaaagaa ctgatgtctt tattcagttg   8100
attctgctaa tctatgaaca tagcatctct ctcaaagcat ttagtctttc tttaatttct   8160
gtcattaatt ttttaaaatt ttcatcctaa agattctgta tatgttttgt tgaatttatg   8220
cttaagcatt tcactttctt ggtaacaatt ataaatgatt ttgtgttttt tattccacta   8280
gttcattttc agtgtgtaga aaagcaatga atttttgtgt gttgatcttt gttcctacat   8340
cttgcaacat tattgaactc atttattagt tctaggaggt tttttcattt ttcttgtaga   8400
taccttgaga ttttctatat agacagtcat gttgtctgca aacaggcaca gttttatttc   8460
ttccttttca atctatatgc cttttttttt ttttttgcct tattgcagtg gctagaactt   8520
ctagcactat gtcaaatagc attggtgaaa gcagacatcc ttgttccttg tcttagagga   8580
acatttggtc tttaatcttg gattgcggcg cctccttttc tcttccaaaa tttctcttgt   8640
ctagttattt gtccagggaa atttgaaagc tcacttactg tgcaagtcag caggaaacaa   8700
ctgggtctgt gcacagcacc tagcaaagtt ctgctctagg aattacactt tggccctgag   8760
gtagatttct acaagaacct taccttctaa gcagcactgg ggttcatctt tttcccagtc   8820
ctcagagccc attttcactc ctgagttctc ccccacaaag gacattttca acgttgagtt   8880
tattactcaa cagaaaatgg aatgaagtcc aagacctaag gagatagaaa ggggaccagt   8940
tatggcatct tctcacccca ggacaccttg ctgcatgtct ctagtgctga acagaccact   9000
ggccttgctc tgtagtttga aatgctcgct gcaaccagaa aggcaccaag ggccagagacc   9060
```

-continued

```
atgctctcct gtctatcacg ccttcaaagc agaatttccc aaaccttgag tcacagtgct   9120
aacacacggg gtgccataac atttttgttg attttggcat tttacaaaaa taaaataaaa   9180
aagttaaaaa tgcattgctc tattcttggg gctggcacac tattgccttt ggccaaatcc   9240
ggtccctgac tgttttttta aataaagttt tattgaaaca caaccatgct cttgtgtaca   9300
tattgtctct tggctgcttc gaagctacaa tagtgttcgc tttttaacac ttacctaaaa   9360
ttactctgta atccatggat ccttaattta tttaaaaaac taatgttaat gagtagcttt   9420
attttcctcc catctaattt aaggcccaca gaacaccttc acttacctca atcctctccc   9480
aacttacatg cttttaatgt catatatgtt aataccgtat acttttaaaa ctttctaaaa   9540
tagcattatt ttatagcatg agtgttcatt tacatttttg catatattta gaattttctt   9600
tgctcttcgt ttcttcttct atttatgact cccctctggg atcattttcc ttctacttga   9660
agtacatagt ttagaactgc actattcaat acagtagcca ctagccatgt gtagctattg   9720
aagtttaaac taagtaaaat tgagtaatat taaaaactca gttccttcat ctcactagcc   9780
acatttcaag tgctcagcag ccacgtgcga ctaatgacta ctgtacatca aacatataga   9840
acatttccat catggcaaag agctctattg atagtgttca tccagagttt ctgttccagg   9900
accaaactga gggttgggct gctatttctc atggcccaat aacaagatgc agatgagctg   9960
gggaggaaga gagtttttat ttctgcnacc atttaccggg agaaggcctg gaaatcatca  10020
ccaggccaac tcaaaattat tacgttttcc agagcttata taccttctaa gctatatgtc  10080
tacgtgtaag tgtgcattca cctgaagacg ttagtgatta acttctttta atctgtaact  10140
aaggtctgag tccggaagat cttcccctgg agcctcagta aatttactta atctaaatgg  10200
gtccaggtgc tggggtaatt acccttatct tgtcccctgc taaatcatgg aggtttgggg  10260
attcctttag agcaccaata aacttgtttg tggaggcctg gggtttcttt ctgacccaca  10320
ataaaacttg tttaatccta aatgggtcct gttaagaatt ccttctttat tttgtcatat  10380
tttaaggccc agaaaaggcc tgggcaaaac tcttgatggg cttttgttac attccagcct  10440
ttgtataaga acactggttt ttaatattta acttaaccat ttagtcagta ctgaaacagt  10500
tgttatagag atctgcatta gtgagacctg gcctgccaca tttccttttc tgaagatctt  10560
atggtagtga tcacctttgt gaaaggaaaa taaatcttgg gacctcaaaa tcactaagcc  10620
aaagaaaaaa gtcaagctgg gaagaatctg acacttaaat ccaacactgc taactcattc  10680
atctcactca ttcattcatt ttattttctt ttttctttct tttttttttt ttttttttga  10740
aacgaagtct tgctctgtca cccaagctgg agtgcagtgg atctcaggtc actgcaacct  10800
ccacctcccg ggttcaagcg attctcctac ctcagactcc tgagtagctg gaattacagg  10860
cacctgccac cacgcctggc taatttttat atttttagta gagacggggt ttcaccatgt  10920
tcatcaggct ggtctcgaac tcctgacctc gtgatccgca ccccccctcgg ccttgtttgc  10980
ttgaggtact gtctaaatgc tggaactgaa aatggcaagc aagacatccc taccccttgag  11040
gaaactgtaa tctagtcgga aatacagatg tcaaccaagt ctcacacaag aanattgtac  11100
aaaaccccta ggaggaaaaa cctatcaccg cctcctatgg aacttaaaac aaaaagaaaa  11160
gtaacaaagg aaatgaatat ttcattctgg aagaacattg aaaaagaaca ggaagaagag  11220
aaagcacaac tcgaactgtc cactagaatt gacaacactc tgacagaatg tctgaacctc  11280
atcgaagggg taagtgaaaa aaataagctc ctccagcttt ggcccaaagt cttataattt  11340
ttaaacatat tcctaaatat aatataggag agatagcctt catctaagta gaaatttagc  11400
```

-continued

```
tactcttgta aatacagagt aataataata atgacatgcc cataaacagt gtcttttgtg  11460
tatctgtgct tttataagca cttagctaag attatctcac ataattatca taaccactgt  11520
tactatgacc actttacaaa caaaactgag gcacaaagaa gttggaaaac taatccaaac  11580
aaactggctc caaaaggaac tttgctttct ttgggtatca agttctgaag agtacacatt  11640
taacattgaa actgaggtca gaaggcaagt ttctatgtaa agttggagta ttctgaatac  11700
tctgggtagc tacaaatagt atttaaattt tatcttggat tctgcagata aggataaaat  11760
agatggtagg caaagagtat gatccttagg agaaattttt cctgaaggaa aaatatatta  11820
ataaaaaatg atggaataaa cttctaagat ccttgcctag agcaaaactc attcagtcct  11880
ttggctggta atgttgaaca tcaacaaaaa aaaggaaaag ttcagtttaa gtctactcca  11940
ggcaacattt tcacaacatc cagttaaata ttaactattt ctctttgtgg aattgaacta  12000
gagttctttt tcttatcctc ttttttggtt gttgtattat ttaaaaatga gtaccttttt  12060
attattgaaa tcatttcaag taatgcagat aaatgatcag ccctctccct gtacaaacat  12120
acatacttag gcatcccaaa cttctctctg gaggtgacca ccattgccag tcattcattc  12180
tgttttcatg catgtccata cagtataggt atgtcgagaa atgaagtatt atatttttgt  12240
gagttgcaat tcttttattc acatttttgt gtactttggt tgtcttttct tgtgttttcc  12300
tagtaccaat gttatgctga cttaggcaga tgagttgagt attttccttt ttgccctata  12360
aactgaaaat agtttgtatg acatgagaat tattttttatt ttttgaaggt ttgataaaaa  12420
cttgcccata aaaatcgtct ggaccggttt cttgaggatg cctgtgttag agcccgcttt  12480
aacctgggct accaatggtt cgtcaagttc tagattctct attaatacct ttttcttgtg  12540
tctttctctg gtctgttttc agccccgagt ctcttagatc tgtcctctaa tattcctatt  12600
gactttactt cattttctaa gtctttatcc ttttgcttta ctttccgaga gacctgctta  12660
accttatctc ccaactcttt tattgaattt catttctttt actatatatt ttttactttg  12720
aatacacctc tctcttcctc acattttccc ccatagtatt ttgtcttcaa ttgacagttc  12780
tactatctta ttactctgga gatattaata atagttttta aatttttatt tatttttatt  12840
ttcaaaacag tgtcttactc tgtcactcac gctggagtgc agtggtgtga tcatggatca  12900
ctgcagcctt gatctctgag ctcaagctat cctcctgctt cagcctccca agtagctgga  12960
accacaggca tgtgtcacca tacccagcta atttttttgt ttttgaggtg gagtctcact  13020
ctgtagcccg gtctggagtg cagtggtgca atctgggctc acagcaacct ctgcctcctg  13080
ggtcctggtt caagcaattc tcctgcctca gcctcctgag tagctgggat tacagaaaca  13140
cactaccatg cccagctaat tttgtatttt ttgtagagac agggtttcac catgttggcc  13200
aggctggtct tgaactcctg accttgtgat ctgcccacct tggcctccca aagtgctggg  13260
attacaggcg tgagccactg cacccggcca ctaattttta aattgttaat aaagacgagg  13320
tcttgctatg ttgcccagta tggtcttgaa ctcctgggct taagtaatcc tcctgcctca  13380
gcctcccaaa gtgttgggat tacaggtgtg agccactgaa tctgacattt tttaaaagtt  13440
ttcttctctt taccaagtct tttttcccct ttctgctttt ttgggttgtt ttattttgat  13500
ctctatcttg ctagaaactt tctgcagacg tttagtaata ctagattttt gagagtgggc  13560
aactggaaag ctgattggaa actctgaata catgggtgag gcttgttggc tgtgagtgtc  13620
attgcttgat gtcctggcaa ggccaatggg tttgggaccc ctactattag tataggcctg  13680
attccctggg aaaggctctt ttgatctcct gcctggagga taaaggcctg gctaccagcc  13740
ttctgtgtgt aatgtgaggg agaagggctg gagtattcaa catcatgctg aatcctttca  13800
```

-continued

```
atgatcatct tgtttttagt aatctcctac cttaactctc tgtcttctgc tagtatggga  13860
aagatgacct gaaaatctaa ccatttattt ttcccccatt aatatcattt tatgattatt  13920
cagaagttaa ataattgtca tgctgtcctc caaaaagact gaatcaacta gcaacaaata  13980
agaattttct cacagctctg ccagcatttt aaaagaatag ctttattgag cccaggaggt  14040
caaggctgca gtgagctgtg attacaccac tctaccccag cctgggtgac agagcaaaac  14100
cctgtctcaa aaaagaaatt taaggaacag ctttattgtt gtaaaataga catacaataa  14160
acagagcaca tatttaaatt gtgcaactta tactttgata taaccctgtg aaaacatcac  14220
cacaatcaag atagtgaata tatttatcac ctcctgatac agtttagctc tgtgtcccca  14280
cctaagtctc atgttgaatt gtaatcccca atgctggggg aggggctttg tgggaggtga  14340
ttgaattgtg gggtgcact tccccccttgc tgttcttgag atagtgaatg agctctcatg  14400
agctcccctt cactcactct ctttcctgct gccatgtgag gatgtgcttg cctcttcttt  14460
gcccttctgc catgatgtgt ttcctgagtc ctccctaacc atgcctcctg tacagcttgc  14520
agaactgtga gtcagttaaa tctcttttct tcataaatta cccagtctca ggtggctctt  14580
tatagcagtg tgaaaaggaa ctaatatacc tcctaagtta cctcaagctt gtttttaatt  14640
ccttctcctc ccttccttca ttgccaagca aacaaccacc tgttttctgt cactatagat  14700
tagtttacat tttgtgggtt tttttttttt ttgagacaag gtctgactct gttgcacagg  14760
agcagagcag cgtatccgcg ttataggaga tgcgaactta agaaatgatg ataaggagac  14820
tttattaaat ataattttga attattttgc cattacagaa attctaatta tttaaaattc  14880
tattcataat ttttaatcac tgtacttccc aagcttagct tagaatcctt ctgtgctgag  14940
gattaatttt aatttgtctt ttataggcct tatctaaaat ccaagaataa ttgccagaat  15000
caaccacctt ctaaatctgt aagtagaaat tagtcttttt aaaaatatgc attcataagt  15060
atgattagta ataaaaataa taaagatgtt agcaacctaa agaacatgta tttgaaaggt  15120
atttcttaca gatataaaaa cagtttggtt taataagaga caatcatttt ttgaaaagta  15180
tgacattttt tgaaaagtag tttagtttta ttaaccaaga aaagcctcaa gtgaacttta  15240
gtcctcttga tagctaacat ttattgaatg cttactgtgt gcctgatact tttctgactt  15300
gcattacctc actgagtcct cacaatctta tgaggctact attagtagcc ccactttaca  15360
gatgagcaaa ctaagtcaca gaaaggttaa ataggtcgta tagctattaa gtgacaaagc  15420
tgagagcctg tgatcttaac cactttggta tgctgccatg aagttaaata gctcagtagt  15480
cattaaaaga gaacatttgc attgaacctt ccaagccact taacaagtat atgcttccta  15540
atcaatttaa tttagctaca ttagatagaa tggtaaagga tccttaactt aaagtttaaa  15600
tggaagaaat tagccctctg aaagaggcac agattattca tctgcaataa aaatctcacc  15660
tttagttttt taaaacatag tttttatctg tgttctgaaa tgtaactaaa acagtgcttc  15720
ctgaagtgaa aaattctcac tggtgagaat tttaataagt tttaatgatt caccaaatca  15780
cttcagtcat atttcagtca tatgcatatg catatataga catataagtt tttatctgtg  15840
ttctgaaatg taactaaaat agtgcttcct gaagtgaaaa attctcactg gtgagaattt  15900
taataagttt taatgattca ccaaatcact tcagtcatat ttcagtcata tgcatatgca  15960
tatgtagaca tatatatgtt gtatgtatac atgacatcat tagacactgt gaaggatagc  16020
aaaatgtata taaggcaaaa tttatgaaca atggtttaac gtttgggaag cactgggtta  16080
cacttttact ttatgcagat tgaaccagta tagtatgcaa gtcttaagga aaaatctact  16140
```

-continued

```
ggaaagggcc ctcattcaga cttcccagag gcttctctgg aagttgacaa tactgacttc  16200
agtacatcag ctcgtaaatg aggatgatac ctaccttatc tgctttacac agttgtaaaa  16260
gtaaaaagtg aactcaggaa gggaattaca gaatttagga gaaactaaaa gcacgatgta  16320
aataatagtc atcattacag ttatataatg cttgacaatt tatataacac tttcgataca  16380
tgacaacaat aactaacacc cagacatgtt tatatacatt acctcactca gaacaaccat  16440
gtgaggaagt tggccatatg ctttaatgtc caaaccagga cacttttgag agtaaaaagc  16500
agtactcttt gaccaacagg cataaatcaa aactatcttg tgaaaaccgg gatatatggc  16560
atccttccta gataatagat acttttacta ttattaattt tgctgtgaat ctaaacctgc  16620
tctaaaaaag ttaattttaa aaagtaatga agtactgata catgctacaa catgggtaaa  16680
tcttgaaaac gttatgctaa gtgaaagaag ccagacagaa aaggccacat attacatgat  16740
tccatttata tgacacatct aaaataggca catctataga catacagaga cagaaagtag  16800
actagcggtt gccaagaact gcagggagca gaagatgggg agtgactgcc aatangaaaa  16860
cgcattacgt tgaatcgcaa tgatatgtgc cactttgcac tctctgtgac atatataatt  16920
atttttaatg cattcatttt tttctcagag tgcattcgtt tgaaaacata gacgggaaat  16980
actggtagtc ttccttgtca gttagaaaca cccaaacaat gaaaaatgaa aaagttgcac  17040
aaatagtctc taaaaacaat gaaactattg cctgaggaat tgaagtttaa aaagaagcac  17100
ataagcaaca acaaggataa tcctagaaaa ccagttctgc tgactgggtg atttcacttc  17160
tctttgcttc ctcatctgga ttggcatatt cctaatatcc cctccagaac tattttccct  17220
gtttgtacta aactgtgtat atcatctgtg tttgtacata gacattaatc tgcacttgtg  17280
atcatggttt tagaaatcat caagcctagg tcagcacctt ttagcttcct gagcaatgtg  17340
aaatacaact ttatgaggat catcaaatac gaattcatcc tgaatgacgc cctcaatcaa  17400
agtataattc gagccaatga tcagtacctc acggctgctg cattacataa tctggatgaa  17460
gcaggtacat taaaatggca ccagacattt ctgtcatcct cccctccttt catttactta  17520
tttatttatt tcaatctttc tgcttgcaaa aaacatacct cttcagagtt ctgggttgca  17580
caattcttcc agaatagctt gaaacacagc acccccataa aaatcccaag ccagggcaga  17640
aggttcaact aaatctggaa gttccacaag agagaagttt cctatctttg agagtaaagg  17700
gttgtgcaca aagctagctg atgtactacc tctttggttc tttcagacat tcttaccctc  17760
aattttaaaa ctgaggaaac tgtcagacat attaaatgat ttactcagat ttacccagaa  17820
gccaatgaag aacaatcact ctcctttaaa aagtctgttg atcaaactca caagtaacac  17880
caaaccagga agatctttat tatctctgat aacatatttg tgaggcaaaa cctccaataa  17940
gctacaaata tggcttaaag gatgaagttt agtgtccaaa aacttttatc acacacatcc  18000
aattttcatg gcggacatgt tttagtttca acagtataca tattttcaaa ggtccagaga  18060
ggcaattttg caataaacaa gcaagacttt ttctgattgg atgcacttca gctaacatgc  18120
tttcaactct acatttacaa attattttgt gttctatttt tctacttaat attatttctg  18180
caattttccc aatattgaca tcgtgtatgt atttgccatt tttaatatca ctagacaatt  18240
caatcaggtt gctacgttgg tcccttgggt ttactctaaa tagcttgatt gcaaatatct  18300
ttgtatatat tattgttttt tctcctatct tgtaatttct ttgagcacat cccaaagagg  18360
aatgcctaga tcaatgggca caaataattt gacagctctt attaaacatt attctgtaag  18420
taaaaactga actacttttc agtatcacta gcaacatatg agtgtatcag cttcctaaac  18480
ccctccatgt taggtcatta tgaacttatg atctaacaaa ttacagggtc ttatcccact  18540
```

-continued

```
aatgaaatta taagagattc aacacttatt cagccccgaa ggattcattc aacgtagaaa  18600
attctaagaa cattaaccaa gtatttacct gcctagtgag tgtggaagac attgtgaagg  18660
acacaaagat gtatagaatt ccattcctga cttccaggta tttacaccat aggtggggac  18720
ctaactacac acacacacac acacacacac acacacacac acacacacac catgcacaca  18780
caatctacat caacacttga ttttatacaa atacaatgaa tttactttct ttttggttct  18840
tctcttcacc agtgaaattt gacatgggtg cttataagtc atcaaaggat gatgctaaaa  18900
ttaccgtgat tctaagaatc tcaaaaactc aattgtttgt gactgcgcaa gaagaaaacc  18960
acccatgctg ctgaaagtca gttgtccttt gtctccaact ttacttcctt tacctctcat  19020
atgtttgtga ataagcccaa taagcagacn cctcctacaa agtgaacctg gtctctttcc  19080
tcctaacagg ggtcttgtaa cacaggtaag acgagttcaa gttttatttc ttgnttttag  19140
aacggtagtg agcggttttc agcntgagac cacacctaag gtaagtagct gaattggggt  19200
tttgtcttgg ctaaagttta acaaccagct ggtcttaatt tctccttacc attagagcac  19260
tcagtaatca tataagttgt gtgatcattc attttgctta actgtttgtt tctgttttta  19320
ttgctgtttc agtctttttc ccattgggtt tgacctactc tatctgactt gatcaaatcc  19380
aaaggaaatt tccaaattat ggggaatgag gcctctgaag tggctaaatt cccaccctcc  19440
cacacacaca aacgtggtat ggtgggggaa aaaacggcca gcaaaagaaa aaaaaaaagg  19500
aaaagatgtt tcattttgac caccaaacgg gctttattta cataacaagg ccaccttttt  19560
gctagccagg ccatactgaa agagcaatgg ctgttgcccc atgctgtggg ttccatagct  19620
aacgttctgc ctttttttcct accacgacag cctgggtttg gttcctaaat caagcctttt  19680
ctggtttgat acttggtaat gctgaaatag cagcaatttg tcctagctga aatatcgtaa  19740
taagatttta aaagatttat tttaaaggac ctcaatagtt aaaagtcagc ttaattaaaa  19800
gctaacatcc aagatgtgtg catgtgtatg tatgcgtctt tgtatttaaa tagccctcat  19860
gttttttttt tctttcctag gaacttgcct ttttttgagc aaaagttttt ttcttctctg  19920
ttgactggat tctgttttct tcatttactt ctgctgtctc tcctttctct tgcaccgtct  19980
gctgcatgag agccctaaaa tagtttataa tagcctgggg ttccttaaag aaaatggaga  20040
aggtgccagg ctccctttta gggagaaact tctatttttc cttatggaat ccctagagtg  20100
taaacagaca agttcatttc agctcttaaa ctgcttgcgt ttgtgttgtg ttacctgatt  20160
tttttgacta ttatattttt gactagctat tgcaacagaa gctactcttg ggttttcaag  20220
gaagattgta gtttagacat gtagaaatgt cttttaaaaa aaaaacaaac ttttttttaa  20280
gtgcactgta aaagcatcat atggtctagc ctcctaataa ttttcccttt ttggagacca  20340
ggattcaggg tgggctctgc ccagagctca gagatccagt taaaagagag gtagtctcgg  20400
ccgggcgtag aggcccagcc tgtaatccca gcactttggg aggccgaggc gggcggatca  20460
cgaggtcagg agatcgagac catcctggcc aacatggtga aaccccgtct ctactaaaaa  20520
tacaaaaatt agctgggtgt ggtggcaggt gcctgtagtc ccagccactc gggagactga  20580
ggaaagagga gaatcgtttg aacccgggag gcggagcttg cagtgagacg agatggcgcc  20640
actgcactcc agcctggcga cagtgagact ccgtctcaaa aaaaaaaaga taggtagact  20700
cgatgttgtc gtacccgagc aagttagagc aacgccacac tttgagacga atttaagagt  20760
cctttatcag ccggcgacca agagacggct aacgctcgaa attctctcgg ccccttggaa  20820
ggggcttgat tttcctttat gctttggttt aggaagggga ggggagctca gttgcaacaa  20880
```

-continued

```
ttctacagga gtaaaaacat gcaaagaaat taaaaagaca agtggttaca gggaaacaaa  20940
cagttccagg tgcaggggct ctaaatctat cataagatgt taggtatggg ggctctgccg  21000
gacacaaact caaggcttta tgctgttatc tcttgagcga aatcctggga acttcgtaca  21060
ttgcttgctt cagtacctta tcagttaatc ggactctttg atatgttggg agtcagcgta  21120
cacaagttaa ctccttgagg aagggggtgg gtaaggagtc cttgatgtct ggtaaatgaa  21180
ggagcgaaat cgagttcctc tggctttctc agctaaggga gagcttattc atgtggaaac  21240
aaggctaagt gattaaggga gaaagggaga gtctgaaaac aaggttaggt attacaatgt  21300
caataaaatt ggtctcctta tacagtccta tggtagattt ctttccatct ttaatctccc  21360
tctagcacca ccagactttt tctctctgta ccttgagatg taaattttgc tatctgaatt  21420
ttcgtctaag agttgtttcc tttaatatgc aaatttaggg ttatttagct gacaactgcc  21480
aaagtagtga aacaagttat caagaacttg aacgtctaag gtaggaaaaa aaaaagtctt  21540
tatgaatcta taagatgtac ttctattggc atgcctaata cgtctatgta tttacgtgtt  21600
gtgtacacag tttttcacta ctgaaaatat atagaggagt tctaattaat tgacttaaga  21660
caataaaagc gcttgaatca aataccttat caggaaaaag gaaaagacaa gtcaaatgct  21720
tgttcaagtc tatataactt aagtaaaatc tttaataaat aagctagctt taacattatt  21780
tgaaatgtct taagaattgc cagcaggttc tgggttacag aactagtggg ggtgcagtgg  21840
ggtgagggtt ggtggggtgg gnggtnnnac nnnnncnccc cccccccccc cccccccccc  21900
cccctccccc cccgccccgn gcgggccgcg cccccccccg cccccccggc ccgcccccg  21960
cggcccccca cccccccccc cccccccccg cgccccgccc cccccccgc gccccccacc  22020
cccccgcccc cccgccccc cccccccccc ccacccccca cacccggccc acacgcaccc  22080
cccaccccga cgcccccgcc cccccccccc cgcagccgac gcccccccc cgcccgcccc  22140
gccccgcacc cccgaccccc cccgccgccc cgcccccgcc cccccccccc ggcccccccc  22200
ccgccggcgc ggcgccccac cccccccccc cagccccgac cgcgcgcccc ccccaccccc  22260
cccccagccc ccgcccccg ccccgacccg gcagtacgct ataattccct cttcacctta  22320
cctcatctgt tctctgatgg atgtactttt ttttttagtt tctaaattcc cttttccttt  22380
gctctggaga tgggtgattg atgtagtctg ggtatttgtt ccctccaaat ctcatgttga  22440
aatgtaatcc ccagtgttgg aggtagggcc tggtgggagg tgtttggatc atgggggcag  22500
atccctcatg aatagcttgg tactgtcctc tcaatagtga atgagttctc ctgagatatg  22560
gttgtttaaa agtgtgtggc actcccccat tgctctcttg ttactgcttt cgacatgtga  22620
catccctgct ccccttcgct ctctgccatg attgaaagtt tcctaaggct tcgccaaaag  22680
ctgagcagat gtgggtgcca tgcttgtaca gcctgcagaa ctgtgagcca aaataaactt  22740
catttccata taaattaccc agcctcagat atttctttat agcaacataa gagtggctta  22800
atacaggctg ggcatggtgg ctcacgcctg taatcccagc actgtgggag gctgaggggg  22860
gtggaacatg aggtcaggag attgagacca ccggctaaca cggtgaaact ccatctctac  22920
taaaaataca aaaaattagt cgggcgtggt ggtgggcgcc tgtagtccca gctactctgg  22980
aggctgaggc aggagaatgg catgaacccg ggaagcggag cttgcagtga gccgagattg  23040
caccactgca ctccagcctg ggcgacaaga gtgaaactcc atttaaaaag aaaaaacaaa  23100
atttcaaaca gaacaaaatg aaaaaaatac caagtgaaag gcccctataa aaacccctct  23160
ggggcccatc ctcccacccc ctcaagtgaa accacattta acaatttggt gcatatcttt  23220
ccaaaccttt tgttgtacac atataaaaaa catacatgct ttgatttggc tcagactgta  23280
```

-continued

```
catagtgttt tccctcttgc attttacact taatatatct ttgacatctt tctatgtcag  23340
tgcatgttgg ctcgatgata ttctatcatt aaataccctt ccaaaaatgg taaaatcatt  23400
ttaaaaaatc attcacacaa gtacatattt acaattttaa aagaaaacag aatcccaaaa  23460
cacaacgaca aacctctaaa aataatctct atctttccac cagcatggaa cagttcattc  23520
ctttttcaca taaaacgaat tatgtgattg gaaagattaa ctctaatcta cacatttata  23580
tacagaatgt tctatttgtt aagcctatct gaaaataaaa aattcagatg attaattcac  23640
ttacacttag aaattaagtc aatatactat gaatacacat tgtgatcagt tataatatga  23700
tgcttcttag tctagggttt caattaaata acagtaaaaa aaattggata aataagacag  23760
ctaataactg aaaaatccag aaattcaaag attatattgc caactaaaac actgccattt  23820
acattttttt ttcctacttg gtagcaaatg ctaatggaat tcaatcctga ttacttaaag  23880
tcagttcaca tcacacattc aatcaggata atacgaacat aatatgccta ctatagcgtt  23940
agattaagac ataaaatttt tttgcttgaa agtaatgact gcgtaccact tgagacattt  24000
gtcaaccact tcagcacatt gtttacgagt gactggatgt ccacaaggaa taaaaacgac  24060
agcaatattt ctatccatac agattttgca aagcttctcc tcttgcaggt gtcttagctg  24120
ctcttcagta ctaatctctt tctgcaatga agtctgactt gattcgtctt gtgtactgtc  24180
tttctgagcc ttcactggat ctgcaatcag aacctcaagt gatttacagt tgctcccaga  24240
tgtctgaatt ttttcctcca ttattttctt aatgtctttg aaactgaacc ccattcatat  24300
agcttcttgt accataggat tatggaagat ggtatcaatt tttctagtta gtgatggcgt  24360
tttttcagca gttcttacca gacactcctc aagtgaatgg gataaatgaa tattgtttat  24420
atattttcgt gtcttctgtt ctaacagata tttacaccct ggatgccatt aacatgttgt  24480
cccaagggtc ttnctgggct ctttctccct ttttaccccc attttcgtag ggatttggtt  24540
aaaacccatg taaaaaatcc aaacaccggc ggggaacggg ggttcaagct cgtatcccca  24600
ccactttggg aacccaaggt ggcaggattg tcggaagcca ggcatttgag cccacccttg  24660
ggaaaaaaaa gagaaccccc atttttttttg aacaaaaacc ccaaccctcc caggaaagaa  24720
ataagtatgg ctgggttgaa gtcaccaaag atggccgact ggctggtcaa gtaactttac  24780
ctgatggttc gtagaatatt taccttcacc caggtgggag aattgcttga gccaaccctc  24840
agtgtggatt caggaacttg atttaattgg tatcgtgatt gtggattaga ttctcaggga  24900
tgcattcact aagtaaaagt gataatagct acttttaagt aaaataatga atgaatcaaa  24960
cactctaaat ccatggtgct atgctaagct ctttctgtat tttatctcat ttgatattac  25020
aaatatttga tgtgttaata gtaatgacta tctccatttt tacaagtaag gaaactgaca  25080
ttgagagatt aaaagactag cacaaatcac aaagtaaatg agatttgaat ccggtcttga  25140
ttccaaactc tacagtattc taaattcaag gagactaaat tataagatgg agagccaatt  25200
ttactttata acagggttag aatggcagaa gagacctgac attcacacct ctagccagtg  25260
catcatcttc ctgtaggcaa atatgcagga aatctataat aagaacgtcc tttggtgaag  25320
gccaggtgca ggggcttaca cttgtaattc cagcactttg ggaggtcaag gtgggagggt  25380
cgcttgatga caggagtttg agaacagcct gggcaacata gtgagaccct gtctctacaa  25440
acaaaaacaa acacaaaaca acttcaagaa aactcctttg gtatggatca gaacaagatg  25500
aattatctat ctgatccaaa tgcttaatga cattaagcca cagtccactc actgccacaa  25560
tagagatata cctgccaatg ccactcaggt aatcccatca aaagtggtaa tgaggtctgc  25620
```

-continued agcatgactt gttcttagtg atcccagcct gagaccttga gattgcagca ttttattcta 25680
catatgcaca aaacatctgt tgaaaaatct tctaaattga tgcaatacat tcgtatcaag 25740
aatacctgtc tgtaatctcc ataaaccctc tcctttctgt tttaaaaaat agtaacagca 25800
tttctcctta catgacaaag aaatgacttc accatctacg aaatagtgaa taggagctgt 25860
gtggaaggaa attagctcta cttcttggtg gagatgagaa gggagtgttc ctctgaaaat 25920
caaggctctt gtcatgctag gagccaaagt cgttttttag agtgtggaca gttgagaaga 25980
taagacaggg accatccact catgtttttc ttattccata ggcctctctc aattgggcaa 26040
agcactccag accttttgga agagtgacac caaaggcaag cacctgcttg gcaggcccct 26100
cagcttctac gcaagtataa gtgagtatat aaaatggggg tacttgtgct gttgagtacc 26160
ttatttccaa atgaggcctg ccggtgtccc tgtggctgtg agaaggcctc tactggatag 26220
gtggaagttg tgtgttctca tcttttctaa ccctggattg acttgcccaa aaggaagcca 26280
ttattaacac tataataaaa ccatccttaa tctgggactc tcttcatgca gtggttctta 26340
accagtgata aacatgagag ttacttttgg agcttaaaaa aattaagatg ctcaaggtct 26400
acccaaactg actgaatctc cagaggtgag gcccagggat gtatactttt gagccagacc 26460
tcagtttacc ctgcagagct cataaggttg cataacaccc tttgtcagcc actctgatga 26520
aaagaaaaat tggtgaggaa taagttttag agaagaagga gcaaaggtgt tcttggccag 26580
tgagagccaa tgacagggaa atgcaaacaa tgtatccaca agaaaggtaa attaccctat 26640
agagcatttt aggataaatg aacatctcat gcctagggtt gagagagggt acaaaaaaaa 26700
aaaaaaaaaa gaccactctg gatacacaac gcgataaatg gaataaagaa ttttttcctt 26760
gtaaattaaa aaaatccttt gttactgagg tataatttaa tctattttat gtatagttca 26820
atgaggtgtt atagataata aatttttttt gtaaattatt atattgtcat atactcatac 26880
attcattttt aaaagtcaga aatgtatata accattaaac ttataaatca ttcagtcatt 26940
cagagatata gatacacgag catattttat atccaccaca ataattatta ccatctcaac 27000
aattccatca cccctcaaat ttcaagcgta ggggttttta aatgtcaaag gagtctactc 27060
agtgggaaga aagttaagga aaaaaccttt ggggctttgg gctccttccc cctggggtta 27120
aaaaggcagg aaattgggct tacccccccct gaaattggga actgaaattt tgggaagttt 27180
aaaaaaaaaa aaatcaagca gccttccttc cttggcttcc caaattgttg ggattacagg 27240
catgagtcag gattcctggc ttagtttaca ttttctagag ttttgtataa atggaaacat 27300
acagaatgta ttttttttgcg gagtggggga gtgtttctat ttctttcttt ccattttccc 27360
cccccncccc ccccgagacg gagtctcgct ctgtctgttg cccaggctgg agtgcagtgg 27420
tgcgatctcg gctcaccgca agctccacct cccgggttca agcaattctc ctgcctcagc 27480
ctcctgagta gctgggatta caggcgcccg ccaccacacc tggctaattt tttttgtatt 27540
tttggtagag acggggtttc accatgttag ccaggatggt ctcgatctcc tgacctcgtg 27600
atctgcccgc ttcggcctcc ctaagtgctg ggattacagg cgtgagccac cgtgcccggc 27660
ccaagtgttt ctatttctta accagctttc atgcaatctt tttttatttt accatctctg 27720
tgatcccact cccaaaggta ctagatgtcg attggtcctt aggatcagct accatttgcc 27780
caactgcttt ccagccttcc aaaaattttt ttcttttttt cttaaagata ctcctgtgtg 27840
aggctcagaa ctcttgaatt gctactgcaa atatgaactc ggtgatgtga atgccaggga 27900
attgcctgat tgatcaaaga aatgtatccc cttctccctc actcttgctg tcttctcatt 27960
tgttttcccc atccttgtgg attcgtgaat ttaaatatcc ctttaatgtt ataatatttt 28020

-continued

```
aatggcgttt ggcgaaaagt acagaattag gtgcaagagt gcatagctgt tattttttt  28080
ttggcctctg agactgttca tatatgcaag ttatttaaca gaaagttctg cagtgacctg  28140
agatgtcagg ggggtctgat agagtacgtt tgaaggcagt tactggaaaa aaataatgcc  28200
atttctggtt tgtacttcgg taagttcaga tgacccaata tattgtttac atgtggcatt  28260
cagtaaaaaa gtagcttccc ctccctttct tcttcctttt ctcctttcct gcttctataa  28320
agcatctgct ttgggaaact tcttaggagg agagcttgcc agcccgtggg taatggagag  28380
gtcttgcaga gataaaagag atgctcccac tcaatgcagg atggtgtgga ggtaaatggg  28440
gatacgtctg gcatcactca ggaatgggcc ttcctggcag ggaaaaaaag ggaggggaaa  28500
gaggaaggga attcnnanat naattgctga atacggggat tccatggcct ggatccagga  28560
agagaacttt gggaggtgtg aacctggaag gcatcanctg atgaggagca gcctgaactc  28620
cggggaggac ctgtttttgg tggcccggaa aaaaatgcct tccacacaca gggaggccac  28680
ccggctgatg ggctgggggt tggacggaca gccctaggac aggcttggga aaccaggctc  28740
aggtagggcc tgcgaggttc tcgctgcgtc tctttccttc ctggtcttag aaaatagaat  28800
ccaaggcctc ttgagagtgg aaggtgggtt gggaggaggg cagatggggc ttaggcccag  28860
gacacccgta gagctactgc ccagctgtct ctcagggact ctgctgaggt cactccaagg  28920
atcattctta gccttgctag acagtactga cagagggaac cgtagtatcg cacccacttc  28980
cttctctttc aatgaaagtt taaaggtcac catttcctct ggcaaaggaa gttccacaaa  29040
tattccattt ccggtcttag aaacagcaag gtatcaagca attgcaaact tcctgtgctg  29100
gggaattccc aaggaagtag gggcagagtt ctggtggaga caaagtgaat tccgagtgat  29160
tagtcagtag cagtagcagt agcagtagca gtagcagtag cagtagcagt agcagtagca  29220
gtagcagtag cagcagcaga accagaattt ccccgcacgt gtctcaggct ctcatttgcc  29280
aactcagtct ctaagtattt ttattggcag gaaaaataaa atagctatga gtgaaataat  29340
tcattagacc tgagcctcca tcaattttgt gtttaaaggc ctgactctct ttacctttcc  29400
ctgggatgga agatgcaaat gttcctgatc tcactgtcaa aaaagaagaa ccagtgggta  29460
tattgtatgc ttgagttcca gccattagtc acaagacata gagatgactg ccatgtgtgt  29520
agactttcta tagactgtgt gctaaacccg acctgccact tccaaggagt agatgaggaa  29580
tgtccatggt tctggggagc cctaccccaa tttggggcag acattccaaa gctcattttc  29640
tgtggagggg gttgatggtt aaaggaacgg ctgggattta ctcttctttc tagggccaag  29700
aaaatgacat gctgcctcca tgtttaatca tccttccccc tgttaataac tatggcttta  29760
agtccccggt tagggccttc ctccaaaatt ggggaaaaaa attcccctcc cccccctaaaa  29820
attttttttt taaaaaaacc ttttttttg ggggttggga aaaaaaccaa aaattttttt  29880
tccccagggg ttttttaatt taaatttctc cccaaaaatt tgtttttttt tttccgcgaa  29940
aaaaagaccc ccccaaaaaa aaaaagtttt ttggcggaaa aaaaaatatt ttttttgtgt  30000
taagaaatgg agaagaaggg gggttttttt tttcttctcc ccccacccgc caaaggaaag  30060
gttgttcaca gattgttttg tgtctcccgc ccatatgtgc ctgcgaaatc atccttccag  30120
aaatatttgc ccctttcttt tgttatagag tggcactgcc ctatatggtg accacttgcc  30180
acatgtggct gttgaacact tgaaattggc ttgtcagaat tgcagtgtaa agtgtaaaac  30240
acataccaaa tttcaaagac atggcacata ataaaaaatg taaaatatct cattaacaat  30300
ttttatattg actgtgtaag taacattttg aatatattgg attaaataca tggatgatgc  30360
```

-continued

```
cccaacaccc acagtccctt atcaagtctc tacttcacat ttttgtactt ctgacttaga  30420
aatagcactg gcgtctaaga gcctattaat gtcgtcaata ggttcttggg aaccacaatt  30480
ttaaacaaaa tgacatataa gaaaacgaat aacattgaac aaaatgacat tattcgagga  30540
cctgctgcat gttgtttcac ttaaagtcag tgtccaagaa actatcagtg acatttagtg  30600
aggaattgct gtccttcctg tttacaggaa cctgggcaag ttacttaatt cctctaagcc  30660
cggtttatat ccctgcaaag agagaaggat aataatcacc agtacttagt gatgtcgtaa  30720
ggagaaaata aaataataaa tatgaaatgg ctgacagtgt ccttgtcaca cagaagatgt  30780
gtgatccaca gtagctgcta ttgtctgcct cacttcacta gtaatggtcc agggaggcct  30840
ttaatgtgca tggtgcagta cattcacatg ttggacatgg gtgaagggaa agaccaggct  30900
catctaaaca caataggatg cttgtggtgt tttgaggagg aatcaaggac tagttatcca  30960
cagctgtaac atgcatggat caaaagagat aaggcacaca aaagactttg tcagtagcaa  31020
agcattacaa aatgcagaga ccagctgtgg gtggtggtga gtcagaccca gcttccctct  31080
gtgcctggct gagtggttct gggcaagtca cgccatctgt cttgatgccc ttccccatct  31140
atagagaggg agcaactgag gccccttcca atactgaagt cctttatttc tgctacttta  31200
gaaatatcca catttttggt aaattcaaat gatccaatga ttccatttcc taatgttcaa  31260
aactagcccc agaaacatct aaatgaatca aacaaataaa atatttattg tgtatgtttt  31320
gattgctgaa acttctattt tagcaacaca cacacacaca cacagaaccc ataagccttc  31380
atctttcctt ggataaacga gccttcctgt ctggccattt aagtcacgat taagtaaatg  31440
atttccaact cgccttttgc agcagttcag atgggtcttt cctgcgtggc agtggccctc  31500
ctgacttatg atttcctgtg tgtcggcctg ttaccactgc agcttaactg aggaaacaag  31560
aacaaaacag cctctgaccc caagagactg ttggaggcaa aggcttcagt cccaagaacc  31620
tcacacgtgg ggagcccgag agcccagccc tgaccttttc tccagtaata acataagaaa  31680
caacaggcac tggccttatt ttggatacaa agagtggtgc ttttccttaa atcttccttt  31740
agtcaggggt accccttcat ggacgcccca acatccatgg ttcctgcttg agtccctgct  31800
tccatattcc tgcacttctc acttgaaata tccctggagt acgttaagca gccaggtttg  31860
gaagttcttg ctgtgcaggc gggtgtgtgc atgtcctctc tctcaacagg acacaagctc  31920
cccaaatcag acggtatgcc tccacgcccc ttcccaagcc tccccagcag caccgagcat  31980
gtgaggggag ctggggccca ggccatgatg ggaagcactc tctgcctaaa gactagggtg  32040
atgcgccctc aactgtggga atgagcccca gctctggtgt ctgcctcggt ttttcctcct  32100
ggacaatcaa catgaactcc tcacccctct tatccacttt gcataaactg aaaataacaa  32160
acccagggtc tttctgtcac aggaaagggt tttttttat aagattaaac agagatgatt  32220
caacacaccc aggatataac acatgggcca tgagtcaagg ccaggcattg ctctggtcag  32280
cctgttgttt gggccccctt ggcagggctc tcccctgaat cttccccctc ttgactcccc  32340
atcaccacag cacgtccagc tttgggtaca aggccagtaa atggggaagg gggtcagatg  32400
acataaagag ccctttcctg tcccattgaa atatatttgg ataacagatg gcatttcccc  32460
ctgtgtcttg cccagggccc agagcctcca cttgctagag gcagacagag gatggagagc  32520
cccttcatta gtgggaggac atcacaggtg ggcaagaaac cacaagcttg cactgaggcc  32580
cagccttgaa atagcagcac ctgccggcac ctgtggtctg gggacagggt cacaggatgg  32640
aggggcctcc taagcctttt atctctatgt actaagtaca acccattttc ccacctcaca  32700
gagccagatc agcctctgtg aggtcctggt ggcaaaagga taattgcctg cccgcctgcc  32760
```

-continued cgcggtgggg tgcttgtgct tgcattcctg ggaaggttgt tgggttactc tgcaataggt 32820
ctctctgacc agctcaccct cctactgcaa acctcaaacc aacttcaaag aagatccagc 32880
acccgcgtag tctaaagact gagtctgaag ctgtcccttc ctgctatgga cttcagattt 32940
tagcccactt gaattgctcc atatcctcca agccatggcc atcccttgac tctctgggct 33000
cccaagcact tgctgccttc atcacacagt ttgagttaag gcagaaagac tggtttccat 33060
gtacactttg tggaagcttt ctcatttctt tatataatct ctgtcctttg tctactgctt 33120
taaaatctag aaattgttta caaacacaaa ggtgatcctt taaaagctca aagctgattg 33180
tgtcaccaat atataccact cttaatggct tcccattaaa ctttgagtaa agactttatg 33240
gagcctacat aaggccatga ctacctggct cttattttcc tcctcatcct catctcacca 33300
actcactctc cactcctata cccctcactc cttccccctc ctctctctga gctccagact 33360
cccaattacc tacttccacc ctttttgacc cccagggact tatctcagcc tggaattttc 33420
cctctttgct ctccactgaa ctgtccactc ccagtctaag acatgtgctt atgtcacacg 33480
cccttaccgt gcttatctca gtttgtaatt atctactcat ttagaaaagt gttgatgaag 33540
gtcttcactg tcagctttca ggatagcagg aatcatagct gattttactt acttaacggg 33600
gtttcattct ttgtaacttt tttttttttt gagatggaga ctcactcttg cccaggctgg 33660
agtgcaatgg catgatctcg gctcactgca acctccacct cctgggttca agtgattctc 33720
ctgcttcagc ctcccgagta gctgggatta cagatgcctg tcaccacgcc cagctaattt 33780
tttgtatttt ttgtaaagac ggggtttcat catgttggcc aggctggtct cgatctcctg 33840
acctcaggcg atccacccac ctcagcctcc caaagtgctg tgattacagg catgagccac 33900
ggcacccagc cactcctttt ttacttatgg gtgagaagcc attagagatc atttcttctt 33960
ttctttctct cttcactaag gcaccagggt cactaagtag taggatactt tgaactagaa 34020
ctcaagaaat tgagttttaa ttttacctca cactctcata tgaattctcc atgtgacctc 34080
gggccatact tcccctgtac cctgtttcct cttttataaa agtaagagtt taaactagat 34140
ggtctccgac atgcatcctt ctctaacata ttctggaacc ttcaataaac taagataaag 34200
cagaataatt aaaacttaat ttaaaagaac acaggaaagg aagcagttac attaagcaaa 34260
agagacatct tcatggttga agaagtgtat gccctggtgt ctggatccca tttaggaaac 34320
ttggtaacct tgcaatcttg ggcagattgc ttaatttctc tagaccatga cttcctcttc 34380
tgtaagatgt gataagaaca tctacctcac aggtttcatg agaggattaa atgagataat 34440
gtattataat cccttgaaca tggtaggctg ttatgttaag tcctttcctc cttctctgta 34500
gctatcatgg aatttaaaaa cacattataa ctagagcatg agttgcgact aaaggctcaa 34560
ttgtctctgc atgtgttggc tcatgcatgc tttattcctc tgaagagctt ttataccaag 34620
tgaaaggaaa taattgcatt tccctgaaaa ttcacaggaa aaagttatgt ttttctcttc 34680
attcaagtga ttctgttaga cccaaccaca tgcaacaatt ttaaagttgc ttccaaatat 34740
atttacaaat atttcctgtc ttcaaggaac aatggcaaga ccatgactca ggttcacatc 34800
cggattccac cactaaccat gtacccaatt acttcagtca ccttcattca ggtcttacat 34860
atcacagaat aaaatcagat ttcatcagag gaggtgaaga cagggagagg agatatttca 34920
atcccttctc cgcaaccccc gttttttttt tttttttaac aaggatccta gagttactga 34980
atgatagcac gtttgagggg gaaagaccct aaggatgatc tttataagcc atcacttggt 35040
gttggtggtg ataaaaaact cgagtatctt tatgcagtgg aaagagaaga ttggactcgg 35100

-continued

```
aatcagaagc ttgagttcaa gcactggttt catcagtctt gtgatcttgg gttggtcact  35160
taacctcttc aagggtcctc agctgtgaaa gaagatagta tcagctaatt cttgtatgtg  35220
cagtgaggag gcagtgagat agtgcaggta aactataaaa caattgtcac atgaaacgca  35280
tcacagtgat tctttggacc cacaagctcc aatcttataa aacatatcca gtcacccacc  35340
aacatagatc atctcacctt gcatatctga ttttgtggat catggggaaa aactgctgat  35400
tcctagcaaa acccatggca taggataagt gcacaataat ttttttttcc taaatgattt  35460
agatgacagt gactcattaa gggtttcctg aggcctcctc agagtcgaga ggtgggtgcc  35520
tgaagccacc caaagtccct gtcacaggat ggctcccaac gcacacacca caggcctgcc  35580
cagtatgttc cactatctac ccagtagagc cctgcccagt acgttccact gtcccttccc  35640
tagaagaggt gactgttgtt cacagtccca gaaaagcggg ctccccaaaa caatgcaagg  35700
acccacctct ctctgaacct cacccaccct agttttcctt taaaaatcaa tttacaagaa  35760
gatcatgtga aggaaaaggt tgggtgatat tctaacccaa gttagctgtt tctcaaccaa  35820
gttctctttg aaaaattcaa caaccacctt tggggaatta tttacaacag aggagtgagg  35880
atgggaccag gataggtatt gcctatgttg gtggaaccag ggtttttttc ctggattacc  35940
aaagagatgg tatgcattgc tcccagaagc taaatatctt caggctttca atggtggcct  36000
tcacctgaaa atgttatccc tgttgaagct ttcaagccag tattttcata agaactatat  36060
tttctttggt gaactgaggc attataatga tgactataca ggttcttgag tgactgaagc  36120
catcattagc attgtcatta tttttgttta gttgcatctc catagcagct cacattcaca  36180
atgtgctttg caattgttcc ttagcaatag ccctcacaag attctcagga ggagagggtt  36240
aatccggatt aacatttctg tgaagcctag cgagattaat cgcaagagtt ttaaaattaa  36300
gtaaggacgc cgggaaacaa atcaatccca gcaaacattt tgttgggatt tatcattcaa  36360
gcaattttac agttatccct gtcaaataca ttaagtgttc aaaattgggc ataggggaa   36420
caaaataata aacccagcca aaacagaata atccctgttt gttcaatgtt ggataaaaaa  36480
gacattacta ttggtgtaag gaaattagat acatcttcca ttatttagta aaattaccat  36540
aacttctaac tttgtggctt taggcagtct agtccacagg caggaaggag gtttgttttg  36600
gcaaatgact gttatcatct tctgtttcaa agctaaacca taaactaagt tcctcccaaa  36660
gttaattcag catatgccca ggaatgaaca aggacagcct ggacgttaga agcaaaatgg  36720
agtcaggtag gtcagatctt cttcactgtc tcagtgatgg cagtttcata actttaaatg  36780
atggctatca cagttttcat aaataatcta gataaacagt taaaataaaa taattaggta  36840
aatgtagtgc gataaatatt agtagacaaa ctcaccataa tttagaatct aaagttaaat  36900
taaataataa tatttcatta tttggtattt tccaagaaaa acatattgta ggaaaccatt  36960
ctttttaaaa aaaaaagtgt ccttttaaaa aggtgaataa tttttgtcta attcaaagtt  37020
tattgaaaag ttatgtataa aacaaggtaa aaggaacaag gaaataaggg aaatgtaaag  37080
aaaattatag aaataaagtg gtattttttg gtaagaaagc ttaaagagaa ataattttag  37140
gtaagaaaga atcttaccta aaattttgtg ctagaataaa gtgactggct aagaaaggga  37200
tgttcaaagc tatttatgac aaacccacag ccaatatcat actgaatggg caaaagctgg  37260
aaacattccc tttgagaact ggcacaagac aaggatgtcc tctctcacca ctcctattca  37320
acatagtatc ggaagttctg gccagggcaa tcaagcaaga gaaagaaata aagggtattc  37380
aaataggaag agaggaagtc aaattttctc cgtttgcaga tgcatgattg catatttaga  37440
aaaccccatc atttcagccc caaaactcct taagctgata agcaacttca gcaaagtctc  37500
```

-continued

```
aggatacaaa atcaatgtgc aaaaatcaca ggcattccta tacaccaata atagactaac  37560
agagagccaa atcatgagtg aactcccatt cacaattgct acaaagagaa taaaatacct  37620
gggaatacaa cttacaatgg acatgaaaga ccttttcagg gtgaactgca aaccactgct  37680
caaggaaata agagaggaaa caagcaaatg gaaaaacatt ccatgcttat ggataggaag  37740
aatcaatatc gtgaaaatgg ccatactgcc caagtaattt atagattcaa tgctatcccc  37800
atcaagctac cattgacttt cttcacagaa ttagaaaaaa ctaatagcca agacaatcct  37860
aagcaaaaag aacaaagctg gaggcattgt gctacctgac ttcaaactat actacaaggc  37920
tgcagtaacc aaaacagcat ggtactggta ccaaaacaga tatatagacc aaaagaacag  37980
aacagaggcc tcagatataa caccacacat ctacaaccat ctgatctttg acaaacctaa  38040
caaaaataag caatggggaa aataattccc tatttaataa atgatgttgg gaaaactggt  38100
tagccatatg ctgaaaactg aaactggacc ccttccttac aacttataca aaaatcaact  38160
caagatggat taaagattta aacatggctg ggcatggtgg ctcacgcctg taatcccagc  38220
actttgggag gccgagatgg gtggatcatg aggtcaggag atggagacca tcctgactaa  38280
cacagtgaaa ccctgtctct actaaaaaat acaaaaaatt agctgggcat ggtggtgggc  38340
gcctgtagtc ccagctactt gggaggctga ggcaggagaa tggtgtgaaa ccaggaggtg  38400
gagcttgcag ggagtggaga tcacgccact gcactccagc ctgggcaaca gagtaagact  38460
ccatctcaaa aaaaaaaaaa aaaaaaaaaa gaaggattta aacataagac ctaaaaccat  38520
aaaaaccata gaagaaaacc taggcaatac cattcaggac ataggcatga gcaaagactt  38580
catgattaga acaccaaaag caattgcaac aaaagccaat tgacaaatgg gatctaatta  38640
aactgaagag cttctgcaca gcaaaagaaa ctattgtcag agtgaacagg caacctacag  38700
aataggagaa aattttttca atctatccat ctgacaaagg gctaatatcc agaatctaca  38760
aggaatttaa acaaatttgc aagaaaaaaa aacccatcaa aaagtgggca aaagatatga  38820
acagacacat ctcagaagaa gacatttatg tggccaacaa acatgaaaaa aagctcatca  38880
tcactggtca ttagagaaat gcaaattgaa accacaatga gataccatct catgccagtt  38940
agaatggcga ttattaaaaa gtcaggaaac aacagatgct ggagaggatg tggagaaata  39000
ggaatgcttt tacactgttg gtgggagtgt cagttagttc aaccattgtg gaagacagtg  39060
tggcaattcc tcaaggatct ggaaccagaa ataccatttg acccagcaat cccattactg  39120
ggtatatacc taaaggatta gaaatcattc tattgtaaag acacatgcac atgtatgttt  39180
attgcagcac tattcacaat agcaaagact tgggaacaac cctaatgccc accaatgata  39240
gactgtgtaa aaaaatgtgg acgtataccc catggaatac tatgcagcca taaaaaagaa  39300
tgagttcatt cttttgcacg gaactggatg aagctggaag ccatcattct cagcaaacta  39360
acacaggaac agaaaaccaa acactgcatg ttctcactca taagtgggag ttgaacaatg  39420
agaacacatg gacacaggga ggggaatgtc acacaccagg gcctgtcagg aggtgggggg  39480
caaggggagg gataacatta ggaaaaatac ctaatataga tgacgggtta atgggtgcag  39540
caaaccacca tggcacatgt acacctacgt aataaacctc catgttcttc acatgtatcc  39600
cagaacgtaa agtaaaattt aaaaaagaaa gaaagaaaga aaaggatgtt cacgacaaac  39660
cagaaagtcc aagcatgtca tgaatagtct gtgtaagtca caataagagg atttatttaa  39720
aaaaactttt atatgataaa gttgtctata attaaaggga aattataatg gtctttctag  39780
agattgggtt gatgttaaaa aactacttat atattaaaaa attggttaga acaatgaaat  39840
```

-continued

```
tttcttacgg ggttgattca ctcttaataa attataagag acttaagaat ttttttttaa  39900
cccaaagttc agcttttatt gcatcttgct gttttaggtt ttctctcccc tttaaaaggg  39960
tgggaaatag taatgccctc cttcaactcc cttcagctca tatacgtttt ttaccctcag  40020
attctgtttg ttgtgtcctg atgctaacaa tgttttctta aaggtctaaa ggaaatgttt  40080
tcttccaaca taatattctg tgcattgcag aaggtctttt cttttgcctt ttggtaactg  40140
gcttaacaga ttttatgttt tattgaaata atttctatgc cattattatt aagttttggt  40200
ttgcttagaa aacactgaga ttaatacaat tttttaaaaa ttatgattat tacatccata  40260
tatctttatg tatgtgcttt taaagtcctt gtgacattga gttctagggc ttgactcctg  40320
ggtcttaaaa ggacaagtcc tgctaaatct taaatactga cagcaattaa aggctcatct  40380
tcaggactgg tagaaaatgc caatcaaaat aaactgcatt cttgaaacac agagccagaa  40440
attaaagcta ttcaactcaa ggcccaggaa ctatagtgga agaggtgggt gtgtgagatt  40500
gtaagggcca attttgagag ataaaataag ttcaatttct ctataaatta atcataatca  40560
ttgatgtcca agccacactg atgcaagatc agcatatggg tcctgtgtca gattaacaag  40620
gttttcttga agcattaacc tactccttaa taaaggttat agaggttata aaaggcttct  40680
ggaagttata gctatggtca agataaaaat ttcatagatt gttaatacaa ttttggaaaa  40740
caaatttaat tggcttcttg ctgtttttat tagggcttat tgtttggaaa attaagtctc  40800
gtctctcaaa gaatgaaggc tttcaccttt tttttttttt tttttaatcc ttgagttatc  40860
actttggtca aatgaatgac ttattttaca atgacctttc atcaagtgtt ttaaaccttt  40920
caaatttgac aaactttcca aaatcaaact acaaattatg tctttttatg acctaatgaa  40980
tcctttaaaa tactaggttc cctaaagtcc aaaaaaaaaa aaaaataaca taatgtggct  41040
tatttggtat aaaaatttta caagaaacat tgtcaaatat aaaatattgt gtggttttgt  41100
ttgggctgta tttgtataaa tatgttattg gtatgtgttc caaaattata ggaaactcct  41160
ataattctga tatgacttgg tgtacattat cagtaataat tataattgtt atggtaaatt  41220
attgtgtgcc atggaggtaa caaatttcct catcaagtgt gtctttgact atggttgccc  41280
taaaactttt tgccattcac agacaattgt cttgctttgg tcctctttag aaggtggttt  41340
tataatcagc tataaaactc taacgggtgc tcttgaatgc aggcttaaga tagctttgga  41400
gactgtgaca tcagaataga ggaaaaactt tcagtattca tggagtgctg aaatattcat  41460
gaatatcaag caaaacagga attaacttca tagatggaac taaaagaatg ctgaagtaat  41520
ctttttgact ttttttctta gaatgttgat ccttcgtttt gtttttcaga gtcnaggaaa  41580
tttttctgtt gagatattga cagctttaac aattaagtat actccagtga acacaatttg  41640
gagcaatcta gtcattcccc agcctgacca attcaatggc ccccatctta gttaaaattc  41700
ctcaccctga caaggcccca tctacgcctc tgacctcatg ccctccactc tcagtcttgc  41760
actcaccctg ccacactcaa gggcttcccc aggttccttc ttagattcca ccgatagctc  41820
agggactttg cacatgctac ggtctctgcc tggctcctcc ccagatcttc tcatgcctag  41880
ctgcttctca tcagcacccc tcagagactg tccctgcccc acctctccag gttccatacc  41940
tgccaccctc ccccaatcac gtaacagttt cttcacagag cgagttacca tcccagtatt  42000
tccctaactt attttttgtg actggtctgt tgcctgtctc caccacaaga acataagctg  42060
catgtgaaca ggagccttgt ctatcttgtc accccagtgg ctgtgacata acctgataca  42120
cattagatgc tcaatgatgt ttgatgaatg aagtgctggt agtccaactg tgtttccttg  42180
tctgtgtaag tatgtctgtt gtggtttcct aagaacctac agctctccca ctgtgactcc  42240
```

-continued

```
tgttctatgg tcctgatttg ctggactaga atcctaacct acatgcttac tcttagtgtc  42300
ctcccccaga ggctgaatcc cagtccctaa acctccacca aatggctaag acctagcttc  42360
caaccagaca ggcctacgct gagacctcag caccgccctt ctgcggtctc atccttaacg  42420
catccttcag ggcccagctt aaatgtctct tctccaagga aggctatcct ctttctgccc  42480
ctcagtgctc tccatgcctc ctctatgcct ccatgcctgc tttcaaccct gcagaagtgg  42540
agaaattgct aatctgctgt gttgacactg tgctggggtg ccttgggcca gggagcaggc  42600
tggtggtgtg ctgatagccc gtggctgtgc ccaggtccat gctcacttcc tgagccccag  42660
tggagtaggc tccctttccc ttattgcagc actcagagga aggacgtgct tcttaggaca  42720
gatctggcca acctctccct cgtgagagaa ggcccagcca tcctcttgcc ctctttcttt  42780
ctcctgcccc cgagtaataa aggtgcctgg tcagagcctt ctagaaggag acccaaacat  42840
ccaccacaca ttcccagttc caaccgtcat ccacatggct ggctgtgcag gtaaacgcag  42900
agtctgtttc acacacccaa ccatctagta ttggatggga ggacagtagc gtgacactct  42960
tctccagcct tgagccctac tgtgggcccc acccaaccca gataccagag gagccctgta  43020
ctgggatgct attggatgct tgtccagtca tgtacaaagt tagccctttg ttatatagag  43080
ttagctacgt acatcttcct ctgtagggaa cccaagaggg gagaagagat atgtagtagg  43140
atttaacctg caaatcctct gctgagcacc ctgcactaca tacagtgggt agcatgtggt  43200
aggtgctcaa taactattga ccgatagatt gaatacaggt aggatggtga cacaatctaa  43260
gatcccaggg gtggggagac cacacgcttg gttagggaga cccaaagtgg accgtgtggc  43320
cagaagagtc ccgcactgca ctctagtgac agtgcagaaa gtcactgtgg gaaatctaga  43380
agtttctaca ggttgctatt tcatcatagc actgtgcagg ccaacccttc ctgctccact  43440
ggctgttggg aaaagctttc tcttttcttc ctagccaggg agctctcaaa gtgttccact  43500
ctctcacctc cacccaggcg tccaggtgtg gaggacactt gccggctgct tgtctgctga  43560
ctcatccctt ggtttcactt ggaaaaccta ccaccagctg gcctctttcc aagcatcagc  43620
ctcctcattt tcttaatccc ttaggtgtga tctcacctcc acacagtaga ttgcctcaag  43680
gcccaattcc aatatgaata aaaatgatta ttttgtcatc ttccaatctt ccttttaaaa  43740
tattatttta taattccctt taggaggatc acctaagtga agactatttt tacctaagaa  43800
atgttaaaat gtaaagacat ggttgtaatc tggggattcc tgttaaaatg gctagcagac  43860
agaagtcaga cgacaggcta gaaatgtgtg aagagtggtt gcctttgaaa ggcggagttg  43920
gtaatgattt tcttccattt ttccatgctt tccaattctc tacaaaggcc ttaatattac  43980
ttcgataacc aggacctctg ataacctgcc cccaccgagt aaagacttag ctgggaaagt  44040
cagcttcatg tgaggtaaaa ggaaccaggt aatacacaat tcccactgcc aactgtcggg  44100
tgtgcaggcc tgagcttcct gcatgtggga ggaaagagaa agaagagaga aactccaaga  44160
tccaagagat ccagcaagaa ggctggagtc tgaggacgca gaaagctgaa tggcacagtt  44220
accactattg tgctgaggtt ctgtggcctc tgggtctctt gacaactggg caaagaccca  44280
cagaaaacta tctctagacc ctacctgtgg gaggggaaag tgcttaagat catttacagg  44340
acagccacct ggacctcaaa tggcttacag ttccttcatc cagagggtct tcatttagta  44400
cataccaggt gctaagctgg gtgctggaga catgacgggg aacccattta ccatggcttt  44460
gttactgtga cattcacatc tagggaaagc cagcaaaggg gagggatcga ggagagcttg  44520
ttaggcagag aaaataccca agggcaaggg agaagccagc ctgttctgag cacacacagt  44580
```

-continued

```
ggttccatct aactgggcct cagtgccagg ttggactgga gatggggctg aggagctgtc  44640
acagagcatt ctggacacag atgtcacata gtcccttgag gttagggtcc ttaggcatgg  44700
cagcattgct ttgagttttt ccttttgtaa tgttgccatt catgacaatg tggaagatgg  44760
gtccttgcag agaagggcag ggctgtgaga ccagttagga gactaagatg tgagccaagg  44820
aaaatgagga acacctgaac actggggcag gtgcagggcc cagagagaag cagatggctt  44880
cctgaggttt taagtaggta gaatcaaggc agctggtaca gatcttttat tacatataaa  44940
ctggaataag ccatctgttc caagacaaaa gagtaggcgg aaaacaatac aagacagaaa  45000
tggaattaga acaaacctgg gaggaatgtg gaattagagt agagagtcca acactggctg  45060
caatcataaa aatgtaaaac aaacaaaaat ttgctaggtg tgcttactta gaaataatta  45120
gctgtcatat taagttcact tgtgttatgg cttaaatgtg tcccccaaaa tgtgatgtgt  45180
tggaaacttg atccccaatg caacagagtt gagagatggg acctttaaaa ggtgattagg  45240
tcataagggt tctgccctca taaatgaatt aatactgtta tcatgagagt agattcctga  45300
taaaaggatg atctctgcct cctccccaca gccctcttgt gcatgctttc ctgcctttcc  45360
accttctgct atgggatgac acagcaagaa ggccctcacc aaatgcagct ccttgatctt  45420
ggactttcca gcctccaaaa ctgtaagcca aacaaatttc tgtttattat aaattaccca  45480
gtctcaggta ttctgttcta gaaacacaaa atggactaag atcattaaat tatcattttt  45540
tatcagactg ttgaaaaata taacagagag taagaggaaa attaccttct ttctttttcc  45600
tttccctgcc tgaccttatt cacctcccat cccagagcat ccatttattc cattgatctt  45660
tactgacatc tattatctga cctacacaat actagacatt aggacaatgt ggcctgcctc  45720
caagaaactc aaataagcca actgagatca gagaggatta atcacctgcc aatgggcaca  45780
aagcaacaag ctgggagcca agtcccaaaa tggggcctgc tgcttccagt tcccctctct  45840
ctgcattgat gtcagcatta tccttcgtcc cagtcctgtc tccactacca ctttcccccct  45900
caaacacaca cacacacaac agccttagat gttttctcca ctgataagta ggtgactcaa  45960
tttgtaagta tataatccaa gaccttctat tcccaagtag aatttatgtg cctgcctgtg  46020
cttttctacc tggatcaagt gatgtctaca gagtagggca gtagcttcat tcatgaactc  46080
attcaacaag cattattcac tgagagcctt gtatttttca ggcatagtgc caacagcagt  46140
gtggacagtg gtgcatcaaa gcctctagtc tcatagaact tagtcttctg gaggatatgg  46200
aaaacagaca acccaaacaa ccaacaaaag agcaagatgc tgcaaaaaaa aaaaaaatga  46260
atagggtgct aagatagaga aaagtgggag agtgctattt agacaaagtg gtaaaaacaa  46320
agccccttgt gagatgagag ctgccgacag gagggggcgg gtcatggttg tgggtttttg  46380
ggtaggacat tcagaggagg gggcgggtcg tggttgtggg tttttgggta ggacattcag  46440
aggaggggc gggtcgtggt tgtgggtttt tgggtaggac attcagagga gggggcgggt  46500
cgtggttgtg ggtttttggg acattcaaaa gagtctgaat gcacccaggc ctacaacttc  46560
aagatggtaa aggacagctc caaggatcag aagaagcatg cttggaactg gggcattttg  46620
agaaggagga aaaatatgca gagactagtg cttgcagagc ttgcatgtgg atttcatttg  46680
aggtacaatg aaaacccatt aatgggtttc acacagtgca atggcctgac ctcacttata  46740
tttcctaaaa tagaaaacag atcagaagga aggcaataga gaagcagaaa gtccaatgag  46800
gaggtttcac agcagtcatg ggggtggggt aaggaaaaga agtggaaaga aacagacaga  46860
attgggttat attttggaga tagaaccaac agaaggaaga ggagaaacaa catttactga  46920
gaagggaaaa agtaggagag gaataggttt gggaaataaa tcctgctgac attggaaacc  46980
```

-continued

```
ccaaggaagc ctcaaaagta tatttacttg ctttagattt aaaagaatag gaaagaagca  47040
tctcaacttg gaatttgaaa tctatttttc cataaaagta ttgttaaatt ctactcatac  47100
tcacaagaaa agtacattct aaagagtata ttgaaagagt ttactgatat acttaggaat  47160
tttgtgtgta tgtgtgtgtg tgtatgcgtg tgtgtgtgtt taaccttcaa ttgttgactt  47220
aaatactgag ataaatgtca tctaaatgct aaattgattt cccaaaggta tgatttgttc  47280
acttggagat caaaatgttt agggggctta gaatcactgt agtgctcaga tttgatgcaa  47340
aatgtcttag gcctatgttg aaggcaggac agaaacaatg tttccctcct acctgcctgg  47400
atacagtaag atactagtgt cactgacaat cttcataact aatttagatc tctctccaat  47460
caactaagga aatcaactct tattaataga ctgggccaca catctactag gcatgtaata  47520
aatgcttgct gaatgaacaa atgaatgaag agcctatagc atcatgttac agccatagtc  47580
ctaaagtgct gtttctcatg aaggccaaat gctaagggat tgagcttcag tcctttttct  47640
aacatcttgt tctctaacag aattctcttc ttttcttcat aggagatgcc tgagataccc  47700
aaaaccatca caggtagtga gaccaacctc ctcttcttct gggaaactca cggcactaag  47760
aactatttca catcagttgc ccatccaaac ttgtttattg ccacaaagca agactactgg  47820
gtgtgcttgg caggggggcc accctctatc actgactttc agatactgga aaaccaggcg  47880
taggtctgga gtctcacttg tctcacttgt gcagtgttga cagttcatat gtaccatgta  47940
catgaagaag ctaaatcctt tactgttagt catttgctga gcatgtantg agccttgtaa  48000
ttctaaatga atgtttacac tctttgtaag agtggaacca acactaacat ataatgttgt  48060
tatttaaaga acaccctata ttttgcatag taccaatcat tttaattatt attcttcata  48120
acaattttag gaggaccaga gctactgact atggctacca aaaagactct acccatatta  48180
cagatgggca aattaaggca taagaaaact aagaaatatg cacaatagca gttgaaacaa  48240
gaagccacag acctaggatt tcatgatttc atttcaactg tttgccttct acttttaagt  48300
tgctgatgaa ctcttaatca aatagcataa gtttctggga cctcagtttt atcattttca  48360
aaatggaggg aataatacct aagccttcct gccgcaacag ttttttatgc taatcaggga  48420
ggtcattttg gtaaaatact tcttgaagcc gagcctcaag atgaaggcaa agcacgaaat  48480
gttatttttt aattattatt tatatatgta tttataaata tatttaagat aattataata  48540
tactatattt atgggaaccc cttcatcctc tgagtgtgac caggcatcct ccacaatagc  48600
agacagtgtt ttctgggata agtaagtttg atttcattaa tacagggcat tttggtccaa  48660
gttgtgctta tcccatagcc aggaaactct gcattctagt acttgggaga cctgtaatca  48720
tataataaat gtacattaat taccttgagc cagtaattgg tccgatcttt gactcttttg  48780
ccattaaact tacctgggca ttcttgtttc attcaattcc acctgcaatc aagtcctaca  48840
agctaaaatt agatgaactc aactttgaca accatgagac cactgttatc aaaactttct  48900
tttctggaat gtaatcaatg tttcttctag gttctaaaaa ttgtgatcag accataatgt  48960
tacattatta tcaacaatag tgattgatag agtgttatca gtcataacta aataaagctt  49020
gcaacaaaat tctctgacac atagttattc attgccttaa tcattatttt actgcatggt  49080
aattagggac aaatggtaaa tgtttacata aataattgta tttagtgtta ctttataaaa  49140
tcaaaccaag attttatatt tttttctcct ctttgttagc tgccagtatg cataaatggc  49200
attaagaatg ataatatttc cgggttcact taaagctcac attacacata cacaaaacat  49260
gtgttcccat ctttatacaa actcacacat acagagctac attaaaaaca actaataggc  49320
```

-continued

```
caggcacggt ggctcagacc tgtaatccca gcactttggg aggccaaggt gggaagatca  49380
cttgaggtca ggagttcaag accagcctag gcaacatagt gagatctcat ctctacaaaa  49440
aaaaaatgaa aaattaaaaa atgagctgga catggtagta cacacctgta gtcccagcta  49500
ctcgggaggc ttgaggtggg aggatcactt gagcctggga gatggaggct gcagtgagcc  49560
ataatcacac cattgcaccc caacctgggc aacagagtga gacccagtct caaaagataa  49620
atttttaaaa atgttaaaaa atatataaaa gagaatttta aaagaacaac taatagatca  49680
aagcatggat gcaagatata tttagttgga aaatcaaggt taaaatcaag ggatcttgga  49740
attaggtgtg gtagatttgg gtaaggagta gtctaagatg accctgtttc ttggtactgg  49800
agactggatg agtggcagcg tcttaaccat atttttggta gaaatatgga ggtcttctcc  49860
attccaggat gaatgatgag taaaatttta ggcatgtaat ttgagctact agaaggacac  49920
tcaattgcag atgtacaatg gggagatgat aacctatctg gaactcagaa aaataactgt  49980
atatagatat gaaagacatc agtaggtatg tagtagataa aatcctaaaa gtgatgtcaa  50040
agggagaaga gaagtatatg gtgaacactg ttgtttgtcc atgcaattgc catctcttct  50100
tcttccttac tgacagaacc ctgatttcac tgagaagtca acatgccctt ccccaattga  50160
tgaatccaat tggttgaaga ttatgttcat tctattctta catgactaag tcacgttgac  50220
ttaatcctat caaatgagat gtcgatctgg aaacaacttc tggaaaagat tttctacctt  50280
gataaaataa agagccatat agatggtcct ttatcttcct tcttccttga atgagatatg  50340
ttctatgagg aagtgaagct tagaactgtg gtcagcaact tgcaacgact gggaagtcag  50400
agccacacaa tgaagaatgc agagtggaag gagaaaaaga gccagcatct ctgacaacat  50460
tgttacaccg agaacctacc tccagatttt aagaaaacaa gaaatgctac tgttattaag  50520
ccatttcact gggtttgcta tgacttgcag tcaaatctag cttaactgat acagagcacc  50580
acagagaact ggtctctcat ttgtctcatc ctgttctttc tagcagccac gactttccta  50640
gggtttcctt agcccaagtc tggctagagc aagactaagt aagacttgat tccttaatgt  50700
ccttttgttt taagaaatat taaagaatta tttttatatt aatatatttt aagaaataag  50760
gaaatacaaa acactgagca agcaacacaa attcaagaaa tcttaaaaag tataatagct  50820
gctcagtctc tgattaacag tgaaatatgg aatcattgta gaaatggcct tggagcgtta  50880
ttctcccagg ccagctatcc ttatggtctg ccccacctcc ctcattgcct aaacagtaag  50940
agagtcccat ggtgagactc aacagtctta gcacagaact tgttacagtc tatttctttt  51000
cttacagtcc tatatatcaa ttccaaatca atgagagtaa agcccaatcc ctgcctttaa  51060
acccaaagga cagaagccca aagcccaaag atattcccta accttctccc cctcctgtcg  51120
ctccctatgt ttaaagctgg ggatctcttt ttcctgtgtc taattatttt cctcattggc  51180
ttgaaaaatc tgataaaaca ttttaggact gtgtataaaa tagaattagc caagtgcaat  51240
gtctttattc agaagaaatt tcatggacgt tgtgcctact ctcttggctt cctggcttca  51300
tggctttcca gatcccacag taagctctgg atagtagaag ttatagtaag actgacttct  51360
aaataaatga agtgacttta accttactga tatggcttaa agaaaaggag tggcctttaa  51420
gatccatgaa cttctcaaac aaaagtgata acgttatctc catgcatata taatactaaa  51480
tataatgcaa ctgagagaag taggctgtgg taagaaagga gacccaagtg ccatctgaag  51540
gcagcactta ccactctgct tcatcccacc gaggaaacaa agcatgagta ttgccagatt  51600
ttcttctgtt tcaagaaaag ccagaaatcc aggtttttgc gtgaaatgtc ctgattttaa  51660
tgttgggaac taatttatat tttgaaataa cattgtgtgg gacaagtgaa cttgtatgtg  51720
```

-continued gaactgcttt ctcccagtgg cgaccagttt ggaccgttga tactcagcaa gttcagccaa 51780
gtgcgccttg tcattgtcag tcatcaaggt gatgtgtgat tggtcaaaca attagttttg 51840
ctcagcatct cgtgtgtttt caaaggacct gagggttcat ttgcccatgc agatcttgta 51900
gtcctgttta ttctattaat ttatcttgca aatctataat gttttatttt aagcagcgag 51960
agccgtggca gcctttggtc tggacccttt ctaatgatca tttagtatca ggctatgtgg 52020
gagttgattg ttttgcattg cctgaaagcc aacagtatca ctcctcctct aggtgtggca 52080
gagatgtgag agagggagac tgacagtctg tgggtgtgta tgcagtgttg ggggaagcga 52140
ggcacagggg acaatactgt ggtgtataaa actagtctaa ggtagcatca ggaagttcat 52200
gaagccaaaa tgattttcat aacagcacaa gacattattt gtttttgcct ccctctcatt 52260
tttttttttt tttgagacag agtcttgctc tgtcatccat gctcgtgtgc agtggtgcaa 52320
tctcggctca ctgcaacctc cacctccagg gttcaagcaa ttctcatgcc tcagcctcct 52380
gagtagctga ttacaggtct gcaccacccc gccggctagt tttgtatttt ttagtagaga 52440
tggggttttg taatgttggc caggctgccc tgtcattttt tttttactag tgtccagtgg 52500
agttttttag ggctacata acatgatact gtcattaatc taatggctaa tgaaagggat 52560
atgtatatgt ttttgtgttt aaaacaaact tctttggggt cctcaataat ttttaagagt 52620
ataaaggggt cctgagatca aagagtttga gttctgctgg actgggacag tggttgtcaa 52680
cccagattgt acattagggt catctgggaa gctttaaaat agtactgatg cccaacctta 52740
ccgcaaacca attaagccag aatctctgtg gatgagaagt cttcattgtc atcatcacca 52800
tgaccatcat cattgtcacc gtcactacac cattatcatc atcatcatat catcttcatt 52860
atcattgtta gtatctccat caccatcatc agcatcacca ttattatcat catcatcatc 52920
cccaccatca tcctcatcgg aacttcacct gcatggagga caatccacta tgcattaggt 52980
gctatgctat ttgctatact ccttattctc acaactgccc agagaggctg atattatctc 53040
actttataac aggaggaatc tggatcggaa aagttaaggt aagctaattc acagagcgag 53100
aagagataga gccaggattc gaaaccagtt ctctgctaca tcaatgttcc cagtccttgc 53160
actattgaga acctctttag ttatgctttc acccctccaa caccacagta aattttttct 53220
ttttttaaaa aaattatact ttaagttata gggtatatgt gcataatgtg caggtttgtt 53280
acatatgtat acatgtgcca tgttggtgtg ctgcactcat taactcgtca tttacattag 53340
gtatatcttc taatgctatc cctccccgct ctccccaccc catgacaggc cctggtgtgt 53400
gatgttcccc accctgtgtc caagtgttct cattgttcag ttcccaccta tgagtgagaa 53460
catgtggtgt ttggttttct gtccttgtga tagtttgctc agaatgatgg tttccagctt 53520
catccacgtc cctacaaagg atatgaactc atcctttttt atggctgcat agtattccat 53580
ggtgtatgtg tgccacattt tcttaatcca gtctatcatt gctggacatt tgggttggtt 53640
ccaagtcttt gctattgtga atagtgccac agtgaacatt catgtgcatg tgtctttata 53700
gcagcatgat ttataatcct ttgggtatat acccagtaat gggatggctg ggtcaaatgg 53760
tatttctagt tctagatcct tgaggaattg ccacactgtc taccacaatg gttgaattag 53820
tttatagccc caccaacagt gtaaaagcat tcctatttct ccacatcctc tccagcacct 53880
gttgtttcgt gactttttag tgattgccat tctaactggc accacagtaa atttttatag 53940
attttataag caaattgtat ttactgtgca agaattggtt tattttttaa accatgtgtt 54000
gcaaacatac aatggttaat tgtgatattt gctcagtaca agatcatcag atcactacac 54060

-continued

```
agacttgagg taattccacc taaaagcaaa gagaactgac cccacattaa ctgagaagtc  54120
tttacttatt tattccctat aaacgagcca atatgaagag aaggccttaa tgtggttaac  54180
tatgtaattt ttttctgact ttttgaaata ctgagaagag ctcatgactc tcccatctcc  54240
taattctacc ttggtggatt ttagactgac cacaactcat gggtaaatga gggaagacga  54300
ataagaaacc ttgctttttt ttcctccttg tttttggctg gctgcagtgg ctcacacctg  54360
taatctcatc actttgggag gccaaggtgg gaagatcact tgagctcagg atttcaaaac  54420
tggcctgggc aacatagtga gaccccatct ctaaaaaaaa aaaaaaaaaa aaaaaaggcg  54480
acaggcggtg cgtgcctgta atcctaccta ctcaagaagc cgaggtggaa agatcacttg  54540
agcatgggag gtcaaagctg cagtgaacct tgattgcacc acttcattcc agcctgggtg  54600
acaaagcagg acgctgcctc aagaaaacaa aaacaaaacc ttaatttttt ggctattctt  54660
ttctggtaag aatggtatag agatggggat gaggatggct attgtatgag agagcaaaca  54720
gggtccaagc agtgctctgg gctgtctaag gaccagtagt cagcttaact tctcaaattt  54780
ccagggaagg agttcggagt ggtagaatat cctgggtatg cccaaagcat caccttgcaa  54840
atagcctgtc atgaataatt tgtttcattt gttatgactg gaaactggct ttgtgtatgc  54900
cagagaatgg gggcaggaaa gagagattgg tgtcttgagc tctctgtgcc tctggggcag  54960
tgatgctttt cctctcatgt ggaaggagag catgactgaa aaggtgcaca aataaggtgt  55020
ctgtgagaga aattaacctt ccagatacag agacacaacc ttccccaaga ggtcctcatt  55080
gctctgcctt ttttcctttt ttttgcttgt tctaccatta ataacagaaa ctgattatga  55140
cctcaaaaga gaggagaaag cgactctccc caccctagag ctagttaacc accatatctt  55200
cctagatatc cttgagagca atgtaacccg tgaactcgtt ttacctgtgt agcagaccaa  55260
gccgcagaca aaatccntca gacaccaaat taaagaagga agggctttat tgggcctgga  55320
gctgcggcaa gactcacgtc tccaacaacc gagctccccg agtgtgcaat tcctgtccct  55380
tttaagggct cacaactcta aggcggtcca catgagagag tcgtgataga ttgagcaagc  55440
agggggtatg tgactggggg ctgcatgcac ctgtagttag aatggaacag aacatgacag  55500
ggatcttcac agtgcttttc ttatgcaaat aaccgattag atcaggggtc gatctttacc  55560
aggcccaggg tgtgtcaccg ggctgtctgc ttgtggattt catttctgcc ttttagttat  55620
tacttctttc tttggaggca gaaattgggc ataagacaat atgaggggtg gtctcctctc  55680
ttacctgcgg ggagtgagct caaactcctt aaaggagtta cctgccttcc atcatcaggg  55740
aagcaggaaa tcttgccttc cttgttggaa gcaagtaaaa ctcaaaacaa acaaagaaaa  55800
aaacagggag ttgtacagca aaataaactt ttgattttga ccaaattttg ggagatcagg  55860
aattctctga aggagatgct ttcagacctc agcaaattgt cctgttggtt tgagccataa  55920
agttagctca tgctggtacc aaacaccagt aggagatttg tcaaaggtaa gaggcatctc  55980
cactcagaat cccttcgtgg ttaccaacat gtgaaccttg gaaatctgag acaggtctca  56040
gttaatttag aaagtttatt ttgccacggt tgaggacacc cacccatgac agagcatcag  56100
gaggtcctga ccacatgtgc tcagggtggt ctgagcacag cttggtttta cacattttag  56160
ggagacatga gacatcagtg aatatatgta agatgtacac tggttccctc cagaaaggca  56220
gaacaacttg aagcagggag ggagcttcca ggtcacaggt aggtgagaga caaacaattg  56280
cattcttctg agtgtctgat tagcctttcc aaaggaggca atcagatatg catttatcac  56340
agtgagcaga ggggtgactt tgaatagaat gggaggcagg tttgccctaa gcagttccca  56400
gcttgacttt tccctttagc ttagtgattt ggaggcccca agatttattt tccttctaca  56460
```

-continued tcactgtggg cagctgacta ggaaagcttt gtaggactgg tgggcagtgt gagagcccag 56520
tggggggtgg tggtcctgtg ccaatggtag caaccacctg tgaggctgag taaactcatt 56580
tcccaacctc ctctagcagc cccagtggag atacagagga agcagactag cgatacaacc 56640
cagcctgaag ttttgtctgg tgagtgtaat ggaataaaaa tgggaagggt gctgaagaga 56700
ccagcaagaa aatggttgaa gagatggggc acagaaatta agctggatca aaaaggacgg 56760
aaaagcagaa agggccgata gagagagggg atatctatgg gttcgcgatt ctgaaaagga 56820
caaatcactg gtgctttgag aagagagagg gtgagaaagc aggaaggctg gaggctgtca 56880
tccaagaggc ggacatctgt gaacatgatt ccaagagtca ccagaccatg gggtggcca 56940
aagggagtgc ctcttctcac ctcctactct taattccttg tactcaagat aataagttcc 57000
cagaagagaa gtacccatat ttaattcatc tgtgtcttcc tagcagtact aaaaatatta 57060
tatgaaaggt atcaaacctt tgagaatgtg tgctgctaaa ttgttaagga tgctggaaaa 57120
ctcaagacgt ccctgatcct gagcctgagt atgagcctgt ggtgagccca atgcaggtct 57180
ccattcagac aaaggcctca gggaacggat gagacctagg gacagagatg catgctggag 57240
cagcattccc catccctact gcagctcagg ccagctgact gctttatgag taaacgttac 57300
cagggaacac tttgcagtct taacacacat gcccacctgt gaccactgat ccctgttggg 57360
tgaccactga catcagagat tcgatggcag caatgaagac aaggctatcc tcattaggaa 57420
ggaaaggaag gaggagggag gagggcaaac gaatctttcc tgcttgtcaa ccacgtccat 57480
ctctgttagg tgatttccca tgtgtgactt tgtttatctt tataataact ctgagaggta 57540
ggtcttgatg tccacatttt gaacatgagg acatccagcc aggaagttga gttctgggga 57600
catagctgag agggcaaagc tacatataaa cccctctttg ttttttctgg cttatccact 57660
gagtgccccc tgcaatccac cagcccattt gtgaagtgca tactataggt aagttggcac 57720
aggaggagtg gatgtgggcg attttgtcac agctctccag gaacttacac actggtgagg 57780
agggccaggt atgttcctga ccagtcacaa tcaaagcaac ctcctactaa tcagggaggc 57840
ttggtacctg gggaatgcta tgttgaaagg ttcttttctg ggttttaaaa tgatgggtct 57900
atttccttat tcttaagatt gcttttttttc tggctagaac ttaaaagaaa ttttcagtaa 57960
aatttccctt ccctggcaca aagtgagctt gaaatgaatt cccaggtggc cttgatactt 58020
taaaatattg cctcctataa aatcaacctt tagaagaagg aagtcaaaga acatgctaga 58080
tttcacaaag gttaattcct tgaaatccag ttatctacag gacaatgttg tcaaagaaaa 58140
aattatttgg ccaggcacgg cggctcatgc ctataatccc agcactttgg gaggctgagg 58200
caggtgatca cctgaggtca ggagttcgag accagcctgg ccaacatggt gaaaccccat 58260
ctctactaaa aatacaaaaa aaattagcca ggtgtggtgg tgggcacctg taatcccagc 58320
tacacgggag gctgaggcag gagaatcgct tgaacccggg aggaggaagt tgcagtgagc 58380
caagttcaag ccactgcacc ccagcctggg caacagagca agactttgtc tccaaaaaaa 58440
aaaaaaattc aatgatattt ttaaattcat ggtaaggaag atttcattca gaaccagcac 58500
agaagatata ggaaacactg caatgggact ttgcggtggg ggagagagat tgaacacaac 58560
tacatataca gcacgggcaa ggacatattc atagccagga agcagagcaa agatcagtgg 58620
atgcgaaatt actaagagga aacatgaaaa ataagggagc ttctgcctaa acccacctaa 58680
ccggatcctt gctgaagaca ggacagggtg attggacacc actttgggga tggtggagga 58740
tggggaatcc agtgagattt caagggtgat gcgatattga acatacaaag ttcttgctaa 58800

-continued

```
aaaaggattt tacaagaaag tgtacaaatg tgcctgggac aaggtgcagg agcccgacgg  58860
agatgtggtc cagcagagaa tatgtgccga gatgataggt gagttctctg acgaaggata  58920
tatgctgatc cagccagggt gaaatgctca gagaaagcac ggaggggcta tgtccgttgc  58980
cccagtctcc acgcggtcaa atctgatccc gttgtgagtg tggccgtttg tagaaagcaa  59040
tcaggggggg tccctcccca atatatattt tttatannat ntgagacagg ttctcactag  59100
gttgcccagg ctggtcttga attcctgcct tcaagtgact ctcccacctt agcctactgc  59160
atagctggga ttacaggcac aaaccactgc atgcagctaa ctttgcttct cattccagca  59220
ctttttattc cactgattat atgtatatgt atatctgcat catctctctc tctctctctc  59280
tctctctctc tctatatata tatatatata tggaaatatc tctctctctc tctatatata  59340
tatatggaaa tatatatctc agtctctcct atcctccttt aatcagtttt gctatcctgt  59400
caattccccc aacgagtgtg atgttgtgaa atatatattt gttcttcatc tcctgtttcc  59460
tgacatacag cttttaaaaa cccttggaat ctctggaata ataagagtgt cttttgcatg  59520
ctaatagatg actgctggct ggcagcccca atgcagtagc ttcatgatgg ggtttgtcac  59580
aggaaagacc aaggcaggat tggagacttg agactgttag ccccactccc caaccactgg  59640
agggagtgga ggggctgaag gttgtgtcag tcaccaatgg ccaatggttc ggtcaatcat  59700
gtgtatgtaa taaagccact cttaaaaacc caaaaaggac agggtttgga agggctccca  59760
gatagctgga cacatgaagg ttcctggagg gtggtgcccc agaggggcat ggaagctcca  59820
cacccctttct cacatgcttt gctctgcgca tctcttcatc tggtgttcat ctgtatcctt  59880
tgtaatatct tttagaataa actggtaaac ttaagtgttt tcctgagttc tgtgagctgc  59940
tctagcaaat tcacggaacc cgagggaagc aaacccagat ttatagccat cagtcagaag  60000
cataggtgac aacctaccac ttgtaactgg cacctgaagt gggaggcagt cttgtgagac  60060
tgagccctca acctgtggga tctaacgcta actccaggta gatagtgttg gagtgaatta  60120
ggacacccaa ctggtgtcgg ctgctggagg actagtggtg ggagaaatcc ccaagcattt  60180
cggtgactag aggtcacaga agaactcagt gttgaggtgt tgtgacagta tggtagggaa  60240
aactgcgtct ggttttttcc ttttacaatc agttaaatat ttaacacaag tctactgtat  60300
attagtaaaa gggttacatt ttttaatgtc ttgacagttg cactttgaca acttccatat  60360
caatcacttt ttttcgtgtc cgtttggaac caaaatcact tgggatacca tgaaccaggc  60420
tgcagcgtat tccccaggcc ttgaaagctt ggaggccatt ttgccagccn taatccctgt  60480
gaataccagg cttcgtggat ttaaaaaata gacttgaggc caggcctggt ggctcacacc  60540
tgtaagccca gcactttggg aggcagaggc ggatagatca caaggttagg agttcgagac  60600
cagcgtggcc aacatggtga aaccccgtct ctactaaata tacaaaaaaa aattagccgg  60660
gcgtgatgtt acacgccagt agtgccagat actcaggagg ctgaggcagg agaaatactt  60720
gaacctggga ggcagaggtt gaaatgagtc aagatcgtgc cactgcactc cagcttgggc  60780
gacagagtga gactcagttt tcaggggagt taaaacaata caaaaaaaga aaaagacttg  60840
aacaatgagg ctccactgga tggatttagg ggaattacag gaagcaggac ctgacggtgc  60900
aatgccacac tccacctgtc cagaattgga cctcaccaag ggaggtctgt ggggacaggg  60960
agaggccctc tgcctccacc ccctcctcta ctccccaaac cctgagtcag gctgaatgta  61020
gtaaacctgg aacagaaaag ttcagtttgg caataggtat ctgaaggact ccaggtgctt  61080
ctcccttgat tcaaaatttt acttataaaa aaaattataa gaaaattcta cttaaaagaa  61140
ataatcaggg aggtacaaca aattgtactt tttttttttt tttttttttt ttgaaatgga  61200
```

-continued

```
gtctcactgt tgcccatgct ggagtacagt agtgtgatct cggctcactg caacctccgc  61260
ctcctaggtt caagtgattt tcctacttca gcctcccaag tagctgcgat tacaggtgtg  61320
tgccaccaca cccggctaat ttttgtattt ttggtagaga cggggtttca ccatgttaac  61380
caagatggtc tcgaactcct gacctcaggt gacccacctg cctcagactc ccaaagtgtt  61440
gggattacag gggtgagcca ctaagcccag ccattgtaca tattttgtgg gtatttacta  61500
aaacattatt caaaatagta aaaaaaaatt gaaataaact ggggactggt taaataattt  61560
tgggtacaac cacatgatgg aatactatac agccattaaa aattacattg aggccaggtg  61620
tggtggctca tgcttgtaat cttagcactt tgggaggcca aagtgggagg attgcttgga  61680
cccaggagct caagaccagc ttgggcaatg tggcaaaacc ctgtctctaa aaaaaaaata  61740
caaaaaaaat taaaaagctg ggtgtggagg cacacacctc tagtcccagc tactcaaagg  61800
gctaaggtgg gaagatcact tgaaccgggg aggtcaaggc tgcagtgacc caaaatcggg  61860
tcattgcact ccagcctggg caacaaagca agaccctgtc tcaaaaaaaa aaaaaataca  61920
ttgaagaata tcttacggta tggataaata ttcattttac agtgatagat gcaaataaaa  61980
gcaaattaca aaatatacag tttaattcca actttgatac tacatatgta tatatgaata  62040
catgcatatg ttatgtatgt atatgtaaat ataacaatat atgttctata tatggatatt  62100
atatatttac acatacatac acacatatat aatatcttct ctagagagca gaaagagagt  62160
agacagataa tgaagatagg atacaactcc agtccagctc aacctagggg acttgtttta  62220
aagcctcagg agagagaagt tgggactaga aagcaaggca gctatttgta agcatctttg  62280
tgtttcatgc tattggggtg ggaaacaaca gcacaacttt tgaaagcccc tttctactca  62340
ccccacaaac tgcagagcag ctttaggacc ctcagagttc aagaagacca tttgcagagt  62400
agaagaagta aaaacatgta tgaacttgac cctgagctca tggactgtgc catgagggaa  62460
attcctaaaa cagcaggaga ggccctggag gaaggcagag gccctgcatc agcaagtcca  62520
ggcaaaagcc tgcattccat agatgctcat ctctctggct ggtgaggtct aaagacgttt  62580
ggtctcaata ttaagtctcg tgagagaggt cacaaaccca gtcccttggc cacaaaagga  62640
aataaattct ggcttgagac attagggagg aacagggcaa ggggaggttc aagaaagttt  62700
taatggatga gatgatattt aagcaaggcc ctggaaaatg agaatttcaa ccaatagcca  62760
tatggtaggt cagaaagcaa agataaggag ggggcaagtg caaggggcaa catcagatat  62820
gaccagggtg tcgtggggca tggctgatgg agaagaagat tagactggag tttgggaatg  62880
ccacagtatc gaggttggat ttaatcctat gggtaataaa gccaactgtt caacccccaa  62940
cccacttgca atatggctcc aaaatagcag gtgtttgata aaatgactac ttttactcta  63000
ctattccctc cctcttaaga agaaaaagaa agtggaggct cagagaaagg cagtggcttg  63060
tcccaatcac actatgattt ggccacaaaa caagaacgaa atgttacacc caaaaatgct  63120
gcctccacct cccttccttg ctttcctccc tgctggacta cagactatct caagagtgac  63180
gtacaccatc agggcttcag cttttccccg aaacaatgcc aaaatattag ccatacgtca  63240
ctgtagtaag agccctgaat tgggaatccc agctttgacg cagacatgct gattgactct  63300
gtgaccattc tcttcacttc tccactctat tcttccccac ctgtaaagtg aggtcctttc  63360
cagttataaa aacagatgat gctattgtcc tgttttgtat ctaatcttgc tgtgttataa  63420
aaaaaaaata aggctctgta cattcatctt ggccaattcc cttcttatct ctacttccca  63480
cagccccttt ttctacagaa aaccagcatt gttcttctgg atccatctct taagaaagcg  63540
```

-continued

```
ctttgcctcc ccggttattt aggtgataag aagtgtccta gatgacagcc ctggaatggg  63600
ctggaggcaa caaaaaagca agtgaaatag acagttacag cgacgacaat aataacaacc  63660
aacacctctc actaaagaga aagaaataaa aaagaaaatt aaaatctgcc gcaatgccca  63720
cacagtcatt gaataactgc atgtgtacag cacttggtta cttttacata cttcatattt  63780
tagccttcat agcagctcac aggggtggat ttaattttta gtccaactcc tgtcacggtg  63840
cctggcacaa gtataataaa tgttctgtga ataaatgacc ctctttttag atgaggaaat  63900
cgaggctcaa ggagaacaag caatgtaatg tccccctcct gttcagccat ctgcctttca  63960
cgccactgaa tgcagtagtc ctcagtgccc tgaacttgac cctcttctgc ttttcggact  64020
ggtccttcta atcccgttgt gactcactac accacctctc ctgcatatga catctacatt  64080
ttaaaacaaa ccgtatggaa ataacacatt agtcggcttg ttcccccacc cccgcaaaaa  64140
aaaaggcctc tttataacag aaacttctca ggctggtagg ggaattttat tcccccattt  64200
atggtagaaa ggccctaacc ttggacctca cgccatagct attcacatgg gggaatgatg  64260
aataacatgg ggagcagcat gtaaatatca ttgagccgta gtccagacct ataacacatc  64320
gggggagctg catgtgcctg tcgagatctg gggaggaac aggaagatca agagttctgt  64380
gtaggacatg ttaagttgaa ggtgcttaca ggatagccag atgaagcatc aggtgtgcag  64440
tcaaagatat gagtctggag cagcacatcc taagtcacct cctgcaccaa cacagaactt  64500
ccaggccact cacttgagct ctcccaaata gtttccaagt gtcattatgt taataaccta  64560
tgagcttgaa caccagattc aaaccccact gcatggcttt taaagaccat ctcaagggct  64620
tgacactcca gggagccaac taaagatgcc tggtcctacc atcaacctcc accccatttt  64680
ttatagaaaa tgtttctacc tgtcctaagg cagggtcctg ccccactccc aggccccttt  64740
agatccccaa tattcctcct ccctgaacca aaaccctcat catcttccag catgggtggg  64800
gcctccattc ttgcttctgc tcccctgagc agaagcaagt ttctcccaac ttgacctgat  64860
tctcctccta agtaccagtc actgctttgt ttctggaatg agagaaaaag acagagtgag  64920
agagacaatc cagaactctt gctcactcac agctaggctg ggcatctggg aggatggctg  64980
tgtccatggg aacctgggaa aagccacacc cttggcaccc tggtcaccca cctgtctccc  65040
tggcagattc cgcactgctc tcttgcaccc tctaccaggg ctaaccggcc tgctcactct  65100
ccccagcatg tcttcccacg cccactctct aattattaca ttcccttcac ataaactgcc  65160
cttctctccc aatcaccaca tgttcacttc ccacccagct gtcaaagtct ggctcaacct  65220
cattcttgaa aaggaaaaaa caaacaaaca aacaaacaaa caagcaaaaa acctatgatg  65280
gattaagaac acacttcatt ccaggaacat gcttatctcc tctaactctc acaacaacta  65340
cagcaggtag gtgttatcac acccatctct caggtgagaa aacaggctca acgagtgcag  65400
gaggacacag caagtcagtg acaaagctta aattcaagcc caagcctgtt ggcaaccaac  65460
gtctgtaccc ttgatagcta cctcatttac caccaaatcc agtggcctca ggcctggctg  65520
cacactggga tcacctggtg cccagaccac atcttagacc agtcatacag aatctcttgg  65580
gctgggatcc tccacggtac attttaaggg tccccaggtg agttccacca tggacccaga  65640
attgaggacc caataccgta taccatctcc ttcttcatct cttctaaggc atctcttact  65700
cgctgtgcac tcccatacca ctttgttcaa tcatccaatc attcattcat tgagtcagtt  65760
agtcaggagc tactcactag tcccctgcca ggtcctagtc atgacatagg gctctgggga  65820
ccaacaagaa gcaggaccca tgcctcctgc tctcatggag cttgctctgc agcagaggaa  65880
gcagtcagtg agatgtagca aatgtgaaat gtgcacagat gggaaaagca aaactttaaa  65940
```

-continued

```
acttttagga caaaatacac aagaaatctt tgcaactttg ggacaggaag gaacaacatt  66000
ccttacacat gacaccaaag gaatcaacca taaataaaaa ggtgatcaat ttgacctcat  66060
ttaagtgtta agctttttc attgagagac accattaaaa attaaaaata catgccacaa  66120
actgggatac aatatttaca acacttatgt ctcacaaagg attagttttc agaatatata  66180
aagaactccc ggccgggtat ggccgcgcac gctggaatct cagcactttg ggaggccagc  66240
ggatcacatg aggtcaggag ttcaagacca gcctggccaa catggcaaaa ctccgtctct  66300
actaaaaata caaaaattag ccaggcatgg tggcgggcgc ctgtaatccc agctactcag  66360
gaaactgagg caggagaatc acttgagccc agaaaacaga agttgcagtg agctgagctc  66420
acatcactgt aagcctcggt gacagagtaa gactgtcaaa aaaacgaaaa caaaaacaaa  66480
aactcctaca aataaataag aaaaaaatag cccagcagga aaaagtatat acatttcata  66540
aaagaataaa tacattctgt cagttttcta acatatattt tttaagagta aatacaaatg  66600
gttaggaaac attttttaaa atgcccaacc tcattaaaaa ttatagaagt gaaaattaag  66660
ccacaataag atacgatttt ataccaaata cagtgtcaac actttgcaag tctgacctca  66720
ccaagtgtta ccagacgtgt gcactgacgt ggctgctgag atactgatgg tgggtgtgta  66780
aatctgtact acaaacaatt gcaataaaat gtaataaata tacaataggt ggagcaggaa  66840
gtgacctgca accatatagc agatagggca ggaaaaagcc tatgaaagct gacatcaaag  66900
ggataagttc cagttaccca gctgaaggga aggagggtgt ttcagataga ggaaggataa  66960
gcatgaccta ttcaaggcca gtgaaagaag cgtgcaacgg ccaagtcagg agaacctgaa  67020
attgtgtcaa agagcttgga tgcaaagagc cgtgggagac tattgggggt tttaagcagg  67080
gatataatat tcattcaagc atgcagtaaa aggtcactgg cacctgccat gggccaggac  67140
tcgggctcta catgattgcg tctgttttgg aaatatcacc ctggctgtga gatgaagaac  67200
aggtaggagg gtcacaaaac ttgaagcaga gagactgttg aggaagtaag ctgtttttgt  67260
gtggactgtg gcaatcacag aggcagagga tataaatgca cagagacaca aggcatgtgg  67320
gaggcagaag gaatcaaata caatgagtga tcagatgtgg ggttagagtg gtgagtgaga  67380
agacatactc aaggtgacac gcccaggtat ctgggtggat ggtaagacat tcatggacta  67440
ggatcgagga angaggtggg gaatgggacc atacctgcag tttataaggg gtggacgagg  67500
gaagattatg cgggagactg agagaggaat agacaaagga atcccggtgc agtattacag  67560
aaactggggt gggagggggt tgtanttcaa aaaggaaaga aaattgtcaa atagtatgaa  67620
atgctgcaga gaaactcacg gatttttttt ttaagcttag aattattcat tgactatgtg  67680
aataagaata acttttatga aagaagtttt gcttaagtag taggaagaag caaaattgtt  67740
gagggctgat gagtgggagg agaagtaatt gaaggcactc tttcaagaga aacaaagcag  67800
aaggtgagga gaatactaat gaaggagtta cggccttcac tattttgttt tgctttagat  67860
aagcaagact tgagtgggtc tggtgaggag aaacaagtag agtacaaagt taaaggagag  67920
acagacagag atagagatag ggacagagag agagacagag acagagcaca aaagagcaag  67980
gtccctgaga acacgggcct tctgtttaaa ccccagccag atgtattgca attcaattcc  68040
agtactaacc acccagagtt tgtgtagact ctacaagtta aagagcatgg tccccaacaa  68100
gactgcttct acgtcagatg ccaggcacac ttcaggggtc cccaagccac tcatgttttt  68160
tgaatgactg ccataagttc aaaaattccc acaattctct cagattcaat aactgggtat  68220
aaccactcat agaactcaag aaaatgctat cattattatt acaattttat tataaaggat  68280
```

-continued

```
acaaatcaga aggactagcc aaatgaggag acacatagag agaggactag taaaaaacag  68340
agcttctgcg tcctaccttc aaggaatcag gatgcaccac cctcccagca catcaagtgc  68400
tcatcaacca ggaagttcct ctgagctcca atgtccagag attttaggga ggattcatta  68460
cataggtatc attgattaaa tcattggcca tgtacttgaa ctcaatctcc agtgtccctc  68520
ttctccctag aggtctgaag ggttggctaa tatcatgtgg ctcaaagccc caactctaat  68580
tacctttttg gtcttttcag ggactagacc ccatcctgaa gctatctaca ggccctgcca  68640
tgagttagct cattaacata acaaagacac ttatattact cagaaaattc caacagtttt  68700
agaagctcca tgtcaggaac ctgggacata gatcaaattc tttttttttt tttttttttg  68760
gagacagggt cttgctgtgt tgcccaggct agagtgcaac gacagatcac agctcaatgc  68820
agcttcaact tcccaggctt aagtgacctt tccaccttaa ccttccaagt atctgggacc  68880
acagaaaatg gctaattatc ctggctgatt tttaaacttt tttttttttgt agggatggga  68940
tcgccctgtg ttgccaaggt tggtctcaaa ctcctgggtt caagcaatca ttctgccctg  69000
gcctctgtga tggttaatac tgagtgtcaa cttgattgga ttgaaggata caaagtatta  69060
tttttgggtg tgtctgtgag ggtgttgcca aaggagatta catttgagtc agtggactgg  69120
gaaagtccac cctttcccag tggactggga gacccaccct caatccaggt aaacacaatc  69180
taatcagctg ccagtgtggt cagaataaaa ggaggcagaa gaacagggaa acactagact  69240
ggcttagtct tccagcctac atctttctct catgctgaat gcttcctacc ctcgaacatc  69300
agcctccaag ttcttcagtt tttggactct tggaccttca accacagatt gaagactgca  69360
gtgttggctt ccctgttttt gaggttttgg gactcagact ggcttccttg ctcctcagct  69420
tgcagatggc caattgtggg actttaactt gtgatcatgt gagtcaatat tccttaataa  69480
actcagatat atatatatgt atcagacata tatatatatc ctattgtata ttatatacag  69540
atatataata tcctattata tacagatata taatatccta ttatatacag gtatatatat  69600
atatatgtat catatatata tatcctattg gttctatccc tcttgagaat cctgactaat  69660
acagcctccc aaaatgctga gattacagga gtgagccaca gccaccatgc ccagccccaa  69720
attcttaatt atacaacaat gggtccagag atcagggcct gggtaggatg cagcaataag  69780
aaaacagatg gtggatgggg acacatgttg gaagtgtggc aggacatggc tgagggaact  69840
cataggatgg tgtctatttt catggctgag tgtgaggaac agcataaggt caaaatttca  69900
ggtcaatggt gagtttttta aattgttgct gtgaacccca aaaatctgac ccaggtctca  69960
gttaatttag aaagtctatt tttccaaggt tgagaacacc cacccactca cgacaagagc  70020
atcaggaggt cctgaccaca tgtgcccaag gtggtaagag cacagcttgg ttttatatat  70080
tttagggaga cgtaagtcat caatcaatat atgtaagatg tacactggtt ctgcctagaa  70140
aggcaggaca acttgaagca gggaggggc ttccatgtca caggtaggtg agagacaaac  70200
agttgcattc tttgagtttc tgattatcct ttccaaagga ggcaatcaga tgtgcaatta  70260
tctcagtgag cagagggatg actttgaata gaaagacagg caggtttgcc ctaagaagtt  70320
cccagcttga ctttttcctt tagctttgtg atttggaggc gccaagattt attttccttt  70380
cacatttccc cccctttcttt tttaagaatc ttttaaagaa agcttttaaa aagaaaatga  70440
gtctctggtc ccaggtttca tctgaattct cgaggggagg atggtttatc ctaaacgggt  70500
ggttctgaat tttgagaaag tgcattgtac aaaagccata cgaatgagga agaattaagg  70560
gccagaacaa aacaagaaga tgagggaaag tttggaactt cttagagact ggctaaatgg  70620
ttgtgaccaa aatgctgata gtgatacgga caatgaagtc cagggtgaca aagtctcaga  70680
```

-continued

```
tggaaatggg gaatttgttg ggaactgggc aaaggtcacc cttgctatga ctcagcaaag  70740
aaattgggtg cattgtgttc atgtcctggg gatctgtgga agtttgaatg taagagtgat  70800
gacttacggt agggtatcta gtggaagaaa cctctaagca acaaagtgtg ttgcttagaa  70860
atttctttct ttcttttttt tttttttttg agctggagtt ttgctgtgtc gcccaggctg  70920
gagcgcagtg gcgcaatctt ggctcacttc aagctctgtc tcctgggttc atgccattct  70980
cctgcctcag cctcccaagt agctgggact acaggcgcct gccaccatac ctggctaatt  71040
ttttagtatt ttagtagaga cgaggtttca ccatgttagc caagatggtc tcaatcttct  71100
gacctcgtga tccacccgcc ttggcctccc aaaatgctgg ggttacaagc atgagccacc  71160
ccgcctggcc tgcttagaaa tttctaagcc aggatatggc ctgtctgctt ctaacagcct  71220
gtgctcaggg gtaaagaaat gacttaaagt tggaacctat gtttaaaatg gaagtagagt  71280
ctaaaaattt ggaaaatttg cagcctggcc ttgtggcaga gaaagaatcc aagtaggctg  71340
cagagcaatc attgctagag agattagcat gactaaaagg gagccaagtg ctaatattca  71400
agacaatgtt aaaaaggcct tgagggcatt tcagagatct atgaagcagc ccctcccatc  71460
acaggtgcag aggtttggtg cactaggccc agaggtttta tgggccanng ccagggccac  71520
actgctatgc acagctttgg gacactgctg cccgcatcca ggccactctg ctctggctcc  71580
acccttggct caaacgggcc aagatagagc ttggaccact gctcccgagg gcacaagcca  71640
taagccttgg tggtttccat gtggtgttaa gcctgcaggt gcccagaatg caagattgag  71700
ggagcttggg cacttccacc taaatttcag aggatgtgtc agaaacccta ggttcccagg  71760
cagaagcatg atacaggggc agagcccttg cagagaacct ctactagggc aatgccaaag  71820
gaaaatgtgg ggttggagtc ctcacacatg gtccccactg gggcactacc tggtgatact  71880
gtgggaatgg ggctgctgcc ctccagaccc cagaatggta gatgcactgg cagctggcac  71940
cctgagcctg gaaaagctgc aggcactcaa ctccaaccca tgagatcagc cacatgggct  72000
actcccaggg aagcccacag aggcagggct gtctaaggcc ttgggagcct acccccttgaa  72060
ccagcttgca ggacatggaa tcaaagatta tgttgcagct ttaaggctta atgttttccc  72120
tgtcaatttc aggcttgtgt gggacctgtt gctttttttt tttttttttt tttttttggt  72180
cacaggtgtt tgaaccagaa caattccatc ttgaataggg gctgggtaaa ataaggctga  72240
gacctactga gctgcattcc taggaggtta ggaattctaa gtcacaggag gagataggag  72300
gtcggcacaa gatacaggta gcgaagacct cgctgataaa ataagttgca gtaaagaagc  72360
cagccaaaac tcacaaagcc aaaatggtga tatggtttgg ctctatgtcc ccacccaaat  72420
ctcatctcaa attataattc ccataatccc cacatgttga ggggaggacc tggttggagg  72480
tgattggatt atggaggcaa tttcccccat gctgttctgg tgatactgag tgagttctca  72540
taagatctaa tggttttata agtgtttgga agttcctcct acacacatgc tcacactctc  72600
tcctgcagct ttatgaagaa ggtacttgct ttcctttctg ccatgattgt aagtttcctg  72660
aggcttccca gctatgcaga actgtgagtc aattaaaccc gttttcttta tacattacca  72720
gtcttgggca gttctttaca gcagtgtgag aactgctggc gatgagagtg acctctggtt  72780
gtcctcactg ctcattatat gctaattata atgtattagc atgccaaaag acactcccac  72840
catgacccca acagtcatgc ctgtgccggt ctcagcacca tgacagttta cagatggcat  72900
agcaacgtct aaaaggtacc ccatatggac taacaagggg aggaaccctc agctctggga  72960
agtgcctacc tcgttcccag aaagcttgtg aataatccac tgcttgttta acatataatt  73020
```

-continued

```
aagaaataac tattaagcat ccttagttca gcagcccaag ctgctgttct gcctatggag  73080
tagccattct ttattccgtt actttcttaa taaaattgct tttactttac tgtatgtact  73140
cgcctggaat tctttcttgt acgaggtcca gagccctctc ttgggtctgg atcgggaccc  73200
ctttctggta acattttgac caatttctcc cttctggaat gggaatgttt acacaatgac  73260
tgtatcactt ttgaatcttg gaagtaaata atttgttttt gactttacag cctcataggt  73320
ggaaggaact tgacttgaat ttcagatgag actttggact ttgggacttt tgggttgggg  73380
ctggaatgag ttaaaagttg gggggattat tgggaaggca cgattttatt ttgcaatatg  73440
agaagcacat gagatttggg ggaccaaggg tggaataata tggtttggat gtttgccccc  73500
tccaaatctc acattgaaat gtaatcccca gtgttgaagt gaggcctgct ggaaaatgtt  73560
tggattacaa ggctgtcgag cacattggat aagacgtgta ggnccccgca gctcgctggt  73620
taattctgtg gctcctgtga ccactattat agcaccaggt ctatgaccag gagaattaga  73680
ctggcattaa atcagaataa gagattttgc acctgcaata gaccttatga cacctaacca  73740
accccattat ttacaattaa acaggaacag agggaatact ttatccaact cacacaagct  73800
gctttcctcc cagatccatg cttttttgcg tttattattt tttagagatg gggcttcac  73860
tatgttgccc acactggact aaaactctgg gcctcaagtg attgtcctgc ctcagcctcc  73920
tgaatagctg ggactacagg ggcatgccat cacacctagt tcatttcctc tatttaaaat  73980
atacatggct taaactccaa ctgggaaccc aaaacattca tttgctaaga gtctggtgtt  74040
ctaccacctg aactaggctg gccacaggaa ttataaaagc tgagaaattc tttaataata  74100
gtaaccaggc aacaccattg aaggctcata tgtaaaaatc catgccttcc tttctcccaa  74160
tctccattcc caaacttagc cactggcttc tggctgaggc cttacgcata cctcccgggg  74220
cttgcacaca ccttcttcta cagaagacac accttgggca tatcctacag aagaccaggc  74280
ttctctctgg tccttggtag agggctactt tactgtaaca gggccagggt ggagaattct  74340
ctcctgaagc tccatcccct ctataggaaa tgtgttgaca atattcagaa gagtaggagg  74400
atcaagactt ctttgtgctc aaataccact gttctcttct ctaccctgcc ctaaccagga  74460
gcttgtcacc ccaaactctg aggtgattta tgccttaatc aagcaaactt ccctcttcag  74520
aaaagatggc tcattttccc tcaaaagttg ccaggagctg ccaagtattc tgccaattca  74580
ccctggagca caatcaacaa attcagccag aacacaacta cagctactat tagaactatt  74640
attattaata aattcctctc caaatctagc cccttgactt cggatttcac gatttctccc  74700
ttcctcctag aaacttgata agtttcccgc gcttcccttt ttctaagact acatgtttgt  74760
catcttataa agcaaagggg tgaataaatg aaccaaatca ataacttctg gaatatctgc  74820
aaacaacaat aatatcagct atgccatctt tcactatttt agccagtatc gagttgaatg  74880
aacatagaaa aatacaaaac tgaattcttc cctgtaaatt ccccgttttg acgacgcact  74940
tgtagccacg tagccacgcc tacttaagac aattacaaaa ggcgaagaag actgactcag  75000
gcttaagctg ccagccagag agggagtcat ttcattggcg tttgagtcag caaaggtatt  75060
gtcctcacat ctctggctat taaagtattt tctgttgttg tttttctctt tggctgtttt  75120
ctctcacatt gccttctcta aagctacagc ctctcctttc ttttcttgtc cctccctggt  75180
ttggtatgtg acctagaatt acagtcagat ttcagaaaat gattctctca ttttgctgat  75240
aaggactgat tcgttttact gagggacggc agaactagtt tcctatgagg gcatgggtga  75300
atacaactga ggcttctcat gggagggaat ctctactatc caaaattatt aggagaaaat  75360
tgaaaatttc caactctgtc tctctcttac ctctgtgtaa ggcaaatacc ttattcttgt  75420
```

-continued

```
ggtgtttttg taacctcttc aaactttcat tgattgaatg cctgttctgg caatacatta  75480
ggttgggcac ataaggaata ccaacataaa taaaacattc taaaagaagt ttacgatcta  75540
ataaaggaga caggtacata gcaaactaat tcaaaggagc tagaagatgg agaaaatgct  75600
gaatgtggac taagtcattc aacaaagttt tcaggaagca caaagaggag gggctcccct  75660
cacagatatc tggattagag gctggctgag ctgatggtgg ctggtgttct ctgttgcaaa  75720
agtcaagatg gccaaagttc cagacatgtt tgaagacctg aagaactgtt acaggtaagg  75780
aataagattt atctcttgtg atttaatgag ggtttcaagg ctcaccaaaa tccagctagg  75840
cataacagtg gccagcatgg gggcaggccg gcagaggttg taaagatgtg tactagtcct  75900
gaagtcagag caggttcaga gaagacccag aaaaactaag cattcagcat gttaaactga  75960
gattacattg gcagggagac cgccatttta gaaaaattat ttttgaggtc tgctgagccc  76020
tacatgaata tcagcatcaa cttagacaca gcctctgttg agatcacatg ccctgatata  76080
agaatgggtt ttactggtcc attctcagga aaacttgatc tcattcagga acaggaaatg  76140
gctccacagc aagctgggca tgtgaactca catatgcagg caaatctcac tcagatgtag  76200
aagaaaggta aatgaacaca aagataaaat tacggaacat attaaactaa catgatgttt  76260
ccattatctg tagtaaatac taacacaaac taggctgtca aaattttgcc tggatatttt  76320
actaagtata aattatgaaa tctgttttag tgaatacatg aaagtaatgt gtaacatata  76380
atctatttgg ttaaaataaa aaggaagtgc ttcaaaacct ttcttttctc taaaggagct  76440
taacattctt ccctgaactt caattaaagc tcttcaattt gttagccaag tccaattttt  76500
acagataaag cacaggtaaa gctcaaagcc tgtcttgatg actactaatt ccagattagt  76560
aagatatgaa ttactctacc tatgtgtatg tgtagaagtc cttaaatttc aaagatgaca  76620
gtaatggcca tgtgtatgtg tgtgacccac aactatcatg gtcattaaag tacattggcc  76680
agagaccaca ctgaaataac aacaattaca ttctcatcat cttattttga cagtgaaaat  76740
gaagaagaca gttcctccat tgatcatctg tctctgaatc aggtaagcaa atgactgtaa  76800
ttctcatggg actgctattc ttacacagtg gtttcttcat ccaaagagaa cagcaatgac  76860
ttgaatctta aatacttttg ttttaccctc actagaggtc cagagacctg tctttcatta  76920
taagtgagac cagctgcctc tctaaactaa tagttgatgt gcattggctt ctcccagaac  76980
agagcagaac tatcccaaat ccctgagaac tggagtctcc tggggcaggc ttcatcagga  77040
tgttagttat gccatcctga gaaaggcccc gcaggccgct tcaccaggtg tctgtctcct  77100
aatgtgatgt gttgtggttg tcttctctga caccagcatc agaggttaga gaaagtctcc  77160
aaacatgaag ctgagagaga ggaagcaagc cagttgaaag tgagaagtct acagccactc  77220
atcaatctgt gttattgtgt ttggagacca caaatagaca ctataagtac tgcctagtat  77280
gtcttcagta ctggctttaa aagctgtccc caaaggagta tttctaaaat attttgagca  77340
ttgttaagca gatttttaac ctcctgagag ggaactaatt ggaaagctac cactcactac  77400
aatcattgtt aacctattta gttacaacat ctcatttttg agcatgcaaa taaatgaaaa  77460
atcttcctaa aaaaatcatc tttttatcct ggaaggagga aggaaggtga gacaaaaggg  77520
agagagggag ggaagcctaa tgaaacacca gttacctaag accagaatgg agatcttcct  77580
cactacctct gttgaataca gcacctactg aaagaacttt cattccctga ccatgaacag  77640
cctctcagct tctgttttcc ttcctcacag aaatccttct atcatgtaag ntatggccca  77700
ctccatgaag gctgcatgga tcaatctgtg tctctgagta tctctgaaac ctctaaaaca  77760
```

-continued

```
tccaagctta ccttcaagga gagcatggtg gtagtagcaa ccaacgggaa ggttctgaag  77820
aagagacggt tgagtttaag ccaatccatc actgatgatg acctggaggc catcgccaat  77880
gactcagagg aaggtaaggg gtcaagcaca ataatatctt tcttttacag ttttaagcaa  77940
gtagggacag tagaatttag gggaaaatta aacgtggagt cagaataaca agaagacaac  78000
caagcattag tctggtaact atacagagga aaattaattt ttatccttct ccaggaggga  78060
gaaatgagca gtggcctgaa tcgagaatac ttgctcacag ccattatttc ttagccatat  78120
tgtaaaggtc gtgtgacttt tagcctttca ggagaaagca gtaataagac cacttacgag  78180
ctatgttcct ctcatactaa ctatgcctcc ttggtcatgt tacataatct tttcgtgatt  78240
cagtttcctc tactgtaaaa tggagataat cagaatcccc cactcattgg attgttgtaa  78300
agattaagag tctcaggctt tacagactga gctagctggg ccctcctgac tgttataaag  78360
attaaatgag tcaacatccc ctaacttctg gactagaata atgtctggta caaagtaagc  78420
acccaataaa tgttagctat tactatcatt attattatta ttttattttt tttttttgag  78480
atggagtctc actctgttgc ccaggctgga gtgcagtggc gcaatcttgg ctcactgcaa  78540
gctctgcctc ctgggttcac gccattttcc tgcctcagcc tcccgagtag ctgggacaac  78600
aggcatgtgc caccatgccc agctaatttt tttgtatttt tagtagagat ggggtttcac  78660
tgtgttagcc aggatggtct ctatttcctg atctcatgat ccgcctgcct tggcctccca  78720
aagtgctggg attacaggcg tgagccaccg cgcccggcct attattatta ttattactac  78780
tactactacc tatatgaata ctaccagcaa tactaattta ttaatgactg gattatgtct  78840
aaacctcaca agaatcctac cttctcattt tacataaaag gaaactaagc tcattgagat  78900
aggtaaactg cccaatggca tacatctgta agtgggagag cctcaaatct aattcagttc  78960
tacctgagta aaaaaatcat ggtttctcct ccatcccttt actgtacaag cctccacatg  79020
aactataaac ccaatattcc tgtttttaag ataataccta agcaataacg catgttcacc  79080
tagaaggttt taaaatgtaa cacaatataa gaaaataaaa atcactcata tcgtcagtga  79140
gagtttacta ctgccagcac tatggtatgt ttccttaaaa tctttgctat acacatacct  79200
acatgtgaac aaatatgtct aacatcaaga ccacactatt tacaacttta tatccagctt  79260
ttctgactta gcaatgtatt gatgacatta tgcatgctta gacctccgta ttctattctc  79320
ggttataaca caatcacagt gatttgtcat atctttccag gatttgttaa tttcacttct  79380
tcagctgttt ccccccttgtt ggctggaact gattttctat cttctgggag aatcttcagc  79440
aagccaactc aggatttgtt gggtgcattt tgtcaagtct aggacccagg ctctgggtga  79500
ctgatttcct ctaattaccg agcaatgtaa aatgaggaag tctgattgtg taaaggtgtt  79560
aaacttttgt gtgacggcaa aactttaata ccatgaatag agattccaga attttccaac  79620
ttctaacggg attcctttca ctccctgaca ttagaatgtt agaaaatcta ccacaaaaca  79680
tctgtgaggc tatcctacaa ggcccgtttt tcaaaatagg tttttacaag gattgctatt  79740
tgggatgata gtttcagaaa ggcgctatca aagttaattg atgatgtgtg caagctgaaa  79800
gttatatgtt agaactagca gtgatttcaa aaatatccct tttaggcttt ttgctaatat  79860
atctgctcat tttcaaagtt cccaatatta taaaactttt taaagcagaa agaagaaccc  79920
tccatttctg ctggcccctt ccctgttcaa ctaaaaagta ttttcccagg caatgctatc  79980
ccaggactca cactccatcc atccatcacc taccataagt tctttgaagg gctcattctg  80040
agcgcttcct gagtgcctgg gatctgttat ttctctccat ttctgctgct gcatggtagt  80100
ccaagtcctc ctcccttttc ccctaggcca tttgaatcat ctgctaattg gttttcctga  80160
```

-continued

```
ttgccacgga aacttcctcc atcccttcct cacatatcag ccacagaagt atctccaaaa  80220
agcaaatctg gtgacatgaa gcccttgcac aaaacccatt cattactggt tccacacctc  80280
ctttgtggat aagttcaagc tcctgagtgt ggcaagcagg gcccacctgg aatcccctgc  80340
cctcctctcc tatcccacgc atcaatcttt cctgtctatt tgcagttcct tgaatgtgat  80400
attctttcta gtctctgtgc ttttgcataa cctgttcttc ctgactggaa actccttctc  80460
ctccttgtag tttggctaat ttctagtctt tcaagactca gctcatgctt cacccccctct  80520
ataacaagtc ctttcccaag ctgggtggtg gatgctcctc tgtgctgtgt gagtcttgaa  80580
catcctcagc aaacctcagc tttgtttgct tgtctccctt gctgtcaatg cacctgattc  80640
agggctggca tatactgttc acctccatga ctggctcatg gtggtgctcc gtgaatatca  80700
tccacccaaa cggatgagag ctaccatgcc atcacttgtg acttccatct ggagctaacc  80760
tcccccgaca ggaaagcgtt tccttaggaa agaatatctt tgggttaaat agaagtagag  80820
actcaccaga agcactatgt ccagctcaga atgaactgct cagtaagcag ccttgtcaat  80880
gaggaggcag caggccagcc ccagaggcct caaagtggga gagtagagaa gcgcagttcc  80940
tgccacaaag gcacagtgga caccttgctc ccctggctgg ctggaagcag atggtgtcca  81000
cctgcttcca tgggaattct gcacctttaa taaagtttta tgggacagga aggtgactgg  81060
cattgacatt gtaacgagga atgggtggtg ccacctttgc tgtgtcttac cagaaatacc  81120
tgtggcaggt aaatttctag agagaccctc ccatttctcc catatagcaa ttttgaaatg  81180
tttcctgagg gctttccaaa ttcatctggg aacataggag ttccagaaag atgaaatcaa  81240
aggtgatggt atgccaaaga aagtagcttt tagaatgact tacattagcc attcatccat  81300
tcagcacacc aggcattcag tttgaggggt gtgtgtgtgt gtgtgcgcgc gcgcgtgcgt  81360
gcatgagtgc atgcgcgcgc gtgtacatag gggaagggaa acaaaacaaa agtacacaag  81420
acatgatagt tgtcctcaag gagtttttgc aaatgttcac aatttaagag aatatgctgt  81480
gctgtggctg gtgtataaac caactgctag ggagaggcct tccacacaca cttggggcaa  81540
atgcgacctc taggactgcc agtggaatct gggcatgctg tttgtggtcg ataaaccctg  81600
gtcccttgat cagggaccta tgtttacttt tcctctccct ggaagtcttc attagtgggc  81660
atccagaagg tcttgcacag ggcagaggga ggcacaaaga caagagtttg aaaccagcct  81720
ggacaacaaa atgagtttct atctttacaa aaaaaatttt taaaaaatta gccaggtagg  81780
attgcatgtg cctgtagtcc cagctattca ggaagctgag gcaggaggat tccctgagac  81840
caggaatttt gaggctgcag tgagctatta agttggcgca aaagtaatcg tggtttttat  81900
cattaaaagt aatggcaaaa cttttaatga caaaaaccgt gattactttt gcaccaattt  81960
aatatgattg cacgactgca ctgtgctcca gcctgggcaa cagagtggga ccctgtcaca  82020
aaataataaa taaataaaat gtaaacatgt aaaaaaaacc ccaaaaacaa aaaaaatggg  82080
tgttgagacc cctgaattga ggaataatag gaaggagtgt gattctgtgt gtgcatgcat  82140
gggtgtgcac cctcagtgcc tgggtggctt accctgggct agttcaggtg gcaaatggtt  82200
ttcctccagc tgggctacca ccatcttccc ccagggcctg tccatgtatt tggtggcaag  82260
atacctatgg actagagtcc ctcctcagag gaaaggctcc tcccatttct ctggctttca  82320
ggtagtagtc catgacttca acaggtcccc actgcaatgt tatgggttag tttaggtggg  82380
gtctcctctg agagcctccc atagcccaaa aggccctgtc ctagctggca ctgcatctcc  82440
ctcttcccag ctctcagcct ttctctttgc tcatcccact ccgcacaggc tttctgcctg  82500
```

-continued

```
atccttggat gtgtcaatcc tgcccctaag ggatgcaagg caatttgtcc ttttattatt  82560
aagatctctc ctgaggccac gtgtggtggc tcacacctgt agtcctagaa ctttggtagg  82620
ccaaggtagg agaattgctt gagctcagga gttccaggct gtagtgaacc atgattgcac  82680
cattgcattc cagcctgtgt gacacagcga gaccctgtct tttttctttt tttttttgag  82740
acagggtctc gctctgtcat ccaggctaga gtgcagcggt gtttttctgc tcactgcagc  82800
ctcaacctgc acattttttg tagagacggt gtcttgctat gttgcccaga gtggcctcaa  82860
actcctgggc tcaagagatc tttccacctc agccttccaa agtgctggga ctacaggcgt  82920
gagctaccgc gcccaacaaa gaccctgtct taaaaagaaa acaaaaataa acaactccct  82980
caagtctttt tttttttttt gagacggagt ctcgctctgt cgcccaggct ggagggcagt  83040
ggcgcaatct tggctcactg caagctctgc ctcccgggtt cacgccattc tcttgcctca  83100
gcctcccgag tagctgggac tacaggtgcc cgccaccacg cctggctaat attttgtatt  83160
tttagtagag atggggtttc actgcgttag ccaggatggt cttgatctcc tcaccttgtg  83220
atccgcccgc ctcggcctcc caaagtgctg ggattacagg catgagccac cgcgcccagc  83280
cagacctctt gagtcttaaa ctcctctgta gttccagcca ccctttagca catgactctg  83340
ttaattttgt tctcactgtc tgaaatcatc tcctgtccac tcttgactga caggtctctg  83400
cactagccca ctgcttaatc agagtaggtc cctgtcaact tattcatatt gtgtccccat  83460
gccagtgtgg atgattaaaa ttgttgagtg gaggctgatc agatgagcca tctccttcca  83520
agtcctcact tgctggctcc tgtcttagtt ttagtcccca ttcttcaaag aacgtgagcc  83580
ctggaaagta ttttagtcat ttagttcagt gcctttggat gggaggatca catccctggg  83640
tcccgtcctg cagactgttt tgctctagct gactaggcag gattccctgc cttctctcac  83700
ttcggcatgg gacttccttc tgaaattgct gctcagtcaa gagaatgacc ttccccaaca  83760
taatcctact ccacagggac ttaaaggtgt gtcagagatc tcttgctcat ctttctggcc  83820
aggtgccaac gtcagtttat agccaaggga caagactagt tagcagatca ggcaggtctt  83880
agaccccagc gtaagtgcca gacttctagc tgcagttgtt cctgcccaca ctgggcgttc  83940
aggtggagag agggcatggc actacactga gctctcggcg aaacccagga ctctgaaatc  84000
tcggtgtcag ccacaggcca ctcttttcag caggacttca gtcagtcctg tcactaggct  84060
gtcgagcaca tggtaggctt taccccaagg agtgtgcttg ctgatagcat gtgtganggg  84120
acgaggagta aataatttct gccttcaaga aattgcaaac tagtaatgga gataaaatca  84180
acagaggaac aattagagta taaggtaaaa tctaagggcc ataagagagg agaagaagta  84240
tgggagttca gaggtagggg gtaaatgagg ggagtaggtg ggtagaaaag gttaaaagta  84300
aataatgatg ggaaggaaga caaaaagacg acaggggtgc caaaggactc ttaacctcat  84360
ctgaacggag ttgccctgtt ttgctctctg atgctcatgt atctatcctt agagacagct  84420
tggcgggcaa tgtagagcgt aggggctgac ataggggggtt ggagtcccac ctccgtgact  84480
tctagcaaat tagcaaactt tgctgctgct aagcctataa ggcggacaga aatgccatct  84540
ttaaagcttg ttatgtaaag tgcctaggac ctcgtaggca tcaacaggaa taatggatga  84600
aacaaaacaa cggtgcgtat cttggagaaa gtggcatctg agcaggagta ttttgaaagg  84660
taggaaaggg ctccaagcac atctaagaga ttagggaacg cagaagcctt agccctgggt  84720
gcagatttaa ccaatcaact tctaaccacc gcaggctgag aggtgtggag tgagagcccc  84780
gccagaggca ggagacccgg gcttcggcca gaccccgcct cctggtacag aggaccacgc  84840
ccggctctgc ctggagccaa atgtggatca aaacagcgcg cagcttccca ctgctggtga  84900
```

-continued aaacccgagc aaggggcctc agtttcttta tccggaacgt ggtgacaatg acatctcttt 84960
gcaaggctgc tgcagggctt tctggaaata cgcccgtgag gtatctgggc ctgcgcacag 85020
cctcccccgc ccaggaccca gacgtctacc tgggggtccc gtctgcgctc ccgggatgga 85080
aaacgcccag gggaaactta ggcaggcgag cggacgggca cctcccgcgg gacgaactca 85140
ctcggtggcc tcctacttcc ccggccgtgt tccaacgcct gagaataacg ggaacagcgg 85200
tcgtactcac cgacagcggc agcagcggta ggcccgggcc ccaccatgac tcttcagtga 85260
cagtttttct tcaaacgccg cgcctgtagc caggaccggc gtgccgcgcg tccacgcgtc 85320
ctcattggct cctgcgggtt tgaaactcgc tagtcgtcag cacgggaggg cgggacaaca 85380
ggcaataggc tctttgcggt tggctctggc cttgagaacc cgaccttggg gccctttgat 85440
tggaagaacg tgcagcgcac ctcggcattg agggcggctt cctcggggcg cggcgccgcc 85500
cgcctctgag tgcgcctgtg agtgcgcctc cgagtgggcg tgggaccctc cgtgggggcc 85560
tcagccgggc tggtggttgg ggggcggtta cgctgaatcc agctggggtt ggcgcgccgg 85620
gagtccctgg gcggagagac agggcggtcc tcccaggatg ctggggccgc tacctgattc 85680
tgtcctttca aagtctcaga ctcacaggag ctgtgaaaaa ataatattat aaagaggaca 85740
tatgggtctt atgcatctaa aggctcctag ttcttagtac tgcagggtgg ctcgtttaat 85800
tgtggtaaaa tatgcataac atcacatata ccattttaac cattttaaag tgttaaattt 85860
ttcaaaaatg tgcagtttag tggtattaag taccctcaca ttgtggcaca gccaccacta 85920
ctgtcctttc cagaactttt tcatcttccc aaatgaaacc ctgtacccgt cactaactcc 85980
gcactcctcc ctcccccagc cccaggcaat caccattcta gtttctgtct ctatggattt 86040
gacaactgta ggtgccatat aagtagaatc atgcagtatt tgttctgtga ctggcttgtt 86100
tcacttagca taaagtattc aaggttcatc catgtgtagc atgtgtcaga atttcctttc 86160
cttttaaggg ggaatagcat ttcgttgtgt ggagatgcca cattttgctt cttggtccat 86220
ccctctccgg acacttgagt tgcttccact ttttggctat tgtgaataat aatatgaaca 86280
tgaatgcaca aataactctt tgagactctc cttttcattc ttttgggtat ataccacgaa 86340
gtggtattgt tggatcaaac ggcaattcta tttttaattt tttgagaaac tgccttactc 86400
ctctcacggt gatctcttgt tcaaggtata ttttcgattt cacctgatca gctgactata 86460
aggccataag gctaacggag aaacgcaggc ctagtttctc ctagttacta ggagatcgca 86520
ggcctcgttg tcctgaatcc ctagacacac ttcattcccc ttgttttaat cctaaatttt 86580
ttttcttttg aagtttgtcc tgtttcatct attctccagt ttcttaaaga ggtctggaaa 86640
atgcttttgg ctccttgtgt atgaaggttc ctcttccatg gatgctggag aagtcgtgtg 86700
tggaggggca gtcatatctg ggcacctgtt ggccaggttc agcttaccag ttgggtactc 86760
agcagggcat gaagccactg cagcagccct tctctttagc cgtaaatagg gagtttggaa 86820
gagagccagg gtttctggat ttatgcattt tgatattttc aatagtgtat taaatgttta 86880
aaataggaaa actgatcatt atttttgtta atgactgaga aagggactcc ttcaccaaca 86940
gtttcagaaa agtgaaggcg gttttgtttt ggtctttgta gaatctaggt ggttgaatgc 87000
atgtcagttg tagaagtcac cttgcctgat atcccacgca gtgctggagt attccacaga 87060
ccccatgtag gtactgcacc tttgcaggta tactgctggt gttggtgagc tgccttacct 87120
gtcctgttat tggagacccc tgcttattag gaaacttaaa atgaactcaa atgagcttcc 87180
ttgcttactg gtcctagtcc tttggagcaa cataggccag ttctgcctcg tttttttcca 87240

-continued

```
tcctttgggt atttgacggt ctattttgta ggacacaaaa tgtgggaaaa tagctaggca  87300
ggtttaaaaa ttctcaactc taccaagcat ggtggcttat gtctgtaatc aatcccagca  87360
ctttgtgaag ctgaggcaag aggattgctt gagcctagga gtttgagacc agactgggca  87420
acatagcaag acctcgtttc ttaaaaaaaa aaaaaaaatt acaaaaatta accaggcatg  87480
gtggcacaca cctgtagtcc cttctactca ggaggctgag gtgggaggat cacttgagcc  87540
caaaagttga aggatgcagt gcactgtggt catgccaccg cactccagca tgggaggcag  87600
agcaagaccc tgtctccaaa taaatacata aattaaattc ttaactcatt catcaaagta  87660
tccactgtag ctttccatca tcctggtgtt gttttttttta gaaggatctg gctccattgc  87720
ccggctagag tgcagtggca tgatctcagc tcactgcagc ccccacctct ctggcttaag  87780
cgatcaccca cttcagtcac ccatctgggt aatttttgta tttttgtag agatggggtt  87840
ttgccatgtt gccccaggtt ggtcttgaac tcctggctca agcgatccat ctgcctccat  87900
ctcctaaagt gttgggatta caggtgtgag ccaccacacc aggacaatcc tggtggcttt  87960
taacggtttt ccattgctct caggctaatg acctataagc cctgcgggc ttggcctttt  88020
actccctcag cattagccac ctcccttagc cttagcccac actactctcc ccttgctcag  88080
tgttatccag acactttgtt ttttcctttc catactcctc tctgtctggg aatccaacct  88140
ttctttctca tttctctagt tgattattat tatttttact ctagcagcct tattgagata  88200
tttacatacc gtacgattct cccacttaca gtgtacaatt caattttcta acattttcat  88260
cacccctaa agaaaccta tactcattag cagtcactcc ccattctccc ctcctctcag  88320
cccctagaaa ccatgaatct actatccatc tctatagatt tgccttctgg acatttcata  88380
tgtatgaaat tatgcaattt gtggtctctg atgggcttct tttgttacca aaatatcatg  88440
ggtttgatct aggtcctgct gctcgctgca cagaaagcca gccactgaga tgacaagtat  88500
tgccaaggaa gaaggcttta gtcaggtgct gcagctgagg agatgggggc tcaatctcaa  88560
atccatctcg ctgacctaaa accaggggtt tggatagcag ggaagaaatg taacaatgcg  88620
taagaaaaca ggaaccaggg aggggcaagg aagcaatcct gatgaatgag tggtccaaag  88680
tctcattgcc tggatgtggt gatctggcga gtttcagttc tttgatactt tttttgagag  88740
gcctgaagtc ttttccccag gaaggaactc aaacaaaaca aatacaagct tccagcttta  88800
agaccagaag cgtcaatttc tatgtttatc cgaaagaaca gtctatggga ctattggtta  88860
agtttcactt tcacttagta tgctgttttc aaggtttatc cacatagcat gtgtcagtac  88920
ttcattcttt tatgactggg tattctattg tgcggatata caatatttta tttgccattc  88980
atcagttgat ggacatctag gttctttcca ctttttggct attatgaata atgctgttat  89040
gaactttcat gtataagttt ttgtgtagac atatgttttc aacactcatg ggtatatacc  89100
taatgagagg aattactgtg tcatacgata attctatctt taaccatttg aggaactgcc  89160
agactgtttt ccaaagcagc tgcagcattt tacattccta ccagcagtgt atgaaagttc  89220
cagtttcttt acatcctcaa caacacttgt tattgtccat cttttaaatt acaaccatcc  89280
tagtggttgt gaaatggtat cacattgtgg tttttatttg tatttccttg atgactaatg  89340
atgttaagca tctttttatg tgtttactgg ccatttgtat atctctattc agagtctttg  89400
ccaattttta aattgggtca gttgtcttct tcctttttttt ttgagatgga gcctcactct  89460
gtttcccagc tggaatacag tggtgtgatc tcagctcact gcaacttcca cctcctgtgt  89520
tcaagtgatt ctggtgcctc agcctcccaa gtagctggga ttacacgcac ctgccaccat  89580
tcccagctaa tttttttctt tgtattttga gtagagacgg ggtttcacca tgttggccag  89640
```

-continued gctagtctct ttgttgactc ttaaccatcc ttcagtctca gacaaaacat ccctttctca 89700
aggattgtga ttagcttgat tatttgctta tctttctccc tgctagtctg taaactgagg 89760
gtaggccact atattcattg ttcttggcac caaatagaaa ctaaattaat gtcttttgaa 89820
tgaatagggc tttctccttt taaagatccc ttcaatacag taaccacact atatataagt 89880
agccacaagc ccattcaata atactactag tncttgcgcc aaaccggctc agcgttacta 89940
tactggtctc aaactcctgg gctcaagcga tctgcccccc tcggcttccc aaagtgttgg 90000
gattataggc gtgagccacg gtgcctggcc tcaaataact atttaagtga aacaaaacta 90060
gtatggcact aatgaaaaat gtataaatcc ataatcgcag agggatttca acttacttct 90120
ttcgattatg taaaggtcaa acagacaaaa gacaatgaca aaacttaatg caatgaacac 90180
ttttgattta atgaacatat attggatatg tacccaagaa ttagagaata catactagtt 90240
ttgagtttat gcagaacatt tacaaaaatt tagtggaagc ctaaattata aaaagttgct 90300
gtcacgtaga ataacacaca aacccctgag tccggaattc aaagccctcc acactctcct 90360
ctacctttgc atctttatcc tccaccacac tgcagtgcat actctgggct actactcact 90420
gttcttgatt caaattccat gttctgtcag ctcaaatcat tctctctgcc tggaataact 90480
acttcataca tattctgcta ttgaattctt gtcttagcac cccatctact ccaagacgat 90540
gtccagttgg ggttactccc tgtcccattt tctttgatta cacttttttt ttctacttcc 90600
attatattat tgatcacatc tgtgccacag tttttgactt tgtgtctgct tttactcttt 90660
tctagaccct gatagctcct gaagggttgg gtcatttctt ttttatttgc tcattcctca 90720
tggcacagtg agtgcttaat aaatggctat tgactgaaat taaactgtat ctaaatggac 90780
atattccact tctgggccat tcattctttc tttctattgg aaccaggaga tggggaacca 90840
taacaaaggt aaggttgtgc catgtgaaag aacatggaac cttcccctga gggccaaaaa 90900
agagcaggga aaggtgcaaa gacaaaatct tccattttta aacaatgtaa gaatgtggtc 90960
cacctcatgc tcaggtggga ctttatcatg acgttatttt tggggactta tagctgcatc 91020
atttacccca tatacattta cctttagtgt agggaactga ggacaggaat tttgttgatg 91080
cagactcttg ctaatgaggc taacacttgg agaattttta tcatgcattc aagaagcttg 91140
ttttacattt cttcattaat actttagttg gtggtttagc tttagttgta ggcttatcag 91200
atatttggag atatcttcat aaacgatggc tttggtttta gaagagttat tctgaagcta 91260
ctatttctgg caataatcaa acagcatggc catttgtttt gtaaggcctt tcctagaata 91320
tgacggtaaa atctacgtgt ggaaaaatgc ttattcttct gtcctctata aatgtgaatc 91380
tagtttgtct tcaaaatgaa atcaagtgat taaaatgtag ttttctaaga agataaatgg 91440
agcaaagcac tctgtgtttc acagtgttgg aaatcactca tccctcataa aactgtccca 91500
actgatcctg actcacatga atgaattaaa ataagagtta ataacatcaa tttacatttt 91560
taaagacact ttcccatgtt ttagactatt ggttggaaaa gctggtaggt gtacaatttg 91620
tggagagttg gctgtttttg tctgtcgttg tttgacgtat ttcaaagcca tatctaattt 91680
tgttgcagaa tggtctgaat tctacaaaaa tgttgagttg tgtagtgtgg agaagtacgg 91740
agccatttac tgaaaggctg gggggaaatg acgagaccct gagataaggc agtagtggtg 91800
cgaacagagt ggaagggagg tagttgagat atgttcagag tagaatcaga atggacatag 91860
tgaacaactg gatgcaggtg gggctgaggg aagcaaagtt gaggataatt ctgagacttc 91920
taggttgatc cactgaagtt acattattca acaccacaag gaaactaggg gaatgagaag 91980

-continued

```
gcatactggt ttgctttgga gtggaagggc agtgatgtaa gaggagttaa tgagttaaag  92040
tttggatatg cctgaacttc aatttgatat gtgcatctga tatacccttg gggtgaccct  92100
ccaggcaatg gttgaacatg tgtatttctt agtaactgat aggcatcaca gactcacatc  92160
agtaaggaag caacagcaaa cttgattgga cgatatacct ggaactcagt accctatgac  92220
tggagcaagt ctctgtcagt gaaatgagga taagaagaat cttgaccttg tggaatatgt  92280
tgttaggaat atatgtgatg aacaacatag gatacttcct acagggctcc acatgtagta  92340
agggctttat aaatgcttga taaatattat tgttgtaatt tatttccaaa gtaagatgcc  92400
actggaggaa tctttggaac ccaaattaat aacaaatagg actggatgca atggctcaca  92460
cctgtaatcc cagcactttg gaaggccaag gcaggaggat ctcttgagcc cagaaattca  92520
agaccagcct gggtgacaca gggagacctt gtatctatga agaattaaaa aaaattaacc  92580
agatgtggtg gtgcacgcct atagtccctg ctgcttgaga ggctgaggtg ggaggattgc  92640
ttgagcccat gaggttgagg ctgcagtgag ccataattgt gccaccacac tccagactgg  92700
gtgacagagt gagaccctat ctcaaataaa taaataaata aataaataaa taagtacaaa  92760
ccagcaaaca ctaatccttt ctagagatta ttgaactctg gagggcagat ctgaatggag  92820
ccagcagagg gacctatgga gatcagcctg gccctggaca gcaccaggca atggggttgc  92880
tagagaggta atggggttga acagggttta agccatgagg tctcaagaat ccgtgaagac  92940
tcagactaat tttttttttt ttgcatgagg attaggtgtt cctaggaatt tcaatgagag  93000
cagggttaat gaaggaatgc agggtaggag agctgaggga aggcatctga gagagcctgg  93060
cttatgaatg gctgcgtcag tatggctcac ctgctttcct tgtatctact tagcagatga  93120
tcccacccca ggcctccagg gccaaggtca tttccacata gtcatgggcc cttgagggcc  93180
tggagcagtg taaggaagac agagtcttaa gaaattgcat taacagtcat ggtgcttggc  93240
aagtgtcgtc atcctatgcc aagcctgatc tgaaggggtg catgctcata ggtagctgct  93300
gcccaagatt acagcagctt cttcaatccc agatccatgc tctcctatat tcatttttcc  93360
aggggttcct gtccttcgac agtgatgaga tgcagaatga cttattgagt tattctcctg  93420
atagttgcca acttttccaa atgacaatgg ggcatggagc ttgagagtgg aaatgaggcc  93480
ctagggatag cgtgcttagg aaaacactcc cagcctgatg taattctggg ggtacaatgg  93540
cattttcatc atcaagactg atgtaaaggg tgactagcag tgagttgggg gtgactcgca  93600
ctggggctag gtttctgatt ctgcctaatc cagacagagc agaagcacta gtgggctggt  93660
agagggcctc cagggcctca cttaatgtcc tggaaaaaca gctccagatt gttggttcac  93720
gttctgagga caagcttggg tactacagga tagagagagt ggtgggagat gccgtggcct  93780
gccctgctga tgcctgccct gccattcctg cgtgtgatgt ctctggggca tcttgccttc  93840
cctgcccaga cctgtagttc agctgagggc atgtggaggc caaatggctt cttagagtgt  93900
tactttcctt gaacagctct gctgggagaa ctggaggagc tagctagtca cggtaactgc  93960
agcagtcaaa ggatcgtccc ggtggaggtg gggtggaaag gtagagaaag agaacatata  94020
gcgttttcct tggagatgtg tgggcatgtc atagaggaaa tacccaattc ctgagccttg  94080
agccctccag gaaaccttgg aatattaggt tagtcatccc caaggaagtc taagaattct  94140
ggtctcaccc atctccttta attcccacaa tgatcctaca tgatattaag gaacacgggc  94200
cagtaaccct ccaagcaatg gatgtggtgg tgaagtttga cctcatgatg gagcggaggt  94260
tggtttgaaa cctaagaatt taatttattg tttcaaactg ttctccactc agcgttatta  94320
aagcatacat aattgacaca taaaaattgt atatgtctac ggtgtacaat gtgatgtttc  94380
```

-continued gatctatgta tacattgtga aatgattaca acaagctaaa taacataccc attcatcgtg 94440
tttcaaagga attaaactca agcacaaaag agaggtgctg ttgaagagta gggctgctct 94500
atctaagtag tatgtctggg gttgtcctgg atcagggtcc ttttgtgcta gtaataaacc 94560
agcccttctg ggctgctcc actttcccca cattttcttc tggagcctcc ctaagaatta 94620
ggacatggcc actttctctg cataggcttc ctacttcaac aaggacaggg cttgtgctgc 94680
cccatgccac ttgagtgtcc ctacagcaca gagctgagtg cacactggct gagtgaggaa 94740
atcccccaga ttaatcttgg ttctaagcat catggctgta tttcacacgt atatgaatta 94800
caaattacag catagtcgaa taaggatttt tgtgctacaa ctggaatccc agattatgca 94860
aattggatag tataatattg aaattcctag gactttttat tagttttaaa aaattataca 94920
agcttagagt aagaaattaa acagtgcaaa agaattcact gtgaaaagta aaatgctctg 94980
tctctgctga gagacagata ttgcagccca gatactactg ggtcaatag tttcctttaa 95040
gcatgccatt ttgatggttt atgggactta cagctcaaga agcttgacac tagggttgat 95100
ctcagaaaat cattgttgca ggtattagat atgaccgtct cataaagata cacacacaga 95160
cacagcgatt ggagatattc actggggctt atgggctgct tgtcctttct gctctgtgcc 95220
taagttgggc tcagagtagc ctggcatcgg ctgtggggag aatgctggca tggggttagc 95280
aggagcccac ttaacatgtc ctaagccacc tggaagagtc cttcaaggag accagactcc 95340
agaggcccta aggaaggaag gacttttgcc cgtttttagg tattctagtc ccagagttta 95400
gggaggaatg gtttggcttt gggtcgtgtg ccccttacc gagtgggatg ggatgtgccc 95460
atgagctgtt gagctggctc ttggagaaga cagcaaaagc gggaataaga ggtcaggaag 95520
ctgtgtggtt gtaggaaatc ccagcagagg gcctgggggt caaaagtggt catggtagtg 95580
acggtggagg ctgaggtggt agaaaatcag aggacaaacc ccatgggctg ctggtgatct 95640
gaccgagctc ctatgctctc ctggttcatt ttaggctctg tagcagcaga tgattggctg 95700
gtgtgagagc agtgcacctg ccatatcagg caatccaaga caagtccaag ctacgctggg 95760
aggaaacctg aaggcagcag caggtagact ggctgaagac agacaggcag gcaacttgtc 95820
aatcagattt gtgtttttaa ggacttttaa ctggggagcc ctccgggaca gatcagatga 95880
gagtgaaatg tgctccgcct tagccggccg ttcgcaattc tgtaaaaggg agagtggttt 95940
tatttatttt taaacatagt caagctgcta aagtatatga tatgtataga tagagtataa 96000
ttaaatactt tcaactacag acaaaatcag gagaatggaa ttaaaaaaca atttacaaat 96060
gggtaatggc agcattgggt tgcgcccacc cacgagaagg cagacaccaa gattctaaga 96120
tcacacgtgg ccagcacttc agacttcaaa tagaattcgt gattatgcat tatttttctc 96180
ggaaagtttt cacttcacta tatgctactt gacacttgct ttcctaagac atccctctat 96240
ttttgagatg actaactcag caattcattt ctctcacgca taagctgtca ctcaacccaa 96300
acccaccaag cctgcattct accctcaata aggtcttggt gtgtaaactg acccacttca 96360
cctagttcct tagccctctc ttgaccagac atgactcttt cataagctag acctataaag 96420
tcagggctct taagtagctg atctctgata gtgccaagtg tcccccactg ttcacatttt 96480
ccactccagc ttctaacagg tgatagactg ctttttgggg gtaggggcac caaaacatat 96540
agacctcatg tttggatgta gacactccag tttctttaaa ttacaactac atattaataa 96600
tgacttccaa gtgtacattt cagtccagat ctctccctgg atccccaaac tttgtaaaac 96660
ccaccgccta gttgatatct tttgatgtct gacaggcatt tcaaatttaa tactgtcaca 96720

-continued aacaaagtta ttgattttca tctctgcatc tgttacaaat ttttcttact ttggtaaata 96780
gcaccccagg ctgtgtcact gccaagaact ttccacagct cttggaataa aattcaaaat 96840
attttccaag gcagaaaggc acagtgtaat ctggctcctg cctacctctc caacctcgta 96900
tcacactagt ctccctgtca ctcacccccct ccaggagctc aggtatcctt aaagtttctt 96960
ttcttttttt tttttttttt ttttttgaaa cagttttgct ctgttgccca ggctggagtg 97020
aagtggcatg atctcaggtc actgcaacct ccgcctcctg ggttcaagtg attcttgtgc 97080
ctcagcctcc caagtagctg caattacagg cgcgtgccac cacacccggc taatttttgt 97140
atttttagta gagatggggt ttcacaatgt tggctaaacc ggtctcaaac tcctgacctc 97200
aagtgatctg accacttcag cctcccaagg tgctgggatt acaggcgtga accattgtac 97260
cctgcctcct tgaagtttct tgatccagac tcattcctgc cttaaggtct tgcatcttca 97320
gtcctcccct caaatgacac ctccatgaag acgcaattac ctgtaattac cgtgtcttat 97380
ttagtcaatg tgttggtttt ctgtctcctc cactacagtg taagctctat gaaggcagaa 97440
accttggcag tccagttccc agcacagtgc ctagcacaca taggtattta ataacacaca 97500
gtaaaattca ccttttagtg tgcaattctg agttttgaca aatgcatcaa gtcatttaag 97560
tctgactatt atcaagctat aagatggttg caacactatc actaattccc tcatgctcct 97620
tggtagtcag tctcacccct aacgcccccc tcctggcaat cactgatccg ttttttgtct 97680
ttatagtttt ggtttttcca gaatgccaat aactaagttt tgaatgaatg aatgctatta 97740
actctcattt ctgactccag agcaacatcc atgcaatatt tattatttca gccccaaata 97800 ctgcccccctc accttcactc caaccaccta cttgatgata caaggtgaga catttggcat 97860
gtgcttcctc catgttccta gcattttccc tatctcctta gccttccttc taatcataaa 97920
cgaagagtga actttccctt tctaaaggca acttactcct aggacctcga tgccataatt 97980
ttgtttctct agtactttct atatatacac caaacaatta gctccagaaa ggtaaagact 98040
cactgtgtgc tcatcactgt gtctcctagc gcctggcaca ctgcaggtgc tgaagaaaca 98100
cctacagaat gagtgaatga atctctccct ctctagactc cttctctttt gtaatcaaac 98160
atgttcaacc tgcaacacag tcttatgacc aatcctctgt tgtctgacct aggctgagct 98220
ccagggctgg gaccctgact tccttattca ccacctcaag gtctctgcac tcacttctct 98280
ttctgctcag gattgttttt cttcttgtca ccagtctttt ctcagactta ggtctcagct 98340
cagacattgc tgttgaaagt acttctactg atccttttat ctaaagcagc cattccagcc 98400
ctactctctt gatcatagca ccctgaatta agttgtttac ttactgtctc ttcaggaggg 98460
caaggagctt ggtggtggtg ttcagggctg taccaagctg taccttgctt caccctgcta 98520
cactttttag caaccatcta attttacatg ctcccttcac tcgtcagaaa tttccttatt 98580
ttctacttca agcaggtata catatgtgct tctcctggga ggctcaccca cttcatgaga 98640
ctacatttgg tcctgggtag aaagtgtaca aaatccactg gctcagtttt aatcaatgta 98700
tgttaatatt aaccaacctg agatcttgat ttccacgcct ggctaatttt gtatttttag 98760
taaaaacagg gtttctccat gttggtcagg ctggtctcga actcccgacc tcaggtgatc 98820
cgctcacctc ggcctcccaa agtgctggga ctacaggcat gagccagcgt gcccggccta 98880
agatcttgat ttctaccatc tgaactctgt atttgaactg actgctcctg cttgagctta 98940
ctggccaaaa cttggcccac tcagactcac ggaagtttct ggttcttccc tggtaacttt 99000
tctgaactta accactggtt tgcttgacaa gagattacca tcttctcact tcctagctat 99060
gtgaactcac ttatctgctc tattgctgtt cagtctagca cggcacttat tgaacgagtg 99120

-continued

```
tctacatctg cacccctac ttcttactca tccattctgt ttcaatttct taaaaagaaa  99180
aaaaaaaagc tattgtaaac atacgattac agaaaatgat ttataacatg tgtatgtacc  99240
acctagccct gtcaagtctt aatatttgtt atatttgctt caaatctttt ttcagactgt  99300
agttaaaaat tacttaggag ccattattta tggcctattt cctgacctag tcttcttgat  99360
ggtcaatttg cctaatcatc ttaagttgca aaagcttaga attaaagcaa agtaccttcg  99420
atcctctgct gttgccttct ttttaatatt tgggtttgtt tgggtcccat ttacggttgt  99480
gacatcagct tgagttttgg gagctgtctt gttcagaaaa tggttctggg gaacagcctt  99540
tttcaacttg gagtccaaag tctgtgcttt ttgctgaaag ccattattgt tatgtttatt  99600
accactggtt ccatttggtc ttatgctagg ggtgcttgga atggctgaat taaatctgcc  99660
aactgtcaaa ttaggcctct ggcttacggc ttttgacttt tgcagtacac atgatgtctg  99720
aggtatacaa acttggctgg acttctgatc ttgcttgatg tttggatgtc tgttgttata  99780
ttcaccctga agcaaactgg ggtatgttct gggtttggtg tgcttcactc tctgttcagt  99840
aacagggtat gaccgtatct tagtttcatt tggtctttca tattgactcc tattaacctt  99900
tatatctttg atgttcttga ctactggttt ctttgatgac tgaactttac taagggtccg  99960
aataaagtga gagggaaccg tccttgaggg ttttactcct ggtcttgcaa gatctgctcc 100020
tctagagagt tgctgtgatt ttactgggaa agtcctgctt tgtgtttctc caacaaattg 100080
tttattaacc ctatctttca gaacagcact attaactgaa cttttgccca aggcttgttt 100140
aggaactaaa ctgttcttgg tttgattata agagtcagtc tttggcttac ttctggtata 100200
taatttagga tctggcttcc tctcaggttc tgttaagata tctagcaagt tctctttgtt 100260
tgtttctttt agaaagttat ccaaagattc gttttcaaca tggatattat tcataaagtc 100320
tatacattta ccatttcctt gatctgttaa ctgctgcttt gtagttttca attgctctat 100380
attaagtgac cccacaggtt ttcttgacag tcctcctgtg gtggactatc tagcttcaca 100440
ctgttgaaaa ctcttgctga aaagcttaga ctatgggtta gaagaaacac attttgaagt 100500
ccgccttttg cccagaagtt ttggtggctc taacttcagc ttctgggacc ctgcagtatt 100560
aggtggtctg ggctggagtt taatgctgat ggacctttta ggtttgacag gcaaaacaac 100620
atggttggta acatcatttt tgggtctaat agtctgaaaa aacaaagaaa atacatatta 100680
aaaaatcctt aacatatctt attgttttta aaataataac tgtgtttaac acatgctaaa 100740
aaaaaaatca tttttagaat ttcatctaag aaagttgaat cctcagaaag taaagaaaga 100800
ctcactaata ggtagttttt gtgttttttt tttttttttt ttttgagaca ggatcttgct 100860
ctgtcaccca gtctggtgtg cagtgatgca atcttggctc attgcaacct ctgcctcctg 100920
ggttgaagca attctcccac cccaacctcg caagtggctg gactacaggc gcatgtcact 100980
acacctggct actttttgt atttttagta aagttggggt ttcaccatat tggccaggtt 101040
ggtcttgaaa tcctgacctc cagtgatcca cgcaccttgg cctcccaaag tgctgggata 101100
acaggtatga gccaccacac ctgtcctaac aggtagtttt tacaacttga gttcctatca 101160
gaagtatatt agaatctttt agcttgacag aattaagcag agatgcagtg aatatacaaa 101220
acttgctctt tcaaaaatga atttgcctca aacagtagtt gttgaatgcc tattatatcc 101280
taagtgccct ccaaagaacc ctgaaaaaat acatacataa tgaacttatg ttagggtacc 101340
tcccaacaaa tctctcctag tactttgtat agccacacta tatgtttttt aaaccactgc 101400
ctttgtaaac atcacagtat cactcaagaa cctctgtctc atccctggag atcagtgaca 101460
```

-continued

```
aggagatagg tggcagatga tgtgaggcct gagatatgct gccacagctc tcaataaaca 101520
tgtaacatct taatagtcat atttgtaaaa tcagccagga cagggtttta aggttagagt 101580
ctatgttaat aataaacaaa tgtttagtca tgtgatttaa gtttggataa gaaaggtagg 101640
actcgattac agagaatttt gaaaactagg gaagggagtt tagaattcat atggtaagta 101700
attgggcaag ccactatgaa ttcctgagca tctctcatga aagcaattac tcagaaagga 101760
gaatttcaca gagatttatg gaatatgttt ccagggtaag atatgggaat gctagagtta 101820
ccactctatt tttgatttga caaatattgt gaagaatcac tacataaact tggcgagtat 101880
gtaaaggatt tctaaccaga accatttggc attgagggca aagaaatgtc tactctggat 101940
gatagcggtg tgtgtggtgt tactaggagt gaaacagcgg agttgggagt gggaggcaga 102000
gagatggatg gtatacccac aatggctata tctggattaa tctttgagca ccaacattta 102060
tatacacctc ggatctctcc atcattgctt actgaagagg tggagggacg ttggcatgaa 102120
agcttccaaa tgtgtttttt tagttgcttt cttatatatt aaaaacgaat tgatataatc 102180
cacaaaccat aaaattcacc attttagtaa gtgcacactt ctgtggattt tagtatagcc 102240
acactattat acagcaatca ccactgtcta attccagaac atattcatca cccctagaaa 102300
gagacttggg tttacttgtt ggcagtccct ccccaggtct acatgtgctc gcaagattgg 102360
atattgaaat atcagcaaga aattaaatga catagtagtc attatgccta aattattgtt 102420
attttttgat tgaaaaaagt tgaatatttc aaatatcaag gtagtagtga gatataataa 102480
agagagagtc agttctaagt atagaattgc tgattcagtt aagctctgtt ctccaacatt 102540
tgggccacat tgaagagacc atgtagctgc tttcagcctc ggtttcctcc tttgcaaaat 102600
ggggattaca ctacctgcct cacagagatg taaacttatg acatgttatc atgattgcca 102660
gggcccacct gttttctttt aaacattgaa atcactgtgc ctgaaacagg gatttccctg 102720
ccctttgtgc aagctccaga aacaggagtc agcctgagtc ccgcagctaa gaacgtggat 102780
tctggtcatt ttctcatagc gaacacactt cacaggtcct tcaagggagt acattttcct 102840
ataactcacc ttaatctcag ttgaagcctc gtttcttatt ttgcactgtg gccaaaaact 102900
aaatctcatt tctttcacgt aaacttcagc aattcaataa tagtacagtc attttatgtt 102960
tcaactgaac caagtcaggg ttccactcct gcctcccctt tctgctctga ggacatccat 103020
gaagtggagg gggtctatgt agcctggagc tattggtgag gggcgatggg tccgtggtgg 103080
tcttggggaa ctgcggggct gtgtctggct ggtctggtgt ctggtgattg gccttgttcc 103140
acgcggttca cgctgcagga cagttcgtgt ccttcttgtc ctaatgatca gcttttaggc 103200
tcacgggcct gtctctgctg agatatggaa taggacagcc tctggatctt ctttaaactc 103260
tcctggggcc acaggggact ctgtttgtgt ctgtgcccac ataggatgat tctgcccaga 103320
cctttgctgc catttcttgc tgttctgctg tttttagtct ctggagggct tgcagtttcc 103380
ttggggtccc tgtggaagca aagcaaagtc ctctccacgc tcagatgtct aaacgtatct 103440
gggttttatc gtccacccat cccagagctc agtctagagg agggggcagc cttcgggttc 103500
tctccttcct cccagagcct cttcctttgc accagggcag cctcttccta tctgttggaa 103560
agggctgtct ggttcttgaa tatagagttg caggtttgag ggtgtaggc tgaggtaagg 103620
caaactatca catggaataa aaattaccct gtgtcaagga acaaccagag ctggacagtt 103680
tttaaatgtg aaaaccaatt ttattcagga ctatggcgag aggtgaagta agacctcagt 103740
atagaactgg gctcaattcc gaatgcagca tgggcaaatg ggaatgtata gcctaggagc 103800
agggtgggaa cctgtggatg aagaattact aaaagggcat atcaggggtg agggggcgtc 103860
```

-continued ctggctacac ccactaacta ctgttgctga agaaaggcct ggtgacatca ctggggaatg 103920
gtgggggatg aagaatccaa tcagatggat attgaggata aggggatctt gataaactgg 103980
cttaggaggg tttttgctaa aactggtttt cataggtaag tccacagaca ggtcttggag 104040
aaagttcagg gacctacggt ttgttcgggc agatgctttg tcatctgtca cactggcact 104100
gtcacctggc tttcctttag tccctccccc ccttttttttt ttctggagta gttttgggag 104160
accagaggag cagggagtta gggagagtag tcagaaaagg ccagagaaaa taaggaggtg 104220
tctgtaggga aaatccttaa atcctctaat taaattaatt taatttattt atctgggaca 104280
aggtctcact ctgttgccca ggctgaagtg cagtggtgtg atctcggctc actgcagcct 104340
cgacctcagg gctcaagcag ttttgccacc tcagcctcct gagtagctgg ggctcacagg 104400
tgtgcactac catgcccggg taatttttgg gttttttttt tttttttttt tttttttttt 104460
tttgtagaga tgaggtttcg ccatgttgcc caggcttggt ctcgaactcc taagtgatcc 104520
atccacgtcg acctcccaaa gtgctgagat tacaggcatg agccactgtg cccggcctaa 104580
attctccaat ttttaaatgc ttccctgttc cctgttccag atttgggata ttgactgctg 104640
ttaaatcagc gatttctccc tgtggagagg tagccaatag gaagcaacaa gagtgaggag 104700
tccttatatc gaaatagagg gtaagagaag agacagatgt tatcttggca gtgatttaag 104760
aacagcgagt ctgtaagcaa agcaaagcaa ggctcccagg tgctgagaaa caatggcttt 104820
ctggggaagc gtctgtgttc agaaccttaa gttggaaaca tctctgaaga tgtttgccat 104880
gaaggttttc ttctgaagtt gagtctttca tcactaggta ggcgtgtttt ggagtctcta 104940
tcaaacagat cctgtgttta ttaggaagct gtggttcata aagccccatg ctaattttgc 105000
aggtagcagg gtggccctgg cctgacccgg ggacagagtg gctgtcctcc ctccaggcag 105060
gaaactctct cctgccacct agtggctgca tacccacatt tcaagggagc ttctgggtgg 105120
tgagtttacc agactatggt ctgaggtaga gttaagcaaa acaaaactaa actgcataaa 105180
gaaacagaaa gaaaatcagg tgttataaaa acaatttggc atttgtttgt gtttcagctc 105240
cgtgtcgatt tattgcttcc acaaatagtg ccgatatgca ccaggcactg ttgtaaaact 105300
gaaaatatgt ttttggatgt gcccagtctg tgagtattaa acgatggttg atttgaaatt 105360
tgctatgatt catatttctg gggtaagat gcaggatttc tttgggggc ctacgatgtg 105420
gcattctaga attctcaaag aatcaaccct ggtgggacca ggaagagctg agctgaggcc 105480
tctctgctca tgtgtactta ctggagatca tggagacagg tgagcctgag tgcacgtctc 105540
accaaagcca cagcagaggg ggaggaggcg gaaagagagc tctctccatt tctgagaagt 105600
taatggtaac aatggcatac atacctactt tacagttgaa attggaaacc acagcattaa 105660
gtgtttccaa tgaaatttgg caatttggga gttttctgag ctgcattgga tgtggttttg 105720
catgctgtta ggatgagcaa gagatgatgg agaacatctt ccttttgagc ttcctcttgg 105780
acgtgggtca ctcccactca tggaattaga aagcttagac ctagacttga atctcacctt 105840
ctcaaggtgc tcccgggcaa atcacttaag atccatcttc ttctcctcct gctccttctc 105900
ctccttctga gttttttttt ttctttccaa aattcaaatg acacggtact ggtagaagaa 105960
aaggtccaag tctgctttta cagctcccct catccccaaa tgtactccga ccccaagatg 106020
accatgttat catttgattg acatccttct agtttcaact catttctttg catgtatatg 106080
cacgtacata tacactattt tattttgcca ggggtcaccg tttagctgca ttaatttctt 106140
ataaaataat ctatatttac ttatggttta cgtaaaacaa catacacatg taagtgtata 106200

-continued gcttgataag tcttcactgt aaaccaaaaa taaaattcga agccccccca accgtctgaa 106260
tggacccctc ttcttggcca agagcattcc aaagttaacc tgaaaaaact agttcaggtc 106320
atgatggaag ggaaggttgg acatgcccca gtataccctt ctcccttttg gaattcagga 106380
aaagctgacc agcattaaca tcaacacaga ccttatgtct gataggaaac tttgacaatc 106440
tattccctct gaagcttgct acccggaggc ttcatctaca agataaaacc ttggtctcca 106500
caaccgctta tcataaccca gacattcctt tctgttgaga ataatttacc ttgtaacctg 106560
gaagctccct gcttcaagtt ccctcacctt tccagattga accaatgtaa accttacatg 106620
cattgattga tgtattatgt ctccctaaga tgaataaaag caagctgtat gttgactgcc 106680
ttcagcacag gttgtcagga cctcctgagg ctgggtcacg gatgcatcct taaccttggc 106740
aaaataaact gtctagattg actgagacct atctcagata ctgttgggtt caaatatata 106800
acttatgaaa ctaatacaca aatcaagtca tagaatattt ccatcactcc tcatctaccc 106860
ccaaatttcc ttatgcgtct ttgcagtcaa cctcccaccc catccccagg caactgcaga 106920
tctacttttt gtctctgcac cttcaactga ccctttctgt gatttcatat gaatggaatc 106980
atgcgctgag cagtcttttg tgtctggctt cttttgctca gcataatgtt tttgaggttt 107040
gtccatgttt ttgtgtttgt caatggttaa tttctctcca ttgcagagta gttttctatt 107100
gtacatgtgt accacaattt gtatatccat tccattgctg atggacattt gatttgtttc 107160
cagattttgg caattatgaa tagagctacc atgaacaccc aggtacaagt ctttgtgtgg 107220
acttatgttt tcatttctct tggaatggaa ctgtcatatc aataagtata tgtttaactt 107280
tgtaagaaac tgacaacaaa ttatctgcga tggttatgcc attttgtttt tctaccagca 107340
atacacgagc atttcagttg ctccacaact ttgccaaaac ttgttttctt taatttggac 107400
atttaagtgg tgtacagagg catctcattg tggttctagt tttctttgcc ctgatgacca 107460
atggtgttga acatcttttc atgtgctttt tgaccattta catatcctct tttgtgaagt 107520
gtctgttcaa atatttttgc ccatttaaaa catttggggg tttgtcttat tattgtgttg 107580
ggagagttcc atatttattt atttattgag atggagtctc actctgttgc ccaggctaga 107640
gtgcagtggc gtgatcttgg ctcactgcaa cctccacttc ctgggttcaa gcaattctcc 107700
tgccttagcc tcctgagtag ctgggattac aggcatgtgc caccacactg gctaagtttt 107760
tgtattttta gtagagatgg ggtttcatca tgttggccag actggtcgca aattcctgac 107820
ctcaagcaat ccacctgcct cggccctaca aagtgctggg attacaagca tgagccactg 107880
tgcctggccc atatttattt tttattcttt attttgtata caagttcttg gtcagataca 107940
ataatacctg gtcagatgag ataatgagtt ggaaaatgct ttgcaaatgg gggagaataa 108000
tttaaatgtt atttatttat taagagcaga ggcccttcct gttgcggtca cagaagccgt 108060
ttgcttcttc tgccttttat aaaccagcag agtcgagcta cacaggctgt ctgtgttggc 108120
tgctattagt taatcagaga gttttttttt tcttgccttg tcattctaat ttgtgacaca 108180
taattagcca caatatgtgt tttcagttgt gacactggcc tgggaaacca agggatgttt 108240
agagtggatt tccttgattt tgcaataatt gtgtgttttt ctgcatcttc tgttaaacac 108300
aaattcatgg aagcaaaaca tggaagcaaa gtaccctgga catcccccct tctttatgaa 108360
attgatttct cttaaatgta atgtttgctt gttcccttac tttaaaagca atttaagagt 108420
ttattgagaa agtgagccct ggaaacatag atgcatagag agaaaattct accaccctca 108480
ggtccctatt gtcttctctc ataaagtgta gtttcagggc cttttagaag tttcttttct 108540
gctctgattt gcatgtttgt gagtgttgct attttaagta tttggatttg gtctgcaaat 108600

-continued cctatgagag atggcaacag agtagggatc tcaaagcctg caggttgtat taagtccagc 108660
agggccttgt atttacaaca gagggtcctt gaagacattc catatattat gctaggggag 108720
tggccaagca aactttaatg tgtccctatg gtgggatatt tggggttaat acctgccctt 108780
ctcttaattt ctttttcttt tcttttttc tttttctttc tttttttttt tgaaatgtag 108840
tcttgctttg tcacccangc tggattggag tgcagtggta tgatctcagc tcactgcaac 108900
ctccacctcc tgggttcaag caattctcct gcctcagcct cccaagtagc tgggactata 108960
ggcacacacc accatgcctg gctagttttt tttttttttt ttgaaacnga atctcgctct 109020
gtcgcccagg cgggactgcg gactgcagtg gcgcaatctc ggcgctcgca tccctcatat 109080
ccatgagtgt tctgtgggcc ctgcctctga aataaatcct gcctttgtct cccagttcac 109140
tccagccacc catcctgggg ctgcaccctc ctccttccaa gccctctccc tttccttcct 109200
ggtgctgcct gtcatgtcaa gcatatgcat cagtgcgacc aggacatttg aaatgcaacc 109260
agtacaattg ggcgcggtta tgcctaccag tttttcttcc ttaaacattt tatatttatg 109320
tttgaaagca tgccaccttt cttcacttgc caacttgaca gatttattag ttgacaacat 109380
ccgctgatag catcagtaat aagttaattg tttttgcaca tgtagcttta attattctca 109440
ttatcattta taggagttat tctttgtaaa gggtaactga gttttccaaa acaaacagaa 109500
atttggggtg ggcccatgga gcgtgactca tgaaatcaga ttcttagaag gacctcggca 109560
agtctctggg ttgctgttaa tgagcctggc tggctgccag ggtgtgtct gccctttatg 109620
aggccaccac tgttcaaatg cttgcctgca gcattacttg cctaggtagt gcttgtttct 109680
actgaactgt cagggatcca attctttgtg gtctaagtaa caatactcag attcacaagg 109740
aattgattaa taagccagaa tgccaatgta ttacattttt gatgaagacc atatttacag 109800
tgattgtatc tgctcaagct caaattagga ttagagttct gacaaataca tatgtgagaa 109860
gtatgaggtt aaatacttga aatttggact tttctagaaa atctgaatgt gattgccatt 109920
cacatacctt tctggggatg atgattcttg tacttttatt ttaaaagaca tagaaaacta 109980
acttaagaat cagattgctt ggctgggcac agtggctcat gcctgtaatg ccagcacttt 110040
gggaggccaa ggtgagtgga ttgcttgagc tcaggagttt gagatcagcc tgggcaacat 110100
ggtgaaatcc catctctacc aaaaatacaa aaaaaaaaaa aaaaacaacc aaaaagaata 110160
aattagctag gtgtgatggt gcgtgcttgt agttccagct acttgggagg atgaggtgga 110220
agaattgctt gagcccagga ggtggaggtt tcagtgagct ggggttgcaa cagtgtactc 110280
cagcctgggc gatagagtga gactccgtct caaaaaaaaa aaaatcagat tgctttattg 110340
ctggttttct ttctaaaact gagattgggt cccatcatcc cctggccccc attggttaat 110400
ggttcctcct ttgtctattg aataaaatac agatgtctgc ttttggcaac atggttgaat 110460
gtagacactg cagggtcttc ctgactcaaa atgagtaagg cttagataaa acacattttg 110520
aaatgcattt ctggatgaac agcaaggaaa ggagatctct taaaatcctc tttctgttcc 110580
cctctcccta ccccctccaa gtgggcttaa gtaggaaggg tggtgagcgg caggtaaaca 110640
cacgtcaaag gcagtcttcc tctctgaggg aaaacacttg tataagcatt gcaatcaatg 110700
ggcctcttta attatgtgcc agtggcaaga gcgggtgctg aacccagggg cctgcctcaa 110760
tccggggcct ttgaggcaga ataaagtggt ctcaggttgt tggcatttcc ttgcccttcc 110820
acccgaagca gacacaaatc ctctctggag gcaagttccc caattcagcc agtacaactc 110880
ccacagacta agatcaatca tgtacaagct cacagacaaa ggtcaccaaa cacacagagc 110940

-continued aataaacaaa ttcatgagtg acgtgaatga gaataaacag aaacaataac caccagctgg 111000
gatgctctaa gtcttcagct gttagaattc ctgaatatag aataaaactg ccacaatggc 111060
aaacatgcat ctagtactta ctgtgtgctg ggttctaaga attttgcaca ttgtgccaga 111120
taccgactca gcttcacact caccctccta ctgtgccctc ttaatttgca ctagattaaa 111180
aggtagaaag gaagaggcag ctattctgtt cttggctgtg cctctggcag cacatgcaaa 111240
atgggcagta acagtggcag tcacaggtaa gtagccttct cacagtgtgg agttaaaggc 111300
atgggactga gacgagcaag gttcctaaag ggacagtggc cagtagatga ccaggggcta 111360
ctggagtggc tgcatggctc tgtggaagct cagaggagcc ttgggtcctg caggtgcagt 111420
agcagctttc tgtagttcct gatctctggg tcccacaatc ttccccgttt ttgctcctcc 111480
acttctaatt ttgtaactga cttccctgtg tgtacttctc tctctgattg aaatagccag 111540
actggtttct gtttcctgat aagacattgt ctggtacgaa cacagtaact catttaatcc 111600
gatatctcta tgaaggaggt acaataatta ttcctatttt acagatgagg aaacacagca 111660
gagaaataaa gtcaattgtc taaggttgca catttagtca agggaagggt tgatataaca 111720
tataattatt tagaaaacat ctaaggaaat aaaaggcata atttaaaaat aaaactaggc 111780
aggtttaaaa aaatgaagta atctataagt aaaaaagtat aattgttgaa atacatatct 111840
tagtggatgg gttaaatagc tgaagaaatg attaatgaac tggaaggtag ttctgaggaa 111900
atcagaattc agcatagata gaaaaaatgg gaatttacaa aagtacacag gaattataaa 111960
agaggttaaa ttatagggag ggtagaatga gaattaacat tggtctaact ggaattttgg 112020
aagaagagaa tagagagaat gaacaaggca atatttaaag aggtggctga gaatttttca 112080
gaaccaacac aaactatgac tttaccagta gagaaaacaa tgtacactga ggaggataaa 112140
taaatatact atgaacaaat tgtaataata atactcaaca aagacaaaga gaagatgtta 112200
aaatcagcaa aaaaagaaag tcagacttag aaagaaatga caatggcaga ctactcaaca 112260
acaacaatgg aatccaaatt cggtcaaaca gtattttctt catgctagca tatagcggga 112320
gtccgctatg ctcctaaaga tttgcacctc tgatctggtt tgtagttagt ctcttttatt 112380
gctttatcct actcaactaa tttttttagt gcctgttttt ttttttttta atgtgtgttg 112440
atgactacaa ttctaaactc attctactga ttcatgggtg ctttaaaatc tgagcagtct 112500
ttcgcattta ctgcctgtga tggcccatcc caccagctaa agtgtgtggc cactgcttac 112560
agcaccatgt gataacgagt aagggagaga tgccgcccag actcttctag gagcagccag 112620
taggaccttc caggggttgc aagcaaacca cagcaatatg tggagtgtgg cagaggatgg 112680
ccccaagagg atgtggcagc ggctagtgca gctcagctta gtctgagagg aaatgctgga 112740
gaggagagcc cagtctgtac aggcatgaca gccacaagga cttcaacagc taacatggct 112800
gagtggactt tatgtgctat ctcattcaga aaacaggagc aatcagaaag gagtcacctc 112860
ctatttgtac cccaggaatt gctaacctac ttgcatctga atgatgtcca tcacttccct 112920
tcatcacctc ctctgggggc tctgcaagga tttgactcct gcattagtga tctgtctcac 112980
ctacgttgtg attcacatga acttactaat gtgctatgtg acaactacca tcttaaacac 113040
aaaaaccctc ttttgattct gtggctccct ccagctaccc ctgcatttct ctgtcccccct 113100
gccccgtctc tgcactcact tttattttac agcaaaacta ctcaagggag tctcagtgct 113160
ccttggctcc atgtctccac ctttcattct ctcctcagtt cactcctgtc aggcttccgt 113220
cctcaagctc ttcttcactt ttgttctagg gccgctgaca tcctctttct tgccaaattc 113280
agtggccagg tcctcactta ctcaactgct cagcattgtt gggcctggtg gaccacattc 113340

-continued tccttcaccc accttttgct gctctctctt ctctccagat gtttctctct tctcactggc 113400
tactcctctt ttgtctcctt tgttagctcc atttcttcct tccaacctca ctgtgctggt 113460
gtgcccagtg ctcagttttt agctattctc tcttttccag tggcattcat tagatggtat 113520
catgtgaccc atggcattat atgccttcta catgacagtt actcctgaat atgaatctca 113580
ggaaagattt ggatttattt ttaattaatt tttttaaatt ttattttaat aaatgaggtc 113640
tctctctgtc atccaggctg gagtgtagta ttgagtgatg tgattatagc tcactgcagc 113700
cttgaaccat gggctcaagt gatcctcctg cctcagcttc ctgagtagct gggactacag 113760
gcatgtgcca ccatgcctgg atgacttttt gtgtgtgtgt gtgtgtgtgg agacagggtc 113820
ttgctctatt gcccaggctg atcacaaact cctggcctca agtgatcctc tcacctcagc 113880
ctcccaaagt gctgggatta caggtgtgag accatcctgg gctaagattc agattttgta 113940
ttcaattgac tgtttgacat cttcacttgg acacctaaga ggtatctcaa atattaatta 114000
acttggccaa aatacagaac ttttgacccc tgcccccaca atacttgccc cttccccaga 114060
cttctccatt tctgttaaat atccccagtt actcaaccct caaacctatg aatgcccttt 114120
gatttctttc tttccctcat ctcctacgtt gacgccatca gctagttttg ttgcctttat 114180
gcccagaata taatcctcac caccttctct cctattgccc gagtataaga tgtcagtttt 114240
tcctgcacag tccattgccc tgacctcctg agtggtttgc ttccactttt gacatttgta 114300
ttcctctttc ccccagggtc aatttttcac agcaagagtg gcattttttt tttttttttt 114360
tttttgagac ggagtctcgc tctgtcgccc aggccggact gcggactgca gtggcgcaat 114420
ctcggctcac tgcaagctcc gcctcccggg ttcacgccat tctcctgcct cagcctcccg 114480
agtagctggg aatacaggcg cccgccaccg cgcccggcta attttttgta tttttagtag 114540
agacggggtt tcaccttgtt agccaggatg gtctcgatct cctgacctca tgatccaccc 114600
gcctcggcct cccaaagtgc tgggattaca ggcgtgagcc accgcgcccg gccaagagtg 114660
gcatttttaa aaccatatat tagatcattg cttttgtgtt tgggaacctc caagggcttt 114720
gcatcatata tcaagttgac acctctccta cccaagcctg gctctttcct gctcctctgt 114780
cctctcagcc cctccaccca ttgttcatgc tgcttcagcc acactggcct tcttgccatg 114840
ccacatttgt gctaagccca catccaatct cggggccttt gcactcgcat ttcctctgct 114900
tggcatgctg taccccagat ctttcatgat tggcagcttc tgtacattca gccacctgct 114960
caagccaccc tttcagaggg ccttccctgg ccacctcacc tgaaatagca cctccgattg 115020
cacccatccg gttattctcc atcctgttct cttgcttggt gattttccat cactgatgag 115080
gaaatgaacc atggaatgct agggctgatg accagaactt tcccccaccc ccacattatt 115140
acagaggagg aaatgaggtc ggaggtaaga tgggcccagg atttctactc ccgcctggac 115200
tgcaggcaca gcactgacct cagctgtgct cactcttggc attcacccaa cccttctatc 115260
tccaactgcc ccatttacca gaaagtgaaa tgttctcaga gacggtgagc cacctgactt 115320
ggacagcagc ccagggcccc tggcaccctg ctttcttcct ccctgccatc ctttcctctc 115380
caagacctac ctttccctgt gattcttgcc cacatgctgc atttcatggt tttatgacct 115440
gatttctgag agggatttga attttcatga ttatttatgt aagcaaatca ttatgcttat 115500
acaaatgaga aaaggagtgc ttctggactt cccagggaca aaatcttgtc acttggcttg 115560
ctttcatatt gctaattaag gacccaggat gtgggtgaga tgtgctaaaa gctgagagga 115620
ggctctggac tctgactatg ggcccacacc cctgggcagg catcacacta gtcctttagg 115680

-continued tcatcctcaa cccagcttcc agttgaatca gatgtttgtg aataactcag caaggctgta 115740
tgggaaatga agaatgaggt ggggaagagg cctgtgcaga agacacactg acttacccct 115800
ctacctctaa ctagggtgtt gtagcagcca cccacccacc aagtctgtct tccagaccac 115860
gtatgctttc ctccaccttt gcatctttta tcttctgcca gcccagatgc ttgctgactc 115920
cagcccaagc ctataggata agctacagcc tgtccctaca gactacgcat tgcagaatct 115980
aagacatcaa gtcaagttcg gaagcacttg ccttctcctc tccaggtaca caggctctcc 116040
tggaaagctg gtagcagctg tggaggtgtg gtgtgttacc tgctgcaggt gcagagaagt 116100
tgacttcaca gcccttcaga aagactgcct tcttccagtt gtatttgtgt acttgcttgg 116160
gtgtggggag gattctcagc tttctccact caaattatca gaccctttcc atttagtggt 116220
agaccatttc cctcgtccag gccaagggca catagtacag agaaataggg agttgttacc 116280
cagggagaga acttggctct aaacctgtaa tagaaaggtc agttctggtc tggagggtca 116340
attttgatct ttggctcaga tccaggaatt ggaaccaagg cttttgaaca ttttaatgca 116400
ggggattaaa aaaatgatac gagtcattca cgaatatatt tgcttaacat ctaaagagat 116460
ccctcaaaac actagaaaaa ataagaacaa aaatctaata aaacaaaatt tgttaaacac 116520
atttaccaaa tttttttttt tggtaaaaat tcaaatgtca taaataaagc taaagttcct 116580
cttgatgact cgctcctctg ccctattcca ctccaagtaa ccactattat cagtcttgcc 116640
aatacccttc cagacctctc tacctctata taccattaga agcacatggt tttgcattga 116700
ggatgtgcag tgttttgttt tacgtaaatg ttatcactct gttcttgttc cataatttgc 116760
ctttttctct caatgatttg cttggctatc tttctatttc agtagcatct cctttctttt 116820
taacttacca ttgtttattt aaccttgcct ctatcaacag atatgtaggt tgtttctagt 116880
tgatttcatt aagtatttat aaacaacgca tcagtagatg tccataaatt tctttacgga 116940
agatggcaag tagtggaatt gctgagccaa agaacatgtt taaaaaaccc aaaaaaacta 117000
gacgctacca attttctctc caaaatggcc atacccactt acccatacag agatgatttg 117060
gaatctggct tcctcacaag gtgagatgcc ttcacagttt cattcttcct ggcatgtctt 117120
ccctttgta tctgagagag ctggcagaat tgtgtcacta aatcaaggat agagggtcaa 117180
atgacagctc aagctcacag gcacctctgc tttcttccca gaccacctgc tttcctgcca 117240
ccagctctgt tccatcttat agaatggttg ccacttgggt gtctgctccg acagccatgt 117300
catcctttgc actgcagtta tgaagcagac agagctagga gaggggcttt gccagcctct 117360
gccctagctt ggagaatttc aaagaaggag ggtattgaga gtgagctgcc gaagactggc 117420
agctccctca actcaacagt tgtccttcca caagaagtca gatacatttt tttgggataa 117480
aatatttaaa aattattatt ttatttctga ataatatatt tacatgattc aaaaatcaaa 117540
ctgtaggcca ggcatggctg cttatgcctg taatcctagc aatttaggag gccgaggcgg 117600
gaggatcact tcagcccagg agttcaagac cagcctgggt aacatagtga gaccctgtat 117660
ctacaaaaat ttaaaaacaa aaattagttg ggcatggtgg ctgatatggt ttggctctgt 117720
gacccaactc aaacctcatg ttgaatttta atcctcaatg ttgagggagg gtcctggtgg 117780
gaggtgattg gatcatgggg gtgggttctc ccttgctgtt ctcatgatag tgagtgagtt 117840
ctcacaagac ctggttattt gaaagtgtgt agcacctccc ccttcactct ctcactctcc 117900
tgctccgcca tagtaagatg tgtgtgtttc ccctttgcct tccgccatga ttgtaagttt 117960
cctgaagcct cccagctatg cttcctgtac agcctgtaga actgtgaatc agttagacct 118020
cttttcttca taaattaccc agtctcaggt cattctttat agcagtgtga gagtggatga 118080

-continued atatagtgcc atatgtttgt attcccagct acccaggagg ctgaggtaag aggattgctt 118140
gagcctggga gtttaaggct gcagtgagcc atgactgtac cactgctctc cagcctgggt 118200
gacagcgaga ccttgtctcc aaaaaaaaaa aacccaaact gtgtaaaatg tgttcataaa 118260
agtgtcttgc tcccacacct gtccctatat atcttattcc tcagcctccg acaactactt 118320
tattcatttc ttatgtatct tccagaatca aaaaaaaaaa atcaaataca agcacagtgg 118380
aatgtattgc ccttcttccc ctccctttttg ttacatcaga gttagcatat cataaatacg 118440
gtctgcattt tcttcttttt cagctatcag catgttttgg agaggatttc atattcgtgc 118500
agacagcatg tattagtcag tccttgcatt gctataagga aatacctgag actgcataat 118560
ttataaagaa aagaggttta attggctcac agcttcgcag gctgttccac aggaagcatg 118620
gcagcatctg cttctgggga ggccttagga agcttttact catgcagaag acaaagcggg 118680
agtggatgtc ttatatggca ggagcaggac tgagagagag agagagagag agaaaggatg 118740
ccacatactt ttaaacaacc agatcttgtg ggaactctgt cacgagaaca gcaccaaagg 118800
gatagtgcta aaccattcat aagaactcca cccccatgat ccaatcaccc cacaccaggc 118860
cccacctcca acatcgggga ttacaatttg acatgagatt tgggctggga cacagaacca 118920
aacaatacca gagtgctttc tcattctttt ctatagctgc ctagtattct atgtccttta 118980
cttcatttag gcagtctctt gttgatagac acttgggtta cttccaattt ttcctattac 119040
aaatgatgtg caatgaataa ttttgatcat tttccatttc acatgggtta tgtccatctg 119100
tgggataaat ctccaggagt gaaattgctg gatcaaaggg gaagtgcact tgtgattttc 119160
atagttagca aattttgttc tataagggtc atatcaattt atagtcccac gcgtaatatt 119220
taacagtggg gatttcccga cagtttgacc aacaaggtct gttgttaaac ttttgatttt 119280
tgtcaatctg atgggaaaat actagtatct caaagtgctt ttaatttgac tttcttatta 119340
caatgttaag catcatttta ctctgcccaa gatcaaatag tattttcttt tctgtgaaca 119400
gactgttaag atcccttgcc tcttgttttg ctggattttt gttctttttt ttcaaatgtt 119460
ttgaggcagt tctttacatg tgaaacaagt tatctcttta tctggggtgt gagttacaac 119520
tacttttcct ctggcttgtt ttgcgctttg actttgcttc tggtgattcc cgcaattctg 119580
aaagtgtact ttttgcatca ttcattctta tacacccatg ctcttgttca cgctggttcc 119640
tctacctgag ggctttttct tttctgcttc tatctgggaa cattttttttg agagagagtc 119700
tcactctctc gcccaggctg gagtagtgca atggcgcgat cttagctcac tgcaacctcc 119760
acctcctggg ttcaagcaat tctcctgcct cagcctccca agtagctggg attacaggag 119820
cccaccacca agcccagcta atttgttgat ttatttattt attttttgta gagatgggag 119880
tctcactatg ttgcccaggc tggtcttgaa ctcctgggct caagcgatcc acccacctcg 119940
gccacccaaa gtgctgggat tacaggcgta agccaccatg cccagcccat gtgtggaaat 120000
cttctgttta tccctttagg cttgattctt atgtcgttct cctccctcct tcctggatac 120060
tcctcttgtt ctttatctta ctctacttgt catgttacct tgtttctgct tataactagc 120120
tgcctctcct atctgaggag ggacttgtga ctgttctcat ctctgtactc ccagctccta 120180
gtacatagcg cttgctcaac agatgtttgg tgcattgata gataaatcac tggtagctgt 120240
tactaccagt cctgactccc tgcagtgctt cagctgatcc tgttccagat gtgcactgaa 120300
tatccttctg ttgaacaaca gaaataaagg ggatgggtga ggaggatagt cttcggtggc 120360
caaggatatt tttaggtact ttgcagcact cagcaatgag gagtgggctt tagtccccca 120420

-continued agaactctca cagccctggg tgtctttact gttcagtgtc aaatccaaga caagtcaatg 120480
atcaggaaag accatttttt tttgttcagt gaagtttatt tcagaatcat tgaacagtat 120540
gatatttggt aatttcataa atattcccac ttaaaatgat cggagcagat atattttcag 120600
tcgtaattaa aggacatgat ttaaagagag cacaccagtc caaattgaaa tgattccata 120660
gctattaaaa aactagggtt ttttacagac aatgatactt tttgccccct ttgaatagat 120720
tagaccaatg aataaaacaa acaaacaaat aaataaataa atagggaagc ggttgctcat 120780
cagaatgtgg gagcgaatga cagagggttt cttagaacca aatgtggccg tggtttctgt 120840
caggcgtgct ttaagtgagt aggagaggtg agagaggcct ggctcaacaa aagggctggg 120900
gattgtccct gaagaaccag agctganttn catcaggagt aacanaggta gatagccgcg 120960
ttgaggttcc acgcagttca aattatgtcc aattatcaac attaatgcac attttcaata 121020
gaacctgttc cggcttttct taggaggggg gcggggagac gttgttctct gggaataagt 121080
gtacgcagga ggctgagaag gcttcattcc atagcattca cttacctcca gctgtagagt 121140
gggcttatca tctttcaaca cgcaggacag gtacagattt ttttctttga ggcccaaggc 121200
cacaggtatt ttgtcattac tttcttctcc ttgtacaaag gacatggaga acaccactga 121260
agaaagaagg gggtcttgtg gttagggaca cagcagtgca gggtcacccc aaccccctagg 121320
ccccatgagt aggatacatg taatttggta gcctctgtgg gaacccacag tgaggttcct 121380
tggcctaaga cacaggataa cttgacttct cacagacaat agcagggtca ttttgttgat 121440
ttagggtttc ccctcaaagg cctgagggtt tctcagagcc tcatagcagt aggaacggag 121500
aatgaaagag ggtctacatt ttaaatgctg aaggaaggaa ggaaggaagc cattgtgtca 121560
ctggctggca atgtgcccat ccacaggagc ggaacaactt gatcaatgtg gaaggaaagg 121620
aaagaggtga ggctgtactt ctgccagaaa tcaggcacca gaactgtttc aggaacagag 121680
agtagcccat gggaagaaac tgggagagga gaggctgagc tgggaaagtg gctccaaaga 121740
gagacactca ttttgatctt cctcagtcac agcagtgtca attggaggcc ctgggatcac 121800
tcttactacc cgattccaaa gaaacaggat tttcttggcc tggctgagag caaatagctt 121860
ccccctgagt gaggctgtcc ttcaaagtca gcagccttag ttgcccacac tcctgtgcag 121920
aggctttggc tactgtggca cgatgccagg cagatcacca cagctaatga tgggttcacc 121980
gcacttgaaa cttttgcccg ttacagcgga gagatataag ttcctgctgg gcggtaaaat 122040
ttccctacaa ggaaccacct ggcattgggt gggacggatg ttggggcaag gggggaagac 122100
tggggagggg gatggacaca ttatcgctcc agcactcttg tttcagcctc aacaacagga 122160
agagagaacc cacaggcagt taggccatgt ccatcaaatg accccatatt gtggaagaat 122220
tgacattgca ctatgcccaa gagacttggg tggacatggt cctgggagtg cttgagccgt 122280
ctaatttctc agggtcacac tcctgttaac aaatgcactg gccagtgcaa tcaaatgtgc 122340
catttctagg accaaagttt gtatattcct ttttaatatt ttttttcact tgtgttgatc 122400
atttgcctta aattaacttt ctactttgtt taaaacatgg agaattagca agctgccagg 122460
aggccaggca gggaaaccag gatgtttcca tttaccttgt tgctcccatat cctgtccctg 122520
gaggtggaga gctttcagtt catatggacc agacatcacc aagctttttt gctgtgagtc 122580
ccggagcgtg cagttcagtg atcgtacagg tgcatcgtgc acataagctt cgttatccca 122640
tgtgtcgaag aagataggtt ctgaaatgtg gagcacatgt tgtttaggta taaaatcaga 122700
agggcaggcc tcgtgaggcg aggtggcaaa atttgatttc ttggaggaca cctgagcata 122760
tacggtcaaa gtctgatgac aacaccagta gggatgaagc tgggagtggg gtggctaaga 122820

-continued

```
acactggacc tgacactatt agacatgggt tccagcttca ggtctattac tgctcactgt 122880
ggccgagcaa cagagctact taggtaaaat ggtgatggtc ataacactag cccacaggga 122940
ggttacgaac ctctggtgac aatgtaagtg aaaggcccct gagaaagagt gagggagttg 123000
caaatgtcag tagccatcaa gatcttcttt aagaatagtt tccactaaag agatgattgc 123060
tttggtttcc agccttcttt gttttgtctc cccgctgggc cttctacctt taaagggctt 123120
tggctctggg ggaattgagt tggctggggc ttgatgactt ccaagaggac acaagtggag 123180
atctactgcc tgctcttggc taactacctt cttcaaagat gaagggaaag aaggtgctca 123240
ggtcattctc ctggaaggtc tgtgggcagg gaaccagcat cttcctcagc ttgtccatgg 123300
ccacaacaac tgacgcggcc tgcctgaagc ccttgctgta gtggtggtcg gagattcgta 123360
gctggatgcc gccatccaga gggcagaggt ccaggtcctg gaaggagcac tgcggagaga 123420
gcgagggagg gagcctggtg aggtggtcct gccaggaacc atgctttgac atcagagagt 123480
agaaagctca gagaggagga aagggcttga aagaatcccg agcttctaaa gatcatccct 123540
ctctgggcca ggcgtggtgg ctcatgcctg taatcccagc actttgggaa gccgaggtgg 123600
atgaatcatt taggtcagga cttcaaaacc agcctggcca acatggcgaa acccottctc 123660
tactaaaaat acaaaaatta gctgggtgtg gtggggtgca cctgtaatcc tagctattca 123720
ggagactgag gaaggagaat cgcttgaact caggaggtgg aggatgcagt aagccaagat 123780
tgtaccactg cactccagcc tgggcaacag agtgagactc tgtctcataa aacaaaacaa 123840
aacaaaacaa aacaaaataa aataaaataa aataaaaaga ttatccctct ctgaagctca 123900
aggaggttaa gggtgtactc aagggcacac agcaggttag aggcagactc aagattagaa 123960
tgtgggcttt ctgacacctt acaggctatt cttttagaat aaatcccatt tctactttgt 124020
tcatcttttt tgtacatgcc ccacctacac catacatgta taccttctct atatcttttt 124080
gtatccctaa tgctgtcaca ctatgatttg ctttttcatg cagatgacca taacattttc 124140
cattcaccta tgctcactca gcaagtattc aatttttcta cactgttctt ttttttcctt 124200
tttcataaca ctgtctcata ggcattctgc aaatcctgtg agagtacttt ttgtgaaatg 124260
ttaccacttt cctcttattc agagaagctc cgtattaagg cttcactgag gttgccttaa 124320
ggcatgataa tggttcaaag gcttgaaaga cagttaaaga gacctgtaag tgcacaaaag 124380
aaagttgagc aggagagaat ttcctgcctg gagcagagcc aagctgctgg aagaggcaat 124440
gggggcaaag gccaggcaga caagccaatg ggctcctccc acagctgcag ccaacaagtt 124500
atgccagtct taaaacttct aaagaaatat gtttttaaca agattgagga ctggattatg 124560
aggctagggg aggctatcac aaactggaat aaaataaagc cagagaaaag tggctgcctt 124620
ccaacctgca caactgacct agctaggctg atggctgggc cacctaggaa ggctactgag 124680
catcatataa aacagaaggg acagcaggaa tataacatgg ctctttgtaa ggatgagtct 124740
gaaaaatgac catttgctgc ccaaatgccc ttagctacaa ctgaaaatat ttcagaactg 124800
gaggttgcag gatgctggaa tctcagagat catccagctc agccctttat ttttcagatg 124860
aggtccaaag cgggtaaaat gacttgtcaa ggtcaaacag caagtgaatg gttttctttc 124920
aagtctcaat tcatcttttt gtttatatca tctatgtctt gttgttataa gcttcacccc 124980
aggtagcaaa aaactattct actcaaaagg ggtagacata tgttagttct caagatcatc 125040
tcttggtttc agagtttaac tcaagtgatt ggcataggct gaatccatct cttaaaagga 125100
taatcaaatt tatgttgaag acttggttgt cttcctacta tgaaatggga aacattatca 125160
```

-continued ctactcctcc cctgtcacca ccaagtgtgg ccaccaccac caacgttagt gagtgactgt 125220
ggtgatatga tgaccaagtg gccaggtcag caagtggtgc agcctgtgtc tcactggaag 125280
aggttaaagt ctttctaaaa caaaatacca tggcatcaaa gtggcccaga actcccttct 125340
ttgagctttc cctgtgttag agcccttcct tgggttggga gttaaaccca tagtcttacc 125400
ttcatctgtt tagggccatc agcttcaaag aacaagtcat cctcattgcc actgtaataa 125460
aaacagggac atgtctcaat tatgtcttct aaacaggttt atttttcctt ccctgtgtac 125520
aagacttgac tgttcataag aaactgcaaa cagcctgcct ctcaaagctg cctgaaacac 125580
ctggcaagtt tcacagtgat atgcgcagaa cagtccagaa ggcagattct aggcctggca 125640
ggtgggcacc ctgggtgctc cctgttggat cttgaggcct aacctctagc ccagcagagt 125700
cagctaaaat ctgagctctc cctctccctc caagccacac tttgcaaagg gattccttgt 125760
attgtgggct tggaatcttt tctccccatt tgcctctgca ggaagccctt gcaacaacac 125820
atctggatag cctccaggtc ccaaggctgg agggacttgt aatgggaaag tagtctttaa 125880
atcagattta cttggcaccc tgtttgccac tgaaagaggc aatttagggg aaaaatctgg 125940
tctccaagca cagataacac tctactcttg aaagaggaga cctgctcatg ttactggtct 126000
cagcgtctcc actgacctgt aataagccat catttcactg gcgagctcag gtacttctgc 126060
catggctgct tcagacacct gtgtaaaaag gagaaaatga gtgacttccc catgacggct 126120
acgttcatgt gtgatttctc tcagcatcca gtgcatggca gtcatgcaaa gaaatgatct 126180
ctgagtaaat gaatgaatgt gtgaaagaga agtcctttgg gtctagagaa aagcatttgc 126240
taaaccaaac cccaactagc aatgtattgg ctaggagagc tggagcagag gctttgacac 126300
taacctttag ggtgtcagct gttagataag cagtatccat tcccagaata tttcccgagt 126360
cataagcatt atattacacc tggcattttt gcaaaaagct gagagaggga ggcagagagg 126420
gaaggagagg gagagacaga gaaagaaaga gagagagaga gagaatatgc atacacacaa 126480
agaggcagag agacagagag actcccttag cacctagttg taaggaagat taaagtcata 126540
cttgagcaat gaagattggc tgaagagaat cccagagcag cctgttgtgc cttgtgcctc 126600
gaagaggttt ggtatctgcc agtttctccc tcgctgtttt tatagctttc aaaagcagaa 126660
gtaggaggct gagaaatttc tctgttgaat acctgatttc acaatcaagt taaaggaaag 126720
gggaaaagag tattggtgga agcttcttag gggaggggac taataaactg agataattct 126780
ctggttcatg gaagggcaag gagtagcaaa ctatgacaca ttttgcaaat gtatcaccat 126840
gcaaatatgc attgttttcc tgacaatcgt tgtgcagttg atgtccacat taaaatactg 126900
gattttccca cgttagaaga atgtttaaat ttagtatatg tgggacaaag tggaagacac 126960
acagatttat acatgcacat acttttcttc attcacttct ttgtacttaa gtttaggaat 127020
cttcccactt acagatggat aaatgggtac aatgaagggc caatagccct ccctgtctgt 127080
attgagggtg tgggtctcta ccttgggtgc tgttctctgc ctcgggagct ctctgtcaat 127140
tgcaggagcc tctgaggaga aaattgacct ttcttggctg gggcagagaa catacggtat 127200
gcagggttca ggctcctgac ggagttgggg caaccctgga gataagctca cacaaccctg 127260
caagaccagg tgctgttacc ctagccaatc tcatggatga accagatcaa tgccagatga 127320
gctctgccta aaatgatttt ttggtgaact ctgaaaagtg gaatattgtt tctgtaagaa 127380
tatccatctg agactctatc tcttggtaat accaagagtt atcagtttct ctttaaccga 127440
gacaccagca aagtgcctgc tccagggtaa tgcccagggg agccctccat ttgtagaatg 127500
aatgagagtc caggttatga acagtgcctg gagtgtagga acaccctcct ttgcctcttt 127560

-continued gacaggtctg catcataaca cttttttttt ttttttgaga cagagtctca ctctgtcgcc 127620
caggctggag tgcagtggca cgatctcggc cccctgcaag ttccgcctcc cgggttcaca 127680
ccattctcct gcctcagcct ccccagcagc tgggactaca ggcacctgcc gccacgcccg 127740
gctaattttt tgtattttta gtagagacag ggtttcacca tgttagccag gatggtctcg 127800
atctcctgac cttgtgatct gcccgcctcg gcctcccaaa gtgttgggat tacaggcgtg 127860
agccaccgtg tccagcctgt aacacttctt atagcactga gttgaaacct tgctcctcct 127920
ggttcctcca ggaaactgaa atctttttga gccaagtcta gcacagtgcc tggcatgtac 127980
attcaggtgg tagagtttgc tgcttgaatg ggtgaatggg aatttgacag catttttatt 128040
caaattagta tgtgccaggt atcgtgctcg ctctgcatta tccaagggag tgagcctctg 128100
tgcaagtatt tgagacacga gggaaatagg ttctactgtg ggaaaaagag catttcatgg 128160
acttgctctc caagcagcct tctgattttt aatttggctc ccagtatctt gatatcagga 128220
gtcagtcaca agaactccat ctttagtaag ttatattttc cacaggaaat ctaaaagctg 128280
ttcaacatgt tagtttcctg tgaatttgat aagccataat ccattcctaa cactgagccc 128340
tcctgaaatt tggtgtctgg tcctgcagat agctaaaagc cctgtctggg tggcctaggg 128400
actcctctgt tttgcctcca caggatccac tttgcaaatt aaccactggt tctcccgttg 128460
taggaactgc caccttcctc agagcctgtc tttcttcctt ccttccttcc ttcctctttc 128520
tttttctttc tctctctctt tctttctttt cttttctttc tttctttctt tctttctttc 128580
tttctttctt tctttctttc tttcttcctt tctttctctt tctctctttc tctctttctc 128640
tttctttctt tctctctccc tccctccctc tctctctttc tttctttttc tttcttttct 128700
cttttctttc tctctttctt tctccctccc tctctctctt tttctttgtc tctccctccc 128760
ttctctctct ctttctcttt ctctctctct ctctcctaga caggatctac ctttatcccc 128820
caggctggag tgcagtggta caatcatgca ttcattgcat gatcacagca gcctcaaacc 128880
cttcctcaga gtctttatgc ggcaaccagc agggtctgga gggttggtgg ctctgtgaac 128940
tctcctgaca gaacacagag atgtctttgg tctgttgatg tgattacaag ctgaacgaag 129000
gaagatcaaa gccagtgaca ggaagggaga tatgcaaggg acccgagcat cagctctgag 129060
ttagtccatt ctgcttctgg gacttgggat acaggtcaga aaccttgagc ttctacttct 129120
ccatcttcca attgtagcat ccaggacctc agaatctgcc agctaagagg agccctaatg 129180
attgtctggt gggatatggt gggaccacag agatgaagac atgaatagct atttgaatgt 129240
gaacagcaga cgaagaaatc aaggctagga gggtggaagt gactcatcca atagcacagt 129300
gtggttgaag cagcactagt atccaggttg catgagcccc tgatgctttc gctcgaggga 129360
aattttggag ccatggggca atgcccccctg acgtaacagt ctccacagtt ctgccatgtc 129420
tcatcctggc cctgtaacct ggacccaaat ctgctaccat cccatccatc tcaggaagtg 129480
aaacctctta tgtcaaatag gttgtgcaac gtatgtatca gatcctgtct tcccaaggag 129540
accgctcagg ccacagcact tccttccgat ccccaatgag cagaaaatat ctcgctataa 129600
acatagttgg cactaaggga gggagtggaa gagtgatgat gatgtagatg gtgatgtagc 129660
cccaaggaag tggaacaagc agagatgggg agctggaaat gccaggatgc tccagctttt 129720
ggggaattat tcagctcttg agtcactaaa gcctttctca gctgcaagtt cctctttacc 129780
ctgtcaggtc attcttccaa gacaggagac tgacatttat tcaaagcagc aagtgccctg 129840
ataccatctt gtgtctaatc atgggcttcg cagccagtta tcaaggttga tctcatctca 129900

-continued ttggtcttca atcattttga acaagaagac aagcaaaata atcatgggtt agttcttata 129960
ttattgtgtg tacatgcagt gatgtctgtt ctttgtagtg agctgttcct tccttgttca 130020
ccctcttgct tagaacagaa ctaagcaatc tgcccccaac attttcccca atttcccatc 130080
tcattcttgg cactggcttc ctaatatttg ttcttatgag tcattttctt gtatcatttc 130140
catgagtccc tctgggatct taaagtatga aaaatgttgt gtgtacccac acctgtcttt 130200
gtggatattt ctctcctttc ccttctgctt ctgggattat ttgggaatgg gcactatgat 130260
ttttatcata tcgcttccac ttcctttatg gcatcatctc caatgggctt cttctccctc 130320
ttggatccag gttctcagat tggggacatg cagagtccaa ggaacattcc attctcctcc 130380
ctggtctaga acaaggaggg cttagatata tgagcaggtg gctggggctg gcgagctatg 130440
tagtctccaa tggcttttcc ctgatgtcgg agttgttatg tcagttctgg gagaccaata 130500
agaccttgtc cttcctttgg atccatcaga aaaagcccct gggtgggtaa gatggatggc 130560
agggctctcc tactctatgt cttttctcac acctagtggg tataagagag gggaccacaa 130620
acagaggggg ctctggtacc acttatccag ggtctggaaa cattttctgt aaagggccag 130680
ataataaatg tttcaggtac aactactcaa ccttgcatca tttcagaaaa gcagtcagat 130740
aatacataaa tgaatgggtg tggctggact tgtcctgcgg tcccctgtct tatatcattg 130800
tattatatca ttttttctta catacaaatt tagaagcaat acttaaaaaa aaaaaagccgt 130860 cctttattga gcacctacta agtgccaggt accttttttt ccctcattat cttattaact 130920
cttcataata acctttaaag tagataatat tgaaccattt gacctatgca gaaactgagg 130980
ttgagacaat aaattattta agaccgcaca aacagtaaat gctggaacta cgactcaaat 131040
atgggttaac tgaaccaaaa ccagatcttt atttctcact tttaattgtt acatatgttt 131100
attgcctcat ctcctgtcca catggtgccc atcggcagac tcctttctca ttctcagtga 131160
ttgagtgaca ttctaaacta cattggcctg gcagattcac ctctgtcccc taaatgtttc 131220
cacattgtcc ttttaggatt gagatcctct ctgttccctt gtcttccctc ctttcttctt 131280
ctggcggtga cgtgctgtgt gaatttgttt ctttctcctc tcagggtagt actgggactt 131340
tccaaatcag ggtttttagt gatctctctt ccctttttctg agtttcttcc ttattcccat 131400
tcactttctc atctataagt ggcagctttg ttgctggagg atttcctttg tccttttatt 131460
cttctttaag actttgtcat aactgtcaaa agcaatccct tgaaggtatc tgtccttgga 131520
attgtgtgct tatgatgctg aaaaatactc tcttcctaaa gctattataa atgctggcta 131580
gctgcaactc ttgaatacaa acacattcag acatgcacac actttctggc tcccaaaaag 131640
aaaaaaaaaa atcaatttat aataattctg atcctttgct tatttccaca aactccatga 131700
aaattgtaca ttgtccaagc aacatttctt aatattctct ttttctctca tatccatttt 131760
ccttactgct gtctccacct atctcttcca aactccctgt taaaatccct gccccagcga 131820
acttttattc aattttgtgg aatggaggct gcactgattt aaattaaaaa aaaaaaaaaa 131880
atccctactc catgtcccag atccctagtt gttttttgtt ttttgttttc ctgagacagg 131940
gtcttgtgtc ttccatgctg gagtgcagtg gcatgatcat ggctcactgc agcctcaacc 132000
tcctgggctc aagtaattct cttgcctcag cctccccagt agctgggagt tcaggtatgt 132060
gctaccatgc ctagctaatt tttttctttt attttgtaga gacacggtct tgccaggttg 132120
cccaggctgg tctagaaccc ctgggcggac gtgatccgcc tgcctcggcc tcccaaagtg 132180
ctgggattac aggcgtgagc cactgctccc ggccttgggt gcaaatttga gctttctcac 132240
ttattagtgt aagacataca gctaatttct aaatcttcca aacctcagat ttttcatcca 132300

-continued tgaagtgagg attattatag agctcactaa taacatggct tcaaaaatat ataatgccaa 132360
aattgagatc aaaataataa atctatatta catgggagat cttaatgtac ctcttatatt 132420
attgatagac taagatgatc aaaaaaatag aaagagagca gtaaggagag caagcattta 132480
atcaatagga ccaatacatt ttaatcaata ggatcctcag gaatatatac agaataccaa 132540
acctaacaac tgcagaaaac atgccaaaca tttaggtaca gacattgttg gaaaatgcaa 132600
tcttgaaacg agtggactga cattcagaag atattaataa gagcactaat gatggggatt 132660
gcaaccatgt ctttactgac ttccagaagc ttcttacagt aaacatgaaa tcacataatt 132720
tcttccactt tcctactgtt tcttgttctg ggctctgtcc tgcttactgt ctaatatctt 132780
ggccccttaa aagttgctaa tcttccaaac ctcattcctg tgactgggcc gctggtcctt 132840
gttcatgggc cttgaaaata ctgactgtac acttatctgg agcatccagt gcctaccacc 132900
tgacccagat tcctcattgc gctcctccct cctccaccta ttggaatttg ctcatacccg 132960
tgtgagaccc ctccctttcc ccccatctga atttttatca agacaacgca ctgccatact 133020
ccctcgtacc ctgctctggg catcagactg aatgtttgtt tccattgagg atctgcagct 133080
gcatcagttt ccccagcacc gtccaacccc ttgagcatgg ctagtcctaa agcagagaat 133140
tagcctttct atccctgctg ctatacatgc tgggacaaat aataagaaat gacagcattt 133200
tatgataatg caggctgcag gaggcaggag gcaggaatca aattcgtgct tatcaaatag 133260
tgctccaatt ctttgaatat tggactatag aatatgtcat ggatctatgc tcaggtgggt 133320
tccctattac tcactccact gaggccaggt tgtgggatta gctgtccaag agggagtttc 133380
agtctcacag catagggtca ttctgagaat tactggccca cacttgtgtg gagacctcca 133440
gagaacagaa tctgggttgg tgccatgtac ttccaggagg agagaagtgg caggatgccc 133500
agccccacaa tcagagggga aggggcagag ccacatgtat gaagatcctc tccccagtac 133560
gtgccaatca cagggcttcc tagcttttgg gccaaggaaa caatgtggga agcaaaaaag 133620
gacaattttc tcctcccttt gcatgaagac tgagcagttt taccagattc ccagggaaac 133680
acccttccac tctgggttga atgtgagtga gagacattca gctggaacac tagaaaaact 133740
atttcctgag ccactcacct ttagccctag aaagtgttgg atttgtcctt catctttgcc 133800
acagtagaga ctgctgatag catcagaact tgggctctgg aattagacag atatgggtac 133860
aaatctgagc tctctcactt attagtgtgg gatgtagagc aacttttaaa atccttccaa 133920
acctcagact tctcatgcat gatgtgagga ttgtaatagg gcccacctaa taggggtttt 133980
tgagaattaa aaaagttatt caatgaacag catttagcaa gatgcctgac cattgagaaa 134040
ataacaaatt gtttattatt attgttatta ttaaacatct ttcctgcacc ttctgactgg 134100
gggcatcgta tcatcagaaa tacttaggat gggatggatt cctgcatggg ctgagtcaag 134160
ggtgcaataa tggaggagtg aagaaggaag aaatggaggc agaaatcccc aggagcccag 134220
catggtacaa ggctgagcta gtgctgcaga gcctccttgg aacagccaca gagcttgcat 134280
ctggccctgg gaggaacctc ttctagctgg caggaccagc cacaacagtg gccaggggat 134340
ttcccagggc gtgggctcct aggagttcat ttggaccaag cctgcctgga gaggggttat 134400
aacagggatc cttccctact ggcaggtgat ttacccctcg gtgagaagct caggcatttg 134460
tttgatggaa ggtggaaggc cctgtgctgg gccagtgact atcagggatg ggcgggtggc 134520
tggaaaatag caaataagac aatatgataa cacagttaac caccacacta tgtgaagcta 134580
caatatgggt atctgtaata gacaattcca atgtagagaa taattctaag gtgtcattct 134640

-continued ccccgccaat gccataagca cacggcctct gcctgggttt ctcactgtgg aatgtcctcc 134700
tggtctcctc atgcccagag agtgggaagt actcctactt taacaccggc tttcctgtca 134760
tctccctgca gccctcctca gccccctctg cacagggagg tttcctccct gctgctgcag 134820
tgctttgtac ttgttagtgg tacctgcaca caggtattgg tgtccttgtc tcaccaccct 134880
acatcactgt aagctcccca ggagcaggct tcctgtttga ctcacctgtg atcctccacc 134940
tcccaccctg tagtgcctca agcattgagg acaatcactg gctgcccctt aacccagaaa 135000
tgctgccgag acaggaggcc atggcccaag ttcctggaat ggggtattac tatgtcagca 135060
caaaggcctt tgcacaaatg aaggctttaa aaatgcagtc ctagtcaggt ggaggagggc 135120
ttataggatt cccaggaatc tggatcattc tcttgagagc tttcccttgt ctctgttaaa 135180
actcacatcc tacggcccaa ataacaacaa aaaatggatg taaattcttg aaataacttg 135240
tggatggggg aacaaggccc accccccaga tctgccagaa gcttcaggtg agggtcccaa 135300
atgccaaaaa gtctggtatc agagaggatg gccagtgacc tggggacaca tgccctttgc 135360
tgtgtcactc aaggagcagc agcctcggcc ccgcacagtg accaggaccc tggcttccca 135420
cgctgggcag gagctggtgt ctgatgaagg gaatgcctgg cagcacgtgc tgtctgtctc 135480
ctcgtgtcag cttacctggc tttgctgcga agaggccact cgcatttctc aatttttat 135540
attttttaa ttttttaaat tttttatttt atttttattt ttatttattt atttattttt 135600
aatttttttt taatttttta aattatgctt taagttttag ggtacatgtg cacattgtgc 135660
aggttagtta catacgcata catgcgccat gctggtgcgc tgcacccact aactcgtcat 135720
ctagcattag gtatatctcc cagtgctatc cctccccct ccccccaccc cacaacagtc 135780
cccagaatgt gatgttcccc ttcctgtgtc catgtgatct cattgaattt ctttaaaggt 135840
ggaatctctc agtggggtct aatctgttca gaaatatcaa aagagtatcc ttgggaatga 135900
ctggaattcc agagtcatct ggtaatcctc ataaaacaac tcctggatgt ctctcagcac 135960
atctcccacc ttgaacgcag gaggctggtt caaatggagg agcatcgctc tactgcactt 136020
tttttttttt ttggcctaaa gtgcaaaagg ggatacgttt catgtaaata aatcaactgc 136080
aaatcgctag ttatgctgag ccctgtcccg tgctgtggac acaaaggaac caaaggcttt 136140
tctccccgcc caacacacac ataacacaca cacaaaatca taaaaacata catacccca 136200
acacataaca acacacaaca cacacacaaa atatatacac acaacacaca ccaaacatgc 136260
ccacaaacct gtgtccagag atagatccta ctggtgggtt tgtggtctcg ctgacttcaa 136320
gaatgaagcc gtggaccttc gcagtgagtg ttacagctct taaagatggc atggatccaa 136380
agagtgagca gtagcaacgt ttactgtgaa gagcaaaagg acaaagcttc cacaacccag 136440
aaggggaccc cagcagggtt gctggttggg gtggccagct tttacttcct tttggcccct 136500
cccatgttct gtttccatcc tatcagagtg ccctttttc aatcctccct gtgattggct 136560
acttttagaa tcctgctgat tggtgcattt tacagagtgc tgattggtgc gttttacaat 136620
ccccttgtaa gacagaaaag ttcctgattg gtgtgtttta caatcctctt gtaagacaga 136680
aaagttcccc aagtccccac tggacccagg aagtccacgt ggcctcacct ttcaactcca 136740
taatggcatg aaaatacata tgttgtacaa aacatacata cacaaagtat acatgcatct 136800
ccccaaatat acacatacca cagaaacata cacacaggaa ctcagctacc tgtcaaaagt 136860
ctgcatggtg attgcctctg cagtgagtag ttagaaaagt gaatttgttt ttcaataaat 136920
tggagtcctt aaaaatcgtt gtaagataga aaatttttaa aagtatataa aataaaatat 136980
gtatgtcctt tggtctagca tttacacatg taggaattta tcctagtgga gtaatcaatg 137040

-continued atatatgcaa agatttggac aagcatatta agcacagaat tatgtatgca tatgtgtgtg 137100
tatatatata tatatctcat acatataata atgtaaaagt gaaaataact cagatgttca 137160
aaattgagga ttagttagac tatgatctgt ccatatgtga catacaagtt agctgcccct 137220
tattctctcg agcttcaacc tcctataaac agtgtccctt gtatatcagt attggtacag 137280
ataatcgaac ttattgaggt tttacatggg gcaataaagg caagagttta tgaatactcc 137340
atactacact aggtagcacc ccctattaaa gacaaactct tctctctcat ttcccttcct 137400
ttccggaacc acttggttga atctctacaa gtctctattg caactgcctc aacatggcac 137460
cctccctgca tctccatctt ccctgtcctg agagcaatgg cctgctgccc ccacactcac 137520
atcctcattc attccagaag tgagcaccac agaagtgcct acagttaccc caaccacctt 137580
cttagaagat aagttagtgt ttgttttgac tttttaaaat ttttacttcc tcttttcctt 137640
cacaatctca tcccatccca agaggtttat caagaagttc tctaaagata tgtgtctcct 137700
tatggaattt aacagaaatc agggatttgt attctagcca tcaagggaat aacatttttc 137760
caggtcttta gacaaataat ggaatacctt gcagtaatta gatacactat tgtagaaaag 137820
tattgatgaa atggaacgat gtttgagata tcatattgag tagaaaaggc aagatacatt 137880
aagtaggaaa tgtatcttac aaaataattt gtcagacaca ctcctatatt tgtatgttat 137940
ataaatgcgt atgtgaagaa aggctagagg atgagaccac agtcttcggt gaagtttaag 138000
agatgatgct gcagcatgct cagaaaggct tggtatagtt ttttccagta attaaggact 138060
gatcttaggt aaattgtcca tcctctctaa actgcaccac cttttgtctg taaaacagga 138120
aggatggtat ttaccccccag ggtcatcaaa ggatttggtt ggagaaaaat aaataaatgg 138180
gctgagccca gacctggcac agtgagagca cagtggttga ctattgtgct ggcctgttgt 138240
tcctgtgtta ttgacatgct gctggtggtg gtccagaagc tattacctta attggttatg 138300
tggatttccc ctcatactga gcagctgtgt gtggtgttgt aaaacatagc catacacagt 138360
aactgacaag ggcaaatgtg atggaaaaat gcaaggaagt gcagataaat agctaatggg 138420
ctgtagaagg aagctagtcc ttggagggct tgatcaagga aggtcctttt gcatgtcacc 138480
tttgaagaag aggggacata gaagaggtat agtgcatccc ggagtgtacc tggaagggaa 138540
catgaaaaga ggacattttt ctctgggaca tggggactcc acttgcatga actctggaat 138600
tggggcaaag aaccatcatg agaacaaggg cttccttgaa cctcccaggc tcattggctg 138660
atctaaaccc tgtgtcccct ctttccttca ctctcctctg ttttctatac ctgtattatt 138720
ggactggact ggaagccacc tgatctatca caagtacctt gaaatgtgtt gaataggtgt 138780
ggcacagtcc ttagcagagt ggcactaccc ccacaggaat ttgtttatac ctttggcatg 138840
gaaaatagca ggaaatgagt gatcactgat aactgaggat gctatttatt attggccaaa 138900
ggaatacttg tgttgtattt gcataaccac tcacaaactg ttgattacaa atgagtacca 138960
gacctagctc cttcaagtaa aggatcttga gaactgaagg caaacagagc tccaggagtc 139020
caagacagag ccacagacca cgaggatccc tggcccaggt aggtggtcct cctgcactgg 139080
ctttcaaggc caacaggatg gatggggaag tagagtagca tctggccatc tagacccttg 139140
ctttttatcc ccactggaag cacatctgaa tttctaaata tgatctctga gacctgccca 139200
gaacaccttg ctctcagccc cagtagcagc ctgctctctc ccaggagggc ttccactaac 139260
aagtagggca ttgctggagg gccaggcaga cactagctta ggaaatccac caaccctgga 139320
aatgctagtc ccttctctga aggctcagaa gactgacttt agagtctaga aaatattggt 139380

-continued ccttgggaac agattttgag tgcaaagaga tggacttcag atggccagat gcactgcttc 139440
tttagggaat tctgtgaaag ctccctgcat ttatcttaat acaggcagca gatttcatga 139500
gtacccccga gggatggccc caggtcctcc agcctgtgag catccttctg tccttcagca 139560
gcaccacagt atctttatat gtctttggat acctacgttt ctgccagaca tctcttgctc 139620
tgatgttctg gctgccaaat tctctgtcaa gcgcctccaa ttttttgtgt cctttgattt 139680
accccaacat gacaaaggca gttgtgcttc atgtattcag ggatactgcc aaaccacaaa 139740
caggttaaaa tcaaatagca gatatccctg ttcctaaaga cccatcagct ctacccacct 139800
gctcctgctc accgtcctta ttgttgagtc ctgaagccct tccttgtcat ttttattttt 139860
tgcatgaaca atttagttcc ctttgtctca ctcctaaacc tttctcaaag gattggattt 139920
gtacacaaac tgcctatctc tgcaatctta gaagtgatat gattctgaac aaatcactta 139980
acttttgatt ttttattggt aagatgggaa taccaatttt tgctccactt ctgtcctatg 140040
ttggcctggg ctgatgttga aagctctcgg tcaactgaga tagggtgtgc agaatttata 140100
tatataaata tatctcctcc aacccctccc aatgaagcaa gtcacgtgag tcaatcctac 140160
cctaagatat tagggattga gcctcctggg acatttggtg gcttaggttt tcatgaaaag 140220
aggttgcaga gcaactgctt tttgttaggc aaagattagg ctactgcaga gactcagcaa 140280
acttctatag aaggtgtcag atggtaagta ttttaggctt tgcttgccag atgatctctc 140340
aactagttaa ccatgctatt gtagcctcga agcagccaga gacgatctgt aaacaagagc 140400
atgtagtgtt ggcataaata tagtaccgcg gcaataagtc tatttactgt aaagttaatc 140460
aaatttacat ttcagaacac ttaatctgca agagtccttt ccaagaccct atacctaatt 140520
ttgtgtttac aattttatat ttgttttctt aaagaagacc accaatataa actatatcca 140580
gccttcatga taagtacata agaaactatg caaataaggg ggaaaaaaaa caaagaaaaa 140640
tacctagttt actaatggtt cacttctgaa tagcacatat tcataatgat acaagcactc 140700
attactagtc taggaaaatg aagatataat tgcattagga agatcaagag gtaggaaatg 140760
tggatgtgtg tggtatagac tagggcagga caaagaacct aaatcctcat tttctaaaga 140820
taattgttaa tacgtaaaac tcaaaattca agaagtaaca gtaaaagcgg tcattaagaa 140880
acaagcacta aacaccagat aggaagcgag agatggggga agagggcaag aatctgatta 140940
ttttttgcaa caaattttgt aaaaccattt gactgtttac atgtagaact tggatctttt 141000
ttaaaaaaca caaaataata atactattat tttttaactg gatttttgaa aaagaagata 141060
aaagtctcat tttagtaatt aaaactcatt ccaggttagt ccactcaaaa cttatattcg 141120
aaaattaaaa ctttgggagg ctgaggcagg cagatcacct gaggttggga gttcgagacc 141180
agcctgacca acacggagaa accccgtctc tactaaaaat acaaaattag ctgggcgttg 141240
tgcatgcctg taatcccagc tactcgggag gctgaggcag gagaattgct tgaacccggg 141300
aggcagaggt tgcagtgagc cgagatcaca ccattgcact ccagcctggg caacaagagt 141360
gaaactccat ctcaaaaaaa aaaaaaaaaa aaaattaaaa cctctggaag ttgagtttgc 141420
agatattcat tatgctcatt tttaacttgt atgtttggaa aatgtcatga tgagaattga 141480
ggttggggga tgagaaaaaa agaaaaacat caaccccaca gcccattcaa ttttcagccc 141540
gacccacagc tccggggaag ggcagcaggt ccatccttca ctctttcttc acctctttcc 141600
cctccttctg gctcttccac ctctaagttg gagcccaaga agaggcactg ggaaatggaa 141660
aagtcttttg tacgtggtac ttgccgggga agctgccatg aagacctggc cccacggtgg 141720
ggagggaatg cccagctgag gcctcgtgcc catgctagga tagactcgtc cagacatgtc 141780

-continued

```
aggtggtctg acagggcaag cagcaggaag tcatgtatga gtatgaactg atctgtatgc 141840
aagggcgggg agaacacgcg gaggaatggg gcgtgagaaa acagcacagt acgtttcttt 141900
agcagctgtc tctgctcagc catgggagtc accagagaaa gaggcttgga ggcgttattt 141960
tcactgtgag atgtgagtgt aaaaaagtgc ccaagacaca gtgagtacca gggagatgcc 142020
ctctttccct acccgaatgc agaatggcca caggccttaa aacacacaca tggttcctca 142080
gaggagagag gcctccacag tggacacccg cattctcccc tggtcagcag cagcagggcg 142140
agtgctgggc catcatgaag cttcacaggc aatgagctct cagcaataac aggaacagtg 142200
cctgggggac tgtagctgca agaccgattt tcatgtaaga tggcctctga ggactccgag 142260
atacaccagg ctgagactag ctggcagctc caagttcttg gtcagaagag aacaggaact 142320
agggaaattg gaattactgt tactacaatt cctttacatc cgcacaacca tgaggtccag 142380
agagtctctc ttattttttt tttaaagaca gggtctcact ctgtcgccca gcctagagtg 142440
cactggtgtg atcatggttc agtacagtct tcacctccca ggctcaagtg accctcctgc 142500
ctcagcctct caagtggctg ggacagcagt tgcatgctac caggcctggc tttttttttt 142560
tttttttttt tttttttttt tcggtagaga ctgggtctct ctgtattgcc caggctagtc 142620
tcgaactcct gggctcaagt gatcctctgg cctcagcctc ccaaagtgtt ggaattacag 142680
gcatgagaca ctgcacccag ccagtatagt cttttaacag ctttattgag gtacggctaa 142740
cattgaaaaa actacacaaa tgtaaagtat gcaatttgat aattttgaca aatgtacaca 142800
ccagtgaaac tatcactaca gtcaaaataa tgaacatatc catcactccc aatttcctca 142860
cgccccttgg taacccctct ctcccaactc cctgccccct aacatcagac aactactgat 142920
gcattctgtc tccataggct catttacatt ttctagaatt ttacataaat aaaatgacag 142980
agtatatact ccttcatgta tggcttcttt cagcccaatt atgtcaagat tcatgcttat 143040
ggctgtgcgt atccttagcc catctctttg tcttgctgag taggatacca ttgcatagac 143100
agaccacagc ttgctcatcc attcactctt gacaacgttg aattgtctct gttttttgca 143160
atgacaaata aggttgctat gtacattcct gtatagacat ttgtaaaagc acagcatttc 143220
atttctcttg ggtaaagacc taaaagtgga aaggctgagt catatggtaa atatatatgt 143280
ctaacttttt aagaaactgt caaactgtta cccaaaggga ttgtacaatt ttacatcccc 143340
accagcagtg tatgaaaatt cccgtacttc cacatcctca ccaatatatg gtgtggtcaa 143400
tctttttaat tttggacatg ntaatgagtg caaaatgagg cccagagtgt ctgaagttac 143460
atttgtatcc tttttggcat ccaaaaacagg tgtcaagcat agaaaaaaca cttgttcctt 143520
gaatggtcag tcatttacaa gtggaattca ttacaaaccg gtagttctac tgggttaaac 143580
tatgccttac tgtcaacagg cacatacaca tacagacaga caggaaggca cagagacaag 143640
gcagagcatt gataagaagg tgacctgggc tctagctctg gcctatcacc tagtaaaata 143700
ttagttaagt agccatgagt aactcactta acttaccaca ggctccattt tcttatctgt 143760
aaaataggaa cattgaaaca gctaatcccc aaggtttgtg gataatcaga attacaaaga 143820
tcaatgacat ttctatgaga gaaacatatt tccaagtatt tgatggagta catcagacac 143880
aaaggaaagg aaactgaata tttttgaggt tttttttttt taccaagaaa ttcacatttt 143940
gttaaatttt cagaactacc tcctgaggaa agtgtagctg cacccattta gaatgataga 144000
aaacatcaat ctgtctgatt ccaaagccaa gttcttgcta caacgagaaa tgaaacaact 144060
ggatccctac agatgcagag acctgggccc cacaaatgtg aattctgttc cctaccgaa 144120
```

-continued

```
tagagttaca gttccataat acagtactcc ctcacttttc cacagtctca cattccacag 144180
tttcagttac ccacagtcaa ctgcaatcca aaaatattaa tgaaaaattc caaaaataaa 144240
caattcagaa gttttaaatt gtgctccatt ctgagtagcg tgataaaatc ttgtgccacc 144300
atcccacctg tccagcttat cgttagtcat tgacatcgtc tgctcctgac atccaaccat 144360
tgacatcatc atgactctat gatccaggat caccgaagca gatgaccctc cttctgacat 144420
atcatcaggc caatatcagc ctaaacactg catcactatg cccacatcag tcacctcact 144480
tcatctcatc aaggaggcaa tggatcacct cacatcatca caagaagaag agtgggtata 144540
gaacaataag ataattttgg ggcaggcatg gtggctcacg cttgtaatcc caatactttg 144600
ggaggccaag gcaggaggat cccttgggcc caggcattca aaaccagcct gggaaacata 144660
gtgagacctc ctctctctgc aaaaaaaaat aaacaaaatt atccagatac agtggtgcat 144720
gcctgtggtc ccagctactc aggaggctaa agtgggagga tcacttggtc ccaggaggtc 144780
gaggcagcag taagctgtga tcgtgccact gcactccagc ctgggcaata aagtgagacc 144840
ctgtctcaaa aaaaaaaggt aattttgaga aagagaccac attcatacaa cttttattat 144900
agtatattgt tagaattgtt ctatttcatt acttattgtt gttaatttct ttctttgcct 144960
aatttttttt tttttttttg agtcggagtt tcactcttgt tgcccaggct gtagtgcaat 145020
gagacgatct cagctcaccg caaatcccgc ctcccgggtt caagtgattc tcctgcctca 145080
gcctcccgag tagctgggat tacaggcgcc tgccaccatg cccagctaat tttgtatttt 145140
tagtagaggc ggggtttctc catgttggtc aggctggtct cgaactcctg acctcaggtg 145200
aggcctcagc ctcctaaagt gctgggatta caggcttgag ccactgcgcc tggcctcttt 145260
gcctaattta taaattaaac attgtcacag gcatgtatta atttatagga aaatcataga 145320
catatagagt tgggtactat ccacagtttc aggcattcac tgaggggctt ggaacacgcc 145380
ctcctcagat gagggggggac tactgtcatc tcctcaatca ttcttgattc aatcctcaac 145440
acaaatggtt tggccaggtc ttgcctctgg agacaaaatt gctaaggatt tagaggggaa 145500
aaaatgtagt tcactgggaa agtcacctct gctccactgg acagcaactt aaaacccagg 145560
ccatgacaag tagaaaggcc acccccactc tccttcacac ctggagtatt caggagtcaa 145620
tcatatttca ggaccaccag gagcaaactg ggaaaaactg agctgccttg aggaaagcaa 145680
tcagctccac aaggggctta agaaacaagc tctgggagga gtggttggag aagagttggg 145740
gacacatcag aaatgccatc aaatttctaa gggctacctc gtggtgtcag acctgtgcat 145800
cttcaaggac ataaacagat gggataagca gatgagattc acagaggaca tcaaaatatt 145860
ggctccccag aagggagaac attctagtaa cagagctgcc cagctgcaga gtggactgtt 145920
tcacaaagca acaggtgccc tgcctcttga atcaccatct tcacaggaat gcagtagaag 145980
ggacttaact cctgccctga agaaaaggtt aggctaggga aacagctcca aaatttttta 146040
aaaggaagca acataggcat ctactgggag ttttctaaag cctttgttta atgaaactaa 146100
agagctggga caggaaatgc caaattaaat taatagagcc ttgctttaag acaatgcaag 146160
tggatggtaa tgaaggaatg agtcttaggc cttggatcaa ccgtattaag caatgctgag 146220
catggagcca attctgttca ctagatttgc tcagaaaggg ccagacgaga aggatttttc 146280
taaaggcacc tactaccaaa aagctgccaa ggcgtccaat ggagcccaga gagaatatgc 146340
taacaataaa aagttgaaca ccctcaataa aaaagggtaa aagtaattaa tagaaaatta 146400
ctgaaagctt ttttgaaacc aaaagtagtc agcattggta aaagtctaca aaagtggaca 146460
ctttcatata atgttggcag gagggtaaaa agacataacc tttttggagg acaatttggc 146520
```

-continued aacagagtac caaaaacctt acaattgaag agaactttgg cctgagtgca gtggctcaca 146580
cctgtaatgc caacactttg gaaggccaag gtgggaggat tgcttgagcc caaaagtttg 146640
agaccagcct ggggtaacac agtaagacct cgtctctatg aaaaataaga aaagttagct 146700
gggcatggtg gcatgtgcct gtggtcccaa ctacttgaga gactgaggca ggaggatcgc 146760
ttgagcctcg gaggtcaagg ctgctgtgag ccatgttcat gcgactgttc tccagtctgg 146820
gtgacagaat gagaccctgt ctcaccagaa aaacaaggca agagagagag agagagagaa 146880
ggagagaaag aaaagaaaga aagaaagaaa gaaagatgga aggaaggaaa gagaagaaag 146940
aaagaagaaa gaaagaaaga aagaaagaaa gaaagaaaga aagaaagaaa gaaagagaaa 147000
gaaagagaaa gaaagggaga gaaagaagga aggaaggaaa gaaagaaagc aagcaagcag 147060
gaaaggaagg aaggaaggaa ggaaggaagg aagaaagaaa aagaaagaaa gaaagaaaga 147120
aagaaagaaa gaaagaaaga aagaaagaga aagaaagaaa aagggagagg gaaagggaaa 147180
agaaaaggac aaagaaaaga cctttgaacc ctgaatttca cttttagaga ttcatcttaa 147240
ggaaattcat tccaatagaa atttatcccc aggattatct aaatatttgc ttttattttc 147300
ttctagtaat tttatggttt aactttctca tgtttaagcc tttaatttat ttggaattta 147360
ttttggtatg agaaagtgtg accttttttt gttttacttt aaaaaaaatg tattacgatt 147420
attattttag agacagggtc ttgctctgtc acccaggcta gagtgcagtg gtgtgatcat 147480
agctcactgc agccttgaac tcctggcctc aagcaattct ccctcttcaa cttaggagta 147540
gctgggacca caggcatgta ccaccatgcc caactaattt tttttatttt ttgtagagac 147600
agagtcttgc ttgttgccca gtcttgcaat gttgtctcaa actcctgggc tcaagtgatc 147660
ctgtcgcccc agcctcccaa agcactggga ttacacgtgt gagccactgc gcccagctgc 147720
ctttttattt tttaattttt cagatgcttt gttggttcca aaatagcact tattaaccca 147780
cgctttcccc ctctggtttt aaatactgca agtttggctt tgaaatacaa cccactgcct 147840
tattcaggct acattcaagg aaatctgaga ccaagagtct gaaggcccag tttccttcct 147900
caaacccagg aggtggtaaa tgtgtcactt ccacactttc tatctatttc taagaactcc 147960
ttctttccaa actctgacat gcccctggct caggtctata gaaattccca gggtccacag 148020
acaaagcaga actcacttat ggggaaatct gggaaatact tatctgttaa acctgcccca 148080
tatggtgact cagattgtct aaagcccaaa gcatcatttt ccaccccaaa ccatttcctc 148140
ctccagactt ctctatttct gtggtccaga gtcaagatct tgatattacc ctagagtccc 148200
ccttctgctc tcctgcatac ccagatgccc ctccctcccc agatccattc tcccaccctc 148260
cctcccatca gtttggtggg cccatcaccg cttcccctgg cccaggctct ccttttgtgc 148320
gcttggagca gcagactgat ctcccagcct tcactcactt catgtggtaa tctgttgtgt 148380
tcatcactgt cagaatcttc tgcatcccct cactactctg ctgaaaacac tctagtggtt 148440
cctcattgct cattaatgaa agtctagata ttaaacgtag aaggcccagc acaatttgcc 148500
cctatgccac ctacctctct aatcttttct ccttactctg acagactctc cgtctgtcat 148560
ttatgtattc ttttattgct ctcttctact tttagtatga actggattta tggatttttt 148620
taacattgct ttcaagtatg gaataaagaa ttttatttat ttatttattt atttatttga 148680
gactgggtct cactctgttg cccaggccag aatgcaatgg tgcagtcata tctcactgta 148740
acctcgaatt cctaggctca agccatcctc ctgcctcagc ctcctaagta gctatgacta 148800
cgggtgtgca tcaccacatc tggctaatgg aataaaatat tacaatgcct aatcttaatt 148860

-continued

```
ttcaaaattt taaattacat tgtacctaat gcccatgcat ttactttttt cagtgggtca 148920
atagccctca ctttggcaaa ggtcccaggc ccaaggtaag gccttacttt ttccaaactc 148980
atcttttgaa agacataagt gcctgtaagt tgtaccacat taggttctag gaatttttca 149040
tcaaagactt tatcagacta ttttcctcta agttgagaaa gagctggggg cagaatatgg 149100
cactgaatga ctgaagagaa ggcactgaaa tcaggccaga ggttgctgga aagagcaatg 149160
aggaacacca gcagcaatga ggagccggtg atgattttgg cttcacaggg aggtgtgtac 149220
cacaccgatt ttatctctac gtggatgaac cacagctgtc ggctcccttg tctccaggac 149280
atcacactct ccacattccc tcccatcttc cggcttctgc ttcccggggc cctcatctgc 149340
cccatcctgg gtgaacactg gtcggtcaac tgctgggcgt accttcccgc tctgcacacc 149400
ctccctggcc accccaccca ctctcacggc tcgcactgca gaggagccgc atctctagct 149460
ccagcccatc tgcctcttct gagctctaac ttcatgtagg cgactcctgc cggtgttgcc 149520
tcacaggccc atcatacttc aaagcatttt cccctcagaa caccatgtcc tggctgctcc 149580
ctccagaaga tacatctctc aagcacatcc ccgcggctct cacctggatg actgcattca 149640
ccttctccca catttgccct cctttggatg tatatagatt gttttaaaat acaaatctga 149700
tgtgcttgct ctcctgcttg aaacacctca aaactgcctt caggataaac cactgccctt 149760
gacatgttca caggttgccc atggcctggc cctgcccatc tcttcagcct catctcatgc 149820
cccttgcccc tcgctctctg ggcttctgcc tccctagccc tcctttaggt tctctaacac 149880
accatagtcc ttctagtgtt ggggcctctg caagtgctgt tcccattgcc tgagacatga 149940
atccctctcc ctatctctac ctgcaccttc atctgattaa tccctaccct tcctactcat 150000
gatgttgctt tctcagggac tctctctgac tttttaaact aatcagggtc tccccagtat 150060
atatcttcat agcactctgt attactcctt tcttaatgac cacctgctgt agactgaatg 150120
tttgtcttcc tccaaaattc atatgttaaa acctagcccc aaatgtgata atatttggag 150180
gaaggctctt tgggaggcag agccctcatg aatgggatta gtagccttat aaaagagacc 150240
cctgagggct cccttgtccc ctccaccgtg taaggatgca acaagaaagt atggtctatg 150300
atccaaaaag cagacccttg ccaggtaccc aatatgctgg cacttgaact tcccagcctc 150360
cagaactgtg agaaataaat ttctattttt cataagccac cgagtctatg gtattttgtt 150420
ataggagcac aaacagactg atgtgccacc caaccatgat tatacgtgta atttatggtt 150480
tctctgctag tagggatgca ccatggggtt aggaaccacg cttttcttat ttcccacaca 150540
gtccttagct ctaagcatgt tcctgaatca aagatcccca tcttttatga atgaaggagt 150600
cagtgaatga attaatgaaa gaactgataa ccctcaataa ttattccagc cttttatacc 150660
tactattaac aagcttgcat tctactccaa atttattggg ctttaactct atttttggcc 150720
agccacattt gacattccct gaagtaaatc tatgctttcc atcctaagtc aaggaaggac 150780
ctggactagt agggccaaga aaggtctaaa ttccatgggt gggagagaga gactaaatct 150840
gaaaggaaga atagattgag caaaggtgta gagattgggg aaggctggac atttggagag 150900
aaggaaaagg aaactgacac taaaccaaac agtctcacaa acacaatctc atccttccaa 150960
aactctgtga agtaagaatt actatcccag ggccaggcac agtggcccat gcctgtaatc 151020
ccagcacttt gggaggccaa ggtgggtgga tcacctgaag tcaggagttc aagaccaacc 151080
tgatcaacat ggtgaaaccc catctctact aaaaatacaa aattagctgg gcatggtggt 151140
gcacacctgt aatcccagct acttgggagg ctgaggcagg agaatcattt gaacctggga 151200
ggtggaggtt gcagtgagca gagatcgtgc cactgcactc cagcctgggt gacagggaga 151260
```

-continued

```
ctccgtctca aaaaaaaaaa aacaaaaaaa aaaccaaaaa aaaaacaaaa aacaagaatt 151320
actatcccag ttttgcagat gaggcaatgg aagctctaaa aagttaagta ggagaaacaa 151380
acatgaaatg tatgtcttat gcttttcctc atcctatttc ctcagcctgg aatgtccatt 151440
ctccctccac tatgcaaatc taactcttca agctaacaca tagcaatgtc tgagaaaccg 151500
tccctgtgtt cactctgtta gcctcacttg ctccctcccc atccctctgt ttcctttctg 151560
ttataacact tctctattct gctggcatca cagtcatctc cacctgcctt cctcacaagt 151620
taaaagcttg ttaagggcaa gtggtgttct ttgccacctc attccccagg gcttctaaca 151680
cagtgcctca tgcatgacag agttgtaaaa caggttacca agctggcttc aggcaggttt 151740
gcatggaact gtgctttaca ggaatacctg ctccccccag gccctgggtc ttcctcctga 151800
gtccaggctc agactctctc atcctgctcg ttctctcttg gggagccaca gtaactttga 151860
gcaactttgc atgggataga atggcctatt aggggcagca caaagacccc atggagggaa 151920
gagtacagaa agggaaaacg ataatcatat ttttttaaga tgtgcatttt cttaacaaaa 151980
tgctctagta cttgtccaga ctttcaaact caaaaaccta agcgtccttt tcttgaagat 152040
catcaaaggc cccagtggtc cttcaggtat gtcaagcttt ctagaaaata aaggtaagtc 152100
ataatcactt aacacacatg gctaaatggc catttccttc taatttatca gcaactgtta 152160
catatttcta tactagaaaa aatttatatt tatactcagg gtggtaagtt aaatttgcca 152220
tcgaagtaaa gcagaaagag cgtagcatgt atgtatatgt aactcaactg tgcatgagac 152280
aaagatgtct tgaggagaat gagtctaaga tgcgcctgag caatagtacc c          152331
```

```
<210> SEQ ID NO 17
<211> LENGTH: 176373
<212> TYPE: DNA
<213> ORGANISM: Homo sapiens
<220> FEATURE:
<221> NAME/KEY: misc_feature
<222> LOCATION: (1)...(176373)
<223> OTHER INFORMATION: n = A,T,C or G

<400> SEQUENCE: 17
```

```
gcacccatgt ttctaaaggg cataccagcc ataataacag gatgggtgag gatatagaca     60
gcagatgaca gagaggagag tgaaagctgg gaatcccagc taaaggcatc aggtttatgg    120
aatgagtagg ggacaatact gtgtgtgttt atacacacat gtatatgtgt gtatatgtat    180
acatgtttat gtatatatat aattatatgg taccatttct aattgacaaa ataatctatc    240
acattttaca ttatcagatt ttacatctat tgttctaaat acactcagtc atcagccctg    300
tgtgtgggct cttacccatc cccatgcaca cctcagctca accactgatg gatggatcat    360
ctgcctatca gaggtggcat attcaggtga atccatggcc acagctgcag cacttcctac    420
ccacgcagaa aggctccaca agaggaggca cacccgctct gactgtccct aagctcctga    480
catcttcacc ccatgaaact gctgctcctg ggtgcttcct gccttgccct gcccaccctt    540
gtactgttct caccattgac acagctggtg cccgatgcac naaaacgaat cgtcactatt    600
gaagcctgtc tctcancgga tcgtgactaa gaaccccctc cttgcttcaa gttgtcctgc    660
ctttctaggc agagccaccc tacatcttaa atatattgat tgatgactta cgtctcccta    720
aaatatataa aaccaagctg tgctcttacc aacttgggca catgtggtca agacctcctg    780
atgctcttgt catgagtggg tgggtgttct caaccttgga aaaataaact ttctaaatta    840
actgagacct gggtcagatt tttggggttc acagcaacaa tttaaaaaac tcaccattga    900
```

-continued

```
cctgaaattt tgaccttatg ctgttcctca cactcctcca tgaaaataga cgccatccta    960
tgagttccct cagccatgtc atgccacact tccaacatgt gtccccatcc accatctgtc   1020
ttcttattgc tgcatcctac ccaggccctg atctctggac ccattgttgt ataattaaga   1080
atttggggct gggcatcgtg gctgtggctc actcctgtga tctcaacatt ttgggaaggt   1140
gtattagtca ggattcctcc gaaggatgca accctaggga tcctctctat gaccctatgt   1200
ctacgcgctc aaccgaccga tttgcgcgaa cctgcccatg cccgaggaca gtgtaatcct   1260
aaaacgtccc ctgaatcata aggatatgag tgcgaaagta cggttccctc tgtcaccact   1320
ttctaacaac gctatgtccg atccgtgcac taaccccgcc caagtcactg aaacactgat   1380
gggcgcttcc tctacaggta tccagggcca ataccactac tcccctcctc cctgtccccc   1440
ttccactctc tagaggccgc ggatgccatc ctctattagc acaaccgaaa acgacggtga   1500
aagtaccacg aagctcacga tctgatcggt cgcccaatgc ggttacaacg gctgtcatcc   1560
caaccccgt cccatcctcc atattgcccc cccctatgag gatggcccta tcatcatgac    1620
ctccaaaatt ctgtcatctc ccgacgtaat gccgcccctc gaacgcctga caccatcaag   1680
tcngtcacct cccaaaatac tcctcctaat caccaggccg agtatccccg gttccacaat   1740
acctccttga gacgggccga tatcacacac nggagtttag gtcaactagt aacaagtggg   1800
atttgcgact caggtctatc taatcctcaa acccacgtcc tggaccccta cacagactgc   1860
cctccctcag tcctctgtgt ggcctcaaga agggtctgga cattcaagtt taaaaatcca   1920
tccaaagaat ctatggaccc agtggtctct ggagtcaatg ttctgaggct cagaagggcc   1980
aggcaggagg gagccgcctc tacacagtcc tgagcagagt gggctgtgtc ccggcacagc   2040
aggggagatc ataaacagaa ttctgccctg ggccctattt aagtaggacc tttaggctgc   2100
cggtgtcatg accacaggtc ccangtctgc acgattggct gtgtgtggaa aatcttcact   2160
ccttgcggcc ttgtccttgg cagagagcac cgctgcttcc tctgatggcc accaggggga   2220
ggcgctcccc tgggaacggt ttgaangga gcctcacccc acacgtgcct tccgtggtac    2280
ccagcaccag ctgctaccca tggttaccca caggcccagc tctgctctga agaaggagga   2340
gtggtggcga tcangccttg tctgcatccc gtggctgccc ctttcttttc tttgggagct   2400
aaccgctcac tgggattaca ggtacgcacc accacgcctg gctaattttg tatttttagt   2460
agagacgggg tttctccgtg ttggtaaggc tggtctcgaa ctcccaacct cagttgatct   2520
gcccgcctca gcctcccaaa gtgctgggat aacaggtgtg agctaccatg cctgggctta   2580
tatgtttcta gtccaaacat ttagctacct tttttttttt tttgagacga agtctcactc   2640
tgttgcccaa gctggagcac agtggcacaa tcgtggctcg ctgcagcctc aacctcctca   2700
ggctcaggtg attctcccac ctcggcctcc ctagtagctg ggactacagg tacgcaccac   2760
tacaccctgc taattttttt gtttttgtat tttttgtaca gatggggttt cttcatgtta   2820
cccangctgg tcttgaactc ctgggctcaa gcaatctgcc tacttcagcc tcccaaagtg   2880
ctaggattac aagcataagc caccataccc ggcctaccta cttttaactt gtggaatttt   2940
ctataaggtc anggatgcct gngggaacaa aagtttctcc cttggtatat gcaagtaaaa   3000
tccacatgct gcctcccagg actgtagctg ttgtctagtc accaggctgg actgcttggc   3060
atgatctcag ctcactacaa cctccacctc ctgggttcaa gggattctcc tgcttcagcc   3120
ttccaagtag ctgggattac aggcatgcac taccatgccc ggctaatttt gtattcttag   3180
tagagacggg gtttcgccat gttggccagg ctgctctcaa actcctgccc tcaagtgatc   3240
tgcctgcctc ggcctcccaa agtgctggga ttacaggcgt gagcccccgg cccacatgta   3300
```

-continued

```
aaagtttata tctctgttgt ttcaccttgt ttttgaccta gtctttcagt gatttgaatc   3360
ttgattcagt cttttgttat tttagtggta cttcccagct ttgtgtcatc tgtggatgac   3420
atatgagtct tgcttcttca tgccaattta agaagactga acgggaatag gtcaaaggca   3480
tggccatgag cgatttctct ccagcttttc atggtgttca gcttcaaatc tattcacata   3540
ttggacctgc aagccatcat cttatccaca ggctatcatc ataggtgaat gtaaattggg   3600
tttaggtggc caagctgaac gtgagatatn ttcagcatgt tctctaaagg cctatcaaag   3660
ctgacatcaa agggataagt tccagttacc cagctgaagg gaaggagggt gtttcagata   3720
gaggaaggat aagcatgacc tattcaaggc cagtgaaaga agcgtgcaac ggccaagtca   3780
ggagaacctg aaattgtgtc aaagagcttg gatgcaaaga gccgtgggag actattgggg   3840
gttttaagca gggatataat attcattcaa gcatgcagta aaaggtcact ggcacctgcc   3900
atgggccagg actcgggctc tacatgattg cgtctgtttt ggaaatatca ccctggctgt   3960
gagatgaaga acaggtagga gggtcacaaa acttgaagca gagagactgt tgaggaagta   4020
agctgttttt gtgtggactg tggcaatcac agaggcagag gatataaatg cacagagaca   4080
caaggcatgt gggaggcaga aggaatcaaa tacaatgagt gatcagatgt ggggttagaa   4140
tggtgagtga naaagacata ctcaaggtga cacgcccagg tatctgggtg gatggtaaga   4200
cattcatgga ctagaatcga agaggaggtg ggatggaca ttccttccgt ttagaggggt    4260
tcaccaggag gatttgccgg aacatggaga ggattaacca ggaatccggt gccttttttcc   4320
aaactgggtt ggaggggggt gaatgctttg gcacgctgtg tagattttag gtgacgggtg   4380
gtgacaatga gtccgtgtcg agcgctgatt ttttcggcct ttagagcgag atttatacaa   4440
tagaatttgg catgagattg gattgctttt agtcagcctc ttatagccta aagtctttga   4500
gtgactagat gacatatcat gtaagttgct gataggtttc cagttttccg ctcctaggtc   4560
tgcatattgt acttttcctc ttactcgact taaccagtac caacccagct tctcaacgga   4620
tttataccat ggcactttaa agccagcatc actgacaatg agcggtgtgg tgttactcgg   4680
tagaatgctc gcaaggtcgg ctaaaattgg tcatgagctt tctttgaaca ttgctctgaa   4740
aacgggaacg ctttctcata aagagtaaca gaacgaccgt gtagtgcgaa tgaagctcgc   4800
cataccataa gtcgtttttg ctcccgaata tcagaccagt caacaagtgt caatgggctc   4860
gtattgcccg aacagattaa gctagcatgc caacgggata aacgagtcgc tcttggtgga   4920
gggggggtgg ggcgcctggt gtttctaaag aggatctcct gccagaaatg gtgtgctgac   4980
actgttgtcc tccttggtgt ggaactttgg tgggaagaaa ggttggaaag ggaaattttg   5040
atccttggat ttaacccgag tttgttactg atgctcacaa gactagggga aggataaagg   5100
caggtgagtc actctaggat ggctcantga gctccacaga gctggaacca caggcaccag   5160
gagggattca gagcaggcct cagtgcacgt cagctgagtg aaccaatgag caggtgatgg   5220
gtccaggcag agccctgtcc tctttaggca aaaacccttg aaacaccgtt cccatcctag   5280
cctgtgttcc acccaaagct ggccagtctc caggccctgc ctgagcccca aggaagtggt   5340
atggtgaaac agaagggcca ttcctgtcca atgtgtgagg aacttcattt cagacttgtt   5400
ggaagccctg atgttcaaaa acctcaatga tatcattcat tttccccatc cattcaatgc   5460
ccatccaatg cccatccgtt caatgcccct tccattcctc ttcagggaaa tgaaaattgt   5520
tcagaaatcc tttctctttc gagaaaccaa ccaaaccaaa accgcgaaat tcactaaact   5580
agccaagaca caatcctggg ttattttcct tttcccaaac ctcctctgtt taaattaatt   5640
```

-continued

```
ctaccctggt tctcggccct tactgcgaag gtgaactcac ctaacctctc ccaaacagag   5700
aagaaacttc tcttggtaaa atgggtttta acacttctaa aaaacccccg ctatggttct   5760
aaaggtaatg gactatggcg tacacaacgt ctcgctcatc gtctgccagg aggctaaggt   5820
atccacggac aatcgctgag caacagtgtc gttgatccat ctctgtacgc acttgtcaac   5880
atggcaggag tacgggagct gcgagaatcc tctctgctga tgtcccacgg agcatgccgt   5940
gagacaacgc cacgaacggc cctcggagan anctactctg caatgaagac gtacgataca   6000
cacgtaggag tcctagctca ccagccgtat ctaggtatac tgtactcgcg gatactcact   6060
cgtgcatgcg gcaatagatc gatacgcagt cgtcacgccc atgctctcag tgtgtgacct   6120
tctggcggta gcgtngtggg cgctattact gtgcgcagca ggcgcntcgt acatgtgtcg   6180
ggtagcgatg ccaggagctg taacatagca agtcgccccc ctactcctat cactatccct   6240
acgctggacc gcactcgaga tctgaacgca cgtcttaacc tgccagtact cgtgagacct   6300
atactgcgca agccttggct aggagatcct gcagcgccgg caaagaatca gctatgatcc   6360
ccttgcgatt atcgcacacg caccatagag tatgtgcata ttaacctctg aatgtgctgc   6420
aagcagacgg ttgctcaaca tatatatgga tgtggggaaa tcgccctggt caccgccact   6480
tggcgtcagg aggcaccagc acgtctgagt gtcacgcacg ttactcggcc gaatggtgaa   6540
ttcatccgtc gtctcgaggg ggtgaaagac ggggagttat gctgtaatgg caccgctcac   6600
cctgggctta tgagcagacc taaccctccc anagtgctgg gattacaggc atgagccacc   6660
gtgcccggcc cagtatctga acttctgtgg ccaggcagaa aaggtcctgt gttactcgtc   6720
tcctttatca ttcatgtcca tattctccca tttgctaaca tttatgtttc tgctccactg   6780
gattctttgg atttttctag aacataccca tgctttgcat tgccttggtc tttgaatatt   6840
tggtccactt ttcctgcaaa gtcccctctc accttatctt cctggtaaac ttccagccaa   6900
cacctcttta ctaaccagag aaacatggtt caactgtgca caggcttgca cagaaactgt   6960
tctcatattg tcttgtcatt gtcaatgtgg cagagatgca ccttagatac ctctttgaga   7020
aaggactcac tgcccagctg cctggcacgt gatgagctga tagctccagc tatagactcc   7080
tttagggtca acctctgctt tccagttgag atcatatcct ttgcagggtg gcctccccag   7140
tgatgactaa ggcagtgtta caatggccta gtcatttcct cccaatgctg gactcccaat   7200
gaaccatctg ctccggagct tcccactggg cagtcagaga ccttagctag tctgcctccg   7260
aatcagaagg ctctctcttg ccactctggc cgctgtgtct aaagattcac ggctgtagtt   7320
ccaactcccg ccgccctcta ctgtgtcctc ttaatggcag tcattcacca tcttcctgtc   7380
cctccccttc atttcttgga tggtgactgt cactttgctg caacagaacc ctgtcccaat   7440
ccttgatggt tcaatacaca catagacatt ctttttaaca gggcggcctc tcaggtcttt   7500
aattttcttc cctccaataa ccttgtgatg atcccccagc ttagccactt actgccagat   7560
cattaccagt aactccagcc cctccttaat tctagtttct aatatcctaa tctgtgacct   7620
cacattccaa cttcttcatt cttatcccct gagtcaaaaa atcctttgat ccatgcaatc   7680
cattaagtca tctacctttt caccattctt cgccccacta gggttctcat tcctttatta   7740
cccatatgaa attccaaggc ctgttggaat cactcccttg cagccactgt caatacttct   7800
gccccttttta cttcatcacc cttatgtggc aaaaccacag ccctggtgga gtcgatcctt   7860
acccctgctc tgtgccaaca gccgcacacg catggctgat ggaggttgga aaaatccaca   7920
catgcagtgg gccctgtatg tccatatacg tatccaacct ccagccttgc atatgcctca   7980
gtgctgcctg acaacacatt atatgttttc cttagttcct tcagtctcct gggtgcctag   8040
```

-continued

```
gtgagtatct cagacatcct tctctctctg caaagctcca acacctccac gtcacattca   8100
actgatgact gtgtctccta tgtcacttag atcacagagg catacataaa caaatcccag   8160
ccactgccag cactctgcac atctgcgagc atggcacccc caatctaggc ctttcctgct   8220
gtcacttggg gtgagctgat tatactcgat cctagtcatt tctacttatg caccttaagg   8280
cctccctcta acattttaat ttaagattga aaaagcaaag attattctgt tttggctgcg   8340
cctatagtaa agtaacccct atgncaaatt ttgacacctt atagtatttg acagggataa   8400
gtataaaatt gcttgattga tacatccaca cccaaatgta tgctgggaat gattttgttt   8460
cacggcactc attacttaat ttttaaaact cttatttaaa tttgcaatgt tttaaatgac   8520
catcacttaa agtagtaatc aacagaggtt aggagaacat aacaatactc tttctcttag   8580
aaaatacaac agaaatataa ttttttacag ttttgctccc aaacttttct ctgtaataac   8640
atgccttact cacctttaca ataggtttgt tgtgagaatc ttgtaatgta aaccctgggt   8700
gttctgtgaa gcatttttaa acttctagtt tacactgact cttattcaag tgtttttaaa   8760
aatatattta aaaaactggc caggtgcagt ggctcacacc tgtaatccca gcactttggg   8820
aggccaaggc gggcagatca caaggtcagg agtttgagac cagcctagcc aacatagtaa   8880
aacctcgtct ctactaaaaa tacaaaaatt agctgggcgt ggtggcgggc gcctgtagtc   8940
ccagctactc aggaggctga ggcagaagaa tcgcttgaac ccgggaggca gaggttgtgg   9000
tgaaccaagt ttgcgccaat gcactgccag cctctgcagn gacagccggg ggcgggccga   9060
gtgatcctaa agcccgctcg cttcacaaca aagcctaaca gtccaatcac ttaatgctgc   9120
atttattcct ggggaagcaa gtctcctttg cactttacac agtgagataa tcagtttctc   9180
atgtggacca ctgggccagg agggcctgac aaagggcagt ctacatttca gactggaaac   9240
tgctcccaga actatttctt tctagttccc acctcggtct gaggtgcctg aggagaggga   9300
ctcaacagag gaagcaggag catagctcaa agtctcagaa catggaagag gaaaagaatc   9360
ctcacaagat tacgtaactt acaggcgtgt tgctgcttca gtagaagttt catctccctc   9420
aatcctgtac acttttccat acattacata ctcaaactgg tcagccctat ggagcaatag   9480
cagcaaagtt attcttaaca gtaattaaca atataaaaga tcccatttaa aaatggttac   9540
tggtcagccg ggcgtggtnn ntcnanaactn taaccccanc actttggaaa gcatgcgggc   9600
gatcccaagt ctgatatcga aacatctgcc taacatgtgc aacccctctc tacaaaatac   9660
aaaaaatatc cgggcttgtg ttggcgccgt tatctcacta cccggagcta agtaagaaat   9720
gctttacctg gaagcgattt ttttacttat atcccctctc ttcaccgggc gcgaccaaat   9780
tctttagtat aggaaagttt attgttttat gcctttgtca aggctctact gtatcttttc   9840
tgtccactca cggttctgaa caacagcagg cgattcctag ccctgtaccc ggggcattgt   9900
ccaacactcg acagggctga attcgtccat aacggtgtgc ccctctggga tataggatga   9960
aatgaattga tctgagtacc tgggatgtaa agttactaaa acgccagcta ggttcacgcc  10020
ccgatgctta aatatgatcg tggcctacac ctcgtccagc agaaaaagta ccctttcttc  10080
aacaccacct cacgatcctc caatttagga gctataaaac tcatgactct ttatttaccc  10140
cctgcagatt ctcaatccaa tagtgtgtgt ctccctgtga actcacggat ataccgattt  10200
tccccacgtc atttccacac gtcgcaatcg cttagtcatc cctatgtatg agaatcatgg  10260
atgactatgt tgaagtccat ctataaagtt caaccccat ctccgtccct gattccccct  10320
ccccaagatc accaacgcga ctcgacatat tgttatcgcc caagggacct cttgcatccc  10380
```

-continued

```
ccatatccac tggtcacctc ccctcttggc tggaagtcac cgggaagttc tccacatgtt  10440
gttgcgagcg atgttcctaa actttagcgc cattgactcg agcatggtca tggctgtttc  10500
ctgagggtgt tcctaaagga tactacgttc cctaaagtcc agagaaaaaa aaaaaagtaa  10560
cataatgtgg cttatttggt ataaaaattt tacaggaagc attgtcaaat atgaaatagt  10620
gtttggtttt gtttgggctg tatttgtata aatatgttat tggtatgtgt tccaaaatta  10680
taggaaactc ctataattct gatatgactt ggtgtacatt atcagtaata attataattg  10740
ttatggtaaa ttattgtgtg ccatggaggt aacaaatttc ctcatcaagt gtgtctttga  10800
ctatggttgc cctaaaactt tttgccattc acagacaatt gtcttgcttt ggtcctcttt  10860
agaaggtggt tttataatca gctataaaac tctaacgggt gctcttgaat gcaggcttaa  10920
gatagctttg gagactgtga catcagaata gaggaaaaac tttcagtatt catggagtgc  10980
tgaaatattc atgaatatca agcaaaacag gaattaactt catagatgga actaaaagaa  11040
tgctgaagta atctttttga ctttttttct taaaatgttg atccttcgtt ttgtttttca  11100
gagtcaagga aatttttctg ttgagatatt gacagctttt aacaattaag tatactccag  11160
tgaacacaat ttggagcata tttgtgtctc tctatatata tttggaaaca atntttgagt  11220
attcttaact tattgcaata ttggttgtct gctataccag taatgggatt gctgggtcaa  11280
atggtatttc tggttccaga tccttgagga attgccacac tgtcttccac aatggttgaa  11340
ctaactgaca ctcccaccaa cagtgtaaaa gcattcctat ttctccacat cctctccagc  11400
atctgttgtt tcctgacttt ttaataatcg ccattctaac tggcatgaga tggtatctca  11460
ttgtggtttc aatttgcatt tctctaatga ccagtgatga tgagcttttt ttcatgtttg  11520
ttggccacat aaatgtcttc ttctgagatg tgtctgttca tatcttttgc ccactttttg  11580
atgggttttt ttttcttgca aatttgttta aattccttgt agattctgga tattagccct  11640
ttgtcagatg gatagattga aaaaattttc tcctattctg taggttgcct gttcactctg  11700
acaatagttt cttttgctgt gcagaagctt ttcagtttaa ttagatccca tttgtcaatt  11760
ggcttttgtt gcaattgctt ttggtgttct aatcatgaag tctttgctca tgcctatgtc  11820
ctgaatggta ttgcctaggt tttcttctat ggtttttatg gttttaggtc ttatgtttaa  11880
atccttcttt tttttttttt tttttttttg agatggagtc ttagtctgtt gcccaggctg  11940
gagagcgagt ggcgtgtctn taggacgcgc atgttgtcta aaggtttgtc ttcctccaaa  12000
attcatatgt taaaacctag ccccaaatgt gataatattt ggaggaaggc tctttgggag  12060
gcagagccct catgaatggg attagtagcc ttataaaaga gacccctgag ggctcccttg  12120
tcccctccac cgtgtaagga tgcaacaaga aagtatggtc tatgatccaa aaagcagacc  12180
cttgccaggt acccaatatg ctggcacttg aacttcccag cctccagaac tgtgagaaat  12240
aaatttctat ttttcataag ccaccgagtc tatggtattt tgttatagga gcacaaacag  12300
actgatgtgc cacccaacca tgattatacg tgtaatttat ggtttctctg ctagtaggga  12360
tgcaccatgg ggttaggaac cacgcttttc ttatttccca cacagtcctt agctctaagc  12420
atgttcctga atcaaagatc cccatctttt atgaatgaag gagtcagtga atgaattaat  12480
gaaagaactg ataaccctca ataattattc cagcctttta tacctactat taaacggttc  12540
tctaaagact ttcaagagct ggattttatg ctttaggtga aggtgataaa gtaaagtgct  12600
ttcactgtgg agggggggcta actgattgga agcccagcga agacccttgg gaacaacatg  12660
ataaatggca tccagggtgt aaatatctgt tagaacagaa gacacgaaaa tatataaaca  12720
atattcattt atcccattca cttgaggagt gtctggtaag aactgctgaa aaaacgccat  12780
```

-continued

```
cactaactag aaaaattgat accatcttcc ataatcctat ggtacaagaa gctatatgaa  12840
tggggttcag tttcaaagac attaagaaaa taatggagga aaaaattcag acatctggga  12900
gcaactgtaa atcacttgag gttctgattg cagatccagt gaaggctcag aaagacagta  12960
cacaagacga atcaagtcag acttcattgc agaaagagat tagtactgaa gagcagctaa  13020
gacacctgca agaggagaag ctttgcaaaa tctgtatgga tagaaatatt gctgtcgttt  13080
ttattccttg tggacatcca gtcactcgta aacaatgtgc tgaagtggtt gacaaatgtc  13140
tcaagtggta cgcagtcatt actttcaagc aaaaaaattt tatgtcttaa tctaacgcta  13200
tagtaggcat attatgttcg tattatcctg attgaatgtg tgatgtgaac tgactttaag  13260
taatcaggat tgaattccat tagcatttgg taccaagtag gaaaaaaaaa tgtaaagcca  13320
gtgcttagac acagccgctg tcttaagaac tgggctagga gtgagcagtg agccaagatc  13380
gcaccattgc acttcagcct gggcaacaag agcaaaactc catctcaaaa aaatacatat  13440
atatatatga cccataaaaa ggagataaat caacacttca gaactgaccc aaacttgcaa  13500
agatactata attaacagaa aaggacagtt tactaagtac tccgtatgtt caacaagtga  13560
aagattaaac atattaagta gagatgtaga agatataaga agatccaaaa tgaactttta  13620
gagttgaaaa ctacaatatt taagataaaa atacactagg tgggattaaa agtagattac  13680
acattgcata agataaaaaa aaatgagcct gaatacagca cagtataaac tatcttaaac  13740
aaaaacacag agagaaaaaa taactttaga gacttagctc ttatcctcta tttgtttcta  13800
aacagaggat aaggggcaga aaaaatgttt gaagaaatca tgatttttaa atttccaact  13860
gagataggaa tagcactggg tagtcacagg aggctggaaa gacccaaaca gcagttaaaa  13920
caggaactag gcaaagaaac caaaggataa cagtaaacct aaactaaggg agagaaaact  13980
gacaaaagct gacttaggat aactgaccct gaatataagc cgcaagtaac caattaaatt  14040
tgttttccaa aattgtatta acaatctatg aaatttttat cttgaccata gctataactt  14100
ccagaagcct tttataacct ctataacctt tattaaggag taggttaatg cttcaagaaa  14160
accttgttaa tctgacacag gacccatatg ctgatcttgc atcagtgtgg cttggacatc  14220
aatgattatg attaatttat agagaaattg aacttatttt atctctcaaa attggccctt  14280
acaatctcac acacccacct cttccactat agttcctggg ccttgagttg aatagcttta  14340
atttctggct ctgtgtttca agaatgcagt ttattttgat tggcattttc taccagtcct  14400
gaagatgaac ctttaattgc tgtcagtatt taagatttag caggacttgt ccttttaaga  14460
accaggagtc aagccctata actcaatgtc acaaggactt taaaagcaca tacataaaga  14520
tatatggatg taataatcat aatttttaaa aaattgtatt aatctcagtg ttttctaagc  14580
aaaccaaaac ttaataataa tggcatagaa attatttcaa taaaacataa aatctgttaa  14640
gccagttacc aaaaggcaaa agaaaagacc ttctgcaatg cacagaatat tatgttggaa  14700
gaaaacattt cctttagacc tttaagaaaa cattgttagc atcaggacac aacaaacaga  14760
atctgagggt aaaaaacgta tatgagctga agggagttga aggagggcat tactatttcc  14820
cacccttttta aaggggagag aaaacctaaa acagcaagat gcaataaaag ctgaactttg  14880
ggttaaaaaa aaattcttaa gtctcttata atttattaag agtgaatcaa ccccgtaaga  14940
aaatttcatt gttctaacca attttttaat atataagtag ttttttaaca tcaacccaat  15000
ctctagaaag accattataa tttcccttta attatagaca actttatcat ataaaagttt  15060
ttttaaataa atcctcttat tgtgacttac acagactatt catgacatgc ttggactttc  15120
```

-continued tggtttgtcg tgaacatcct tttctttctt tctttctttt ttaaatttta ctttacgttc 15180
tgggatacat gtgaagaaca tggaggttta ttacgtaggt gtacatgtgc catggtggtt 15240
tgctgcaccc attaacccgt catctatatt aggtattttt cctaatgtta tccctcccct 15300
tgccccccac ctcctgacag gccctggtgt gggacatccc ctccctgtgt ccatgtgttc 15360
tcaatgttca ctcccactta tgattgagaa ctgcagtgtt tggttttctg ttcgctaaat 15420
ataagctatg ataaaacagt tggccctctg tatcatgggt ttcacaactg tggattcaac 15480
taactgtgga tgaaaaatac ttgggaaaaa aagaatggct gcatctgtac tgcacaagtg 15540
cgtgctttta ttctcgtcat tattccctaa gcaatacaat ataacaacta tttatatagc 15600
atttacgctg tattaggtat tataagtaat ctagagatga tttgaagtat acaggaggat 15660
gtgcttaggt tacatgcaaa tattatgcca ctttatataa ggcccttgag cctcctcaga 15720
ttttggtatc catggcagtc ctggagtcaa ttctcctgca acatctccat ttgttcagat 15780
tctcttctat atcatgttta tatcagaaaa tctacataag attttttaat gtgttcatat 15840
aggttttgtg tatttttggt tgttaatccc tagatatatg cagtatttat tgctattatg 15900
agtagtgttt ctttaccatg tattctagtt ggttattgct gacagagaaa tgttgctggt 15960
gtttctaagt taccttgttt ctaacaacct tgctgaactc ttattagttc tcatagtttt 16020
taattaatct ttcttagttc tgataacata atctgcaaat aatgacaatt ttatatcttt 16080
ctttccaatg cttatatctc tcagtcctct ttatcccaaa gtattttcca ggatctccac 16140
tataacatta aatagtaata agaatttctg tcttgttact gatcttaagg agaataaatt 16200
taaatttcct ctgtcaggtt ttatgcttga tatagatttg tgatatatag cctttcacag 16260
gttaaaaaaa aatgctttcc tagtagtcct aatttttaa aaaaatcatc ataaatagat 16320
gttgaacatt atcaaatgct ttttctgcat ctatagagat aatcatatgg ttttttacta 16380
tttattaatg taatgaatta gaccaatttt ctaatgccaa ctctttcttg tatttgtagg 16440
gtaaatccta tgggatcata aaatactttt aatacattgt tagatttgaa gagttaacgc 16500
cttatttaga acgttttcag tcacatccat aagtgaaatg gcactatagt gtctattact 16560
attatatttt tctggttctg aaaccaaaat tatactcacc tcatacagta agttgggcaa 16620
cttttgttct ttttttctga aacaatttgt gtatagaaga aattaactgt tccttgaaag 16680
tttgataata atcatccaga aaattatccc catctagggc ttttacaaaa aggagactct 16740
agaatgccat ttcggtttcc ttgatgtgta ttggcctctt tcatttaggc ttttggattt 16800
tttagggcat tttttcacta taggcttttt accggcataa acttcaggtt ggatgttcgg 16860
tcaaagtggt ccggcgatgc gaaaacgaga gggctcgagg actgggcaga gaactatttg 16920
aaggtatctc tcaggggaaa ccaagcggaa ggcggggagt aaaattggga gggagcgacg 16980
gccttcaaag aaggggcttg cattagatcg gcgagatccg ggagggtctg gtggggagaa 17040
atgactagag gacaaatcta atggagagac agacggagat agatatcgtg acagagagag 17100
ggacagtgac agcgcacaac agtgcagggt ccatgagtac aaggccctta agtgtacacc 17160
ccagccggag tcatggcaat tcgattcctg tactgaccac ccaggatttg ggtagactgt 17220
acgagttaat gagcatggtc cccaacaaga ctgcttcgac ctcagatgca aagcacactt 17280
caggggtccc caagccactc atgtttttttg aatgactgcc ataagttcaa aaattcccac 17340
aattctctca gattcaataa ctgggtataa ccactcatag aactcaagaa aatgctatca 17400
ttattattac aattttatta taaaggatac aaatcagaag gactagccaa atgaggagac 17460
acatagagag aggactagta aaaaacagag cttctgcgtc ctaccttcaa ggaatcagga 17520

-continued tgcaccaccc tcccagcaca tcaagtgctc atcaaccagg aagttcctct gagctccaat 17580
gtccagagat tttagggagg attcattaca taggtatcat tgattaaatc attggccatg 17640
tacttgaact caatctccag tgtccctctt ctccctagag gtctgaaggg ttggctaata 17700
tcatgtggct caaagcccca actctaatta ccttttttggt cttttcaggg actagacccc 17760
atcctgaagc tatctacagg ccctgccatg agttagctca ttaacataac aaagacactt 17820
atattactca gaaaattcca acagttttag aagctccatg tcaggaacct gggacataga 17880
tcaaattctt tttttttttt tttttttgga gacagggtct tgctgtgttg cccaggctag 17940
agtgcaacga cagatcacag ctcaatgcag cttcaacttc ccaggcttaa gtgacctttc 18000
caccttaacc ttccaagtat ctgggaccac agaaaatggc taattatcct ggctgatttt 18060
taaacttttt tttttgtag ggatgggatc gccctgtgtt gccaaggttg gtctcaaact 18120
cctgggttca agcaatcatt ctgccctggc ctctgtgatg gttaatactg agtgtcaact 18180
tgattggatt gaaggataca aaataatatt tttgggtgtg tctgtgaagg tttcgccaaa 18240
agacattact ttgagtcagt ggacggggaa atccccccctt ccccatggga cggggagacc 18300
cccctccatc caggtaaaaa aatctaatca cctgcaatgt ggcagaaata aaggagggaa 18360
aaaacgggga cccctanatg ggttattctc cacctaattc ttcccccagg ccatgtattt 18420
catttctaca gaccctgaga tgaatttgtc attgccacgg ggtcctgaag ttcaaatact 18480
ctatttggta tcctgcccct gtggttaact gtgatcattt cactcacctt gtttatgatg 18540
agaggtgcca ccatctggcc tcctccactc tgcaatcctg ttaattccta tcaaagctga 18600
aaacctgctg cagcacccac accatcacct ccagcctaga gagggaagct accagtgagc 18660
tctcctggat gccggtgtgc ccctcgccaa tacatttctt cttagtccct tggtcatcct 18720
gaggtgtgtg attaatggac agctatgtgg attgcacata atagatgtac tccagcatct 18780
tcatccctga ttttccttta cagaaatcac tcaaccttag caacatgtga aaatcaccta 18840
aggacattct ttaaatccct ctgtccacat ggcaacacaa accacttaaa taagaatctc 18900
cagggagtca ctcaagcatc aatgtttttt aaagctccaa ttttaaggat cattacatta 18960
tgtcgaagaa attatagtat ttcagcctta ctgactgtaa accaccacca tatctaagca 19020
tccattagtc aacctagcag acaataaact aacattacct ccaggtactc aaatcaattc 19080
attgcatccc aaatcccaga tgggcccacc cttattgaca aattcagccc aatcttggtt 19140
gaacacattt agaatatatt tccatgaaca atatccggtt gacgagtttc tttaactttt 19200
tggagtttaa gccatttcct ttcacagtag ccttgttaat tccctgtcaa tgctccatgg 19260
gggtcatgaa gagacctctt attaactgtg aagcaacttg gctcaggtgc agacactcaa 19320
atgcttcaca tgcagtggga aaagagagtg attgtctact ttaaaaagaa ctgagtcttt 19380
attcagtcga ttcttctaat ctatgaacat agcatctctc tcaaagcatt tagtccttct 19440
ttaatttctg tcattaattt tttaaaattt tcatcctaaa gattctgtat atgttttgtt 19500
gaatttatgc ttaagcattt cactttcttg gtaacaatta taaatgattt tgtgtttttt 19560
attccactag ttcattttca gtgtgtagaa aagcaatgaa tttttgtgtg ttgatctttg 19620
ttccaacatc ttgcaacatt attgaactca tttattagtt ctaggaggtt ttttcatttt 19680
tcttgtagat accttgagat tttctatata gacagtcatg ttgtctgcaa acaggcacag 19740
ttttatttct tccttttcaa tctatatgcc tttttttttt tttttgcctt attgcagtgg 19800
ctagaacttc tagcactatg tcaaatagca ttggtgaaag cagacatcct tgttccttgt 19860

-continued

```
cttagaggaa catttggtct ttaatcttga tttaaaaaat tccttgcact aagttaccgt  19920
gttttgcggg agggagaggt ggggtgaggt ggggatttcc cctaatgttt acaagctggg  19980
attttctttt tcctgtgtct aattattttc ctcattggct tgaaaaatct gataaaacat  20040
tttaggactg tgtataaaat agaattagcc aagtgcaatg tctttattca gaagaaattt  20100
catggacgtt gtgcctactc tcttggcttc ctggcttcat ggctttccag atcccacagt  20160
aagctctgga tagtagaagt tatagtaaga ctgacttcta aataaatgaa gtgactttaa  20220
ccttactgat atggcttaaa gaaaaggagt ggcctttaag atccatgaac ttctcaaaca  20280
aaagtgataa cgttatctcc atgcatatat aatactaaat ataatgcaac tgagagaagt  20340
aggctgtggt aagaaaggag acccaagtgc catctgaagg cagcacttac cactctgctt  20400
catcccaccg aggaaacaaa gcatgagtat tgccagattt tcttctgttt caagaaaagc  20460
cagaaatcca ggtttttgcg tgaaatgtcc tgattttaat gttgggaact aatttatatt  20520
ttgaaataac attgtgtggg acaagtgaac ttgtatgtgg aactgctttc tcccagtggc  20580
gaccagtttg gaccgttgat actcagcaag ttcagccaag tgcgccttgt cattgtcagt  20640
catcaaggtg atgtgtgatt ggtcaagcaa ttaattttgc tcagcatctc gtgtgttttc  20700
aaaagaactg aaggttcatt tgctttcaga gcacaatgcg tattcatagt atattgactt  20760
aatttctaag tgtaagtgaa ttaatcatct gaatttttta ttttcagata ggcttaacaa  20820
atagaacatt ctgtatataa atgtgtaaat tagagttaat ctttccaatc acataattcg  20880
ttttatgtga aaaaggaatg aactgttcca tgctggtgga aagatagaga ttatttttag  20940
aggtttgtcg ttgtgttttg ggattctgtt ttcttttaaa attgtaaata tgtacttgtg  21000
tgaatgattt tttaaaatga ttttaccatt tttggaaggg tatttaatga tagaatatca  21060
tcgagccaac atgcactgac atagaaagat gtcaaagata tattaagtgt aaaatgcaag  21120
agggaaaaca ctatgtacag tctgagccaa atcaaagcat gtatgttttt tatatgtgta  21180
caacaaaagg tttggaaaga tatgcgccga attgttaaat gtggtttcac ttgagggggt  21240
gggaggatgg ggccccagag gggtttttat gggggccttt cacttggtat ttttttcatt  21300
ttgttctgtt tgaaattttg ttttttcttt ttaaatggag tttcactctt gtcgcctagg  21360
ctgcaatgta gtggcgtgaa ctcagctcac tgcaacctcc gcctcccagg ttcaagtgat  21420
tctcctgcct cagcctccca tgcctcctgt gtagctggga ttacaggcac ccatcaccat  21480
gcctggctaa tttttgtatt ttcagtagag atggggtttc accatgttgg ccaggctggt  21540
ctgtaattcc tgacctcaag tgatccaccc accttggcct cccaaagtgc tgggatttca  21600
ggtgtgagcc accacgccca gccctgttta aatttttttat aagtatgtac tacttttgta  21660
atcagaatta ttagaaagca ttttactgat ttaaaagctt agacatgttc aaatgcctgc  21720
aaaactactt aacactcagc tttagttttt ctaatccaaa aaggccgggc agttaatctt  21780
tttggtgcca atgtgaaatt taaacggttt tatgtttttc ctgtgttgtg aatgaaaaat  21840
atttctgagt ggtggttttt tgacaggtag accatgtctt gtcttgtttc aaaataagta  21900
tttctgattt tgtaaaatga aatatacaat atgtcacaga tcttccaatt aagtagtaag  21960
ggtttatcct taatccttgc taatttaagc ttgcataagt cactttacta aaagatcttt  22020
gttaagctag tattttaaac atctgtcagc ttatgtaggt aaaagtagaa gcatgtttgt  22080
acactgttgt agttatagtg acagctttcc atgttgaggt tctcatatca ccttgtatct  22140
tgaagtttca tgtgagtttt taccattagg atgattaaga tgtatatagg acaaaatatt  22200
aagtctttcc tttacctaag tttgctttct tgactagtaa tagtagtaga tatttctgta  22260
```

-continued

```
ataaatgttc tctcaagatc cttaaaatct cttggaaatt ataaaattat tggaaagaca  22320
agaacagttt ttattcatta tatgcattat tatcgctttc tcaagaaaag ggaactggag  22380
caattaaaca tatgtaattt ttttttaaaa aaccctaaac ctaaacatct acctatatac  22440
aaaaattaat taacaatgga tcatggactc caatgtaaaa catgaaactc taaacttcta  22500
gaaaaaaaac tggagaaaac ctttggtacc tatgacaagg cacagttttt agacttaaca  22560
ctagaagtgt gaactataca agaaaaaatt aataatttga accttatgaa aatcaaatta  22620
tttgctctcc aaaagaccct gttaagagga tgaaaactaa attacagatt gagagaaaat  22680
atttgtaaat cacatatttg acaatggact tgtatctaaa atatctaaag aactctcaaa  22740
actcaacatt aaaaaaaata tctaattaga aaatgagtga acattttacg aaaggggcct  22800
tatagattag caaataaaac acttgaaaag atactcagca tcactagcca ttagaaaaat  22860
gcatattaaa accacaataa tgtatcgcta cacacatata agaatggttt atgaaaaaat  22920
agtgatgaca ccaactgtta gtgaagatgt ggagaaacac tcatacattg ctggtagaaa  22980
tgtaaaatgg catagccact gtggaaaatt atttggcagt tccttttaaa actaaaaatc  23040
aatctaccac acaacccagc aatttcatta cagggcatat atcccagaga aatgaagatt  23100
tatgatcaca caaaaatctg tacacaaatg ttttatggtc actttattca taatagccaa  23160
aacctggaaa ctatccaaat gtccttcaat gggcaaagga ttaaacacac tgtgatacat  23220
ccataccatg gaatactact cagcaataat aaggaaagaa ttactgctac acacaagttg  23280
gattaaactc aaggaaattg tgctgagtga aaaattaaca agccaatctc aaaggacaca  23340
tacttcatga ttccatttgt ataacattaa ttaacacaat taattacaga gatggagaac  23400
agaatagtgg ttgccaggga ttatacatgg tggacgcggt gaggcgggcc tccacgcctt  23460
ggagatgaag gggctacac cctttaaagc acacccacga gagagttttg tgcggagggg  23520
cccaatttaa gtactccgcc ccgggggggg aacacagggg caaacaaaaa aaattggcct  23580
tgggggtgac caaacacaca aaaaaaaaac aaacacacaa aaaaacaacn atgggtggga  23640
ggattaatcg ccaaatctga gtaagctatc tggacagtac caatatcgat ttcccagttt  23700
tgatgttgta ctataataat gcaagatgtt aacattggaa gaagctggct gaagggggct  23760
caggaactct ctggacattt ctttgtacct tcctgtgaat ccatcattat tacaaaatag  23820
gacattttct aaaggttaaa tcattttaat tttaaaatgt ccctgttact gttgaaactc  23880
acatctccat atactgatca agaacagcac taatggcccc tggcctccag gaattcacaa  23940
ttcctactga cttttctttg aaaccttggc caagtcgctt ctcttctctg gtcctcaatt  24000
tttcatcttc aaaatgaaga ttgaatgact attaaaatct cttgcaattc ttgagatgaa  24060
gggtcctaaa ggaactgaag aggatgccat gtaatgtaaa tatgggtttt tactccatca  24120
gccagccaag acagagggca gacaccaaga catggtaacc aaggaggcca tgtgtaaaca  24180
aagaccattt agacttatgc tctggccttt gcagcccaac tggtgtggcc agttggtggg  24240
gtatgaagaa aatggggcct tccaggaacc atgttgagtg gagataagca gggaggaatg  24300
cagaagacat gggggcagtg ccagtctcag cccgagccag ctacacccac acatggttat  24360
gaaagactga cagcctgtaa gntgaacaca gccctgcctc tcttagatag gcgcaaatat  24420
gatctcagat gtggatttac tgtaaagttc atcaaattta aatttcagaa cacttaatct  24480
gcaagagtcc tttccaagac cctataccta attttgtgtt tacaatttta tatttgtttt  24540
cttaaagaag accaccaata taaactatat ccagccttca tgataagtac ataggaaact  24600
```

-continued

```
atgcaaataa gggggaaaaa aaacaaagaa aaatacctag tttactaatg gttcacttct  24660
gaatagcaca tattcataat gatacaagca ctcattacta gtctaggaaa atgaagatat  24720
aattgcatta ggaagatcaa gaggtaggaa atgtggatgt gtgtggtata gactagggca  24780
ggacaaagaa cctaaatcct cattttctaa agataattgt taatacgtaa aactcaaaat  24840
tcaagaagta acagtaaaag cggtcattaa gaaacaagca ctaaacacca gataggaagc  24900
gagagatggg ggaagagggc gacaatctga ttattttttg caacaaattt tgtaaaacca  24960
tttgactgtt tacatgtaga acttggatct tttttaaaaa acacaaaata ataatactat  25020
tattttttaa ctggattttt gaaaaagaag ataaaagtct cattttagta attaaaactc  25080
attccaggtt agtccactca aaacttatat tcgaaaatta aaactttggg aggctgaggc  25140
aggcagatca cctgaggttg ggagttcgag accagcctga ccaacacgga gaaaccccgt  25200
ctctactaaa aatacaaaat tagctgggcg ttgtgcatgc ctgtaatccc agctactcgg  25260
gaggctgagg caggagaatt gcttgaaccc gggaggcaga ggttgcagtg agccgagatc  25320
acaccattgc actccagcct gggcaacaag agtgaaactc catctcaaaa aaaaaaaaaa  25380
aaaaaaatta aaacctctgg aagttgagtt tgcaaatatt cattatgctc atttttaact  25440
tgtatgtttg gaaaatgtca tgatgaaaat tgaggttggg ggatgagaaa aaaagaaaaa  25500
catcaacccc acagcccatt caattttcag cccgacccac agctccgggg aagggcagca  25560
ggtccatcct tcactctttc ttcacctctt tcccctcctt ctggctcttc cacctctaat  25620
ttggagccca aaaaaaggca ctgggaaatg gaaaagtctt ttgtacgtgg tacttgccgg  25680
ggaagctgcc atgaaaacct ggccccacgg tggggaggga atgcccanct gaggcctcgt  25740
gcccatgcta ggatagactc gtccaaacat gtcaggtggt ctgacagggc aagcancang  25800
aaatcatgta tgagtatgaa ctgatctgta tgcaagggcg gggagaacac gcggaggaat  25860
ggggcgtgag aaaacagcac agtacgtttc tttagcagct gtctctgctc agccatggga  25920
ggtcacagag aaagaggctt ggaggcgtta ttttcactgt gagatgtgag tgtaaaaaag  25980
tgcccaagac acagtgagta ccagggagat gccctctttc ctacccgaat gcagaatggc  26040
cacaggcctt aaaacacaca catgggtcct cagaggagag aggcctccac agtggacacc  26100
cgcattctcc cctggtcagc agcagcaggg cgagtgctgg gccatcatga agcttcacag  26160
gcaatgagct ctcagcaata acaggaacag tgcctggggg actgtagctg caagaccgat  26220
tttcatgtaa gatggcctct gaggactccg agatacacca ggctgagact agctggcagc  26280
tccaagttgt tggtcagaag agaacaggaa ctagggaaat tggaattact gttactacaa  26340
ttcctttaca tccgcacaac catgaggtcc agcgatttc tattattttt ttttttaaga  26400
cagggtctca gtatgtcgcc cagcatagag tgcattgatg tgatcatggt tcagtacagt  26460
attcacgtcc caggctcaag tgaccctcct gcctcagcct ctcaagtggc tgggacagca  26520
gttgcatgct accaggccag gctttttttt tttttttttt tagtttctgt agagcacata  26580
gcggttaaca atggcacagg gaaacaaaca gttccaggtg caggggctct aaatctatca  26640
taagatgtta ggtatggggg ctctgccgga cacaaactca aggctttatg ctgttatctc  26700
ttgagcgaaa tcctgggaac ttcgtacatt gcttgcttca gtaccttatc agttaatcgg  26760
actctttgat atgttgggag tcagcgtaca caagttaact ccttgaggaa gggggtgggt  26820
aaggagtcct tgatgtctgg taaatgaagg agcgaaatcg agttcctctg gctttctcag  26880
ctaagggaga gcttattcat gtggaaacaa ggctaagtga ttaagggaga aagggagagt  26940
ctgaaaacaa ggttaggtat tacaatgtca ataaaattgg tctccttata cagtcctatg  27000
```

-continued

```
gtagatttct ttccatcttt aatctccctc tagcaccacc agactttttc tctctgtacc  27060
ttgagatgta aattttgcta tctgaatttt cgtctaagag ttgtttcctt taatatgcaa  27120
atttagggtt atttagctga caactgccaa agtagtgaaa caagttatca agaacttgaa  27180
cgtctaaggt aggaaaaaaa aaagtcttta tgaatctata agatgtactt ctattggcat  27240
gcctaatacg tctatgtatt tacgtgttgt gtacacagtt tttcactact gaaaatatat  27300
agaggagttc taattaattg acttaagaca ataaaagcgc ttgaatcaaa taccttatca  27360
ggaaaaagga aaagacaagt caaatgcttg ttcaagttta tataacttaa gtaaaatctt  27420
taataaataa gctagcttta acattatttg aaatgtctta agaattgcca gcaggttctg  27480
ggttacagaa ctagtggggg tgcagtgggg tgagggttgg tggggtgggg ggtggtacgg  27540
gggctttgtt ttttcttgct gccccttct gggttgggga agtggcagga ccttggcagc  27600
accccgagcc ggcatggcgt taataatgga gggatgccag acccaagtgg ctaaggcccg  27660
gctgcagagc caagttggca tttccagact ggggctcggg ccgcaccctc tccaggaccc  27720
tccccttgta ccgagcagat tgtcgcgggc agtttgggcc agctgtcctg gcgtggaatt  27780
tcccaaattc aacaaatcct ccaagaaatc aatccatcca ttcatccatc catccatcca  27840
tccatccatc catccatcca tccgtggcag attatgaagc atggatcatt acttttggga  27900
tgtggatata ttcagttaac aaggagcagc tttcaagagc tggattttat gctttgggtg  27960
aagtttagaa acactagctc ccacacctca tgtgctctag cgcctcttac ctcatgccct  28020
ccactctcag tcttgcactc accctgccac actcaagggc ttccccaggt tccttcttag  28080
attccaccga tagctcaggg actttgcaca tgctacggtc tctgcctggc tcctccccag  28140
atcttctcat gcctagctgc ttctcatcag cacccctcag agactgtccc tgccccacct  28200
ctccaggttc catacctgcc accctccccc aatcacgtaa cagtttcttc acagagcgag  28260
ttaccatccc agtatttccc taacttattt tttgtgactg gtctgttgcc tgtctccacc  28320
acaagaacat aagctgcatg tgaacaggag ccttgtctat cttgtcaccc cagtggctgt  28380
gacataacct gatacacatt agatgctcaa tgatgtttga tgaatgaagt gctggtagtc  28440
caactgtgtt tccttgtctg tgtaagtatg tctgttgtgg tttcctaaga acctacagct  28500
ctcccactgt gactcctgtt ctatggtcct gatttgctgg actagaatcc taacctacat  28560
gcttactctt agtgtcctcc cccagaggct gaatcccagt ccctaaacct ccaccaaatg  28620
gctaagacct agcttccaac cagacaggcc tacgctgaga cctcagcacc gcccttctgc  28680
ggtctcatcc ttaacgcatc cttcagggcc cagcttaaat gtctcttctc caaggaaggc  28740
tatcctcttt ctgcccctca gtgctctcca tgcctcctct atgcctccat gcctgctttc  28800
caaccctgca gaggtggaga agttgctaat ctgctgtgtt gacatgtgct ggggtgcctt  28860
gggccaggga gcaggctggt ggtgtgctga tagcccgtgg ctgtgcccag gtccatgctc  28920
acttcctgag ccccagtgga gtaggctccc tttcccttat tgcagcactc agaggaagga  28980
cgtgcttctt aggacagatc tggccaacct ctccctcgtg agagaaggcc cagccatcct  29040
cttgccctct ttctttctcc tgcccccgag taataaaggt gcctggtcag agccttctag  29100
aaggagaccc aaacatccac cacacattcc cagttccaac cgtcatccac atggctggct  29160
gtgcaggtaa acgcagagtc tgtttcacac acccaaccat ctagtattgg atgggaggac  29220
agtagcgtga cactcttctc cagccttgag ccctactgtg ggccccaccc aacccagata  29280
ccagaggagc cctgtactgg gatgctattg gatgcttgtc cagtcatgta caaagttagc  29340
```

-continued

```
ccttttgttat atagagttag ctacgtacat cttcctctgt agggaaccca agaggggaga  29400
agagatatgt agtaggattt aacctgcaaa tcctctgctg agcaccgtgc actacataca  29460
gtgggtagca tgtggtaggt gctcaataac tattgaccga tctattgaat acacgtaaga  29520
tcgtgacact atctaaaacg nggggtgtgg gggaaaaacc ccccccttgt ttaggaaacc  29580
caaattggac cgtgttggcg cgcgattgtg ctaaagatca tgcatgcctg atcaaacgtc  29640
cccatatggc gtctcagagt caactccttc cccatcagtg ccctgacttc ggcataacaa  29700
acctggcagg ttaagtgatt aatcggtcct gtacaactgt agcccttagc aggaagcact  29760
aagcttcgtt ttcatttatt tcttccctgg aactgcaaga aatgagggat gccttccgcc  29820
atgaagtttt gctgattgtc cactttgttc tcaaggagat attcacagtt tttaatttgt  29880
ctttctctcc tgcatggtct ccaaacctgt ccaaagaagc cagctggctc catcatctgt  29940
aaaatcacca ttgtcaccag agcacttgac ttcctgttgc cctacaatcc acctgcactt  30000
tatttcctgc caccatgata atgtagtgtt actacatttt acattcagct gtaagaaatg  30060
ttacattcat ttacttaaat caaattaagt ctgctcactc agtcccccac agtgaccaac  30120
ttataaaaga gaaggtacat ttcagtcatc actgaggttc tctctaccac tggaaaactg  30180
aggaagggtc tggagtccac agtggttaac atcattgcct ctgtttttttc tcctactcaa  30240
tgtaaccatc caaggttact cacaaattca caaaaagagg tcttcacctc tgctctcaag  30300
acccagaggg ctgggttcta aactcaaagg ccaatgttcc ccaacttttt gcattgtttc  30360
aacattgggg aaaactcgag gggattcaag aatggttata taagttttgt ggaaaaatgt  30420
ataatttttt aaaattaaaa tacaaagtat tatggaaagc actaaatatt gaatttatat  30480
aaatattcca aatattttc taaattttta gtgagaaact tgagcttgct tctgtgagat  30540
atttatttta aaacagattt gacacttaaa atgtctaatc aagcctttta aaccatgatc  30600
tatctcttca aattcttcag atgccaccat caataaagaa actttgttca cacaagtaag  30660
tggtagcaaa tggcagggtg tttatcattt tttttttttc ttttttttgag acggagtctc  30720
gctctgtcgc ccaggctgga gtgcagtggc gcgatctcag ctcactgcaa gttccacctg  30780
ctgggttcac gcccttctcc tgcctcagcc tcccgagtag ctgggactac aggcacctgc  30840
caccacgccc ggctaatttt ttgtattttt agtagagacg gggtttcacc gtgttagcca  30900
ggatggtctc gatctcctga cctcgtgatc cgcccgcctc ggcctcccaa agtgctggga  30960
tgacaggcgt gagccaccgc gcccccgccg tgtttatcat tttttgcctg atgaaatttt  31020
ccttgccact actctggatg gtttgataca tttaaattgt gcttccaggg tacaattatc  31080
ctttaaatct atacctcttt cctttctttt attgacaaat ataatgttac acttttctgt  31140
cattgcagcc acaccaccag tacacagatc ccaacagagt tgtaatattt tattagtttc  31200
agagtttcaa tattttatca ctttcaatac ttcatgtgca ggagttttat ttggtacttc  31260
tttacaaaat aaatgatgtg cttccaagca tttcttttca ataattccaa tcaatgttat  31320
taactgagta atactagtat ctgtttattc ataaattcac aggaaatgct tttttactta  31380
ttagtctttg gaattctgtt gtttgtataa acatctttca tgatggcttt gtgtctacca  31440
atagcactat tgccaaaagg caccttttttc ttgttccttt acttcactgg tccgaagcct  31500
ggtaccaaca actaccacac agactgggaa atgagcaatt ttgccacgtg cccttagcta  31560
ttaatggtgg cactccataa ctagcatctt aagctcaatt tcatgaaaga aatgtgtttc  31620
ttattttgta cttgcaggca ctttttaaac ttgtaatctt ttattcatac tttaaaatta  31680
aaacagagta atagaaccca tagaaggaaa tcaataccca cgagtccata ctgatataaa  31740
```

-continued

```
taaatagtta cataaataaa tggggggaga aataacagct cttccttaca gaaaaatttc  31800
aattaataaa tgaagaagga attagggaaa tacaacgtta ccattaagca accacagtaa  31860
taatcattac aggcaatatc caaaaataaa ttccaaagcc agtgggcaaa agtttgagga  31920
gatacaggat attaacatag tctccaaata gctcatgcta tttataaatt acaaaaggaa  31980
acataacaac tgtatagtga agaaactcag cagacaccac cttagccaag tgatcaaggt  32040
taacgtcact agtaataggg cttgttgaca tactggactc caatctgata cactgataag  32100
gacacatgac ttctgcagta ttcttaccaa aaacagaatt ctaatgtaat taaggaaaat  32160
gtcagacaaa cctattctga gaaacattct ataaaacaac taaccaatac tttcaaaatt  32220
gtcaaggtca taaagaccag gcgatggtca cagatttgag gagactaagg agatacaaca  32280
actaaataca caaatggaac catggcattc ttgattggat cttgaaacag aaaaaggata  32340
ttaggaagaa aagctgatga aattctaata cattctgtag tttaattaat agtattgtac  32400
caatattaat ttcctagatt tgatcattat actatggtta agtttttaac attagaggaa  32460
tctgggagaa tggtatatat gaactccact gttcattcaa ctttttcagt aactattatt  32520
tcaaaataaa gttgggagcg gcggcccacg ctgatctcta aagctttaga ccacattggc  32580
tcgagcatgg tcatggccgt ttcctggacg tcttagcgct atattataaa gaaatattca  32640
cctccctgct gagcttacag ggtgtaccta atgtccaaca atatgaaatc tcttcaatga  32700
attgcagcac gtccatatat aacccacatg gaagctgtcc tctttcctca ccttcgaact  32760
tcccatgcca aagagggacc tcttggactc aaatacatct tagcaatata gaagatgctg  32820
gagacttgta ggagaagtgg agagggttta cagtgtagcc ccacagaaaa caacttatga  32880
ccccatcagt cacttgtccc ttttttccat gcctcagtct agtcaggaaa ccactagatc  32940
ctggatggct tcttctccct tcccctcctt tctcttctcc tctccctccc ttgctcctcc  33000
ttcctccatc acccactcct tacttccaac caaaacttga ctagctccag tctcatccct  33060
ccttattgaa aactatttta ctcagccctc ctccccccact cctgcccaat ctttattcct  33120
tacctacatc agacttcacc aaaacaaagg ccaggataat aaacaggaca aactctttca  33180
aacacatttt aatgaccata ttttgttatt ttggtacaat ttgaggagtc ccaatcccca  33240
gggaagacta acaagaagtt ctcctaacaa aggtgggtct cccccttacta aaaactcctg  33300
taatggctga aaagagcatg aggttttctg catatcatta cacattcaat agaacgtcat  33360
gcagctgtta aaaatgatct gtagaaggct atcttgtgac agaaaggcat tggagatata  33420
ctgttagtga caaaaaatagg ttataaatga atttttccat gcatgcctct atatttataa  33480
atacacacac ataaaagaca ggaaggacag acattaaaca ttcatagtgc ttaagatgat  33540
gcatagtata atagttagga ccatggcctt tgggacagaa aactacagcc tctctcccac  33600
ttatcagcca tgggaccttg ggcaatttgc tcagcctcaa agcccctgtt cctttatctg  33660
tgtgctgggg ttgttgtaag agttaagtgc aatacacaga gagagagaga gtacctaaca  33720
tgtattatgt gctcagtcaa tatgcatcat agtactcatt gttacatatg ttcctaagtg  33780
ctttatacgt tttttcccta agttgaccat ctgtttttgg cattatgaaa cataatgatc  33840
ctaacaaatt aaaattaaaa acataaagaa tatttgcccc aaaaaaaataa agaacatgaa  33900
ttcttcaagt agccaagggg ccatagacag aagtaagccc ttggtggggc ttagttgaga  33960
gaagtctcca gaaggtcttt cgtgtgttaa agaagagggt aacagggagg aggtggggag  34020
agatgttaac tgagtctaaa tgagcacctg gaagaagaga tgggacaggc cacttctgcc  34080
```

-continued

```
tggactccct gattgttaag aagaatgaaa aagagcagaa gtcttccctg agcccaactt  34140
cactccctga cttaacctag tctttgcccc ttccctctca ctcatggcta ctttctgtgg  34200
tcaccttgtt gtagaaatgg atgtgcagcc acctcatctt tttctacctc cttcacatgt  34260
tttagataat ttaatgtagt agaagacggt tacagcaaaa aattacaaaa atcaaaatat  34320
ctctgctatc tactgttgca tttctaacca tcccaaaaca gtagctgaaa acagcactcg  34380
tggtcgagcg cggtgactca tgcctttaat tccagatact ccggaggctg aggcaagaga  34440
atcacttgaa cccggaaggt ggaggttgca gtgactcaag atcatgccac tgcactccag  34500
cctgggtgac acagtgagac tccgtctcaa aaaaaaaaaa aaaaaaagca ctcgtgtatt  34560
ttgttcaaga tctgtggttt gggcagggca gggctcaatg aggacatctc gtctccgttc  34620
ccgcagtgtc aggaagtgta actgagactg gagggtcaca cagaagatgg ctccctcaag  34680
tggccagcaa attggtgctt acaattgaca gggagctgtt gaccaagggc cccaattcct  34740
cttcctatgg ccccttctcg ggctgcatgg gcttctttac agaatggcag ctggattcca  34800
agagcaagta tcacaaccta cagaagagtg gaggaatatt gaaagttcac agtctcttaa  34860
gacgttggcc cagaaactgg caaaagcttc atttctgcca tgttctattg atcagtcaca  34920
gaacctgcac caattcaaga ggagaacata tagaggacat ctctcaatgg gataagtgtc  34980
aacaaatttg catctatcac aatctgtctt ttgggtacaa actatttcta ttcctccatt  35040
atgcaaaata tactcacaac ctcccagggg tcgcaaaagc ctcatccatt tatggcaaat  35100
gtggcccttt taatttatat aaaataattt gcgggggctt cctttatatt tttaactccc  35160
ctgcgtgcag agaagtgatt taaagccctt cagaaagaat gctttattcc cgtggaattt  35220
ggtaacttgc ttgggtgtgg ggaggtttgt cagctttctc cactcaaatt atcagaccct  35280
ttccatttag tggtagacca tttccctcgt ccaggccaag ggcacatagt acagagaaat  35340
agggagttgt tacccaggga gagaacttgg ctctaaacct gtaatagaaa ggtcagttct  35400
ggtctggagg gtcaattttg atctttggct cagatccagg aattggaacc aaggcttttg  35460
aacattttaa tgcaggggat taaaaaaatg atacgagtca ttcacgaata tatttgctta  35520
acatctaaag agatccctca aaacactaga aaaaataaga acaaaaatct aataaaacaa  35580
aatttgttaa acacatttac caaatttttt tttttggtaa aaattcaaat gtcataaata  35640
aagctaaagt tcctcttgat gactcgctcc tctgccctat tccactccaa gtaaccacta  35700
ttatcagtct tgccaatacc cttccagacc tctctacctc tatataccat tagaagcaca  35760
tggttttgca ttgaggatgt gcagtgtttt gttttacgta aatgttatca ctctgttctt  35820
gttccataat ttgccttttt ctctcaatga tttgcttggc tatctttcta tttcagtagc  35880
atctcctttc tttttaactt accattgttt atttaacctt gcctctatca acagatatgt  35940
aggttgtttc tagttgattt cattaagtat ttataaacaa cgcatcagta gatgtccata  36000
aatttcttta cggaagatgg caagtagtgg aattgctgag ccaaagaaca tgtttaaaaa  36060
acccaaaaaa actagacgct accaattttc tctccaaaat ggccataccc acttacccat  36120
acagagatga tttggaatct ggcttcctca caaggtgaga tgccttcaca gtttcattct  36180
tcctggcatg tcttcccttt tgtatctgag agagctggca gaattgtgtc actaaatcaa  36240
ggatagaggg tcaaatgaca gctcaagctc acaggcacct ctgctttctt cccagaccac  36300
ctgctttcct gccaccagct ctgttccatc ttatagaatg gttgccactt gggtgtctgc  36360
tccgacagcc atgtcatcct ttgcactgca gttatgaagc agacagagct aggagagggg  36420
ctttgccagc ctctgcccta gcttggagaa cttcaaaaaa ggagggtatt gaagttgaac  36480
```

-continued

```
tcccccaaaa aggggtggtc cccacacctc aaaaagtggt gcctccgaaa gaaatgtaaa  36540
attcgtgtgg ggggggaaaa aggttattta gaaattgttg gcttgtcgtg ccgaaagtat  36600
gtgtggttac ggggagtacg gaaatttcga ggggtggggg cgaggccgtg tgtcctttag  36660
cccggggttt tcccgtcgca tgtttaaggg gggggaagag gggggatgtt ttctttccgc  36720
gaaggttttt gaagaacggc gtggcccccc accgccacta ctcaaccggc cgttcacgaa  36780
acaactcgcc acatccacta acccgctggc tcaccaccca ccgccctccc gatcccccca  36840
atccaaactc aacccccacc accaagcgcc tccccccctcc cccaccctcc agctcagccc  36900
caacctacca ccaaccccga ctcgcccacc gaaaaccaac agcaaaccca aatgcccaca  36960
aaaccagtgt ccaaaccctc cttcccatca gtttggtggg cccatcaccg cttcccctgg  37020
cccaggctct ccttttgtgc gcttggagca gcagactgat ctcccagcct tcactcactt  37080
catgtggtaa tctgttgtgt tcatcactgt cagaatcttc tgcatcccct cactactctg  37140
ctgaaaacac tctagtggtt cctcattgct cattaatgaa agtctagata ttaaacgtag  37200
aaggcccagc acaatttgcc cctatgccac ctacctctct aatcttttct ccttactctg  37260
acagactctc cgtctgtcat ttatgtattc ttttattgct ctcttctact tttagtatga  37320
actggattta tggatttttt taacattgct ttcaagtatg gaataaagaa ttttatttat  37380
ttatttattt atttatttga gactgggtct cactctgttg cccaggccag aatgcaatgg  37440
tgcagtcata tctcactgta acctcgaatt cctaggctca agccatcctc ctgcctcagc  37500
ctcctaagta gctatgacta cgggtgtgca tcaccacatc tggctaatgg aataaaatat  37560
tacaatgcct aatcttaatt ttcaaaattt taaattacat tgtacctaat gcccatgcat  37620
ttactttttt cagtgggtca atagccctca ctttggcaaa ggtcccaggc ccaaggtaag  37680
gccttacttt ttccaaactc atcttttgaa agacataagt gcctgtaagt tgtaccacat  37740
taggttctag gaatttttca tcaaagactt tatcagacta ttttcctcta agttgagaaa  37800
gagctggggg cagaatatgg cactgaatga ctgaagagaa ggcactgaaa tcaggccaga  37860
ggttgctgga aagagcaatg aggaacacca gcagcaatga ggagccggtg atgattttgg  37920
cttcacaggg aggtgtgtac cacaccgatt ttatctctac gtggatgaac cacagctgtc  37980
ggctcccttg tctccaggac atcacactct ccacattccc tcccatcttc cggcttctgc  38040
ttcccggggc cctcatctgc cccatcctgg gtgaacactg gtcggtcaac tgctgggcgt  38100
accttcccgc tctgcacacc ctccctggcc accccaccca ctctcacggc tcgcactgca  38160
gaggagccgc atctctagct ccagcccatc tgcctcttct gagctctaac ttcatgtagg  38220
cgactcctgc cggtgttgcc tcacaggccc atcatacttc aaagcatttt cccctcagaa  38280
caccatgtcc tggctgctcc ctccagaaga tacatctctc aagcacatcc ccgcggctct  38340
cacctggatg actgcattca ccttctccca catttgcccc ctcctttgga tgtatataga  38400
ttgttttaaa atacaaatct gatgtgcttg ctctcctgct tgaaacacct caaaactgcc  38460
ttcaggataa accactgccc ttgacatgtt cacaggttgc ccatggcctg gccctgccca  38520
tctcttcagc ctcatctcat gccccttgcc cctcgctctc tgggcttctg cctccctagc  38580
cctcctttag gttctctaac acaccatagt ccttctagtg ttggggcctc tgcaagtgct  38640
gttcccattg cctgagacat gaatccctct ccctatctct acctgcacct tcatctgatt  38700
aatccctacc cttcctactc atgatgttgc tttctcaggg actctctctg actttttaaa  38760
ctaatcaggg tctccccagt atatatcttc atagcactct gtattactcc tttcttaatg  38820
```

-continued

```
accacctgct gtagacagaa tgtttgtctt cctccaaaat catatgtaaa accttccacc  38880
agagcgatga ttagagaagc ctcccgactg acattcagaa gatattaata agagcactaa  38940
tgatggggat tgcaaccatg tctttactga cttccagaag cttcttacag taaacatgaa  39000
atcacataat ttcttccact ttcctactgt ttcttgttct gggctctgtc ctgcttactg  39060
tctaatatct tggcccctta aaagttgcta atcttccaaa cctcattcct gtgactgggc  39120
cgctggtcct tgttcatggg ccttgaagat actgactgta cacttatctg gagcatccag  39180
tgcctaccac ctgacccaga ttcctcattg cgctcctccc tcctccacct aatgggattt  39240
gctcataccc gtgtgggacc cctcccattt tccccaactg aatacttatc aagacaacgc  39300
attgccatac tccctcgtac cctgctctgg gcatcagact gaatgtttgt ttccattgag  39360
gatctgcagc tgcatcagtt tccccagcac cgtccaaccc cttgagcatg gctagtccta  39420
aagcagagaa ttagcctttc tatccctgct gctatacatg ctgggacaaa taataagaaa  39480
tgacagcatt ttatgataat gcaggctgca ggaggcagga ggcaggaatc aaattcgtgc  39540
ttatcaaata gtgctccaat tctttgaata ttggactata gaatatgtca tggatctatg  39600
ctcaggtggg ttccctatta ctcactccac tgaggccagg ttgtgggatt agctgtccaa  39660
gagggagttt cagtctcaca gcatagggtc attctgagaa ttactggccc acacttgtgt  39720
ggagacctcc agagaacaga atctgggttg gtgccatgta cttccaggag gagagaagtg  39780
gcaggatgcc cagccccaca atcagagggg aaggggcaga gccacatgta tgaagatcct  39840
ctccccagta cgtgccaatc acagggcttc ctagcttttg ggccaaggaa acaatgtggg  39900
aagcaaaaaa ggacaatttt ctcctccctt tgcatgaaga ctgagcagtt ttaccagatt  39960
cccagggaaa caccccttcca ctctgggttg aatgtgagtg agagacattc agctggaaca  40020
ctagaaaaac tatttcctga gccactcacc tttagcccta gaaagtgttg gatttgtcct  40080
tcatctttgc cacagtagag actgctgata gcatcagaac ttgggctctg gaattagaca  40140
gatatgggta caaatctgag ctctctcact tattagtgtg ggatgtagag caacttttaa  40200
aatccttcca aacctcagac ttctcatgca tgatgtgagg attgtaatag ggcccaccta  40260
ataggggttt ttgagaatta aaaaagttat tcaatgaaca gcatttagca agatgcctga  40320
ccattgagaa aataacaaat tgtttattat tattgttatt attaaacatc tttcctgcac  40380
cttctgactg ggggcatcgt atcatcagaa atacttagga tgggatggat tcctgcatgg  40440
gctgagtcaa gggtgcaata atggaggagt gaagaaggaa gaaatggagg cagaaatccc  40500
caggagccca gcatggtaca aggctgagct agtgctgcag agcctccttg gaacagccac  40560
agagcttgca tctggccctg gaggaacctc ttctagctgg caggaccagc cacaacagtg  40620
gccaggggat ttcccagggc gtgggctcct caggagttca tttggaccaa gcctgcctgg  40680
agaggggtta taacagggat ccttccctac tggcaggtga tttacccctc ggtgagaagc  40740
tcaggcattt gtttgatgga aggtggaagg ccctgtgctg ggccagtgac tatcagggat  40800
gggcgggtgg ctggaaaata gcaaataaga caatatgata acacagttaa ccaccacact  40860
atgtgaagct acaatatggg tatctgtaat agacaattcc aatgtagaga ataattttaa  40920
ggtgtcattc tccccgccaa tgccataagc acacggcctc tgcctgggtt tctcactgtg  40980
gaatgtcctc ctggtctcct catgcccaga gagtgggaag tactcctact ttaacaccgg  41040
ctttcctgtc atttccntgc agccctcctc agccccctct gcacagggag gtttcctccc  41100
tgctgctgca gtgctttgta cttgttagtg gtacctgcac acaggtattg gtgtccttgt  41160
ctcaccaccc tacatcactg taagctcccc aggagcaggc ttcctgtttg actcacctgt  41220
```

-continued

```
gatcctccac ctcccaccct gtagtgcctc aagcattctg tagagcacat ggacgccgac  41280
taataagtac ttcattattt gggtattttc caagaacaac atattgtagg aaaccattct  41340
ttctaaaaaa aaaagtgtcc ttttaaaaag gtgaataatt tttgtctaat tcaaagttta  41400
ttgaaaagtt atgtataaaa caaggtaaaa ggaacaagga aataagggaa atgtaaagaa  41460
aattatagaa ataaagtggt attttttggt aagaaagctt aaagagaaat aattttaggt  41520
aagaaagaat cttacctaaa attttgtgct agaataaagt gactggctaa gaaagggatg  41580
ttcaaagcta tttatgacaa acccacagcc aatatcatac tgaatgggca aaagctggaa  41640
acattccctt tgagaactgg cacaagacaa ggatgtcctc tctcaccact cctattcaac  41700
atagtatcgg aagttctggc cagggcaatc aagcaagaga aagaaataaa gggtattcaa  41760
ataggaagag aggaagtcaa attttctccg tttgcagatg catgattgca tatttagaaa  41820
accccatcat ttcagcccca aaactcctta agctgataag caacttcagc aaagtctcag  41880
gatacaaaat caatgtgcaa aaatcacagg cattcctata caccaataat agactaacag  41940
agagccaaat catgagtgaa ctcccattca caattgctac aaagagaata aaatacctgg  42000
gaatacaact tacaatggac atgaaagacc ttttcagggt gaactgcaaa ccactgctca  42060
aggaaataag agaggaaaca aacaaatgga aaaacattcc atgcttatgg ataggaagaa  42120
tcaatatcgt gaaaatggcc atactgccca agtaatttat agattcaatg ctatccccat  42180
caagctacca ttgactttct tcacagaatt agaaaaaact aatagccaag acaatcctaa  42240
gcaaaaagaa caaagctgga ggcattgtgc tacctgactt caaactatac tacaaggctg  42300
cagtaaccaa aacagcatgg tactggtacc aaaacagata tatagaccaa aagaacagaa  42360
cagaggcctc agatataaca ccacacatct acaaccatct gatctttgac aaacctaaca  42420
aaaataagca atggggaaaa taattcccta tttaataaat gatgttggga aaactggtta  42480
gccatatgct gaaaactgaa actggacccc ttccttacaa cttatacaaa aatcaactca  42540
agatggatta aagatttaaa catggctggg catggtggct cacgcctgta atcccagcac  42600
tttgggaggc cgagatgggt ggatcatgag gtcaggagat ggagaccatc ctgactaaca  42660
cagtgaaacc ctgtctctac taaaaaatac aaaaaattag ctgggcatgg tggtgggcgc  42720
ctgtaatccc agctacttgg gaagctaagg caggagaatg gtgtgaaccc aggaagtgga  42780
ggttgcagtg agccaagatc acgccactgc actctagcct gggcaacaga gtgagactcc  42840
atctcaataa ataaataaat atggaactct cccaacacaa taataagaca aacccccaaa  42900
tgttttaaat gggcaaaaat atttgaacag acacttcaca aaagaggata tgtaaatggt  42960
caaaaagcac atgaaaagat gttcaacacc attggtcatc agggcaaaga aaactagaac  43020
cacaatgaga tgcctctgta caccacttaa atgtccaaat taaagaaaac aagttttggc  43080
aaagttgtgg agcaactgaa atgctcgtgt attgctggta gaaaaacaaa atggcataac  43140
catcgcagat aatttgttgt cagtttctta caaagttaaa catatactta ttgatatgac  43200
agttccattc caagagaaat gaaaacataa gtccacacaa agacttgtac ctgggtgttc  43260
atggtagctc tattcataat tgccaaaatc tggaaacaaa tcaaatgtcc atcagcaatg  43320
gaatggatat acaaattgtg gtacacatgt acaatagaaa actactctgc aatggagaga  43380
aattaaccat tgacaaacac aaaaacatgg acaaacctca aaaacattat gctgagcaaa  43440
agaagccaga cacaaaagac tgctcagcgc atgattccat tcatatgaaa tcacagaaag  43500
ggtcagttga aggtgcagag acaaaaagta gatctgcagt tgcctgggga tggggtggga  43560
```

-continued

```
ggttgactgc tctgacgcgt aaggaaattt gggggtaggt gggggatggt gggaatattt  43620
tttgaattga attgggtaat agttttaata ggtaaaatat tggaccccac agtatttgag  43680
ataggtttca gtcaatttag acagtttatt ttgccaaggt taaggatgca tccgtgaccc  43740
agcctcagga ggtcctgaca acctgtgctg aaggcagtca acatacagct tgcttttatt  43800
catcttaggg agacataata catcaatcaa tgcatgtaag gtttacattg gttcaatctg  43860
gaaaggtgag ggaacttgaa gcagggagct tccaggttac aaggtagatt attctcaaca  43920
gaaaggaatg tctgggttat gataagcggt tgtggagacc aaggttttat cttgtagatg  43980
aagcctccgg gtagcaagct tcagagggaa tagattgtca aagtttccta tcagacataa  44040
ggtctgtgtt gatgttaatg ctggtcagct tttcctgaat tccaaaaggg agaagggtat  44100
actggggcat gtccaacctt cccttccatc atgacctgaa ctagtttttt caggttaact  44160
ttggaatgct cttggccaag aagaggggtc cattcagatg gttggggggg cttagaattt  44220
tatttttggt ttacagtgaa gacttttcaa gctagacact taaatgagta tgttgcaaaa  44280
tggcaatttc ttagcacggc gacgtcctaa agaaatgcta aggtaactca attaactatg  44340
ctagaaaaga gagttaagta tttaggagga tttaatatgg tgttaaagtt gtgaaaatca  44400
aaatggagac actaatgtta agaaaaccct gataaatgga gccagggaag gccatgaaga  44460
aagagttctc acacttgtat ccctgatcat gaaaaagact ctgcaaaaaa caaaaccttg  44520
cacaaaggcc attgcaacct tacacaaaaa atactacttt aaaaggacat gtgcccagca  44580
actgcctgtc caacctcaga ctggcaatat ctttgttatt gatcttagta gcccagcata  44640
actatttcaa aacagtgatg taatgctcat ttttttttctt ttgaaaactt ttgtcttcct  44700
gtaaaaacct ttgtcttctt tacttaccct gaatatgcac agagtttact atggagtgca  44760
tattcctgtt gcaatgctct attcccaaac aaacatcatt ttcttttaga gagcctctct  44820
ctgtttgtga tttaggttgg tgatgtaaag caatggcata actgaacact gattcaaaga  44880
aaagtggctt ttctctttgt tgtattaaaa agaggcctta taaataggat agtaagattt  44940
gtaagttgaa cttaaagcat gaagaaaatt taggggccag gcagggtggc tcacacctgt  45000
aatcccagca ctttgggagg ccaagacagg aggattgctt gagcccagga gttcaagacc  45060
agtctggtca acacagacct catctttact aaaaataaaa aaattaggcc aggtgcagtg  45120
gctcatgcct gtaatcccag cactttggga ggccaaggcg ggaggatcac ttgaggtcag  45180
gagttcgtga ccagcctggt caacacgatg aaaccccatc tctactaaaa atacaaaaaa  45240
attagctggg tgtggtggcg ggcacctgca atcccagcta ctcgggaggc ttcaggcagg  45300
ggaatcactt gaacctggga ggcggacatt gcagtgagct gagatagtcc cactgcactc  45360
cagcctgggc gactcagcaa gactctgcct caaaaaaaaa aaaaaaaatt agtcaggtgt  45420
ggtagcacac agctgtggtc ccagctactc gggaggctga ggtgggagga tcatctgagc  45480
ccaggaggtc aaggctgcgg taagagctga gattgtacta ctgcattcca gcaggggcta  45540
caaagtgaga ccctgtctca aaaaaagaaa aagaaaaaga aaattatgtt tttaaattta  45600
taattataat aaatttaatt acataaattt aagctcaagt aattgtaaat attctttctg  45660
tgcacataag ttattcttgt attgacccca caggagctgg ccattcttca agtcagaagg  45720
cctgagagag gagctgccca ggtggtcttc atggggctgt gcggccagtc atcccccaca  45780
ggttgacaat ccttgtgtac ttcatcctcg ttggatcctc tgtatccctg acgatgagca  45840
actgtgaggc ccgtttcagc actgagttcc agtcaggaaa acatccaccc acccaccaca  45900
cgctcacact tacacacaca ttcacacatg cacacacgtt ctggctccga aaaagaaaaa  45960
```

-continued

```
aaaaaagcaa tttaaaataa ttctgatcct ttgcttattt ccacaaactc catgaaaatt  46020
gtacattgtc caagcaacat ttcttaatat tctctttttc tctcatatcc attttcctta  46080
ctgctgtctc cacctttctc ttccaaactc cctgttaaaa tccctgcccc agcgaacttt  46140
tattcaattt tgtggaatgg aggctgctct gatttaaatt aaaaaaaaaa aaaaaatccc  46200
tactccatgt cccagatccc tagttgtttt ttgttttttg ttttcctgag acagggtctt  46260
gtgtcttcca tgctggagtg cagtggcatg atcatggctc actgcagcct caacctcctg  46320
ggctcaagta aatctcttgc gtcagccctc cccagtagct gggagttcag gtatgtgcta  46380
ccatgcctag ctaatttttt tcttttattt tgtagagaca cggtcttgcc aggttgccca  46440
ggctggtata gaacccctgg gcttaagtga tcctcctgcc tcggcttccc aaagtgctgg  46500
gattacaagt gtgaggcact gcacccaggc tggatccctg catttttaca gatttagcat  46560
cacaaaagtc taaacaatta gactgactaa ggcagaactg cccttatgac agcagacata  46620
agaaggaaaa ggccaaaaca ctgtgttaaa aattatccaa atgtgaggaa aaggcaaaga  46680
gagtaggtgt gccttttag tgtctaagct gcctgcccaa ggggcatctg atgctctcag  46740
gcaggagtcc acaaattttt ttttgtaaaa gatcagatag taaatctttt cagcgtgaag  46800
agcatgaggt ctctgtcaca aatactcaac caccattaca acatgaaagc agccaacaga  46860
caacacatga caaatgagtg tggctgtgtt ccagtaaatc ttgattacaa aaacaggcaa  46920
gaggccagag ctgacccatg ggccatagtt tgctgacccc ttctgtaaag gaaagtattt  46980
ttgtttgact tgctgtttac cattgattga acacaaggct ctgtagagtt acttgttaac  47040
ttgcagaaga ttgatgagtg gcaagtaatt tttattcacc agaatatann attattctgt  47100
tcagtagata agataaaccc actgttatat tactgtcttg tttagaatgt gactttgatt  47160
catttttca caaattcata ttattgccct aatttgtata taagtatgct tcttttaaaa  47220
atatatattt tttaataaat ttgagacagg gtctcactag gttgcccagc cttttgctat  47280
aatgagagca taaagtgaat ttcacacttt agcctagtgc atagatggga ttacaggcac  47340
aaaccactgc atgcagctaa ctttgcttct cattccagca cgttctattc cnnngntttt  47400
catatacgcg tctcttaatg ccgcattcag cccaagtttt cttcagtgtt aaggtttttg  47460
ttactctgtg cccaaatgtc cttccaaaaa ggttaagttt ttttaccttc ctgccaacat  47520
tatatgaaag tgtccacttt tgtagacttt taccaatgct gactactttt ggtttcaaaa  47580
aagctctcag taattttcta ttaattactt ttaccctttt ttattgaggg tgttcaactt  47640
tttattgtta gcatattctc tctgggctcc attggacgcc ttggcagctt tttggtagta  47700
ggtgccttta gaaaagtcct tctcgtctgg ccctttctga gcaaatctag tgaacagaat  47760
tggctccatg ctcagcattg cttaatacgg ttgatccagg gcctaggact cattccttca  47820
ttaccatcca cttgcattgt cttaaagcaa ggctctatta atttaatttg gcatttcctg  47880
tcccagctct ttagtttcat taaacaaagg ctttagaaaa ctcccagtag atgcctatgt  47940
tgcttccttt taaaaaattt tggagctgtt tccctagcct aaccttttct tcagggcagg  48000
agttaagtcc cttctactgc attcctgtga agatggtgat tcaagaggca gggcacctgt  48060
tgctttgtga aacagtccac tctgcagctg ggcagctctg ttactagaat gttctccctt  48120
ctggggagcc aatattttga tgtcctctgt gaatctcatc tgcttatccc atctgtttat  48180
gtccttgaag atgcacaggt ctgacaccac gaggtagccc ttagaaattt gatggcattt  48240
ctgatgtgtc cccaactctt ctccaaccac tcctcccaga gcttgtttct taagcccctt  48300
```

-continued gtggagctga ttgctttcct caaggcagct cagtttttcc cagtttgctc ctggtggtcc 48360
tgaaatatga ttgactcctg aatactccag gtgtgaagga gagtgggggt ggcctttcta 48420
cttgtcatgg cctgggtttt aagttgctgt ccagtggagc agaggtgact ttcccagtga 48480
actacatttt ttcccctcta aatccttagc aattttgtct ccagaggcaa gacctggcca 48540
aaccatttgt gttgaggatt gaatcaagaa tgattgagga gatgacagta gtcccccctc 48600
atctgaggag ggcgtgttcc aagcccctca gtgaatgcct gaaactgtgg atagtaccca 48660
actctatatg tctatgattt tcctataaat taatacatgc ctgtgacaat gtttaattta 48720
taaattaggc aaagaggcca ggcgcagtgg ctcaagcctg taatcccagc actttaggag 48780
gctgaggcct cacctgaggt caggagttcg agaccagcct gaccaacatg gagaaacccc 48840
gcctctacta aaaatacaaa attagctggg catggtggca ggcgcctgta atcccagcta 48900
ctcgggaggc tgaggcagga gaatcacttg aacccgggag gcgggatttg cggtgagctg 48960
agatcgtctc attgcactac agcctgggca acaagagtga aactccgact caaaaaaaaa 49020
aaaaaaaatt aggcaaagaa agaaattaac aacaataagt aatgaaatag aacaattcta 49080
acaatatact ataataaaag ttgtatgaat gtggtctctt tctcaaaatt accttttttt 49140
tttgagacag ggtctcactt tattgcccag gctggagtgc agtggcacga tcacagctta 49200
ctgctgcctc gacctcctgg gaccaagtga tcctcccact ttagcctcct gagtagctgg 49260
gaccacaggc atgcaccact gtatctggat aattttgttt attttttttt gcagagagag 49320
gaggtctcac tatgtttccc aggctggttt tgaatgcctg ggcccaaggg atcctcctgc 49380
cttggcctcc caaagtattg ggattacaag cgtgagccac catgcctgcc ccaaaattat 49440
cttattgttc tatacccact cttcttcttg tgatgatgtg aggtgatcca ttgcctcctt 49500
gatgagatga agtgaggtga ctgatgtggg catagtgatg cagtgtttag gctgatattg 49560
gcctgatgat atgtcagaag gagggtcatc tgcttcggtg atcctggatc atagagtcat 49620
gatgatgtca atggttggat gtcaggagca gacgatgtca atgactaacg ataagctgga 49680
caggtgggat ggtggcacaa gattttatca cgctactcag aatggagcac aatttaaaac 49740
ttctgaattg tttattttg gaatttttca ttaatatttt tggattgcag ttgactgtgg 49800
gtaactgaaa ctgtggaatg tgagactgtg gaaaagtgag ggagtactgt attatggaac 49860
tgtaactcta ttcggtaggg gaacagaatt cacatttgtg gggcccaggt ctctgcatct 49920
gtagggatcc aattgtttca tttctcgttg tagcaaaaac ttggctttgg aatcagacag 49980
attgatgttt gctatcattc taaatgggtg cagctacact ttcctcaaga ggtagttctg 50040
aaaatttaac aaaatgtgaa tttcttggta aaaaaaaaaa acctcaaaaa tattcagttt 50100
cctttccttt gtgtctgatg tactccatca aatactggga aatatgtgtc tctcatagaa 50160
atgtcatgga tctttgtaat tctgattatc cacaaacctt ggggattagc tgtttcaatg 50220
ttcctatttt acagataaga aaatggagcc tgtggtaagt taagtgagtt actcatggct 50280
acttaactaa tattttacta ggtgataggc cagagctaga gcccaggtca ccttcttatc 50340
aatgctctgc cttgtctctg tgccttcctg tctgtctgta tgtgtatgtg cctgttgaca 50400
gtaaggcata gtttaaccca gtagaactac cggtttgtaa tgaattccac ttgtaaatga 50460
ctgaccattc aaggaacaag tgttttttct atgcttgaca cctgttttgg atgccaaaaa 50520
ggatacaaat gtaacttcag acactctggg cctcattttg cactcattag catgtccaaa 50580
attaaaaaga ctgaccacac caaatattgg tgaggatgtg gaagaacggg aactttcata 50640
cactgctggt ggggatgtaa aatggtacaa tccctttggg taacagtttg acagtttctt 50700

-continued

```
aaaaagttag acatatatat ttaccatatg actcagccct tccacttcta ggtctttacc  50760
caagagaaat gaaatgctgt gcttttacaa atgtctatac aggaatgtac atagcaacct  50820
tatttgtcat tgcaaaaaac agagacaatt caacgttgtc aagagtgaat ggatgagcaa  50880
gctgtggtct gtctatgcaa tggtatccta ctcagccaga caaagatatg gctaatgaca  50940
acaatgtcat gcataagatg acgatggcct gggtgattga tgcaaacaag gataaagaaa  51000
ataatcaatt ttgtccccat tttcaaagac agatagcagc agcaagagtg taagtctgag  51060
gaaagtcata ttccttcctc ctacaacata gcacacacac ttacaaaaac aatacacaga  51120
ctcctggcca atggacttca aaactgagga ggatcattaa atttaaatgt tcaccgctgc  51180
atgaaatctc cctgggtcct gccctccctt ccccaccctc ctccacttgg gccggggcac  51240
agcagtgatt ctctcacctc tcagagtgag ccagtgttgg ctgcattgaa ggctccagat  51300
atgcaaacag ggcagatatt cctggaccag ggtgcacaga gtgaggctcc aacgcaccct  51360
attaactgca tgaaggatga atgagcctct ggtatgggct gggacagaaa aaaggattca  51420
aggggcccaa aagggtttgg gtggaaccta ccaggagcgg cagtacagac tccttgggaa  51480
ggtggccatg atttagccac attcaccaat aggataatct ggagaatttc ctagcttgag  51540
tttctgggag aaagcagatt tctggattat ctggtgacag gtaacagggc cgagttcatc  51600
cacagccacc tgcagtgtta gcaccttaag ctgagttcct tgcaccagga tgctgtcacg  51660
cccagtcagt gtgagacggt tcttggctga aggactgaaa agcttgggta agtgacttca  51720
cctaagcctc tatctcttgc tcccgtaagt cagggctcat tgtggctcct tgcaggcttg  51780
acttcagggt taacagagaa aatgaaggta caagtgcctt gtgaactctg aaactccaaa  51840
ccagtcattc tcaaagtgcc gtccaccagt ctagcacatc agcatcactg gaagcttgtt  51900
tgaaatgtaa attatcaggt cctccagagc tatgtatgaa ttagaaactc tgggaatggg  51960
gccctgcaat ctatttcaac aggtcctcca ggtgattctg atgcaagtta aagcctgaga  52020
aactctgtcc tatacaaatg gatgtcaact caagctgctc ttcagaatca cctatagcac  52080
ttgttcaccc gaatccctga gaatggagct tcaggactgc tatttctcaa agtttgcctg  52140
gtgatcctga gatggggttt gggggacaga gatccaaggt gctaccaggt gtgaggaatt  52200
gttagaaggc aaacctggct gtcatctagg gtgcttaaag ggtacagatc ctaggattct  52260
gcctcttaca gctgaatcag actttcctag aatgggattg ctgtccaatg gcatgcctcc  52320
tgggtgactc tgatgtatag cctgggctgg gaaccaccag aggattatct tccattgacc  52380
aagctgacaa actcgcttaa ggctctgagt ttcacacttg attttctagc ccctgtcctt  52440
ccatggatca cctgcccccct tccctcctaa tcaggagcac agtcagtgga tgcactaatg  52500
tggcctctcc ttggctgcag ggaacaggtg gaaatgtggc cataggtgtg cagggctgcc  52560
tgccatgtat taatagctac agatttgaaa gatccaagga caagagacta gaaaaaaatt  52620
taaaacagcc aagcattggc ccagtaatgg catttcagaa atccaccaaa atattaagat  52680
gctttttgaa aaatatccag agcactcatg taaaagtgct taattattaa taaaagctga  52740
catgtgttgg gtacttcctg tgggtctggc actaggctaa ttatgttttt aggagttgac  52800
tcaaatgctc cctgtcataa ttatgtgaaa aaatataatt attagctcca tggtacaaat  52860
taaggagagg ttacataaat aaaaaggaat gatactcaaa ttagtaacca gagcccatgc  52920
tcttaaacac tatgctatta tttgtggact cttacatagg tggcaaaagt caaaggctag  52980
attgacttct gtccacttcc agccaagatg aagtacaaga ttcagataca cccttccgca  53040
```

-continued

```
ttaaacaact taggaatcag acaaaatata caaagcattg tttgttacac attggataac  53100
agacagcact agatagtcgt gtctgagaaa agcggtgaaa tgagctgagt cttagaattg  53160
ccccagttta ctaaggggca tagtaagggc atagctgcag cacaaagaag cagaacccaa  53220
cagagactgg cgttcacctg agttgagaaa accaagttga aaatttagga acactaacac  53280
agatatgtag gcaagagtat cagagaggag acagttgtag ggaaaaagag agctttacag  53340
agagacagcg agagctccag agacccgcag aagattgccc tgacgtcact agctgagtac  53400
cgatcagtgc atacatgtaa ggatattact caatatgtgg aaaagaacag aaggaatgat  53460
gtccaaagct cacccaaaga caggaatcat ttatgtttcc accagccaga gtggaacaac  53520
cttgtaacgc atatggagta ctcaaacgaa tatttcctca ataataagtt caaattaact  53580
gagactaaag cctgcccgct ttgtctggac atgcctaaca aagctttgag ggaagcctca  53640
aaagaatgaa accgtgtcca agtaatttaa ctgtgtccca gaaaaaaatt caagaacatt  53700
taaataaata ttaaaatatg atcaaaccca gcaaggttaa attcaaaatg tctggcatcc  53760
attaaaaaat taccagcctt gaaaattggc gggaaaatat tattcataat gaaaagaaaa  53820
agcaatcaac agaaacaggc ctagaaagta tacatatgat aaaattagca gacattaaat  53880
ggttatgatt aatttatttt atatgttaaa gaaggtagag aagagcataa gcacattaaa  53940
gagagacagg aaagtcccag tactcacaca gggccaggag cagttttcac cagtcaggtg  54000
ggaaaacttc atatttcatg gagcattggt agagtacaca gtgtcttgcc ttagtagagg  54060
gataaatgct gttctgttcc cgcctaaccc atcttgaaag aaaatctgaa aggatcaaac  54120
tgtattcaag taacctaatc acatcccagc acacagctcg actagttata aaaacacaaa  54180
atattaatat ctagaaacac aaaaataata tctagcaccc aacaaggtaa aattcacaat  54240
gtctagcatt caattgaaat tttctaggcc atcaaagaag cagtaaaata tgacctataa  54300
ggccgggcac attggctcat gcctgtaatc ccagcactct gggaggccaa ggtgggtggc  54360
tcacccggag gtcaggagtt caagaccagc ctggtcaaca tggtgagacc tcatctctac  54420
taaaaatata aaaattagcc cagcatggtg gtgggcgcct gtaatcccag ctactcagga  54480
ggttgaggca ggagaatcgc ttgaacctgg gagaaggaga ccgcagtgag ccaagatggc  54540
accaatgcac tgcagcctca ttagagaaca tcgggaagga aactaaaggc ttatttaaag  54600
cgcgagaccg tggcgccttt ggactggacc ctttctaatg atcatttagt atcaggctat  54660
gtgggagttg accgttttgc atagcctgaa agccaacagt atcactcctc ctctaggtgt  54720
ggcagagatg tgagagaagg agactgacag tctgtgggtg tgtatgcagt gttgggggaa  54780
gcgaggcaca ggggacaata ctgtggtgta gaaaactagt ctaaggtagc atcaggaaat  54840
tcatgaaacc aaaatgaatt tcataacagc acaagacatt atttgttttt gcctccctct  54900
catttttttt ttttttgaa acagagtctt gctctgtcat ccatgctcgt gtgcagtggt  54960
gcaatctcgg ctcactgcaa cctccacctc cagggttcaa gcaattctca tgcctcagcc  55020
tcctgagtag ctgattacag gtctgcacca ccccgccggc tagtttttgt atttttagta  55080
gagatggggt tttgtaatgt tggccaggct gccctgtcat ttttttttta ctagtgtcca  55140
gtggagtttt ttaggggcta cataacatga tactgtcatt aatctaatgg ctaatgaaag  55200
ggatatgtat atgtttttgt gtttaaaaca aacttctttg ggtcctcaa taatttttaa  55260
gagtataaag gggtcctgag atcaaagagt ttgagttctg ctggactggg acagtggttg  55320
tcaacccaga ttgtacatta gggtcatctg ggaagcttta aaatagtact gatgcccaac  55380
cttaccgcaa accaattaag ccagaatctc tgtggatgag aagtcttcat tgtcatcatc  55440
```

-continued

```
accatgacca tcatcattgt caccgtcact acaccattat catcatcatc atatcatctt  55500
cattatcatt gttagtatct ccatcaccat catcagcatc accattatta tcatcatcat  55560
catccccacc atcatcctca tcggaacttc acctgcatgg aggacaatcc actatgcatt  55620
aggtgctatg ctatttgcta tactccttat tctcacaact gcccagagag gctgatatta  55680
tctcacttta taacaggagg aatctggatc ggaaaagtta aggtaagcta attcacagag  55740
cgagaagaga tagagccagg attcgaaacc agttctctgc tacatcaatg ttcccagtcc  55800
ttgcactatt gagaacctct ttagttatgc tttcacccct ccaacaccac agtaaatttt  55860
ttcttttttt aaaaaaatta tactttaagt tatagggtat atgtgcataa tgtgcaggtt  55920
tgttacatat gtatacatgt gccatgttgg tgtgctgcac tcattaactc gtcatttaca  55980
ttaggtatat cttctaatgc tatccctccc cgctctcccc accccatgac aggccctggt  56040
gtgtgatgtt ccccaccctg tgtccaagtg ttctcattgt tcagttccca cctatgagtg  56100
agaacatgtg gtgtttggtt ttctgtcctt gtgatagttt gctcagaatg atggtttcca  56160
gcttcatcca cgtccctaca aaggatatga actcatcctt ttttatggct gcatagtatt  56220
ccatggtgta tgtgtgccac attttcttaa tccagtctat cattgctgga catttgggtt  56280
ggttccaagt ctttgctatt gtgaatagtg ccacagtgaa cattcatgtg catgtgtctt  56340
tatagcagca tgatttataa tcctttgggt atatacccag taatgggatg gctgggtcaa  56400
atggtatttc tagttctaga tccttgagga attgccacac tgtctaccac aatggttgaa  56460
ttagtttata gccccaccaa cagtgtaaaa gcattcctat ttctccacat cctctccagc  56520
acctgttgtt tcgtgacttt ttagtgattg ccattctaac tggcaccaca gtaaattttt  56580
atagatttta taagcaaatt gtatttactg tgcaagaatt ggtttatttt ttaaaccatg  56640
tgttgcaaac atacaatggt taattgtgat atttgctcag tacaagatca tcagatcact  56700
acacagactt gaggtaattc cacctaaaag caaagagaac tgaccccaca ttaactgaga  56760
agtctttact tatttattcc ctataaacga gccaatatga agagaaggcc ttaatgtggt  56820
taactatgta atttttttct gactttttga aatactgaga agagctcatg actctcccat  56880
ctcctaattc taccttggtg gattttagac tgaccacaac tcatgggtaa atgagggaag  56940
acgaataaga aaccttgctt ttttttcctc cttgtttttg gctggctgca gtggctcaca  57000
cctgtaatct catcactttg ggaggccaag gtgggaagat cacttgagct caggatttca  57060
aaactggcct gggcaacata gtgagacccc atctctaaaa aaaaaaaaaa aaaaaaaaaa  57120
ggcgacgggc ggtgcgtgcc tgtaatccta cctactcaaa aagccgaggt ggaaagatca  57180
cttgagcatg ggaggtcaaa gctgcagtga accttgattg caccacttca ttccagcctg  57240
ggtgacaaag caggacgctg cctcaaaaaa acaaaaacaa aaccttaatt ttttggctat  57300
tcttttctgg taagaatggt atagagatgg ggatgaggat ggctattgta tgagagagca  57360
aacagggtcc aagcagtgct ctgggctgtc taaggaccag tagtcagctt aacttctcaa  57420
atttccaggg aaggagttcg gagtggtaga atatcctggg tatgcccaaa gcatcacctt  57480
gcaaatagcc tgtcatgaat aatttgtttc atttgttatg actggaaact ggctttgtgt  57540
atgccagaga atgggggcag gaaagagaga ttggtgtctt gagctctctg tgcctctggg  57600
gcagtgatgc ttttcctctc atgtggaagg agagcatgac tgaaaaggtg cacaaataag  57660
gtgtctgtga gagaaattaa ccttccagat acagagacac aaccttcccc aagaggtcct  57720
cattgctctg cctttttttcc ttttttttgc ttgttctacc attaataaca gaaactgatt  57780
```

-continued

```
atgacctcaa aagagaggag aaagcgactc tccccaccct agagctagtt aaccaccata  57840
tcttcctaga tctcagttca agagtcactt ccatccccaa taaaagccct tgagtgctga  57900
gcacctctcc gtcatagcat ttgtcctagg ggtttttgta cattttcttg tgtgaaactt  57960
gggttgacat ctgtatttcc gactagatta cagtttcctc aagggtaggg atgtcttgct  58020
tgccattttc agttccagca tctagacagt acctcaagca aacaaggccg aggggggtgc  58080
ggatcacgag gtcaggagtt cgagaccagc ctgatgaaca tggtgaaacc ccgtctctac  58140
taaaaatata aaaattagcc aggcgtggtg gcaggtgcct gtaattccag ctactcagga  58200
gtctgaggta ggagaatcgc ttgaacccgg gaggtggagg ttgcagtgac ctgagatcca  58260
ctgcactcca gcttgggtga cagagcaaga cttcgtctca aaaaaaaaaa aaaaaaaaga  58320
aagagaaaag aacatcaaat gaatgaatga gtgagatgaa tgagttagca gtgttggatt  58380
taagtgtcag attcttccca gcttgacttt tttctttggc ttagtgattt tgaggtcnca  58440
agatttattt tcctttcaca aaggtgatca ctaccataag atcttcagaa aaagaatgtg  58500
gcaagccang tctcactaat gcaaatctct ataacaactg tatcagtact gaggtgtcat  58560
aaatatggac cgatagatga atacaggtag gatgggacac aatctaagat cccagggggg  58620
ggagaccaca cgcttggtta gggagaccca aagtggaccg tgtggccaga agagtcccgc  58680
actgcactct agtgacagtg cagaaagtca ctgtgggaaa tctagaagtt tctacaggtt  58740
gctatttcat catagcactg tgcaggccaa cccttcctgc tccactggct gttgggaaaa  58800
gctttctctt ttcttcctag ccagggagct ctcaaagtgt tccactctct cacctccacc  58860
caggcgtcca ggtgtggagg acacttgccg gctgcttgtc tgctgactca tcccttggtt  58920
tcacttggaa aacctaccac cagctggcct ctttccaagc atcagcctcc tcattttctt  58980
aatcccttag gtgtgatctc acctccacac agtagattgc ctcaaggccc aattccaata  59040
tgaataaaaa tgattatttt gtcatcttcc aatcttcctt ttaaaatatt attttataat  59100
tccctttagg aggatcacct aagtgaagac tatttttacc taagaaatgt taaaatgtaa  59160
agacatggtt gtaatctggg gattcctgtt aaaatggcta gcagacagaa gtcagacgac  59220
aggctagaaa tgtgtgaaga gtggttgcct ttgaaaggcg gagttggtaa tgattttctt  59280
ccatttttcc atgctttcca attctctaca aaggccttaa tattacttcg ataaccagga  59340
cctctgataa cctgccccca ccgagtaaag acttagctgg gaaagtcagc ttcatgtgag  59400
gtaaaaggaa ccaggtaata cacaattccc actgccaact gtcgggtgtg caggcctgag  59460
cttcctgcat gtgggaggaa agagaaagaa gagagaaact ccaagatcca agagatccag  59520
caagaaggct ggagtctgag gacgcagaaa gctgaatggc acagttacca ctattgtgct  59580
gaggttctgt ggcctctggg tctcttgaca actgggcaaa gacccacaga aaactatctc  59640
tagaccctac ctgtgggagg ggaaagtgct tcagatcatc tacaggacag ccacctggac  59700
ctcaaatggc ttacagttcc ttcatccaga gggtcttcat ctagtacata ccaggtgcta  59760
agcctgggtg ctggagacat gacggggaac ccatttacca tggctttgtt actgtgacat  59820
tcacatctag ggaaagccag caaaggggag ggatcgagga gagcttgtta ggcagagaaa  59880
atacccaagg gcaagggaga agccagcctg ttctgagcac acacagtggt tccatctaac  59940
tgggcctcag tgccaggttg gactggagat ggggctgagg agctgtcaca gagcattctg  60000
gacacagatg tcacatagtc ccttgaggtt agggtcctta ggcatggcag cattgctttg  60060
agtttttcct tttgtaatgt tgccattcat gacaatgtgg aagatgggtc cttgcagaga  60120
agggcagggc tgtgagacca gttaggagac taagatgtga gccaaggaaa atgaggaaca  60180
```

-continued

```
cctgaacact ggggcaggtg cagggcccag agagaagcag atggcttcct gaggttttaa  60240
gtaggtagaa tcaaggcagc tggtaaagat cttttattac atataaactg gaataagcca  60300
tctgctccaa gacaaaagag taggcggaaa acaatacaag acagaaatgg aattagaaca  60360
aacctgggag gaatgtggaa ttagagtaga gagtccaaca ctggctgcaa tcataaaaat  60420
gtaaaacaaa caaaaatttg ctaggtgtgc ttacttagaa ataattagct gtcatattaa  60480
gttcacttgt gttatggctt aaatgtgtcc cccaaaatgt gatgtgttgg aaacttgatc  60540
cccaatgcaa cagagttgag agatgggacc tttaaaaggt gattaggtca taagggttct  60600
gccctcataa atgaattaat actgttatca tgagagtaga ttcctgataa aaggatgatc  60660
tctgcctcct ccccacagcc ctcttgtgca tgctttcctg cctttccacc ttctgctatg  60720
ggatgacaca gcaagaaggc cctcaccaga tgcagctcct tgatcttgga ctttccagcc  60780
tccagaactg taagccaaac aaatttctgt ttattataaa ttacccagtc tcaggtattc  60840
tgttctagaa gcacaaaatg gactaagatc attagattat catttttat cagactgttg  60900
aagtgaaaaa taaaaatcaa ataaagaaat taagagagct gcatgcagca gctcatgcct  60960
ataatcccag cactttggga ggccaaggca ggtggattgc ctgagctcag gagtttcaga  61020
ccagcctggg caacacggtg aaaccctgtt tctactaaaa tacaaaaaac taggccgggc  61080
gcggtggctc acgtctgtaa tcccagcact ttgggaggcc gaggcgggtg gatcatgagg  61140
tcaggagatc gagaccatcc tggctaacaa ggtgaaaccc cgtctctact aaaaatacaa  61200
aaaaaattag ccgggcgcgg tggcgggcgc ctgtagtccc agctactcgg gaggctgagg  61260
caggagaatg gcgtgaaacc cgggaagcgg agcttgcagt gagccgagat tgcgccactg  61320
cagtccgcag tcccgcctgg gcgacagagc gagactccgt ctcaaaaaaa aaaaaaaaaa  61380
ctagccaggc atggtggtgt gtgcctatag tcccagctac ttgggaggct gaggcaggag  61440
aattgcttga acccaggagg tggaggttgc agtgagctga gatcatacca ctgcactcca  61500
atccagcctg ggtgacaaag caagactaca tttcaaaaaa aaaaagaaag aaaaagaaaa  61560
aaagaaaaga aaaagaaatt aagagaaggg caggtattaa ccccaaatat cccaccatag  61620
ggacacatta aagtttgctt ggccactccc ctagcataat atatggaatg tcttcaagga  61680
ccctctgttg taaatacaag gccctgctgg acttaataca acctgcaggc tttgagatcc  61740
ctactctgtt gccatctctc ataggatttg cagaccaaat ccaaatactt aaaatagcaa  61800
cactcacaaa catgcaaatc agagcagaaa agaaacttct aaaaggccct gaaactacac  61860
tttatgagag aagacaatag ggacctgagg gtggtagaat tttctctcta tgcatctatg  61920
tttccagggc tcactttctc aataaactct taaattgctt ttaaagtaag ggaacaagca  61980
aacattacat ttaagagaaa tcaatttcat aaagaagggg ggatgtccag ggtactttgc  62040
ttccatgttt tgcttccatg aatttgtgtt taacagaaga tgcagaaaaa cacacaatta  62100
ttgcaaaatc aaggaaatcc actctaaaca tcccttggtt tcccaggcca gtgtcacaac  62160
tgaaaacaca tattgtggct aattatgtgt cacaaattag aatgacaagg caagaaaaaa  62220
aaaactctct gattaactaa tagcagccaa cacagacagc ctgtgtagct cgactctgct  62280
ggtttataaa aggcagaaga agcaaacggc ttctgtgacc gcaacaggaa gggcctctgc  62340
tcttaataaa taaataacat ttaaattatt ctccccccatt tgcaaagcat tttccaactc  62400
attatctcat ctgaccaggt attattgtat ctgaccaaga acttgtatac naaataaaga  62460
ataaaaaata aatatgggcc angcacagtg gctcatgctt gtaatcccan cactttggga  62520
```

-continued

```
ggcccaggcg ggtggatcac ttgaggtcag tagtttgaga ccagtctggc cgacatggcg  62580
aaaccccgtc tctactaaaa atacaaaaat tagcccggca tggtggcaca tgcctgtaat  62640
cccaactact tgggaggctg aggcacgaga attgcttgaa ctcgagaggc ggaggttgca  62700
gtgagccgag actgcggcca ttgccctcca gcctgggcga tgagagcgaa acttcatcga  62760
aaaaacaaaa acaaaacaaa acaaaaaaca ccttagaaga agcgttcctc ctcttgcttt  62820
ctgaagacac tctacgctga aacagtaact ttcaataaac catctcttct caccgcactc  62880
tgcgacttgc cttgaattcc tttgtgtgca agatccaata agcctctctt gcggtctgga  62940
tgagaaccct ttttttggaa tactctgaca caacaaattg cagaaagaaa gtctcacatg  63000
tataaaataa gcaaaaagat tctctggcat ctgaagaaac aatttccttg tcaatattag  63060
tatcactata agtgtagaac aacctgttgt atgatgctac ataaagtata tgaatctgaa  63120
tactgttgga tacaaaggga gactatnnaa tgtaatacgt cgcccgaaat gactacactg  63180
ttggtgatct ttctttcaag aagcanaata ttgcctcnaa catcctgtac atggtataaa  63240
attttaccca gcaagaacac caatacaacg gggggggcgt tctttgtgag gggtggggag  63300
gtcaattttt tggaacctgc agcaggtaac acacaaaact tccacagctg ctaccagctt  63360
tccaggagag cctgtgtacc tggagaggag aaggcaagtg cttccgaact tgacttgatg  63420
tcttagattc tgcaatgcgt agtctgtagg gacaggctgt agcttatcct ataggcttgg  63480
gctggagtca gcaagcatct gggctggcag aagataaaag atgcaaaggt ggaggaaagc  63540
atacgtggtc tggaagacag acttggtggg tgggtggctg ctacaacacc ctagttagag  63600
gtagaggggt aagtcagtgt gtcttctgca caggcctctt ccccacctca ttcttcattt  63660
cccatacagc cttgctgagt tattcacaaa catctgattc aactggaagc tgggttgagg  63720
atgacctaaa ggactagtgt gatgcctgcc caggggtgtg ggcccatagt cagagtccag  63780
agcctcctct cagcttttag cacatctcac ccacatcctg ggtccttaat tagcaatatg  63840
aaagcaagcc aagtgacaag attttgtccc tgggaagtcc agaagcactc cttttctcat  63900
ttgtataagc ataatgattt gcttacataa ataatcatga aaattcaaat ccctctcaga  63960
aatcaggtca taaaaccatg aaatgcagca tgtgggcaag aatcacaggg aaaggtaggt  64020
cttggaaaag aaaggatggc agggaggaag aaagcagggt gccaggggcc ctgggctgct  64080
gtccaagtca ggtggctcac cgtctctgag aacatttcac tttctggtaa atggggcagt  64140
tggagataga agggttgggt gaatgccaag agtgagcaca gctgaggtca gtgctgtgcc  64200
tgcagtccag gcgggagtag aaatcctggg cccatcttac ctccgacctc atttcctcct  64260
ctgtaataat gtgggggtgg gggaaagttc tggtcatcag ccctagcatt ccatggttca  64320
tttcctcatc agtgatggaa aatcaccaag caagagaaca ggatggagaa taaccggatg  64380
ggtgcaatcg gaggtgctat ttcaggtgag gtggccaggg aaggccctct gaaagggtgg  64440
cttgagcagg tggctgaatg tacagaagct gccaatcatg aaagatctgg ggtacagcat  64500
gccaagcaga ggaaatgcga gtgcaaaggc cccgagattg gatgtgggct tagcacaaat  64560
gtggcatggc aagaaggcca gtgtggctga agcagcatga acaatgggtg gaggggctga  64620
gaggacagag gagcaggaaa gagccaggct tgggtaggag aggtgtcaac ttgatatatg  64680
atgcaaagcc cttggaggtt cccaaacaca aaagcaatga tctaatatat ggttttaaaa  64740
atgccactct tggccgggcg cggtggctca cgcctgtaat cccagcactt tgggaggccg  64800
aggcgggtgg atcatgaggt caggagatcg agaccatcct ggctaacaag gtgaaacccc  64860
gtctctacta aaaatacaaa aaattagccg ggcgcggtgg cgggcgcctg tagtcccagc  64920
```

-continued

```
tactcgggag gctgaggcag gagaatggcg tgaacccggg aggcggagct tgcagtgagc  64980
cgagattgcg ccactgcagt ccgcagtccg gcctgggcga cagagcgaga ctccgtctca  65040
aaaaaaaaaa aaaaaaaaaa atgccactct tgctgtgaaa aattgaccct gggggaagga  65100
ggagtagaaa tgtcaaaagt ggaagcagac cactcaggag gtcagggcaa tggactgtgc  65160
aggagagact gacatcttag actcgggcaa taggagagaa ggtggtgagg attatattct  65220
gggcataaag gcaacagaac tagctgatgg cgtcaacgta ggagatgagg gaaagaaaga  65280
aatcaaaggg cattcatagg tttgagggtt gagtaactgg ggatatttaa cagaaatgga  65340
gaagtctggg gaaggggcaa gtattgtggg ggcaggggtc aaaagttctg tattttggcc  65400
aagttaatta atatttgaga tacctcttag gtgtccaagt gaagatgtca aacagtcaat  65460
tgaatacaaa atctgaatct tagcccagga tggtctcaca cctgtaatcc cagcactttg  65520
ggaggctgag gtgagaggat cacttgaggc caggagtttg tgatcagcct gggcaataga  65580
gcaagaccct gtctccacac acacacacac acacaaaaag tcatccaggc atggtggcac  65640
atgcctgtag tcccagctac tcaggaagct gaggcaggag gatcacttga gcccatggtt  65700
caaggctgca gtgagctata atcacatcac tcaatactac actccagcct ggatgacaga  65760
gagagacctc atttattaaa ataaaattta aaaaaattaa ttaaaaataa atccaaatct  65820
ttcctgagat tcatattcag gagtaactgt catgtagaag gcatataatg ccatgggtca  65880
catgatacca tctaatgaat gccactggaa aagagagaat agctaaaaac tgagcactgg  65940
gcacaccagc acagtgaggt tggaaggaag aaatggagct aacaaaggag acaaaagagg  66000
agtagccagt gagaagagag aaacatctgg agagaagaga gagcagcaaa aggtgggtga  66060
aggagaatgt ggtccaccag gcccaacaat gctgagcagt tgagtaagtg aggacctggc  66120
cactgaattt ggcaagaaag aggatgtcag cggccctaga acaaaagtga agaagagctt  66180
gaggacggaa gcctgacagg agtgaactga ggagagaatg aaaggtggag acatggagcc  66240
aaggagcact gagactccct tgagtagttt tgctgtaaaa taaaagtgag tgcagagacg  66300
gggcaggggg acagagaaat gcaggggtag ctggagggag ccacagaatc aaaagagggt  66360
ttttgtgttt aagatggtag ttgtcacata gcacattagt aagttcatgt gaatcacaac  66420
gtaggtgaga cagatcacta atgcaggagt caaatccttg cagagccccc agaggaggtg  66480
atgaagggaa gtgatggaca tcattcagat gcaagtaggt tagcaattcc tggggtacaa  66540
ataggaggtg actcctttct gattgctcct gttttctgaa tgagatagca cataaagtcc  66600
actcagccat gttagctgtt gaagtccttg tggctgtcat gcctgtacag actgggctct  66660
cctctccagc atttcctctc agactaagct gagctgcact agccgctgcc acatcctctt  66720
ggggccatcc tctgccacac tccacatatt gctgtggttt gcttgcaacc cctggaaggt  66780
cctactggct gctcctagaa gagtctgggc ggcatctctc ccttactcgt tatcacatgg  66840
tgctgtaagc agtggccaca cactttagct ggtgggatgg gccatcacag gcagtaaatg  66900
cgaaagactg ctcagatttt aaagcaccca tgaatcagta gaatgagttt agaattgtag  66960
tcatcaacac acattaaaaa aaaaaaaaac aggcactaaa aaaattagtt gagtaggata  67020
aagccataaa agatattaac tacaacccag ataggaggtg caaaattgtc cttacataaa  67080
tcagatggaa aaagttgaaa gcagataaga taaaataggt aagcatgaca tttaaaaggt  67140
attcatggga cgtggttaca aaaccaactc acaactaaaa agtcttagga cctctcgctg  67200
acttaggagc ctgatcccaa ctttgagaat gactcagtgt gttaccctgt ggctagtgta  67260
```

-continued

```
gaccaatgat cctgtctcag agtcactagc caacagccca tatcaagtaa ttgaaacttt  67320
gactcagaaa cctcagtgtc agaacctttg acttaggaac cacctgtagt ggttaactgc  67380
aatttgcacc ccttagttca gggctttaca acaccggggg cggggagggg gaaggcatag  67440
agctgatgac ctaaaggaaa cccattgcag caacgctttt gtgttaagtt tacaaataag  67500
tgttgtttta gaatcctcca ggtaatgcct ttgttattta atgtgtctga gacaattctg  67560
cacattaaag aatataaaat attaccttgt aattccaatt tgaaatgtgt aattgacatt  67620
agacttctat tttaatttga aatgtctaaa acaatgtggt taagtttgta aaaggtgtgt  67680
gaattttgag tctgatttac tacatttttt tttaattttc tttttttttg gagttttagg  67740
gattgcttag atggctagaa agatcgctag gcacatgtcc gatgtgtgta cgtgtgtgca  67800
aataccgtgc ctttttttgtt ttcttttgtt gaaacagagt ctcactctgt cgcccaggct  67860
agaatgtagt ggcgtgatgt cagctcactg caacctccgc ctcccaggtt ccagtgattc  67920
tcccgcctca gcctcccaag taactgggat tacaggcgcc caccaacacg cccagctaat  67980
ttttgtattt ttagtagaga cggggtttca ccatgttggc caggctggtc tctaactcct  68040
gacctcgaga tccacccacc tcgacctccc aaagtgctgg gattacaggc atgagccacc  68100
atgcctggcc aatactgtgc cattttatta tcagggactt gagcatccat ggattttggc  68160
atccataggg gtcctgtaac caatactgca caaataccaa gggacaactg tattctaaaa  68220
agaccaaaaa ttaataagca ggacgctgaa ggtaattgcc ccaataaagt catgatccct  68280
tgcccagtgt ctgaacctca gccagttttc atactcagga cctattggct gcagaggtgg  68340
taggaaccat atgagaatcc tgcaatatca tggcaagtat gcactttaat gatatctgca  68400
gtccttcccc aaaaggacct tacatttacc atactgctat gtcctgcgtg agagggtaat  68460
actcagattt tttttttttt tttttttaca caacgtctta ctgtgttgcc cacactggag  68520
tgcactggct cgatcttagc tcactgcaac ttctgttttc tgggctcaag tgattctcct  68580
gcctcagttt cctgagtagc tgggattaca ggcgcccgcc accatgcctg gctaattttt  68640
gtatttttag tagagacgga gttttgccat gttggccagg ctggtcttga actcctgacc  68700
tcatgtgatc cgctggcctc ccaaagtgct gagattccag cgtgcgcggc catacccggc  68760
cgggaattct ttatatattc tgaaaactaa tcctttgtga gacataagtg ttgtaaatat  68820
tgtatcccag tttgtggcat gtatttttaa tttttaatgg tgtctctcaa tgaaaaaagc  68880
ttaacactta aatgaggtca aattgatcac ctttttattt atggttgatt cctttggtgt  68940
catgtgtaag gaatgttgtt ccttcctgtc ccaaagttgc aaagatttct tgtgtatttt  69000
gtcctaaaag ttttaaagtt ttgcttttcc catctgtgca catttcacat ttgctacatc  69060
tcactgactg cttcctctgc tgcagagcaa gctccatgag agcaggaggc atgggtcctg  69120
cttcttgttg gtccccagag ccctatgtca tgactaggac ctggcagggg actagtgagt  69180
agctcctgac taactgactc aatgaatgaa tgattggatg attgaacaaa gtggtatggg  69240
agttcacagc gagtaagaga tgccttagaa gagatgaaga aggagatggt atagggtagt  69300
ggttctcaat tctgggtcca tggtggactc acctggggac ccttaaaatg taccgtggag  69360
gatcccagcc caagagattc tgtatgactg gtctaagatg tggtctgggc accaggtgat  69420
cccagtgtgc agccaggcct gaggccactg gatttggtgg taaatgaggt aactatcaag  69480
ggtacagacg ttggttgcca acaggcttgg gcttgaattt aagctttgtc actgacttgc  69540
tgtgtcctcc tgcactcgtt gagcctgttt tctcacctga gagatgggtg tgataacacc  69600
tacctgctgt agttgttgtg agagttagag gagataagca tgttcctgga atgaagtgtg  69660
```

-continued

```
ttcttaatcc atcataggtt ttttgcttgt ttgtttgttt gtttgtttgt tttttccttt  69720
tcaagaatga ggttgagcca gactttgaca gctgggtggg aagtgaacat gtggtgattg  69780
ggagagaagg gcagtttatg tgaagggaat gtaataatta gagagtgggc gtgggaagac  69840
atgctgggga gagtgagcag gccggttagc cctggtagag ggtgcaagag agcagtgcgg  69900
aatctgccag ggagacaggt gggtgaccag ggtgccaagg gtgtggcttt tcccaggttc  69960
ccatggacac agccatcctc ccagatgccc agcctagctg tgagtgagca agagttctgg  70020
attgtctctc tcactctgtc tttttctctc attccagaaa caaagcagtg actggtactt  70080
aggaggagaa tcaggtcaag ttgggagaaa cttgcttctg ctcaggggag cagaagcaag  70140
aatggaggcc ccacccatgc tggaagatga tgagggtttt ggttcaggga ggaggaatat  70200
tggggatcta aaggggcctg ggagtggggc aggaccctgc cttaggacag gtagaaacat  70260
tttctataaa aaatggggtg gaggttgatg gtaggaccag gcatctttag ttggctccct  70320
ggagtgtcaa gcccttgaga tggtctttaa aagccatgca gtggggtttg aatctggtgt  70380
tcaagctcat aggttattaa cataatgaca cttggaaact atttgggaga gctcaagtga  70440
gtggcctgga agttctgtgt tggtgcagga ggtgacttag gatgtgctgc tccagactca  70500
tatctttgac tgcacacctg atgcttcatc tggctatcct gtaagcacct tcaacttaac  70560
atgtcctaca cagaactctt gatattcctg ttcctccccc agttcctcag ttcttaccaa  70620
atgttcttcc agttacccaa ttgctcaagt aaaaaatcta agtccttctc ttggatttct  70680
gcctgttccc tcaacatccc acctatccat gagtgttctg tgggccctgc ctctgaaata  70740
aatcctgcct ttgtctccca gttcactcca gccacccatc ctggggctgc accctcctcc  70800
ttccaagccc tctccctttc cttcctggtg ctgcctgtca tgtcaagcat atgcatcagt  70860
gcgaccagga catttgaaat gcaaccagta caattgggcg cggttatgcc taccagtttt  70920
tcttccttaa acattttata tttatgtttg aaagcatgcc acctttcttc acttgccaac  70980
ttgacagatt tattagttga caacatccgc tgatagcatc agtaataagt taattgtttt  71040
tgcacatgta gctttaatta ttctcattat catttatagg agttattctt tgtaaagggt  71100
aactgagttt tccaaaacaa acagaaattt ggggtgggcc catggagcgt gactcatgaa  71160
atcagattct tagaaggacc tcggcaagtc tctgggttgc tgttaatgag cctggctggc  71220
tgccaggggt gtgtctgccc tttatgaggc caccactgtt caaatgcttg cctgcagcat  71280
tacttgccta ggtagtgctt gtttctactg aactgtcagg gatccaattc tttgtggtct  71340
aagtaacaat actcagattc acaaggaatt gattaataag ccagaatgcc aatgtattac  71400
atttttgatg aagaccatat ttacagtgat tgtatctgct caagctcaaa ttaggattag  71460
agttctgaca aatacatatg tgagaagtat gaggttaaat acttgaaatt tggacttttc  71520
tagaaaatct gaatgtgatt gccattcaca tacctttctg ggatgatgga ttcttgtact  71580
tttattttaa aagacataga aaactaactt aagaatcaga ttgcttggct gggcacagtg  71640
gctcatgcct gtaatgccag cactttggga ggccaaggtg agtggattgc ttgagctcag  71700
gagtttgaga tcagcctggg caacatggtg aaatcccatc tctaccaaaa atacaaaaaa  71760
aaaaaaaaaa acaaccaaaa agaataaatt agctaggtgt gatggtgcgt gcttgtagtt  71820
ccagctactt gggaggatga ggtggaagaa ttgcttgagc ccaggaggtg gaggtttcag  71880
tgagctgggg ttgcaacagt gtactccagc ctgggcgata gagtgagact ccgtctcaaa  71940
aaaaaaaaaa tcagattgct ttattgctgg ttttctttct aaaactgaga ttgggtccca  72000
```

-continued

```
tcatcccctg gcccccattg gttaatggtt cctcctttgt ctattgaata aaatacagat  72060
gtctgctttt ggcaacatgg ttgaatgtag acactgcagg gtcttcctga ctcaaaatga  72120
tttaggctta gataaaacac atttggaaat gcatttctgg attaacacca aggaaaggag  72180
atctctttaa atccccttc tgttcccccc tccctacccc ctccaattgg gcttaagtaa  72240
gaagggtggt tacccgctag taaacccct tcgaaggggg tcttctcctc taagggaaaa  72300
cccttgtttt gacatttgct tcaatgggcc cttgtatttt gttccttgct aaacgggtgc  72360
taaaccaggg gcctcctctt aaggctttta gaatatttgc acactttaga aatggaaatg  72420
tttttggggg gcgagttgtc ttaatatttc atttttctag cttgtgtgac atccttttga  72480
aagcagcaat tctggccttt gtgagagatg gtgaatgcct gcaggtgtgt ggaccagtgc  72540
gtcccttcct tcctacatgc acggccccca gctgggccca gcagagtgct gttacagaat  72600
aatttccaag ggctgtgtct ctaacctttg gtcttgtccc ccattgctgt agatttggcc  72660
aattgacttc ataagtgcct cttatgaaca tagatgttgg caatggaagt tgaggaccag  72720
tcagtggttg ttttattgaa cacacagcgt aaatcccaac acaatgctga cctaagagaa  72780
ttccagccac tctgattctc agtctcttta tatctgaaag ggttctgttc cactttttcc  72840
cagatcaaaa tgtccctgca gctactcagc agagctgtcg caacttatac gtagaagagg  72900
taacagtcca caaacagaaa ggcacaggac gagagtggtc tgggtgatgc ttcctgtggg  72960
ggaaaaggtg atgagggtgc atctgcacac ctatgttcat aggtaagtct gggaggaggt  73020
gacctcccct ttggttgagg tgctgaggcg tcttgttaga atggcactat tccatttatc  73080
tgatgcagtc tgtgggaatt ttgtggtatg gccaccacag gtaccatgct gggaacaatg  73140
ccagatactg cctgctaagc cacagcatga gtcacatgag catttgtggg ctttgggaac  73200
taaagttatt gaacgatagt tatctgaaaa ggaatttagg gaaaggggac tttagtccag  73260
cgaacagttt gcaaaccagg gggaaggcag ccttcagcgt aaaatgaaga cgtgtgtgcc  73320
ccaaataaca aagggagagt ttgtctttta gagagtaaat gtccacgcaa ggttccactt  73380
aggcaaatga aagatgcaaa cttgcttagt tctgatttgt ttacatttgc tgaattcgga  73440
ttggtccgtg caggcttttc tgggaactcc aaatacatgt atgacctcta gtcatacatg  73500
gcaaatggcc gcttggctct aatttgaatt taggcccagt tagtcactca ggattaacct  73560
ttttcagggt tcacagctct gaacaatgga cttagacctg caggacataa tctgttccta  73620
actctgggac tacctgtgcc ttttgactgt gcccagtgag cagctgtggc tctgggccca  73680
gacccacagg gcgataaggc acagaggtac gcatggagca ggctgtcctt gctgagtgat  73740
catgaagata cacttacata gagcagcact tttccttcca gtctttgtga tttaactcat  73800
tagatcctta taacaagagt cagtcctcta tttaacccat gaagcacagg tggagtccaa  73860
gcttagtttg tgaaggatga gccaaaagga ttcttctctt gtagacctca agctcagctc  73920
tctccatggg ccctggagta ggtgagaagg cctctgtctt ccagagccca ctgccaatca  73980
tctacatttt ctgttagccc aattctagga cattgcttta ccaactgaag ggtgagaact  74040
atcataagtt ataaaaatca attgaaaaac aaaaaggtac agaacagaaa ataaaagatg  74100
agaatctatt aaacatagtg atgttactgg aaaagggggt ctcaaaccag accccaagag  74160
agagtccttg gatttcacac aggaaagaac tcaaggtgag ttgcagggtg cggtgaattg  74220
agagagttta ttgaaagcta ttccattaca aagtagagca tcctcagaca gcaagtggag  74280
gaacatgcca tcattaaatt tttcttatat aggaatcttg tctatataaa gactaaacta  74340
agctgtggct atgtgtgggt gggccgacag catgaaaaca tttattctcc tattgattta  74400
```

-continued

```
aagagaacta tccttgacat tttagtgtgt ttaagtacat caaagcataa ctataattat  74460
cttgaaagca tatattttta tagggattgg gacatctggg ctttctgttg ttgtagaagt  74520
ttgtccttgc agggattacc aagccacttc cttagctgta aacatcttag ggccatgggt  74580
cctgactggc aaggaatgtg tcttgctagt tttaagatgg gcttgatttg aaaatggtgt  74640
ccatctggct ctcctaggct cctgctttcc taacagtaag ggtaaatgct atgttatgaa  74700
atgtcatttc tgcctttagc ttgcaaactc ttgatggtga aattctcctg tccgttttca  74760
gtggggtatt tattctgcat ccacgtcttc acaaggagct gaaaacaaat tggatggaag  74820
caactgggtt ttatgggaca cgttaatgtt ttaatgtcat ttggtgtgga attcagatgt  74880
ccaagcaaca ttttacacta caaatctgca actttaataa tcactcaaag tacctgaacc  74940
tcaatgcttt cagacagact tggtataaag ccaccacctc tttctattat ggcagcccta  75000
tcctgaggac acaaatttct gcagggcttc tggcatatct ctgattaaac aaatgtcaac  75060
aaggttaaaa caaatgtcat ctctgatttg tttgttttaa agcctggatt tactcattga  75120
atatttcact cctactagca tgtcttgtag tagttttctt cagggaccct aattattgct  75180
attaaaaata tgtgtgcagc tacatgtttt ttttttatca atttgcaatg aaaactttaa  75240
ttgaataatc tattagtgtt attatttgaa agtgaaatct tttccttttg ctttcttgtt  75300
ctcacacata gtgcagacag tttccacacg ggctcataaa aggaatgatt ctgccttgtg  75360
tgaacttttt gcctttattg ttaattgcac cattttgtga ctggcttctt gaccctgttg  75420
taaccaagct cataatgtac attatttctt attttgcagt tgtagacact tgaggaagtt  75480
cccattcttt gtttcttctt gcttttgttc cctgtgataa ctttttcatg cagacatttt  75540
tttttttttt ttttttgaga ccgagtcttg ctctgtcatc caggctggag tgcagtggca  75600
tgatcttggc tcactgcaac ctctgcctcc caggttcaag agattctcct gcttcagcct  75660
ttctagtagc taggattgca ggcgtgcact accacaccca gctaaatttt tcaaattagc  75720
caccccacct ggctaatttt tgtattttta gtagagacag ggtttcaacc atgttggcca  75780
ggctggtctc gaccaggtga tccacccgcc ttagcctcgc atagttgcag gtgctattct  75840
gagctcaggg ctctggcagc tacaagccca agatgcggtc tccaacatgt ggccattcaa  75900
tgtcatggcg ccctctactg gtcctgggaa gcgcagctct gccagtagct ccagcagggc  75960
acagctgtta agtcgtgatg ttctacaggt gaccaaaggg caatctctgg actccttagc  76020
cgctaggtcc tctctgtagc aggacccagg agaaggcagg ggctgaggat ggctctctta  76080
gacatttgtg atgaaccaaa cgtgtgcatt catgaaactt ctgtgagcaa gcaggtgagt  76140
agagttgggt tataaaaagt cttagggtct cactacagag atggacttgc tgtgtagatg  76200
gtgcagagcc gctgaagagt tctacttggg gtaatggtgt gattgggttt gcgttttagg  76260
aagatttctt ggccagaatg aggcgggcaa cccagagcag ggagtggcca catgtgggtg  76320
tgcagttatg ggccactaat ccaggtgata aatggtgtct ctgaacttca ggtgggggtg  76380
ccacatgtct ccatctgctc tgtacccttg agactggcct tatgggctgc cttagtggtc  76440
tgttgtcctc tatctcctgg ttgggctcag gcaatgggag atcagaggga ggaaagagag  76500
cttggttaga gtgcacccgc gccccttcag gttggcagtg gccacattcc cctatacaga  76560
aggccacagt ttctgtcagt ggccctccca cagccccagc tttctcagtg ggccagccac  76620
ctccccatcc cttgctcctc ctcctccaga gagggttgtg gatttccact gtcagcagtg  76680
cctggagctc caccatctcc tgctgcttcc tctggacctg cctgcagttt tataaataac  76740
```

-continued

```
ctttccttac attacctcta gcatgcacct tttgtgtgta tactctgccc cctgtcagca  76800
catgactcat gccaaagagt ttgaattttt ttctccaggc aacgggaggt cattggagga  76860
ttttagacat tgagaacaga tgtgtattgt ggaaatatct gtctgactga agtgaccagg  76920
atggtccaaa agagcgagaa tttgaggcaa gcaaaccatc agcaggccag cagcagaaat  76980
ccaggtcata aacagggaag ctgaggctca cagggttgga tcagggaatg ggagagggaa  77040
gccaaacaat tccatgagca tgtcagttgc acatatgact tggtaactat ttttattttt  77100
atttttatgt tttgagacag agtctcgctc tgtcacacag gccagagtgt agtggcatga  77160
tcacagctct ctgcaacctc tgcctcctag gttcaaacaa ttctcctgcc tcaaccttcc  77220
aggtagctgg gactacaggt gcgcaccact acacccaact aagttgtgta tttttagtag  77280
agatgagcat tcacgctgtt gccttagaca cggaatattg attatttgac cagaaattca  77340
tgcagctaac cgtgacccct ggcaaaataa aatagtgtat atgtacgtgc atatacatgc  77400
aaagaaatga gttgaaacta gaaggatgtc aatcaaatga taacatggtc atcttggggt  77460
cggagtacat ttggggatga ggggagctgt aaaagcagac ttggaccttt tcttctacca  77520
gtaccgtgtc atttgaattt tggaaagaaa aaaaaaaact cagaaggagg agaaggagca  77580
ggaggagaag aagatggatc ttaagtgatt tgcccgggag caccttgaga aggtgagatt  77640
caagtctagg tctaagcttt ctaattccat gagtgggagt gacccacgtc caagaggaag  77700
ctcaaaagga agatgttctc catcatctct tgctcatcct aacagcatgc aaaaccacat  77760
ccaatgcagc tcagaaaact cccaaattgc caaatttcat tggaaacact taatgctgtg  77820
gtttccaatt tcaactgtaa agtaggtatg tatgccattg ttaccattaa cttctcagaa  77880
atggagagag ctctctttcc gcctcctccc cctctgctgt ggctttggtg agacgtgcac  77940
tcaggctcac ctgtctccat gatctccagt aagtacacat gagcagagag gcctcagctc  78000
agctcttcct ggtcccacca gggttgattc tttgagaatt ctagaatgcc acatcctagg  78060
ccccccaaag aaatcctgca tcttaccccc agaaatatga atcatagcaa atttcaaatc  78120
aaccatcgtt taatactcac agactgggca catccaaaaa catattttca gttttacaac  78180
agtgcctggt gcatatcggc actatttgtg gaagcaataa atcgacacgg agctgaaaca  78240
caaacaaatg ccaaattgtt tttataacac ctgattttct ttctgtttct ttatgcagtt  78300
tagttttgtt ttgcttaact ctacctcaga ccatagtctg gtaaactcac cacccagaag  78360
ctcccttgaa atgtgggtat gcagccacta ggtggcagga gagagtttcc tgcctggagg  78420
gaggacagcc actctgtccc cgggtcaggc cagggccacc ctgctacctg caaaattagc  78480
atggggcttt atgaaccaca gcttcctaat aaacacagga tctgtttgat agagactcca  78540
aaacacgcct acctagtgat gaaagactca acttcagaag aaaaccttca tggcaaacat  78600
cttcagagat gtttccaact taaggttctg aacacagacg cttccccaga aagccattgt  78660
ttctcagcac ctgggagcct tgctttgctt tgcttacaga ctcgctgttc ttaaatcact  78720
gccaagataa catctgtctc ttctcttacc ctctatttcg atataaggac tcctcactct  78780
tgttgcttcc tattggctac ctctccacag ggagaaatcg ctgatttaac agcagtcaat  78840
atcccaaatc tggaacaggg aacagggaag catttaaaaa ttggagaatt taggccgggc  78900
acagtggctc atgcctgtaa tctcagcact ttgggaggtc gacgtggatg gatcacttag  78960
gagttcgaga ccaagcctgg gcaacatggc gaaacctcat ctctacaaaa aaaaaaaaaa  79020
aaaaaaaaaa aaaaaaaaac ccaaaaatta gccgggcatg gtagtgcaca cctgtgagcc  79080
ccagctactc aggaggctga ggtggcaaga ctgcttgagc cctgaggtcg aggctgcagt  79140
```

-continued gagccgagat cacaccactg cacttcagcc tgggcaacag agtgagacct tgtcccagat 79200
aaataaatta aattaattta attagaggat ttaaggattt tccctacaga cacctcctta 79260
ttttctctgg ccttttctga ctactctccc taactccctg ctcctctggt ctcccaaaac 79320
tactccagaa aaaaaaaagg gggggaggga ctaaaggaaa gccaggtgac agtgccagtg 79380
tgacagatga caaagcatct gcccgaacaa accgtaggtc cctgaacttt ctccaagacc 79440
tgtctgtgga cttacctatg aaaaccagtt ttagcaaaaa ccctcctaag ccagtttatc 79500
aagatcccct tatcctcaat atccatctga ttggattctt catcccccac cattccccag 79560
tgatgtcacc aggcctttct tcagcaacag tagttagtgg gtgtagccag gacgccccct 79620
cacccctgat atgccctttt agtaattctt catccacagg ttcccaccct gctcctaggc 79680
tatacattcc catttgccca tgctgcattc ggaattgagc ccagttctat actgaggtct 79740
tacttcacct ctcgccatag tcctgaataa aattggtttt cacatttaaa aactgtccag 79800
ctctggttgt tccttgacac agggtaattt ttattccatg tgatagtttg ccttacctca 79860
gcctacaccc ctcaaacctg caactctata ttcaagaacc agacagccct ttccaacaga 79920
taggaagagg ctgccctggt gcaaaggaag aggctctggg aggaaggaga gaacccgaag 79980
gctgccccct cctctagact gagctctggg atgggtggac gataaaaccc agatacgttt 80040
agacatctga gcgtggagag gactttgctt tgcttccaca gggaccccaa ggaaactgca 80100
agccctccag agactaaaaa cagcagaaca gcaagaaatg gcagcaaagg tctgggcaga 80160
atcatcctat gtgggcacag acacaaacag agtcccctgt ggccccagga gagtttaaag 80220
aagatccaga ggctgtccta ttccatatct cagcagagac aggcccgtga gcctaaaagc 80280
tgatcattag gacaagaagg acacgaactg tcctgcagcg tgaaccgcgt ggaacaaggc 80340
caatcaccag acaccagacc agccagacac agccccgcag ttccccaaga ccaccacgga 80400
cccatcgccc ctcaccaata gctccaggct acatagaccc cctccacttc atggatgtcc 80460
tcagagcaga aaggggaggc aggagtggaa ccctgacttg gttcagttga aacataaaat 80520
gactgtacta ttattgaatt gctgaagttt acgtgaaaga aatgagattt agtttttggc 80580
cacagtgcaa aataagaaac gaggcttcaa ctgagattaa ggtgagttat aggaaaatgt 80640
actcccttga aggacctgtg aagtgtgttc gctatgagaa aatgaccaga atccacgttc 80700
ttagctgcgg gactcaggct gactcctgtt tctggagctt gcacaaaggg cagggaaatc 80760
cctgtttcag gcacagtgat ttcaatgttt aaaagaaaac aggtgggccc tggcaatcat 80820
gataacatgt cataagttta catctctgtg aggcaggtag tgtaatcccc attttgcaaa 80880
ggaggaaacc gaggctgaaa gcagctacat ggtctcttca atgtggccca aatgttggag 80940
aacagagctt aactgaatca gcaattctat acttagaact gactctctct ttattatatc 81000
tcactactac cttgatattt gaaatattca acttttttca atcaaaaaat aacaataatt 81060
taggcataat gactactatg tcatttaatt tcttgctgat atttcaatat cccatgccag 81120
gaatattgaa agctcagctc cttaagagct gactatggca tcaactccca acaaccatcc 81180
ttccagaaat attttcccct ttcttttgtt atagagtggc actgccctat atggtgacca 81240
cttgccacat gtggctgttg aacacttgaa attggcttgt cagaattgca gtgtaaagtg 81300
taaaacacat accaaatttc aaagacatgg cacataataa aaaatgtaaa atatctcatt 81360
aacaattttt atattgactg tgtaagtaac attttgaata tattggatta aatacatgga 81420
tgatgcccca acacccacag tcccttatca agtctctact tcacattttt gtacttctga 81480

-continued

```
cttagaaata gcactggcgt ctaagagcct attaatgtcg tcaataggtt cttgggaacc  81540
acaattttaa acaaaatgac atataagaaa acgaataaca ttgaacaaaa tgacattatt  81600
cgaggacctg ctgcatgttg tttcacttaa agtcagtgtc caagaaccta tcagtgacat  81660
ttagtgagga cttgctgtcc ttcctgttta caggaacctg ggcaagttac ttaattcctc  81720
taagcctggt ttatatccct gcaaagagag aaggataata atcaccagta cttagtgatg  81780
tcgtaaggag aaaataaaat aataaatatg aaatggctga cagtgtcctt gtcacacaga  81840
agatgtgtga tccacagtag ctgctattgt ctgcctcact tcactagtaa tggtccaggg  81900
aggcctttaa tgtgcatggt gcagtacatt cacatgttgg acatgggtga agggaaagac  81960
caggctcatc taaacacaat aggatgcttg tggtgttttg aggaggaatc aaggactagt  82020
tatccacagc tgtaacatgc atggatcaaa agagataagg cacacaaaag actttgtcag  82080
tagcaaagca ttacaaaatg cagagaccag ctgtgggtgg tggtgagtca gacccagctt  82140
ccctctgtgc ctggctgagt ggttctgggc aagtcacgcc atctgtcttg atgcccttcc  82200
ccatctatag agagggagca actgaggccc cttccaatac tgaagtcctt tatttctgct  82260
actttagaaa tatccacatt tttggtaaat tcaaatgatc caatgattcc atttcctaat  82320
gttcaaaact agccccagaa acatctaaat gaatcaaaca aataaaatat ttattgtgta  82380
tgttttgatt gctgaaactt ctattttagc aacacacaca cacacacaca gaacccataa  82440
gccttcatct ttccttggat aaacgagcct tcctgtctgg ccatttaagt cacgattaag  82500
taaatgattt ccaactcgcc ttttgcagca gttcagatgg gtctttcctg cgtggcagtg  82560
gccctcctga cttatgattt cctgtgtgtc ggcctgttac cactgcagct taactgagga  82620
aacaagaaca aaacagcttc tgaccccaag agactgttgg aggcaaaggc ttcagtccca  82680
agaacctcac acgtggggag cccgagagcc cagccctgac cttttctcca gtaataacat  82740
aagaaacaac aggcactggc cttattttgg atacaaagag tggtgctttt ccttaaatct  82800
tcctttagtc agggctaccc cttcatggac gccccaacat ccatggttcc tgcttgagtc  82860
cctgcttcca tattcctgca cttctcactt gaaatatccc tggagtacgt taagcagcca  82920
ggtttggaag ttcttgctgt gcaggcgggt gtgtgcatgt cctctctctc aacaggacac  82980
aagctcccca aatcagacgg tatgcctcca cgccccttcc caagcctccc cagcagcacc  83040
gagcatgtga ggggagctgg ggcccaggcc atgatgggaa gcactctctg cctaaagact  83100
agggtgatgc gccctcaact gtgggaatga gccccagctc tggtgtctgc ctcggttttt  83160
cctcctggac aatcaacatg aactcctcac ccctcttatc cactttgcat aaactgaaaa  83220
taacaaaccc agggctcttt ctgtcacagg aaagggtttt tttttataaa attaaacaga  83280
gatgattcaa cacacccagg atataacaca tgggccatga atcaagggca gcattgctct  83340
ggtcagcctg ttgtttgggc ccccttggca gggctctccc ctgaatcttc ccctcttgac  83400
tcccatcanc acagcactcc anctttgtgt tacaggcgat aaatgggaaa ggggtaaatc  83460
attcttaatt agagaaacgc tcattaaact agacacccaa attctctggg gggggatcat  83520
tcttacaagc atgcccttct ctcttaaaga gagagcactt ttttcgcaaa taatgctgcc  83580
atgaacatac ggggtgcatg tatcttcgta atagaatgat ttctattttg gggggtatgt  83640
acccagcaat aggattgctg ggtcaaatgg tatttctggt tctagatctt cgagatcttc  83700
cacaccgtct tccacaatgg ttgaactaat tcacattcct accaacagtg tgaaagcatt  83760
cctatttctc tgcaacctcg ccagcacctg ttatttcttg actttttaat aatcgtcatt  83820
ctgactagca tgagagacag tatctcgttg aggatttgat gtgcattttg ctaatgatca  83880
```

-continued

```
gtgatgttga gcttttttttc atatgttttt tggctgcaag aatgtcttct tttgagaagt  83940
gtctgttcat gtcctttgcc cactttttaa tgggggtttg ttttttcttg taaatttgtt  84000
taagctcctt atagactcac aataacaaag acatgggatc aacctaaatg tccatcaatg  84060
atataacgga taaagaaaat gtggtacata tataccatgg aatagtatgc agccataaaa  84120
aagaatggga tcatatcctt tgaaaggaca tggatgagct ggaaaccatg atcctcagca  84180
aactatgcaa gaacagaaaa caattgttgc atgctctcac ttataagtgg gagctgaaca  84240
ctgagaacac agggacacag agaggggaac aacacacatt tggggcctgt caggggtgag  84300
gtgggggagg gagagcatta ggaaaaatag ctaatgcatg ctgggcttaa tacctaggtg  84360
atgggttgac aggtgcagca aatcactgtg gcacacattt acctatgtaa caaacctgca  84420
catcctgcac acgtacccca ggacttcaaa ataaagagag acaatacttc tcccttaagt  84480
gtctactgtt gctttgcaat aaaaacttcc tgcctttcac ttcactctga cttgtccctg  84540
aattctttct cgtgatggtg tcaagaacgt ggacactggc tggggctgga gactcaccag  84600
catccggaga ccctcctgag ccctccagca atacaacttt gacacaaact atgaaatcac  84660
agatccaaga agctcaaaga acccaagcac aggaaacatg atgaaactac atgaaggaac  84720
atcagaattg aattgttcaa aatcagtgat aaagagtaaa tcttaaaagc aaccagaaca  84780
aaatatccat catatacgca gaaataaaga taagtatgac agcagattta caaatagaaa  84840
aaaaaacaag tgcagcaaca gaaacaaact atcaatccat aattctatac ctagtgaaaa  84900
tttctttcaa aacaaaggtg aaataaaaaa attattttca ggaatacaaa agcgaaaaaa  84960
ttaatcacta gcattcatca ctgcaagaaa tgttaaagga agtcctttag gcagaaagaa  85020
aatgatacaa ggtgaatatt tggatccctg caaggaacta aaaagatcca gaactgataa  85080
cttaatgggt aaacatgtaa ttttcatcaa caagtgaatg aataaacaaa tcatgatata  85140
tccatatgat agactactac ttagaataca aaagaagaac tacttatgca tgtgataaca  85200
tgaatgatat tcaaaattat tattgagtga aagacaccag atcaaaacaa agtacatact  85260
gtatgattct gtttatataa aactctataa attgcatgct cttctatagt gacagaaaga  85320
agatcagtgg ctgcctgcag acaggaagag attacaaacg gaaatgagaa ttccttaaga  85380
gatgatggac atgctcatta cccatcatat gtatacagcc ataatggttt tacagataca  85440
tatatatgta cacgccaaca taaatataag ttatcaaatt acagtaagtt ctgacttaat  85500
gtcactaggt tcctggaaac tttgacttta agcaaaatga tgtacagtga aaccaatttt  85560
accataggct aattgatata aagatgagtt aggtttttgg tttttttttt tttgacatga  85620
agtctcgctc tatcgcccag gcaggagaag aagagttagg ttttacagca tgtttctggt  85680
cacaagaaca tcatcaaact tgtaaataaa ggcacaaaac acttctaata ttaaatatca  85740
aaataaatat gagttataca gaatttaaga aagattaata aaaacaagta aaatcattat  85800
ttatgggatt tttggtaatc agtgagttat gtggtcatag tggaagtggg ttaagtcaag  85860
aaataaatgt ttgcaaaaca aaaattttaa agatcctctc ctaccaccac acaaaaaaca  85920
agaaaacacg gtgggctcgc taagcacttt tgtaccactc gtatcttatg cgtttgtatg  85980
attattgtaa atgctttatg ataattttta gagacagggt ctcactctgt gtctcaggct  86040
ggagtgaagt ggtgcaatca tagctcactg cagtctcaac ctcccggatt caagagatcc  86100
tcccacctca gcctccagtg tagctaggac tacagttgtg tgccaccatg cccatctatc  86160
ttcttttta ttttttgtag agacaggggt tgtgctttgt tgcccaggct agtcttcaac  86220
```

-continued

```
tcctgggctc aagcaatcct cctgcctcag cctcccaaaa tgctgggatt tcggacatga  86280
gccagcagca ccttgcccag cattttattt cataataatt ataagtcatt ccttcattca  86340
tcttacaacc cacttgttcc agttcaggat ctcgggtgac cagaacctat taacgttcac  86400
gcacaagtca gaaaccagcc ctggacagga caccatccta ccgcagggag aacttacaca  86460
cccacactca ctcagactgg gaccatgcaa agaacctaac gtgcactttg gaatgtgtgt  86520
tccataccca ctagaacagc taaaatttaa aagactgacc atacttgagt gttgaacagg  86580
atgtgacaca actaaatctt ttaagcgctt ctgcgtaaat ggcacagccg ctttggaaaa  86640
cagttggcag tttttcaagt taaatatacc caaactctat gatccacttc tcaacaatca  86700
aacaagagaa ataaaagcaa tgtctacaca aagatgtata cacaaatgtt cattgcagcc  86760
ttaattatac tagccccaag ttgaaacaag ccaaatgtcc attaccagat gactggaaca  86820
tacaaattgt ggtatattga tacaatgaaa tactacttag taataaaaaa gaaagagcta  86880
ttaacataag caacaacatg gatgaatctg aaaacaatta tgctaagtga aaacagccac  86940
acaaaagtta catactgtat gatcacatct acataaaatt acagaaaagg caaactaatc  87000
tatagacaga aaagcagatg agtggttacc tagggatggg gcagaaggga cgaaaggatg  87060
gattgcaaaa tagcacaaaa atattggagg gatgacaaat atattcatta tcttgattgt  87120
ggggatagtt taatgggtat atatagagat caaagctcat ctaattatac actttaaata  87180
tatgtatttc attgtgcatc agttattcat caacaagact ataaaataat atatgcctac  87240
atacattttt aaatattcaa aatctcacag ttatatacat aaatgcaact gaatatgtat  87300
tcagatgttt taacaagcag aaaggactga ttaaactcat gacagcggct gtttctggga  87360
agggtgtagg agacaagaga tggaaaagag gatgagagcc agaagagacc cttgtaatgt  87420
ttcctttctt ttagtaaaaa tatattgaca gttaaagctg agaggtgaga ataatagtct  87480
catggctttt gtgtccttaa aatttcacaa actaagtgaa atgggagaaa gcaaaaaaat  87540
aaacttaaat aaatgttata ttgcccaaaa agagatttaa aatggaggtt agacacatga  87600
gacttacgtt ctcaaaaaag tagaatctgc agggaagttt aacaactata aagaattaaa  87660
atctagcttc taccagccca aagcctaaaa tgttctgctt tattcttcct tattataatt  87720
cataggtaat atattttatg tttgcaaatg aatgcagtga tattagatct ctaagaggtg  87780
ctaaaaatga aaagtacata ttccaatttt tcccaatttt ccttctcttt ccatgaatga  87840
aaaatataca tatttgatga tttccaagtt tatacaaccg atctttctct tagttttctc  87900
ttaccaaatt ccctccctca ctcagccacc agccagtcca actgtgctac ctgcacagca  87960
gccctcatac catccacact ctcatcagga tcctgcctga cctgcgagga gcagcagcaa  88020
gaaggagaca gaacctccac gctgagcatc tcagggcttt ctcagagact ccagaggacc  88080
ctgataggga cagagcctgg ccagcaatcc atgctgccag ctgtatgatt gtgggcatgt  88140
aaattctcaa ctgaaaatgg gtgtaataat aacatgttct tcccagaatg agctttatga  88200
agatcatata gctgtttgga actcagacaa gcactggtag gaatacaaac aggggagcca  88260
acagcctata aataatactt taagaaaggg catgaatgta attacttagg aacaaaaggc  88320
aaagtggaga gatgcctagg actgagctgg acaagctgca ccctttagtg gctcagccca  88380
tgggctgaca aggaaaatgg aggagctacc aaagaaggtg gaaggattct gggagagtgg  88440
ccctcaccct gcccagggca gggctcagtg ggagagaggg agatctgtta taaatgctgc  88500
caggaggtcg agtcatgtga gaatgtccat gtgaaaacat ccactgtgtg tatctaaaga  88560
gagtggctgt aaaacaggtc agggtcaaag gtcttattgt ctcagatgtt atctgcatgc  88620
```

-continued

```
attgtctcac gaccaagaaa actaaggagc atggacacaa agggttaggt tgaagcaaaa  88680
atttaataag tgaaagaaga aggctctctg cagtggagag gggagtctga gtgggttgcc  88740
actttgacag ctgaatccaa aagcttttat aagaaactct tctcatatct gcagctgttt  88800
gagtaacttc tcttacctat aaaactgtct gtataactct cccttatcta tgcagctgtg  88860
ggatgtctcc aggtaagcat aaagtgtagc ttctcttgtt tgtataactg tgggtttgtt  88920
ttaggcaagc ccccatcccc tccctgtgta agctcccatg gagcccacca tgtgcatatc  88980
tgagaagtgg aggaagcttt ctctgggagc tcactgatcg tacaaagaac aagaggcttc  89040
tgtgccgctt atctattcag gtgcagcctg agttttcccc aggctgctct atttttgcct  89100
gtagctatga tttttcaggc aggctgcttc tctgaagact agccttaact gtctacctat  89160
cagatttttc cttttcttct ccctcagctg gttcccctca ccaaggctga gcaagtgaaa  89220
aggagggcac agggcaggcc agtagtgagc agcaacaagg aactaagaca gcagaaacca  89280
ctcttcacac ctgggttgaa aggggtgggg agccaggact acagctcagg taagaacata  89340
ggtaaagaga tactgttgtt gtgttgtttt taactatgag aagcattgag ctttaaattt  89400
ctacaggaag gatccagttc agacaggagc acccaatatt cagaagagaa gaacatggtg  89460
taaaggtcct gggaaggctg agaggattgg gactcagaat ccagagcaga agccgtctgt  89520
gaacagaaga aggacctccc ccagtgtagc aagagggagg gaggagggac agatgccaag  89580
atggttcagg aagaaggttt ggtggtaaat gtgaggctgt gctcacctgc tggcttcaat  89640
tttctcttta aaatgtcaga tggaatcatt tgatgaaggc catgccatgc aatgaaatgg  89700
cagtctgagg catggagcag ctccagctta gcccgtgttt agggtaatta tggctccaac  89760
ccaggagatg aatatgacta gggaaagtga agtccaaaaa caaatggtct caagttgact  89820
gtgagtcttc tgggaggctg agacgacagg tggggttgac aagggaaggg gaacccacct  89880
gctgaaaaac atcaggctgt tggctggggg aggggtgagg cctgtgttgt agagatggat  89940
ggatgcctaa agttgggtaa aggtttcaac tctaccctct gctgggtgtg gaaataaaca  90000
aagaccaccc aaatgagaac aaacaaagac tatttatcca gagcttgctc tgacaaggga  90060
gtcggcaacc atcacttgct tggcagagac tcagaagtaa gcaggggaga aagcctcata  90120
gcagaaagaa gggaagtctt catgtatgcc ctgagtggca gctgtagatg tgggtgagtt  90180
gcaggtggct aactagaaat gggggactcc tgtgtgattg attaggagca tgtttggctt  90240
tctctggttg gtcctacatt ggaagaggga acaaaaaatt tagggcagtt gtcagttatt  90300
aatcaagtgt tggccatttt tgactgactg ttacaggagt gactggctcc ctggattgtt  90360
tgctagaaat agtggtcttc acttcctgca agtctgactt tctggtaata ggcttcctgg  90420
gttggctatt gtggataata agtgggtttc ctgagctgat ttctgcagat tgtggatcag  90480
agttatttta tataaacagt ctgaccattt tccactggca tattccatct tccaagagct  90540
ggccaagctg ctgtcttatc tgtctccccc agcccctcca ctctggctgt gaaaatacaa  90600
gccactaggt gaggaatggg gacaattgaa gactgaaagc ttttctttgc tgggttcgca  90660
gagctgagga aagaaatgac aacatccaag tgtctgccct gggccagttt taggactgta  90720
gtggtaatgc aaggactgtg tgagtttata ttttcatttg tctctctaac taaggtggaa  90780
aaaaaaaaac agaaaattgt ctgtctgcag tctctgcaaa agtctaacac tgtgcttccc  90840
aacattgcag ccattagcca caggtgagta tcaagcactt taaatgagac tggtccaaac  90900
tgagatgtgc tctgagaata aaacacacag cagatttcaa agacctagta catgccctga  90960
```

-continued

```
tttcaagcta tattacaaag ctgtggtaat caaaacagta tggcattggg aaaaaaatag  91020
acacattggt caatgtgaca gaatagagag cccagaaata aacccgtgca tgtatagtca  91080
actaatcttt gacaagagta ccaagaatac acaatgggga aagtctcttc aataagtggt  91140
gttgggaaaa ctagatatcc acatgcaaaa gaaagaaatt agacccttgt attacacaaa  91200
atctaaaatt aattcaaaat agaaaaagac ttacatgtaa gatctaaaac cataaaactc  91260
ctagaagaaa acatagggaa agagctcctt gacactggca ttagcagtaa tttttcagat  91320
ataacatcaa aagtacaggc aatgaaagca aaaacaagtg agagtatatc aaactaaaaa  91380
gtttctgcac agcataaaca atcaacagag taaagacatg acgtatggaa tgagagaaaa  91440
tattgacatc tgacaaaggg ttaatatcca aaatatataa gtaattcaca caactcagta  91500
acaaaagcca aataacctga cttttttta aaatgggcaa agtacctgaa taggtattcc  91560
tcaaaagaag acatacaaat ggccaagaga tgtatgaaaa gctgcttaac ataactaatc  91620
atcagagaaa tacacaaatc aaaacaagat atcatctcac acctgttaga atggctatta  91680
ttaaaaaatg agataagtgt tggccaggtg tggaggaaag gaaacccttg tacattattc  91740
ataggaatgt aaattagtac agccattatg gagaacagta tggagattcc ctaacaaaat  91800
taaaaataga attaccatat gacccagcaa ttccacttca aggaatacat tcaaatacta  91860
tcagtatctc aataagatac ttgcactcct atgttcgttg cagcgttatt caccatagcc  91920
aagatacaga aacaagttaa atgtccatca acagataaat ggataaagaa aatcaggtac  91980
atatatatat acaatggaat attattcagc aaaatcctga catctgagat aacctggata  92040
aacctggagg acattatgct aagtaaaatc aaagcctgac acagaaagac aaataccaca  92100
taatctcact tacatatgaa atatgaaaat gttaatttta tggaaacaga gtagaatggt  92160
agttgccaga gcctgagagt agagaaaatg agatgcttgt caaatcaaat catcacattg  92220
aatatatata atctatttgt caattaaata ttttaagaat aaaaaatacc tggcaccaaa  92280
aaaagaatgc aaaatgtctc aacaatgtta tatgtattgc attttgaagt gataataatt  92340
tgaatattag gttaaataaa atatatttga aaaattaact tcacctattt ctttccattt  92400
ttgttaacat aggtacaaaa aaaaattaaa attacctatg tggctcatgt aggtggctca  92460
cattatactt tgatgacact atacaggctg gtgaccatat atctcttaga ctagtctaag  92520
tgatttaaca gtggttccag aaagatccag gtttaacacc aatgaaaggg ccagctggct  92580
tagcccagct tgtgtgggaa atgttgggga gtggtttaag acagggaaaa gcaaaacttt  92640
tgatgctatt gactttttga aaaatctttt gtggctgaaa aaaccaaaac attattgctc  92700
gagtgtgtct ctaaagcctt tcccccattg gctccactat acgcactctc ctggtttcct  92760
cccctctagc cgctgtcttt ggtctccttt ctgattttgc tgcgtcctct gtcccctgaa  92820
tgattgcttc tccactacgg ggtgattttg ctccccaggg gacatttggc aatatctgga  92880
gaggtctatg gttgtgtttg agggtgttgc tactgccatc tagtggggag aggctaaaga  92940
tgctgttaat gcccaggaca gtccccataa cacagaatta ttcagctcaa aatatccatg  93000
gtgccaagat caagaaaccc tgctcaaata ttagcatgtg ctgaaggccc ttctctttcc  93060
tttagcaata tctgcctcct tagggatctt ttctagtctc agtggtttaa catttaaaat  93120
cccaaattag gcaataaatt gggccccaaa cttcgttagt ataaaatgta gaactgtgtt  93180
attagaaggc taataaaatg acctggtgag catctgcagc tagcctctga gcaattctgg  93240
ggaccacgtg caagataaat ccatctgttc cctctctgta atgtggcgct accttgtggc  93300
cgatttttcc tcgggttaaa tatctctggg gatgcaactt gtcgtggtta atggctgtgt  93360
```

-continued

```
gaggccagcg cgtggtgata aaggaatcaa tcaagacaat attgaattta gaaaggcaga  93420
tttatttaga gaaaaggaga gatacgttgc aagggagcaa tgggcaatac agcagaggga  93480
aggctgtctg caaagaggca agggctacgt atgacgtagg gctgcttagg ctgaatgctt  93540
gcagacaaga tgcttgcgtg caggtgggct gtgagctgag tgcttgggtg ctagtgagcc  93600
attggcagct gaccctattt cttggaacat tcgctccctg caagcatttt aatgttaaac  93660
cgccaggtca gtttgaattt tctttttttct tttttttttt ttttttttgc ctttagtagg  93720
acctgccgtt gtgagactat ctgaggtaaa ttagacaccc tcctggttta agtcaccgct  93780
ccagtgacta ggcagggagc tcttccttga agagggtgtg ggcagtgggt actttgcatg  93840
ttgtccacac caggcgagct gctgcttcag ggcctttgca tttgctcttt tctttgccca  93900
aaatgcactt ctctcactgt tcacatgatt tttctccctc ttttcctttt agtctttgct  93960
taaatatcac cttctaggga ggccttccca caccacctct tcaagatttg agggtatgca  94020
cccccacccc tagccttctt atccctctcc actgctttct tctcaaagca cttgttacgt  94080
tcaaataaaa tagattagtt actttatagt tctaatttta ctattttttg tttacttcat  94140
caatacccat gtaatctctg gaaggaacgt ttctttttgt agtgtatttc tagcacctag  94200
aacagtactt ggcacatggc aggtgttcaa aagtatttgt tgattatttt ctcaaagggc  94260
atggagtctt agaagtttga gaacacagtt ctaagcacag ctgtttagag actatggatg  94320
atgctaatgg ctgtattccc agtaggtggg gcaattctca aattgacctg gaatccttga  94380
gatctgggga cagtcaccaa gcactgggct ctgtggggag agatgtgctg gtttttagag  94440
aggagaatag catcctgggg gacttggccc cagggctttc ctgtcccaat ctcttcccaa  94500
ctgagtccca gaggcaggag gccttgtctg tagctggtca gtcctgtaac tgtttccctc  94560
ccatctacac agatgcaaag aaggctgaga aaagcaagct gtcaggtgag caggggccct  94620
gactcctccc cagaaggcac tcagaacttc catagggcaa ctggaaagaa ggttctactt  94680
cctcaccggc agctgttgct ggggaaaaaa ccagcctcag gccctaccct gtgctgagaa  94740
cctgaatcca gtatcaggtt ctccaacaaa cttggatcca gctgaccctc acaaggggtc  94800
agatgcaacc ttgtagcata tggaaaatgg cagcaaggtc cttgtgtgga ctatgcctag  94860
aatctaaatt aagacaaggc ctcagagggg ctaagtgaca tctgtctcca aagtttcaca  94920
gctagtgtgt gactaaatct tgattccacc ctctcaggtt ttaccataat cccaaaaaag  94980
gttgaaacaa gaaaagttat ctttgggcaa ttacctcttt ctgttccttg ctttacctac  95040
taatgttcta ggctcaccct ctggtctgca atctcactga actgacagat ccctcatggc  95100
ctaaagggtt ttcacactgg gttgactagg ctctcccatt gcctgtccta ctgtctaagg  95160
cacctcctgg gtagggtgcc cagcgtcatt ctgatgctgc ctgactttcc ttccagctac  95220
ttttgaaact tggtatccat ggcagaggct taaagggcat gttccaggta cttttatttc  95280
caaattcccc agtggcatca aggaaatcag catctctgga tagctctact aaggcttagt  95340
tctcattgtc caatctagct cctgggtcat gggaggcatt caggaaatat ttgagtgtaa  95400
gagtgagttg ctttacctcc agaatatcct tccaatggct ctgaagcagg ctgtggagtc  95460
ctgctggctg atcacagttc acaggtggct cccaaacctg tggtctacat ccatcctttg  95520
tcagtgtcac tgccattgtc ccacaaatgt catttgggcc tagcccctgg gatagtaatc  95580
agtctttaca tagatataca ttgtgcttta catccacagt aattctgagt ggaccttaaa  95640
ataaattcca tgtcaggtct caccagccca tgggttacag atggggttac ctttcagcct  95700
```

-continued

```
tgtaaggtgc cccgtctttg agtgtagaca tggactcaca acgagtccac tcctgctgtt  95760
cctctgctct tgctgaggct tctgctgctg ctgctgctgc tttgcagagg ctggccagct  95820
gtggtgcctg aggcacctgt gtcttcacag caccaacttg catggtggcc acggtgtagt  95880
tggaaaggga tgcttagatg ggaggccaat gggagctgct tcaggaggca aatccaagtc  95940
acagagatcg agtcaccgag agcatagtaa actcaaaatc ccttcttctg cttaataact  96000
gagatgctgt cactgggtta acctcaccaa gccttgtttt gtcttcactt agagtgattt  96060
ctgtcttaga aggctcctca tatccttctg ggaaggcttt ctagtgagtc cacagatagc  96120
tggaccaggc atgtccagaa ataatctgat tctcacattt gagttagcca gcgttcccag  96180
ctatatcccc attttgtgtc tatataagtt accaaagccc acaaggatat taggtggctc  96240
cttagtttgc tttatgatta tgccttgtgt gtgtgtgtgt gtgagtgtgt acgcctatga  96300
ggattccttc tctcccgttc ttgctatggc ttctcttccc cactgatggg ctgtagttcc  96360
ctgtcctttt gactttgggc ttagtcatgt gactttttg ccaagggaat gtgggcagaa  96420
gtaactggga gccagtccca agctaaggcc ttgggaagca tggtgagcct atgccagctc  96480
cctcagaact ccttcccttg gccatgaaga gagaataacc tggattgtac cttcagccca  96540
tgtcctagaa tacaaacatg gagaataatg aacttgactc aaaggctgaa gggcagctga  96600
gcccacatga ggtcaattga actgcagcta cctacagacc tgaaagtgaa ataaacatgt  96660
ataagtctct gacgtttggg gtttgtttac atagcattat tgtagcagaa acttaaataa  96720
tactggggc taaatatagt ggaccagtga cagcacagaa tggtaaaatg gagtgattgt  96780
tacttacatc acaacccttc atctctgttg atggacacta aaatcaaagt ggcaattact  96840
cagagttggg agtcattgag ttgcatcatt gttgtttaga atcattgaca gtttgagctc  96900
taagtgatta cagagatggt ttcctcagct acaggtaaat aaacaaaggc acagagaagt  96960
aaagtgactt ctagagggct tcattgatat ttagcagcag aatcagagct aaacaatgag  97020
tctctcatct ccagcctttc tattcttgtt tcctaggttg ggattttggg aaatagtgca  97080
gagagattag cagtagtgac atggaacaat gtgagcctca gcttccatcc ctgaggctgc  97140
cttcatctgc cagggaaatg tctctgtgtg cagccttgcc ctctgcacac agtgtgtatg  97200
gccacctgaa taagtgtcct ttcatagcga ctaatggatt gaaatgggtg ctagagcagt  97260
gcttctaaaa actccatgta ttaatcatct aggggtctta ccaaaaacgc atgcagattc  97320
tgattcagta ggtctggagt ggggcttgac attctgcact tgtaacacat ggaccacact  97380
ttgagtagca atgtattaga tcattccagt ggaaacatgt atgagtgatg gaatgaacag  97440
atataattaa tccaggtctg gtaagtgagg tactgataca tattaagttg aagtgaattt  97500
cacatcaaaa ataatggtta cacagtgact tttactgccc ccaaattctt tccttttgag  97560
tggtttcaaa gtgaactgag ccagccaggt taagtccctg gtttagtgtg tgattagaag  97620
atttgatcca gctttctcct ccttctaatt ctttaaatat gcaatggcct tctagaaact  97680
tgtctctcag gctccccatg agccacctgt cttaatatct tcccccccag gacatttcct  97740
gggtcaagga aggaatcagg gactaggaaa agtagaaagg ttgcctgaca gtgagaaact  97800
ttttgcactc ctatttgttc aattctaaaa tgtgggtatt gttggggctt ctaattggaa  97860
tctaacctga aattcaggca tgtctagcta tatatgacca agaattagga tgagttcact  97920
agaagcctat tttcaggaga gcggtcagtt aaattgaagt ttatgggttt atggtaatgg  97980
gttggggagt ttacttcatt agcaatagca acgtttttga atcagagaag tgattttgaa  98040
cacactgtac atagttttct cacttagatt tatctctggg tcaacccttg ttggacctat  98100
```

-continued

```
attagaatca tttagtgaag aaaaggtggg tgtcattagg aaaagagcca tttattcaaa  98160
tgttctgttt gacattaggg cactggcaag actacagaat caatagatat ttaaaaacag  98220
ccaggtgcgg tggctcacgc ctgtaatccc agcgtgattt gggattactt tgggaggctg  98280
aagcgggtgg attgcctgag ctcaggaatt caagaccagc ctggtcaaca cggtgaaacc  98340
ctatctctac taaaatacaa aaaattagcc gggcatggtg gcaggcgcct ataatcccag  98400
ctacttggga ggctgaggca ggagaatcgc ttgaacccag gaggcggatg ttgtcatgag  98460
ctgagatcgc gccattgcac tcaagccagg gcaagaataa caagactctg tctcacaaca  98520
aacaagcgaa catacgaaac aaacgtaaca tccaaactag caggtacatg ccgtgccagt  98580
catgacccat ggtcataaga tgtctacagc tcaggaagca gctgcacaat gcctgcatag  98640
acaaactctt atgaaagcag aatgtcctga tgtctccata acacataaca gtgtatgctt  98700
ttattatggt catactctag ctgtgatgta cctacgctct aatatgccaa cgatagtttt  98760
ctttaaatca tcaacataat aaatgtcatg ctgtcagtcc cccacatgta gacataactt  98820
agctggtaca tggataagaa acctatatta gataacctta ggccaggtgt ggtggctcat  98880
gcctgtaatc ccagcacttt ggggaggccg aagcgggtgg atcacgaggt caggagatcg  98940
agaccaccct ggctaacaca gtgaaacccc gtctctacta aaaatacaaa aaaaaattaa  99000
ccgggcatgg tggcaggcac ctgtggtccc agctactcag gaagctgagg cgggagaatg  99060
gcgtgaaccc aggaggcgga ggttgcagta agccgagatc acaccactgc actccagcct  99120
gggggacaga gcgcaagatt tcgtctccca acccaaaaan cnannnnaaa tttgcaccca  99180
aatctgacta attccagagc caattccaat ttagaatcgt tatatctccc tggtgaactg  99240
aagcttttat ctttaaggag acacactctt tatgtctacc aatgcttatt gccttaaagt  99300
ccactttgtc agatacagct gctttctttt aattagtttt tgtgtggtat atctctttcc  99360
atcctttttc tttcagcctt ctccattctt acattttaga tatatttctt ttttcttttt  99420
tttttgagag agagtctcac tctctcgccc aggctggagt agtgcaatgg cgcgatctta  99480
gctcactgca acctccacct cctgggttca agcaattctc ctgcctcagc ctcccaagta  99540
gctgggatta caggagccca ccaccaagcc cagctaattt gttgtatttt tagaagagat  99600
gaggtttcgc catgttggcc aggctggtct cgaactcctg acctcaggtc atccacccac  99660
ctcggctttc ccaaagtgtt ggtattacag gcgcgagcca ccatgcccag ctgattttag  99720
ctgtatctca aaaacagcat gggttctgtt tgctttcctt attcagcttt ataatgtaaa  99780
tcatttacat caaacatcta atacaccatg gactgtaaaa cacagccata ttttatgtat  99840
gaattaaaaa aaaaaacacc accaattagt tcctgagaca cacaccttaa caatatctct  99900
gtgatgtgca taaatcaatc acatcagttt ctctgcacct caaaatttct ttcctcaatt  99960
ctcagagata tggcaatttc tctggtttta cattcccaga agcaaagaaa aagtacacag 100020
cttcttcaag tcatgagtag cttctttttt atagctcttg gtgtttgcaa aaaagattgg 100080
aattgcttca ctaatactaa attttcattc tgctgctctg tttctatgac aagtcagagg 100140
gcatcttttt gaagacattc taaacagcaa ttaaactcaa aacatgtaat gacaatgaca 100200
cacaaaactc aactgatgac caaatgaaga gttccagcca agttgacaca agctggctga 100260
cagagcttgt aatacacaca gcttggcata tgcctcgcca tttcagagat gtaaaaatag 100320
gaataaatgt tttcccttaa atcaatgaaa tagagcattt ggactgaaaa tctacgacag 100380
ttatagtgtt ttctattcat tattctcatt ctgtttcttc tccccttgc tttcttttag 100440
```

-continued tttgaatatt ttctatcatt tcatttttct tcctactagt ttgaaactta tgcatttatt 100500
ttctattttt tagcacttac ctaaaattac tctgtaatcc atggatcctt aatttattta 100560
aaaaactaat gttaatgagt agctttattt tcctcccatc taatttaagg cccacagaac 100620
accttcactt acctcaatcc tctcccaact tacatgcttt taatgtcata tatgttaata 100680
ccgtatactt ttaaaacttt ctaaaatagc attattttat agcatgagtg ttcatttaca 100740
tttttgcata tatttagaat tttctttgct cttcgtttct tcttctattt atgactcccc 100800
tctgggatca ttttccttct acttgaagta catagtttag aactgcacta ttcaatacag 100860
tagccactag ccatgtgtag ctattgaagt ttaaactaag taaaattgag taatattaaa 100920
aactcagttc cttcatctca ctagccacat ttcaagtgct cagcagccac atgtgactaa 100980
tgactactgt acagcaaaca tatagaacat ttccatcatg gcaaagagct ctattgatag 101040
tgttcatcca gagtttctgt tccaggacca aactgagggt tgggctgcta tttctcatgg 101100
cccaataaca agatgcagat gagctgggga ggaagagagt ttttatttct gcaaccagtt 101160
acagggagaa ggcctggaaa tcatcaccag gccaactcaa aattatgacg ttttccagag 101220
cttatatacc ttctaagcta tatgtctacg tgtaagtgtg cattcacctg aagacgtaag 101280
tgattaactt cttttaatct gtaactaagg tctgagtccg gaagatcttc ccctggagcc 101340
tcagtaaatt tacttaatct aaatgggtcc aggtgctggg gtaattaccc ttatcttgtc 101400
ccctgctaaa tcatggaggt ttggggaatt ccctttagag caccattaac ctgtttgttg 101460
aaggcctggg aatttcctcc aaacccccat taaacctgtt taatcccaaa ttggttccgt 101520
taaaaattcc ctccttaatt tgtccaattt taaaggccca aaaaaggctg gggcaaactc 101580
ctgaatggcc tttgttacat tccaaccttt gtttaaaaac accggttttt aatatttaac 101640
ttaaccattt aatctctact gaaacacttg ttatataaat ctgcattaat gagaactggc 101700
ctgcgccata tctccttctc agaatatctt agggttgtga tcccctgtgt gaagagaata 101760
tatctctgga gatctcaatc tctctacccc aaaaaaaatc tcactcggag aaaactcaga 101820
ctcttatctc cacagcgcta tctctctcct ctccgcttgt ctaagatggt gctccttgtt 101880
gctgtgcctg ctttcatcct gggatctccc ttcaccatca ggattgcctt cacctcattc 101940
cagtcttgga tctttcttct tgtttcttga gtattttttt tttttttttg ctgcattccc 102000
ttcagtggcc tcttgggaaa agatgtgtag ggagaaaaat tttctttaga aacttgcata 102060
tctgacaata tatttatcct atcctgacat ttggtagata gttcagctgg gtacagaatt 102120
ctaattaatt ttccttcctg atttataaga cattgctcca ttttcttctg gcttccaata 102180
ttgctgctga gaagtctgac accattcaaa tgcctgattt tttccatgtg attgttgttt 102240
tctgtctgga gtgttgtagg attgcctctt tatctacagt gttctgaaat ttcatgacgt 102300
aggtctttct tcattcatta tggtagacac tcagtgggcc atttaatcgg gaaaaacatg 102360
tgttcttcaa gttctacaaa ctttattact tcctttttct tgtgtctttc tctggtctgt 102420
tttcagcccc gagtctctta gatctgtcct ctaatattcc tattgacttt acttcatttt 102480
ctaagtcttt atccttttgc tttactttcc gagagacctg cttaacctta tctcccaact 102540
cttttattga atttcatttc ttttactata tattttttac tttgaataca cctctctctt 102600
cctcacattt tcccccatag tattttgtct tcaattgaca gttctactat cttattactc 102660
tggagatatt aataatagtt tttaaatttt tatttatttt tattttcaaa acagtgtctt 102720
actctgtcac tcaggctgga gtgcagtggt gtgatcatgg atcactgcag ccttgatctc 102780
tgagctcaag ctatcctcct gcttcagcct cccaagtagc tggaaccaca ggcatgtgtc 102840

-continued

```
accataccca gctaattttt ttgtttttga ggtggagtct cactctgtag cccggtctgg 102900
agtgcagtgg tgcaatctgg gctcacagca acctctgcct cctgggtcct ggttcaagca 102960
attctcctgc ctcagcctcc tgagtagctg ggattacaga aacacactac catgcccagc 103020
taatttttgt atttttgtag agacaggttt caccatgttg ggcagcctgg gtctgaactc 103080
ctgacttgtg atctgcccac ttgggctccc caaagtgttg ggattacagg cgtgagccac 103140
tgcacccggc cactaatttt taaattgtta ataaagacga ggtcttgcta tgttgcccag 103200
tatggtcttg aactcgtggg cttaagtaat cttctgcctc agcctcccaa agtgttggga 103260
ttacaggtgt gagccactga atctgacatt ttttaaaagt tttcttctct ttaccaagtc 103320
ttttttcccc tttctgcttt tttgggttgt tttattttga tctctatctt gctagaaact 103380
ttctgcagac gtttagtaat actagatttt tgagagtggg caactggaaa gctgattgga 103440
aactctgaat acatgggtga ggcttgttgg ctgtgagtgt cattgcttga tgtcctggca 103500
aggccaatgg gtttgggacc cctactatta gtataggcct gattccctgg gaaaggctct 103560
tttgatctcc tgcctggagg ataaaggcct ggctaccagc cttctgtgtg taatgtgagg 103620
gagaagggct ggagtattca acatcatgct gaatcctttc aatgatcatc ttgtttttag 103680
taatctccta ccttaactct ctgtcttctg ctagtatggg aaagatgacc tgaaaatcta 103740
accatttatt tttcccccat taatatcatt ttatgattat tcagaagtta aataattgtc 103800
atgctgtcct ccaaaaagac tgaatcaact agcaacaaat aagaattttc tcacagctct 103860
gccagcattt taaaagaata gctttattga gcccaggagg tcaaggctgc agtgagctgt 103920
gattacacca ctctacccca gcctgggtga cagagcaaaa ccctgtctca aaaaagaaat 103980
ttaaggaaca gctttattgt tgtaaaatag acatacaata aacagagcac atatttaaat 104040
tgtgcaactt atactttgat ataaccctgt gaaaacatca ccacaatcaa gatagtgaat 104100
atatttatca cctcctgata cagtttagct ctgtgtcccc acctaagtct catgttgaat 104160
tgtaatcccc aatgctgggg gaggggcttt gtgggaggtg attgaattgt gggggtgcac 104220
ttccccccttg ctgttcttga gatagtgaat gagctctcat gagctcccct tcactcactc 104280
tctttcctgc tgccatgtga ggatgtgctt gcctcttctt tgcccttctg ccatgatgtg 104340
tttcctgagt cctccctaac catgcctcct gtacagcttg cagaactgtg agtcagttaa 104400
atctcttttc ttcataaatt acccagtctc aggtggctct ttatagcagt gtgaaaagga 104460
actaatatac ctcctaagtt acctcaagct tcttcttaat tccttctcct cccttccttc 104520
attgccaagc aaacaaccac ctgttttctg tcactataga ttagtttaca ttttgtgggt 104580
tttttttttt tttgagacaa ggtctcactc tgttgcccag gatggagtgc agtggtgcga 104640
tcatagctca ttgcagcctt gaactcctag tttcaagtgg tcctcccact tcagcctcct 104700
gagtacctgg gactacaggg gtacaccacc acaactggct taaaaaattt tttaaataaa 104760
aatggggtct tgttatgttt ctcaggctgg tctcgaactc ctcgcctcaa gcagccctcc 104820
ctccttggcc tcccaaattg ttgggattac aggcatgagt catgactcct ggcctagttt 104880
acattttcta gagttttgta taaatggaaa catacagaat gtattttttt gcggagtggg 104940
ggagtgtttc tatttctttc tttctttttt cttttttttt tttttttttt gagacggagt 105000
ctcgctctgt ctgttgccca ggctggagtg cagtggtgcg atctcggctc accgcaagct 105060
ccacctcccg ggttcaagca attctcctgc ctcagcctcc tgagtagctg ggactacagg 105120
cgcccgccac cacacctggc taattttttt tgtatttttg gtagagacgg ggtttcacca 105180
```

-continued tgttagccag gatggtctcg atctcctgac ctcgtgatct gcccgcttcg gcctccctaa 105240
gtgctgggat tacaggcgtg agccaccgtg cccggcccaa gtgtttctat ttcttaacca 105300
gctttcatgc aatctttttt tattttacca tctctgtgat cccactccca aaggtactag 105360
atgtcgattg gtccttagga tcagctacca tttgcccaac tgctttccag ccttccaaaa 105420
atttttttct ttttttctta aagatactcc tgtgtgaggc tcagaactct tgaattgcta 105480
ctgcaaatat gaactcggtg atgtgaatgc cagggaattg cctgattgat caaagaaatg 105540
tatccccttc tccctcactc ttgctgtctt ctcatttgtt ttccccatcc ttgtggattc 105600
gtgaatttaa atatcccttt aatgttataa tattttaatg gcgtttggcg aaaagtacag 105660
aattaggtgc aagagtgcat agctgttatt ttttttttgg cctctgagac tgttcatata 105720
tgcaagttat ttaacagaaa gttctgcagt gacctgagat gtcagggggg tctgatagag 105780
tacgtttgaa ggcagttact ggaaaaaaat aatgccattt ctggtttgta cttcggtaag 105840
ttcagatgac ccaatatatt gtttacatgt ggcattcagt aaaaaagtag cttcccctcc 105900
ctttcttctt ccttttctcc tttcctgctt ctataaagca tctgctttgg gaaacttctt 105960
aggaggagag cttgccagcc cgtgggtaat ggagaggtct tgcagagata aaagagatgc 106020
tcccactcaa tgcaggatgg tgtggaggta aatggggata cgtctggcat cactcaggaa 106080
tgggccttcc tggcagggaa gagaagggag gggaaagagg aagggagtca aagatgaatt 106140
gctgaatacg gggattccag ggcctggagc caggaagaga actttgggag gtgtgaacct 106200
ggagggcatc agctgatgag gagcagcctg aagtccgggg aggacctgtt tttggtggcc 106260
aggaagaaag tgccttccac acacagggag gccacaaggc tgatgggctg gggggttggaa 106320 ggacagccct aggacaggct tgggaagcag gctcaggtag ggactgcgag gttcttgttg 106380
agtctttttc attcctggtc ttagaaaata gaatccaagg cctcttgaga gtggaaggtg 106440
ggttgggagg agggcagatg gggcttaggc ccaggacacc cgtagagcta ctgcccagct 106500
gtctctcagg gactctgctg aggtcactcc aaggatcatt cttagccttg ctagacagta 106560
ctgacagagg gaaccgtagt atcgcaccca cttccttctc tttcaatgaa agtttaaagg 106620
tcaccatttc ctctggcaaa ggaagttcca caaatattcc atttccggtc ttagaaacag 106680
caaggtatca agcaattgca aacttcctgt gctggggaat tcccaaggaa gtaggggcag 106740
agttctggtg gagacaaagt gaattccgag tgattagtca gtagcagtag cagtagcagt 106800
agcagtagca gtagcagtag cagtagcagt agcagtagca gtagcagtag cagcagcaga 106860
accagaattt ccccgcacgt gtctcaggct ctcatttgcc aactcagtct ctaagtattt 106920
ttattggcag gaaaaataaa atagctatga gtgaaataat tcattagacc tgagcctcca 106980
tcaattttgt gtttaaaggc ctgactctct ttacctttcc ctgggatgga agatgcaaat 107040
gttcctgatg tcactgtcaa aaaagaagaa ccagtgggta tattgtatgc ttgagttcca 107100
gccatttgtc acaatagata gagatgactg ccatgtgtgt agactttcta tagactgtgt 107160
gctaaacccg acctgccact tccaaggagt agatgaggaa tgtccatggt tctggggagc 107220
cctaccccaa tttggggcag acattccaaa gctcattttc tgtggagggg gttgatggtt 107280
aaaggacggc ctgggagtaa ctcgtctgta ctagggccca ggagagttac atgctgcttc 107340
ccatgttatt catcattccc ccatgtgaat agctatggcg tgaggtccaa ggttagggcc 107400
tttctaccat aaatggggga ataaaattcc cctaccagcc tgagaagttt ctgttataaa 107460
gaggcttttt ttttgcgggg gtgggggagc aagccgacta atgtgttatt tccatacggt 107520
ttgttttaaa atgtagatgt catatgcagg agaggtggtg tagtgagtca caacgggatt 107580

-continued

```
agaaggacca gtccgaaaag cagaagaggg tcaagttcag ggcactgagg actactgcat 107640
tcagtggcgt gaaaggcaga tggctgaaca ggagggggac attacattgc ttgttctcct 107700
tgagcctcga tttcctcatc taaaaagagg gtcatttatt cacagaacat ttattaaact 107760
tgtgccaggc accgtgccag gagctggact aaaaattaaa tccacccctg tgagctgctc 107820
tgaaggctaa aatatgaagt atgtaaaagt aaccaagtgc tgtacacatg cagctattca 107880
atgactgtgt gggcattgcg gcagatttta attttctttt ttatttcttt ctctttagtg 107940
agaggtgttg gttgttatta ttgtcgtcgc tgtaactgtc tatttcactt gctttttgt 108000
tgcctccagc ccattccagg gctgtcatct aagacacttc ttatcaccta aataaccggg 108060
gaggcaaagc gctttcttaa gagatggatc cagaagaaca atgctggttt tctgtagaaa 108120
aaggggctgt gggaagtaga gataagaagg gaattggcca agatgaatgt acagagcctt 108180
attttttttt tataacacag caagattaga tacaaaacag gacaatagca tcatctgttt 108240
ttataactgg aaaggacctc actttacagg tggggaagaa tagagtggag aagtgaagag 108300
aatggtcaca gagtcaatca gcatgtctgc gtcaaagctg ggattcccaa ttcagggctc 108360
ttactacagt gacgtatggc taatattttg gcattgtttc ggggaaaagc tgaagccctg 108420
atggtgtacg tcactcttga gatagtctgt agtccagcag ggaggaaagc aaggaaggga 108480
ggtggaggca gcatttttgg gtgtaacatt tcgttcttgt tttgtggcca aatcatagtg 108540
tgattgggac aagccactgc ctttctctga gcctccactt tctttttctt cttaagaggg 108600
agggaatagt agagtaaaag tagtcatttt atcaaacacc tgctattttg gagccatatt 108660
gcaagtgggt tgggggttga acacttggct ttattaccca taggattaaa tccaacctcg 108720
atactgtggc attcccaaac tccagtctaa tcttcttctc catcagccat gccccacgac 108780
accctggtca tatctgatgt tgccccttgc acttgccccc tccttatctt tgctttctga 108840
cctaccatat ggctattggt tgaaattctc attttccagg gccttgctta aatatcatct 108900
catccattaa aactttcttg aacctcccct tgccctgttc ctccctaatg tctcaagcca 108960
gaatttattt ccttttgtgg ccaagggact gggtttgtga cctctctcac gagacttaat 109020
attgagacca aacgtcttta gacctcacca gccagagaga tgagcatcta tggaatgcag 109080
gcttttgcct ggacttgctg atgcagggcc tctgccttcc tccagggcct ctcctgctgt 109140
tttaggaatt tccctcatgg cacagtccat gagctcaggg tcaagttcat acatgttttt 109200
acttcttcta ctctgcaaat ggtcttcttg aactctgagg gtcctaaagc tgctctgcag 109260
tttgtggggt gagtagaaag gggctttcaa aagttgtgct gttgtttccc accccaatag 109320
catgaaacac aaagatgctt acaaatagct gccttgcttt ctagtcccaa cttctctctc 109380
ctgaggcttt aaaacaagtc ccctaggttg agctggactg gagttgtatc ctatcttcat 109440
tatctgtcta ctctctttct gctctctaga gaagatatta tatatgtgtg tatgtatgtg 109500
taaatatata atatccatat atagaacata tattgttata tttacatata catacataac 109560
atatgcatgt attcatatat acatatgtag tatcaaagtt ggaattaaac tgtatatttt 109620
gtaatttgct tttatttgca tctatcactg taaaatgaat atttatccat accgtaagat 109680
attcttcaat gtattttttt tttttttgaa acagggtctt gctttgttgc ccaggctgga 109740
gtgcaatgac ccgatcttgg gtcactgcag ccttgacctc cccggctcaa gtgatcttcc 109800
caccttagcc ctctgagtag ctgggactaa aggtgtgtgc ctccacaccc agctttttaa 109860
tttttttgt atttttttt taaagacagg gttttgccac attgcccaag ctggtcttga 109920
```

-continued gctcctgggt ccaagcaatc ctcccacttt ggcctcccaa agtgctaaga ttacaagcat 109980
gagccaccac acctggcctc aatgtaattt ttaatggctg tatagtattc catcatgtgg 110040
ttgtacccaa aattatttaa ccagtcccca gtttatttca attttttttt actattttga 110100
ataatgtttt agtaaatacc cacaaaatat gtacaatggc tgggcttagt ggctcacccc 110160
tgtaatccca acactttggg agtctgaggc aggtgggtca cctgaggtca ggagttcgag 110220
accatcttgg ttaacatggt gaaaccccgt ctctaccaaa aatacaaaaa ttagccgggt 110280
gtggtggcac acacctgtaa tcgcagctac ttgggaggct gaagtaggaa aatcacttga 110340
acctaggagg cggaggttgc agtgagccga gatcacacta ctgtactcca gcatgggcaa 110400
cagtgagact ccatctcaaa aaaaaaaaaa aaaaaaaaaa agtacaattt gttgtacctc 110460
cctgattatt tcttttaagt agaattttct tataattttt tttataagta aaattttgaa 110520
tcaagggaga agcacctgga gtccttcaga tacctattgc caaactgaac ttttctgttc 110580
caggtttact acattcagcc tgactcaggg tttggggagt agaggagggg gtggaggcag 110640
agggcctctc cctgtcccca cagacctccc ttggtgaggt ccaagtctgg acaggtggag 110700
tgtggcattg caccgtcagg tcctgcttcc tgtaattccc ctaaatccat ccagtggagc 110760
ctcattgttc aagtcttttt tttttttttt tttttttaac tcccctgaag acggagtctc 110820
actctgtcgc ccaggctgga gtgcagtggc acgatcttga ctcatttcaa cctctgcctc 110880
ccaggttcaa gtaattctcc tgcctcagcc tcctgagtag ctggcactac aggcgtgtac 110940
catcacgccc ggctaatttt tttttgtatt tttagtagag acggggtttc accatgttgg 111000
ccaggctggt ctcgaactcc taaccttgtg atctacccgc ctctgcctcc caaagtgctg 111060
ggcttacagg tgtgagccac caggcctggc ctcaagtcta ttttttaact ccaggaggcc 111120
tggtattcag agggattagg gctggcagaa gggcctcaaa gctttcaagg cctggggaat 111180
aggctgcagc ctggttcagg gtaacccaag tgattttggt tccaaaggga caggaaaaaa 111240
agtgattgat atggaagttg tcaaagtgca actgtcaaga cattaaaaaa tgtaaccctt 111300
ttactaatat acagtagact tgtgttaaat atttaactga ttgtaaaagg aaaaaaccag 111360
acgcagtttt ccctaccata ctgtcacaac acctcaacac tgagttcttc tgtgacctct 111420
agtcaccgaa atgcttgggg atttctccca ccactagtcc tccagcagcc gacaccagtt 111480
gggtgtccta attcactcca acactatcta cctggagtta gcgttagatc ccacaggttg 111540
agggctcagt ctcacaagac tgcctcccac ttcaggtgcc agttacaagt ggtaggttgt 111600
cacctatgct tctgactgat ggctataaat ctgggtttgc ttccctcggg ttccgtgaat 111660
ttgctagagc agctcacaga actcaggaaa acacttaagt ttaccagttt attctaaaag 111720
atattacaaa ggatacagat gaacaccaga tgaagagatg cgcagagcaa agcatgtgag 111780
aaggggtgtg gagcttccat gcccctctgg ggcaccaccc tccaggaacc ttcatgtgtc 111840
cagctatctg ggagcccttc caaaccctgt cctttttggg tttttaagag tggctttatt 111900
acatacacat gattgaccga accattggcc attggtgact gacacaacct tcagcccctc 111960
cactccctcc agtggttggg gagtggggct aacagtctca agtctccaat cctgccttgg 112020
tctttcctgt gacaaacccc atcatgaagc tactgcattg gggctgccag ccagcagtca 112080
tctattagca tgcaaaagac actcttatta ttccagagat tccaagggtt tttaaaagct 112140
gtatgtcagg aaacaggaga tgaagaacaa atatatattt cacaacatca cactcgttgg 112200
gggaattgac aggatagcaa aactgattaa aggaggatag gagagactga gatatatatt 112260
tccatatata tatatagaga gagagagaga tatttccata tatatatata gatctagaga 112320

-continued gagagagaga tagagagaga agagtctttc cacacatttg ggggagcagt tccggaggta 112380
cagcccggac aggagatgtg agaagatcgt ggttantgtt cccctggtcc agaacccctc 112440
caagtgggct taagtaggaa gggtggtgag cggcaggtaa acacacgtca aaggcagtct 112500
tcctctctga gggaaaacac ttgtataagc attgcaatca atgggcctct ttaattatgt 112560
gccagtggca agagcgggtg ctgaacccag gggcctgcct caatccgggg cctttgaggc 112620
agaataaagt ggtctcaggt tgttggcatt tccttgccct tccacccgaa gcagacacaa 112680
atcctctctg gaggcaagtt ccccaattca gccagtacaa ctcccacaga ctaagatcaa 112740
tcatgtacaa gctcacagac aaaggtcacc aaacacacag agcaataaac aaattcatga 112800
gtgacgtgaa tgagaataaa cagaaacaat aaccaccagc tgggatgctc taagtcttca 112860
gctgttagaa ttcctgaata tagaataaaa ctgccacaat ggcaaacatg catctagtac 112920
ttactgtgtg ctgggttcta agaattttgc acattgtgcc agataccgac tcagcttcac 112980
actcaccctc ctactgtgcc ctcttaattt gcactagatt aaaaggtaga aaggaagagg 113040
cagctattct gttcttggct gtgcctctgg cagcacatgc aaaatgggca gtaacagtgg 113100
cagtcacagg taagtagcct tctcacagtg tggagttaaa ggcatgggac tgagacgagc 113160
aaggttccta aagggacagt ggccagtaaa tgaccagggg ctactggagt ggctgcatgg 113220
ctctgtggaa gctcagagga gccttgggtc ctgcaggtgc agtagcagct ttctgtagtt 113280
cctgatctct gggtcccaca atcttccccg tttttgctcc tccacttcta attttgtaac 113340
tgacttccct gtgtgtactt ctctctctga ttgaaatagc cagactggtt tctgtttcct 113400
gataagacat tgtctggtac gaacacagta actcatttaa tccgatatct ctatgaagga 113460
ggtacaataa ttattcctat tttacagatg aggaaacaca gcagaaaaat aaagtcaatt 113520
gtctaaggtt gcacatttag tcaagggaag ggttgatata acatataatt atttagaaaa 113580
catctaagga aataaaaggc ataatttaaa aataaaacta ggcaggttta aaaaaatgaa 113640
gtaatctata agtaaaaaag tataattgtt gaaatacata tcttagtgga tgggttaaat 113700
agctgaagaa atgattaatg aactggaagg tagttctgag gaaatcagaa ttcagcatag 113760
atagaaaaaa tgggaattta caaaagtaca caggaattat aaaagaggtt aaattatagg 113820
gagggtagaa tgagaattaa cattggtcta actggaattt tggaagaaga gaatagagag 113880
aatgaacaag gcaatattta aagaggtggc tgagaatttt tcagaaccaa cacaaactat 113940
gactttacca gtagagaaaa caatgtacac tgaggaggat aaataaatat actatgaaca 114000
aattgtaata ataatactca acaaagacaa agagaagatc ttaaaatcag caaaaaaaga 114060
aagtcagact tagaaagaaa tgacaatggc agactactca acaacaacaa tggaaaccaa 114120
attcagtgaa acagtatttt caaaatgcat atttaatcta tctttgaaga ataagggtga 114180
aaagggtgaa aattgctgcc ttatacaaaa tatcaacatt aacaaaaagt aatgaaggta 114240
atataaaaat gttttcaaat aaacaaaact gagagagttt accaccaaca agcattcatt 114300
aaatggactt ttaaatgcag tttttaggaa gaaggaaaac aattcctaag gaaggtctga 114360
gatgcaaaaa ggaattatga acaaagaaat tgttaaaatt ataggtgaat taaaaaaact 114420
gcctgcataa atgataataa tgacaatgat gctattaata atgagttgat aaggataaag 114480
aaaaggacag aattaaaata ctagaaaaca agcatgctgg aaaggattca ggaattactt 114540
gaaggttaaa gttctagggt ccttctatcc ttctagaggg gagtcaatat attaattttt 114600
gaccgtcact tacacagtga aaaactttaa ggataaccat aaaaaaatag aaatagagag 114660

-continued tataacttct gaaacagtca agggaaaaat atggaataag aaaactgacc aaaaaacatc 114720
tcagtcaatc aaaaaaaaaa aaaaaaagaa agaaaaggtt cggaaggaga aaatcaaagc 114780
atagaaaaag cgggacaaat agaagtggaa aagaaaaagg tagaagaaac aggtccagaa 114840
atatcactga tgcactaaat caccattaaa agatgaaaac aaatgaacaa catcaaaaaa 114900
ttctagtgac tgtagtagtg ctgatcagaa taggctctaa gataagatgc attattgtga 114960
gtcaacttgt gatgatgaaa ggtttaattc accagaaaga cacaattata aacttgtaat 115020
caaatagttt tattttattt actttattta tttatttttt ttgagacagg atcttgttct 115080
gttgctcagg ctggagtgca gtggcttgat ctcagctcac tgcagcctcc acctcttgag 115140
gctcaagctt tcttcctgcc ttagcctcat gagtagctgg gtccacaggc acacaccacc 115200
aagccctgct aatttttgta ttttttgtag agatggggtt tcaccatgtt accaggctgg 115260
tctcaaactc ctgggctcaa gcgatctgcc cccctcggct tcccaaagtg ttgggattat 115320
aggcgtgagc cacggtgcct ggcctcaaat aactatttaa gtgaaacaaa actagtatgg 115380
cactaatgaa aaatgtataa atccataatc gcagagggat ttcaacttac ttctttcgat 115440
tatgtaaagg tcaaacagac aaaagacaat gacaaaactt aatgcaatga acacttttga 115500
tttaatgaac atatattgga tatgtaccca agaattagag aatacatact agttttgagt 115560
ttatgcagaa catttacaaa aatttagtgg aagcctaaat tataaaaagt tgctgtcacg 115620
tagaataaca cacaaacccc tgagtccgga attcaaagcc ctccacactc tcctctacct 115680
ttgcatcttt atcctccacc acactgcagt gcatactctg ggctactact cactgttctt 115740
gattcaaatt ccatgttctg tcagctcaaa tcattctctc tgcctggaat aactacttca 115800
tacatattct gctattgaat tcttgtctta gcaccccatc tactccaaga cgatgtccag 115860
ttggggttac tccctgtccc attttctttg attacacttt ttttttctac ttccattata 115920
ttattgatca catctgtgcc acagtttttg actttgtgtc tgcttttact cttttctaga 115980
ccctgagagc tcctgaaggg ttgggtcatt tcttttttat ttgctcattc ctcatggcac 116040
agtgagtgct taataaatgg ctattgactg aaattaaact gtatctaaat ggacatattc 116100
cacttctggg ccattcattc tttctttcta ttggaaccag gagatgggga accataacaa 116160
aggtaaggtt gtgccatgtg aaagaacatg gaaccttccc ctgagggcca aaaaagagca 116220
gggaaaggtg caaagacaaa atcttccatt tttaaacaat gtaagaatgt ggtccacctc 116280
atgctcaggt gggactttat catgacgtta tttttgggga cttatagctg catcatttac 116340
cccatataca tttaccttta gtgtagggaa ctgaggacag gaattttgtt gatgcagact 116400
cttgctaatg aggctaacac ttggagaatt tttatcatgc attcaagaag cttgttttac 116460
atttcttcat taatacttta gttggtggtt tagctttagt tgtaggctta tcagatattt 116520
ggagatatct tcataaacga tggctttggt tttagaagag ttattctgaa gctactattt 116580
ctggcaataa tcaaacagca tggccatttg ttttgtaagg cctttcctaa aatatgacgg 116640
taaaatctac gtgtggaaaa atgcttattc ttctgtcctc tataaatgtg aatctagttt 116700
gtcttcaaaa tgaaatcaag tgattaaaat gtagttttct aagaagataa atggagcaaa 116760
gcactctgtg tttcacagtg ttggaaatca ctcatccctc ataaaactgt cccaactgat 116820
cctgactcac atgaatgaat taaaataaga gttaataaca tcaatttaca tttttaaaga 116880
cactttccca tgttttagac tattggttgg aaaagctggt aggtgtacaa tttgtggaga 116940
gttggctgtt tttgtctgtc gttgtttgac gtatttcaaa gccatatcta attttgttgc 117000
agaatggtct gaattctaca aaaatgttga gttgtgtagt gtggagaagt acggagccat 117060

-continued ttactgaaag gctgggggga aatgacgaga ccctgagata aggcagtagt ggtgcgaaca 117120
gagtggaagg gaggtagttg agatatgttc agagtagaat cagaatggac atagtgaaca 117180
actggatgca ggtgggggct gaggaagcaa agttgaggat aattctgaga cttctaggtt 117240
gatccactga agttacatta ttcaacacca caaggaaact aggggaatga gaaggcatac 117300
tggtttgctt tggagtggaa gggcagtgat gtaagaggag ttaatgagtt aaagtttgga 117360
tatgcctgaa cttcaatttg atatgtgcat ctgatatacc cttggggtga ccctccaggc 117420
aatggttgaa catgtgtatt tcttagtaac tgataggcat cacagactca catcagtaag 117480
gaagcaacag caaacttgat tggacgatat acctggaact cagtacccta tgactggagc 117540
aagtctctgt cagtgaaatg aggataagaa gaatcttgac cttgtggaat atgttgttag 117600
gaatatatgt gatgaacaac ataggatact tcctacaggg ctccacatgt agtaagggct 117660
ttataaatgc ttgataaata ttattgttgt aatttatttc caaagtaaga tgccactgga 117720
ggaatctttg gaacccaaat taataacaaa taggactgga tgcaatggct cacacctgta 117780
atcccagcac tttggaaggc caaggcagga ggatctcttg agcccagaaa ttcaagacca 117840
gcctgggtga cacagggaga ccttgtatct atgaagaatt aaaaaaaatt aaccagatgt 117900
ggtggtgcac gcctatagtc cctgctgctt gagaggctga ggtgggagga ttgcttgagc 117960
ccatgaggtt gaggctgcag tgagccataa ttgtgccacc acactccaga ctgggtgaca 118020
gagtgagacc ctatctcaaa taaataaata aataaataaa taaataagta caaaccagca 118080
aacactaatc ctttctagag attattgaac tctggagggc agatctgaat ggagccagca 118140
gagggaccta tggagatcag cctggccctg gacagcacca ggcaatgggg ttgctagaga 118200
ggtaatgggg ttgaacaggg tttaagccat gaggtctcaa gaatccgtga agactcagac 118260
taattttttt ttttttgcat gaggattagg tgttcctagg aatttcaatg agagcagggt 118320
taatgaagga atgcagggta ggagagctga gggaaggcat ctgagagagc ctggcttatg 118380
aatggctgcg tcagtatggc tcacctgctt tccttgtatc tacttagcag atgatcccac 118440
cccaggcctc cagggccaag gtcatttcca catagtcatg ggcccttgag ggcctggagc 118500
agtgtaagga agacagagtc ttaagaaatt gcattaacag tcatggtgct tggcaagtgt 118560
cgtcatccta tgccaagcct gatctgaagg ggtgcatgct cataggtagc tgctgcccaa 118620
gattacagca gcttcttcaa tcccagatcc atgctctcct atattcattt ttccaggggt 118680
tcctgtcctt cgacagtgat gagatgcaga atgacttatt gagttattct cctgatagtt 118740
gccaactttt ccaaatgaca atggggcatg gagcttgaga gtggaaatga ggccctaggg 118800
atagcgtgct taggaaaaca ctcccagcct gatgtaattc tgggggtaca atggcatttt 118860
catcatcaag actgatgtaa agggtgacta gcagtgagtt gggggtgact cgcactgggg 118920
ctaggtttct gattctgcct aatccagaca gagcagaagc actagtgggc tggtagaggg 118980
cctccagggc ctcacttaat gtcctggaaa aacagctcca gattgttggt tcacgttctg 119040
aggacaagct tgggtactac aggatagaga gagtggtggg agatgccgtg gcctgccctg 119100
ctgatgcctg ccctgccatt cctgcgtgtg atgtctctgg ggcatcttgc cttccctgcc 119160
cagacctgta gttcagctga gggcatgtgg aggccaaatg gcttcttaga gtgttacttt 119220
ccttgaacag ctctgctggg agaactggag gagctagcta gtcacggtaa ctgcagcagt 119280
caaaggatcg tcccggtgga ggtggggtgg aaaggtagag aaagagaaca tatagcgttt 119340
tccttggaga tgtgtgggca tgtcatagag gaaataccca attcctgagc cttgagccct 119400

-continued ccaggaaacc ttggaatatt aggttagtca tccccaagga agtctaagaa ttctggtctc 119460
acccatctcc tttaattccc acaatgatcc tacatgatat taaggaacac gggccagtaa 119520
ccctccaagc aatggatgtg gtggtgaagt ttgacctcat gatggagcgg aggttggttt 119580
gaaacctaag aatttaattt attgtttcaa actgttctcc actcagcgtt attaaagcat 119640
acataattga cacataaaaa ttgtatatgt ctacggtgta caatgtgatg tttcgatcta 119700
tgtatacatt gtgaaatgat tacaacaagc taaataacat acccattcat cgtgtttcaa 119760
aggaattaaa ctcaagcaca aaagagaggt gctgttgaag agtagggctg ctctatctaa 119820
gtagtatgtc tggggttgtc ctggatcagg gtccttttgt gctagtaata aaccagccct 119880
tctggggctg ctccactttc cccacatttt cttctggagc ctccctaaga attaggacat 119940
ggccactttc tctgcatagg cttcctactt caacaaggac agggcttgtg ctgccccatg 120000
ccacttgagt gtccctacag cacagagctg agtgcacact ggctgagtga ggaaatcccc 120060
cagattaatc ttggttctaa gcatcatggc tgtatttcac acgtatatga attacaaatt 120120
acagcatagt cgaataagga tttttgtgct acaactggaa tcccagatta tgcaaattgg 120180
atagtataat attgaaattc ctaggacttt ttattagttt taaaaaatta tacaagctta 120240
gagtaagaaa ttaaacagtg caaaagaatt cactgtgaaa agtaaaatgc tctgtctctg 120300
ctgagagaca gatattgcag cccagatact actggggtca atagtttcct ttaagcatgc 120360
cattttgatg gtttatggga cttacagctc aagaagcttg acactagggt tgatctcaga 120420
aaatcattgt tgcaggtatt agatatgacc gtctcataaa gatacacaca cagacacagc 120480
gattggagat attcactggg gcttatgggc tgcttgtcct ttctgctctg tgcctaagtt 120540
gggctcagag tagcctggca tcggctgtgg ggagaatgct ggcatggggt tagcaggagc 120600
ccacttaaca tgtcctaagc cacctggaag agtccttcaa ggagaccaga ctccagaggc 120660
cctaaggaag gaaggacttt tgcccgtttt taggtattct agtcccagag tttagggagg 120720
aatggtttgg ctttgggtcg tgtgcccctt taccgagtgg gatgggatgt gcccatgagc 120780
tgttgagctg gctcttggag aagacagcaa aagcgggaat aagaggtcag gaagctgtgt 120840
ggttgtagga aatcccagca gagggcctgg gggtcaaaag tggtcatggt agtgacggtg 120900
gaggctgagg tggtagaaaa tcagaggaca aaccccatgg gctgctggtg atctgaccga 120960
gctcctatgc tctcctggtt cattttaggc tctgtagcag cagatgattg gctggtgtga 121020
gagcagtgca cctgccatat caggcaatcc aagacaagtc caagctacgc tgggaggaaa 121080
cctgaaggca gcagcaggta gactggctga agacagacag gcaggcaact tgtcaatcag 121140
atttgtgttt ttaaggactt ttaactgggg agccctccat gacagatcag atgagagagg 121200
aatctgggtc cgcccatgtg tcaagctacc agagggtccc atcggtgctt ggatcttctt 121260
tgaagctggg tctgaggttt gcaggtagag ggtgagctgg tcagagggac ctattgcaga 121320
gctaaccaac accttcccag gaatgcaagc acaagcaccc caccgcgggc aggcgggcag 121380
gcacttctcc ttttgccacc aggacctcac agaggctgat ctggctctgt gaggtgggaa 121440
aatgggttgt acttagtaca tagagataaa aggcttagga ggcccctcca tcctgtgacc 121500
ctgtccccag accacaggtg ccggcaggtg ctgctatttc aaggctgggc ctcagtgcaa 121560
gcttgtggtt tcttgcccac ctgtgatgtc ctcccactaa tgaaggggct ctccatcctc 121620
tgtctgcctc tagcaagtgg aggctctggg ccctgggcaa gacacagggg gaaatgccat 121680
ctgttatcca aatatatttc aatgtgacag gaaagctgtc tttagagcac agcgcatgtg 121740
ctctacattg atcccaggag tttgagacaa cattgcaaga ctgggcaaca agcaagactc 121800

-continued tgtctctaca aaaaataaaa aaaattagtt gggcatggtg gtacatgcct gtggtcccag 121860
ctactcctaa gttgaagagg gagaattgct tgaggccagg agttcaaggc tgcagtgagc 121920
tatgatcaca ccactgcact ctancctggg tgacagagca agaccctgtc tctaaaataa 121980
taatcgtaat acattttttt taaagtaaaa caaaaaaagg tcacactttc tcataccaaa 122040
ataaattcca aataaattaa aggcttaaac atgagaaagt taaaccataa aattactaga 122100
agaaaataaa agcaaatatt tagataatcc tggggataaa tttctttgga atgaatttcc 122160
ttaagatgaa tctctaaaag tgaaattcag ggttcaaagg tcttttcttt gtccttttct 122220
tttccctttc cctctccctt tttctttctt tctctttctt tctttctttc tttctttctt 122280
tctttctttc tttatctttc ttccttcctt ccttccttcc ttccttcctt tcctgcttgc 122340
ttgctttctt tctttccttc cttccttctt tctctccctt tctttctctt tctttctctt 122400
tctttctttc tttctttctt tctttctttc tttctttctt tctttctact ttctttcttc 122460
tctttccttc cttccatctt tctttctttc tttctttctt ttctttctct ctttctctct 122520
ctctctctct ctttcttttt ttttctggtg agacagggtc tcattctgtc actcagactg 122580
gagaacagtc gcatgaacat ggctcacagc agccttgacc tcctgggttc aagcaattct 122640
cctgcctcag tctctcaagt agctgagacc acaggcaccc accaccaaac ctggctaatt 122700
tttgtatttt tagtagagat ggggtttcac cacattggcc aggctggtct tgaactcctg 122760
acctcaggtg atctgcctgc cttggccttc tgaagtgctg ggattacagg ctgggcctct 122820
acgcccggcc gagactacct ctcttttaac tggatctctg agctctgggc agagcccacc 122880
ctgaatcctg gtctccaaaa agggaaaatt attaggaggc tagaccatat gatgctttta 122940
cagtgcactt aaaaaaaagt ttgttttttt tttaaaagac atttctacat gtctaaacta 123000
caatcttcct tgaaaaccca agagtagctt ctgttgcaat agctagtcaa aaatataata 123060
gtcaaaaaaa tcaggtaaca caacacaaac gcaagcagtt taagagctga aatgaacttg 123120
tctgtttaca ctctagggat tccataagga aaaatagaag tttctcccta aaagggagcc 123180
tggcaccttc tccattttct ttaaggaacc ccaggctatt ataaactatt ttagggctct 123240
catgcagcag acggtgcaag agaaaggaga gacagcagaa gtaaatgaag aaaacagaat 123300
ccagtcaaca gagaagaaaa aaacttttgc tcaaaaaaag gcaagttcct aggaaagaaa 123360
aaaaaaacat gagggctatt taaatacaaa gacgcataca tacacatgca cacatcttgg 123420
atgttagctt ttaattaagc tgacttttaa ctattgaggt cctttaaaat aaatctttta 123480
aaatcttatt acgatatttc agctaggaca aattgctgct atttcagcat taccaagtat 123540
caaaccagaa aaggcttgat ttaggaacca aacccaggct gtcgtggtag gaaaaaaggc 123600
agaacgttag ctatggaacc cacagcatgg ggcaacagcc attgctcttt cagtatggcc 123660
tggctagcaa aaaggtggcc ttgttatgta aataaagccc gtttggtggt caaaatgaaa 123720
catcttttcc tttttttttt tcttttgctg gccgtttttt cccccaccat accacgtttg 123780
tgtgtgtggg agggtgggaa tttagccact tcagaggcct cattccccat aatttggaaa 123840
tttcctttgg atttgatcaa gtcagataga gtaggtcaaa cccaatggga aaaagactga 123900
aacagcaata aaaacagaaa caaacagtta agcaaaatga atgatcacac aacttatatg 123960
attactgagt gctctaatgg taaggagaaa ttaagaccag ctggttgtta aactttagcc 124020
aagacaaaac cccaattcag ctacttacct agggttgggt ctcaggctga agaccgctca 124080
ctaccgttct agaagcaaga aataaaactt gaactcgtct tacctgtgta gcaggacaag 124140

-continued

```
ccgcagacaa aatccctcag acaccaaatt aaagaaggaa gggctttatt gggcctggag 124200
ctgcggcaag actcacgtct ccaacaaccg agctccccga gtgtgcaatt cctgtccctt 124260
ttaagggctc acaactctaa ggcggtccac atgagagagt cgtgatagat tgagcaagca 124320
gggggtatgt gactgggggc tgcatgcacc tgtagttaga atggaacaga acatgacagg 124380
gatcttcaca gtgcttttct tatgcaaata accgattaga tcaggggtcg atctttacca 124440
ggcccagggt gtgtcaccgg gctgtctgct tgtggatttc atttctgcct tttagttatt 124500
acttctttct ttggaggcag aaattgggca taagacaata tgaggggtgg tctcctctct 124560
tacctgcggg gagtgagctc aaactcctta aaggagttac ctgccttcca tcatcaggga 124620
agcaggaaat cttgccttcc ttgttggaag caagtaaaac tcaaaacaaa caaagaaaaa 124680
aacagggagt tgtacagcaa aataaacttt tgattttgac caaattttgg gagatcagga 124740
attctctgaa ggagatgctt tcagacctca gcaaattgtc ctgttggttt gagccataaa 124800
gttagctcat gctggtacca aacaccagta ggagatttgt caaaggtaag aggcatctcc 124860
actcagaatc ccttcgtggt taccaacatg tgaaccttgg aaatctgaga caggtctcag 124920
ttaatttaga aagtttattt tgccacggtt gaggacaccc acccatgaca gagcatcagg 124980
aggtcctgac cacatgtgct cagggtggtc tgagcacagc ttggttttac acattttagg 125040
gagacatgag acatcagtga atatatgtaa gatgtacact ggttccctcc agaaaggcag 125100
aacaacttga agcagggagg gagcttccag gtcacaggta ggtgagagac aaacaattgc 125160
attcttctga gtgtctgatt agcctttcca aaggaggcaa tcagatatgc atttatcaca 125220
gtgagcagag gggtgacttt gaatagaatg ggaggcaggt ttgccctaag cagttcccag 125280
cttgactttt ccctttagct tagtgatttg gaggccccaa gatttatttt ccttctacat 125340
cactgtgggc agctgactag gaaagctttg taggactggt gggcagtgtg agagcccagt 125400
ggggggtggt ggtcctgtgc caatggtagc aaccacctgt gaggctgagt aaactcattt 125460
cccaacctcc tctagcagcc ccagtggaga tacagatgaa gcagactagc gatacaaccc 125520
agcctgaagt tttgtctggt gagtgtaatg gaataaaaat gggaagggtg ctgaagagac 125580
cagcaagaaa atggttgaag agatggggca cagaaattaa gctggatcaa aaaggacgga 125640
aaagcagaaa gggccgatag agagagggga tatctatggg ttcgcgattc tgaaaaggac 125700
aaatcactgg tgctttgaga agagagaggg tgagaaagca ggaaggctgg aggctgtcat 125760
ccaagaggcg gacatctgtg aacatgattc caagagtcac cagaccatgg gggtggccaa 125820
agggagtgcc tcttctcacc tcctactctt aattccttgt actcaagata ataagttccc 125880
agaagagaag tacccatatt taattcatct gtgtcttcct agcagtacta aaaatattat 125940
atgaaaggta tcaaaccttt gagaatgtgt gctgctaaat tgttaaggat gctggaaaac 126000
tcaagacgtc cctgatcctg agcctgagta tgagcctgtg gtgagcccaa tgcaggtctc 126060
cattcagaca aaggcctcag ggaacggatg agacctaggg acagagatgc atgctggagc 126120
agcattcccc atccctactg cagctcaggc cagctgactg ctttatgagt aaacgttacc 126180
agggaacact ttgcagtctt aacacacatg cccacctgtg accactgatc cctgttgggt 126240
gaccactgac atcagagatt cgatggcagc aatgaagaca aggctatcct cattaggaag 126300
gaaaggaagg aggagggagg agggcaaacg aatctttcct gcttgtcaac cacgtccatc 126360
tctgttaggt gatttcccat gtgtgacttt gtttatcttt ataataactc tgagaggtag 126420
gtcttgatgt ccacattttg aacatgagga catccagcca ggaagttgag ttctggggac 126480
atagctgaga gggcaaagct acatataaac ccctctttgt tttttctggc ttatccactg 126540
```

-continued agtgcccccct gcaatccacc agcccatttg tgaagtgcat actataggta agttggcaca 126600
ggaggagtgg atgtgggcga ttttgtcaca gctctccagg aacttacaca ctggtgagga 126660
gggccaggta tgttcctgac cagtcacaat caaagcaacc tcctactaat cagggaggct 126720
tggtacctgg ggaatgctat gttgaaaggt tcttttctgg gttttaaaat gatgggtcta 126780
tttccttatt cttaagattg cttttttttct ggctagaact taaaagaaat tttcagtaaa 126840
atttcccttc cctggcacaa agtgagcttg aaatgaattc ccaggtggcc ttgatacttt 126900
aaaatattgc ctcctataaa atcaaccttt agaagaagga agtcaaagaa catgctagat 126960
ttcacaaagg ttaattcctt gaaatccagt tatctacagg acaatgttgt caaagaaaaa 127020
attatttggc caggcacggc ggctcatgcc tataatccca gcactttggg aggctgaggc 127080
aggtggatca cctgaggtca ggagttcgag accagcctgg ccaacatggt gaaaccccat 127140
ctctactaaa aatacaaaaa aaattagcca ggtgtggtgg tgggcacctg taatcccagc 127200
tacacgggag gctgaggcag gagaatcgct tgaacccggg aggaggaagt tgcagtgagc 127260
caagttcaag ccactgcacc ccagcctggg caacagagca agactttgtc tccaaaaaaa 127320
aaaaaaattc aatgatattt ttaaattcat ggtaaggaag atttcattca gaaccagcac 127380
agaagatata ggaaacactg caatgggact ttgcggtggg ggagagagat tgaacacaac 127440
tacatataca gcacgggcaa ggacatattc atagccagga agcagagcaa agatcagtgg 127500
atgcgaaatt actaagagga aacatgaaaa ataagggagc ttctgcctaa acccacctaa 127560
ccggatcctt gctgaagaca ggacagggtg attggacacc actttgggga tggtggagga 127620
tggggaatcc agtgagattt caagggtgat cagatattga acatagaagg ttcttgctaa 127680
aaaaggagtt tacaagaaag tgtacaaatg tgcctgggag aaggttcagg agcctgacta 127740
aaatttggtc aagcagagaa tatttgccaa gataatagct aagtcttctg acaaacaata 127800
gatgctaagc cagcaagggt gatgtgctca gagaaagcac tgagggctta tttccttttc 127860
ccccaatctc cactcagtca agtctagtcc ccttgtcaat gtagccattt gtaagaatgc 127920
aatcaggcag ggtcccatct cctagtgaca ggactgactg aagttctgct gaagagagtg 127980
gcctggggct gacaccgaga tttcagagtc ctgggtttcg ccgagagctc agtgtagtgc 128040
catgccctct ctccacctga acgcccagtg tgggcaggaa caactgcagc tagaagtctg 128100
gcacttacgc tggggtctaa gacctgcctg atctgctaac tagtcttgtc ccttggctat 128160
aaactgacgt tggcacctgg ccagaaagat gagcaagaga tctctgacac acctttaagt 128220
ccctgtggag taggattatg ttggggaagg tcattctctt gactgagcag caatttcaga 128280
aggaagtccc atgccgaagt gagagaaggc agggaatcct gcctagtcag ctagagcaaa 128340
acagtctgca ggacgggacc cagggatgtg atcctcccat ccaaaggcac tgaactaaat 128400
gactaaaata ctttccaggg ctcacgttct ttgaagaatg gggactaaaa ctaagacagg 128460
agccagcaag tgaggacttg gaaggagatg gctcatctga tcagcctcca ctcaacaatt 128520
ttaatcatcc acactggcat ggggacacaa tatgaataag ttgacaggga cctactctga 128580
ttaagcagtg ggctagtgca gagacctgtc agtcaagagt ggacaggaga tgatttcaga 128640
cagtgagaac aaaattaaca gagtcatgtg ctaaagggtg gctggaacta cagaggagtt 128700
taagactcaa gaggtctggc tgggcgcggt ggctcatgcc tgtaatccca gcactttggg 128760
aggccgaggc gggcggatca caaggtgagg agatcaagac catcctggct aacgcagtga 128820
aaccccatct ctactaaaaa tacaaaatat tagccaggcg tggtggcggg cacctgtagt 128880

-continued

```
cccagctact cgggaggctg aggcaagaga atggcgtgaa cccgggaggc agagcttgca 128940
gtgagccaag attgcgccac tgccctccag cctgggcgac agagcgagac tccgtctcaa 129000
aaaaaaaaaa aagacttgag ggagttgttt atttttgttt tctttttaag acagggtctt 129060
tgttgggcgc ggtagctcac gcctgtagtc ccagcacttt ggaaggctga ggtggaaaga 129120
tctcttgagc ccaggagttt gaggccactc tgggcaacat agcaagacac cgtctctaca 129180
aaaaatgtgc aggttgaggc tgcagtgagc agaaaaacac cgctgcactc tagcctggat 129240
gacagagcga gaccctgtct cggaaaaaaa aagaaaaaag acagggtctc gctgtgtcac 129300
acaggctgga atgcaatggt gcaatcatgg ttcactacag cctggaactc ctgagctcaa 129360
gcaattctcc taccttggcc taccaaagtt ctaggactac aggtgtgagc caccacacgt 129420
ggcctcagga gagatcttaa taataaaagg acaaattgcc ttgcatccct taggggcagg 129480
attgacacat ccaaggatca ggcagaaagc ctgtgcggag tgggatgagc aaagagaaag 129540
gctgagagtt gtgaagaggg agatgcagtg ccagctagga caggcctttt tgggctatgg 129600
gaggttttca gaggagaccc cacctaaact aacccataac attgcagtgg ggacctgttg 129660
aagtcatgga ctactacctg aaagccagag aaatgggagg agcctttcct ctgaggaggg 129720
actctagtcc ataggtatct tgccaccaaa tacatggaca ggccctgggg gaagatggtg 129780
gtagcccagc tggaggaaaa ccatttgcca cctgaactag cccagggtaa gccacccagg 129840
cactgagggt gcacacccat gcatgcacac acagaatcac actccttcct attattcctc 129900
aattcagggg tctcaacacc cattttttttt gtttttgggg ttttttttac atgtttacat 129960
tttatttatt tattattttg tgacagggtc ccactctgtt gcccaggctg gagcacagtg 130020
cagtcgtgca atcatattag attggtgcaa aagtaatcac ggtttttgtc attaaaagtt 130080
ttgccattac ttttaatgat aaaaaaccacg attacttttg acgcaactta aaagctcact 130140
gcagcctcaa aattcctggt ctcagggaat cctcctgcct cagcttcctg aatagctggg 130200
actacaggca catgcaatcc tacctggcta attttttaaa aattttttttt gtaaagatag 130260
aaactcattt tgttgtccag gctggtttca aactcttgtc tttgtgcctc cctctgccct 130320
gtgcaagacc ttctggatgc ccactaatga agacttccag ggagaggaaa agtaaacata 130380
ggtccctgat caagggacca gggtttatcg accacaaaca gcatgcccag attccactgg 130440
cagtcctaga ggtcgcattt gccccaagtg tgtgtggaag gcctctccct agcagttggt 130500
ttatacacca gccacagcac agcatattct cttaaattgt gaacatttgc aaaaactcct 130560
tgaggacaac tatcatgtct tgtgtacttt tgttttgttt cccttcccct atgtacacgc 130620
gcgcgcatgc actcatgcac gcacgcgcgc gcgcacacac acacacacac ccctcaaact 130680
gaatgcctgg tgtgctgaat ggatgaatgg ctaatgtaag tcattctaaa agctactttc 130740
tttggcatac catcaccttt gatttcatct ttctggaact cctatgttcc cagatgaatt 130800
tggaaagccc tcaggaaaca tttcaaaatt gctatatggg agaaatggga gggtctctct 130860
agaaatttac ctgccacagg tatttctggt aagacacagc aaaggtggca ccacccattc 130920
ctcgttacaa tgtcaatgcc agtcaccttc ctgtcccata aaactttatt aaaggtgcag 130980
aattcccatg gaagcaggtg gacaccatct gcttccagcc agccagggga gcaaggtgtc 131040
cactgtgcct ttgtggcagg aactgcgctt ctctactctc ccactttgag gcctctgggg 131100
ctggcctgct gcctcctcat tgacaaggct gcttactgag cagttcattc tgagctggac 131160
atagtgcttc tggtgagtct ctacttctat ttaacccaaa gatattcttt cctaaggaaa 131220
cgctttcctg tcgggggagg ttagctccag atggaagtca caagtgatgg catggtagct 131280
```

-continued ctcatccgtt tgggtggatg atattcacgg agcaccacca tgagccagtc atggaggtga 131340
acagtatatg ccagccctga atcaggtgca ttgacagcaa gggagacaag caaacaaagc 131400
tgaggtttgc tgaggatgtt caagactcac acagcacaga ggagcatcca ccacccagct 131460
tgggaaagga cttgttatag agggggtgaa gcatgagctg agtcttgaaa gactagaaat 131520
tagccaaact acaaggagga gaaggagttt ccagtcagga agaacaggtt atgcaaaagc 131580
acagagacta gaaagaatat cacattcaag gaactgcaaa tagacaggaa agattgatgc 131640
gtgggatagg agaggagggc aggggattcc aggtgggccc tgcttgccac actcaggagc 131700
ttgaacttat ccacaaagga ggtgtggaac cagtaatgaa tgggttttgt gcaagggctt 131760
catgtcacca gatttgcttt ttggagatac ttctgtggct gatatgtgag gaagggatgg 131820
aggaagtttc cgtggcaatc aggaaaacca attagcagat gattcaaatg gcctagggga 131880
aaagggagga ggacttggac taccatgcag cagcagaaat ggagagaaat aacagatccc 131940
aggcactcag gaagcgctca gaatgagccc ttcaaagaac ttatggtagg tgatggatgg 132000
atggagtgtg agtcctggga tagcattgcc tgggaaaata ctttctagtt gagacaggga 132060
agtgggccag cagaaatgga gggcttcttc tttttgcttt aaatactttt ataatatttg 132120
gaactttgaa aatgagcaga tatattagca aaaagcctaa aagggatatt tttgaaatca 132180
ctgctagttc taacatataa ctttcagctt gcacacatca tcaattaact ttgatagcgc 132240
ctttctgaaa ctatcatccc aaatagcaat ccttgtaaaa acctattttg aaaaacgggc 132300
cttgtaggat agcctcacag atgttttgtg gtagattttc taacattcta atgtcaggga 132360
gtgaaaggaa tcccgttaga agttggaaaa ttctggaatc tctattcatg gtattaaagt 132420
tttgccgtca cacaaaagtt taacaccttt acacaatcag acttcctcat tttacattgc 132480
tcggtaatta gaggaaatca gtcacccaga gcctgggtcc tagacttgac aaaatgcacc 132540
caacaaatcc tgagtggcct tgctgaggac ttctcccaga agatagaaaa ctcagttcca 132600
gccaacaagg gggaagcagc tgaagaagtg aaattaacaa agtcctggaa ggaaatgacc 132660
aaatcatctt tgattgtgta ataaccagag agtagaatac agctacgaca gacattttgg 132720
gagagaagca ttttatcata gcttttagaa gagaatattt ttcagcatca taagcacaca 132780
attccaagac agatactttc aagggattgt tttgacgatg ttnnggtttt gggaccccat 132840
tcaaacttca tgttgaattt taatcttcaa tgttgagcga ggtcctgtgg gagggtgatt 132900
ggatcatggg ggtgggttct cccttgctgt tctcaatgat agtgagtgag ttctcacaag 132960
acctggttat ttgaaagtgt gtagcacctc tccccttcat tctctcactc gtcactgctc 133020
cgccatagta agatgtgtgt gtttcccctt tgccttccgc catgattgta agtttcctga 133080
agcctcccag ctatgcttcc tgtacagcct gtagaactgt gaatcagtta gacctctttt 133140
cttcataaat tacccagtct caggtcattc tttatagcag tgtgagagtg gatgaatata 133200
gtgccatatg tttgtattcc cagctaccca ggaggctgag gtaagaggat tgcttgagcc 133260
tgggagttta aggctgcagt gagccatgac tgtaccactg ctctccagcc tgggtgacag 133320
cgagaccttg tttccaaaaa aaaaaaaccc aaactgtgta aaatgtgttc ataaaagtgt 133380
cttgctccca cacctgtccc tatatatctt attcctcagc ctccgacaac tactttattc 133440
atttcttatg tatcttccag aatcaaaaaa aaaaaaatcaa atacaagcac agtggaatgt 133500
attgcccttc ttcccctccc ttttgttaca tcagagttag catatcataa atacggtctg 133560
cattttcttc tttttcagct atcagcatgt tttggagagg atttcatatt cgtgcagaca 133620

-continued

```
gcatgtatta gtcagtcctt gcattgctat aaggaaatac ctgagactgc ataatttata 133680
aagaaaagag gtttaattgg ctcacagctt cgcaggctgt tccacaggaa gcatggcagc 133740
atctgcttct ggggaggcct taggaagctt ttactcatgc agaagacaaa gcgggagtgg 133800
atgtcttata tggcaggagc aggactgaga gagagagaga gagagagaaa ggatgccaca 133860
tacttttaaa caaccagatc ttgtgggaac tctgtcacga gaacagcacc aaagggatag 133920
tgctaaacca ttcataagaa ctccaccccc atgatccaat caccccacac caggccccac 133980
ctccaacatc ggggattaca atttgacatg agatttgggc tgggacacag aaccaaacaa 134040
taccagagtg ctttctcatt cttttctata gctgcctagt attctatgtc ctttacttca 134100
tttaggcagt ctcttgttga tagacacttg ggttacttcc aatttttcct attacaaatg 134160
atgtgcaatg aataatttg atcattttcc atttcacatg ggttatgtcc atctgtggga 134220
taaatctcca ggagtgaaat tgctggatca aaggggaagt gcacttgtga ttttcatagt 134280
tagcaaattt tgttctataa gggtcatatc aatttatagt cccacgcgta atatttaaca 134340
gtggggattt cccgacagtt tgaccaacaa ggtctgttgt taaacttttg atttttgtca 134400
atctgatggg aaaatactag tatctcaaag tgcttttaat ttgactttct tattacaatg 134460
ttaagcatca ttttactctg cccaagatca aatagtattt tcttttctgt gaacagactg 134520
ttaagatccc ttgcctcttg ttttgctgga tttttgttct ttttttcaa atgttttgag 134580
gcagttcttt acatgtgaaa caagttatct ctttatctgg ggtgtgagtt acaactactt 134640
ttcctctggc ttgttttgcg ctttgacttt gcttctggtg attcccgcaa ttctgaaagt 134700
gtacttttg catcattcat tcttatacac ccatgctctt gttcacgctg gttcctctac 134760
ctgagggctt tttcttttct tttctatctg ggaacatttt ttagagacag ggtctcactc 134820
tgtcatccac gctggagtgc aatggtgcga tcacagctca ctgcagtctt gaacttctgg 134880
gctcaagcaa tcctccagtg tcagcttccc aagtagctag gactacaggt gcatgccagc 134940
atgcctggct gattgtttta tttatttatt tattttttgt agagatggga gtctcactat 135000
gttgcccagg ctggtcttga actcctgggc tcaagcgatc tttctgcccc tgccacccaa 135060
agtgctggga ttacaggcgt aagccaccat gcccagccca tgtgtggaaa tcttctgttt 135120
atccctttag gcttgattct tatgtcgttc tcctccctcc ttcctggcta ctcctcttgt 135180
tctttatctt actctacttg tcatgttacc ttgtttctgc ttataactag ctgcctctcc 135240
tatctgagga gggacttgtg actgttctca tctctgtact cccaggtcct agtacatagc 135300
gcttgctcaa cagatgtttg gtgcattgat agataaatca atggtagctg ttaataccag 135360
tcctgactcc ctgcagtgct tcagctgatc ctgttccaga tgtgcactga atatctttct 135420
gttgaacaac agaaataaag gggatgggtg aggaggatag tcttcggtgg ccaaggatat 135480
ttgtaggtac tttgcagcac tcagcaatga ggagtgggct ttagtccccc aagaactctc 135540
acagccctgt ttgtctttac tgttcagtgt caaatccaag acaagtcaat gatcaggaaa 135600
gaccttttt tttcttcagt gaagtttatt tcagaaccat tgaacagtat gatatttgct 135660
catttataaa tattcccatt taaataatct gagcttatat attttcagtc ttaattaaag 135720
gacttgattt aaagagagca caccagtcca aattgaattg attccatagc tattaaaaac 135780
taggctcttt tacagacact gctacttctt gcccccttg aataaattag accaatgaat 135840
aaaacaaaca aacaaataaa taaataaata gggaagcggt tgctcatcag aatgtgggag 135900
cgaatgacag agggtttctt agaaccaaat gtggccgtgg tttctgtcag gcgggcttta 135960
agtgagtagg agaggtgaga gaggcctggc tcaacaaaag ggctggggat tggccctgaa 136020
```

-continued aggagagagc tgactgtcct ggctgatgga caggagatcc tcttagcact accctaaggc 136080
aggcagttgg gcattggtgt agacaacagg aaagtccagg ctatagccgt actcaaaaac 136140
ctttctgttc cctttctgcc agccctaggg attgagtcca cattcagcac aggactctct 136200
gggtacagct ctctttagga agacacaaat tgcatggtga agtcagttat atcctggccg 136260
cctttggtcc ctcccaggaa gacgggcatg ttttctgctt gagaggtgct gatgtaccag 136320
ttggggaact gggcagactc aaattccagc ttgttattga tttctatctt gttgaagaca 136380
aatcgctttt ccatcttctt ctttgggtaa tttttgggat ctacactctg cagcgaaaga 136440
gaaagaagaa tttttgtggg gcaagggaca aaaatgctat gggaaagatg ttctttgggt 136500
tggccagaaa ggaaactgac gagcaggtca catgatcagg agccacactc ctgagttgta 136560
actgggcccc caactttctg tgtgattatt aaaagagccc ttcttctttt ctaaaactta 136620
gtgccaaatg ctgaggagca taatgtaggt gagaattttt tttttttggg ggggtgaaaa 136680
ttaagctaga gcttcttgaa gtacctagtt tccaggggct ttttattgta tttttcctta 136740
tggtcctaga atgacatcaa cttggaaatg aagcttttgc tgagaaagct ggaggtgata 136800
gtggtggtga ttttgggagt ggagtggacg tgataatggg accctttaag tcatctattt 136860
cccaaggtgt ctatcaaatg agagcagccc taacaatata taatctgttg gggttgtaac 136920
tatggtagga cataataaca tcggcaaaat gatttaattt tctgcagcag gattgaaggt 136980
tgcacgcagt taaaaattat gttaaattta tttacattaa tgcaaaattg tcaaatagac 137040
ctgttcccag cttttcctag ggatgggggc ggggagaagg tggttgtctg ggaataagtg 137100
gtagcaggag gctgagaagg gcttcattcc atagcattca cttacctcca gctgtagagt 137160
gggcttatca tctttcaaca cgcaggacag gtacagattc ttttccttga ggcccaaggc 137220
cacaggtatt ttgtcattac tttcttctcc ttgtacaaag gacatggaga acaccactga 137280
agaaagaagg gggtcttgtg gttagggaca cagcagtgca gggtcacccc aacccctagg 137340
ccccatgagt aggatacatg taatttggta gcctctgtgg gaacccacag tgaggttcct 137400
tggcctaaga cacaggataa cttgacttct cacagacaat agcagggtca ttttgttgat 137460
ttagggtttc ccctcaaagg cctgagggtt tctcagagcc tcatagcagt aggaacggag 137520
aatgaaagag ggtctacatt ttaaatgctg aaggaaggaa ggaaggaagc cattgtgtca 137580
ctggctggca atgtgcccat ccacaggagc ggaacaactt gatcaatgtg gaaggaaagg 137640
aaagaggtga ggctgtactt ctgccagaaa tcaggcacca gaactgtttc aggaacagag 137700
agtagcccat gggaagaaac tgggagagga gaggctgagc tgggaaagtg gctccaaaga 137760
gagacactca ttttgatctt cctcagtcac agcagtgtca attggaaggc cctgggatca 137820
ctcttactac ccgattccaa agaaacagga ttttcttggc ctggctgaga gcaaatagct 137880
tccccttga gtgaggctgt ccttcaaagt cagcagcctt agttgcccac actcctgtgc 137940
agaggctttg gctactgtgg cacgatgcca ggcagatcac cacagctaat gatgggttca 138000
ccgcacttga aacttttgcc cgttacagcg gagagatata agttcctgct gggcggtaaa 138060
atttccctac aaggaaccac ctggcattgg gtgggacgga tgttggggca agggggggaag 138120
actggggagg gggatggaca cattatcgct ccagcactct tgtttcagcc tcaacaacag 138180
gaagagagaa cccacaggca gttaggccat gtccatcaaa tgaccccata ttgtggaaga 138240
attgacattg cactatgccc aagagacttg ggtggacatg gtcctgggag tgcttgagcc 138300
gtctaatttc tcagggtcac actcctgtta acaaatgcac tggccagtgc aatcaaatgt 138360

-continued gccatttcta ggaccaaagt ttgtatattc ctttttaata ttttttttca cttgtgttga 138420
tcatttgcct taaattaact ttctactttg tttaaaacat ggagaattag caagctgcca 138480
ggaagccagg cagggaaacc aggatgtttc catttacctt gttgctccat atcctgtccc 138540
tggaggtgga gagctttcag ttcatatgga ccagacatca ccaagctttt ttgctgtgag 138600
tcccggagcg tgcagttcag tgatcgtaca ggtgcatcgt gcacataagc ctcgttatcc 138660
catgtgtcga agaagatagg ttctgaaatg tggagcacat gttgtttagg tataaaatca 138720
gaagggcagg cctcgtgagg caaggtggca aaatttgatt tcttggagga cacctgagca 138780
tatacggtca aagtctgatg acaacaccag tagggatgaa gctgggagtg ggtggctaa 138840 gaacactgga cctgacacta ttagacatgg gttccagctt caggtctatt actgctcact 138900
gtggccgagc aacagagcta cttaggtaaa atggtgatgg tcataacact agcccacagg 138960
gaggttacga acctctggtg acaatgtaag tgaaaggccc ctgagaaaga gtgagggagt 139020
tgcaaatgtc agtagccatc aagatcttct ttaagaatag tttccactaa agagatgatt 139080
gctttggttt ccagccttct ttgttttgtc tccccgctgg gccttctacc tttaaagggc 139140
tttggctctg ggggaattga gttggctggg gcttgatgac ttccaagagg acacaagtgg 139200
agatctactg cctgctcttg gctaactacc ttcttcaaag atgaagggaa agaaggtgct 139260
caggtcattc tcctggaagg tctgtgggca gggaaccagc atcttcctca gcttgtccat 139320
ggccacaaca actgacgcgg cctgcctgaa gcccttgctg tagtggtggt cggagattcg 139380
tagctggatg ccgccatcca gagggcagag gtccaggtcc tggaaggagc actgcggaga 139440
gagcgaggga gggagcctgg tgaggtggtc ctgccaggaa ccatgctttg acatcagaga 139500
gtagaaagct cagagaggag gaaagggctt gaaagaatcc cgagcttcta aagatcatcc 139560
ctctctgggc caggcgtggt ggctcatgcc tgtaatccca gcactttggg aagccgaggt 139620
ggatgaatca tttaggtcag gacttcaaaa ccagcctggc caacatggcg aaaccccttc 139680
tctactaaaa atacaaaaat tagctgggtg tggtggggtg cacctgtaat cctagctatt 139740
caggagactg aggaaggaga atcgcttgaa ctcaggaggt ggaggatgca gtaagccaag 139800
attgtaccac tgcactccag cctgggcaac agagtgagac tctgtctcat aaaacaaaac 139860
aaaacaaaac aaaacaaaat aaaataaaat aaaataaaaa gattatccct ctctgaagct 139920
caaggaggtt aagggtgtac tcaagggcac acagcaggtt agaggcagac tcaagactag 139980
aatgtgggct ttctgacacc ttacaggcta ttcttttaga ataaatccca tttctacttt 140040
gttcatcttt tttgtacatg ccccacctac accatacatg tataccttct ctatatcttt 140100
ttgtatccct aatgctgtca cactatgatt tgctttttca tgcagatgac cataacattt 140160
tccattcacc tatgctcact cagcaagtat tcaatttttc tacactgttc ttttttttcc 140220
tttttcataa cactgtctca taggcattct gcaaatcctg tgagagtact ttttgtgaaa 140280
tgttaccact ttcctcttat tcagagaagc tccgtattaa ggcttcactg aggttgcctt 140340
aaggcatgat aatggttcaa aggcttgaaa gacagttaaa gagacctgta agtgcacaaa 140400
agaaagttga gcaggagaga atttcttgcc tggagcagag ccaagctact ggaagaggca 140460
atgggggcaa aggccaggca gacaagccaa tgggctcctc ccacagctgc agccaacaag 140520
ttatgccagt cttaaaactt ctaaagaaat atgtttttaa caagattgag gactggatta 140580
tgaggctagg ggaggctatc acaaactgga ataaaataaa gccagagaaa agtggctgcc 140640
ttccaacctg cacaactgac ctagctaggc tgatggctgg gccacctagg aaggctactg 140700
agcatcatat aaaacagaag ggacagcagg aatataacat ggctctttgt aaggatgagt 140760

-continued ctgaaaaatg accatttgct gcccaaatgc ccttagctac aactgaaaat atttcagaac 140820
tggaggttgc aggatgctgg aatctcagag atcatccagc tcagcccttt atttttcaga 140880
tgaggtccaa agcgggtaaa atgacttgtc aaggtcaaac agcaagtgaa tggttttctt 140940
tcaagtctca attcatcttt ttgtttatat catctatgtc ttgttgttat aagcttcacc 141000
ccaggtagca aaaaactatt ctactcaaaa ggggtagaca tatgttagtt ctcaagatca 141060
tctcttggtt tcagagttta actcaagtga ttggcatagg ctgaatccat ctcttaaaag 141120
gataatcaaa tttatgttga agacttggtt gtcttcctac tatgaaatgg gaaacattat 141180
cactactcct cccctgtcac caccaagtgt ggccaccacc accaacgtta gtgagtgact 141240
gtggtgatat gatgaccaag tggccaggtc agcaagtggt gcagcctgtg tctcactgga 141300
agaggttaaa gtctttctaa aacaaaatac catggcatca aagtggccca gaactccctt 141360
ctttgagctt tccctgtgtt agagcccttc cttgggttgg gagttaaacc catagtctta 141420
ccttcatctg tttagggcca tcagcttcaa agaacaagtc atcctcattg ccactgtaat 141480
aaaaacaggg acatgtctca attatgtctt ctaaacaggt ttattttttcc ttccctgtgt 141540
acaagacttg actgttcata agaaactgca aacagcctgc ctctcaaagc tgcctgaaac 141600
acctggcaag tttcacagtg atatgcgcag aacagtccag aaggcagatt ctaggcctgg 141660
caggtgggca ccctgggtgc tccctgttgg atcttgaggc ctaacctcta gcccagcaga 141720
gtcagctaaa atctgagctc tccctctccc tccaagccac actttgcaaa gggattcctt 141780
gtattgtggg cttggaatct tttctcccca tttgcctctg caggaagccc ttgcaacaac 141840
acatctggat agcctccagg tcccaaggct ggagggactt gtaatgggaa agtagtcttt 141900
aaatcagatt tacttggcac cctgtttgcc actgaaagag gcaatttagg ggaaaaatct 141960
ggtctccaag cacagataac actctactct tgaaagagga gacctgctca tgttactggt 142020
ctcagcgtct ccactgacct gtaataagcc atcatttcac tggcgagctc aggtacttct 142080
gccatggctg cttcagacac ctgtgtaaaa aggagaaaat gagtgacttc cccatgacgg 142140
ctacgttcat gtgtgatttc tctcagcatc cagtgcatgg cagtcatgca aagaaatgat 142200
ctctgagtaa atgaatgaat gtgtgaaaga gaagtccttt gggtctagag aaaagcattt 142260
gctaaaccaa accccaacta gcaatgtatt ggctaggaga gctggagcag aggctttgac 142320
actaaccttt agggtgtcag ctgttagata agcagtatcc attcccagaa tatttcccga 142380
gtcataagca ttatattaca cctggcattt ttgcaaaaag ctgagagagg gaggcagaga 142440
gggaaggaga gggagagaca gagaaagaaa gagagagaga gagagaatat gcatacacac 142500
aaagaggcag agagacagag agactccctt agcacctagt tgtaaggaag attaaagtca 142560
tacttgagca atgaagattg gctgaagaga atcccagagc agcctgttgt gccttgtgcc 142620
tcgaagaggt ttggtatctg ccagtttctc cctcgctgtt tttatagctt tcaaaagcag 142680
aagtaggagg ctgagaaatt tctctgttga atacctgatt tcacaatcaa gttaaaggaa 142740
aggggaaaag agtattggtg gaagcttctt aggggagggg actaataaac tgagataatt 142800
ctctggttca tggaagggca aggagtagca aactatgaca cattttgcaa atgtatcacc 142860
atgcaaatat gcattgtttt cctgacaatc gttgtgcagt tgatgtccac attaaaatac 142920
tggattttcc cacgttagaa gaatgtttaa atttagtata tgtgggacaa agtggaagac 142980
acacagattt atacatgcac atacttttct tcattcactt ctttgtactt aagtttagga 143040
atcttcccac ttacagatgg ataaatgggt acaatgaagg gccaatagcc ctccctgtct 143100

-continued

```
gtattgaggg tgtgggtctc taccttgggt gctgttctct gcctcgggag ctctctgtca 143160
attgcaggag cctctgagga gaaaattgac ctttcttggc tggggcagag aacatacggt 143220
atgcagggtt caggctcctg acggagttgg ggcaaccctg gagataagct cacacaaccc 143280
tgcaagacca ggtgctgtta ccctagccaa tctcatggat gaaccagatc aatgccagat 143340
gagctctgcc taaaatgatt ttttggtgaa ctctgaaaag tggaatattg tttctgtaag 143400
aatatccatc tgagactcta tctcttggta ataccaagag ttatcagttt ctctttaacc 143460
gagacaccag caaagtgcct gctccagggt actgcccagg ggagccctcc atttgtagaa 143520
tgaatgagag tccaggttat gaacagtgcc tggagtgtag gaacaccctc ctttgcctct 143580
ttgacaggtc tgcatcataa cacttttttt ttttttttga gacagagtct cactctgtcg 143640
cccaggctgg agtgcagtgg cacgatctcg gccccctgca agttccgcct cccgggttca 143700
caccattctc ctgcctcagc ctccccagca gctgggacta caggcacctg ccgccacgcc 143760
cggctaattt tttgtatttt tagtagagac agggtttcac catgttagcc aggatggtct 143820
cgatctcctg accttgtgat ctgcccgcct cggcctccca aagtgttggg attacaggcg 143880
tgagccaccg tgtccagcct gtaacacttc ttatagcact gagttgaaac cttgctcctc 143940
ctggttcctc caggaaactg aaatcttttt gagccaagtc tagcacagtg cctggcatgt 144000
acattcaggt ggtagagttt gctgcttgaa tgggtgaatg ggaatttgac agcattttta 144060
ttcaaattag tatgtgccag gtatcgtgct cgctctgcat tatccaaggg agtgagcctc 144120
tgtgcaagta tttgagacac gagggaaata ggttctactg tgggaaaaag agcatttcat 144180
ggacttgctc tccaagcagc cttctgattt ttaatttggc tcccagtatc ttgatatcag 144240
gagtcagtca caagaactcc atctttagta agttatattt tccacaggaa atctaaaagc 144300
tgttcaacat gttagtttcc tgtgaatttg ataagccata atccattcct aacactgagc 144360
cctcctgaaa tttggtgtct ggtcctgcag atagctaaaa gccctgtctg ggtggcctag 144420
gggactcctc tgttttgcct ccacaggatc cactttgcaa attaaccact ggttctcccg 144480
ttgtaggaac tgccaccttc ctcagagcct gtctttcttc cttccttcct tccttcctct 144540
ttctttttct ttctctctct ctttctttct tttcttttct ttctttcttt ctttctttct 144600
ttctttcttt ctttctttct ttctttcttc ctttctttct ctttctctct ttctctcttt 144660
ctctttcttt ctttctctct ccctccctcc ctctctctct ttctttcttt ttctttcttt 144720
tctcttttct ttctctcttt ctttctccct ccctctctct ctttttcttt gtctctccct 144780
cccttctctc tctctttctc tttctctctc tctctctcct agacaggatc tacctttatc 144840
ccccaggctg gagtgcagtg gtacaatcat gcattcattg catgatcaca gcagcctcaa 144900
acccttcctc agagtcttta tgcggcaacc agcagggtct ggagggttgg tggctctgtg 144960
aactctcctg acagaacaca gagatgtctt tggtctgttg atgtgattac aagctgaacg 145020
aaggaggatc aaagccagtg acaggaaggg agatatgcaa gggacccgag catcagctct 145080
gagttagtcc attctgcttc tgggacttgg gatacaggtc agaaaccttg agcttctact 145140
tctccatctt ccaattgtag catccaggac ctcagaatct gccagctaag aggagcccta 145200
atgattgtct ggtgggatat ggtgggacca cagagatgaa gacatgaata gctatttgaa 145260
tgtgaacagc agacgaagaa atcaaggcta ggagggtgga agtgactcat ccaatagcac 145320
agtgtggttg aagcagcact agtatccagg ttgcatgagc ccctgatgct ttcgctcgag 145380
ggaaattttg gagccatggg gcaatgcccc ctgacgtaac agtctccaca gttctgccat 145440
gtctcatcct ggccctgtaa cctggaccca aatctgctac catcccatcc atctcaggaa 145500
```

-continued gtgaaacctc ttatgtcaaa taggttgtgc aacgtatgta tcagatcctg tcttcccaag 145560
gagaccgctc aggccacagc acttccttcc gatccccaat gagcagaaaa tatctcgcta 145620
taaacatagt tggcactaag ggagggagtg gaagagtgat gatgatgtag atggtgatgt 145680
agccccaagg aagtggaaca agcagagatg gggagctgga aatgccagga tgctccagct 145740
tttggggaat tattcagctc ttgagtcact aaagcctttc tcagctgcaa gttcctcttt 145800
accctgtcag gtcattcttc caagacagga gactgacatt tattcaaagc agcaagtgcc 145860
ctgataccat cttgtgtcta atcatgggct tcgcagccag ttatcaaggt tgatctcatc 145920
tcattggtct tcaatcattt tgaacaagaa gacaagcaaa ataatcatgg gttagttctt 145980
atattattgt gtgtacatgc agtgatgtct gttctttgta gtgagctgtt ccttccttgt 146040
tcaccctctt gcttagaaca gaactaagca atctgccccc aacattttcc ccaatttccc 146100
atctcattct tggcactggc ttcctaatat ttgttcttat gagtcatttt cttgtatcat 146160
ttccatgagt ccctctggga tcttaaagta tgaaaaatgt tgtgtgtacc cacacctgtc 146220
tttgtggata tttctctcct ttcccttctg cttctgggat tatttgggaa tgggcactat 146280
gatttttatc atatcgcttc cacttccttt atggcatcat ctccaatggg cttcttctcc 146340
ctcttggatc caggttctca gattggggac atgcagagtc caaggaacat tccattctcc 146400
tccctggtct agaacaagga gggcttagat atatgagcag gtggctgggg ctggcgagct 146460
atgtagtctc caatggcttt tccctgatgt cggagttgtt atgtcagttc tgggagacca 146520
ataagacctt gtccttcctt tggatccatc agaaaaagcc cctgggtggg taagatggat 146580
ggcagggctc tcctactcta tgtcttttct cacacctagt gggtataaga gaggggacca 146640
caaacagagg gggctctggt accacttatc cagggtctgg aaacattttc tgtaaagggc 146700
cagataataa atgtttcagg tacaactact caaccttgca tcatttcaga aaagcagtca 146760
gataatacat aaatgaatgg gtgtggctgg acttgtcctg cggtcccctg tcttatatca 146820
ttgtattata tcatttttc ttacatacaa atttagaagc aatacttaaa aaaaaaaagc 146880
cgtcctttat tgagcaccta ctaagtgcca ggtacctttt tttccctcat tatcttatta 146940
actcttcata ataaccttta aagtagataa tattgaacca tttgacctat gcagaaactg 147000
aggttgagac aataaattat ttaagaccgc acaaacagta aatgctggaa ctacgactca 147060
aatatgggtt aactgaacca aaaccagatc tttatttctc acttttaatt gttacatatg 147120
tttattgcct catctcctgt ccacatggtg cccatcggca gactcctttc tcattctcag 147180
tgattgagtg acattctaaa ctacattggc ctggcagatt cacctctgtc ccctaaatgt 147240
ttccacattg tccttttagg attgagatcc tctctgttcc cttgtcttcc ctcctttctt 147300
cttctggcgg tgacgtgctg tgtgaatttg tttctttctc ctctcagggt agtactggga 147360
ctttccaaat cagggttttt aatgatctct cttcnctttt ctgaatttct tccttattcc 147420
cattcacttt ctcatctata agtggcanct ttgttgctgg aagatatccc ttgtgcaggg 147480
attnctcttt aanaatttgt cnnnaccgtg atcgtcaacc tcccaccctg tagggcctca 147540
agcattgagg acaatcactg gctgcccatt aacccagaaa tgttgccgag acaggaggcc 147600
gtggcccaag ttcctggaat ggggtattat tatgtcagca caaaggcctt tgcacaaatg 147660
aaggctttaa aaatgcagtc ctagtcaggt ggaggagggc ttataggatt cccaggaatc 147720
tggatcattc tcttgagagc tttcccttgt ctctgttaaa actcacatcg tacggcccaa 147780
ataacaacaa aaaatggatg taaattcttg aaataacttg tggatggggg aacaaggccc 147840

-continued acccccccaga tctgccagaa gcttcaggtg agggtcccaa atgccaaaaa gtctggtatc 147900
agagaggatg gccagtgacn tggggacaca tgccctttgc tgtgtcactc aaggagcagc 147960
agcttcggcc ccgcacagtg accaggaccc tggcttccca cgctgggcag gagctggtgt 148020
ctgatgaagg gaatgcctgg cagcacgtgc tgtctgtctc ctcgtgtcag cttacctggc 148080
tttgctgcga agaggccact tgcatttctt tattttttat attttttaa tttttaaat 148140
tttttatttt atttttattt ttatttattt atttattttt aattttttt taatttttta 148200
aattatgctt taagttttag ggtacatgtg cacattgtgc aggttagtta catacgcata 148260
catgcgccat gctggtgcgc tgcacccact aactcgtcat ctagcattag gtatatctcc 148320
caggttaatc cctcccccc tccccccacc ccacaacagt ccccagaatg tgatgttccc 148380
cttcctgtgt ccatgtgatc tcattgaatt tctttaaagg tggaatctct cagtggggtc 148440
taatctgttc agaaatatca aaagagtatc cttgggaatg actggaattc cagagtcatc 148500
tggtaatcct cataaaacaa ctcctggatg tctctcagca catctcccac cttgaacgca 148560
ggaggctggt tcaaatggag gagcatcgct ctactgcact tttttttttt tttggcctaa 148620
agtgcaaaag gggatacgtt tcatgtaaat aaatcaactg caaatcgcta gttatgctga 148680
gccctgtccc gtgctgtgga cacaaaggaa ccaaaggctt ttctccccgc ccaacacaca 148740
cataacacac acacaaaatc ataaaaacat acataccccc aacacataac aacacacaac 148800
acacacacaa aatatataca cacaacacac accaaacatg cccacaaacc tgtgtccaaa 148860
aataaatcct actggtgggt ttgtggtctc cctaacttca aaaatgaagc cgtggacctt 148920
cgcagtgagt gttacagctc ttaaagatgg catggatcca aagagtgagc agtagcaacg 148980
tttactgtga agagcaaaag gacaaagctt ccacaaccca gaaggggacc ccagcagggt 149040
tgctggttgg ggtggccagc ttttacttcc ttttggcccc tcccatgttc tgtttccatc 149100
ctatcagagt gcccttttt caatcctccc tgtgattggc tacttttaga atcctgctga 149160
ttggtgcatt ttacagagtg ctgattggtg cgttttacaa tccccttgta agacagaaaa 149220
gttcctgatt ggtgtgtttt acaatcctct tgtaagacag aaaagttccc caagtcccca 149280
ctggacccag gaagtccacc tggcctcacc tttcaactcc ataatggcat gaaaatacat 149340
atgttgtaca aaacatacat acacaaagta tacatgcatc tccccaaata tacacatacc 149400
acagaaacat acacacagga actcagctac ctgtcaaaag tctgcatggt gattgcctct 149460
gcagtgagta gttagaaaag tgaatttgtt tttcaataaa ttggagtcct taaaaatcgt 149520
tgtaagatag aaaattttta aaagtatata aaataaaata tgtatgtcct ttggtctagc 149580
atttacacat gtaggaattt atcctagtgg agtaatcaat gatatatgca aagatttgga 149640
caagcatatt aagcacagaa ttatgtatgc atatgtgtgt gtatatatat atatatctca 149700
tacatataat aatgtaaaag tgaaaataac tcagatgttc aaaattgagg attagttaga 149760
ctatgatctg tccatatgtg acatacaagt tagctgcccc ttattctctc gagcttcaac 149820
ctcctataaa cagtgtccct tgtatatcag tattggtaca gataatcgaa cttattgagg 149880
ttttacatgg ggcaataaag gcaagagttt atgaatactc catactacac taggtagcac 149940
cccctattaa agacaaactc ttctctctca tttcccttcc tttccggaac cacttggttg 150000
aatctctaca agtctctatt gcaactgcct caacatggca ccctccctgc atctccatct 150060
tccctgtcct gagagcaatg gcctgctgcc cccacactca catcctcatt cattccagaa 150120
gtgagcacca cagaagtgcc tacagttacc ccaaccacct tcttagaaga taagttagtg 150180
tttgttttga ctttttaaaa tttttacttc ctcttttcct tcacaatctc atcccatccc 150240

-continued aagaggttta tcaagaagtt ctctaaagat atgtgtctcc ttatggaatt taacagaaat 150300
cagggatttg tattctagcc atcaagggaa taacattttt ccaggtcttt agacaaataa 150360
tggaatacct tgcagtaatt agatacacta ttgtagaaaa gtattgatga aatggaacga 150420
tgtttgagat atcatattga gtagaaaagg caagatacat taagtaggaa atgtatctta 150480
caaaataatt tgtcagacac actcctatat ttgtatgtta tataaatgcg tatgtgaaga 150540
aaggctagag gatgagacca cagtcttcgg tgaagtttaa gagatgaggc tgcagcatgc 150600
tcagaaaggc ctgggttata gttcttccag taattaagga tgtgatcttg ggtaaattgt 150660
ccatcctctc taaactgcac caccttttgt ctgtaaaaca ggaaggatgg tatttacccc 150720
cagggtcatc aaaggatttg gttggagaaa aataaataaa tgggctgagc ccagacctgg 150780
cacagtgaga gcacagtggt tgactattgt gctggcctgt tgttcctgtg ttattgacat 150840
gctgctggtg gtggtccaga agctattacc ttaattggtt atgtggattt cccctcatac 150900
tgagcagctg tgtgtggtgt tgtaaaacat agccatacac agtaactgac aagggcaaat 150960
gtgatggaaa aatgcaagga agtgcagata aatagctaat gggctgtaga aggaagctag 151020
tccttggagg gcttgatcaa ggaaggtcct tttgcatgtc acctttgaag aagaggggac 151080
atagaagagg tatagtgcat cccggagtgt acctggaagg gaacatgaaa agaggacatt 151140
tttctctggg acatggggac tccacttgca tgaactctgg aattggggca aagaaccatc 151200
atgagaacaa gggcttcctt gaacctccca ggctcattgg ctgatctaaa ccctgtgtcc 151260
cctctttcct tcactctcct ctgttttcta tacctgtatt attggactgg actggaagcc 151320
acctgatcta tcacaagtac cttgaaatgt gttgaatagg tgtggcacag tccttagcag 151380
agtggcacta cccccacagg aatttgttta tacctttggc atggaaaata gcaggaaatg 151440
agtgatcact gataactgag gatgctattt attattggcc aaaggaatac ttgtgttgta 151500
tttgcataac cactcacaaa ctgttgatta caaatgagta ccagacctag ctccttcaag 151560
taaaggatcc tgagaactga aggcaaacag agctccagga gtccaagaca gagccacaga 151620
ccacgaggat ccctggccca ggtaggtggt cctcctgcac tggctttcaa ggccaacagg 151680
atggatgggg aagtagagta gcatctggcc atctagaccc ttgcttttta tccccactgg 151740
aagcacatct gaatttctaa atatgatctc tgagacctgc ccagaacacc ttgctctcag 151800
ccccagtagc agcctgctct ctcccaggag ggcttccact aacaagtagg gcattgctgg 151860
agggccaggc agacactagc ttaggaaatc caccaaccct ggaaatgcta gtcccttctc 151920
tgaaggctca gaagactgac tttagagtct agaaaatatt ggtccttggg aacagatttt 151980
gagtgcaaag agatggactt cagatggcca gatgcactgc ttctttaggg aattctgtga 152040
aagctccctg catttatctt aatacaggca gcagatttca tgagtacccc cgagggatgg 152100
ccccaggtcc tccagcctgt gagcatcctt ctgtccttca gcagcaccac agtatcttta 152160
tatgtctttg gatacctacg tttctgccag acatctcttg ctctgatgtt ctggctgcca 152220
aattctctgt caagcgcctc caattttttg tgtcctttga tttaccccaa catgacaaag 152280
gcagttgtgc ttcatgtatt cagggatact gccaaaccac aaacaggtta aaatcaaata 152340
gcagatatcc ctgttcctaa agacccatca gctctaccca cctgctcctg ctcaccgtcc 152400
ttattgttga gtcctgaagc ccttccttgt catttttatt ttttgcatga acaatttagt 152460
tccctttgtc tcactcctaa acctttctca aaggattgga tttgtacaca aactgcctat 152520
ctctgcaatc ttagaagtga tatgattctg aacaaatcac ttaactttg atttttttatt 152580

-continued

```
ggtaagatgg gaataccaat ttttgctcca cttctgtcct atgttggcct gggctgatgt 152640
tgaaagctct cggtcaactg agatagggtg tgcagaattt atatatataa atatatctcc 152700
tccaacccct cccaatgaag caagtcacgt gagtcaatcc taccctaaga tattagggat 152760
tgagcctcct gggacatttg gtggcttagg ttttcatgaa aagaggttgc agagcaactg 152820
ctttttgtta ggcaaagatt aggctactgc agagactcag caaacttcta tagaaggtgt 152880
cagatggtaa gtattttagg ctttgcttgc cagatgatct ctcaactagt taaccatgct 152940
attgtagcct cgaagcagcc agagacaata tgtaaacaag agcatggctg tgtttcaata 153000
aaactttatt taaaaaaaca gtcagggacc ggatttggcc aaaggccata gtgtgccagc 153060
cccaagacta gagcaatgca cttttaactt ttttatttta tttttgtaaa atgccaagat 153120
ccacaaaaat gctattgcac cccgtgtgtt agcactgtga ctcaaggttt gggaaattct 153180
gctttgaagg cgtgatagac aggagagcat ggtctggccc cttggtgcct ttctggttgc 153240
agcgagcatt tcaaactaca gagcaaggcc agtggtctgt tcagcactag agacatgcag 153300
caaggtgtcc tggggtgaga agatgccata actggtcccc tttctatctc cttaggtctt 153360
ggacttcatt ccattttctg ttgagtaata aactcaacgt tgaaaatgtc ctttgtgggg 153420
gagaactcag gagtgaaaat gggctctgag gactgggaaa aagatgaacc ccagtgctgc 153480
ttagaaggta aggttcttgt agaaatctac ctcagggcca aagtgtaatt cctagagcag 153540
aactttgcta ggtgctgtgc acagacccag ttgtttcctg ctgacttgca cagtaagtga 153600
gctttcaaat ttccctggac aaataactag acaagagaaa ttctggaaga gaaaaggaag 153660
ctttgcttca gtgtccaggc acatcaggta gtagataaaa ggatcgtcct cacctacaga 153720
tttggggctt tagcatcctg tttgccaact ggatggttgc atatgcttca aaatgcacct 153780
cttccctccc aacattccca agtggaagag aagcctccga tgagaaggaa ctctctaagg 153840
ctgggctgaa caaatgaccc aggcacaggg catctgagta ttccatgagg aacacatttg 153900
ggtgttgccc atgggggaca ataggaggag gcttttgacc caaatgattg tctactgagg 153960
tgtgacggga gaggcctgtg acatgccaga ggccaaaccc gtgatccagt tcatctctat 154020
tctatgtttc tgaagaggga agctatgatt taatgtcatt actatcatgc tgctctagta 154080
tttctcagca catacacaga agagggaatt aaatggtcct tgataccccct aaatccttgg 154140
aaaatccgaa ttgcatatgc taacctcact gcgtctgact gcagacccgg ctgtaagccc 154200
cctggaacca ggcccaagcc tccccgccat gaattttgtt cacacaagta aggcctcggg 154260
gtgaggtgat gggggtggct gaggtgcgag ggtggggatg ggggatggag ccattgggtc 154320
ctcttacagg gtgagagaat tgtagaatgg ggacacctaa gggtgctgga tggggctgaa 154380
gtctttcctt tgtggaagca aatcccatta ggagataact ctgggaaaga tgagcccggg 154440
gaggggcagg tgatgctcac ctgctaagag gcaaagggca aggaagagtt tgtgcctggg 154500
aaccttccag gtgcctcttc tgaccatagc caagagactg gagacacaga cctcctccca 154560
gcactgagga caaacagcca tggggccagt gggggtgcag ggacacccac accactaagg 154620
gctcagggcg gcgccttcag agcctgaacc ttcctctcat gctgccattt gaacaccaca 154680
acaccctaat aggaaactgt taacattgcc actgttcagg tgtggaaacc gagacagaca 154740
gtggagattc cctgccctag gtgacacagg taataagtga cagatgtgga aatttaaagg 154800
tactataacg tctgtctgcc tgactcaggc ttaaggctcc catcacctcc tcttctcagg 154860
acagagtcag gaggcctcag cctgagcccc agctctagtg caggttcatg tgggaatact 154920
gagcctcact agtacaatgg cagagaggac caaatgggac caggtgtgta agggtgcctg 154980
```

-continued gcacagttgg gggaggctgc tgtcgcttct ccaccgctgc tgctgcagtt acctttgatg 155040
ttttagtttt gttgtagtta caccattgct ggctttggat ctgcactgtg tccactccag 155100
gtggaaccac gcacacaagc ctctctgtcg ggcctgtcct gacttctcct tgtcagggct 155160
gggatctcct tcaaatctgg cggaagtggt tctccaagtc tggtcctcaa acgtcagcag 155220
catcagcgcc tagaagtgtt aggaatacac attcccaggc cccaccacag acctcctgcc 155280
tcagaaactc agggcgctga ggctctaggg gctgctttaa caagccttcc aggttatcgt 155340
gacgcacctt gaaagtctga gagctactgc cctacagaaa gttactagtg ccctaaagct 155400
ggcgctggca ctgatgttac tgctgctgtt ggagtacaac ttccctatag aaaacaactg 155460
ccagcacctt aagaccactc acaccttcag agtggccttg agaaagattt ggggtcaagg 155520
atcatgagcg agaacaccac ttaagaggat agtgaactag tctgcatgtg agacgctgag 155580
atcctatgtc aggctgtgat aggagggaaa cagaaaccaa aggaaagaac agctttaaga 155640
agcgcttaag aggtacaaag taaaatgatg gtgctagaaa agtagcttct taaaaagagc 155700
attttccagt ctcaccctgg actaactgaa tgagaatctc aggagtgtga ggcccaggta 155760
tccatggtct taaaatgcca cccaccaggt gattcccagt gtgcaccagg ggtgagagtc 155820
acagccttag gccatgccac tcaaagggtg tcttcagacc agcagcaccc acagctctgg 155880
gagtgcatca gaaagacaga ggcttggcac cacccacacc tactgaacca tagtttgcag 155940
gtgatttctt gcacattaaa gtgtgggaaa tggaaaagct tagagttcag ctagctcggt 156000
gactctcagt caacctgcac ctgctccatg aactcagact gcctgggatg ggcccagaaa 156060
agctcctgag gagattctga tgtaaggcag ggctgataac catggatctc atctgacccc 156120
atatcactgg ggagttactt aggatcttgc ctggggccag tcatctcttc catagacact 156180
gagagtgtcc acgatgcttg gggcactaca gggtgggagg tggaggatca cgggtgagtc 156240
agataggaag cctgctcctg gggagcttac agtgctatag ggcagcaagc caaggatgcc 156300
aatacctgtg tgcaggtacc actgacgagt gcagagcgct gcagcaccag agaggaagct 156360
accctgtgca gagggggctg aggagggctg cagggagatg acaggaaagc cggtgttaca 156420
ggaggagtcc tccccactct ttgggcatga ggagaccagg aggacattct acagtgagaa 156480
acccaggcag aggccatgtg cttatggcat gggaaaagaa tgacacctta gacttattct 156540
ctacattaga attgcctacc acagataccc atattatagc ttcacatagt gtggtggtta 156600
ctgtgttttc atattgtcac atttgccatt ttccagccac ccacccattc ttgacagtca 156660
ctggcccagc ctgggggccc ctgttcttta tcaaacaagt gcctgagctc tttgcagagg 156720
tgagggtcac ctgtccaatc agaggccagg agggaacgtt ccctttttaag accctactct 156780
aggcaggcct ggcccaaatg agttgctagg agcccacgcc ctaagaaccc tctgagcact 156840
gttgtggctg gtcctgctgc tagaagttgt tcctccaggg ccaggtgcaa gatttgtggc 156900
ttttcaaagg agccactaaa gctccagctc agccttgcac ggtgctgggc tcctgggggc 156960
ttcctgcctc caaccctccc aactcttcca tcaccgctcc cttagcctgg ccagtgcagg 157020
gatctgttcc actctaggca ctgctgaggg aatgatgcct ccagtcagag ggtgcaaaaa 157080
agagagttaa gaaaaacaat gattataaaa agtccttttt atacgccaga cattttcttt 157140
gctcaggcta agtgctactt atttgagtaa gcattttagt tctcataact cctctctcaa 157200
gtaggtgctg ctattacttt catttcacag atgaggacat tgaggtttgg agagacttag 157260
taacttgtcc tctgtcctac agcagagctg ggatttgaat ctatctgtcc aaatctggaa 157320

-continued cccatttgct tgcacagaaa gcttaattgc ttgtcccagc aagatagaaa gcctgggagt 157380
ggaagaaata ttcagtggct gtgatgtctg agcccacagg cagggtggag agctagggct 157440
ggggcccttg gacgtgggga agaaagggct gagtcttcca ttttcaatgt gaagtgttga 157500
tatctggtga tattgatcta ggtccaaagg tgaagaactt aaacccgaag aaattcagca 157560
ttcatgacca ggatcacaaa gtactggtcc tggactctgg gaatctcata gcagttccag 157620
ataaaaacta catacgccca ggtgactctc agttttggct gtgttttctg cctccaccta 157680
gcaggggtaa ggcctcctgc taggtgggct caactccatg ctataccatg ccccatctcc 157740
agcaggtggt ggaagcgagg aggagaggcc ccagggacta gggcatcaga tgaagggtct 157800
ctagcaatga ccagatctga aagtagtctt tctggaaggg ctggagaaaa agaaggaggc 157860
agacacttag actggaagaa gaggaggctt aaaccggtgt gatggaggga gaagtggacc 157920
acagagtcaa gggagaggga ctgtgcatca ggcctgaaac cccagcagac aggagagacc 157980
tttccctgct ctcagaaccc acacatgttc tgactgtctt tttccagaga tcttctttgc 158040
attagcctca tccttgagct cagcctctgc ggagaaagga agtccgattc tcctgggggt 158100
ctctaaaggg gagttttgtc tctactgtga caaggataaa ggacaaagtc atccatccct 158160
tcagctgaag gtgagagttc tagctcagtt tcctgggcct ttggctaccc caaagtaaaa 158220
ggccaagatc ctcaatgcct ctcgctttcc tgcaaattct tatcttggcc aatataacag 158280
ggacatccac ctttctggaa gcaccaggca gaagagcccc ataacttctt ctctggttcc 158340
ttgccccttc tagggaagga ggagagactc ctcacagcgg ggagacagca aggagctgag 158400
cacctgttct cctctcctgg gctcactggt cctggccctg ggcgggtggc ggtcccctcc 158460
tgctgtggcc ctccatgtgg caagcaacac aattgggcca ggaccctggc gtgctgctgt 158520
agggtaggag ggtgtgaggg agcactcgga gggcagtgtg tctgccctgc aaatttagtc 158580
ctggatggag catcctttca cttgagggga gaaatcttag gaagctgaat tagatacaga 158640
tctaagccat attctctaat tttaaaaact atagagctga gattttggta tccatctgac 158700
tcttacgtct ctctctctct ctctctctct ctcagtttat ttttaatctg ggggacaaga 158760
aggcctggaa aagagggcat gattgcttat catcccttaa ataccagtac caaggctgac 158820
acgtcatctt tcccaaggac catctgcctt ctctcttttc ctcctctcct gtgtaaaggc 158880
ctggaggatg agcacatgtg ctgtgttttc ctccctctca aagcctgtgc tatctaatta 158940
atccctttta cctcacagaa ggagaaactg atgaagctgg ctgcccaaaa ggaatcagca 159000
cgccggccct tcatctttta tagggctcag gtgggctcct ggaacatgct ggagtcggcg 159060
gctcaccccg gatggttcat ctgcacctcc tgcaattgta atgagcctgt tggggtgaca 159120
gataaatttg agaacaggaa acacattgaa ttttcatttc aaccagtttg caaagctgaa 159180
atgagcccca gtgaggtcag cgattaggaa actgccccat tgaacgcctt cctcgctaat 159240
ttgaactaat tgtataaaaa caccaaacct gctcactaaa ctttctgtca ttgggtttca 159300
tttctcattc atgctttaag gatttgtgtt tttaggatat agcaagaagc ttgtttaatt 159360
acaaagttct gggttggaaa gagaccggct tctgcttgtg tactgctacc ctgaaccatc 159420
agacatgcat gtgtgtgtca tatgctatga tgtggccagt ctgagtgcaa tacttgcagc 159480
gggaaggagc agctgggtgc atgctgtgct ctagaattag tctttcctac tggggtttgg 159540
tagattctga gggcattgat cctggggcag aagtggctga gtctgtgtct agggtacagt 159600
gtgcaagaaa gaaatgtaac agcaagtcac aatccagcca agtgatagtg gaaaaggggt 159660
agttaggtcc cagataagga gcagggtgac ttgacctgtg ggaaaggcac agagacaagg 159720

-continued aatctgggtc agatgacagc caggagacca ggtgagggag gagccaggta ctgtctggga 159780
ggcttgtcaa caagggcatg gtcctatcac taagcagggc tcagatcctc ataatggggg 159840
agtggaaggc tggccgaaca gaaatcaggg cctggaaaca gagtgagggg gtggagacag 159900
gagactgagg cttggaaatt agtttattag ttttagctct tcagttacaa gcaataataa 159960
tagcttctag cttatttaag caacaagtat actacaaaag gagctttcta gaaggatatt 160020
gggtatattc atttcttact gctgctgtaa caaattacca ccaacttagt ggtttaaaca 160080
atgcaatgta ttatcttgca gttatggagg tcagtctgga atgtgtctca ctgggccaaa 160140
atcaaagtat cagcaggata gcattgcttt gggaggctct aggggagagt caatttcctt 160200
gccttttcca gcttccagag gccacctgca ttccttggct agtggcccac tcccatcttc 160260
gctgcttggg tttttctcac actgctttgc tctgaccctc ctgccttcct ctttcacata 160320
taagaacgct tgcaatttac atcgggctca cgtcaatatc caggatactc tcccgtctca 160380
aagaggctta actttaatca cagatgcaaa gtcccttttg ctatgtcatg taacatatac 160440
acagggtctg ggattagaa tgtggacatt ttcggggtgc cattattctg cctatcatgt 160500
gaagtaactt tcaaaatgga aagacatgct gaagaaaaag tcagggattt ctggcaggcc 160560
agaaatgaca gaaggcagaa aacgttggtc ccatcactca gatgggtaag agccaatcat 160620
gctttttgtc agttagcaaa agattgagat tccaagcaaa gcatgcaact gccctagttt 160680
gggtcatgtg tcgactcctt ggtcagtgaa gggcagcaca ccttgatcaa tactccctcc 160740
aagactgtat ccaacgaggc cagtgatgtt cctcaaagca gagctagaga gctaatccca 160800
ggagagaggc gtgtgggtgg tgggcaggaa gacaaagctc agccgtaaag gagtagtagg 160860
gacagcaccc taggcatgga ggctcaagtg agatgatacc catgggaaaa gctctgataa 160920
ggtcagctcc ttctgtttct gatcctgatg gtgatggtga tcaacaccag cccagtgaca 160980
aaaaagtaca tagtatattt agtagatgtt tcccacacag agaaatggta aatattcaag 161040
gcgaggaata ctccaaacat cctaccttga tcattacaca ttccgtgcat gtaatgagta 161100
cttgcatgta tgccataaat atgtgaaata ttatgtatca ctatataaaa gaaaaaaaaa 161160
tgtggccagg tgacatccat attttggaga ggaaggcatg tcttcttcat aatatcacaa 161220
aactattttc acaacaaaga cacagctgtt caaattagtc tctgagccgg ggctgtctca 161280
tggcagtgag gactctggtt cccttacaga ctagcagaaa ggagatgggg cttactgacc 161340
atggccttga ggaggctgaa catgcaggcc aaatggagac acagacagcc tgggcttggt 161400
cctgctccat ccccttccaa cctgatgaga tatagtgagt cactatgacg tgggtcactc 161460
atgcttcctg tgaggctcca ccaagacagc aagtgcatca acaccttacg gaagcacaag 161520
gccctgtttg ttgttgactt catgaaaggc atggttgtgg tgatcgcatt gagtaggctt 161580
ttgggtgaga ggtgaaaaac cccaactatc atgcattgca gccctctggt ggaaactgtg 161640
cttcaggctc taaatttcag gctctagact gactccagga tgagtatttg gaagctgaag 161700
tcaatctgtg gtctcttctc ctgtagagca ggagtcagca cttttcatag agtgccagat 161760
tctatatatc ctgccacatg ctctgttgtt acagaacaaa gaaggccata gacagcatgg 161820
ctgtgttggc aaatacacaa aacaggcaat aagctgtatt tggcctttag gctgcagttt 161880
gccaacccct gcactaacac agagcttaaa ggtggtggtg gtgtgctgga gctagcttat 161940
atcagcttgc aatagccaat tgctaacatc tcttccaaac tctgtgtctg tgccttgatg 162000
ttgatagttt gaaattggct accccattta atgctgcaat cttttctcac cccagcacta 162060

-continued ctgactcccc tttgccctgt cttatttttc tcactctaac atgctgtata gttttcttct 162120
tacatttatt gtttgtgtct tccactagca tgtatgtccc acaagttctt tgctctgtga 162180
tgtatcccaa gaacccactg cagtgcttgg cacttgtagg aactccataa gatttttata 162240
aatgaagaaa ggaagaaaaa agagagggag ggaaaaagga aaggaagcct tctatttaaa 162300
tgatggcctt ctccatattt ctatagtaat atgacttccc ttgcaaaggg ggatgcattt 162360
tggaaaatgt gtataaataa actcaggtgg ttttgaattt cattttccta actgtaattg 162420
taatcattgg tctttatgtt tagtgaaaaa gttttggccc ttatgcctca cacctgagaa 162480
tcccaaagta ttggtttgtt agagctccca tagagaacca taaactgggt ggcttaaaac 162540
aacagaaatg tatcgtctcc tggttcagga ggccaaagtc tgaactccag gtgttggttc 162600
attctgagag ctctgagaga gaatctgttc caggcttccc ttcagtttgt ggtagctcca 162660
gggttccttg gctggtggca gcaaaactcc agtctctgcc cccatcttca catgactgtc 162720
ttctctctgt gtttctgtgt ccagattgtc ctataaggac agagtcatac tgaattaggg 162780
ctcactcgaa tgacttcatc ttaagttgaa ctgtatctgt aaagacctta tttccaagta 162840
aggtcacatt cacagctact gggggatagg acctcaacat atctttttgg gggacataat 162900
tcaactcata atacccaaca tgataactgt tcatcccatg aaatttaatg tctctcaaaa 162960
ggtgatctca gggcatttaa tctgtgacag aaactcccat aggaaacatt ccaaccagaa 163020
gctcctttca cagctggtca ctcctcctac cccatccgag gtcctggggc agggtgaggc 163080
aggtggggac aagaagaagg ctgtctcggg tgtagaaaga gaagaccctt attcacccgg 163140
cactctgttc atgaatgagc tatccagcat aggatataat aaatcgcttt aggagtggta 163200
gactccaaac attttttttgg tcccagttat cctaatcaat taaacaaact ctagaaccca 163260
tcttgaagtg caggcattgg gacattatga aacttacaca gaattcaaaa atttacaagg 163320
gctaaataaa acagggtctg acatctaata ttttcttccc acattcccat gcactgtctg 163380
gctcaaccat ccccaaccct cactctcatc ctggtggaca catgcctagt gatgtgatca 163440
gctggttcac agggggctgg tgatggtgga tatacagctt ttgccaattt ccatggcata 163500
actactccaa atatggccaa tttcaaacta ccaacatgaa ggcacagaca cagagtttgg 163560
aagagatgtt agcaattggc tattgcaagc tgatataagc tagctccagc acagcaccac 163620
cgctaccttt aagctccttg tgttagtgca agggttggca aactgcagcc taaaggccaa 163680
atacagctta ctgcctgttt tgtgtatttg ccaacacagc catgctgtct atggccttct 163740
ttgttctgta acaacagagc atgtggcagg atatatagaa tctggcagtc tttaataagt 163800
gctgactcct gctctacagg agaacacaga ttgtcttcag cttccaaaca ttcatctctg 163860
agtcagtcta gagcctgaaa tttagactga agcacagttt ccaccagagg gctgcaatgc 163920
atgatagttg gggttttcac ctctcaccca aaagcctact caattttttta ctgcaaaaac 163980 atgttatcat cattattttt tacttagccc acctttcctt ggcaattttc cataggaaaa 164040
tgcattctaa atttcaacta atcaggggac ttggagcctc tggacacccc cttgttcctt 164100
gcccacagtc ccttgcagaa ggtgccttat cagagcggct ccatgcaggg gctcaggaca 164160
ggatcagatg tcagttgcac caagggggca gggacagatc ctctctgctg accatgcaga 164220
agggactgtt cagtgcaccg tcatggtcct ggtgatttct ggtccataag ggaattttca 164280
catgcatcgg gtgattgtca catcagcaca acactgtgag gaaggcagag tgagaatttg 164340
tgtgcccatt ttataggtga gaaaacagat gcagagacat taagtaactt caccacagtc 164400
atgcgggttt taagtggcag actttcaggt gttgtgactc ctagtccaga gttctttgca 164460

-continued ctgcccctga ggtgctaaaa ctctactgtg ctttaagact cacttgggga gcttcctaaa 164520
aagagagatt gcacaacctg agattcttgt ttaactgttt tgggatgtag ctcagggatc 164580
tagctgcctt aaaaaaaaaa actcccaagt aattctgatg caagcggttc ttttttgtcc 164640
acctttgaag aaacactgcc tcctccccat acatttcatt agaaaatggt aacatgtttt 164700
tcagcctgag agccatttct gggtgaccgg acgtcggcag cccgctgtac tagctttcag 164760
tctaggctta aacacacatg ataggagatg tcctactcca gatgatatga gtctgaacca 164820
tggaaaaatt ccattgtgtg gcacatctgg tgggtgtgca ctgtccccag cagtgaggca 164880
cccagtgaag acagcagctg ggagaggctt agttacatgc agtgggacag tgtgggctag 164940
actgctgagc cctctgcagt ttactctgtg tcaggcaatg agggtgaaag gctgatcaga 165000
cccacgtgca gaccataccc tccagggaga cagatatcag tcaggacaac cccaagtgta 165060
gctggagaag cagtgcccag gtatgaccgg atgtgtatcc aaccaggaaa tctgcatata 165120
aatataagag gagaaaatga acagatgttg ctcttatatg tagatattta tgaagagcat 165180
ataattttgt tttgtgtgtt ttaagaagtt tataagtatg ccttaaaaat gtatagtata 165240
tactgtaggt attttttcca ttagatattt tgtttttcat acttatccac attgacattg 165300
tagcaacagt ataatataac aacctcctct acaaaagcag aaggaagtga agctttggaa 165360
ggaagcaccc agtgagcttg cccctttcag gtgggtgcag tgagcaggag tcagtgaggt 165420
tgagatcctt tgagaggagg caatcattaa ccaggaaatc tgcactgcat cctggccaca 165480
cctaaccctt ggacaatggt gcttggagcg ccttccagct cttaaggctt gcgatttctt 165540
tctctcactc ttcacccacg atgattaaat cttctcctac agagttggac aataaagcct 165600
tgagttcctg cctcccctgg tgtgatcacg aggcatagac atggccagga acatgtaggt 165660
gtctttgaaa gctgaacaag ttagtaaatt tcaaacctca tttcacccac cagtaaaatg 165720
ggaataataa taaacctatt ttacataggg ttgacaagag gagtaaagag ggattcaatg 165780
aaagttcgtt attatcattt gtagtagcag tgttgataat atcaactgaa agttcattat 165840
cattattagt agcagtattg ataaccctct tttctgtgcc ttctcactgg tgggcccagg 165900
ccatcagcaa tgcccagggt gtcatggatc tctgctgcat cgggcaccag ctgtgtcaat 165960
ggtgagaaca gtacaagggt gggcagggca aggcaggaag cacccaggag cagcagcttc 166020
atggggtgaa gatgtcagga gcttagggac agtcagagcg ggtgtgcctc ctcttgtgga 166080
gcctttctgc gtgggtagga actgctgcag ctgtggccat ggattcacct gaatatgggt 166140
ggaattaggc attcagctgg gttagctgtg cctagaagga ggaactctaa actgagaact 166200
tgtccctatt gccacctctg ataggcagat gatccatcca tcagtggctg agctgaggtg 166260
tgcatgggga tgggtaagag cccacacaca gggctgatga ctgagtctat ttagaacaat 166320
agatgtaaaa tctgataatg taaaatgtga tagattattt tgtcaattag aaatggtacc 166380
atataattat atatatacat aaacatgtat acatatacac acatatacat gtgtgtataa 166440
acacacacag tattgtcccc tactcattcc ataaacctga tgcctttagc tgggattccc 166500
agctttcact ctcctctctg tcatctgctg tctatatcct ccccatcctg taattctggc 166560
ttatatgcca cttcctccct aaagccctcc ctcaatccct tgctggaagt gacattttcc 166620
tctttgagct gcccctgctt gtgctttggt gaggtcagct gtattgcagt accttgtatt 166680
gtggttgtca catcatcgta tagaattaat ttctgacaca ttccgtattt ttcaaagggc 166740
ctagtgtggg gctttaacag taactacgcc accacgccca gttaattttt tgtatttttg 166800

-continued gtggagacaa ggtttcacca tgttggccgg gctggtttcg aactcctgac ttcaggtgat 166860
ctgtctgcct cagcctcctg gagtgctagg attgcaggca tgagccactg cacccagcca 166920
cctatcaaaa ttttaagtgc catttttatt ttttattttt tgtagaaatg gacaagctga 166980
tcgcaaaatt cacatggaat tgcaggaggt tccaaatagc caaaacaatc ttgaaaaaga 167040
agaacaaagt tggaggattt acactttcca gtttcaagac ttagctctta gctacaaagc 167100
tacagtaatc agaacactat ggtcctggca taagtgatgc tggacaggtg agccccaaag 167160
tgggacttaa cctgtgaagg ttcttggcct tgcccaggaa ggaattcaag ggcaagccaa 167220
tgggacaaga aaacagcttt attgaagggg cagtattaca gctccagccc tgttacagct 167280
ccagccctgt tacaactctg actactcctg cacagaaggg ctaccctgta ggcagagagt 167340
agcaactcag ggcagttttg cagtcattta tatccacttt taacacatgc agattaaggg 167400
acaatttatg cagaaatttc tacggaattg gtaataactt ttgggtcatg gagtcatcat 167460
ggaagggggg cggggaactc cctggtgttg ccatgatgac ggtaaactga tatggcgaac 167520
tggtgggtat gtcacatgaa aagctccttc caccccagcc ctgtttcaat tagtcctcgg 167580
tttggtccag tgtccaagtc ctgcctccag agtcaagtcc cacccctac ctcttaagga 167640 gagatgtaaa tacatggaat agaattgaga gtccagaaat aatctcatac atctatgatc 167700
aattgatttt cagcaaaggt gccaagacca ttcaatgagg gaaagaatca tattttttc 167760 aacaaatggt gctggataac cacatgtgaa agaatgcaac tgggccctta tctcacacca 167820
tatacagaaa ttaactcaaa atggctcaaa cacttacatg taagagctaa aactataata 167880
ttcttagaag aaaacaggga tatatcttta tgaccttgga tttgctggct gattcttaaa 167940
tgacactgaa agcacaagca acaaaagaaa aaaaaatagg taaattggac ctcatcaaaa 168000
tttaaaactt ttatgctggg tgcacacctg taatcccagc actttgggag gctgaggcag 168060
gaggatctct tgagcccaag aagctgaggc tacagtgagc cgaaattgtg ccactgcact 168120
ccagcctggg tgacagagca agaccctgtc tcgaataaat aaataaacaa atatataatt 168180
atagatctct ggatcttgcc ttcggagact gactcaacta actggtctgg gtgggagccc 168240
agccatttgt attttttgaa aactctccaa atgattttac tgtgcagcca aggttgagaa 168300
tcactgtatc atagggttgg actcctaact ggaaacagtt tgcaccatca ggtgtcgcag 168360
cattctgata atagttaagc tttcctccta gattttctga tattagatga gtcatgttta 168420
caagttttta ccaagagaca aactatcttt ctgcccttac tttctctctt atactattct 168480
aatcccagaa ccctttggaa cttccactga gagatgaatc tagaaagtga ctctcttggc 168540
tacaacagag agtaatgttg gcctgtttgt gccagatcca gttggtgctg gtggtgggac 168600
agcacctccc tgaaatcccc tcctctcccg tcagattcag tcccccattt gcatcacgta 168660
caatcatcac tatgggtttc tattaccttg ctagggcatt tggaggtacc atatatacca 168720
actattagtt ttgagccatg gttcccaaag tgtggactgt agggcacctc agcacactca 168780
cgaggtgtca tgggatattt aaatattctg aagaaaacac agtgacatct gtcaggcccg 168840
tgaaaaccgt tggcattaaa ttgtctcaac ccaattgctt aagaagcaga actggccagg 168900
cacggtggct cacatctgta atcccagcac tttgggaggc cgaggcgggc agatcacgag 168960
gtcaggagtt cgagaccagc ctgaccaaca tagtgaaacc ccgtctctac taaaaatata 169020
aaaattagcc atgcatggtg gcatgcacct gtaaccccag ctactcagga ggctgaggca 169080
ggagaattgc ttgaacctgg gaagcggagg ttgtagtgag ccaaaatcgt gccactgcac 169140
tccagcttgg gtgatagtga gactacatct caaaaaaaaa aaaatgagag agagagagag 169200

-continued aagcagaacc atcaggtgtt tcttttggct taaagtactc tgtgaagaaa ttcctgggac 169260
acgaaggata ccatgaactg agagattttg ggaacctctg ctttagaagc tggaggtagc 169320
attccttggg cacagtactg ccttgggatc agcaaatcct tttgatggtg catttaggtg 169380
tggcaagaca gctcttagag tgggaccggg atgtgcttgg agacagaggg aactagattg 169440
agctgcccga taaagacatg ccagcctggc agagtgtagt gactcatgtc tgtaatccta 169500
gtgctttggg aggctgaagt gggaggattg cttgaggcca ggggtttgag atcagcctgg 169560
gaaacaacaa gacctctaca aaaaaaaaag aaaaaaaaaa ttaaccacat gtggtggcat 169620
gcacctgtag tcccagctac ctggcaggct gaggtaggag gatcacttga gcccaggaag 169680
gtaaggatac attgagccat gactgtgcca ctgcactcta gcctgggtga cagaaagaga 169740
ctctgtctca gaaataaatt aaataaataa ataaatatat agtggccatg acatccctag 169800
aaagacaagg tcctgggaat aggtagaagc caagggaaat gagaaatgag agggggccct 169860
ggagctggaa ctgggggagc aggatggcct ctgagaagtt cctgatagtg gtgtcactga 169920
tgtgtctgat gtttagttgt aattatttgc tgggcccctg tcatccctca tatctgatag 169980
ctctttgcta gtcaaagtgt ggtctgggga tcagcggcat cagcatcact tgagaacttg 170040
ttagagatgc agaatctaga gccccacccg ggacccagaa acagagcctg cattttaaca 170100
agctccccag gtgattctca cacacactcg catttgagaa gcactgggct agttgacaga 170160
ttctcaggca tggctgacat tgaaatatcc agggagcagg cttggcatta ggatgtttaa 170220
aagtcctcca ggtgtttcta aagccaggtt tgaggaatta ctgggctgat acaaatgttt 170280
tgtgatgatg ctttgtgtgt gtgtgtgtgt gtgtgtgtgt gtgtgtgtgt gtgtgtgtgt 170340
gtgtgtgtag ggaattctgg gtcacttggc accaacacag gaaacaatgg aaatatgtga 170400
gccatgacag aaaggtcagg agataaaaga aattagtgac atgagaggta ctcctcaggt 170460
gttaggaaag agggtagagc aaaccaggtt ttccaccata tgttggatag ggggtcaagt 170520
aaatttctac ttaaaaatta caaacagggg ctgggcgcgg tggctcatgc ctgtaatccc 170580
gcactttggg aggctgagga gggcggatca caaggtcaag agattgagac catcctggcc 170640
aacacggtga aaccgtgtct ccactaaaaa tacaaaaatt agctgggcat ggtggtgcgt 170700
gcctttattc ccagctactc gggaggctga ggcaggagaa tcgcttgaac ctgggaggtg 170760
gaggttgcag tgggccgaga tcgcaccact gcaatccaga gcgagactgt gtcaaaaaaa 170820
aaaaaaaaaa gaaaattcca aacaggatga ccctaagcct gcaggacttg gagacatcta 170880
ggtgactgat actcagtcac aaaacataat tggtcacagg cctgatgaaa tgcacagcag 170940
accttcagat ggtatgcact caagtgatat ccacaagtcc acctaaagaa atgctatatt 171000
cagacatttg gcatcaatct ctatcaaaca aagatagtcc aaagcaatgg gttccaaaaa 171060
cactttccta agacaaattc tctatttgct tttaatatca gtcatcccag cccttggaat 171120
agaggagcaa atgataccag tggtacccta ccacaatgca ccaaggtatt atactctcat 171180
gctccatttt ctccctctgt ctacatcact aataactcat tgatttctgg tgcaagccct 171240
gctgggagaa aaagtctact cttgtacctt ggagcaagtt gctcagagta ggtatcgagg 171300
ataaaatttg gaaagttaga aaagctatta gaaggagatc ctagtagttg aaaacacagc 171360
ctggccaagt caatgatgct atttcatctc cccagccttg catgtccata gctaaggaag 171420
acaatttagg cttgggctag aggatgggaa agggcaaaat tactgatgcc acagcccaga 171480
gaggtattct agtaatctga gggtgaggac cacatacctg gttcagggac gtacagtgtt 171540

-continued

```
gacagctgtg agtggatgcc tggagttctg gcgtgtcttc tagcacaatg atacctgaga 171600
ctcttgcatc attgggaata ataaaatggg agtggataga tatgaaatta tgatggcaat 171660
aagcaatcag ctaatagctt cattgatggg acagattaaa gatggctgca aatcctttgg 171720
tccaggtttg ggatataggc agcatttgta ttggaatgct gatagtctga ggccatgaaa 171780
agtccacctg cagtagtggt aggaggaaca agcctcactt tcttcaatgt gtgtgactgc 171840
tgtcttgatt ccctgggtgg ccagttccat tcgtgtggtt ctttggtcca cttgactctg 171900
gggtggctct gtgatggctt gaccaataca atgtagtgga aatgatgctg tcatcatttc 171960
cagcctcttc cagccttaag gaactggcaa cttttatttc tgtcccttgg aatacttgtt 172020
cttgcaaccc atccatcata cagtgagaaa ttctaagctg ccccattaag aggcccacat 172080
ggtgataaat tggggtctta catacagccc tagctgtgct cctagctgac aaacagtagc 172140
aacttgtcac caggcgagtg aaccacttag gactgtatac tccagcccca gttgagcaat 172200
gtggaacaga gtaaaccatc tcagcttagc cctgcccaaa ctgcagaatt atgagcaaaa 172260
taatccccta ggctttgggc tgatttgttc cagattactg gaacagaatt tggtaccagg 172320
ggtgaggtgc tacagcaatg aaagcttaag acacgtgact ttggttttgg gtctgagtgg 172380
caggggaact tggcaggcct caaggaaact tttagggagg gttgaagcat agtgaggaaa 172440
acagtagggg aagctagagg aaaaaatgat gcttggtatg tagtggtggg aagtttagca 172500
aaactcgcct gatgtaatgt gggaaattgt aagaactcag aacgatttaa gggcatgttt 172560
tataggtcct ttaagaaact tctaggccag gcgcagtggc tcatgtctgt aatcccagca 172620
ctttgggagg ctgaggtggg cggatcacaa ggtcaggaga tcgagacaat cctggctaac 172680
attgtgaaac cccgtctcta ctaaaactac aaaaaaaaat tagccgggca tggtggcggg 172740
tgcctgtagt cccagctact agggaggctg aggcagaaga atggcgtgaa cctgggatgt 172800
ggatcttgaa gtgagcccag attgtgccac tgcactccag cctgggcaac agagtgagac 172860
tccgtctcaa accgaaaaaa aaaaaaaaaa aaagaaactt ctagggctgg tcccgtggaa 172920
gcctcacaca tggtacacaa aggctgtctt gaaaagaaac gtaagtgtgt tttttggttt 172980
aataaaattg attataaatg gataatgcaa aacattttaa agaattttac tagcttacat 173040
tagcagattt ggatccagtg attgttacat tctggtactg agcccctgaa ttacttcttt 173100
gagtaaggca ttataccaaa gctattgata gttgggctta tagggtgtat gtttgaagaa 173160
ctactaatgt caaaaccaat atttcacggt cgacaagagg acatcagaac tggtaatcct 173220
tattaccatg actggctgga cagaatactc aatgtaatgg gatttcctgc aaataaagac 173280
ggggaagatg taaaaaagat gcctgaacat tcaacattaa tgaaagattt cagaagaaat 173340
atgtatacta actgcagcct tatcaagtat atggaaaaac acaaagttaa accagatagt 173400
aaagcattcc acttgcttca gaagtttctt actatggacc caataaagtg aattacctga 173460
gaacggggtc cctgtttctt cgaagaccca cttcctacat cagacgtttt caacagttgt 173520
caaatcccct acccaaaatg agaattttta acagaagaag aacctgatga caaaggagcc 173580
aaaaagaacc accaccggca gcagggccat aaccacacga atggaactgg ccacccagga 173640
atcaagacaa cggtcacaca cagggacccc cgttgaagaa agtgaggctt gttcctccta 173700
ccactacctc aggtggactt ttcacggcct cagactatcc gcgttccaat ccacatgctg 173760
cctatatccc aaccctggac caagcacatc ccagccgaag agcagtgtag gatactcagc 173820
tacctcccag caggctccac aggacccacg tcagacacac gggtactgag ctgcatcgga 173880
atcttgtccg tgcactgttg tgaatgctgc agggctgact gtgcagctct ccgtgggaac 173940
```

-continued ctggtatggg ccatgagaat gtactgtaca accacacctg cccagtagcc aagttccttc 174000
caccgctttt cacagatcgg ggtagtggct tccagtttgt acctattttg gagttagacc 174060
tgaaaagaaa gcgctagcac agtttgtgtt gtggatttgc tactttcata gttaacttga 174120
cctggctcag actgaccagt actttttttt ccgtgacagt ctatagcagt tgaagctgag 174180
aatgtgctag gggcaagcgt ttgtcttcat atgtcatgaa ttcctccagt gtaacaacat 174240
tatctgacca atagtacaca cacagacaca aggtttaact ggtacttgaa aacatacagt 174300
aggtgttaac tcagtgaaat aaccaggact caaagtaaga ttattttggt acacctttct 174360
tgttagtgtc ttatcagtga gttgattcat tttctacatt aatcagtgtt ttctgaccaa 174420
gaatattgct tggatttttc tgaaagtaca aaaagccaca tagttttttt cagaaaggtt 174480
tcaaaactcc taaagattaa tttccaagta taagtttgtt tttattttca atctatgact 174540
tgactggtat taaagctgct atttgatagt aattagatat attctcattg atataaacct 174600
gtttggttca gcaaacaaac taaaatgatt gtcacagaca atgctttatt tttcctgttg 174660
gtgttgcttg tgggaaaaag aaagagagat cagattgtta ctgtgtctgt gtagaaagaa 174720
gtagacatag gagactccat tttgttctgt actaagaaaa attcttctgc cttgagatgc 174780
tgttaatcta tataacctta cccccaaccc tgtgctctct gaaacatgtg ctgtgtccac 174840
tcagggttaa atggattaag ggcggtgcaa gatgtgcttt gttaaacaga tgcttgaagg 174900
cagcatgctc gtaagagtca tcaccactcc ctaatctcaa gtacccaggg acacaaacac 174960
tgctgaaggc cgcagggacc tctgcctagg aaagccaggt attgtccaag gtttctcccc 175020
atgtgatagt ctgaaatatg gcctcgtggg aggggaaaga cctgaccgtc cccagcccg 175080
acacccgtaa agggtctgtg ctgaggagga ttagtatacg aggaaggaac gcctctttgc 175140
agttgagaca agaggaaggc atctgtcttc tgcccgtccc tgggcaatgg aatgtctcgg 175200
tataaaaccc gattttatgt tccatctact gagatagggg aaaaccacct tagggctgga 175260
ggtgggacat gcggcagcaa tactgctctt taagacattg agatgtttat gtgtatgcat 175320
atctaaagca cagcacttaa ttctttacct tgtctatgtt gcagagacct ttgttcacgt 175380
gtttatctgc tgaccttctc tccactatta tcctatgacc ctgccacatc cccctctccg 175440
agaaacaccc aagaatgatc aataaatact aagggaactc agaggccggc gggatcctcc 175500
atatactgaa cgcttgtccc ctgggccccc ttatttcttt ctctatactt ggtctctgtg 175560
tctttttctt ttccaagtct ctcgttccac ctaatgagaa acacccacag gtgtaaaggg 175620
gcaacccacc ccttcattgc tgatttgtga gcgtgcttta aggtgaaaaa agcatgaatg 175680
ttaacttcct taaaaaggta cagcatccaa ttcaaatatt tttgtcctga ttttaatgct 175740
agttgatgta gtgctattaa aattttgttc aacatggaca cagagagggg aacaacacat 175800
accagggcct gttgcggggt ggggatgagg ggagggaact tagaggacag gtgaacaggt 175860
gcagcagatc accatggccc acatatacct atttaacaaa cctgcacgtt ctgcacacgt 175920
atcccatttc tttttttttt taagaaatag aaaaaaaaat aaaattttgt tcactgattc 175980
ttccatttta aaacttgttt gcatgtggtt taggatgccc ttacttcagc aaaggagaag 176040
gaataggagg gccttagaat ttttgaggga aaaaaaccct ataacataca ttgtactgta 176100
tcaaactatt ttacatgaat gacacaagta ttctgaataa aaaaataatt gaacattgtt 176160
aagaacaagg tgtcatgtaa tttatttttc ataaataaaa aaattatagt ggcttagact 176220
gaaaggaaca gagaatttaa aaaattaaaa agaagcctta gtatattttt gtatatagtt 176280

-continued

```
tccatgtgcc atatttgcca taattggatg agaatttttt gacctctggc agggtgaccc 176340

tatattttca ntntataaag cgtgcatcat acc                             176373


<210> SEQ ID NO 18
<211> LENGTH: 185
<212> TYPE: PRT
<213> ORGANISM: Artificial sequence
<220> FEATURE:
<221> NAME/KEY: synthetically generated
<222> LOCATION: (1)...(185)
<223> OTHER INFORMATION: human sequence predicted using an alignment
      algorithm which predicts presence of alternatively spliced exons
      for a protein of interest in a stretch of genomic DNA
<220> FEATURE:
<221> NAME/KEY: VARIANT
<222> LOCATION: (1)...(185)
<223> OTHER INFORMATION: Xaa = Any Amino Acid

<400> SEQUENCE: 18

Met Val Leu Lys Cys His Pro Pro Gly Asp Ser Gln Cys Ala Pro Gly
  1               5                  10                  15

Val Arg Val Thr Ala Leu Gly His Ala Thr Gln Arg Val Ser Ser Asp
             20                  25                  30

Gln Gln His Pro Gln Leu Trp Glu Cys Ile Arg Lys Thr Glu Ala Trp
         35                  40                  45

His His Pro His Leu Leu Asn His Ser Leu Gln Pro Gly Gly Pro Cys
     50                  55                  60

Ser Leu Ser Asn Lys Cys Leu Ser Ser Leu Gln Arg Ser Ala Ser Ala
 65                  70                  75                  80

Glu Lys Gly Ser Pro Ile Leu Leu Gly Val Ser Lys Gly Glu Phe Cys
                 85                  90                  95

Leu Tyr Cys Asp Lys Asp Lys Gly Gln Ser His Pro Ser Leu Gln Leu
            100                 105                 110

Lys Glu Lys Leu Met Lys Leu Ala Ala Gln Lys Glu Ser Ala Arg Arg
        115                 120                 125

Pro Phe Ile Phe Tyr Arg Ala Gln Val Gly Ser Trp Asn Met Leu Glu
    130                 135                 140

Ser Ala Ala His Pro Gly Trp Phe Ile Cys Thr Ser Cys Asn Cys Asn
145                 150                 155                 160

Glu Pro Val Gly Ile Xaa Asn Xaa Val Asp Phe Asp Leu Leu Gly Lys
                165                 170                 175

Ala Gln Lys Arg Gly Thr Gly Ser Glu
            180                 185
```